US008206914B2

(12) United States Patent
Liu et al.

(10) Patent No.: US 8,206,914 B2
(45) Date of Patent: Jun. 26, 2012

(54) EVOLVING NEW MOLECULAR FUNCTION

(75) Inventors: David R. Liu, Lexington, MA (US); Zev J. Gartner, Santa Cruz, CA (US); Jeffrey B. Doyon, Allston, MA (US); Christopher T. Calderone, Boston, MA (US); Matthew W. Kanan, Cambridge, MA (US); Xiaoyu Li, Cambridge, MA (US); Thomas M. Snyder, Cambridge, MA (US); Daniel M. Rosenbaum, Burlingame, CA (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 12/834,072

(22) Filed: Jul. 12, 2010

(65) Prior Publication Data
US 2011/0190141 A1 Aug. 4, 2011

Related U.S. Application Data

(63) Continuation of application No. 10/950,367, filed on Sep. 24, 2004, now Pat. No. 7,771,935, which is a continuation of application No. 10/643,752, filed on Aug. 19, 2003, now Pat. No. 7,491,494.

(60) Provisional application No. 60/404,395, filed on Aug. 19, 2002, provisional application No. 60/419,667, filed on Oct. 18, 2002, provisional application No. 60/432,812, filed on Dec. 11, 2002, provisional application No. 60/444,770, filed on Feb. 4, 2003, provisional application No. 60/457,789, filed on Mar. 26, 2003, provisional application No. 60/469,866, filed on May 12, 2003, provisional application No. 60/479,494, filed on Jun. 18, 2003.

(51) Int. Cl.
*C12Q 1/68* (2006.01)
(52) U.S. Cl. ........................................................ 435/6.1
(58) Field of Classification Search .................. None
See application file for complete search history.

(56) References Cited

U.S. PATENT DOCUMENTS

| | | | |
|---|---|---|---|
| 4,683,202 A | 7/1987 | Mullis | |
| 4,863,857 A | 9/1989 | Blalock et al. | |
| 5,162,218 A | 11/1992 | Schultz | |
| 5,270,170 A | 12/1993 | Schatz et al. | |
| 5,449,602 A | 9/1995 | Royer et al. | |
| 5,539,082 A | 7/1996 | Nielsen et al. | |
| 5,547,835 A | 8/1996 | Koster | |
| 5,559,000 A | 9/1996 | Janda et al. | |
| 5,573,905 A | 11/1996 | Lerner et al. | |
| 5,574,141 A | 11/1996 | Seliger et al. | |
| 5,597,697 A | 1/1997 | Diamond | |
| 5,605,798 A | 2/1997 | Koster | |
| 5,622,824 A | 4/1997 | Koster | |
| 5,637,682 A | 6/1997 | Nieuwlandt et al. | |
| 5,639,603 A | 6/1997 | Dower et al. | |
| 5,660,988 A | 8/1997 | Duck et al. | |
| 5,677,195 A | 10/1997 | Winkler et al. | |
| 5,691,141 A | 11/1997 | Koster | |
| 5,698,685 A | 12/1997 | Summerton et al. | |
| 5,708,153 A | 1/1998 | Dower et al. | |
| 5,719,262 A | 2/1998 | Buchardt et al. | |
| 5,721,099 A | 2/1998 | Still et al. | |
| 5,723,289 A | 3/1998 | Eaton et al. | |
| 5,723,598 A | 3/1998 | Lerner et al. | |
| 5,770,358 A | 6/1998 | Dower et al. | |
| 5,770,367 A | 6/1998 | Southern et al. | |
| 5,786,461 A | 7/1998 | Buchardt et al. | |
| 5,789,160 A | 8/1998 | Eaton et al. | |
| 5,789,162 A | 8/1998 | Dower et al. | |
| 5,789,172 A | 8/1998 | Still et al. | |
| 5,811,238 A | 9/1998 | Stemmer et al. | |
| 5,840,485 A | 11/1998 | Lebl et al. | |
| 5,843,701 A | 12/1998 | Gold et al. | |
| 5,846,839 A | 12/1998 | Gallop et al. | |
| 5,851,765 A | 12/1998 | Koster | |
| 5,858,660 A | 1/1999 | Eaton et al. | |
| 5,872,003 A | 2/1999 | Koster | |
| 5,922,545 A | 7/1999 | Matheakis et al. | |
| 5,925,517 A | 7/1999 | Tyagi et al. | |
| 5,945,325 A | 8/1999 | Arnold et al. | |
| 5,958,691 A | 9/1999 | Pieken et al. | |
| 5,958,703 A | 9/1999 | Dower et al. | |
| 5,986,053 A | 11/1999 | Ecker et al. | |
| 5,998,140 A | 12/1999 | Dervan et al. | |

(Continued)

FOREIGN PATENT DOCUMENTS
DE 19646372 6/1997
(Continued)

OTHER PUBLICATIONS

Acevedo et al., "Non-Enzymatic Transcription of an Oligodeoxynucleotide 14 Residues Long" *J. Mol. Biol.* 197: 187-193 (1987). Alvarez et al., "Photocleavable Protecting Groups as Nucleobase Protections Allowed the Solid-Phase Synthesis of Base-Sensitive Sate-Prooligonucleotides" *J. Org. Chem.* 64: 6319-6328 (1999).
Anderson et al. "A Comparison of Selected mRNA and Protein Abundances in Human Liver" *Electrophoresis* 18: 533-537 (1997).
Arap et al., "Steps Toward Mapping the Human Vasculature by Phage Display" *Nat. Med.* 8(2) 121-127 (2002).
Arnold et al., "Directed Evolution of Biocatalysts" *Curr. Opin. Chem. Biol.* 3: 54-59 (1999).

(Continued)

*Primary Examiner* — Kenneth R. Horlick
*Assistant Examiner* — David Thomas
(74) *Attorney, Agent, or Firm* — Goodwin Procter LLP

(57) ABSTRACT

Nature evolves biological molecules such as proteins through iterated rounds of diversification, selection, and amplification. The power of Nature and the flexibility of organic synthesis are combined in nucleic acid-templated synthesis. The present invention provides a variety of template architectures for performing nucleic acid-templated synthesis, methods for increasing the selectivity of nucleic acid-templated reactions, methods for performing stereoselective nucleic acid-templated reactions, methods of selecting for reaction products resulting from nucleic acid-templated synthesis, and methods of identifying new chemical reactions based on nucleic acid-templated synthesis.

19 Claims, 114 Drawing Sheets

U.S. PATENT DOCUMENTS

| | | | |
|---|---|---|---|
| 6,037,120 | A | 3/2000 | Benner |
| 6,043,031 | A | 3/2000 | Koster et al. |
| 6,048,698 | A | 4/2000 | Eaton et al. |
| 6,060,596 | A | 5/2000 | Lerner et al. |
| 6,074,823 | A | 6/2000 | Koster |
| 6,080,826 | A | 6/2000 | Grubbs et al. |
| 6,103,476 | A | 8/2000 | Tyagi et al. |
| 6,127,154 | A | 10/2000 | Mosbach et al. |
| 6,140,053 | A | 10/2000 | Koster |
| 6,140,493 | A | 10/2000 | Dower et al. |
| 6,140,496 | A | 10/2000 | Benner |
| 6,143,497 | A | 11/2000 | Dower et al. |
| 6,150,097 | A | 11/2000 | Tyagi et al. |
| 6,165,717 | A | 12/2000 | Dower et al. |
| 6,175,001 | B1 | 1/2001 | Barbas et al. |
| 6,194,144 | B1 | 2/2001 | Koster |
| 6,194,550 | B1 | 2/2001 | Gold et al. |
| 6,207,446 | B1 | 3/2001 | Szostak et al. |
| 6,214,553 | B1 | 4/2001 | Szostak et al. |
| 6,225,450 | B1 | 5/2001 | Koster |
| 6,238,871 | B1 | 5/2001 | Koster |
| 6,287,765 | B1 | 9/2001 | Cubicciotti |
| 6,291,160 | B1 | 9/2001 | Lerner et al. |
| 6,291,161 | B1 | 9/2001 | Lerner et al. |
| 6,368,874 | B1 | 4/2002 | Gallop et al. |
| 6,391,593 | B1 | 5/2002 | Weston et al. |
| 6,436,635 | B1 | 8/2002 | Fu et al. |
| 6,511,809 | B2 | 1/2003 | Baez et al. |
| 6,607,878 | B2 | 8/2003 | Sorge |
| 6,680,192 | B1 | 1/2004 | Lerner et al. |
| 7,070,928 | B2 | 7/2006 | Liu et al. |
| 7,223,545 | B2 | 5/2007 | Liu et al. |
| 7,442,160 | B2 | 10/2008 | Liu et al. |
| 7,491,494 | B2 | 2/2009 | Liu et al. |
| 7,557,068 | B2 | 7/2009 | Liu et al. |
| 7,771,935 | B2 | 8/2010 | Liu et al. |
| 2001/0036638 | A1 | 11/2001 | Nolan et al. |
| 2002/0034757 | A1 | 3/2002 | Cubicciotti |
| 2002/0038000 | A1 | 3/2002 | Gold et al. |
| 2002/0064779 | A1 | 5/2002 | Landegren et al. |
| 2002/0064798 | A1 | 5/2002 | Nolan et al. |
| 2003/0099945 | A1 | 5/2003 | Eaton et al. |
| 2003/0104389 | A1 | 6/2003 | Sergeev |
| 2003/0113738 | A1 | 6/2003 | Liu et al. |
| 2003/0143561 | A1 | 7/2003 | Pedersen et al. |
| 2004/0014090 | A1 | 1/2004 | Neri et al. |
| 2004/0049008 | A1 | 3/2004 | Pedersen et al. |
| 2004/0180412 | A1 | 9/2004 | Liu et al. |
| 2005/0009050 | A1 | 1/2005 | Nadeau et al. |
| 2005/0025766 | A1 | 2/2005 | Liu et al. |
| 2005/0042669 | A1 | 2/2005 | Liu et al. |
| 2005/0142583 | A1 | 6/2005 | Liu et al. |
| 2005/0221316 | A1 | 10/2005 | Pedersen et al. |
| 2005/0227281 | A1 | 10/2005 | Liu et al. |
| 2005/0233381 | A1 | 10/2005 | Liu et al. |
| 2005/0281819 | A9 | 12/2005 | Liu et al. |
| 2006/0223086 | A1 | 10/2006 | Liu et al. |
| 2006/0246450 | A1 | 11/2006 | Franch et al. |
| 2008/0318807 | A1 | 12/2008 | Liu et al. |
| 2009/0035824 | A1 | 2/2009 | Liu et al. |
| 2009/0149347 | A1 | 6/2009 | Liu et al. |
| 2010/0152099 | A1 | 6/2010 | Lee et al. |
| 2011/0059458 | A1 | 3/2011 | Huang et al. |

FOREIGN PATENT DOCUMENTS

| | | |
|---|---|---|
| EP | 0324616 | 7/1989 |
| EP | 0643778 | 3/1995 |
| EP | 0604552 | 2/1997 |
| EP | 0773227 | 5/1997 |
| WO | WO-9105058 | 4/1991 |
| WO | WO-9202536 | 2/1992 |
| WO | WO-9306121 | 4/1993 |
| WO | WO-9320242 | 10/1993 |
| WO | WO-9609316 | 3/1996 |
| WO | WO-99/43853 A1 | 9/1999 |
| WO | WO-0023458 | 4/2000 |
| WO | WO-0032823 | 6/2000 |
| WO | WO-0047775 | 8/2000 |
| WO | WO-0061775 | 10/2000 |
| WO | WO-0116352 | 3/2001 |
| WO | WO-02074929 | 9/2002 |
| WO | WO-02102820 | 12/2002 |
| WO | WO-02103008 | 12/2002 |
| WO | WO-03031591 | 4/2003 |
| WO | WO-03078050 | 9/2003 |
| WO | WO-03078445 | 9/2003 |
| WO | WO-03078446 | 9/2003 |
| WO | WO-03078625 | 9/2003 |
| WO | WO-03078626 | 9/2003 |
| WO | WO-03078627 | 9/2003 |
| WO | WO-03082901 | 10/2003 |
| WO | WO-04001042 | 12/2003 |
| WO | WO-2004010101 | 1/2004 |
| WO | WO-2004013070 | 2/2004 |
| WO | WO-2004016767 | 2/2004 |
| WO | WO-2004024929 | 3/2004 |
| WO | WO-2004039825 | 5/2004 |
| WO | WO-2004056994 | 7/2004 |
| WO | WO-2004074429 | 9/2004 |
| WO | WO-2004074501 | 9/2004 |
| WO | WO-2004083427 | 9/2004 |
| WO | WO-2004110964 | 12/2004 |
| WO | WO-2005003778 | 1/2005 |

OTHER PUBLICATIONS

Arnold et al, "Design by Directed Evolution" *Acc. Chem. Res.* 31: 125-131 (1998).

Bain et al. "Ribosome-Mediated Incorporation of a Non-Standard Amino Acid into a Peptide Through Expansion of the Genetic Code" *Nature* 356: 537-539 (1992).

Baldwin et al. "Enzymes in Synthetic Organic Chemistry" *Tetrahedron Organic Chemistry Series* 12:1-40, 1994.

Ban et al., "The Complete Atomic Structure of the Large Ribosomal Subunit at 2.4 Å Resolution" *Science* 289: 905-920 (2000).

Bannwarth et al., "A Simple and Effective Chemical Phosphyorylation Procedure for Biomolecules" *Helv. Chim. Acta* 70: 175-186 (1987).

Barbas et al., "Phage Display: A Laboratory Manual" Cold Spring Harbor Laboratory Press New York 736 pages (2001) (copy not enclosed).

Barbas et al., *Chem. Int. Ed.* vol. 37, 1998. 2872-2875 Benner Reviews.

Becker et al., "Synthesis, Sar and In Vivo Activity of Novel Thienopyridine Sulfonamide Pyrrolidinones as Factor Za Inhibitors" *Bioorg. Med. Chem. Lett.* 9: 2753-2758 (1999).

Berger et al., "Universal Bases for Hybridization, Replication and Chain Termination" *Nucleic Acids Research* 28(15): 2911-2914 (2000).

Blanco et al., "A Method for Detecting Protein-DNA Interactions at Sites of Chromatin Replication" *Analytical Biochemistry* 163: 537-545 (1987).

Bogarad et al., "A Hierarchical Approach to Protein Molecular Evolution" *Proc. Natl. Acad. Sci. USA* 96: 2591-2595 (1999).

Böhler et al., "Template Switching Between PNA and RNA Oligonucleotides" *Nature* 376: 578-581 (1995).

Bolli et al., "Pyranosyl-RNA: Chiroselective Self-Assembly of Base Sequences by Ligative Oligomerization of Tetranucleotide-2'3'-Cyclophosphates (with a Commentary Concerning the Origin of Biomolecular Homochirality)" *Chem. Biol.* 4: 309-320 (1997).

Boschelli et al., "Synthesis of Amphotericin B. 2. Fragment C-D of the Aglycone" *Tetrahedron Lett.* 26: 5239-5242 (1985).

Bostwick et al., "RPR120844, A Novel, Specific Inhibitor of Coagulation Factor Xa Inhibits Venous Thrombosis in the Rabbit" *Thromb Haemost* 81: 157-160 (1999).

Brenner et al., "Encoded Combinatorial Chemistry" *Proc. Natl. Acad. Sci.* 89: 5381-5383 (1992).

Brenner et al., "In Vitro Cloning of Complex Mixtures of DNA on Microbeads: Physical Separation of Differentially Expressed cDNAs" *Proc. Natl. Acad. Sci. USA* 97(4): 1665-1670 (2000).

Bresler et al., "Stability of Peptidyl-tRNA—The Intermediate of Protein Synthesis" *Biochimica et Biophysica Acta* 155: 465-475 (1968).

Brooks et al., "Antiintegrin αvβ3 Blocks Human Breast Cancer Growth and Angiogenesis in Human Skin" *J. Clin. Invest.* 96: 1815-1822 (1995).

Brooks et al., "Disruption of Angiogenesis by PEX, a Noncatalytic Metalloproteinase Fragment with Integrin Binding Activity" *Cell* 92: 391-400 (1998).

Brooks et al., Integrin $α_vβ_3$ Antagonists Promote Tumor Regression by Inducing Apoptosis of Angiogenic Blood Vessels *Cell* 79: 1157-1164 (1994).

Bruick et al., "Template-Directed Ligation of Peptides to Oligonucleotides" *Chem. Biol.* 3: 49-56 (1996).

Cadwell et al., "Randomization of Genes by PCR Mutagenesis" *PCR Methods Appl.* 2: 28-33 (1992).

Celewicz et al., "Mass Spectrometry of Some Derivatives of 5-(Indol-2-yl) Pyrimidine" *Pol. J. Chem.* 72: 725-734 (1998).

Chan et al., "Intra-tRNA distance measurements for nucleocapsid protein-dependent tRNA unwinding during priming of HIV reverse transcription" *Proc. Natl. Acad. Sci. USA* 96: 459-464 (1999).

Chen et al., "Template-Directed Synthesis on Oligodeoxycytidylate and Polydeoxycytidylate Templates" *J. Mol. Biol.* 181: 271-279 (1985).

Cho et al., "An Unnatural Biopolymer" *Science* 261: 1303-1305 (1993).

Choi et al., "Inhibition of Neointimal Hyperplasia by Blocking $α_vβ_3$ Integrin with a Small Peptide Antagonist Gpen GRGDSPCA" *J. Vasc. Surg.* 19: 125-134 (1994).

Choi-Sledeski et al., "Sulfonamidopyrrolidinone Factor Xa Inhibitors: Potency and Selectivity Enhancements via P-1 and P-4 Optimization" *J. Med. Chem.* 42: 3572-3587 (1999).

Collado et al., "Diastereoselective Functionalization of 5-Hydroxy Prolinates by Tandem Horner-Emmons-Michael Reaction" *Tetrahedron Lett.* 35: 8037 (1994).

Compton, "Nucleic Acid Sequence-Based Amplification" *Nature* 350: 91-92 (1991).

Czlapinski et al., "Nucleic Acid Template-Directed Assembly of Metallosalen-DNA Conjugates" *J. Am. Chem. Soc.* 123: 8618-8619 (2001).

Davis, "Intermediates in Amino Acid Biosynthesis" *Adv. Enzymol.* 16: 287-295 (1955).

Dechantsreiter et al., "N-Methylated Cyclic RGD Peptides as Highly Active and Selective $α_vβ_3$ Integrin Antagonists" *J. Med. Chem.* 42: 3033-3040 (1999).

Dewey et al., "New Uridine Derivatives for Systematic Evolution of RNA Ligands b Exponential Enrichment" *J. Am. Chem. Soc.* 117: 8474-8475 (1995).

Dietz et al., Photochemical Reduction of 5-Bromouracil by Cystine Derivatives and Coupling of 5-Bromouracil to Cystine Derivatives: Photochemistry and Photobiology 49(2): 121-129 (1989).

Drews, "Drug Discovery: A Historical Perspective" *Science* 287: 1960-1964 (2000).

Eaton, "The Joys of In Vitro Selection: Chemically Dressing Oligonucleotides to Satiate Protein Targets" *Current Opinion in Chemical Biology* 1: 10-16 (1997).

El-Dorry, "Purification of mRNA Coding for Rat-Liver Fructose-1,6-bisphosphatase by polysome immunoabsorption" *Biochimica et Biophysica Acta* 867: 252-255 (1986).

Eliseev et al., "Dynamic Combinatorial Chemistry: Evolutionary Formation and Screening of Molecular Libraries" *Combinatorial Chemistry in Biology* 243: 159-172 (1999).

Ellis et al., "Functional Analysis of the T-Cell Restricted Protein Tyrosine Kinase TxK" *Biochem. J.* 335: 277-284 (1998).

Ewing et al., "Design and Structure—Activity Relationships of Potent and Selective Inhibitors of Blood Coagulation Factor Xa" *J. Med. Chem.* 42: 3557-3571 (1999).

Famulok et al., "Oligonucleotide Libraries-Variatio Delectat" *Curr. Opin. Chem. Biol.* 2: 320-327 (1998).

Fenn et al., "Direct Quantitation of Biotin-Labeled Nucleotide Analogs in RNA Transcripts" *Analytical Chemistry* 190: 78-83 (1990).

Fleet et al., "Enantiospecific Synthesis of Shikimic Acid from D-Mannose: Formation of a Chiral Cyclohexene by Intramolecular Olefination of a Carbohydrate-Derived Intermediate" *J. Chem. Soc. Perkins. Trans.* I: 905-908 (1984).

Fleischer et al., "Conversion of Aliphatic and Alicyclic Polyalcohols to the Corresponding Primary Polyamines" *J. Org. Chem.* 36(20): 3042-3044 (1971).

Francis et al., "Combinatorial Libraries of Transition-Metal Complexes, Catalysts and Materials" *Curr. Opin. Chem. Biol.* 2: 422-428 (1998).

Francis et al., "Discovery of Novel Catalysts for Alkene Epoxidation from Metal-Binding Combinatorial Libraries" *Angew. Chem. Int. Ed. Engl.* 38: 937-941 (1999).

Frankel et al., "Encodamers: Unnatural Peptide Oligomers Encoded in RNA" *Chemistry and Biology* 10: 1043-1050 (2003).

Friedlander et al., "Definition of Two Angiogenic Pathways by Distinct αv Integrins" *Science* 270: 1500-1502 (1995).

Fruchart et al., "A New Linker for the Synthesis of C-Terminal Peptide α-oxo-Aldehydes" *Tetrahedron Lett.* 40: 6225 (1999).

Fruchtel et al., "Organic Chemistry on Solid Supports" *Angew. Chem. Int. Ed. Engl.* 35: 17-42 (1996).

Gad, "Synaptic Vesicle endocytosis studied in a living synapse" Nobel Institute for Neurophysiology, Karolinska Institutet, Sweden 1-48 (2000).

Gallop et al., "Applications of Combinatorial Technologies to Drug Discovery, 1. Background and Peptide Combinatorial Libraries" *J. Med. Chem.* 37: 1233-1251 (1994).

Gartner et al., "The Generality of DNA-Templated Synthesis as a Basis for Evolving Non-Natural Small Molecules" *J. Am. Chem. Soc.* 123: 6961-6963 (2001).

Gat et al., "Reading DNA Differently" *Biopolymers* 48: 19-28 (1998).

Gevorkian et al. "Rapid Communication Identification of Autoimmune Thrombocytopenic Purpura-Related Epitopes using Phage-Display Peptide Library" *Clin. Immunol. Immunopathol* 86: 305-309 (1998).

Geyer et al., "Conformational Analysis of a Cyclic RGD Peptide Containing a Ψ[CH2-NH] Bond: A Positional Shift in Backbone Structure Caused by a Single Dipeptide Mimetic" *J. Am. Chem. Soc.* 116: 7735-7743 (1994).

Gilbertson et al., "Asymmetric Catalysis with Libraries of Palladium β-Turn Phosphine Complexes" *J. Am. Chem. Soc.* 122: 6522-6523 (2000).

Gocke, "Mechanism of Quinolone Mutagenicity in Bacteria" *Mutation Research* 248: 135-143 (1991).

Gordon et al., Applications of Combinatorial Technologies to Drug Discovery. 2. Combinatorial Organic Synthesis, Library Screening Strategies, and Future Directions, *J. Med. Chem.* 37(10): 1385-1401 (1994).

Gourlain et al., "Enhancing the Catalytic Repertoire of Nucleic Acids. II. Simultaneous Incorporation of Amino and Imidazolyl Functionalities by Two Modified Triphosphates During PCR" *Nucleic Acids Res.* 29: 1898-1905 (2001).

Greene et al., "Protective Groups in Organic Synthesis", 780 pages Wiley & Sons (1999) (copy not enclosed).

Grubina et al., "Summer Research Report: DNA-Templated Synthesis of a Synthetic Small Molecule Library" *The Nucleus* 10-14, Jan. 2004.

Gryaznov et al., "Chemical Ligation of Oligonucleotides in the Presence and Absence of a Template" *J. Am. Chem. Soc.* 115: 3808-3809 (1993).

Gryaznov et al., "Template Controlled Coupling and Recombination of Oligonucleotide Blocks Containing Thiophosphoryl Groups" *Nucleic Acids Research* 21(6): 1403-1408 (1993).

Guatelli et al., "Isothermal, In Vitro Amplification of Nucleic Acids by a Multienzyme Reaction Modeled After Retroviral Replication" *Proc. Natl. Acad. Sci.* 87: 1874-1878 (1990).

Gyllensten et al., "Generation of Single-Stranded DNA by the Polymerase Chain Reaction and its Application to Direct Sequencing of the HLA-DQA locus", *PNAS* 85: 7652-7656 (1988).

Haaima et al., "Peptide Nucleic Acids (PNAs) Containing Thymine Monomers Derived from Chiral Amino Acids: Hybridization and Solubility Properties of D-Lysine PNA" *Angew. Chem. Int. Ed. Engl.* 35: 1939-1942 (1996).

Haeuptle et al., "Translation Arrest by Oligodeoxynucleotides Complementary to mRNA Coding Sequences Yields Polypeptides of Predetermined Length" *Nucleic Acids Research* 14(3): 1427-1448 (1986).

Hamburger et al., "Peptidyl-tRNA XI. The Chemical Synthesis of Phenylalanine-Containing Oligopeptidyl-tRNA" *Biochimica et Biophysica Acta*, 213: 115-123 (1970).

Haubner et al. "Structural and Functional Aspects of RGD-Containing Cyclic Pentapeptides as Highly Potent and Selective Integrin $\alpha v \beta_3$ Antagonists" *J. Am. Chem. Soc.* 118: 7461-7472 (1996).

Herrera-Estrella et al., "VirD Proteins of Agrobacterium Tumefaciens are Required for the Formation of a Covalent DNA—Protein Complex at the 5' Terminus of T-Strand Molecules" *The EMBO Journal* 7(13): 4055-4062 (1988).

Herrlein et al., "A Covalent Lock for Self-Assembled Oligonucleotide Conjugates" *J. Am. Chem. Soc.* 117: 1-151-10152 (1995).

Heywood et al., "A Study of Muscle Polyribosomes and the Coprecipitation of Polyribosomes with Myosin" *J. Biol. Chem.* 7: 3289-3296 (1968).

Heywood et al., "The Identification of Polyribosomes Synthesizing Myosin" *PNAS* 57: 1002-1009 (1967).

Hirama et al., "Asymmetric Induction in the Intramolecular Conjugate Addition of - or δ-Carbamoyloxy-, β-Unsaturated Esters. A New Method for Diastereoselective Amination and Divergent Synthesis of 3-Amino-2,3,6-Trideoxyhexoses" *Heterocycles* 28: 1229-1247 (1989).

Hirama et al., "Intramolecular Michael Addition of O-Carbamates to α,β Unsaturated Esters: A New Diastereoselective Amination in an Acyclic System" *J. Am. Chem. Soc.* 107: 1797-1798 (1985).

Hooper et al., "Mode of Action of the New Quinolones: New Data" *Eur. J. Clin. Microbiol. Infect. Dis.* 10(4): 223-231 (1991).

Houdebine et al., "Purification of the mRNAs for Ewe $\alpha_s$-Casein and β-Casein by Immunoprecipitation of Polysomes" *Eur. J. Biochem.* 63: 9-14 (1976).

House et al., "The Chemistry of Carbanions. XVII. The Addition of Methyl Organometallic Reagents to Cyclohexenone Derivatives" *J. Org. Chem.* 33: 949 (1968).

Hughes, "Application of Polymer-Bound Phosphonium Salts as Traceless Supports for Solid" *Tetrahedron Lett.* 37: 7595-7598 (1996).

Hyrup et al., "Peptide Nucleic Acids (PNA): Synthesis, Properties and Potential Applications" *Bioorganic & Medical Chemistry* 4(1): 5-23 (1996).

Illuminati et al., "Ring Closure Reactions of Bifunctional Chain Molecules" *Acc. Chem. Res.* 14: 95-102 (1981).

Inoue et al., "Oligomerization of (Guanosine 5' -Phosphor)-2-Methylimidazolide on Poly(C): An RNA Polymerase Model" *J.Mol. Biol.* 162: 201-217 (1982).

Inoue et al., "Substituent Control of the Poly(C)—Directed Oligomerization of Guanosine 5'—Phosphoroimidazolide" *J. Am. Chem. Soc.* 103: 7666-7667 (1981).

Inoue et al., "Template-Directed Synthesis on the Pentanucleotide CpCpGpCpC" *J. Mol. Biol.* 178: 669-676 (1984).

International Search Report for Application No. PCT/US02/08546 dated Dec. 17, 2002.

International Search Report for Application No. PCT/US03/25984 dated Jan. 18, 2005.

Ito et al., "Acetone-Sensitized Photocoupling of 5-Bromouridine to Trytophan Derivatives via Electron-Transfer Process" *J. Amer. Chem. Soc.* 102: 7535-7541 (1980).

Jemth et al., "Kinetic Characterization of Recombinant Human Glutathione Transferase T1-1, A Polymorphic Detoxication Enzyme" *Arch. Biochem. Biophys.* 348(2): 247-54 (1997).

Johansson et al., "Regioselective Reductive Ring-Opening of 4-Methoxybenzylidene Acetals of Hexopyranosides. Access to a Novel Protecting-Group Strategy. Part 1" *J. Chem. Soc. Perkins Trans.* I: 2371-2374 (1984).

Johnson et al. "Evidence for Posttranslational O-Glycosylation of Fetuin" *Biochemistry* 25: 5518-5525 (1986).

Johnston et al., "RNA-Catalyzed RNA Polymerization: Accurate and General RNA-Templated Primer Extension" *Science* 292: 1319-1325 (2001).

Jost et al., "Quantitative Precipitation of Short Oligonucleotides with Low Concentrations of Cetyltrimethylammonium Bromide" *Nucleic Acids Res.* 17: 2143 (1989).

Kahl et al., "Introducing Structural Diversity in Oligonucleotides via Photolabile, Convertible C5-Substituted Nucleotides" *J. Am. Chem. Soc.* 121(4): 597-604 (1999).

Keiler et al., "Role of a Peptide Tagging System in Degradation of Proteins Synthesized from Damaged Messenger RNA" *Science* 271: 990-993 (1996).

King et al., "Bis (Dialkylamino) Phosphines" *J. Org. Chem.* 49: 1784-1789 (1984).

Kinoshita et al., "Enzymatic Synthesis of Code Regions for Encoded combinatorial Chemistry (ECC)" *Nucleic Acids Symposium Series* 34: 201-202 (1995).

Kuntz et al., "Combinatorial Catalyst Discovery" *Current Opinion in Chemical Biology* 3: 313-319 (1999).

Kupsch et al., "Isolation of Human Tumor-Specific Antibodies by Selection of an Antibody Phage Library on Melanoma Cells" *Clin Cancer Res.* 5: 925-931 (1999).

Latham et al. "The Application of a Modified Nucleotide in Aptamer Selection: Novel Thrombin Aptamers Containing 5-(Pentynyl)-2'-Deoxyuridine" *Nucleic Acids Res.* 22: 2817-2822 (1994).

Leadley et al., "Pharmacodynamic Activity and Antithrombotic Efficacy of RPR120844, a Novel Inhibitor of Coagulation Factor Xa" *J. Cardiovasc. Pharmacol.* 34: 791-799 (1999).

Lee et al., "Enhancing the Catalytic Repertoire of Nucleic Acids: a Systematic Study of Linker Length and Rigidity" *Nucleic Acids Res.* 29: 1565-1573 (2001).

Leon et al., "Covalent Coupling of 4-Thiouridine in the Initiator Methionine tRNA to Specific Lysine Residues in *Escherichia coli* Methionyl-tRNA Synthetase" *Biochemistry* 26: 7113-7121 (1987).

Li et al. "DNA-Catalyzed Polymerization" *J. Am. Chem. Soc.* 124: 746-747 (2002).

Li et al., "A Catalytic DNA for Porphyrin Metallation" *Nat. Struct. Biol.* 3: 743-747 (1996).

Li et al., "Capping DNA with DNA" *Biochemistry* 39: 3106-3114 (2000).

Li et al., "Chemical Self-Replication of Palindromic Duplex DNA" *Nature* 369: 218-221 (1994).

Li et al., "Phosphorylating DNA with DNA" *Proc. Natl. Acad. Sci. USA* 96: 2746-2751 (1999).

Li et al., "Toward an Efficient DNAzyme" *Biochemistry* 36: 5589-5599 (1997).

Lin et al. "Formation of an Amino-Acid-Binding Pocket Through Adaptive Zippering-Up of a Large DNA Hairpin Loop" *Chem. Biol.* 5: 555-572 (1998).

Lin et al. "Structural Basis of DNA Folding and Recognition in an AMP-DNA Aptamer Complex: Distinct Architectures But Common Recognition Motifs for DNA and RNA Aptamers Complexed to AMP" *Chem. Biol.* 4: 817-832 (1997).

Liu et al. "Generating New Molecular Function: A Lesson from Nature" *Angew. Chem. Intl. Ed. Eng.* 38: 37-54 (1999).

Loss, "Spin-based Quantum Information Processing in Nanostructures" Dept. of Phys., Univ. of Basel, Switzerland, 2002.

Luo et al., "Analysis of the Structure and Stability of a Backbone-Modified Oligonucleotide: Implications for Avoiding Product Inhibition in Catalytic Template-Directed Synthesis" *J. Am. Chem. Soc.* vol. 120, No. 13: 3019-3031 (1998).

Luther et al., "Surface-Promoted Replication and Exponential Amplification of DNA Analogues" *Nature* 396: 245-248 (1998).

Lynn et al., "Water-Soluble Ruthenium Alkylidenes: Synthesis, Characterization, and Application to Olefin Metathesis in Protic Solvents" *J. Am. Chem. Soc.* 122: 6601-6609 (2000).

Lynn et al., Living Ring-Opening Metathesis Polymerization in Water *J. Am. Chem. Soc.* 12: 1627-1628 (1998).

MacLean et al., "Encoded Combinatorial Chemistry Synthesis and Screening of a Library of Highly Functionalized Pyrrolidines" *Proc. Natl. Acad. Sci. USA* 94: 2805-2810 (1997).

Magid, "Nucleophilic and Organometallic Displacement Reactions of Allylic Compounds: Stereo- and Regiochemistry" *Tetrahedron* 36: 1901-1930 (1980).

Mahal et al., "Engineering Chemical Reactivity on Cell Surfaces Through Oligosaccharide Biosynthesis" *Science* 276: 1 125-1 128 (1997).
Maignan et al., "Crystal Structures of Human FactorXa Complexed with Potent Inhibitors" *J. Med. Chem.* 43: 3226-3232 (2000).
Marks et al., "Molecular Evolution of Proteins on Filamentous Phage" *J. Biol.Chem.* 267(23): 16007-16010 (1992).
Marlowe et al., "Design, Synthesis and Structure-Activity Relationship of a Series of Arginine Aldehyde Factor Xa Inhibitors. Part 1: Structures Based on the (D)-Arg-Gly-Arg Tripeptide Sequence" *Bioorg. Med. Chem. Lett.* 10: 13-16 (2000).
Mattheakis et al., "An In Vitro Polysome Display System for Identifying Ligands from Very Large Peptide Libraries" *Proc. Natl. Acad. Sci. USA* 91: 9022-9026 (1994).
Mel'nikov et al., "Solubilization of DNA-Cationic Lipid Complexes in Hydrophobic Solvents. A Single-Molecule Visualization by Fluorescence Microscopy" *Langmuir* 15: 1923-1928 (1999).
Minshull et al., "Protein Evolution by Molecular Breeding" *Curr. Opin. Chem. Biol.* 3: 284-290 (1999).
Mirza et al., "Synthesis of Shikimic Acid and Its Phosphonate Analogue Via Knoevenagel Condensation" *Tetrahedron Lett.* 32: No. 33, 4111-4114 (1991).
Miyamoto-Sato et al., "Highly stable and efficient mRNA templates for mRNA-protein fusions and C-terminally labeled proteins" *Nucleic Acids Research* vol. 31 No. 15 e78 (2003).
Mohr et al., "Synthesis of Water-Soluble, Aliphatic Phoshines and Their Application to Well-Defined Ruthenium Olefin Metathesis Catalysts" *Organometallics* 15: 4317-4325 (1996).
Muth et al., "A Single Adenosine with a Neutral pKa in the Ribosomal Peptidyl Transferase Center" *Science* 289: 947-950 (2000).
Nagasaka et al.,"Wittig Reactions of 1-Alkoxycarbonyl-2-Hydroxypyrrolidines and -Piperidines: Synthesis of (±)—Hygrine and ((±)-2-Epilasubine II" *Heterocycles* 29: 155 (1989).
Nakano et al., "General Acid-Base Catalysis in the Mechanism of a Hepatitis Delta Virus Ribozyme" *Science* 287: 1493-1497 (2000).
Nazarenko et al., "A closed tube format for amplification and detection of DNA based on energy transfer" *Nucleic Acid Research* 25(12): 2516-2521 (1997).
Nemoto et al., "In vitro virus: Bonding of mRNA bearing puromycin at the 3'-terminal end to the C-terminal end of its encoded protein on the ribosome in vitro" *European Biochemical Societies Letters* 414: 405-408 (1997).
Nissen et al., "The Structural Basis of Ribosome Activity in Peptide Bond Synthesis" *Science* 289: 920-930 (2000).
Nolte et al., "Mirror-Design of L-Oligonucleotide Ligands Binding to L-Arginine" *Nature Biotechnology* 14: 1116-1121 (1996).
Norris et al., "Mechanistic Studies of the 5-lodouracil Chromophore Relevant to Its Use in Nucleoprotein Photo-Cross-Linking" *J. Amer. Chem. Soc.* 118: 5796-5803 (1996).
Olofson et al., "Selective N-Dealkylation of Teritiary Amines with Vinyl Chloroformate: An Improved Synthesis of Naloxone" *Tetrahedron Lett.* 18: 1567-1570 (1977).
Olofson et al., "Use of the Vinyloxycarbonyl Group for Amino Protection in Peptide Synthesis" *Tetrahedron Lett.* 18: 1563-1566 (1977).
Olofson et al., "Value of Vinyloxycarbonyl Unit in Hydroxyl Protection: Application to the Synthesis of Nalorphine" *Tetrahedron Lett.* 18: 1571-1574 (1977).
Orgel et al., "Unnatural Selection in Chemical Systems" *Acc. Chem. Res.* 28: 109-118 (1995).
Pagratis et al., "Potent 2'-Amino-, and 2'-Fluoro-2'-Deoxyribonucleotide RNA Inhibitors of Keratinocyte Growth Factor" *Nature Biotechnology* 15: 68-72 (1997).
Pasqualini et al., "Aminopeptidase N Is a Receptor for Tumor-homing Peptides and a Target for Inhibiting Angiogenesis" *Cancer Res.* 60: 722-727 (2000).
Pasqualini et al., "Organ Targeting In Vivo Using Phage Display Peptide Libraries" *Nature* 380: 364-366 (1996).
Pedersen et al., "A Method for Directed Evolution and Functional Cloning of Enzymes" *Proc. Natl. Acad. Sci. USA* 95: 10523-10528 (1998).

Perrin et al., "Bridging the Gap Between Protein and Nucleic Acids: A Metal-Independent RNAseA Mimic with Two Protein-Like Functionalities" *J. Am. Chem. Soc.* 123: 1556-1563 (2001).
Perrin et al., "Expanding the Catalytic Repertoire of Nucleic Acid Catalysts: Simultaneous Incorporation of Two Modified Deoxyribonucleoside Triphosphates Bearing Ammonium and Imidazolyl Functionalities" *Nucleosides & Nucleotides* 18: 377-391 (1999).
Pfaff et al., "Selective Recognition of Cyclic RGD Peptides of NMR Defined Conformation of αIIbβ3, α5β1 Integrins" *J. Biol. Chem.* 269: 20233-20238 (1994).
Polacek et al., "Ribosomal Peptidyl Transferase can Withstand Mutations at the Putative Catalytic Nucleotide" *Nature* 411: 498-501 (2001).
Püschl et al., "Peptide Nucleic Acids (PNAs) with a Functional Backbone" *Tetrahedron Lett.* 39: 4707-4710 (1998).
Rai et al., "Development of Potent and Selective Factor Xa Inhibitors" *Bioorg. Med. Chem. Lett.* 11: 1797-1800 (2001).
Rembold et al., "Single-Strand Regions of Poly(G) Act as Templates for Oligo(C) Synthesis" *J. Mol. Evol.* 38: 205-210 (1994).
Roberts et al., "RNA-Peptide Fusions for the In Vitro Selection of Peptides and Proteins" *Proc. Natl. Acad. Sci. USA* 94: 12297-12302 (1997).
Rodriguez et al., "Template-Directed Extension of a Guanosine 5'-Phosphate Covalently Attached to an Oligodeoxycytidylate Template" *J. Mol. Evol.* 33: 477-482 (1991).
Saiki et al., "Enzymatic Amplification of β-Globin Genomic Sequences and Restriction Site Analysis for Diagnosis of Sickle Cell Anemia" *Science* 230: 1350-1354 (1985).
Sakthivel et al., "Expanding the Potential of DNA for Binding and Catalysis: Highly Functionalized dUTP Derivatives That Are Substrates for Thermostable DNA Polymerases" *Angew. Chem. Int. Ed.* 37: 2872-2875 (1998).
Salas et al., "Biosynthetic Polydeoxynucleotides as Direct Templates for Polypeptide Synthesis" *Journal of Biological Chemistry* 243(5): 1012-1015 (1968).
Santoro et al., "A General Purpose RNA-Cleaving DNA Enzyme" *Proc. Natl. Acad. Sci. USA* 94: 4262-4266 (1997).
Saxon et al., "A 'Traceless' Staudinger Ligation for the Chemoselective Synthesis of Amide Bonds" *Organic Letters* 2(14): 2141-2143 (2000).
Scharf et al., "Direct Cloning and Sequence Analysis of Enzymatically Amplified Genomic Sequences" *Science* 233: 1076-1078 (1986).
Scheffer et al., "Selection and Characterisation of a Phage-Displayed Human Antibody (Fab) Reactive to the Lung Resistance-Related Major Vault Protein" *Br. J. Cancer* 86: 954-962 (2002).
Schmidt et al., "Information Transfer from DNA to Peptide Nucleic Acids by Template-Directed Syntheses" *Nucleic Acids Research* 25(23): 4792-4796 (1997).
Schmidt-Dannert et al., "Directed Evolution of Industrial Enzymes" *Trends Biotechnol.* 17: 135-136 (1999).
Scholl et al., "Synthesis and Activity of a New Generation of Ruthenium-Based Olefin Metathesis Catalysts Coordinated with 1,3-Dimesityl-4,5-Dihydroimidazol-2-Ylidene Ligands" *Org. Lett.* 1(6): 953-956 (1999).
Schultze et al., Three-Dimensional Solution Structure of the Thrombin-Binding DNA Aptamer d(GGTTGGTGTGGTTGG) *J. Mol. Biol.* 235: 1532-1547 (1994).
Schwartz et al., "Template-Directed Synthesis of Novel, Nucleic Acid-Like Structures" *Science* 228: 585-587 (1985).
Scott, "How Were Porphyrins and Lipids Synthesized in the RNA World?" *Tetrahedron Lett.* 38: 4961-4964 (1997).
Seeberger et al., "Solid-Phase Oligosaccharide Synthesis and Combinatorial Carbohydrate Libraries" *Chem. Rev.* 100: 4349-4393 (2000).
Seeberger, P.H., Ed., "Solid Support Oligosaccharide Synthesis and Combinatorial Carbohydrate Libraries" Wiley-Interscience: New York 2001 (copy not enclosed).
Seela et al., "Oligonucleotides Containing 7-Deazaadenines: The Influence of the 7-Substituent Chain Length and Charge on the Duplex Stability" *Helv. Chem. Acta.* 82: 1878-1898 (1999).

Seela et al., "Palladium-Catalyzed Cross Coupling of 7-Iodo-2' Deoxytubercidin with Terminal Alkynes" *Synthesis*: 726-730 (1996).
Shao et al., "Random-Priming in Vitro Recombination: An Effective Tool for Directed Evolution" *Nucleic Acids Research* 26(2): 681-83 (1998).
Sheppard et al., "A DNA Enzyme with N-Glycosylase Activity" *Proc. Natl. Acad. Sci. USA* 97: 7802-7807 (2000).
Shimizu et al., "Search for Chiral Catalysts Through Ligand Diversity: Substrate-Specific Catalysts and Ligand Screening on Solid Phase" *Angew. Chem. Int. Ed.* 36(16): 1704-1707 (1997).
Shishido et al., "1,2-Asymmetric Induction in Intramolecular Michael Reaction. A Novel and Enantioselective Route to (+) Geissman Lactone" *J. Chem. Soc. Perkins Trans.* I: 993-1004 (1987).
Siegel et al., "Isolation of Cell Surface-Specific Human Monoclonal Antibodies Using Phage Display and Magnetically-Activated Cell Sorting: Applications in Immunohematology" *J. Immunol. Methods* 206: 73-85 (1997).
Smith, G., "Filamentous Fusion Phage: Novel Expression Vectors That Display Cloned Antigens on the Virion Surface" *Science* 228: 1315-1317 (1985).
Smith, G., "The Progeny of Sexual PCR" *Nature* 370: 324-325 (1995).
Soumillion et al., "Selection of β-Lactamase on Filamentous Bacteriophage by Catalytic Activity" *J. Mol. Biol.* 237: 415-22 (1994).
Stemmer, "DNA Shuffling by Random Fragmentation and Reassembly: In Vitro Recombination for Molecular Evolution" *Proc. Natl. Acad. Sci. USA* 91: 10747-10751 (1994).
Stemmer, "Rapid Evolution of a Protein In Vitro by DNA Shuffling" *Nature* 370: 389-391 (1994).
Still et al., "Chemical Consequences of Conformation in Macrocyclic Compounds," *Tetrahedron* 37: 3981-3996 (1981).
Summerer D. et al., "DNA-Templated Synthesis: More Versatile Than Expected" *Angewandte Chemie. Int'l Edit.*, Verlag Chemie. Weinheim, DE, vol. 41, No. 1: 89-90 (2002).
Supplementary European Search Report for Application No. EP 02 75 3671 dated Sep. 21, 2004.
Sutherlin et al., "Stereoselective Synthesis of Dipyranyl C-Disaccharides" *Tetrahedron Lett.* 34(31): 4897-4900 (1993).
Tamura et al., "Oligonucleotide-Directed Peptide Synthesis in a Ribosome- and Ribozyme-Free System" *Proc. Natl. Acad. Sci. USA* 98: 1393-1397 (2001).
Tarasow et al., "Dressed for Success: Realizing the Catalytic Potential of RNA" *Biopolymers* 48: 29-37 (1998).
Tseng-Law et al., "Identification of a Peptide Directed Against the Anti-CD34 Antibody, 9C5, by Phage Display and Its Use in Hematopoietic Stem Cell Selection" *Exp. Hematol* 27: 936-945 (1999).
Uhlmann et al., "Synthesis and Properties of PNA/DNA Chimeras" *Angew. Chem. Int. Ed.* Engl. 35: 2632-2635 (1996).
Vacca, "New Advances in the Discovery of Thrombin and Factor Xa Inhibitors" *Curr. Opin. Chem. Biol.* 4: 394-400 (2000).
Van Gelder et al., PNAS, 85: 77652-77656 (1988).
Varner et al., "Review: $\alpha_v\beta_3$: The Integrin Angiogenesis and Apoptosis" *Cell Adhes Commun* 3: 367-374 (1995).
Visscher et al., "Template-Directed Synthesis of Acyclic Oligonucleotide Analogs" *Journal of Molecular Evolution* 28: 3-6 (1988).
Walder et al., "Complementary Carrier Peptide Synthesis: General Strategy and Implications for Prebiotic Origin of Peptide Synthesis" *Proc. Nat. Acad. Sci. USA* 76(1): 51-55 (1979).
Wells et al., "Rapid Evolution of Peptide and Protein Binding Properties in Vitro" *Curr. Opin. Struct. Biol.* 2: 597-604 (1992).
Wermuth et al., "Stereoisomerism and Biological Activity of the Selective and Superactive $\alpha_v\beta_3$ Integrin Inhibitor Cyclo (-RGDfV -) and Its Retro-Inverso Peptide"*J. Am. Chem. Soc.* 119: 1328-1335 (1997).
Wiegand et al., "Selection of RNA Amide Synthases" *Chemistry and Biology* 4: 675-683 (1997).
Wilson et al., "In Vitro Selection of Functional Nucleic Acids" *Annu. Rev. Biochem.* 68: 611-647 (1999).
Winter et al., "Making Antibodies by Phage Display Technology" *Annu. Rev. Immunol.* 12: 433-455 (1994).

Wong et al., "Enzymes in Synthetic Organic Chemistry" 388 pages Pergamon: *Tetrahedron Organic Chemistry Series* 12: 1994 (Index only enclosed).
Woodward et al., "Asymmetric Total Synthesis of Erythromycin. 1. Synthesis of an Erythronolide A Seco Acid Derivative via Asymmetric Induction" *J. Am. Chem. Soc.* 103: 3210-3213 (1981).
Xu et al., "Nonenzymatic Autoligation in Direct Three-Color Detection of RNA and DNA Point Mutations" *Nature Biotechnology* 19: 148-152 (2001).
Xu et al., "Rapid and Selective Selenium-Mediated Autoligation of DNA Strands" *J. Am. Chem. Soc.* 122: 9040-9041 (2000).
Zarling et al., "Mapping of Lymphocyte Surface Polypeptide Antigens by Chemical Cross-Linking with Bsocoes" *J. Immunology* 124: 913-920 (1980).
Zhan et al. "Chemical Amplification through Template-Directed Synthesis" *J. Am. Chem. Soc.* vol. 119, No. 50: 12420-12421 (1997) see entire document.
Zhang et al., "Lactone and Lactam Library Synthesis by Silver Ion-Assisted Orthogonal Cyclization of Unprotected Peptides" *J. Am. Chem. Soc.* 121: 3311-3320 (1999).
Zhao et al., "A Methodological Comparison: The Advantage of Phosphorimidates in Expanding the Sugar Nucleotide Repertoire" *J. Org. Chem.* 63: 7568-7572 (1998).
Zhao et al., "Molecular Evolution by Staggered Extension Process (StEP) in Vitro Recombination" *Nature Biotechnology* 16(3): 258-61 (1998).
Zhao et al., "Optimization of DNA Shuffling for High Fidelity Recombination" *Nucleic Acids Research* 25(6): 1307-1308 (1997).
Schmidt et al., "Information Transfer from Peptide Nucleic Acids to RNA by Template-Directed Syntheses" *Nucleic Acids Research* 25(23): 4797-4802 (1997).
Dewey et al., "Integrated drug discovery technology in a test tube," www.currentdrugdiscovery.com (Jul. 2002).
Kanavarioti et al., *Journal of Organic Chemistry* vol. 64, pp. 8323-8333 (Oct. 1999).
Letter from Mr. Iver P. Cooper to the Office of Naval Research, dated May 25, 2004.
Letter from the Office of Naval Research to Mr. Iver P. Cooper, dated Feb. 1, 2005.
Appeal letter and memorandum to the General Counsel of the Navy on behalf of Mr. Iver P. Cooper, dated Apr. 1, 2005.
Letter from the Office of the General Counsel of the Navy to Mr. Iver P. Cooper, dated Aug. 5, 2005.
Slides 1, 2, 3, and 30 of Professor David Liu's slide presentation entitled "Unnatural Molecule Evolution.", 2000.
Plaintiff's Complaint, filed Nov. 18, 2005, *Iver P. Cooper v. U.S. Department of Navy*, Case 1:05-cv-02252-EGS.
Defendants Answer to Plaintiff's Complaint, filed Feb. 10, 2006, *Iver P. Cooper v. U.S. Department of Navy*, Case 1:05-cv-02252-EGS.
Motion of Plaintiff Iver Cooper for Summary Judgment, filed May 15, 2006, *Iver P. Cooper v. U.S. Department of Navy*, Case 1:05-cv-02252-EGS.
Plaintiff's Memorandum of Points & Authorities of Plantiff Iver Cooper in Support of his Motion for Summary Judgment, filed May 15, 2006, *Iver P. Cooper v. U.S. Department of Navy*, Case 1:05-cv-02252-EGS.
Defendant's Motion for Summary Judgment, filed May 15, 2006, *Iver P. Cooper v. U.S. Department of Navy*, Case 1:05-cv-02252-EGS.
Defendant's Memorandum of Law in Support of Defendant's Motion for Summary Judgment, filed May 15, 2006, *Iver P. Cooper v. U.S. Department of Navy*, Case 1:05-cv-02252-EGS.
Defendant's Opposition to Plaintiff's Cross Motion for Summary Judgment, filed Jun. 21, 2006, *Iver P. Cooper v. U.S. Department of Navy*, Case 1:05-cv-02252-EGS.
Plaintiff's Memorandum of Points & Authorities of Plantiff Iver Cooper in Opposition to Defendants Motion for Summary Judgment, filed Jun. 21, 2006, *Iver P. Cooper v. U.S. Department of Navy*, Case 1:05-cv-02252-EGS.
Defendant's Reply to Plaintiffs Opposition to Defendant's Motion for Summary Judgment, *Iver P. Cooper v. U.S. Department of Navy*, Case 1:05-cv-02252-EGS, 2006.

Plaintiff's Reply in Support of His Motion for Summary Judgment, *Iver P. Cooper v. U.S. Department of Navy*, Case 1:05-cv-02252-EGS, 2006.

Kang and Rokita, "Site Specific and photo-induced alkylation of DNA by a dimethylanthraquinone-oligodeoxynucleotide conjugate," *Nucleic Acid Res.* (Oct. 15, 1996) 24(20): 3896-902.

Supplementary European Partial Search Report for European Patent Application No. 03788662 dated Feb. 22, 2006 (2 pages).

Landegren et al. (1988) *Science* 241 (4869): 1077-1080.

Li et al. (2004) "DNA-templated organic synthesis: nature's strategy for controlling chemical reactivity applied to synthetic molecules," *Angewandte Chemie* (Intl. Ed. In English) 43(37): 4848-70.

New England Biolabs 1998/99 Catalog. Cover and p. 284.

Podyminogin et al., "Sequence-specific covalent modification of DNA by cross-linking oligonucleotides. Catalysis by RecA and implication for the mechanism of synaptic joint formation," *Biochemistry* (Oct. 10, 1995) 34(40): 13098-108.

International Search Report for Application No. PCT/US06/02420 dated Jul. 28, 2006 (3 pages).

Dorner et al. (1984) *Journal of Virology* 50(3): 507-514.

Brooker, Genetics Analysis and Principles ed. 1, 1999, Menlo Park, CA, pp. 326, 368, 372, 373, and 379.

Gartner et al. (2001) Supporting Materials (2 pages) for "The Generality of DNA-Templated Synthesis as a Basis for Evolving Non-Natural Small Molecules" *J. Am. Chem. Soc.* 123: 6961-6963(2001).

Stryer (1995) *Biochemistry*, 4th Edition, Chapter 37.

Rohatgi et al. (1996) *J. Am. Chem. Soc.* 118:3332-39.

Rohatgi et al. (1996) *J. Am. Chem. Soc.* 118:3340-44.

Suga et al. (1998) *J. Am. Chem. Soc.* 120: 1151-1156.

Suga et al. (1998) *Biochem.* 37: 10118-25.

Lee et al. (2000) *Nature Struct. Biol.* 7: 28-33.

Bartel et al. (1993) *Science* 261 1411-18.

Xu et al. (1999) *Nucl. Acids Res.* 27: 875-81.

Ekland et al. (1995) *Science* 269: 364-70.

Jenne et al. (1998) *Chem. Biol.* 5: 23-34.

Goodwin et al. (1992) *J. Am. Chem. Soc.* 114: 9197-98.

Xu et al. (1998) *Nucl. Acids Res.* 26(13): 3159-64.

Homepage of David R. Liu (http://evolve.harvard.edu) available at Mar. 11, 2000 according to the Wayback Machine (http://web.archive.org).

Homepage of David R. Liu (http://evolve.harvard.edu) available at Oct. 15, 2000 according to the Wayback Machine (http://web.archive.org).

Opposition to European Patent No. EP1423400, filed May 9, 2007 (Communication issued from EPO on May 15, 2007).

Harris et al. (1999) "Directed Molecular Evolution," Origins of Life and Evolution of the Biosphere 29: 425-435.

Gartner Z.J. et al., "Expanding the Reaction Scope of DNA-Templated Synthesis" *Angewandte Chemie* (2002), vol. 41, No. 10, pp. 1796-1800.

Gartner Z.J. et al., "Multistep Small-Molecule Synthesis Programmed by DNA Templates" *Journal of the American Chemical Society*, (2002) vol. 124, No. 35, pp. 10304-10306.

European Patent Office (EPO) Examination Report; European Application No. EP 03788662.9, mailed Nov. 21, 2007 (15 pages).

Tyagi et al. (1996) "Molecular Beacons: Probes that Fluoresce Upon Hybridization," *Nature Biotechnology* 14(1): 303-08.

Mag et al. (1991) "Synthesis and Selective Cleavage of an Oligodeoxynucleotide Containing a Bridged Internucleotide 5'-Phosphorothioate Linkage," *Nucl. Acids Res.*

Kuimelis et al. (1995) "Cleavage Properties of an Oligonucleotide Containing a Bridged Internucleotide 5'-Phosphothioate RNA Linkage," *Nucl. Acids Res.* 23(23): 4753-60.

Metelev et al. (2001) "New Chemically Reactive dsDNAs Containing Single Internucleotide Monophosphoryldithio links: reactivity of 5'-mercapto-oligodeoxyribonucleotides," *Nucl. Acids Res.* 29(19): 4062-69.

Calderone et al. (2002) "Directing Otherwise Incompatible Reactions in a Single Solution by Using DNA-Templated Organic Synthesis," *Angewandte Chemie* 41(21): 4104-08.

Arnold et al. (1989) "Assay Formats Involving Acridinium-Ester-Labeled DNA Probes" *Clin. Chem.* 35(8): 1588-94.

Balachander et al. (1990) "Monolayer Transformation by Nucleophilic Substitution: Applications to the Creation of New Monolayer Assemblies," *Langmuir* 6(11): 1621-1627.

Knight et al. (1999) "Accuracy of Genotyping of Single-Nucleotide Polymorphisms by PCR-ELISA Allele-Specific Oligonucleotide Hybridization Typing and by Amplification Refractory Mutation System," *Clinical Chemistry* 45(10): 1860-1863.

Tamura et al. (Jul. 11, 2003) "Peptide Synthesis with a Template-like RNA guide and aminoacyl phosphate adaptors" *Proc. Natl. Acad. Sci. USA* 100(15): 8666-8669.

Gartner et al.(2003) "Two-Enabling Architectures for DNA-templated Organic Synthesis," *Angewandte Chemie* 42(12): 1370-75.

Sando et al. (2002) "Quencher as leaving group: Efficient detection of DNA-joining reactions," *JACS* 124(10): 2096-97.

Ma et al. (2000) "Nucleic acid-triggered catalytic drug release," *PNAS USA*: 97(21): 11159-63.

Amato (1992) "Speeding Up a Chemical Game of Chance," *Science* 257:330-331.

European Search Report for European Application No. EP06016511.5, mailed on Jul. 24, 2009, 4 pages.

end-of-helix (E)
n=1
1 base end-of-helix (E)
n=10
10 bases end-of-helix (E)
n=20
20 bases hairpin (H)
n=1
1 base omega, 3-base
constant region (Ω-3)
n=10
3 bases
7 base loop omega, 5-base
constant region (Ω-5)
n=20
5 bases
15 base loop T architecture (T)
n=1
1 base

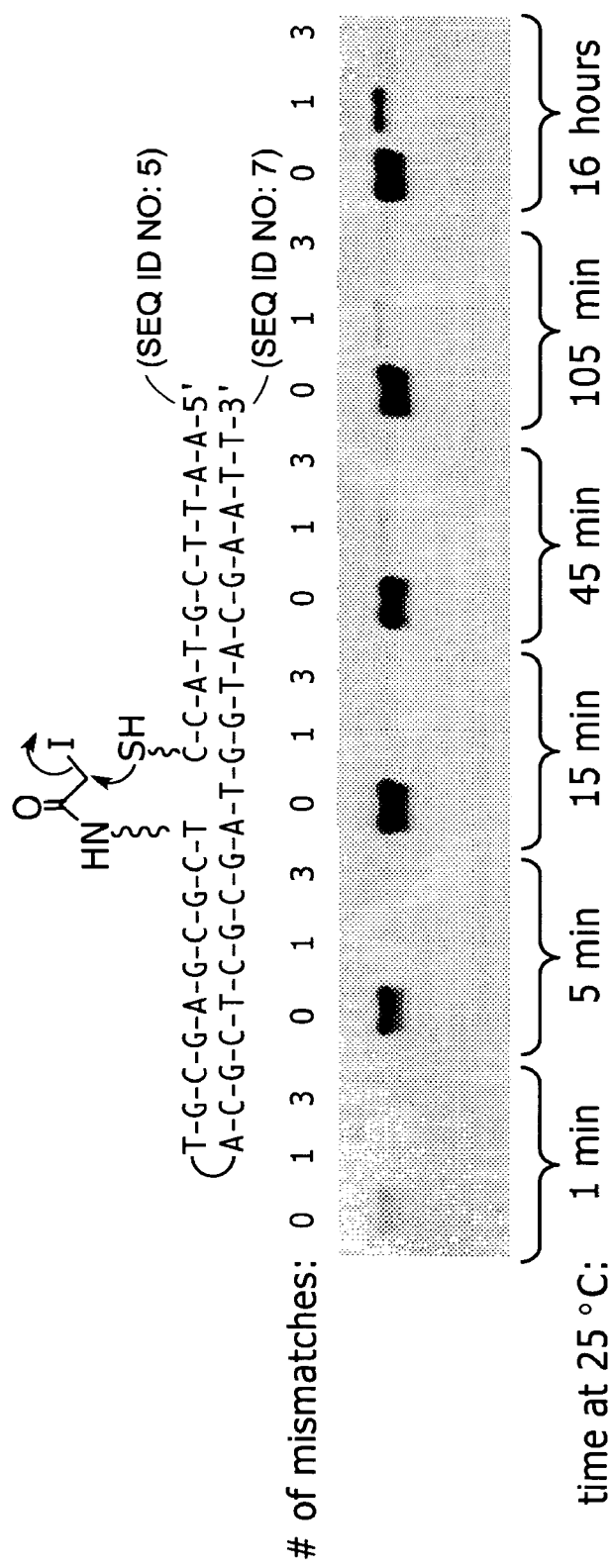
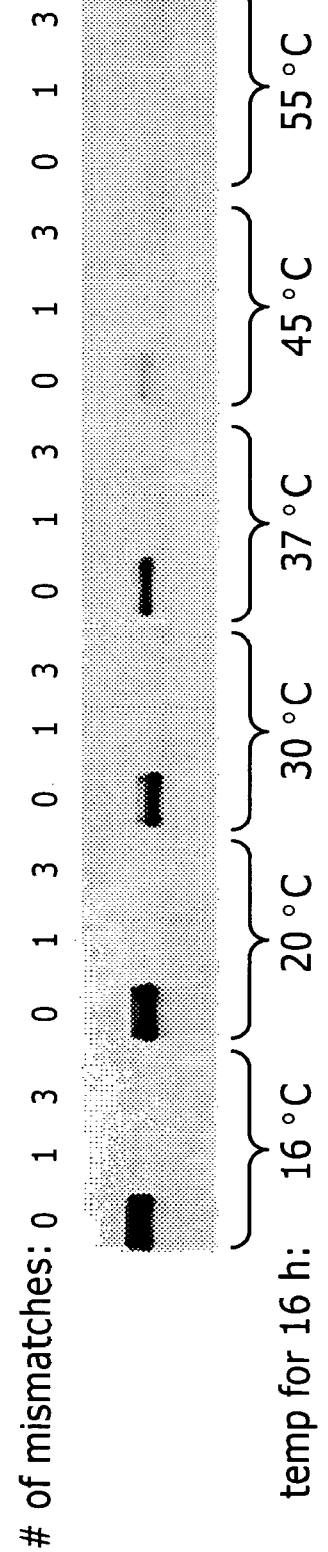
FIG. 17A
FIG. 17B

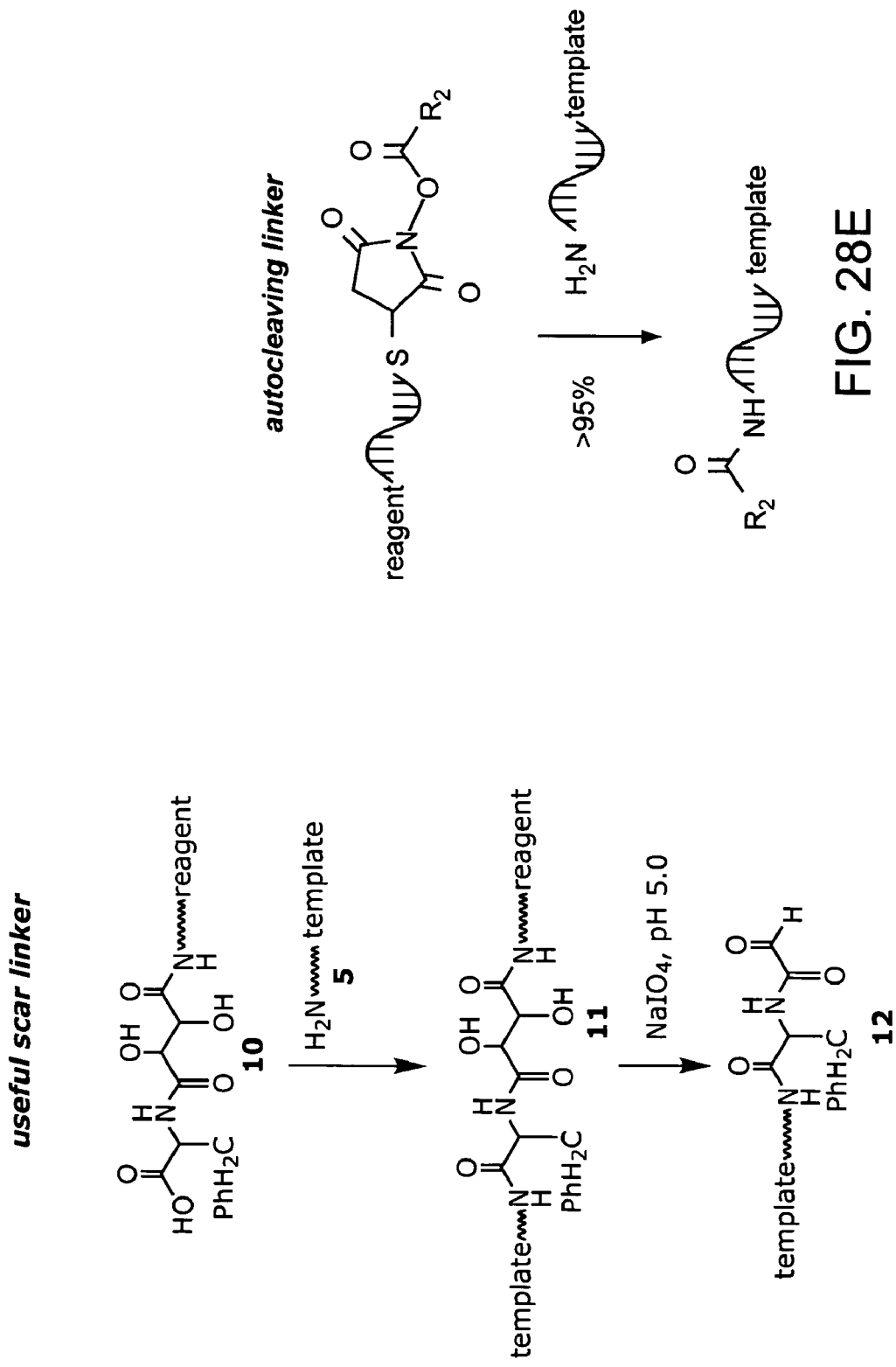

| Architecture | Buffer | $T_m$ (°C) |
|---|---|---|
| E ($n$ = 10) | PBS | 45 |
| Ω ($n$ = 10) | PBS | 46 |
| E ($n$ = 10) | HSP | 55 |
| Ω ($n$ = 10) | HSP | 54 |
| E ($n$ = 20) | PBS | 40 |
| Ω ($n$ = 20) | PBS | 39 |

FIG. 36

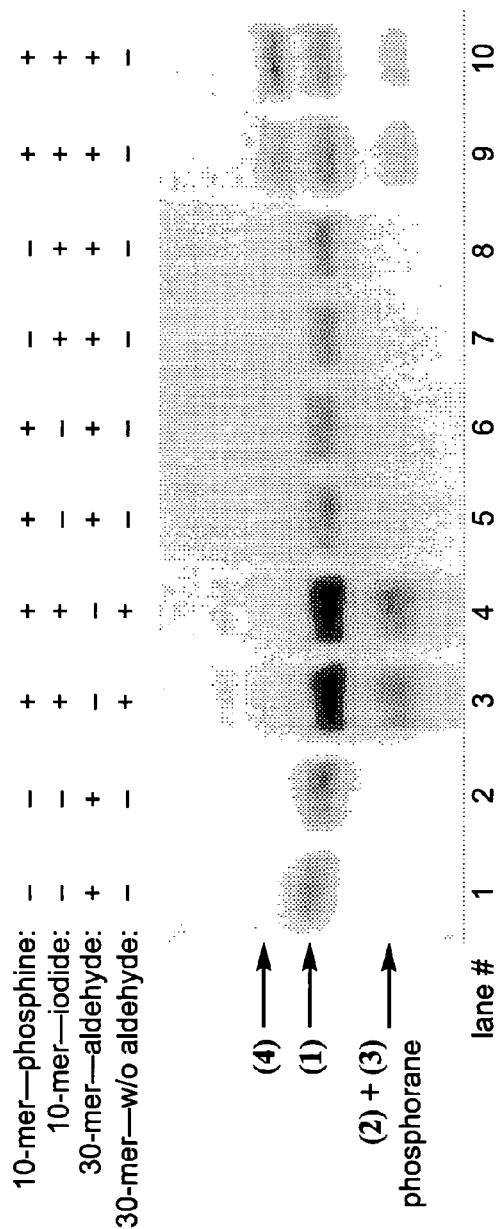
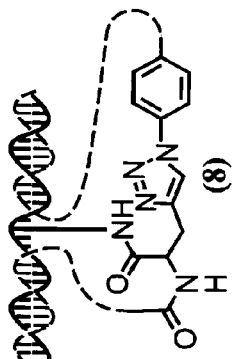
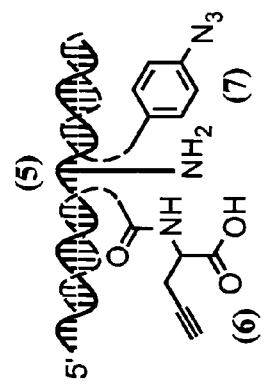
FIG. 38B
FIG. 38C

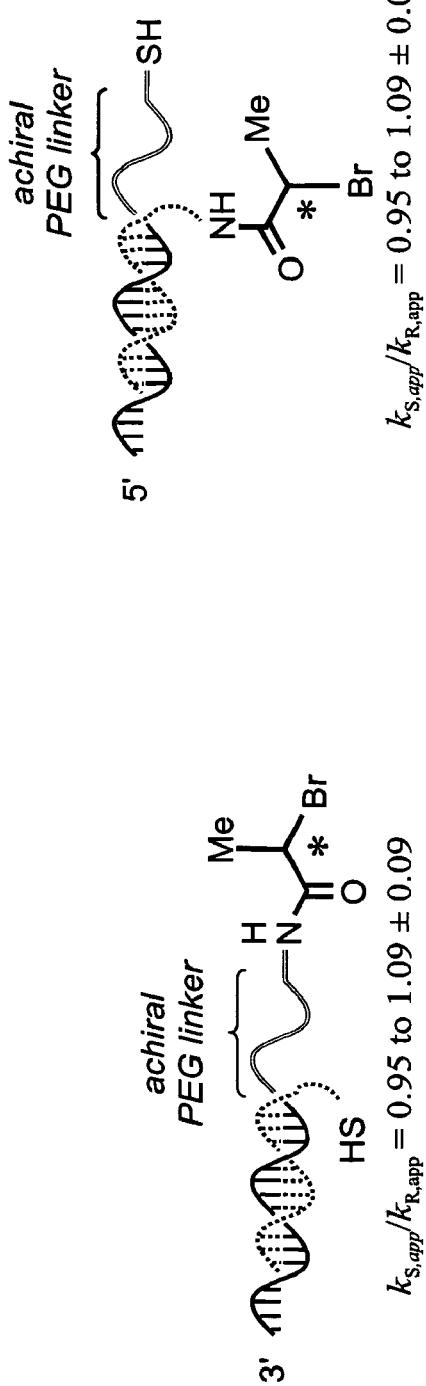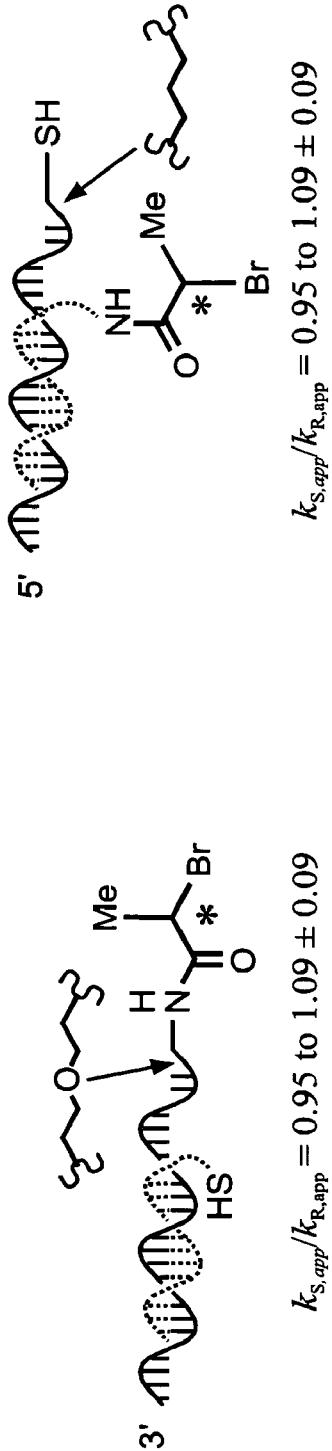
FIG. 43A
FIG. 43B
FIG. 43C
FIG. 43D
$k_{S,app}/k_{R,app} = 0.95$ to $1.09 \pm 0.09$

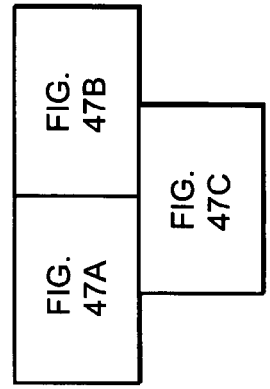

| FIG. 48A |
| FIG. 48B |

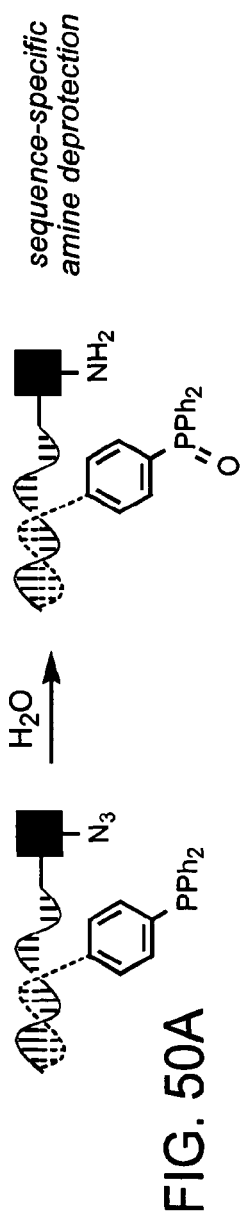
FIG. 50A
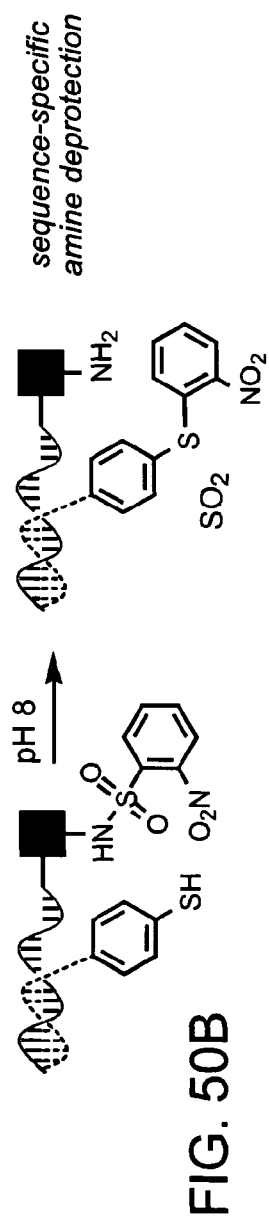
FIG. 50B
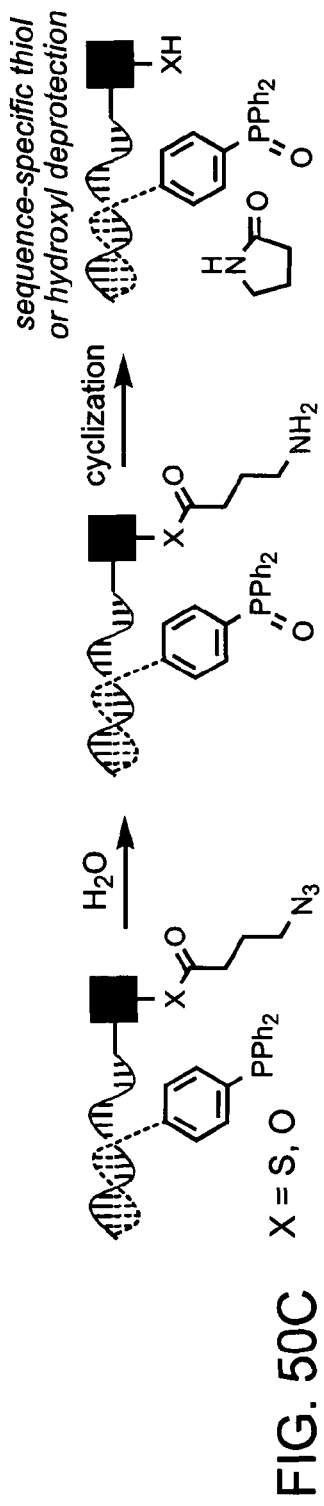
FIG. 50C  X = S, O

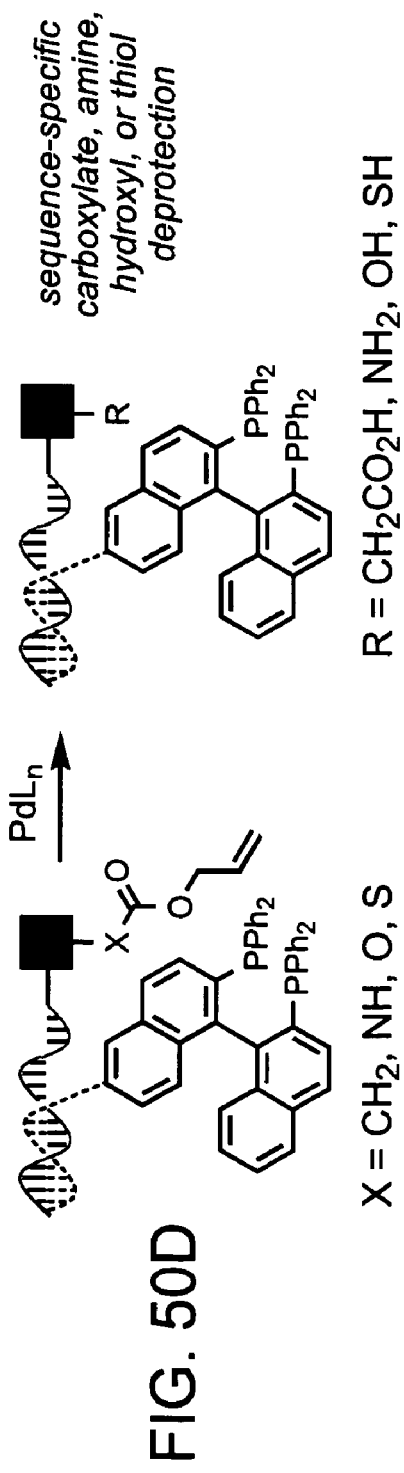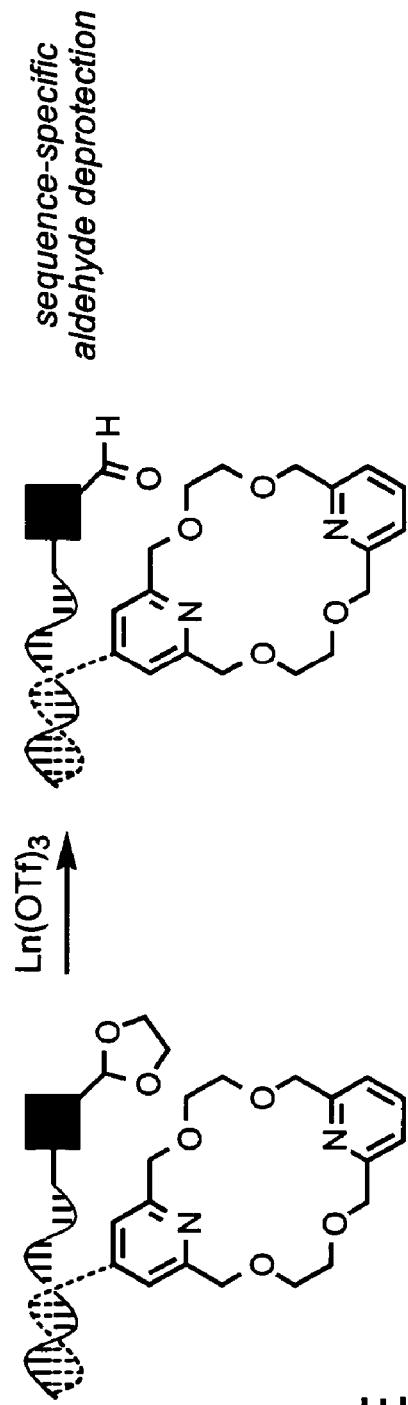
FIG. 50D
FIG. 50E

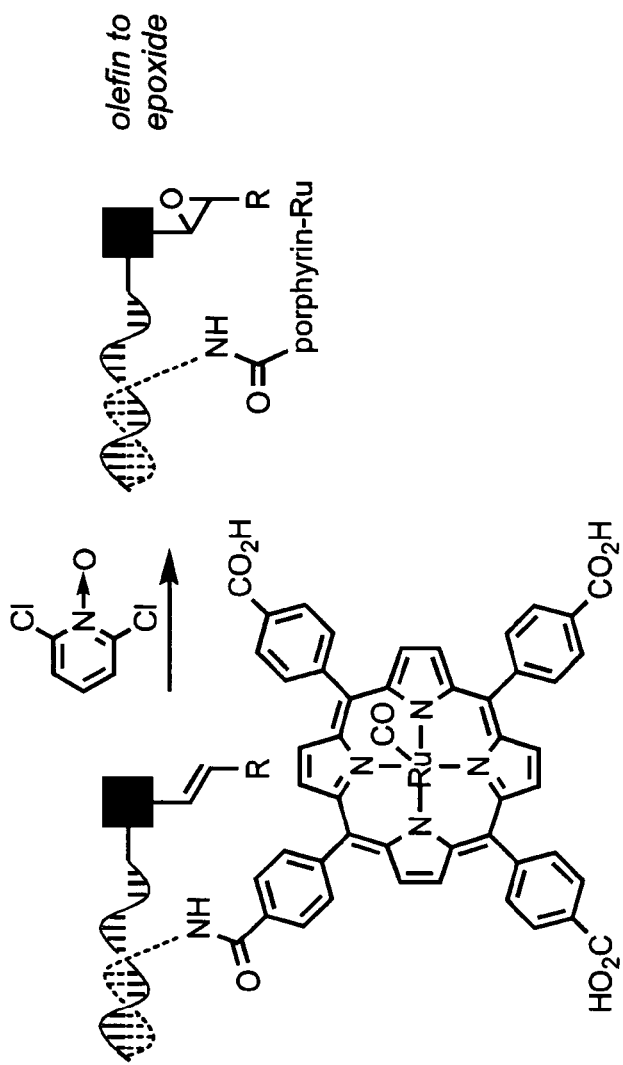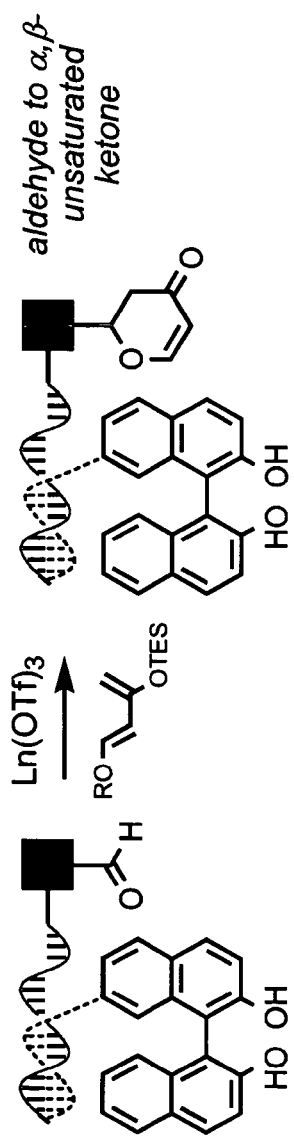
FIG. 51A
FIG. 51B

X, Y = groups for coupling (see Fig. 1)

R =

Evolving Plastics

- Ring-opening metathesis polymerization (ROMP, R. Grubbs) is mediated by a ruthenium catalyst
- ROMP is aqueous-compatible and is a living polymerization R' = 2'-deoxyribose-5'-triphosphate

| DNA-linked molecule | target protein | predicted activity | enrichment factor | sensitivity (mol) |
|---|---|---|---|---|
| 1 | glutathione S-transferase | $K_d = 10\ \mu M$ | 2,500 | $10^{-20}$ |
| 3 | carbonic anhydrase | $K_d = 0.9$ nM | 330 | $10^{-20}$ |
| 4 | streptavidin | $K_d = 40$ fM | 4,400 | $10^{-18}$ |
| 5 | papain | $IC_{50} = 14\ \mu M$ | 64 | $10^{-16}$ |
| 5 | chymotrypsin | $IC_{50} = 290$ nM | 76 | $10^{-16}$ |
| 6 | papain | $IC_{50} = 270$ nM | 98 | $10^{-18}$ |
| 6 | trypsin | $K_d = 100$ nM | 125 | $10^{-17}$ |

SEQUENCE LISTING

```
<160> NUMBER OF SEQ ID NOS: 125

<210> SEQ ID NO 1
<211> LENGTH: 64
<212> TYPE: DNA
<213> ORGANISM: Artificial Sequence
<220> FEATURE:
<223> OTHER INFORMATION: Template Encoding Parent Molecule 1

<400> SEQUENCE: 1
cgagcagcac cagcgcactc cgcctggatc cgccccgggt gcacgcgact cctacgggct      60
ccaa                                                                  64

<210> SEQ ID NO 2
<211> LENGTH: 64
<212> TYPE: DNA
<213> ORGANISM: Artificial Sequence
<220> FEATURE:
<223> OTHER INFORMATION: Template Encoding Parent Molecule 2

<400> SEQUENCE: 2
cgagcagcac cagcgagtcc cgcctgggga tgccccgggt gggcgcgact ccaacgggct      60
ccaa                                                                  64

<210> SEQ ID NO 3
<211> LENGTH: 64
<212> TYPE: DNA
<213> ORGANISM: Artificial Sequence
<220> FEATURE:
<223> OTHER INFORMATION: Recombined Daughter Template

<400> SEQUENCE: 3
cgagcagcac cagcgcactc cgcctgggga tgccccgggt gggcgcgact cctacgggct      60
ccaa                                                                  64

<210> SEQ ID NO 4
<211> LENGTH: 64
<212> TYPE: DNA
<213> ORGANISM: Artificial Sequence
<220> FEATURE:
<223> OTHER INFORMATION: Recombined Daughter Template

<400> SEQUENCE: 4
```

```
cgagcagcac cagcgagtcc cgcctggatc cgccccgggt gcacgcgact ccaacgggct    60
ccaa                                                                 64

<210> SEQ ID NO 5
<211> LENGTH: 10
<212> TYPE: DNA
<213> ORGANISM: Artificial Sequence
<220> FEATURE:
<223> OTHER INFORMATION: Synthetic oligonucleotide linked to a thiol
      reagent

<400> SEQUENCE: 5
aattcgtacc                                                           10

<210> SEQ ID NO 6
<211> LENGTH: 11
<212> TYPE: DNA
<213> ORGANISM: Artificial Sequence
<220> FEATURE:
<223> OTHER INFORMATION: Template E

<400> SEQUENCE: 6
tggtacgaat t                                                         11

<210> SEQ ID NO 7
<211> LENGTH: 31
<212> TYPE: DNA
<213> ORGANISM: Artificial Sequence
<220> FEATURE:
<223> OTHER INFORMATION: Template H

<400> SEQUENCE: 7
tcgcgagcgt acgctcgcga tggtacgaat t                                   31

<210> SEQ ID NO 8
<211> LENGTH: 20
<212> TYPE: DNA
<213> ORGANISM: Artificial Sequence
<220> FEATURE:
<223> OTHER INFORMATION: Template

<400> SEQUENCE: 8
tggtacgaat tcgactcggg                                                20

<210> SEQ ID NO 9
<211> LENGTH: 10
<212> TYPE: DNA
<213> ORGANISM: Artificial Sequence
<220> FEATURE:
<223> OTHER INFORMATION: Synthetic oligonucleotide linked to a thiol
      reagent

<400> SEQUENCE: 9
cccgagtcga                                                           10

<210> SEQ ID NO 10
<211> LENGTH: 50
<212> TYPE: DNA
<213> ORGANISM: Artificial Sequence
<220> FEATURE:
<223> OTHER INFORMATION: Template

<400> SEQUENCE: 10
tggtgcggag ccgccgtgac gggtgatacc acctccgagc cgaggagccg               50
```

```
<210> SEQ ID NO 11
<211> LENGTH: 50
<212> TYPE: DNA
<213> ORGANISM: Artificial Sequence
<220> FEATURE:
<223> OTHER INFORMATION: Template
<220> FEATURE:
<221> NAME/KEY: misc_feature
<222> LOCATION: (17)..(17)
<223> OTHER INFORMATION: N is A, C, T or G
<220> FEATURE:
<221> NAME/KEY: misc_feature
<222> LOCATION: (19)..(19)
<223> OTHER INFORMATION: N is A, C, T or G
<220> FEATURE:
<221> NAME/KEY: misc_feature
<222> LOCATION: (21)..(21)
<223> OTHER INFORMATION: N is A, C, T or G
<220> FEATURE:
<221> NAME/KEY: misc_feature
<222> LOCATION: (23)..(24)
<223> OTHER INFORMATION: N is A, C, T or G

<400> SEQUENCE: 11
tggtgcggag ccgccgncna ncnngatacc acctccgagc cgaggagccg            50

<210> SEQ ID NO 12
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 12
cacccgtcac                                                        10

<210> SEQ ID NO 13
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(3)
<223> OTHER INFORMATION: N is A, T, C or G
<220> FEATURE:
<221> NAME/KEY: misc_feature
<222> LOCATION: (5)..(5)
<223> OTHER INFORMATION: N is A, T, C or G
<220> FEATURE:
<221> NAME/KEY: misc_feature
<222> LOCATION: (7)..(7)
<223> OTHER INFORMATION: N is A, T, C or G
<220> FEATURE:
<221> NAME/KEY: misc_feature
<222> LOCATION: (9)..(9)
<223> OTHER INFORMATION: N is A, T, C or G

<400> SEQUENCE: 13 cnngntngnc                                                        10

<210> SEQ ID NO 14
<211> LENGTH: 11
<212> TYPE: DNA
<213> ORGANISM: Artificial Sequence
<220> FEATURE:
<223> OTHER INFORMATION: Template 1a-1c

<400> SEQUENCE: 14
tggtacgaat t                                                      11
```

```
<210> SEQ ID NO 15
<211> LENGTH: 17
<212> TYPE: DNA
<213> ORGANISM: Artificial Sequence
<220> FEATURE:
<223> OTHER INFORMATION: Template 2a-2c

<400> SEQUENCE: 15
ttaacgagag atagtct                                                    17

<210> SEQ ID NO 16
<211> LENGTH: 23
<212> TYPE: DNA
<213> ORGANISM: Artificial Sequence
<220> FEATURE:
<223> OTHER INFORMATION: Template 3a-3c

<400> SEQUENCE: 16
tatctacaga gtagtctaat gac                                             23

<210> SEQ ID NO 17
<211> LENGTH: 14
<212> TYPE: DNA
<213> ORGANISM: Artificial Sequence
<220> FEATURE:
<223> OTHER INFORMATION: Synthetic oligonucleotide 4a-4c

<400> SEQUENCE: 17
cagcaattcg tacc                                                       14

<210> SEQ ID NO 18
<211> LENGTH: 16
<212> TYPE: DNA
<213> ORGANISM: Artificial Sequence
<220> FEATURE:
<223> OTHER INFORMATION: Synethetic oligonucleotide 5a-5c

<400> SEQUENCE: 18
ctcagctctc tcgtta                                                     16

<210> SEQ ID NO 19
<211> LENGTH: 18
<212> TYPE: DNA
<213> ORGANISM: Artificial Sequence
<220> FEATURE:
<223> OTHER INFORMATION: Synthetic oligonucleotide 6a-6c

<400> SEQUENCE: 19
ggctcagcct ctgtagat                                                   18

<210> SEQ ID NO 20
<211> LENGTH: 11
<212> TYPE: DNA
<213> ORGANISM: Artificial Sequence
<220> FEATURE:
<223> OTHER INFORMATION: Template 15

<400> SEQUENCE: 20
tatagatcag c                                                          11

<210> SEQ ID NO 21
<211> LENGTH: 11
<212> TYPE: DNA
<213> ORGANISM: Artificial Sequence
<220> FEATURE:
<223> OTHER INFORMATION: Template 17

<400> SEQUENCE: 21
```

-continued ttaacgagag a                                                 11

<210> SEQ ID NO 22
<211> LENGTH: 11
<212> TYPE: DNA
<213> ORGANISM: Artificial Sequence
<220> FEATURE:
<223> OTHER INFORMATION: Template 18

<400> SEQUENCE: 22
tatctacaga g                                                 11

<210> SEQ ID NO 23
<211> LENGTH: 11
<212> TYPE: DNA
<213> ORGANISM: Artificial Sequence
<220> FEATURE:
<223> OTHER INFORMATION: Template 19

<400> SEQUENCE: 23
tcctgatgta a                                                 11

<210> SEQ ID NO 24
<211> LENGTH: 11
<212> TYPE: DNA
<213> ORGANISM: Artificial Sequence
<220> FEATURE:
<223> OTHER INFORMATION: Template 20

<400> SEQUENCE: 24
taagatctgc t                                                 11

<210> SEQ ID NO 25
<211> LENGTH: 15
<212> TYPE: DNA
<213> ORGANISM: Artificial Sequence
<220> FEATURE:
<223> OTHER INFORMATION: Synthetic oligonucleotide linked to a
      functional group 21

<400> SEQUENCE: 25
tcagcgctga tctat                                             15

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide linked to functional
      group 22

<400> SEQUENCE: 26
agggctcagc aattcgtacc                                        20

<210> SEQ ID NO 27
<211> LENGTH: 25
<212> TYPE: DNA
<213> ORGANISM: Artificial Sequence
<220> FEATURE:
<223> OTHER INFORMATION: Synthetic oligonucleotide linked to a
      functional group 23

<400> SEQUENCE: 27
acgtaagggc tcagctctct cgtta                                  25

<210> SEQ ID NO 28

```
<211> LENGTH: 31
<212> TYPE: DNA
<213> ORGANISM: Artificial Sequence
<220> FEATURE:
<223> OTHER INFORMATION: Synthetic oligonucleotide linked to a
      functional group 24

<400> SEQUENCE: 28
ttccagccgt aagggctcag cctctgtaga t                              31

<210> SEQ ID NO 29
<211> LENGTH: 35
<212> TYPE: DNA
<213> ORGANISM: Artificial Sequence
<220> FEATURE:
<223> OTHER INFORMATION: Synthetic oligonucleotide linked to a
      functional group 25

<400> SEQUENCE: 29
ggcatttccg acctaagggc tcagcttaca tcagg                          35

<210> SEQ ID NO 30
<211> LENGTH: 40
<212> TYPE: DNA
<213> ORGANISM: Artificial Sequence
<220> FEATURE:
<223> OTHER INFORMATION: Synthetic oligonucleotide linked to a
      functional group 26

<400> SEQUENCE: 30
tctatggcat ttccgacgta agggctcagc agcagatctt                     40

<210> SEQ ID NO 31
<211> LENGTH: 48
<212> TYPE: DNA
<213> ORGANISM: Artificial Sequence
<220> FEATURE:
<223> OTHER INFORMATION: Template
<220> FEATURE:
<221> NAME/KEY: misc_feature
<222> LOCATION: (11)..(16)
<223> OTHER INFORMATION: N is A, T, C or G.
<220> FEATURE:
<221> NAME/KEY: misc_feature
<222> LOCATION: (22)..(27)
<223> OTHER INFORMATION: N is A, T, C or G.
<220> FEATURE:
<221> NAME/KEY: misc_feature
<222> LOCATION: (33)..(38)
<223> OTHER INFORMATION: N is A, T, C or G.

<400> SEQUENCE: 31
tcggacgtgt nnnnnngagt cnnnnnnctc agnnnnnngt agacatgc            48

<210> SEQ ID NO 32
<211> LENGTH: 15
<212> TYPE: DNA
<213> ORGANISM: Artificial Sequence
<220> FEATURE:
<223> OTHER INFORMATION: Synthetic oligonucleotide linked to NH2

<400> SEQUENCE: 32
tgggctcgat gacgg                                                15

<210> SEQ ID NO 33
<211> LENGTH: 16
<212> TYPE: DNA
<213> ORGANISM: Artificial Sequence
<220> FEATURE:
<223> OTHER INFORMATION: Synthetic oligonucleotide linked to biotin
```

```
<400> SEQUENCE: 33
tacgtagcgg cgtcgc                                                    16

<210> SEQ ID NO 34
<211> LENGTH: 51
<212> TYPE: DNA
<213> ORGANISM: Artificial Sequence
<220> FEATURE:
<223> OTHER INFORMATION: Template
<220> FEATURE:
<221> NAME/KEY: misc_feature
<222> LOCATION: (17)..(36)
<223> OTHER INFORMATION: N is A, T, C or G

<400> SEQUENCE: 34
tacgtagcgg cgtcgcnnnn nnnnnnnnnn nnnnnccgt catcgagccc a              51

<210> SEQ ID NO 35
<211> LENGTH: 16
<212> TYPE: DNA
<213> ORGANISM: Artificial Sequence
<220> FEATURE:
<223> OTHER INFORMATION: Primer 1

<400> SEQUENCE: 35
tggtgcggag ccgccg                                                    16

<210> SEQ ID NO 36
<211> LENGTH: 37
<212> TYPE: DNA
<213> ORGANISM: Artificial Sequence
<220> FEATURE:
<223> OTHER INFORMATION: Primer

<400> SEQUENCE: 36
ccactgtccg tggcgcgacc ccggctcctc ggctcgg                             37

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
ccactgtccg tggcgcgacc c                                              21

<210> SEQ ID NO 38
<211> LENGTH: 19
<212> TYPE: DNA
<213> ORGANISM: Artificial Sequence
<220> FEATURE:
<223> OTHER INFORMATION: Synthetic oligonucleotide linked to SH

<400> SEQUENCE: 38
cccgagtcga agtcgtacc                                                 19

<210> SEQ ID NO 39
<211> LENGTH: 19
<212> TYPE: DNA
<213> ORGANISM: Artificial Sequence
<220> FEATURE:
<223> OTHER INFORMATION: Synthetic oligonucleotide linked to SH

<400> SEQUENCE: 39
gggctcagct tccccataa                                                 19
```

<210> SEQ ID NO 40
<211> LENGTH: 10
<212> TYPE: DNA
<213> ORGANISM: Artificial Sequence
<220> FEATURE:
<223> OTHER INFORMATION: Synthetic oligonucleotide linked to SH

<400> SEQUENCE: 40
aaatcttccc                                                           10

<210> SEQ ID NO 41
<211> LENGTH: 10
<212> TYPE: DNA
<213> ORGANISM: Artificial Sequence
<220> FEATURE:
<223> OTHER INFORMATION: Synthetic oligonucleotide linked to SH

<400> SEQUENCE: 41
aattcttacc                                                           10

<210> SEQ ID NO 42
<211> LENGTH: 60
<212> TYPE: DNA
<213> ORGANISM: Artificial Sequence
<220> FEATURE:
<223> OTHER INFORMATION: E Template

<400> SEQUENCE: 42
cgcgagcgta cgctcgcgat ggtacgaatt cgactcggga ataccacctt cgactcgagg    60

<210> SEQ ID NO 43
<211> LENGTH: 31
<212> TYPE: DNA
<213> ORGANISM: Artificial Sequence
<220> FEATURE:
<223> OTHER INFORMATION: H Template

<400> SEQUENCE: 43
cgcgagcgta cgctcgcgat ggtacgaatt c                                   31

<210> SEQ ID NO 44
<211> LENGTH: 10
<212> TYPE: DNA
<213> ORGANISM: Artificial Sequence
<220> FEATURE:
<223> OTHER INFORMATION: Clamp Oligonucleotide

<400> SEQUENCE: 44
attcgtacca                                                           10

<210> SEQ ID NO 45
<211> LENGTH: 20
<212> TYPE: DNA
<213> ORGANISM: Artificial Sequence
<220> FEATURE:
<223> OTHER INFORMATION: Template 1

<400> SEQUENCE: 45
tggtacgaat tcgactcggg                                                20

<210> SEQ ID NO 46
<211> LENGTH: 16
<212> TYPE: DNA
<213> ORGANISM: Artificial Sequence
<220> FEATURE:
<223> OTHER INFORMATION: Synthetic oligonucleotides 2 and 3 matched

```
<400> SEQUENCE: 46
gagtcgaatt cgtacc                                                    16

<210> SEQ ID NO 47
<211> LENGTH: 16
<212> TYPE: DNA
<213> ORGANISM: Artificial Sequence
<220> FEATURE:
<223> OTHER INFORMATION: Synthetic oligonucleotides 2 and 3 mismatched

<400> SEQUENCE: 47
gggctcagct tcccca                                                    16

<210> SEQ ID NO 48
<211> LENGTH: 30
<212> TYPE: DNA
<213> ORGANISM: Artificial Sequence
<220> FEATURE:
<223> OTHER INFORMATION: Templates 4 and 5

<400> SEQUENCE: 48
ggtacgaatt cgactcggga ataccacctt                                     30

<210> SEQ ID NO 49
<211> LENGTH: 10
<212> TYPE: DNA
<213> ORGANISM: Artificial Sequence
<220> FEATURE:
<223> OTHER INFORMATION: Synthetic oligonucleotides 6-9 matched, n=10

<400> SEQUENCE: 49
tcccgagtcg                                                           10

<210> SEQ ID NO 50
<211> LENGTH: 10
<212> TYPE: DNA
<213> ORGANISM: Artificial Sequence
<220> FEATURE:
<223> OTHER INFORMATION: Synthetic oligonucleotide 6 matched, n=0

<400> SEQUENCE: 50
aattcgtacc                                                           10

<210> SEQ ID NO 51
<211> LENGTH: 10
<212> TYPE: DNA
<213> ORGANISM: Artificial Sequence
<220> FEATURE:
<223> OTHER INFORMATION: Synthetic oligonucleotides 6-9 mismatched

<400> SEQUENCE: 51
tcacctagca                                                           10

<210> SEQ ID NO 52
<211> LENGTH: 20
<212> TYPE: DNA
<213> ORGANISM: Artificial Sequence
<220> FEATURE:
<223> OTHER INFORMATION: Templates 11, 12, 14, 17, 18, 20

<400> SEQUENCE: 52
ggtacgaatt cgactcggga                                                20

<210> SEQ ID NO 53
<211> LENGTH: 20
```

```
<212> TYPE: DNA
<213> ORGANISM: Artificial Sequence
<220> FEATURE:
<223> OTHER INFORMATION: Synthetic oligonucleotides 10, 13, 16, 19
      matched

<400> SEQUENCE: 53
tcccgagtcg aattcgtacc                                              20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucletides 10, 13, 16, 19
      mismatched

<400> SEQUENCE: 54
gggctcagct tccccataat                                              20

<210> SEQ ID NO 55
<211> LENGTH: 10
<212> TYPE: DNA
<213> ORGANISM: Artificial Sequence
<220> FEATURE:
<223> OTHER INFORMATION: Synthetic oligonucleotide 15 matched

<400> SEQUENCE: 55
aattcgtacc                                                         10

<210> SEQ ID NO 56
<211> LENGTH: 10
<212> TYPE: DNA
<213> ORGANISM: Artificial Sequence
<220> FEATURE:
<223> OTHER INFORMATION: Synthetic oligonucleotide 15 mismatched

<400> SEQUENCE: 56
tcgtattcca                                                         10

<210> SEQ ID NO 57
<211> LENGTH: 30
<212> TYPE: DNA
<213> ORGANISM: Artificial Sequence
<220> FEATURE:
<223> OTHER INFORMATION: Template for n=10 vs. n=0 comparison

<400> SEQUENCE: 57
tagcgattac ggtacgaatt cgactcggga                                   30

<210> SEQ ID NO 58
<211> LENGTH: 30
<212> TYPE: DNA
<213> ORGANISM: Artificial Sequence
<220> FEATURE:
<223> OTHER INFORMATION: E or Omega Template

<400> SEQUENCE: 58
ggtacgaatt cgactcggga ataccacctt                                   30

<210> SEQ ID NO 59
<211> LENGTH: 48
<212> TYPE: DNA
<213> ORGANISM: Artificial Sequence
<220> FEATURE:
<223> OTHER INFORMATION: H Template

<400> SEQUENCE: 59
```
cgcgagcgta cgctcgcggg tacgaattcg actcgggaat accacctt         48

<210> SEQ ID NO 60
<211> LENGTH: 29
<212> TYPE: DNA
<213> ORGANISM: Artificial Sequence
<220> FEATURE:
<223> OTHER INFORMATION: T Template
<220> FEATURE:
<221> NAME/KEY: misc_feature
<222> LOCATION: (14)..(14)
<223> OTHER INFORMATION: N is c(dt-nh2)

<400> SEQUENCE: 60
ggtacgaatt cgancgggaa taccaccett         29

<210> SEQ ID NO 61
<211> LENGTH: 10
<212> TYPE: DNA
<213> ORGANISM: Artificial Sequence
<220> FEATURE:
<223> OTHER INFORMATION: E or H synthetic oligonucleotide (n=1)

<400> SEQUENCE: 61
aattcgtacc         10

<210> SEQ ID NO 62
<211> LENGTH: 10
<212> TYPE: DNA
<213> ORGANISM: Artificial Sequence
<220> FEATURE:
<223> OTHER INFORMATION: E or H synthetic nucleotide (n=10)

<400> SEQUENCE: 62
tcccgagtcg         10

<210> SEQ ID NO 63
<211> LENGTH: 10
<212> TYPE: DNA
<213> ORGANISM: Artificial Sequence
<220> FEATURE:
<223> OTHER INFORMATION: E or H synthetic oligonucleotide (n=20)

<400> SEQUENCE: 63
aaggtggtat         10

<210> SEQ ID NO 64
<211> LENGTH: 10
<212> TYPE: DNA
<213> ORGANISM: Artificial Sequence
<220> FEATURE:
<223> OTHER INFORMATION: Mismatched E or H synthetic oligonucleotide

<400> SEQUENCE: 64
tccctgatcg         10

<210> SEQ ID NO 65
<211> LENGTH: 13
<212> TYPE: DNA
<213> ORGANISM: Artificial Sequence
<220> FEATURE:
<223> OTHER INFORMATION: Omega-3 synthetic oligonucleotide (n=10)

<400> SEQUENCE: 65
tcccgagtcg acc         13

```
<210> SEQ ID NO 66
<211> LENGTH: 13
<212> TYPE: DNA
<213> ORGANISM: Artificial Sequence
<220> FEATURE:
<223> OTHER INFORMATION: Omega-4 synthetic oligonucleotide (n=10)

<400> SEQUENCE: 66
tcccgagtcg acc                                                          13

<210> SEQ ID NO 67
<211> LENGTH: 15
<212> TYPE: DNA
<213> ORGANISM: Artificial Sequence
<220> FEATURE:
<223> OTHER INFORMATION: Omega-5 synthetic oligonucleotide (n=10)

<400> SEQUENCE: 67
tcccgagtcg gtacc                                                        15

<210> SEQ ID NO 68
<211> LENGTH: 13
<212> TYPE: DNA
<213> ORGANISM: Artificial Sequence
<220> FEATURE:
<223> OTHER INFORMATION: Omega-3 synthetic oligonucleotide (n=20)

<400> SEQUENCE: 68
aaggtggtat acc                                                          13

<210> SEQ ID NO 69
<211> LENGTH: 14
<212> TYPE: DNA
<213> ORGANISM: Artificial Sequence
<220> FEATURE:
<223> OTHER INFORMATION: Omega-4 synthetic oligonucleotide (n=20)

<400> SEQUENCE: 69
aaggtggtat tacc                                                         14

<210> SEQ ID NO 70
<211> LENGTH: 15
<212> TYPE: DNA
<213> ORGANISM: Artificial Sequence
<220> FEATURE:
<223> OTHER INFORMATION: Omega-5 synthetic oligonucleotide (n=20)

<400> SEQUENCE: 70
aaggtggtat gtacc                                                        15

<210> SEQ ID NO 71
<211> LENGTH: 13
<212> TYPE: DNA
<213> ORGANISM: Artificial Sequence
<220> FEATURE:
<223> OTHER INFORMATION: Mismatched Omega-3 synthetic oligonucleotide

<400> SEQUENCE: 71
tccctgatcg acc                                                          13

<210> SEQ ID NO 72
<211> LENGTH: 14
<212> TYPE: DNA
<213> ORGANISM: Artificial Sequence
<220> FEATURE:
<223> OTHER INFORMATION: Mismatched Omega-4 synthetic oligonucleotide

<400> SEQUENCE: 72
```

```
tccctgatcg tacc                                                    14

<210> SEQ ID NO 73
<211> LENGTH: 15
<212> TYPE: DNA
<213> ORGANISM: Artificial Sequence
<220> FEATURE:
<223> OTHER INFORMATION: Mismatched Omega-5 synthetic oligonucleotide

<400> SEQUENCE: 73
tccctgatcg gtacc                                                   15

<210> SEQ ID NO 74
<211> LENGTH: 10
<212> TYPE: DNA
<213> ORGANISM: Artificial Sequence
<220> FEATURE:
<223> OTHER INFORMATION: Synthetic T-oligonucleotide (n=1)

<400> SEQUENCE: 74
ggtattcccg                                                         10

<210> SEQ ID NO 75
<211> LENGTH: 10
<212> TYPE: DNA
<213> ORGANISM: Artificial Sequence
<220> FEATURE:
<223> OTHER INFORMATION: Synthetic T-oligonucleotide (n=2)

<400> SEQUENCE: 75
tggtattccc                                                         10

<210> SEQ ID NO 76
<211> LENGTH: 10
<212> TYPE: DNA
<213> ORGANISM: Artificial Sequence
<220> FEATURE:
<223> OTHER INFORMATION: Synthetic T-oligonucleotide (n=3)

<400> SEQUENCE: 76
gtggtattcc                                                         10

<210> SEQ ID NO 77
<211> LENGTH: 10
<212> TYPE: DNA
<213> ORGANISM: Artificial Sequence
<220> FEATURE:
<223> OTHER INFORMATION: Synthetic T-oligonucleotide (n=4)

<400> SEQUENCE: 77
ggtggtattc                                                         10

<210> SEQ ID NO 78
<211> LENGTH: 10
<212> TYPE: DNA
<213> ORGANISM: Artificial Sequence
<220> FEATURE:
<223> OTHER INFORMATION: Synthetic T-oligonucleotide (n=5)

<400> SEQUENCE: 78
aggtggtatt                                                         10

<210> SEQ ID NO 79
<211> LENGTH: 10
<212> TYPE: DNA
<213> ORGANISM: Artificial Sequence
```

```
<220> FEATURE:
<223> OTHER INFORMATION: Synthetic T-oligonucleotide (n=-1)

<400> SEQUENCE: 79
gtcgaattcg                                                                10

<210> SEQ ID NO 80
<211> LENGTH: 10
<212> TYPE: DNA
<213> ORGANISM: Artificial Sequence
<220> FEATURE:
<223> OTHER INFORMATION: Synthetic T-oligonucleotide (n=-4)

<400> SEQUENCE: 80
aattcgtacc                                                                10

<210> SEQ ID NO 81
<211> LENGTH: 31
<212> TYPE: DNA
<213> ORGANISM: Artificial Sequence
<220> FEATURE:
<223> OTHER INFORMATION: Template

<400> SEQUENCE: 81
tcgcgagcgt acgctcgcga ggtacgaatt c                                        31

<210> SEQ ID NO 82
<211> LENGTH: 11
<212> TYPE: DNA
<213> ORGANISM: Artificial Sequence
<220> FEATURE:
<223> OTHER INFORMATION: Synthetic oligonucleotide linked to a
      functional group

<400> SEQUENCE: 82
gaattcgtac c                                                              11

<210> SEQ ID NO 83
<211> LENGTH: 23
<212> TYPE: DNA
<213> ORGANISM: Artificial Sequence
<220> FEATURE:
<223> OTHER INFORMATION: Synthetic oligonucleotide linked to a
      functional group

<400> SEQUENCE: 83
tacgctcgcg atggtacgaa ttc                                                 23

<210> SEQ ID NO 84
<211> LENGTH: 23
<212> TYPE: DNA
<213> ORGANISM: Artificial Sequence
<220> FEATURE:
<223> OTHER INFORMATION: Template

<400> SEQUENCE: 84
gaattcgtac atagcgctcg cat                                                 23

<210> SEQ ID NO 85
<211> LENGTH: 11
<212> TYPE: DNA
<213> ORGANISM: Artificial Sequence
<220> FEATURE:
<223> OTHER INFORMATION: Synthetic oligonucleotide linked to a
      functional group

<400> SEQUENCE: 85
```

-continued

```
tgtacgaatt c                                                       11

<210> SEQ ID NO 86
<211> LENGTH: 48
<212> TYPE: DNA
<213> ORGANISM: Artificial Sequence
<220> FEATURE:
<223> OTHER INFORMATION: Template

<400> SEQUENCE: 86
gaattctgga cacttagcta ttcatcgagc gtacgctcga tgaatagc               48

<210> SEQ ID NO 87
<211> LENGTH: 15
<212> TYPE: DNA
<213> ORGANISM: Artificial Sequence
<220> FEATURE:
<223> OTHER INFORMATION: Synthetic oligonucleotide linked to a
      functional group

<400> SEQUENCE: 87
taagtgtcca gaatt                                                   15

<210> SEQ ID NO 88
<211> LENGTH: 48
<212> TYPE: DNA
<213> ORGANISM: Artificial Sequence
<220> FEATURE:
<223> OTHER INFORMATION: Template
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (9)..(9)
<223> OTHER INFORMATION: 5-methyl cytosine
<220> FEATURE:
<221> NAME/KEY: modified_base
<222> LOCATION: (11)..(11)
<223> OTHER INFORMATION: 5-methyl cytosine
<220> FEATURE:
<221> NAME/KEY: modified_base
<222> LOCATION: (13)..(13)
<223> OTHER INFORMATION: 5-methyl cytosine
<220> FEATURE:
<221> NAME/KEY: modified_base
<222> LOCATION: (15)..(15)
<223> OTHER INFORMATION: 5-methyl cytosine
<220> FEATURE:
<221> NAME/KEY: modified_base
<222> LOCATION: (17)..(17)
<223> OTHER INFORMATION: 5-methyl cytosine
<220> FEATURE:
<221> NAME/KEY: modified_base
<222> LOCATION: (19)..(19)
<223> OTHER INFORMATION: 5-methyl cytosine
<220> FEATURE:
<221> NAME/KEY: modified_base
<222> LOCATION: (21)..(21)
<223> OTHER INFORMATION: 5-methyl cytosine
<220> FEATURE:
<221> NAME/KEY: modified_base
<222> LOCATION: (23)..(23)
<223> OTHER INFORMATION: 5-methyl cytosine
<220> FEATURE:
<221> NAME/KEY: modified_base
<222> LOCATION: (25)..(25)
<223> OTHER INFORMATION: 5-methyl cytosine
<220> FEATURE:
<221> NAME/KEY: modified_base
<222> LOCATION: (39)..(39)
<223> OTHER INFORMATION: 5-methyl cytosine
<220> FEATURE:
<221> NAME/KEY: modified_base
```

```
<222> LOCATION: (41)..(41)
<223> OTHER INFORMATION: 5-methyl cytosine
<220> FEATURE:
<221> NAME/KEY: modified_base
<222> LOCATION: (43)..(43)
<223> OTHER INFORMATION: 5-methyl cytosine
<220> FEATURE:
<221> NAME/KEY: modified_base
<222> LOCATION: (45)..(45)
<223> OTHER INFORMATION: 5-methyl cytosine
<220> FEATURE:
<221> NAME/KEY: modified_base
<222> LOCATION: (47)..(47)
<223> OTHER INFORMATION: 5-methyl cytosine

<400> SEQUENCE: 88
gaattccgcg cgcgcacgcg cgcgcggagc gtacgctccg cgcgcgcg          48

<210> SEQ ID NO 89
<211> LENGTH: 15
<212> TYPE: DNA
<213> ORGANISM: Artificial Sequence
<220> FEATURE:
<223> OTHER INFORMATION: Synthetic oligonucleotide linked to a
      functional group
<220> FEATURE:
<221> NAME/KEY: modified_base
<222> LOCATION: (3)..(3)
<223> OTHER INFORMATION: 5-methyl cytosine
<220> FEATURE:
<221> NAME/KEY: modified_base
<222> LOCATION: (5)..(5)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (9)..(9)
<223> OTHER INFORMATION: 5-methyl cytosine

<400> SEQUENCE: 89
tgcgcgcgcg gaatt                                              15

<210> SEQ ID NO 90
<211> LENGTH: 11
<212> TYPE: DNA
<213> ORGANISM: Artificial Sequence
<220> FEATURE:
<223> OTHER INFORMATION: Template

<400> SEQUENCE: 90
ggtacgaatt c                                                  11

<210> SEQ ID NO 91
<211> LENGTH: 11
<212> TYPE: DNA
<213> ORGANISM: Artificial Sequence
<220> FEATURE:
<223> OTHER INFORMATION: Synthetic oligonucleotide linked to a
      functional group

<400> SEQUENCE: 91
gaattcgtac c                                                  11

<210> SEQ ID NO 92
<211> LENGTH: 11
<212> TYPE: DNA
<213> ORGANISM: Artificial Sequence
<220> FEATURE:
<223> OTHER INFORMATION: Template
```

```
<400> SEQUENCE: 92
gaattcgtac a                                                         11

<210> SEQ ID NO 93
<211> LENGTH: 11
<212> TYPE: DNA
<213> ORGANISM: Artificial Sequence
<220> FEATURE:
<223> OTHER INFORMATION: Synthetic oligonucleotide linked to a
      functional group

<400> SEQUENCE: 93
tgtacgaatt c                                                         11

<210> SEQ ID NO 94
<211> LENGTH: 22
<212> TYPE: DNA
<213> ORGANISM: Artificial Sequence
<220> FEATURE:
<223> OTHER INFORMATION: Template

<400> SEQUENCE: 94
acgctcgcga tggtacgaat tc                                             22

<210> SEQ ID NO 95
<211> LENGTH: 11
<212> TYPE: DNA
<213> ORGANISM: Artificial sequence
<220> FEATURE:
<223> OTHER INFORMATION: Synthetic oligonucleotide linked to a
      functional group

<400> SEQUENCE: 95
gaattcgtac c                                                         11

<210> SEQ ID NO 96
<211> LENGTH: 22
<212> TYPE: DNA
<213> ORGANISM: Artificial Sequence
<220> FEATURE:
<223> OTHER INFORMATION: Template

<400> SEQUENCE: 96
gaattcgtac atagcgctcg ca                                             22

<210> SEQ ID NO 97
<211> LENGTH: 11
<212> TYPE: DNA
<213> ORGANISM: Artificial Sequence
<220> FEATURE:
<223> OTHER INFORMATION: Synthetic oligonucleotide linked to a
      functional group

<400> SEQUENCE: 97
tgtacgaatt c                                                         11

<210> SEQ ID NO 98
<211> LENGTH: 23
<212> TYPE: DNA
<213> ORGANISM: Artificial Sequence
<220> FEATURE:
<223> OTHER INFORMATION: Template

<400> SEQUENCE: 98
tacgctcgcg atggtacgaa ttc                                            23
```

```
<210> SEQ ID NO 99
<211> LENGTH: 11
<212> TYPE: DNA
<213> ORGANISM: Artificial Sequence
<220> FEATURE:
<223> OTHER INFORMATION: Synthetic oligonucleotide linked to a
      functional group

<400> SEQUENCE: 99
gaattcgtac c                                                              11

<210> SEQ ID NO 100
<211> LENGTH: 23
<212> TYPE: DNA
<213> ORGANISM: Artificial Sequence
<220> FEATURE:
<223> OTHER INFORMATION: Template

<400> SEQUENCE: 100
gaattcgtac atagcgctcg cat                                                 23

<210> SEQ ID NO 101
<211> LENGTH: 11
<212> TYPE: DNA
<213> ORGANISM: Artificial Sequence
<220> FEATURE:
<223> OTHER INFORMATION: Synthetic oligonucleotide linked to a
      functional group

<400> SEQUENCE: 101
tgtacgaatt c                                                              11

<210> SEQ ID NO 102
<211> LENGTH: 48
<212> TYPE: DNA
<213> ORGANISM: Artificial Sequence
<220> FEATURE:
<223> OTHER INFORMATION: Template

<400> SEQUENCE: 102
gaattctgga cacttagcta ttcatcgagc gtacgctcga tgaatagc                      48

<210> SEQ ID NO 103
<211> LENGTH: 16
<212> TYPE: DNA
<213> ORGANISM: Artificial Sequence
<220> FEATURE:
<223> OTHER INFORMATION: Synthetic oligonucleotide linked to a
      functional group

<400> SEQUENCE: 103
taagtgtcca gaattc                                                         16

<210> SEQ ID NO 104
<211> LENGTH: 48
<212> TYPE: DNA
<213> ORGANISM: Artificial Sequence
<220> FEATURE:
<223> OTHER INFORMATION: Template
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (9)..(9)
<223> OTHER INFORMATION: 5-methyl cytosine
<220> FEATURE:
<221> NAME/KEY: modified_base
```

```
<222> LOCATION: (11)..(11)
<223> OTHER INFORMATION: 5-methyl cytosine
<220> FEATURE:
<221> NAME/KEY: modified_base
<222> LOCATION: (13)..(13)
<223> OTHER INFORMATION: 5-methyl cytosine
<220> FEATURE:
<221> NAME/KEY: modified_base
<222> LOCATION: (15)..(15)
<223> OTHER INFORMATION: 5-methyl cytosine
<220> FEATURE:
<221> NAME/KEY: modified_base
<222> LOCATION: (17)..(17)
<223> OTHER INFORMATION: 5-methyl cytosine
<220> FEATURE:
<221> NAME/KEY: modified_base
<222> LOCATION: (19)..(19)
<223> OTHER INFORMATION: 5-methyl cytosine
<220> FEATURE:
<221> NAME/KEY: modified_base
<222> LOCATION: (21)..(21)
<223> OTHER INFORMATION: 5-methyl cytosine
<220> FEATURE:
<221> NAME/KEY: modified_base
<222> LOCATION: (23)..(23)
<223> OTHER INFORMATION: 5-methyl cytosine
<220> FEATURE:
<221> NAME/KEY: modified_base
<222> LOCATION: (25)..(25)
<223> OTHER INFORMATION: 5-methyl cytosine
<220> FEATURE:
<221> NAME/KEY: modified_base
<222> LOCATION: (39)..(39)
<223> OTHER INFORMATION: 5-methyl cytosine
<220> FEATURE:
<221> NAME/KEY: modified_base
<222> LOCATION: (41)..(41)
<223> OTHER INFORMATION: 5-methyl cytosine
<220> FEATURE:
<221> NAME/KEY: modified_base
<222> LOCATION: (43)..(43)
<223> OTHER INFORMATION: 5-methyl cytosine
<220> FEATURE:
<221> NAME/KEY: modified_base
<222> LOCATION: (45)..(45)
<223> OTHER INFORMATION: 5-methyl cytosine
<220> FEATURE:
<221> NAME/KEY: modified_base
<222> LOCATION: (47)..(47)
<223> OTHER INFORMATION: 5-methyl cytosine

<400> SEQUENCE: 104
gaattccgcg cgcgcacgcg cgcgcggagc gtacgctccg cgcgcgcg         48

<210> SEQ ID NO 105
<211> LENGTH: 15
<212> TYPE: DNA
<213> ORGANISM: Artificial Sequence
<220> FEATURE:
<223> OTHER INFORMATION: Synthetic oligonucleotide linked to a
      functional group
<220> FEATURE:
<221> NAME/KEY: modified_base
<222> LOCATION: (3)..(3)
<223> OTHER INFORMATION: 5-methyl cytosine
<220> FEATURE:
<221> NAME/KEY: modified_base
<222> LOCATION: (5)..(5)
<223> OTHER INFORMATION: 5-methyl cytosine
<220> FEATURE:
<221> NAME/KEY: modified_base
<222> LOCATION: (7)..(7)
<223> OTHER INFORMATION: 5-methyl cytosine
<220> FEATURE:
<221> NAME/KEY: modified_base
<222> LOCATION: (9)..(9)
<223> OTHER INFORMATION: 5-methyl cytosine
```

```
<400> SEQUENCE: 105
tgcgcgcgcg gaatt                                                       15

<210> SEQ ID NO 106
<211> LENGTH: 11
<212> TYPE: DNA
<213> ORGANISM: Artificial Sequence
<220> FEATURE:
<223> OTHER INFORMATION: Olignucleotide used to generate products

<400> SEQUENCE: 106
tatctacaga g                                                           11

<210> SEQ ID NO 107
<211> LENGTH: 17
<212> TYPE: DNA
<213> ORGANISM: Artificial Sequence
<220> FEATURE:
<223> OTHER INFORMATION: Oligonucleotide used to generate products

<400> SEQUENCE: 107
tatctacaga gtagtct                                                     17

<210> SEQ ID NO 108
<211> LENGTH: 23
<212> TYPE: DNA
<213> ORGANISM: Artificial Sequence
<220> FEATURE:
<223> OTHER INFORMATION: Oligonucleotide used to generate products

<400> SEQUENCE: 108
tatctacaga gtagtctaat gac                                              23

<210> SEQ ID NO 109
<211> LENGTH: 14
<212> TYPE: DNA
<213> ORGANISM: Artificial Sequence
<220> FEATURE:
<223> OTHER INFORMATION: Oligonucleotide used to generate products

<400> SEQUENCE: 109
cagcctctgt agat                                                        14

<210> SEQ ID NO 110
<211> LENGTH: 16
<212> TYPE: DNA
<213> ORGANISM: Artificial Sequence
<220> FEATURE:
<223> OTHER INFORMATION: Oligonucleotide used to generate products

<400> SEQUENCE: 110
ctcagcctct gtagat                                                      16

<210> SEQ ID NO 111
<211> LENGTH: 18
<212> TYPE: DNA
<213> ORGANISM: Artificial Sequence
<220> FEATURE:
<223> OTHER INFORMATION: Oligonucleotide used to generate products

<400> SEQUENCE: 111
ggctcagcct ctgtagat                                                    18

<210> SEQ ID NO 112
<211> LENGTH: 42
<212> TYPE: DNA
```

-continued

<213> ORGANISM: Artificial Sequence
<220> FEATURE:
<223> OTHER INFORMATION: GSH-Template (1)

<400> SEQUENCE: 112
gcctctgcga ccgttcggaa gcttcgcgag ttgcccagcg cg            42

<210> SEQ ID NO 113
<211> LENGTH: 42
<212> TYPE: DNA
<213> ORGANISM: Artificial Sequence
<220> FEATURE:
<223> OTHER INFORMATION: MLF-template (2a)

<400> SEQUENCE: 113
gcctctgcga ccgttcggga attccgcgag ttgcccagcg cg            42

<210> SEQ ID NO 114
<211> LENGTH: 18
<212> TYPE: DNA
<213> ORGANISM: Artificial Sequence
<220> FEATURE:
<223> OTHER INFORMATION: Primer 1

<400> SEQUENCE: 114
gcctctgcga ccgttcgg                                       18

<210> SEQ ID NO 115
<211> LENGTH: 18
<212> TYPE: DNA
<213> ORGANISM: Artificial Sequence
<220> FEATURE:
<223> OTHER INFORMATION: Primer 2

<400> SEQUENCE: 115
cgcgctgggc aactcgcg                                       18

<210> SEQ ID NO 116
<211> LENGTH: 36
<212> TYPE: DNA
<213> ORGANISM: Artificial Sequence
<220> FEATURE:
<223> OTHER INFORMATION: Phenyl sulfonamide-template (3)

<400> SEQUENCE: 116
cgatgctagc gaaggaagct tccactgcac gtctgc                   36

<210> SEQ ID NO 117
<211> LENGTH: 36
<212> TYPE: DNA
<213> ORGANISM: Artificial Sequence
<220> FEATURE:
<223> OTHER INFORMATION: MLF-template

<400> SEQUENCE: 117
cgatgctagc gaagggaatt cccactgcac gtctgc                   36

<210> SEQ ID NO 118
<211> LENGTH: 36
<212> TYPE: DNA
<213> ORGANISM: Artificial Sequence
<220> FEATURE:
<223> OTHER INFORMATION: Biotin-template (4b)

<400> SEQUENCE: 118
cgatgctagc gaagggaatt cccactgcac gtctgc                   36

<210> SEQ ID NO 119
<211> LENGTH: 15
<212> TYPE: DNA
<213> ORGANISM: Artificial Sequence
<220> FEATURE:
<223> OTHER INFORMATION: Primer 1

<400> SEQUENCE: 119
cgatgctagc gaagg                                                    15

<210> SEQ ID NO 120
<211> LENGTH: 15
<212> TYPE: DNA
<213> ORGANISM: Artificial Sequence
<220> FEATURE:
<223> OTHER INFORMATION: Primer 2

<400> SEQUENCE: 120
gcagacgtgc agtgg                                                    15

<210> SEQ ID NO 121
<211> LENGTH: 36
<212> TYPE: DNA
<213> ORGANISM: Artificial Sequence
<220> FEATURE:
<223> OTHER INFORMATION: Chymostatin-template (5)

<400> SEQUENCE: 121
gcagtcgact cgaccggatc cggctacgac gtgcac                             36

<210> SEQ ID NO 122
<211> LENGTH: 36
<212> TYPE: DNA
<213> ORGANISM: Artificial Sequence
<220> FEATURE:
<223> OTHER INFORMATION: Antipain-template (6)

<400> SEQUENCE: 122
gcagtcgact cgacccagct gggctacgac gtgcac                             36

<210> SEQ ID NO 123
<211> LENGTH: 36
<212> TYPE: DNA
<213> ORGANISM: Artificial Sequence
<220> FEATURE:
<223> OTHER INFORMATION: Biotin-template (4a)

<400> SEQUENCE: 123
gcagtcgact cgaccaagct tggctacgac gtgcac                             36

<210> SEQ ID NO 124
<211> LENGTH: 15
<212> TYPE: DNA
<213> ORGANISM: Artificial Sequence
<220> FEATURE:
<223> OTHER INFORMATION: Primer 1

<400> SEQUENCE: 124
gcagtcgact cgacc                                                    15

<210> SEQ ID NO 125
<211> LENGTH: 15
<212> TYPE: DNA
<213> ORGANISM: Artificial Sequence
<220> FEATURE:
<223> OTHER INFORMATION: Primer 2

```
<400> SEQUENCE: 125
gtgcacgtcg tagcc                                                     15
```

EVOLVING NEW MOLECULAR FUNCTION

PRIORITY INFORMATION

This application is a continuation of U.S. patent application Ser. No. 10/950,367, filed Sep. 24, 2004, which is a continuation of U.S. patent application Ser. No. 10/643,752, filed Aug. 19, 2003, which claims the benefit of (i) U.S. Provisional Patent Application No. 60/404,395, filed Aug. 19, 2002, (ii) U.S. Provisional Patent Application No. 60/419,667, filed Oct. 18, 2002, (iii) U.S. Provisional Patent Application No. 60/432,812, filed Dec. 11, 2002, (iv) U.S. Provisional Patent Application No. 60/444,770, filed Feb. 4, 2003, (v) U.S. Provisional Patent Application No. 60/457,789, filed Mar. 26, 2003, (vi) U.S. Provisional Patent Application No. 60/469,866, filed May 12, 2003, and (vii) U.S. Provisional Patent Application No. 60/479,494, filed Jun. 18, 2003, the disclosures of each of which are incorporated by reference herein. The application is also related to U.S. Provisional Patent Application Nos. 60/277,081 (filed Mar. 19, 2001), 60/277,094 (filed Mar. 19, 2001), 60/306,691 (filed Jul. 20, 2001), and 60/353,565 (filed Feb. 1, 2002), as well as to U.S. patent application Ser. Nos. 10/101,030 (filed Mar. 19, 2002) and 10/102,056 (filed Mar. 19, 2002), and to International Patent Application serial number US02/08546 (filed Mar. 19, 2002).

GOVERNMENT FUNDING

This invention was made with Government support under the Office for Naval Research under Contract No. N00014-00-1-0596 and Grant No. 00014-03-1-0749. The United States Government has certain rights in the invention.

BACKGROUND OF THE INVENTION

The classic "chemical approach" to generating molecules with new functions has been used extensively over the last century in applications ranging from drug discovery to synthetic methodology to materials science. In this approach, researchers synthesize or isolate candidate molecules, assay these candidates for desired properties, determine the structures of active compounds if unknown, formulate structure-activity relationships based on available assay and structural data, and then synthesize a new generation of molecules designed to possess improved properties. While combinatorial chemistry methods (see, for example, Eliseev et al. (1999) COMBINATORIAL CHEMISTRY IN BIOLOGY 243: 159-172; Kuntz et al. (1999) CURRENT OPINION IN CHEMICAL BIOLOGY 3: 313-319; Liu et al. (1999) ANGEW. CHEM. INTL. ED. ENG. 38: 36) have increased the throughput of this approach, its fundamental limitations remain unchanged. Several factors limit the effectiveness of the chemical approach to generating molecular function. First, the ability to accurately predict the structural changes that will lead to new function is often inadequate due to subtle conformational rearrangements of molecules, unforeseen solvent interactions, or unknown stereochemical requirements of binding or reaction events. The resulting complexity of structure-activity relationships frequently limits the success of rational ligand or catalyst design, including those efforts conducted in a high-throughput manner. Second, the need to assay or screen, rather than select, each member of a collection of candidates limits the number of molecules that can be searched in each experiment. Finally, the lack of a way to amplify synthetic molecules places requirements on the minimum amount of material that must be produced for characterization, screening, and structure elucidation. As a result, it can be difficult to generate libraries of more than roughly $10^6$ different synthetic compounds.

In contrast, Nature generates proteins with new functions using a fundamentally different method that overcomes many of these limitations. In this approach, a protein with desired properties induces the survival and amplification of the information encoding that protein. This information is diversified through spontaneous mutation and DNA recombination, and then translated into a new generation of candidate proteins using the ribosome. Unlike the linear chemical approach described above, the steps used by Nature form a cycle of molecular evolution. Proteins emerging from this process have been directly selected, rather than simply screened, for desired activities. Because the biomolecules that encode evolving proteins (e.g., DNA) can be amplified, a single protein molecule with desired activity can in theory lead to the survival and propagation of the DNA encoding its structure.

Acknowledging the power and efficiency of Nature's approach, researchers have used molecular evolution to generate many proteins and nucleic acids with novel binding or catalytic properties (see, for example, Minshull et al. (1999) CURR. OPIN. CHEM. BIOL. 3: 284-90; Schmidt-Dannert et al. (1999) TRENDS BIOTECHNOL. 17: 135-6; Wilson et al. (1999) ANNU. REV. BIOCHEM. 68: 611-47). Proteins and nucleic acids evolved by researchers have demonstrated value as research tools, diagnostics, industrial reagents, and therapeutics, and have greatly expanded the understanding of the molecular interactions that endow proteins and nucleic acids with binding or catalytic properties (see, Famulok et al. (1998) CURR. OPIN. CHEM. BIOL. 2: 320-7).

Despite Nature's efficient approach to generating function, Nature's molecular evolution is limited to two types of "natural" molecules (proteins and nucleic acids) because thus far the information in nucleic acids can only be translated into proteins or into other nucleic acids. Unfortunately, many synthetic molecules of interest do not in general have nucleic acid or protein backbones. An ideal approach to generating functional molecules merges the most powerful aspects of molecular evolution with the flexibility of synthetic chemistry. Clearly, enabling the evolution of non-natural synthetic small molecules and polymers, much as Nature evolves biomolecules, would lead to much more effective methods of discovering new synthetic ligands, receptors, and catalysts difficult or impossible to generate using rational design.

Although these concepts have been brought together to permit nucleic acid-templated synthesis of small molecules (see, for example, Gartner & Liu (2001) J. AM. CHEM. SOC. 123: 6961-6963) there is still an ongoing need for improvements in these core technologies to permit the more efficient synthesis, selection, amplification, and evolution of molecules of interest.

SUMMARY OF THE INVENTION

The invention provides a variety of methods and compositions that expand the scope of template-directed synthesis, selection, amplification and evolution of molecules of interest. During nucleic acid-templated synthesis, the information encoded within a nucleic acid template is used to bring two or more reactants together into reactive proximity. These methods permit the creation of, for example, small molecule and polymer libraries that have not been possible to create to date using conventional combinational chemistries.

In one aspect, the invention provides a method of performing nucleic acid-templated synthesis using a template having an "omega" or "Ω" type architecture. This type of template permits distance-dependent nucleic acid-templated reactions to be encoded by bases far removed from the associated reactive unit. The method involves providing (i) a template comprising a first reactive unit associated with a first oligonucleotide comprising a codon and (ii) a transfer unit comprising a second reactive unit associated with a second oligonucleotide comprising an anti-codon that is capable of annealing to the codon. The codon and/or the anti-codon include first and second regions spaced apart from one another. The oligonucleotides then are annealed together to bring the reactive units into reactive proximity. When the oligonucleotides anneal to one another, the codon (or anti-codon) with the spaced-apart regions produce a loop of oligonucleotides not annealed to the corresponding anti-codon (or codon). A covalent bond-forming reaction then is induced between the reactive units to produce the reaction product.

In one embodiment, at least one of the reactive units are attached adjacent a terminal region of its corresponding oligonucleotide. In another embodiment, the codon or anti-codon is disposed more than one base away (for example, 10, 20, 30 bases or more) from its corresponding reactive unit. The first spaced apart region typically is disposed directly adjacent a terminus of its corresponding oligonucleotide. The first spaced apart region preferably includes, for example, three, four, or five nucleotides, although other embodiments (e.g., more than five nucleotides) are also envisioned. The second region may be disposed, for example, at least twenty or at least thirty bases away from its corresponding reactive unit. More particularly, the end of the second region closest to the reactive unit may be disposed, for example, at least ten, twenty, thirty or more bases from the end of the oligonucleotide attached to its reactive unit. The template may include additional (e.g., 2, 3, 4, or more than 4) codons, in which case a corresponding number of transfer units can be annealed to the template, optionally permitting multi-step or alternative syntheses.

In another aspect, the invention provides a method of performing a nucleic acid-templated synthesis using a template having a "T" type architecture. The T architecture permits two nucleic acid-templated reactions to take place on a single template in a single step. The method involves providing (i) a template comprising a first reactive unit (e.g., a scaffold molecule) associated with a first oligonucleotide having a codon, and (ii) a transfer unit comprising a second reactive unit associated with a second oligonucleotide having an anti-codon capable of annealing to the codon. The first reactive unit is attached, preferably covalently, to an attachment site intermediate the proximal and distal ends of the first oligonucleotide of the template. During synthesis, the oligonucleotides of the template and transfer unit are annealed to one another to bring the reactive units into reactive proximity, and a covalent bond-forming reaction between the reactive units is induced.

In one embodiment of the T type architecture, the template also includes a second, different codon capable of annealing to a second, different anti-codon sequence of a second, different transfer unit. In this embodiment, the first codon is located proximal to the attachment site and the second codon, if present, is located distal to the attachment site. If a second transfer unit comprising a third reactive unit associated with a third oligonucleotide having a second, different anti-codon sequence capable of annealing to the second codon is provided, the second transfer unit may bind to the template at the second codon position. Accordingly, when the first and second transfer units are combined with the template, the first anti-codon of the first transfer unit anneals to the first codon of the template and the second anti-codon of the second transfer unit anneals to the second codon of the template. This system permits two reactions to occur simultaneously or sequentially on a single template in a single step.

In another aspect, the invention provides a series of methods for increasing reaction selectivity between reactants in a templated synthesis. In one approach, the method comprises providing a template and at least two transfer units. The template comprises a first reactive unit associated with a first oligonucleotide comprising a predetermined codon sequence. The first transfer unit comprises a second reactive unit associated with a second oligonucleotide comprising an anti-codon sequence capable of annealing to the codon sequence. The second transfer unit comprises a third reactive unit, different from the second reactive unit. The third reactive unit, however, is associated with a third oligonucleotide that lacks an anti-codon sequence capable of annealing to the codon sequence. The template and transfer units are mixed under conditions to permit annealing of the second oligonucleotide to the first oligonucleotide, thereby to enhance covalent bond formation between the second and first reactive units relative to covalent bond formation between the third and first reactive units.

This method may be particularly helpful when the second and third reactive units are each capable of reacting independently with the first reactive unit. Furthermore, the method may also be helpful when the second and third reactive units are capable of reacting with one another, for example, to modify or inactivate one another. Accordingly, this type of method permits a series of otherwise incompatible reactions to occur in the same solution, for example, where a reaction between the second and third reactive units is incompatible with a reaction between the second reactive unit and the first reactive unit. The method may enhance covalent bond formation between the first and second reactive units by at least 2-fold, at least 5-fold, at least 10-fold, or at least 50-fold relative to covalent bond formation between the first and third reactive units. Collectively, these advantages permit a one-pot ordered multi-step synthesis, in which a sequence of reactions is programmed by the sequence of a template oligonucleotide. Thus, a sequence of at least 2, 3, 4, 5, 6, or more reactions can take place in an ordered manner in a single solution, even when the reactants would interfere with each other using conventional, non-templated chemistries.

In one embodiment, the template, the first transfer unit, and/or the second transfer unit are associated with a capturable moiety, for example, biotin, avidin, or streptavidin. If a capturable moiety is present, the method may include capturing the capturable moiety as a way to enrich a reaction product from a reaction mixture.

In another approach, the method comprises providing (i) a template comprising a first oligonucleotide having first and second codon sequences (ii) a first transfer unit, (iii) a second transfer unit, and (iv) a third transfer unit. The first transfer unit comprises a first reactive unit associated with a second oligonucleotide comprising a first anti-codon sequence capable of annealing to the first codon sequence. The second transfer unit comprises a second reactive unit associated with a third oligonucleotide comprising a second anti-codon sequence capable of annealing to the second codon sequence. The third transfer unit comprises a third reactive unit associated with a fourth oligonucleotide sequence that lacks an anti-codon sequence capable of annealing to the first or second codon sequences. The template, first transfer unit, second transfer unit, and third transfer unit then are mixed under conditions to permit (i) annealing of the first anti-codon sequence to the first codon sequence and (ii) annealing of the second anti-codon sequence to the second codon sequence thereby to enhance covalent bond formation between the first and second reactive units relative to covalent bond formation between the third reactive unit and the first reactive unit and/or between the third reactive unit the second reactive unit. This type of method may be particularly useful for producing non-natural polymers by nucleic acid-templated synthesis.

In one embodiment, the template is associated with a capturable moiety, for example, biotin, avidin, or streptavidin. The capturable moiety may also be a reaction product resulting from a reaction between the first and second reactive units when the first and second reactive units are annealed to a template. If a capturable moiety is present, the method may include capturing the capturable moiety as a way to enrich a reaction production from the reaction mixture.

This type of method is also helpful when the third reactive unit is capable of reacting with the first and/or second reactive units. In other words, the reaction between the first and third reactive units and/or between the second and third reactive units may be incompatible with the reaction between the first and second reactive units. The method may enhance covalent bond formation between the first and second reactive units by at least 2-fold, at least 5-fold, at least 10-fold, or at least 50-fold relative to covalent bond formation between the first and third reactive units.

In another aspect, the invention provides a series of methods for performing stereoselective nucleic acid-templated synthesis. The stereoselectivity of the synthesis may result from the choice of a particular template, transfer unit, reactive unit, hybridized template and transfer unit, stereoselective catalyst, or any combination of the above. The resulting product may be at least 60%, at least 70%, at least 80%, at least 90%, at least 95%, at least 98%, or at least 99% stereochemically pure.

Generally, the method involves providing (i) a template comprising a first oligonucleotide that optionally is associated with a reactive unit and (ii) one or more transfer units, each comprising a second oligonucleotide associated with a reactive unit. Annealing of the first and second oligonucleotides brings at least two reactive units into reactive proximity and to react to produce a reaction product where the reaction product contains a chiral center and is of at least 60%, more preferably at least 80%, and more preferably at least 95% stereochemically pure at the chiral center. It is contemplated that this method can be accomplished when one reactive unit is associated with the template and the other reactive unit is associated with the transfer unit. Also, it is contemplated that this method can be accomplished when the template does not provide a reactive unit and two transfer units when they anneal to the template provide the two reactive units that come into reactive proximity to produce the reaction product.

In one approach, the method involves providing at least two templates and at least one transfer unit. One template includes a first oligonucleotide associated with a first reactive unit comprising a first stereochemical configuration, and the other template includes another first oligonucleotide associated with another first reactive unit having a second, different stereochemical configuration. The transfer unit comprises a second reactive unit associated with a second oligonucleotide including a sequence complementary to a sequence of the first oligonucleotide of the template. The first and second oligonucleotides then are annealed under conditions to permit the second reactive unit of the transfer unit to react preferentially with either the first reactive unit of the first stereochemical configuration or the first reactive unit of the second stereochemical configuration to produce a reaction product.

The resulting reaction product may have a particular stereochemical configuration. In one embodiment, a stereochemical configuration or macromolecular conformation of the first oligonucleotide of the template determines which one of the first reactive units reacts with the second reactive unit.

In a second approach, the method involves providing at least one template and at least two transfer units. The template includes a first oligonucleotide associated with a first reactive unit. One transfer unit comprises a second oligonucleotide associated with a second reactive unit having a first stereochemical configuration, and the other transfer unit comprises another second oligonucleotide associated with a second reactive unit having a second, different stereochemical configuration. A sequence of the second oligonucleotides is complementary to a sequence of the first oligonucleotide. The first and second oligonucleotides then are annealed under conditions to permit the first reactive unit of the template to react preferentially with either the second reactive unit having the first stereochemical configuration or with the second reactive unit having the second stereochemical configuration to produce a reaction product.

The resulting reaction product may have a particular stereochemical configuration. In one embodiment, a stereochemical configuration or macromolecular conformation of the second oligonucleotide determines which of the second reactive units reacts with the first reactive unit.

In a third approach, the method involves providing at least one template and at least two transfer units, wherein one or optionally both of the transfer units comprise a pair of reactive units with one reactive unit of the pair having a first stereochemical configuration and the other reactive unit of the pair having a second, different stereochemical configuration. The template comprises a first oligonucleotide comprising a first codon sequence and a second codon sequence. One transfer unit of a first pair of transfer units includes a second oligonucleotide with a first anti-codon sequence associated with a first reactive unit having a first stereochemical configuration. The other transfer unit of the first pair of transfer units includes another second oligonucleotide associated with a second stereochemical configuration of the first reactive unit. The second transfer unit includes a third oligonucleotide with a second anti-codon sequence associated with a second reactive unit. The template, the first pair of transfer units, and the second transfer unit are annealed to permit a member of the first pair of transfer units to react preferentially with the second transfer unit to produce a reaction product. The resulting reaction product may have a particular stereochemical configuration.

In one embodiment, a stereochemical configuration or macromolecular conformation of the second oligonucleotide determines which member of the first pair of transfer units reacts preferentially to produce the reaction product.

In one embodiment, the method involves providing a template and at least two pairs of transfer units. The template comprises a first oligonucleotide comprising first and second codon sequences. One transfer unit of the first pair comprises a second oligonucleotide with a first anti-codon sequence associated with a first reactive unit having a first stereochemical configuration. The other transfer unit of the first pair comprises the second oligonucleotide with the first anti-codon sequence associated with a first reactive unit having a second, different stereochemical configuration. One transfer unit of the second pair of transfer units comprises a third oligonucleotide having a second, different anti-codon sequence associated with a second reactive unit having a first stereochemical configuration. The other transfer unit of the second pair comprises the third oligonucleotide with the second anti-codon sequence associated with the second reactive unit having a second, different stereochemical configuration. The template, the first pair of transfer units and the second pair of transfer units are annealed to permit a member of the first pair of transfer units to react preferentially with a member of the second pair of transfer units to produce a reaction product.

In one embodiment, a stereochemical configuration or macromolecular conformation of the second oligonucleotide determines which member of the first pair of transfer units reacts preferentially to produce the reaction product. In addition, a stereochemical configuration or macromolecular conformation of the third oligonucleotide determines which member of the second pair of transfer units reacts preferentially to produce the reaction product.

In another aspect, the invention provides a method for enriching a product of a templated synthesis reaction. The method comprises providing a first library of molecules comprising a plurality of reaction products associated with a corresponding plurality of oligonucleotides, wherein each oligonucleotide comprises a nucleotide sequence indicative of the associated reaction product. A portion of the reaction products in the first library are capable of binding to a preselected moiety. The first library then is exposed to the binding moiety under conditions to permit reaction product capable of binding the binding moiety to do so. Unbound reaction products are removed, and bound reaction product is eluted from the binding moiety to produce a second library of molecules enriched at least 10-fold, more preferably at least 50-fold, relative to the first library, for reaction products that bind the binding moiety.

In one embodiment, the binding moiety, for example, a target biomolecule, for example, a protein, is immobilized on a solid support. In another embodiment, the second library is enriched at least 100-fold or at least 1,000-fold for reaction products that bind to the binding moiety. Furthermore, it is contemplated that the steps of exposing the library to the binding moiety, removing unbound reaction products, and eluting bound reaction products can be repeated (e.g., repeated one, two, three or more times). Repetition of these steps preferably yields a second library enriched at least 1,000-fold, more preferably, at least 10,000-fold, or, more preferably, at least 100,000-fold, for reaction products that bind to the binding moiety.

In one embodiment, the oligonucleotide attached to the selected library member includes a first sequence that identifies a first reactive unit that produced the reaction product bindable by the preselected binding moiety. Preferably, the oligonucleotide also includes a second sequence that identifies a second reactive unit that produced the reaction product bindable by the preselected binding moiety. By sequencing the oligonucleotide attached to the selected library member it is possible to determine what reactants reacted with one another to produce the reaction product. Accordingly, using this approach it is possible to deduce the structure of the selected library member from the reaction history.

The method may further comprise the step of amplifying the oligonucleotide associated with the enriched reaction product and, preferably, determining the sequence of the amplified oligonucleotide. Furthermore, the reaction product can be further characterized by using information encoded within the sequence of the oligonucleotide. For example, the sequence of the oligonucleotide may be determined and then from the sequence it is possible to determine what reactive units reacted to produce the reaction product. Using a similar approach, it is possible to identify the existence of new chemical reactions that produced the reaction product.

In another aspect, the invention provides a variety of methods for identifying the existence of new chemical reactions. One approach involves, providing a library of molecules comprising a plurality of reaction products associated with a corresponding plurality of oligonucleotides, wherein each oligonucleotide includes a nucleotide sequence indicative of an associated reaction product. A particular reaction product associated with its corresponding oligonucleotide then is selected, and characterized. Following characterization of the reaction product and identification of the reactive units that reacted to create the reaction product, it is possible to identify one or more new chemical reactions necessary to produce the reaction product.

In one embodiment, the method further includes, after selecting the reaction product, amplifying its corresponding oligonucleotide. The amplified oligonucleotide can then be sequenced to identify what reactive units reacted to produce the reaction product. The oligonucleotide may also be amplified for use in preparing more of the selected reaction product. In other embodiments, the oligonucleotide may be mutated, and the resulting mutated oligonucleotide may be used in the creation of a second generation library.

A second approach involves providing (i) a template and (ii) a first transfer unit. The template comprises a first reactive unit associated with a first oligonucleotide comprising a codon. The transfer unit comprises a second reactive unit associated with a second oligonucleotide comprising an anti-codon capable of annealing to the codon. The oligonucleotides are annealed to bring the first and second reactive units into reactive proximity. A covalent bond-forming reaction is induced between the reactive units to produce a reaction product. The reaction product then is characterized, and a new chemical reaction necessary to make the reaction product is identified using information encoded by the template to identify the first and second reactive units that reacted to produce the reaction product. The method may also include the step of selecting the reaction product prior to its characterization.

In a third approach, the invention involves providing at least (i) a template, (ii) a first transfer unit and (iii) a second transfer unit. The first transfer unit comprises a first reactive unit associated with a first oligonucleotide. The second transfer unit comprises a second reactive unit associated with a second oligonucleotide. The template includes sequences capable of annealing to the first and second oligonucleotides. During the method, the oligonucleotides are annealed to the template to bring the reactive units into reactive proximity and a covalent bond-forming reaction is induced between the reactive units to produce a reaction product. The reaction product then is characterized, for example, by using information encoded by the template to identify the first and second reactive units that reacted with one another to produce the reaction product. Based on the characterization, it is then possible to identify one or more new chemical reactions that were necessary to make the reaction product. The method may also include the step of selecting the reaction product prior to its characterization.

Although the methods of the invention are useful with small numbers of templates and transfer units, use of larger numbers of templates (e.g., 10, 50, 100, 1000, or more) and of transfer units for each codon (e.g., 10, 20, 30, 50, or more) permits the synthesis of large libraries of molecules that can be screened simultaneously using the sensitivity afforded by amplification.

DEFINITIONS

The term, "associated with" as used herein describes the interaction between or among two or more groups, moieties, compounds, monomers, etc. When two or more entities are "associated with" one another as described herein, they are linked by a direct or indirect covalent or non-covalent interaction. Preferably, the association is covalent. The covalent association may be, for example, but without limitation, through an amide, ester, carbon-carbon, disulfide, carbamate, ether, thioether, urea, amine, or carbonate linkage. The covalent association may also include a linker moiety, for example, a photocleavable linker. Desirable non-covalent interactions include hydrogen bonding, van der Waals interactions, dipole-dipole interactions, pi stacking interactions, hydrophobic interactions, magnetic interactions, electrostatic interactions, etc. Also, two or more entities or agents may be "associated with" one another by being present together in the same composition.

The term, "biological macromolecule" as used herein refers to a polynucleotide (e.g., RNA, DNA, RNA/DNA hybrid), protein, peptide, lipid, or polysaccharide. The biological macromolecule may be naturally occurring or non-naturally occurring. In a preferred embodiment, a biological macromolecule has a molecular weight greater than about 5,000 Daltons.

The terms, "polynucleotide," "nucleic acid", or "oligonucleotide" as used herein refer to a polymer of nucleotides. The polymer may include, without limitation, natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages). Nucleic acids and oligonucleotides may also include other polymers of bases having a modified backbone, such as a locked nucleic acid (LNA), a peptide nucleic acid (PNA), a threose nucleic acid (TNA) and any other polymers capable of serving as a template for an amplification reaction using an amplification technique, for example, a polymerase chain reaction, a ligase chain reaction, or non-enzymatic template-directed replication.

The term, "small molecule" as used herein, refers to an organic compound either synthesized in the laboratory or found in nature having a molecular weight less than 10,000 grams per mole, optionally less than 5,000 grams per mole, and optionally less than 2,000 grams per mole.

The terms "small molecule scaffold" or "molecular scaffold" as used herein, refer to a chemical compound having at least one site or chemical moiety suitable for functionalization. The small molecule scaffold or molecular scaffold may have two, three, four, five or more sites or chemical moieties suitable for functionalization. These functionalization sites may be protected or masked as would be appreciated by one of skill in this art. The sites may also be found on an underlying ring structure or backbone.

The term, "transfer unit" as used herein, refers to a molecule comprising an oligonucleotide having an anti-codon sequence associated with a reactive unit including, for example, but not limited to, a building block, monomer, monomer unit, molecular scaffold, or other reactant useful in template mediated chemical synthesis.

The term, "template" as used herein, refers to a molecule comprising an oligonucleotide having at least one codon sequence suitable for a template mediated chemical synthesis. The template optionally may comprise (i) a plurality of codon sequences, (ii) an amplification means, for example, a PCR primer binding site or a sequence complementary thereto, (iii) a reactive unit associated therewith, (iv) a combination of (i) and (ii), (v) a combination of (i) and (iii), (vi) a combination of (ii) and (iii), or a combination of (i), (ii) and (iii).

The terms, "codon" and "anti-codon" as used herein, refer to complementary oligonucleotide sequences in the template and in the transfer unit, respectively, that permit the transfer unit to anneal to the template during template mediated chemical synthesis.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions may be conducted simultaneously.

DESCRIPTION OF THE DRAWINGS

FIGS. 17A-17B depict various mismatch reactions analyzed by denaturing PAGE. FIG. 17A depicts results of reactions in which H templates linked to an iodoacetamide group were reacted with thiol reagents containing 0, 1, or 3 mismatches at 25° C. FIG. 17B depicts results of reactions in which the reactions in FIG. 17A were repeated at the indicated temperatures for 16 hours.

FIGS. 23A-23D are schematic representations of exemplary DNA-templated reactions.

FIG. 26A is a schematic representation showing a model for distance-independent nucleic acid-templated synthesis. FIG. 26B depicts the results of denaturing PAGE of a DNA-templated Wittig olefination between complementary aldehyde-linked template 11 and phosphorous ylide reagent 13 from FIG. 23B with either zero bases (lanes 1-3) or ten bases (lanes 4-6) separating annealed reactants.

FIG. 36 is a table showing the melting temperatures of selected template-reagent combinations using the omega (Ω) and end-of-helix (E) architectures.

FIGS. 38A-38C depict two DNA-templated reactions on a single template in one solution mediated by templates having a T architecture.

FIG. 42A corresponds to the reaction shown in FIG. 39A; FIG. 42B corresponds to the reaction shown in FIG. 39B; FIG. 42C corresponds to the reaction shown in FIG. 44A and FIG. 42D corresponds to the reaction shown in FIG. 44B.

FIGS. 43A-43F are a schematic representations showing template and reagent structures that incorporate achiral, flexible linkers.

FIGS. 50A-50E are schematic representations of exemplary nucleic acid-templated deprotections useful in the practice of the invention.

FIGS. 51A-51B are schematic representations of exemplary nucleic acid-templated functional group interconversions useful in the practice of the invention.

FIG. 78A is a schematic representation of an exemplary scheme for the in vitro selection of synthetic polymers containing polymerase-accepted metal-binding nucleotides that catalyze Heck reactions. FIG. 78B is a schematic representation of an exemplary scheme for the in vitro selection of synthetic polymers containing polymerase-accepted metal-binding nucleotides that catalyze hetero Diels-Alder reactions. FIG. 78C is a schematic representation of an exemplary scheme for the in vitro selection of synthetic polymers containing polymerase-accepted metal-binding nucleotides that catalyze aldol reactions.

DESCRIPTION OF CERTAIN EMBODIMENTS OF THE INVENTION

Nucleic-acid templated synthesis as described herein permits the production, selection, amplification and evolution of a broad variety of chemical compounds such as synthetic small molecules and non-natural polymers. In nucleic acid-templated synthesis, the information encoded by a DNA or other nucleic acid sequence is translated into the synthesis of a reaction product. The nucleic acid template typically comprises a plurality of coding regions which anneal to complementary anti-codon sequences associated with reactive units, thereby bringing the reactive units together in a sequence-specific manner to create a reaction product. Since nucleic acid hybridization is sequence-specific, the result of a nucleic acid-templated reaction is the translation of a specific nucleic acid sequence into a corresponding reaction product.

Figures 1, 1A:
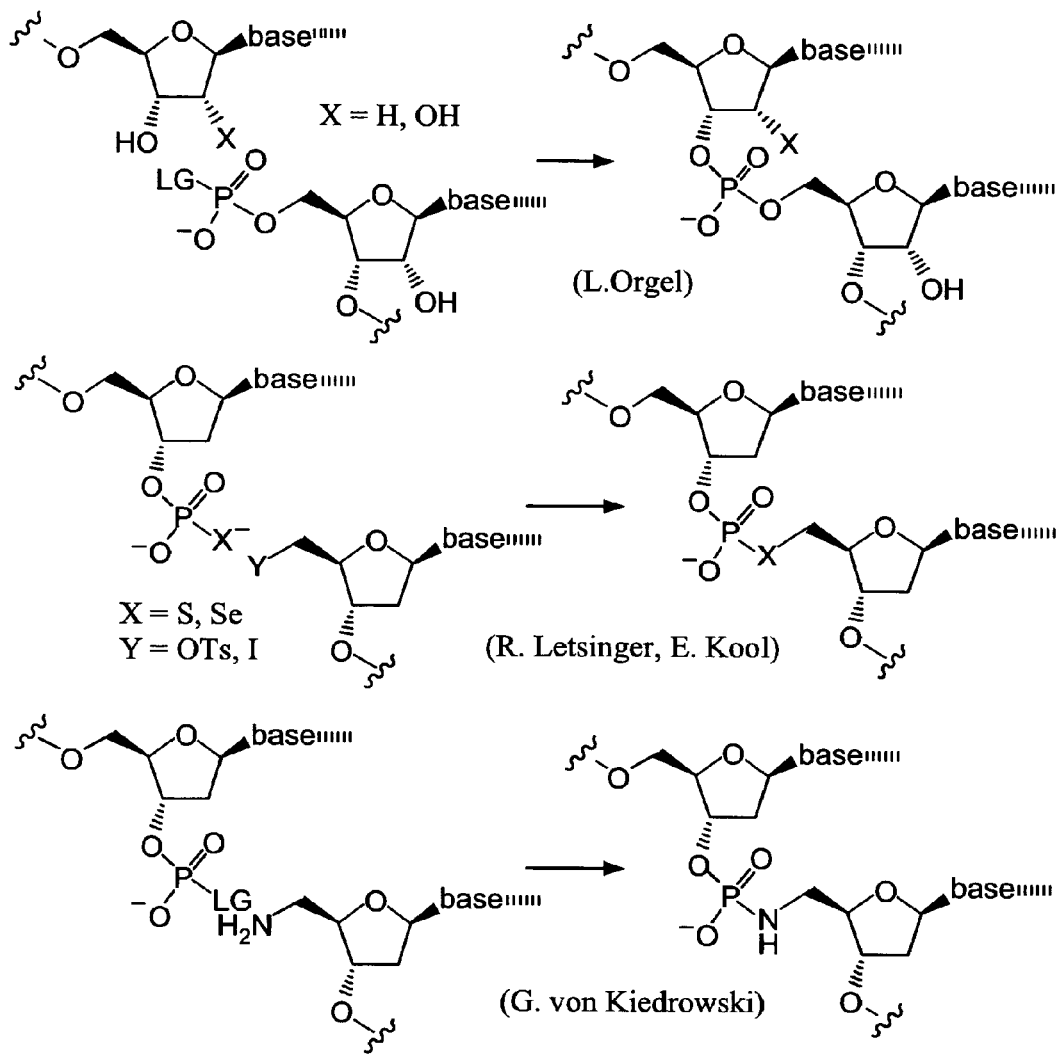
FIG. 1 depicts known sequence-specific oligomerizations of complimentary oligonucleotides catalyzed by single-stranded nucleic acid templates.
Figure 1B:
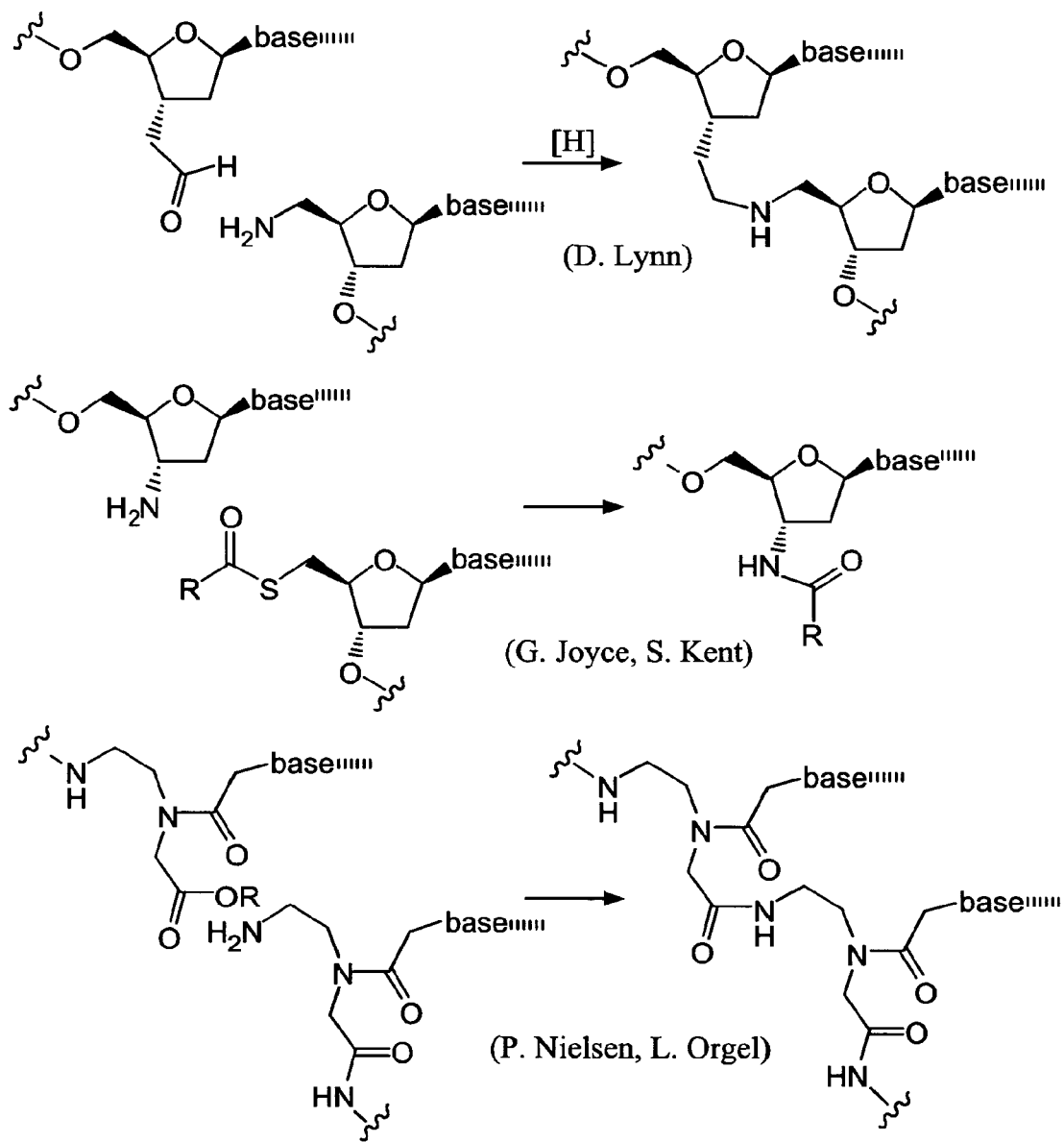

As shown in FIG. 1, the ability of single stranded nucleic acid templates to catalyze the sequence-specific oligomerization of complementary oligonucleotides has been demonstrated (Inoue et al. (1981) J. AM. CHEM. SOC. 103: 7666; Inoue et al. (1984) J. MOL. BIOL. 178: 669-76). This discovery was soon followed by findings that DNA or RNA templates can catalyze the oligomerization of complementary DNA or RNA mono-, di-, tri-, or oligonucleotides (Inoue et al. (1981) J. AM. CHEM. SOC. 103: 7666; Orgel et al. (1995) ACC. CHEM. RES. 28: 109-118; Rembold et al. (1994) J. MOL. EVOL. 38: 205; Rodriguez et al. (1991) J. MOL. EVOL. 33: 477; Chen et al. (1985) J. MOL. BIOL. 181: 271). DNA or RNA templates have since been shown to accelerate the formation of a variety of non-natural nucleic acid analogs, including peptide nucleic acids (Bohler et al. (1995) NATURE 376: 578), phosphorothioate- (Herrlein et al. (1995) J. AM. CHEM. SOC. 117: 10151-10152), phosphoroselenate- (Xu et al. (2000) J. AM. CHEM. SOC. 122: 9040-9041; Xu et al. (2001) NAT. BIOTECHNOL. 19: 148-152) and phosphoramidate- (Luther et al. (1998) NATURE 396: 245-8) containing nucleic acids, non-ribose nucleic acids (Bolli et al. (1997) CHEM. BIOL. 4: 309-20), and DNA analogs in which a phosphate linkage has been replaced with an aminoethyl group (Gat et al. (1998) BIOPOLYMERS 48: 19-28). Nucleic acid templates can also catalyze amine acylation between nucleotide analogs (Bruick et al. (1996) CHEM. BIOL. 3: 49-56).

Although nucleic acid templates have been demonstrated to accelerate the formation of a variety of non-natural nucleic acid analogues, nearly all of these reactions were designed to proceed through transition states closely resembling the natural nucleic acid backbone (FIG. 1), typically affording products that preserve the same six-bond backbone spacing between nucleotide units. The motivation behind this design presumably was the assumption that the rate enhancement provided by nucleic acid templates depends on a precise alignment of reactive groups, and the precision of this alignment is maximized when the reactants and products mimic the structure of the DNA and RNA backbones. Evidence in support of the hypothesis that nucleic acid-templated synthesis can only generate products that resemble the nucleic acid backbone comes from the well-known difficulty of macrocyclization in organic synthesis (Illuminati et al., (1981) ACC. CHEM. RES. 14: 95-102; Woodward et al. (1981) J. AM. CHEM. SOC. 103: 3210-3213). The rate enhancement of intramolecular ring closing reactions compared with their intermolecular counterparts is known to diminish quickly as rotatable bonds are added between reactive groups, such that linking reactants with a flexible 14-carbon linker hardly affords any rate acceleration (Illuminati et al. (1981) supra).

Because synthetic molecules of interest do not in general resemble nucleic acid backbones, the use of nucleic acid-templated synthesis to translate nucleic acid sequences into synthetic molecules is useful broadly only if synthetic molecules other than nucleic acids and nucleic acid analogs can be synthesized in a nucleic acid-templated fashion. Significantly, as shown herein, nucleic acid-templated synthesis is indeed a general phenomenon and can be used for a variety of reactions and conditions to generate a diverse range of compounds, specifically including compounds that are not, and do not resemble, nucleic acids or nucleic acid analogs. More specifically, the present invention extends the ability to amplify and evolve libraries of chemical compounds beyond natural biopolymers. The ability to synthesize chemical compounds of arbitrary structure allows researchers to write their own genetic codes incorporating a wide range of chemical functionality into novel backbone and side-chain structures, which permits the development of novel catalysts, drugs, and polymers, to name a few examples. For example, the direct amplification and evolution of molecules by genetic selection permits the discovery of entirely new families of artificial catalysts which possess activity, bioavailability, solvent, or thermal stability, or other physical properties (such as fluorescence, spin-labeling, or photolability) that may be difficult or impossible to achieve using the limited set of natural protein and nucleic acid building blocks. Similarly, developing methods to amplify and directly evolve synthetic small molecules by iterated cycles of mutation and selection permits the isolation of novel ligands or drugs with properties superior to those isolated by traditional rational design or combinatorial screening drug discovery methods. Additionally, applying this approach to the identification and development of polymers of significance in material science can permit the evolution of new plastics or other polymers.

In general, nucleic acid-templated synthesis as performed herein involves 1) providing one or more nucleic acid templates optionally associated with a reactive unit, and 2) contacting the one or more nucleic acid templates with one or more transfer units including an anti-codon associated with a reactive unit. The anti-codons of the transfer units are designed to hybridize to the nucleic acid template. In certain embodiments of the invention, the transfer unit comprises a single moiety simultaneously incorporating the hybridization capability of the anti-codon unit and the chemical functionality of the reaction unit. After the transfer units have hybridized to the nucleic acid template in a sequence-specific manner, the reactive units present on the transfer units and/or the nucleic acid template come into reactive proximity to react and generate a reaction product. Preferably, the oligonucleotide portion of the transfer unit is removed once the reactive units have reacted to generate the reaction product or an intermediate of the reaction product. Significantly, the sequence of the nucleic acid template can later be determined, to permit decoding of the synthetic history of the attached reaction product and, thereby, its structure. This method may be used to synthesize one molecule at a time or may be used to synthesize thousands to millions of compounds using combinatorial methods.

Figure 2:
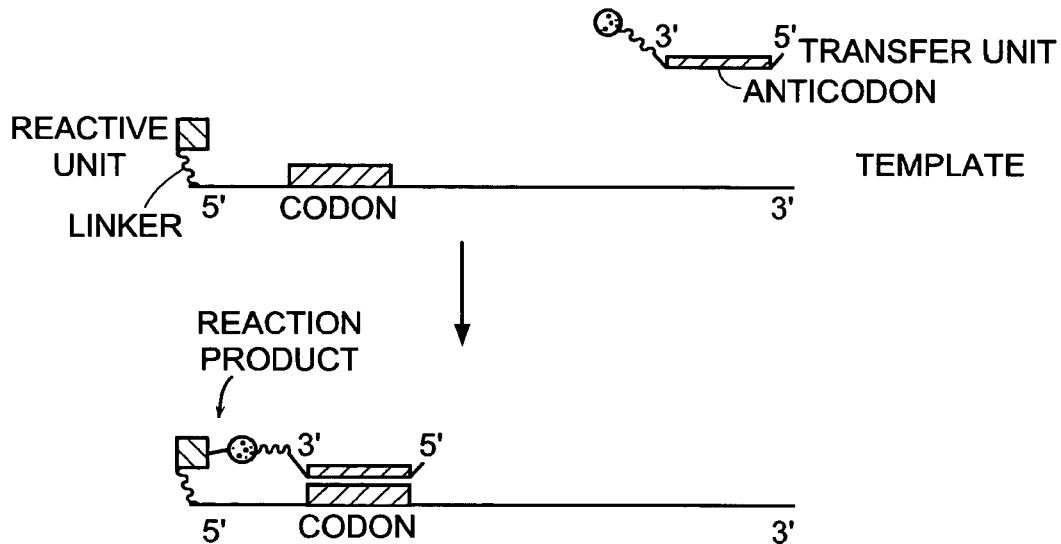
FIG. 2 is a schematic representation of one embodiment of nucleic acid-templated synthesis where a reactive unit is attached to a template at the start of synthesis.

In one embodiment, the template molecule optionally is associated with a reactive unit prior to interaction with any transfer units. Thus, as shown in FIG. 2, the template can be connected by a covalent bond to a reactive unit, either directly or via a linker. Alternatively, the template can be connected by a noncovalent linkage. For example, the template can be biotinylated, generally at a fixed location on the molecule, and can stably interact with a reactive unit associated with an avidin or streptavidin moiety. For ease of synthesis, the reactive unit is preferably placed at or near the 5' end of the template in some embodiments as shown in FIG. 2. In other embodiments, placement of the reactive unit at an internal position of the template or at the 3' end is preferred. The template molecule also includes at least one codon capable of annealing to an anti-codon of a transfer unit. During synthesis, the transfer unit anneals to the codon, bringing its reactive unit into reactive proximity with the reactive unit of the template to produce a reaction product.

Figure 3:
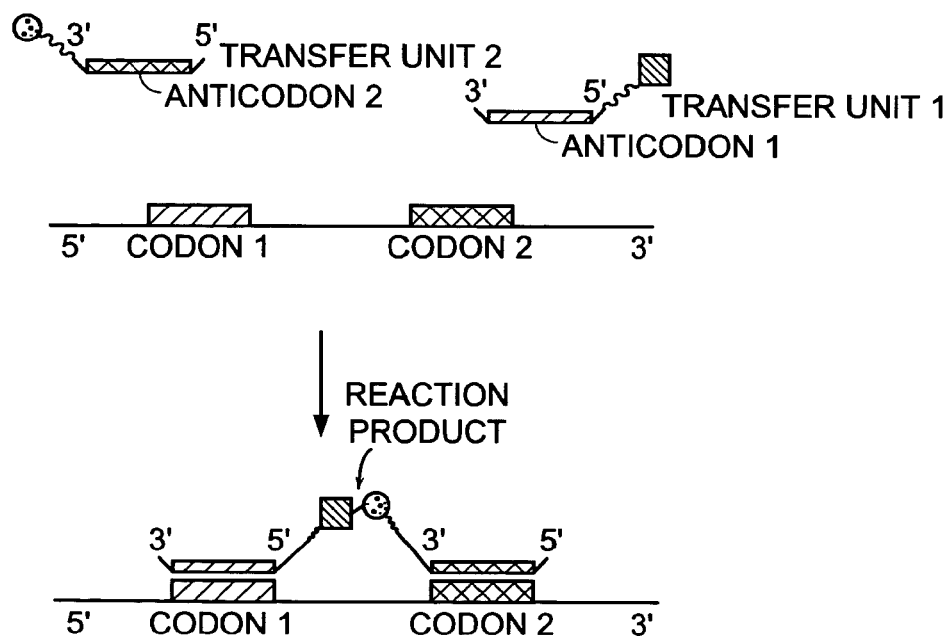
FIG. 3 is a schematic representation of a second embodiment of nucleic acid-templated synthesis where a reactive unit is not attached to the template at the start of synthesis.

In another embodiment, as shown in FIG. 3, the template is not initially associated with a reactive unit, but permits the nucleic acid-templated synthesis of at least two reactive units disposed with two transfer units. The template molecule includes at least two codons, each capable of annealing to a different anti-codon disposed within each transfer unit. The anti-codon in each transfer unit anneals to the corresponding codon in the template to bring the reactive units of each transfer unit into reactive proximity with one another to produce a reaction product.

Figure 4:
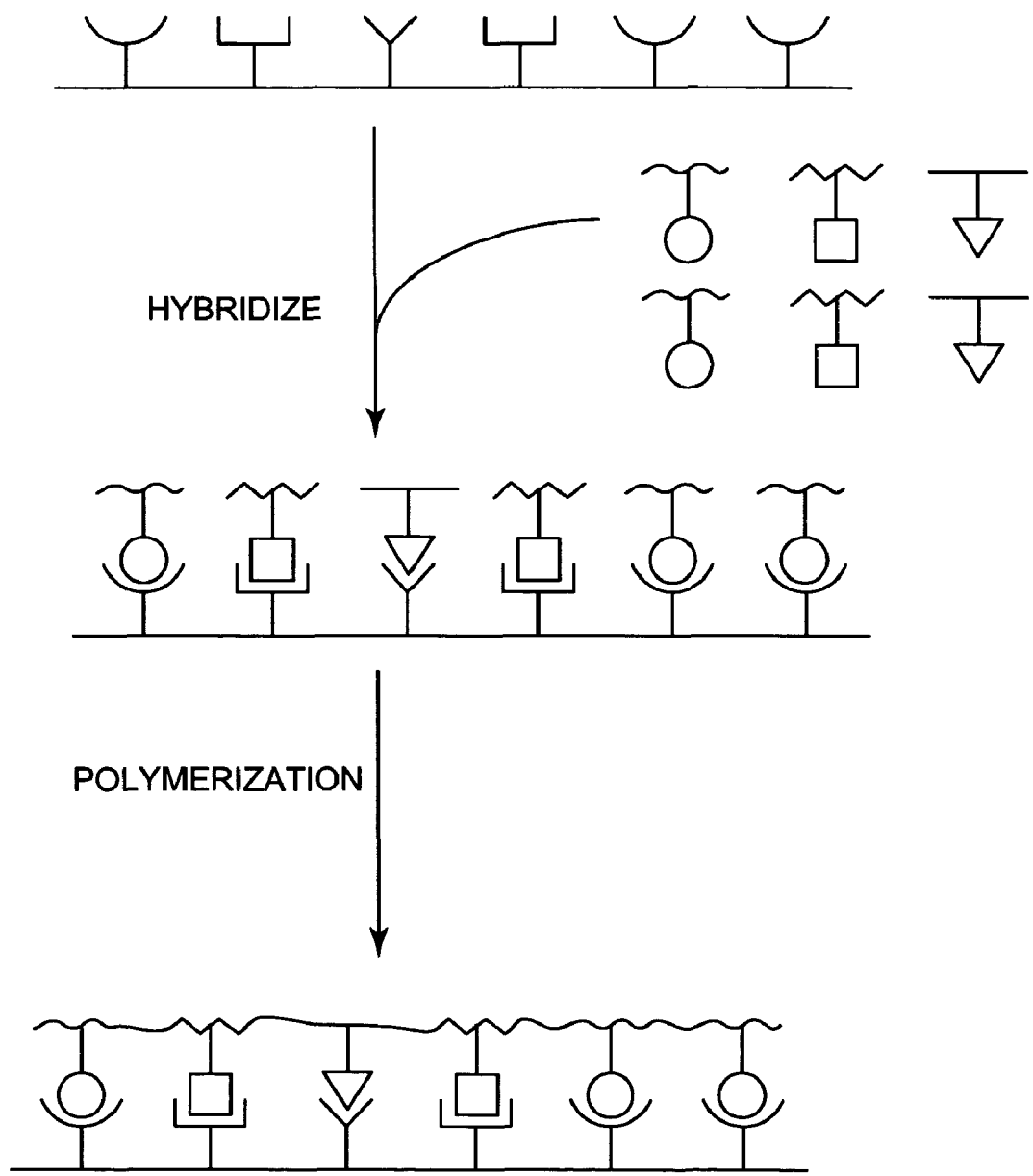
FIG. 4 is a schematic representation of a third embodiment of nucleic acid-templated synthesis suitable for polymer synthesis.

In another embodiment, as shown in FIG. 4, the template can bring together, either simultaneously or sequentially, a plurality of transfer units in a sequence-specific manner. The reactive units on each annealed transfer unit can then be reacted with one another in a polymerization process to produce a polymer. Using this approach it is possible to generate a variety of non-natural polymers. The polymerization may be a step-by step process or may be a simultaneous process whereby all the annealed monomers are reacted in one reaction sequence.

I. Template Considerations

The nucleic acid template can direct a wide variety of chemical reactions without obvious structural requirements by sequence-specifically recruiting reactants linked to complementary oligonucleotides. As discussed, the nucleic acid mediated format permits reactions that may not be possible using conventional synthetic approaches. During synthesis, the template hybridizes or anneals to one or more transfer units to direct the synthesis of a reaction product, which during certain steps of templated synthesis remain associated with the template. A reaction product then is selected or screened based on certain criteria, such as the ability to bind to a preselected target molecule. Once the reaction product has been identified, the associated template can then be sequenced to decode the synthetic history of the reaction product. Furthermore, as will be discussed in more detail below, the template may be evolved to guide the synthesis of another chemical compound or library of chemical compounds.

(i) Template Format

The template may be based on a nucleic acid sequence, for example, a DNA, an RNA, a hybrid of DNA and RNA, or a derivative of DNA and RNA, and may be single- or double-stranded. The design of a particular template may vary depending upon the type of nucleic acid templated synthesis contemplated.

FIG. 5 shows a variety of templates that may be useful in the practice of the invention. FIGS. 5A-C are schematic representations of templates including two codons for interaction with complementary anti-codons of two transfer units. These templates can be used in the type of nucleic acid-templated synthesis where no reactive units are linked to the template at the initiation of synthesis; for example, when two transfer units anneal to the template to bring their reactive units into reactive proximity to create a reaction product. One such example is polymerization. Nevertheless, the templates can be associated with a reactive unit prior to annealing of the transfer units. FIGS. 5D-F are schematic representations of templates that can be used in the type of nucleic acid-templated synthesis where one reactive unit is linked to the template at the initiation of synthesis, for example, when one transfer unit anneals to the template to bring its reactive unit into reactive proximity with the other reactive unit linked to the template to create a reaction product.

Figure 5A:
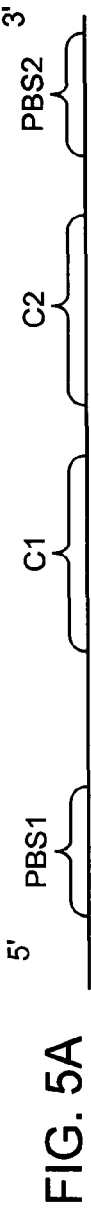
FIGS. 5A-F are schematic representations of various exemplary templates useful in nucleic acid-templated synthesis.

FIG. 5A shows a template comprising in a 5' to 3' direction, a nucleotide sequence encoding a first primer binding site (PBS1) or a sequence complementary thereto, a nucleotide sequence encoding a first codon (C1) that anneals to an anti-codon sequence of a first transfer unit, a nucleotide sequence encoding a second codon (C2) that anneals to an anti-codon sequence of a second, different transfer unit, and a nucleotide sequence encoding a second primer binding site (PBS2) or a sequence complementary thereto. The primer binding sites, although optional, are preferred in some embodiments to facilitate PCR-based amplification of templates. As will be discussed in more detail below, the C1 sequence is selected so as to minimize cross-reactivity with the anti-codon sequence of the second transfer unit, and the C2 sequence is selected so as to minimize cross-reactivity with the anti-codon sequence of the first transfer unit. As shown in FIG. 5A, the C1 and C2 sequences are separated by one or more intervening bases. In other words the C1 and C2 sequences do not directly abut one another. During nucleic acid templated synthesis, both the first and second transfer units are capable of binding to the template at the same time.

Figure 5B:

FIG. 5B shows a template similar to that shown in FIG. 5A, except there are no intervening bases disposed between C1 and C2. In other words, the C1 and C2 sequences directly abut one another. As with the template of FIG. 5A, during nucleic acid templated synthesis, both the first and second transfer units are capable to binding to the template at the same time.

Figure 5C:

FIG. 5C shows a template similar to those shown in FIGS. 5A and 5B, except that the sequence of C1 overlaps the sequence of C2. Unlike the templates of FIGS. 5A and 5B, during nucleic acid templated synthesis, the first and second transfer units cannot both bind to the template at the same time. Thus, unless the template is associated with a reactive unit prior to the initiation of synthesis, a third codon should normally be present, so that two reactive units can anneal simultaneously to the template to permit the reaction to proceed. This type of template can require a step-by-step approach to the synthesis of the reaction product. For example, the transfer units with anti-codons to C1 are added first, allowed to hybridize and react, and then removed before the transfer units with anti-codons to C2 are added.

Figure 5D:
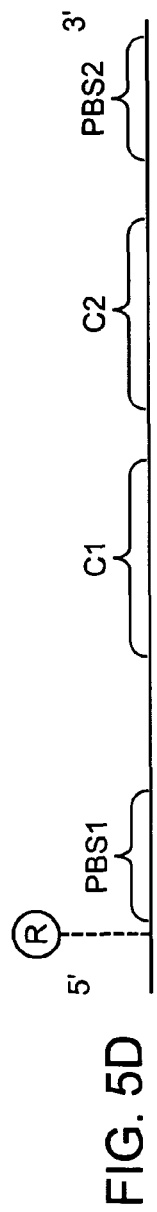
Figure 5E:
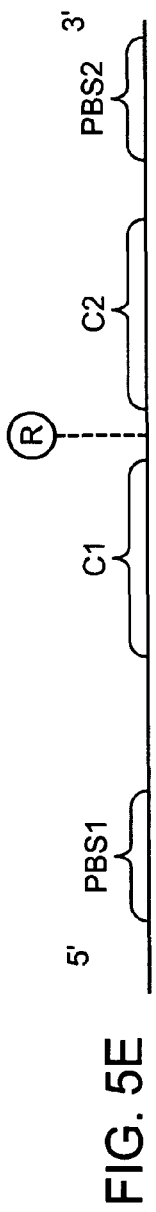
Figure 5F:
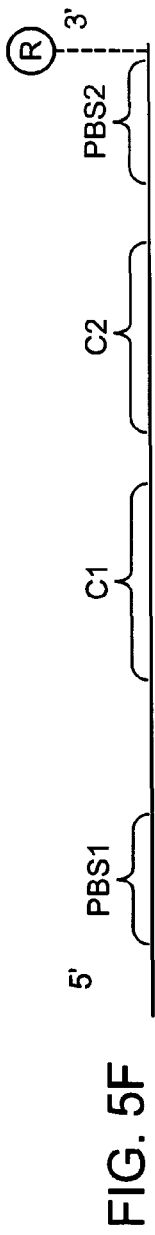

FIGS. 5D-5F show templates similar to the template shown in FIG. 5A, except that the template also includes a reactive unit (R) associated with, for example, covalently linked to, the template. It is understood, however, that the templates shown in both FIG. 5B and FIG. 5C may also comprise a reactive unit (R) associated with the corresponding template, as shown in FIGS. 5D-5F. To the extent that a template is associated with a reactive unit, the nucleotide sequence of the template further comprises a sequence of nucleotides or sequence tag that uniquely identifies the reactive unit associated with the template. Following template mediated synthesis, the reactive unit actually attached to the template that participated in the reaction to generate the reaction product may be identified by reading the sequence of the sequence tag.

In FIG. 5D, R is linked to the template at a location in the vicinity of the 5' terminal end, for example, at the 5' end of the template or downstream of the 5' end of the template. In FIG. 5E, R is linked to the template at a location between the 5' terminal end and the 3' terminal end. In this particular case, R is located at a position between C1 and C2, and represents an example of the T type template architecture discussed in more detail below. In FIG. 5F, R is linked to the template at a location in the vicinity of the 3' terminal end, for example, at the 3' end of the template or upstream of the 3' end of the template.

It is contemplated that each of the templates shown in FIGS. 5A-F, may comprise one or more restriction endonuclease sites. For example, with reference to FIG. 5A, the template may comprise a restriction endonuclease site disposed between (i) PBS1 and C1, (ii) C1 and C2, and (iii) C2 and PBS2. The restriction endonuclease sites facilitate the use of nucleic acid cassettes to easily introduce various sequences to replace the PBS1 sequence, the C1 sequence, the C2 sequence, the PBS2 sequence, or any combination thereof.

In addition, the template may also incorporate a hairpin loop on one end terminating in a reactive unit that can interact with one or more reactive units associated with transfer units. For example, a DNA template can comprise a hairpin loop terminating in a 5'-amino group, which may or may not be protected. The amino group may act as an initiation point for formation of an unnatural polymer, or may be modified to bind a small molecule scaffold for subsequent modification by reactive units of other transfer units.

The length of the template may vary greatly depending upon the type of the nucleic acid-templated synthesis contemplated. For example, in certain embodiments, the template may be from 10 to 10,000 nucleotides in length, from 20 to 1,000 nucleotides in length, from 20 to 400 nucleotides in length, from 40 to 1,000 nucleotides in length, or from 40 to 400 nucleotides in length. The length of the template will of course depend on, for example, the length of the codons, the complexity of the library, the complexity and/or size of a reaction product, the use of spacer sequences, etc.

(ii) Codon Usage

It is contemplated that the sequence of the template may be designed in a number of ways without going beyond the scope of the present invention. For example, the length of the codon must be determined and the codon sequences must be set. If a codon length of two is used, then using the four naturally occurring bases only 16 possible combinations are available to be used in encoding the library. If the length of the codon is increased to three (the number Nature uses in encoding proteins), the number of possible combinations increases to 64. If the length of the codon is increased to four, the number of possible combinations increases to 256. Other factors to be considered in determining the length of the codon are mismatching, frame-shifting, complexity of library, etc. As the length of the codon is increased up to a certain point the number of mismatches is decreased; however, excessively long codons likely will hybridize despite mismatched base pairs.

Although the length of the codons may vary, the codons may range from 2 to 50 nucleotides, from 2 to 40 nucleotides, from 2 to 30 nucleotides, from 2 to 20 nucleotides, from 2 to 15 nucleotides, from 2 to 10 nucleotides, from 3 to 50 nucleotides, from 3 to 40 nucleotides, from 3 to 30 nucleotides, from 3 to 20 nucleotides, from 3 to 15 nucleotides, from 3 to 10 nucleotides, from 4 to 50 nucleotides, from 4 to 40 nucleotides, from 4 to 30 nucleotides, from 4 to 20 nucleotides, from 4 to 15 nucleotides, from 4 to 10 nucleotides, from 5 to 50 nucleotides, from 5 to 40 nucleotides, from 5 to 30 nucleotides, from 5 to 20 nucleotides, from 5 to 15 nucleotides, from 5 to 10 nucleotides, from 6 to 50 nucleotides, from 6 to 40 nucleotides, from 6 to 30 nucleotides, from 6 to 20 nucleotides, from 6 to 15 nucleotides, from 6 to 10 nucleotides, from 7 to 50 nucleotides, from 7 to 40 nucleotides, from 7 to 30 nucleotides, from 7 to 20 nucleotides, from 7 to 15 nucleotides, from 7 to 10 nucleotides, from 8 to 50 nucleotides, from 8 to 40 nucleotides, from 8 to 30 nucleotides, from 8 to 20 nucleotides, from 8 to 15 nucleotides, from 8 to 10 nucleotides, from 9 to 50 nucleotides, from 9 to 40 nucleotides, from 9 to 30 nucleotides, from 9 to 20 nucleotides, from 9 to 15 nucleotides, from 9 to 10 nucleotides. Codons, however, preferably are 3, 4, 5, 6, 7, 8, 9 or 10 nucleotides in length.

In one embodiment, the set of codons used in the template maximizes the number of mismatches between any two codons within a codon set to ensure that only the proper anti-codons of the transfer units anneal to the codon sites of the template. Furthermore, it is important that the template has mismatches between all the members of one codon set and all the codons of a different codon set to ensure that the anti-codons do not inadvertently bind to the wrong codon set. For example, with regard to the choice of codons n bases in length, each of the codons within a particular codon set (for example, C1 in FIG. 5A) should differ with one another by k mismatches, and all of the codons in one codon set (for example, C1 in FIG. 5A) should differ by m mismatches with all of the codons in the other codon set (for example, C2 in FIG. 5A). Exemplary values for n, k, and m, for a variety of codon sets suitable for use on a template are summarized in Table 1.

TABLE 1

| n | k | m |
|---|---|---|
| 2 | 1 | 1 |
| 3 | 1 | 1 |
| 3 | 2 | 1 |
| 3 | 2 | 2 |
| 4 | 1 | 1 |
| 4 | 2 | 1 |
| 4 | 2 | 2 |
| 4 | 3 | 1 |
| 4 | 3 | 2 |
| 4 | 3 | 3 |
| 5 | 1 | 1 |
| 5 | 2 | 1 |
| 5 | 2 | 2 |
| 5 | 3 | 1 |
| 5 | 3 | 2 |
| 5 | 3 | 3 |
| 5 | 4 | 1 |
| 5 | 4 | 2 |
| 5 | 4 | 3 |
| 5 | 4 | 4 |
| 6 | 1 | 1 |
| 6 | 2 | 1 |
| 6 | 2 | 2 |
| 6 | 3 | 1 |
| 6 | 3 | 2 |
| 6 | 3 | 3 |
| 6 | 4 | 1 |
| 6 | 4 | 2 |
| 6 | 4 | 3 |
| 6 | 4 | 4 |
| 6 | 5 | 1 |
| 6 | 5 | 2 |
| 6 | 5 | 3 |
| 6 | 5 | 4 |
| 6 | 5 | 5 |
| 7 | 1 | 1 |
| 7 | 2 | 1 |
| 7 | 2 | 2 |
| 7 | 3 | 1 |
| 7 | 3 | 2 |
| 7 | 3 | 3 |
| 7 | 4 | 1 |
| 7 | 4 | 2 |
| 7 | 4 | 3 |
| 7 | 4 | 4 |
| 7 | 5 | 1 |
| 7 | 5 | 2 |
| 7 | 5 | 3 |
| 7 | 5 | 4 |
| 7 | 5 | 5 |
| 7 | 6 | 1 |
| 7 | 6 | 2 |
| 7 | 6 | 3 |
| 7 | 6 | 4 |
| 7 | 6 | 5 |
| 7 | 6 | 6 |
| 8 | 1 | 1 |
| 8 | 2 | 1 |
| 8 | 2 | 2 |
| 8 | 3 | 1 |
| 8 | 3 | 2 |
| 8 | 3 | 3 |
| 8 | 4 | 1 |
| 8 | 4 | 2 |

TABLE 1-continued

| n | k | m |
|---|---|---|
| 8 | 4 | 3 |
| 8 | 4 | 4 |
| 8 | 5 | 1 |
| 8 | 5 | 2 |
| 8 | 5 | 3 |
| 8 | 5 | 4 |
| 8 | 5 | 5 |
| 8 | 6 | 1 |
| 8 | 6 | 2 |
| 8 | 6 | 3 |
| 8 | 6 | 4 |
| 8 | 6 | 5 |
| 8 | 6 | 6 |
| 8 | 7 | 1 |
| 8 | 7 | 2 |
| 8 | 7 | 3 |
| 8 | 7 | 4 |
| 8 | 7 | 5 |
| 8 | 7 | 6 |
| 8 | 7 | 7 |
| 9 | 1 | 1 |
| 9 | 2 | 1 |
| 9 | 2 | 2 |
| 9 | 3 | 1 |
| 9 | 3 | 2 |
| 9 | 3 | 3 |
| 9 | 4 | 1 |
| 9 | 4 | 2 |
| 9 | 4 | 3 |
| 9 | 4 | 4 |
| 9 | 5 | 1 |
| 9 | 5 | 2 |
| 9 | 5 | 3 |
| 9 | 5 | 4 |
| 9 | 5 | 5 |
| 9 | 6 | 1 |
| 9 | 6 | 2 |
| 9 | 6 | 3 |
| 9 | 6 | 4 |
| 9 | 6 | 5 |
| 9 | 6 | 6 |
| 9 | 7 | 1 |
| 9 | 7 | 2 |
| 9 | 7 | 3 |
| 9 | 7 | 4 |
| 9 | 7 | 5 |
| 9 | 7 | 6 |
| 9 | 7 | 7 |
| 9 | 8 | 1 |
| 9 | 8 | 2 |
| 9 | 8 | 3 |
| 9 | 8 | 4 |
| 9 | 8 | 5 |
| 9 | 8 | 6 |
| 9 | 8 | 7 |
| 9 | 8 | 8 |
| 10 | 1 | 1 |
| 10 | 2 | 1 |
| 10 | 2 | 2 |
| 10 | 3 | 1 |
| 10 | 3 | 2 |
| 10 | 3 | 3 |
| 10 | 4 | 1 |
| 10 | 4 | 2 |
| 10 | 4 | 3 |
| 10 | 4 | 4 |
| 10 | 5 | 1 |
| 10 | 5 | 2 |
| 10 | 5 | 3 |
| 10 | 5 | 4 |
| 10 | 5 | 5 |
| 10 | 6 | 1 |
| 10 | 6 | 2 |
| 10 | 6 | 3 |
| 10 | 6 | 4 |
| 10 | 6 | 5 |
| 10 | 6 | 6 |
| 10 | 7 | 1 |
| 10 | 7 | 2 |
| 10 | 7 | 3 |
| 10 | 7 | 4 |
| 10 | 7 | 5 |
| 10 | 7 | 6 |
| 10 | 7 | 7 |
| 10 | 8 | 1 |
| 10 | 8 | 2 |
| 10 | 8 | 3 |
| 10 | 8 | 4 |
| 10 | 8 | 5 |
| 10 | 8 | 6 |
| 10 | 8 | 7 |
| 10 | 8 | 8 |
| 10 | 9 | 1 |
| 10 | 9 | 2 |
| 10 | 9 | 3 |
| 10 | 9 | 4 |
| 10 | 9 | 5 |
| 10 | 9 | 6 |
| 10 | 9 | 7 |
| 10 | 9 | 8 |
| 10 | 9 | 9 |
| 11 | 1 | 1 |
| 11 | 2 | 1 |
| 11 | 2 | 2 |
| 11 | 3 | 1 |
| 11 | 3 | 2 |
| 11 | 3 | 3 |
| 11 | 4 | 1 |
| 11 | 4 | 2 |
| 11 | 4 | 3 |
| 11 | 4 | 4 |
| 11 | 5 | 1 |
| 11 | 5 | 2 |
| 11 | 5 | 3 |
| 11 | 5 | 4 |
| 11 | 5 | 5 |
| 11 | 6 | 1 |
| 11 | 6 | 2 |
| 11 | 6 | 3 |
| 11 | 6 | 4 |
| 11 | 6 | 5 |
| 11 | 6 | 6 |
| 11 | 7 | 1 |
| 11 | 7 | 2 |
| 11 | 7 | 3 |
| 11 | 7 | 4 |
| 11 | 7 | 5 |
| 11 | 7 | 6 |
| 11 | 7 | 7 |
| 11 | 8 | 1 |
| 11 | 8 | 2 |
| 11 | 8 | 3 |
| 11 | 8 | 4 |
| 11 | 8 | 5 |
| 11 | 8 | 6 |
| 11 | 8 | 7 |
| 11 | 8 | 8 |
| 11 | 9 | 1 |
| 11 | 9 | 2 |
| 11 | 9 | 3 |
| 11 | 9 | 4 |
| 11 | 9 | 5 |
| 11 | 9 | 6 |
| 11 | 9 | 7 |
| 11 | 9 | 8 |
| 11 | 9 | 9 |
| 11 | 10 | 1 |
| 11 | 10 | 2 |
| 11 | 10 | 3 |
| 11 | 10 | 4 |
| 11 | 10 | 5 |
| 11 | 10 | 6 |
| 11 | 10 | 7 |
| 11 | 10 | 8 |
| 11 | 10 | 9 |
| 11 | 10 | 10 |

TABLE 1-continued

| n | k | m |
|---|---|---|
| 12 | 1 | 1 |
| 12 | 2 | 1 |
| 12 | 2 | 2 |
| 12 | 3 | 1 |
| 12 | 3 | 2 |
| 12 | 3 | 3 |
| 12 | 4 | 1 |
| 12 | 4 | 2 |
| 12 | 4 | 3 |
| 12 | 4 | 4 |
| 12 | 5 | 1 |
| 12 | 5 | 2 |
| 12 | 5 | 3 |
| 12 | 5 | 4 |
| 12 | 5 | 5 |
| 12 | 6 | 1 |
| 12 | 6 | 2 |
| 12 | 6 | 3 |
| 12 | 6 | 4 |
| 12 | 6 | 5 |
| 12 | 6 | 6 |
| 12 | 7 | 1 |
| 12 | 7 | 2 |
| 12 | 7 | 3 |
| 12 | 7 | 4 |
| 12 | 7 | 5 |
| 12 | 7 | 6 |
| 12 | 7 | 7 |
| 12 | 8 | 1 |
| 12 | 8 | 2 |
| 12 | 8 | 3 |
| 12 | 8 | 4 |
| 12 | 8 | 5 |
| 12 | 8 | 6 |
| 12 | 8 | 7 |
| 12 | 8 | 8 |
| 12 | 9 | 1 |
| 12 | 9 | 2 |
| 12 | 9 | 3 |
| 12 | 9 | 4 |
| 12 | 9 | 5 |
| 12 | 9 | 6 |
| 12 | 9 | 7 |
| 12 | 9 | 8 |
| 12 | 9 | 9 |
| 12 | 10 | 1 |
| 12 | 10 | 2 |
| 12 | 10 | 3 |
| 12 | 10 | 4 |
| 12 | 10 | 5 |
| 12 | 10 | 6 |
| 12 | 10 | 7 |
| 12 | 10 | 8 |
| 12 | 10 | 9 |
| 12 | 10 | 10 |
| 12 | 11 | 1 |
| 12 | 11 | 2 |
| 12 | 11 | 3 |
| 12 | 11 | 4 |
| 12 | 11 | 5 |
| 12 | 11 | 6 |
| 12 | 11 | 7 |
| 12 | 11 | 8 |
| 12 | 11 | 9 |
| 12 | 11 | 10 |
| 12 | 11 | 11 |
| 13 | 1 | 1 |
| 13 | 2 | 1 |
| 13 | 2 | 2 |
| 13 | 3 | 1 |
| 13 | 3 | 2 |
| 13 | 3 | 3 |
| 13 | 4 | 1 |
| 13 | 4 | 2 |
| 13 | 4 | 3 |
| 13 | 4 | 4 |
| 13 | 5 | 1 |
| 13 | 5 | 2 |
| 13 | 5 | 3 |
| 13 | 5 | 4 |
| 13 | 5 | 5 |
| 13 | 6 | 1 |
| 13 | 6 | 2 |
| 13 | 6 | 3 |
| 13 | 6 | 4 |
| 13 | 6 | 5 |
| 13 | 6 | 6 |
| 13 | 7 | 1 |
| 13 | 7 | 2 |
| 13 | 7 | 3 |
| 13 | 7 | 4 |
| 13 | 7 | 5 |
| 13 | 7 | 6 |
| 13 | 7 | 7 |
| 13 | 8 | 1 |
| 13 | 8 | 2 |
| 13 | 8 | 3 |
| 13 | 8 | 4 |
| 13 | 8 | 5 |
| 13 | 8 | 6 |
| 13 | 8 | 7 |
| 13 | 8 | 8 |
| 13 | 9 | 1 |
| 13 | 9 | 2 |
| 13 | 9 | 3 |
| 13 | 9 | 4 |
| 13 | 9 | 5 |
| 13 | 9 | 6 |
| 13 | 9 | 7 |
| 13 | 9 | 8 |
| 13 | 9 | 9 |
| 13 | 10 | 1 |
| 13 | 10 | 2 |
| 13 | 10 | 3 |
| 13 | 10 | 4 |
| 13 | 10 | 5 |
| 13 | 10 | 6 |
| 13 | 10 | 7 |
| 13 | 10 | 8 |
| 13 | 10 | 9 |
| 13 | 10 | 10 |
| 13 | 11 | 1 |
| 13 | 11 | 2 |
| 13 | 11 | 3 |
| 13 | 11 | 4 |
| 13 | 11 | 5 |
| 13 | 11 | 6 |
| 13 | 11 | 7 |
| 13 | 11 | 8 |
| 13 | 11 | 9 |
| 13 | 11 | 10 |
| 13 | 11 | 11 |
| 13 | 12 | 1 |
| 13 | 12 | 2 |
| 13 | 12 | 3 |
| 13 | 12 | 4 |
| 13 | 12 | 5 |
| 13 | 12 | 6 |
| 13 | 12 | 7 |
| 13 | 12 | 8 |
| 13 | 12 | 9 |
| 13 | 12 | 10 |
| 13 | 12 | 11 |
| 13 | 12 | 12 |
| 14 | 1 | 1 |
| 14 | 2 | 1 |
| 14 | 2 | 2 |
| 14 | 3 | 1 |
| 14 | 3 | 2 |
| 14 | 3 | 3 |
| 14 | 4 | 1 |
| 14 | 4 | 2 |
| 14 | 4 | 3 |
| 14 | 4 | 4 |
| 14 | 5 | 1 |
| 14 | 5 | 2 |

TABLE 1-continued

| n | k | m |
|---|---|---|
| 14 | 5 | 3 |
| 14 | 5 | 4 |
| 14 | 5 | 5 |
| 14 | 6 | 1 |
| 14 | 6 | 2 |
| 14 | 6 | 3 |
| 14 | 6 | 4 |
| 14 | 6 | 5 |
| 14 | 6 | 6 |
| 14 | 7 | 1 |
| 14 | 7 | 2 |
| 14 | 7 | 3 |
| 14 | 7 | 4 |
| 14 | 7 | 5 |
| 14 | 7 | 6 |
| 14 | 7 | 7 |
| 14 | 8 | 1 |
| 14 | 8 | 2 |
| 14 | 8 | 3 |
| 14 | 8 | 4 |
| 14 | 8 | 5 |
| 14 | 8 | 6 |
| 14 | 8 | 7 |
| 14 | 8 | 8 |
| 14 | 9 | 1 |
| 14 | 9 | 2 |
| 14 | 9 | 3 |
| 14 | 9 | 4 |
| 14 | 9 | 5 |
| 14 | 9 | 6 |
| 14 | 9 | 7 |
| 14 | 9 | 8 |
| 14 | 9 | 9 |
| 14 | 10 | 1 |
| 14 | 10 | 2 |
| 14 | 10 | 3 |
| 14 | 10 | 4 |
| 14 | 10 | 5 |
| 14 | 10 | 6 |
| 14 | 10 | 7 |
| 14 | 10 | 8 |
| 14 | 10 | 9 |
| 14 | 10 | 10 |
| 14 | 11 | 1 |
| 14 | 11 | 2 |
| 14 | 11 | 3 |
| 14 | 11 | 4 |
| 14 | 11 | 5 |
| 14 | 11 | 6 |
| 14 | 11 | 7 |
| 14 | 11 | 8 |
| 14 | 11 | 9 |
| 14 | 11 | 10 |
| 14 | 11 | 11 |
| 14 | 12 | 1 |
| 14 | 12 | 2 |
| 14 | 12 | 3 |
| 14 | 12 | 4 |
| 14 | 12 | 5 |
| 14 | 12 | 6 |
| 14 | 12 | 7 |
| 14 | 12 | 8 |
| 14 | 12 | 9 |
| 14 | 12 | 10 |
| 14 | 12 | 11 |
| 14 | 12 | 12 |
| 14 | 13 | 1 |
| 14 | 13 | 2 |
| 14 | 13 | 3 |
| 14 | 13 | 4 |
| 14 | 13 | 5 |
| 14 | 13 | 6 |
| 14 | 13 | 7 |
| 14 | 13 | 8 |
| 14 | 13 | 9 |
| 14 | 13 | 10 |
| 14 | 13 | 11 |
| 14 | 13 | 12 |
| 14 | 13 | 13 |
| 15 | 1 | 1 |
| 15 | 2 | 1 |
| 15 | 2 | 2 |
| 15 | 3 | 1 |
| 15 | 3 | 2 |
| 15 | 3 | 3 |
| 15 | 4 | 1 |
| 15 | 4 | 2 |
| 15 | 4 | 3 |
| 15 | 4 | 4 |
| 15 | 5 | 1 |
| 15 | 5 | 2 |
| 15 | 5 | 3 |
| 15 | 5 | 4 |
| 15 | 5 | 5 |
| 15 | 6 | 1 |
| 15 | 6 | 2 |
| 15 | 6 | 3 |
| 15 | 6 | 4 |
| 15 | 6 | 5 |
| 15 | 6 | 6 |
| 15 | 7 | 1 |
| 15 | 7 | 2 |
| 15 | 7 | 3 |
| 15 | 7 | 4 |
| 15 | 7 | 5 |
| 15 | 7 | 6 |
| 15 | 7 | 7 |
| 15 | 8 | 1 |
| 15 | 8 | 2 |
| 15 | 8 | 3 |
| 15 | 8 | 4 |
| 15 | 8 | 5 |
| 15 | 8 | 6 |
| 15 | 8 | 7 |
| 15 | 8 | 8 |
| 15 | 9 | 1 |
| 15 | 9 | 2 |
| 15 | 9 | 3 |
| 15 | 9 | 4 |
| 15 | 9 | 5 |
| 15 | 9 | 6 |
| 15 | 9 | 7 |
| 15 | 9 | 8 |
| 15 | 9 | 9 |
| 15 | 10 | 1 |
| 15 | 10 | 2 |
| 15 | 10 | 3 |
| 15 | 10 | 4 |
| 15 | 10 | 5 |
| 15 | 10 | 6 |
| 15 | 10 | 7 |
| 15 | 10 | 8 |
| 15 | 10 | 9 |
| 15 | 10 | 10 |
| 15 | 11 | 1 |
| 15 | 11 | 2 |
| 15 | 11 | 3 |
| 15 | 11 | 4 |
| 15 | 11 | 5 |
| 15 | 11 | 6 |
| 15 | 11 | 7 |
| 15 | 11 | 8 |
| 15 | 11 | 9 |
| 15 | 11 | 10 |
| 15 | 11 | 11 |
| 15 | 12 | 1 |
| 15 | 12 | 2 |
| 15 | 12 | 3 |
| 15 | 12 | 4 |
| 15 | 12 | 5 |
| 15 | 12 | 6 |
| 15 | 12 | 7 |
| 15 | 12 | 8 |
| 15 | 12 | 9 |
| 15 | 12 | 10 |
| 15 | 12 | 11 |

TABLE 1-continued

| n | k | m |
|---|---|---|
| 15 | 12 | 12 |
| 15 | 13 | 1 |
| 15 | 13 | 2 |
| 15 | 13 | 3 |
| 15 | 13 | 4 |
| 15 | 13 | 5 |
| 15 | 13 | 6 |
| 15 | 13 | 7 |
| 15 | 13 | 8 |
| 15 | 13 | 9 |
| 15 | 13 | 10 |
| 15 | 13 | 11 |
| 15 | 13 | 12 |
| 15 | 13 | 13 |
| 15 | 14 | 1 |
| 15 | 14 | 2 |
| 15 | 14 | 3 |
| 15 | 14 | 4 |
| 15 | 14 | 5 |
| 15 | 14 | 6 |
| 15 | 14 | 7 |
| 15 | 14 | 8 |
| 15 | 14 | 9 |
| 15 | 14 | 10 |
| 15 | 14 | 11 |
| 15 | 14 | 12 |
| 15 | 14 | 13 |
| 15 | 14 | 14 |

Using an appropriate algorithm, it is possible to generate sets of codons that maximize mismatches between any two codons within the same set, where the codons are n bases long having at least k mismatches between any two codons. Since between any two codons, there must be at least k mismatches, any two subcodons of n−(k−1) bases must have at least one mismatch. This sets an upper limit of $4^{n-k+1}$ on the size of any (m, k) codon set. Such an algorithm preferably starts with the $4^{n-k+1}$ possible subcodons of length n−(k−1) and then tests all combinations of adding k−1 bases for those that always maintain k mismatches. All possible (m, k) sets can be generated for n≦6. For n>6, the $4^{n-k+1}$ upper limits of codons cannot be met and a "full" packing of viable codons is mathematically impossible. In addition to there being at least one mismatch k between codons within the same codon set, there should also be at least one mismatch m between all the codons of one codon set and all the codons of another codon set. Using this approach, different sets of codons can be generated so that no codons are repeated.

By way of example, four (n=5, k=3, m=1) sets, each with 64 codons, can be chosen that always have at least one mismatch between any two codons in different sets and at least three mismatches between codons in the same set.

TABLE 2

Sequences of (5, 3, 1) Codon Set 1

| Codon Seq. | Codon Seq. | Codon Seq. | Codon Seq. | Codon Seq. | Codon Seq. |
|---|---|---|---|---|---|
| CCCTC | CCGAG | CCTCT | CCAGA | CGCGT | CGGCA |
| CGTAC | CGATG | CTCCG | CTGGC | CTTTA | CTAAT |
| CACAA | CAGTT | CATGG | CAACC | GCCCA | GCGGT |
| GCTTG | GCAAC | GGCAG | GGGTC | GGTGA | GGACT |
| GTCTT | GTGAA | GTTCC | GTAGG | GACGC | GAGCG |
| GATAT | GAATA | TCCGG | TCGCC | TCTAA | TCATT |
| TGCTA | TGGAT | TGTCG | TGAGC | TTCAC | TTGTG |
| TTTGT | TTACA | TACCT | TAGGA | TATTC | TAAAG |
| ACCAT | ACGTA | ACTGC | ACACG | AGCCC | AGGGG |
| AGTTT | AGAAA | ATCGA | ATGCT | ATTAG | ATATC |
| AACTG | AAGAC | ATCA | AAAGT | | |

TABLE 3

Sequences of (5, 3, 1) Codon Set 2

| Codon Seq. | Codon Seq. | Codon Seq. | Codon Seq. | Codon Seq. | Codon Seq. |
|---|---|---|---|---|---|
| CCCAC | CCGTG | CCTGT | CCACA | CGCCT | CGGGA |
| CGTTC | CGAAG | CTCGG | CTGCC | CTTAA | CTATT |
| CACTA | CAGAT | CATCG | CAAGC | GCCGA | GCGCT |
| GCTAG | GCATC | GGCTG | GGGAC | GGTCA | GGAGT |
| GTCAT | GTGTA | GTTGC | GTACG | GACCC | GAGGG |
| GATTT | GAAAA | TCCCG | TCGGC | TCTTA | TCAAT |
| TGCAA | TGGTT | TGTGG | TGACC | TTCTC | TTGAG |
| TTTCT | TTAGA | TACGT | TAGCA | TATAC | TAATG |
| ACCTT | ACGAA | ACTCC | ACAGG | AGCGC | AGGCG |
| AGTAT | AGATA | ATCCA | ATGGT | ATTTG | ATAAC |
| AACAG | AAGTC | AATGA | AAACT | | |

TABLE 4

Sequences of (5, 3, 1) Codon Set 3

| Codon Seq. | Codon Seq. | Codon Seq. | Codon Seq. | Codon Seq. | Codon Seq. |
|---|---|---|---|---|---|
| CCCTG | CCGAC | CCTCA | CCAGT | CGCAT | CGGTA |
| CGTGC | CGACG | CTCCC | CTGGG | CTTTT | CTAAA |
| CACGA | CAGCT | CATAG | CAATC | GCCAA | GCGTT |
| GCTGG | GCACC | GGCTC | GGGAG | GGTCT | GGAGA |
| GTCGT | GTGCA | GTTAC | GTATG | GACCG | GAGGC |
| GATTA | GAAAT | TCCGC | TCGCG | TCTAT | TCATA |
| TGCCA | TGGGT | TGTTG | TGAAC | TTCAG | TTGTC |
| TTTGA | TTACT | TACTT | TAGAA | TATCC | TAAGG |
| ACCCT | ACGGA | ACTTC | ACAAG | AGCGG | AGGCC |
| AGTAA | AGATT | ATCTA | ATGAT | ATTCG | ATAGC |
| AACAC | AAGTG | AATGT | AAACA | | |

TABLE 5

Sequences of (5, 3, 1) Codon Set 4

| Codon Seq. | Codon Seq. | Codon Seq. | Codon Seq. | Codon Seq. | Codon Seq. |
|---|---|---|---|---|---|
| CCCAG | CCGTC | CCTGA | CCACT | CGCTT | CGGAA |
| CGTCC | CGAGG | CTCGC | CTGCG | CTTAT | CTATA |
| CACCA | CAGGT | CATTG | CAAAC | GCCTA | CGAT |
| GCTCG | GCAGC | GGCAC | GGGTG | GGTGT | GGACA |
| GTCCT | GTGGA | GTTTC | GTAAG | GACGG | GAGCC |
| GATAA | GAATT | TCCCC | TCGGG | TCTTT | TCAAA |
| TGCGA | TGGCT | TGTAG | TGATC | TTCTG | TTGAC |
| TTTCA | TTAGT | TACAT | TAGTA | TATGC | TAACG |
| ACCGT | ACGCA | ACTAC | ACATG | AGCCG | AGGGC |
| AGTTA | AGAAT | ATCAA | ATGTT | ATTGG | ATACC |
| AACTC | AAGAG | AATCT | AAAGA | | |

Similarly, four (n=6, k=4, m=2) sets as shown below, each with 64 codons, can be chosen that always have at least two mismatches between any two codons in different codon sets and at least four mismatches between codons in the same codon set.

TABLE 6

Sequences of (6, 4, 2) Codon Set 1

| Codon Seq. | Codon Seq. | Codon Seq. | Codon Seq. | Codon Seq. | Codon Seq. |
|---|---|---|---|---|---|
| CCCTCC | TCGAAC | CCGCTG | TCTCCA | CGGTAT | TCATTT |
| CCAGAA | TGCACT | CGCCGA | TGGGTA | CTCAAG | TGTTGC |
| CGTGCG | TGACAG | CGAATC | TTCCTC | CTACCT | TTGTCG |
| CTGGGC | TTTGAT | CTTTTA | TTAAGA | CATCAC | TACTAA |
| CACGTT | TAGCGT | CAGACA | TATATG | GCGGCT | TAAGCC |
| CAATGG | ACCCAT | GCCATA | ACGTGA | GGCGAC | ACTGTC |
| GCTTAG | ACAACG | GCACGC | AGCTTG | GGATCA | AGGCCC |
| GGGAGG | AGTAAA | GGTCTT | AGAGGT | GTTACC | ATCGCA |
| GTCTGT | ATGATT | GTGCAA | ATTCGG | GAGTTC | ATATAC |
| GTAGTG | AACAGC | GACCCG | AAGGAG | TCCGGG | AATTCT |
| GATGGA | AAACTA | GAAAAT | CCTAGT | | |

TABLE 7

Sequences of (6, 4, 2) Codon Set 2

| Codon Seq. | Codon Seq. | Codon Seq. | Codon Seq. | Codon Seq. | Codon Seq. |
|---|---|---|---|---|---|
| CCCCTC | TCGGGC | CCGTCG | TCTTTA | CGGCGT | TCACCT |
| CCAAGA | TGCGTT | CGCTAA | TGGACA | CTCGGG | TGTCAC |
| CGTATG | TGATGG | CGAGCC | TTCTCC | CTATTT | TTGCTG |
| CTGAAC | TTTAGT | CTTCCA | TTAGAA | CATTGC | TACCGA |
| CACACT | TAGTAT | CAGGTA | TATGCG | GCGATT | TAAATC |
| CAACAG | ACCTGT | GCCGCA | ACGCAA | GGCAGC | ACTACC |
| GCTCGG | ACAGTG | GCATAC | AGCCCG | GGACTA | AGGTTC |
| GGGGAG | AGTGGA | GGTTCT | AGAAAT | GTTGTC | ATCATA |
| GTCCAT | ATGGCT | GTGTGA | ATTTAG | GAGCCC | ATACGC |
| GTAACG | AACGAC | GACTTG | AAGAGG | TCCAAG | AATCTT |
| GATAAA | AAATCA | GAAGGT | CCTGAT | | |

TABLE 8

Sequences of (6, 4, 2) Codon Set 3

| Codon Seq. | Codon Seq. | Codon Seq. | Codon Seq. | Codon Seq. | Codon Seq. |
|---|---|---|---|---|---|
| CCCGAC | TCGCCC | CCGAGG | TCTAAA | CGGGCT | TCAGGT |
| CCATCA | TGCCAT | CGCATA | TGGTGA | CTCCCG | TGTGTC |
| CGTTAG | TGAACG | CGACGC | TTCAGC | CTAAAT | TTGGAG |
| CTGTTC | TTTTCT | CTTGGA | TTACTA | CATACC | TACGCA |
| CACTGT | TAGATT | CAGCAA | TATCGG | GCGTAT | TAATAC |
| CAAGTG | ACCACT | GCCCGA | ACGGTA | GGCTCC | ACTTGC |
| GCTGCG | ACACAG | GCAATC | AGCGGG | GGAGAA | AGGAAC |
| GGGCTG | AGTCCA | GGTAGT | AGATTT | GTTCAC | ATCTAA |
| GTGGTT | ATGCGT | GTGACA | ATTATG | GAGGGC | ATAGCC |
| GTATGG | AACCTC | GACAAG | AAGTCG | TCCTTG | AATGAT |
| GATTTA | AAAAGA | GAACCT | CCTCTT | | |

TABLE 9

Sequences of (6, 4, 2) Codon Set 4

| Codon Seq. | Codon Seq. | Codon Seq. | Codon Seq. | Codon Seq. | Codon Seq. |
|---|---|---|---|---|---|
| CCCAGC | TCGTTC | CCGGAG | TCTGGA | CGGATT | TCAAAT |
| CCACTA | TGCTGT | CGCGCA | TGGCAA | CTCTTG | TGTACC |
| CGTCGG | TGAGTG | CGATAC | TTCGAC | CTAGGT | TTGAGG |
| CTGCCC | TTTCTT | CTTAAA | TTATCA | CATGTC | TACATA |
| CACCAT | TAGGCT | CAGTGA | TATTAG | GCGCGT | TAACGC |
| CAAACG | ACCGTT | GCCTAA | ACGACA | GGCCTC | ACTCAC |
| GCTATG | ACATGG | GCAGCC | AGCAAG | GGAAGA | AGGGGC |
| GGGTCG | AGTTTA | GGTGAT | AGACCT | GTTTGC | ATCCGA |
| GTCACT | ATGTAT | GTGGTA | ATTGCG | GAGAAC | ATAATC |

TABLE 9-continued

Sequences of (6, 4, 2) Codon Set 4

| Codon Seq. | Codon Seq. | Codon Seq. | Codon Seq. | Codon Seq. | Codon Seq. |
|---|---|---|---|---|---|
| GTACAG | AACTCC | GACGGG | AAGCTG | TCCCCG | AATAGT |
| GATCCA | AAAGAA | GAATTT | CCTTCT | | |

Codons can also be chosen to increase control over the GC content and, therefore, the melting temperature of the codon and anti-codon. Codons sets with a wide range in GC content versus AT content may result in reagents that anneal with different efficiencies due to different melting temperatures. By screening for GC content among different (m, k) sets, the GC content for the codon sets can be optimized. For example, the four (6, 4, 2) codon sets set forth in Tables 6-9 each contain 40 codons with identical GC content (i.e., 50% GC content). By using only these 40 codons at each position, all the reagents in theory will have comparable melting temperatures, removing potential biases in annealing that might otherwise affect library synthesis. Longer codons that maintain a large number of mismatches such as those appropriate for certain applications such as the reaction discovery system can also be chosen using this approach. For example, by combining two (6, 4) sets together while matching low GC to high GC codons, (12, 8) sets with 64 codons all with 50% GC content can be generated for use in reaction discovery selections as well as other application where multiple mismatches might be advantageous. These codons satisfy the requirements for encoding a 30×30 matrix of functional group combinations for reaction discovery.

Figure 6A:
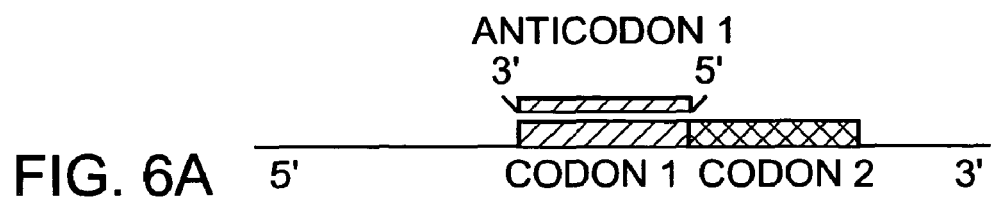
FIGS. 6A-E are schematic representations of desirable and undesirable possible interactions between a codon of a template and an anti-codon of a transfer unit.
Figure 6B:
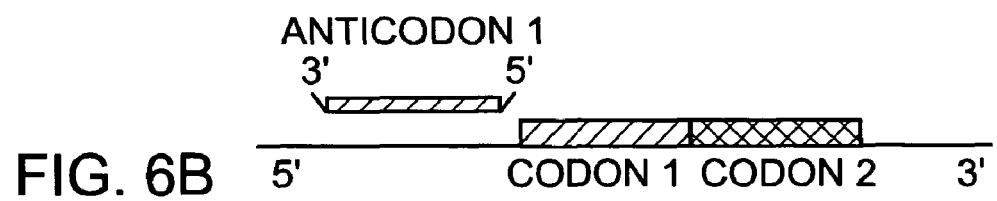
Figure 6C:
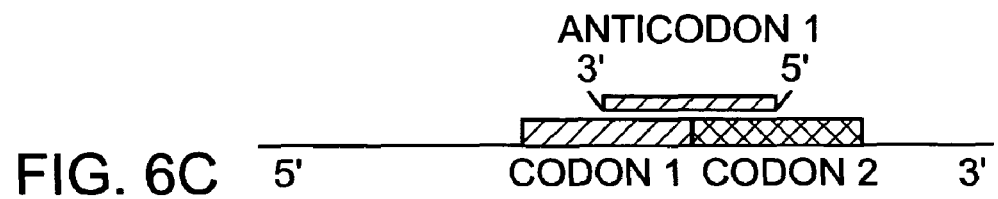
Figure 6D:
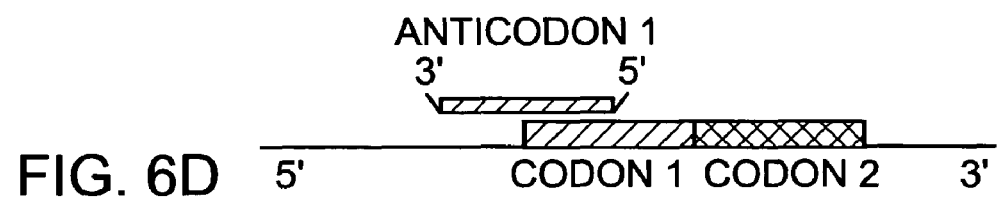
Figure 6E:
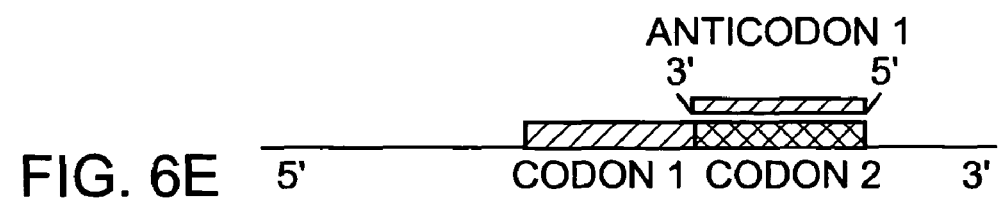

Although an anti-codon is intended to bind only to a codon, as shown in FIG. 6A, an anti-codon may also bind to an unintended sequence on a template if complementary sequence is present. Thus, an anti-codon may inadvertently bind to a non-codon sequence as shown in FIG. 6B. Alternatively, as shown in FIGS. 6C and 6D, an anti-codon might inadvertently bind out-of-frame by annealing in part to one codon and in part to another codon (FIG. 6C) or to a non-codon sequence (FIG. 6D). Finally, as shown in FIG. 6E, an anti-codon might bind in-frame to an incorrect codon, an issue addressed by the codon sets described above by requiring at least one base difference distinguishing each codon. In Nature, the problems of noncoding sequences and out-of-frame binding (FIGS. 6B-D) are avoided by the ribosome. The nucleic acid-templated methods described herein, however, do not take advantage of the ribosome's fidelity. Therefore, in order to avoid erroneous annealing as in FIGS. 6B-D, the templates can be designed such that sequences complementary to anti-codons are found exclusively at in-frame codon positions. For example, codons can be designed to begin, or end, with a particular base (e.g., "G"). If that base is omitted from all other positions in the template (i.e., all other positions are restricted to T, C, and A), only perfect codon sequences in the template will be at the in-frame codon sequences. Similarly, the codon may be designed to be sufficiently long such that its sequence is unique and does not appear elsewhere in a template.

When the nucleic acid-templated synthesis is used to produce a polymer, spacer sequences may also be placed between the codons to prevent frame shifting. More preferably, the bases of the template that encode each polymer subunit (the "genetic code" for the polymer) may be chosen from Table 10 to preclude or minimize the possibility of out-of-frame annealing. These genetic codes reduce undesired frameshifted nucleic acid-templated polymer translation and differ in the range of expected melting temperatures and in the minimum number of mismatches that result during out-of-frame annealing.

TABLE 10

Representative Genetic Codes for Nucleic Acid-templated Polymers That Preclude Out-Of-Frame Annealing

| Sequence | Number of Possible Codons |
|---|---|
| VVNT | 36 possible codons |
| NVVT | 36 possible codons |
| SSWT | 8 possible codons |
| SSST | 8 possible codons |
| SSNT | 16 possible codons |
| VNVNT or NVNVT | 144 possible codons |
| SSSWT or SSWST | 16 possible codons |
| SNSNT or NSNST | 64 possible codons |
| SSNWT or SWNST | 32 possible codons |
| WSNST or NSWST | 32 possible codons | where, V = A, C, or G, S = C or G, W = A or T, and N = A, C, G, or T

As in Nature, start and stop codons are useful, particularly in the context of polymer synthesis, to restrict erroneous anti-codon annealing to non-codons and to prevent excessive extension of a growing polymer. For example, a start codon can anneal to a transfer unit bearing a small molecule scaffold or a start monomer unit for use in polymer synthesis; the start monomer unit can be masked by a photolabile protecting group as shown in Example 9A. A stop codon, if used to terminate polymer synthesis, should not conflict with any other codons used in the synthesis and should be of the same general format as the other codons. Generally, a stop codon can encode a monomer unit that terminates polymerization by not providing a reactive group for further attachment. For example, a stop monomer unit may contain a blocked reactive group such as an acetamide rather than a primary amine as shown in Example 9A. In other embodiments, the stop monomer unit can include a biotinylated terminus that terminates the polymerization and facilitates purification of the resulting polymer.

(iii) Template Architecture

As discussed previously, depending upon the type of nucleic acid-templated synthesis contemplated, the template may be further associated (for example, covalently coupled) with a particular reactive unit. Various templates useful in nucleic acid-templated synthesis are shown in FIGS. 7A-7G, and include templates referred to as the "end-of helix" or "E" templates (see, FIG. 7A-C), "Hairpin" or "H" templates (see, FIG. 7D), "Omega" or "Ω" templates (see, FIG. 7E-F), or "T" templates (see, FIG. 7G).

Figure 7A:
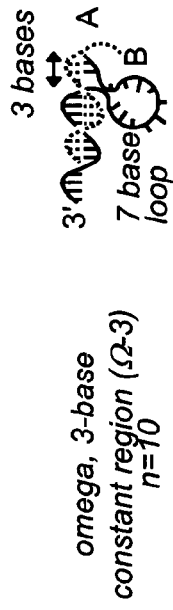
FIGS. 7A-G are schematic representations of various template architectures useful in nucleic acid-templated synthesis.
Figure 7B:
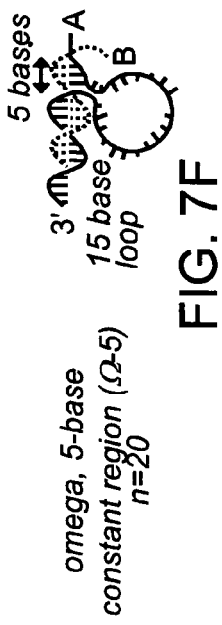
Figure 7C:
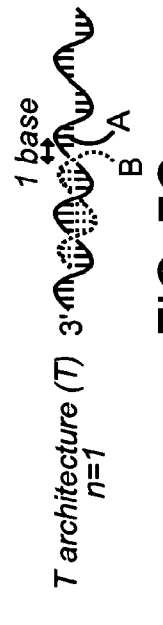
Figure 7D:
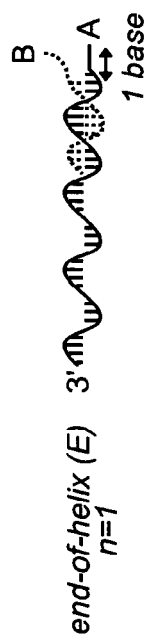
Figure 7E:
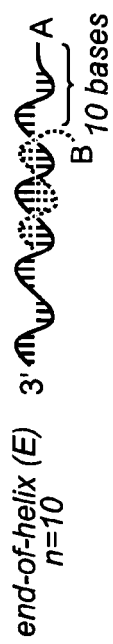
Figure 7F:
Figure 7G:
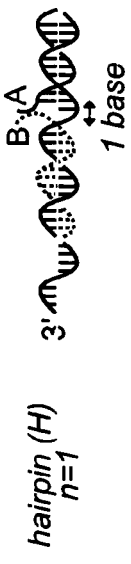

FIGS. 7A-C show E type template architectures where the reactive units on the annealed templates (denoted by A) and transfer units (denoted by B) are separated by 1 base (FIG. 7A), 10 bases (FIG. 7B) and 20 bases (FIG. 7C). FIG. 7D, shows a H type template architecture where the reactive unit is attached to the template (denoted by A) and the template folds back on itself to create a hairpin loop stabilized by a plurality of intramolecular bonds. As shown, the reactive units on the annealed template (denoted by A) and the transfer unit (denoted by B) are separated by 1 base. FIGS. 7E-F show omega type template architecture where the codon for the transfer unit, bearing reactive unit B, is separated from reactive unit A on the template by 10 intervening template bases (FIG. 7E) or by 20 bases (FIG. 7F). In FIG. 7E, the omega template comprises a three base constant region (Ω-3) and creates a seven base loop when the transfer unit anneals to the template. In FIG. 7F, the omega template includes a five base constant region (Ω-5) and creates a fifteen base loop when the transfer unit anneals to the template. The loop gets larger as transfer units anneal to codons further away from the constant region of the template. FIG. 7G shows a T-type template architecture where the reactive units on the annealed template (denoted by A) and the transfer unit (denoted by B) are separated by 1 base. In FIG. 7G, reactive unit A is attached at a location intermediate the 5' and 3' terminal ends of the template. Using this architecture, it is contemplated that the reactive unit may be attached to the template at a location at least 10, 20, 30, 40, 50, 60, 70 bases or more downstream of the 5' end of the template and/or at least 10, 20, 30, 40, 50, 60, 70 bases or more upstream of the 3' end of the template.

The ability of the E type template architecture and the H type template architecture to facilitate nucleic acid mediated chemical syntheses is described in detail in Example 1. However, as a result of performing nucleic acid mediated syntheses, it has been discovered that certain reactions, referred to as distance dependent reactions, do not proceed efficiently when the annealed reactive units on the template and transfer unit are separated by even small numbers of bases. Using the E and H type templates, certain distance dependent reactions may only be encoded by template bases at the reactive end of the template. The new Ω type template overcomes the distance dependence problems that can be experienced with the E and H type templates (see, Example 5). Furthermore, it has been discovered that the presence of double-stranded nucleic acids between annealed reactive units can greatly reduce the efficiency of templated reactions because the flexibility of a single-stranded template is required. This may hinder performing two or more reactions in a single nucleic acid templated step using the E or H architectures even though the template may contain enough bases to encode multiple reactions. The new T type template overcomes this problem that can be experienced with the E and H type templates (see, Example 5).

Ω Templates

The omega architecture permits distance dependent reactions to be directed efficiently by nucleotide bases far away from the reaction end of the template, effectively overcoming their distance dependence. By way of example, in the omega architecture, five bases of the template are held constant at the 5'-end of the template (see, FIG. 7F). The transfer units contain at their 3'-ends the complementary five bases but otherwise possess sequences that complement distal coding regions of the template. This permits the transfer unit to anneal to the distal coding regions of the template while still placing the reactive group of the transfer unit in close proximity by looping out large numbers of template bases that would ordinarily prevent a distance dependent reaction from proceeding. The omega architecture retains sequence specificity because the five bases of the transfer unit that complement the end of the template are insufficient by themselves to anneal to the template at room temperature.

The usefulness of this type of template architecture is apparent, for example, in nucleic acid-templated reductive amination reactions. These reactions are strongly distance dependent and very little product is produced when the reaction is attempted using the hairpin or end-of-helix architectures with more than one base of distance between the annealed amine and aldehyde groups. In contrast, product forms efficiently using the omega architecture even when a region of the template 20 bases away from the reactive end is used to recruit the reagent (see, Example 5). No product is observed when the coding region of the transfer unit is mismatched, despite the presence of five bases at the end of the transfer unit that are complementary to the end of the template.

By enabling distance-dependent nucleic acid mediated reactions to be encoded by bases far away from the reactive end of the template, the omega architecture expands the types of reactions that can be encoded anywhere on the template.

T Templates

The T architecture permits a single template to encode two distance-dependent reactions and in addition permits a template to undergo two different nucleotide-templated reactions in a single solution or in "one-pot." Using this architecture, the template can present a molecular scaffold through the non-Watson-Crick face of a base located in the center, rather than the end, of the template (see, FIG. 7G). This permits two transfer units to anneal to either side of the reactive unit attached to the template and react either simultaneously or in successive steps to give the product of two nucleotide-templated transformations. As expected, distance dependent reactions tolerate this architecture when reactive groups are proximal. Thus, the T-type architecture permits two sequence-specific nucleic acid-templated reactions to take place on one template in one solution, i.e., in one step. In addition to reducing the number of separate DNA-templated steps needed to synthesize a target structure, this architecture may permit three- or more component reactions commonly used to build structural complexity in synthetic libraries.

The omega and T architectures permit a broader range of template mediated reactions that can be performed in fewer steps with other template architectures and are especially useful in distance-dependent reactions. The variety of available architectures provide significant flexibility in the placement of reactive units on templates, particularly for the synthesis of small molecules. It is contemplated that the reactive unit including, for example, molecular scaffold may be associated with a template at any site along the template including the 5'-end (e.g., end-of-helix architecture, omega architecture), the 3'-end (e.g., end-of-helix architecture, omega architecture), at the end of a hairpin loop (e.g., hairpin architecture), or in the middle of the template (e.g., T architecture). Preferably, the molecular scaffold is attached covalently to the template. However, in certain embodiments, the molecular scaffold, like the other reactive units, can be brought to the template using a transfer unit, in which case the molecular scaffold is only associated with the template through a non-covalent (here, hydrogen bonding) interaction. It is contemplated, however, that under certain circumstances it may be advantageous to covalently link the molecular scaffold or another reactive unit to the template to produce a T- or E-type template architecture. For reactions that are not distance dependent, the position of the molecular scaffold along the template is more flexible because the reactive units brought to the template by the transfer units are able to react with the scaffold even if the scaffold and reactive group are separated by many bases.

(iv) Template Synthesis

The templates may be synthesized using methodologies well known in the art. For example, the nucleic acid sequence may be prepared using any method known in the art to prepare nucleic acid sequences. These methods include both in vivo and in vitro methods including PCR, plasmid preparation, endonuclease digestion, solid phase synthesis (for example, using an automated synthesizer), in vitro transcription, strand separation, etc. Following synthesis, the template, when desired may be associated (for example, covalently or non covalently coupled) with a reactive unit of interest using standard coupling chemistries known in the art.

By way of example, it is possible to create a library of templates via a one-pot modular ligation reaction using oligonucleotide cassettes shown as discussed, for example, in Example 9C. Specifically, it is possible to combine short oligonucleotides representing all transfer unit annealing regions together with T4 DNA ligase in a single solution. Due to the sequence design of the oligonucleotide termini, the desired assembled template library is the only possible product when the ligation is complete. This strategy requires 2n×m short oligonucleotides to assemble a library of $n^m$ templates, where n refers to the number of different sequences per codon position and m refers to the number of codons per library member. Thus, for a two-codon template with 64 possible sequences per codon, 2×64×2 (256) oligonucleotides are required to assemble a library of $64^2$ (4096) templates. The one-pot assembly of the templates for the 83-membered macrocyclic fumaramide library is discussed in Example 9B. Excellent yields of the desired template library resulted from a 4 hour ligation reaction. Following ligation, T7 exonuclease was added to degrade the non-coding template strand (the desired coding strand is protected by its non-natural 5'-aminoethylene glycol linker). This procedure can provide 20 nmoles of the 5' functionalized single-stranded template library (sufficient material for thousands of DNA-templated library syntheses and selections) in about 6 hours. The constant 10-base primer binding regions at the ends of each template were sufficient to permit PCR amplification of as few as 1,000 molecules ($10^{-21}$ mol) of template from this assembled material.

Figure 8:
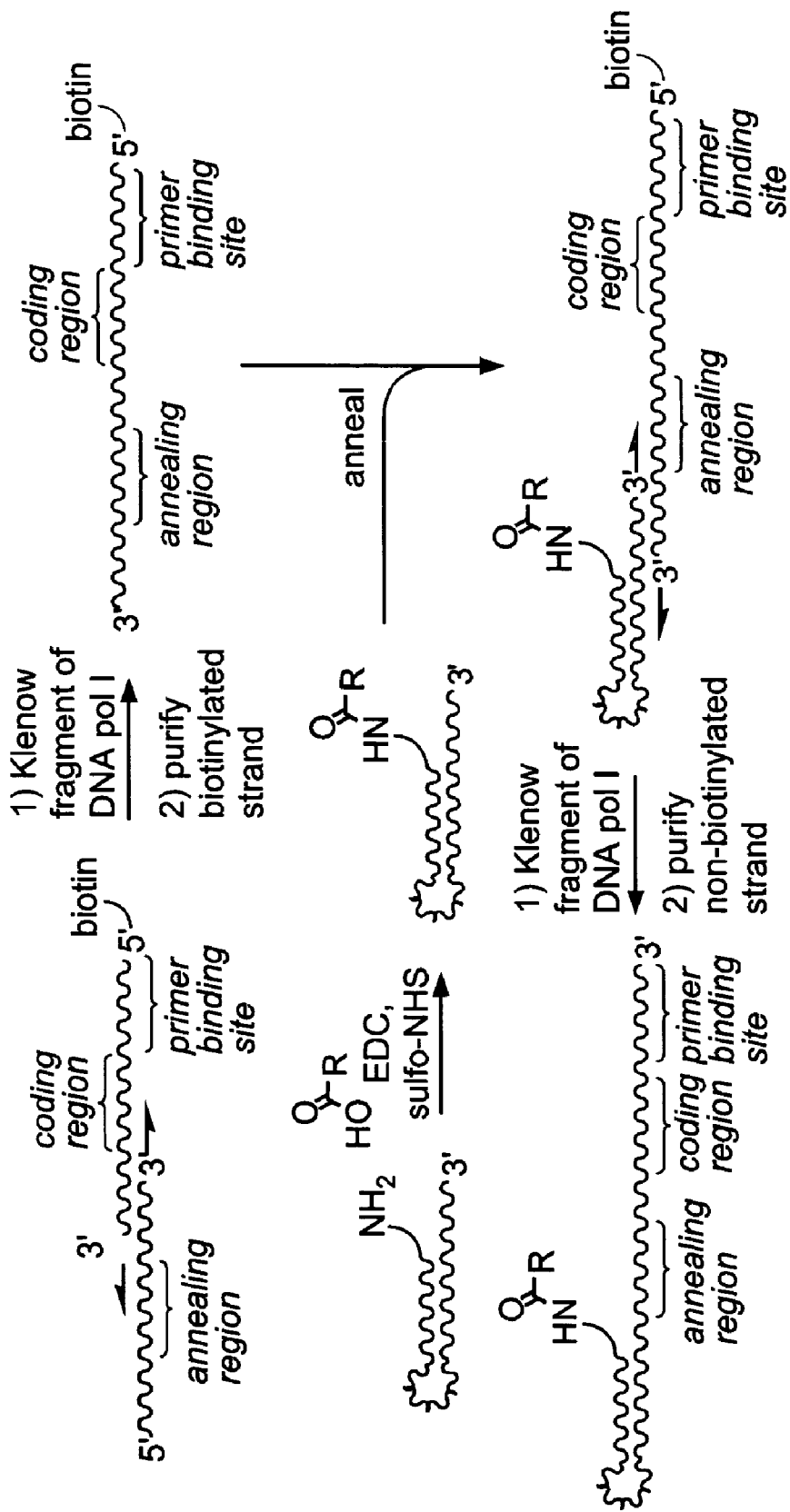
FIG. 8 is a schematic representation of a method for producing a template, containing, from the 5'-end to the 3'-end, a small molecule functional group, a DNA hairpin, an annealing region, a coding region, and a PCR primer binding site.

Another approach for synthesizing templates is shown in FIG. 8. In particular, FIG. 8 shows a protocol for producing a template containing in a 5' to 3' direction, a small molecule reactant, a hairpin loop, an annealing region, a coding region, and a primer binding site. This type of protocol may be used to synthesize a wide variety of templates, in particular, H type templates useful in the practice of the invention.

An efficient method to synthesize a large variety of templates is to use a "split-pool" technique. The oligonucleotides are synthesized using standard 3' to 5' chemistries. First, the constant 3' end is synthesized. This is then split into n different vessels, where n is the number of different codons to appear at that position in the template. For each vessel, one of the n different codons is synthesized on the (growing) 5' end of the constant 3' end. Thus, each vessel contains, from 5' to 3', a different codon attached to a constant 3' end. The n vessels are then pooled, so that a single vessel contains n different codons attached to the constant 3' end. Any constant bases adjacent the 5' end of the codon are now synthesized. The pool then is split into m different vessels, where m is the number of different codons to appear at the next (more 5') position of the template. A different codon is synthesized (at the 5' end of the growing oligonucleotide) in each of the m vessels. The resulting oligonucleotides are pooled in a single vessel. Splitting, synthesizing, and pooling are repeated as required to synthesize all codons and constant regions in the oligonucleotides.

II. Transfer Units

A transfer unit comprises an oligonucleotide containing an anti-codon sequence and a reactive unit. The anti-codons are designed to be complementary to the codons present in the template. Accordingly, the sequences used in the template and the codon lengths should be considered when designing the anti-codons. Any molecule complementary to a codon used in the template may be used, including natural or non-natural nucleotides. In certain embodiments, the codons include one or more bases found in nature (i.e., thymidine, uracil, guanidine, cytosine, and adenine). Thus, the anti-codon can include one or more nucleotides normally found in Nature with a base, a sugar, and an optional phosphate group. Alternatively, the bases may be connected via a backbone other than the sugar-phosphate backbone normally found in Nature (e.g., non-natural nucleotides).

As discussed above, the anti-codon is associated with a particular type of reactive unit to form a transfer unit. The reactive unit may represent a distinct entity or may be part of the functionality of the anti-codon unit. In certain embodiments, each anti-codon sequence is associated with one monomer type. For example, the anti-codon sequence ATTAG may be associated with a carbamate residue with an isobutyl side chain, and the anti-codon sequence CATAG may be associated with a carbamate residue with a phenyl side chain. This one-for-one mapping of anti-codon to monomer units allows the decoding of any polymer of the library by sequencing the nucleic acid template used in the synthesis and allows synthesis of the same polymer or a related polymer by knowing the sequence of the original polymer. By changing (e.g., mutating) the sequence of the template, different monomer units may be introduced, thereby allowing the synthesis of related polymers, which can subsequently be selected and evolved. In certain preferred embodiments, several anti-codons may code for one monomer unit as is the case in Nature.

In certain other embodiments, where a small molecule library is to be created rather than a polymer library, the anti-codon generally is associated with a reactive unit or reactant used to modify a small molecule scaffold. In certain embodiments, the reactant is linked to the anti-codon via a linker long enough to allow the reactant to come into reactive proximity with the small molecule scaffold. The linker preferably has a length and composition to permit intramolecular reactions but yet minimize intermolecular reactions. The reactants include a variety of reagents as demonstrated by the wide range of reactions that can be utilized in nucleic acid-templated synthesis (see, Examples 2, 4 and 7) and can be any chemical group, catalyst (e.g., organometallic compounds), or reactive moiety (e.g., electrophiles, nucleophiles) known in the chemical arts.

Additionally, the association between the anti-codon and the reactive unit, for example, a monomer unit or reactant, in the transfer unit may be covalent or non-covalent. The association maybe through a covalent bond and, in certain embodiments, the covalent bond may be severable.

Thus, the anti-codon can be associated with the reactant through a linker moiety (see Example 3). The linkage can be cleavable by light, oxidation, hydrolysis, exposure to acid, exposure to base, reduction, etc. Fruchtel et al., (1996) ANGEW. CHEM. INT. ED. ENGL. 35: 17 describes a variety of linkages useful in the practice of the invention. The linker facilitates contact of the reactant with the small molecule scaffold and in certain embodiments, depending on the desired reaction, positions DNA as a leaving group ("auto-cleavable" strategy), or may link reactive groups to the template via the "scarless" linker strategy (which yields product without leaving behind an additional atom or atoms having chemical functionality), or a "useful scar" strategy (in which a portion of the linker is left behind to be functionalized in subsequent steps following linker cleavage).

With the "autocleavable" linker strategy, the DNA-reactive group bond is cleaved as a natural consequence of the reaction. In the "scarless" linker strategy, DNA-templated reaction of one reactive group is followed by cleavage of the linker attached through a second reactive group to yield products without leaving behind additional atoms capable of providing chemical functionality. Alternatively, a "useful scar" may be utilized on the theory that it may be advantageous to introduce useful atoms and/or chemical groups as a consequence of linker cleavage. In particular, a "useful scar" is left behind following linker cleavage and can be functionalized in subsequent steps.

The anti-codon and the reactive unit (monomer unit or reactant) may also be associated through non-covalent interactions such as ionic, electrostatic, hydrogen bonding, van der Waals interactions, hydrophobic interactions, pi-stacking, etc. and combinations thereof. To give but one example, an anti-codon may be linked to biotin, and a monomer unit linked to streptavidin. The propensity of streptavidin to bind biotin leads to the non-covalent association between the anti-codon and the monomer unit to form the transfer unit.

The specific annealing of transfer units to templates permits the use of transfer units at concentrations lower than concentrations used in many traditional organic syntheses. Thus, transfer units can be used at submillimolar concentrations (e.g. less than 100 µM, less than 10 µM, less than 1 µM, less than 100 nM, or less than 10 nM).

III. Chemical Reactions

A variety of compounds and/or libraries can be prepared using the methods described herein. In certain embodiments, compounds that are not, or do not resemble, nucleic acids or analogs thereof, are synthesized according to the method of the invention. In certain other embodiments, compounds that are not, or do not resemble, proteins, peptides, or analogs thereof, are synthesized according to the method of the invention.

(i) Coupling Reactions for Small Molecule Synthesis

In some embodiments, it is possible to create compounds such as small molecules using the methods described herein. These small molecules may be like natural products, non-polymeric, and/or non-oligomeric. The substantial interest in small molecules is due in part to their use as the active ingredient in many pharmaceutical preparations although they may also be used, for example, as catalysts, materials, or additives.

In synthesizing small molecules using the method of the present invention, an evolvable template also is provided. The template can include a small molecule scaffold upon which the small molecule is to be built, or a small molecule scaffold may be added to the template. The small molecule scaffold can be any chemical compound with two or more sites for functionalization. For example, the small molecule scaffold can include a ring system (e.g., the ABCD steroid ring system found in cholesterol) with functionalizable groups coupled to the atoms making up the rings. In another example, the small molecule may be the underlying structure of a pharmaceutical agent such as morphine, epothilone or a cephalosporin antibiotic. The sites or groups to be functionalized on the small molecule scaffold may be protected using methods and protecting groups known in the art. The protecting groups used in a small molecule scaffold may be orthogonal to one another so that protecting groups can be removed one at a time.

In this embodiment, the transfer units comprise an anti-codon associated with a reactant or a building block for use in modifying, adding to, or taking away from the small molecule scaffold. The reactants or building blocks may be, for example, electrophiles (e.g., acetyl, amides, acid chlorides, esters, nitriles, imines), nucleophiles (e.g., amines, hydroxyl groups, thiols), catalysts (e.g., organometallic catalysts), or side chains. The transfer units are allowed to contact the template under hybridizing conditions. As a result of oligonucleotide annealing, the attached reactant or building block is allowed to react with a site on the small molecule scaffold. In certain embodiments, protecting groups on the small molecule template are removed one at a time from the sites to be functionalized so that the reactant of the transfer unit will react at only the desired position on the scaffold.

The reaction conditions, linker, reactant, and site to be functionalized are chosen to avoid intermolecular reactions and accelerate intramolecular reactions. Sequential or simultaneous contacting of the template with transfer units can be employed depending on the particular compound to be synthesized. In certain embodiments of special interest, the multi-step synthesis of chemical compounds is provided in which the template is contacted sequentially with two or more transfer units to facilitate multi-step synthesis of complex chemical compounds.

After the sites on the scaffold have been modified, the newly synthesized small molecule remains associated with the template that encoded its synthesis. Decoding the sequence of the template permits the deconvolution of the synthetic history and thereby the structure of the small molecule. The template can also be amplified in order to create more of the desired small molecule and/or the template can be evolved (mutagenized) to create related small molecules. The small molecule can also be cleaved from the template for purification or screening.

(ii) Coupling Reactions for Polymer Synthesis

In certain embodiments, polymers, specifically unnatural polymers, are prepared according to the method of the present invention. The unnatural polymers that can be created using the inventive method and system include any unnatural polymers. Exemplary unnatural polymers include, but are not limited to, peptide nucleic acid (PNA) polymers, polycarbamates, polyureas, polyesters, polyacrylate, polyalkylene (e.g., polyethylene, polypropylene), polycarbonates, polypeptides with unnatural stereochemistry, polypeptides with unnatural amino acids, and combination thereof. In certain embodiments, the polymers comprise at least 10, 25, 75, 100, 125, 150 monomer units or more. The polymers synthesized using the inventive system may be used, for example, as catalysts, pharmaceuticals, metal chelators, or catalysts.

In preparing certain unnatural polymers, the monomer units attached to the anti-codons may be any monomers or oligomers capable of being joined together to form a polymer. The monomer units may be, for example, carbamates, D-amino acids, unnatural amino acids, PNAs, ureas, hydroxy acids, esters, carbonates, acrylates, or ethers. In certain embodiments, the monomer units have two reactive groups used to link the monomer unit into the growing polymer chain, as depicted in FIG. 4. Preferably, the two reactive groups are not the same so that the monomer unit may be incorporated into the polymer in a directional sense, for example, at one end may bean electrophile and at the other end a nucleophile. Reactive groups may include, but are not limited to, esters, amides, carboxylic acids, activated carbonyl groups, acid chlorides, amines, hydroxyl groups, and thiols. In certain embodiments, the reactive groups are masked or protected (Greene et al. (1999) PROTECTIVE GROUPS IN ORGANIC SYNTHESIS 3rd Edition, Wiley) so that polymerization may not take place until a desired time when the reactive groups are deprotected. Once the monomer units are assembled along the nucleic acid template, initiation of the polymerization sequence results in a cascade of polymerization and deprotection steps wherein the polymerization step results in deprotection of a reactive group to be used in the subsequent polymerization step.

The monomer units to be polymerized can include two or more monomers depending on the geometry along the nucleic acid template. The monomer units to be polymerized must be able to stretch along the nucleic acid template and particularly across the distance spanned by its encoding anti-codon and optional spacer sequence. In certain embodiments, the monomer unit actually comprises two monomers, for example, a dicarbamate, a diurea, or a dipeptide. In yet other embodiments, the monomer unit comprises three or more monomers. Example 9C, for example, discloses the synthesis of PNA based polymers wherein each monomer unit comprises four PNA molecules.

The monomer units may contain any chemical groups known in the art. Reactive chemical groups especially those that would interfere with polymerization, hybridization, etc., are preferably masked using known protecting groups (Greene et al. (1999) supra). In general, the protecting groups used to mask these reactive groups are orthogonal to those used in protecting the groups used in the polymerization steps.

It has been discovered that, under certain circumstances, the type of chemical reaction may affect the fidelity of the polymerization process. For example, distance independent chemical reactions (for example, reactions that occur efficiently when the reactive units are spaced apart by intervening bases, for example, amine acylation reactions) may result in the spurious incorporation of the wrong monomers at a particular position of a polymer chain. In contrast, by choosing chemical reactions for template mediated syntheses that are distance dependent (for example, reactions that become inefficient the further the reactive units are spaced part via intervening bases, for example, reductive amination reactions), it is possible control the fidelity of the polymerization process. Example 9 discusses in detail effect of using distance dependent chemical reactions to enhance the fidelity of the polymerization process during template mediated synthesis.

(iii) Functional Group Transformations

Nucleic acid-templated synthesis can be used to effect functional group transformations that either (i) unmask or (ii) interconvert functionality used in coupling reactions. By exposing or creating a reactive group within a sequence-programmed subset of a library, nucleic acid-templated functional group interconversions permit the generation of library diversity by sequential unmasking. The sequential unmasking approach offers the major advantage of enabling reactants that would normally lack the ability to be linked to a nucleic acid (for example, simple alkyl halides) to contribute to library diversity by reacting with a sequence-specified subset of templates in an intermolecular, non-templated reaction mode. This advantage significantly increases the types of structures that can be generated.

One embodiment of the invention involves deprotection or unmasking of functional groups present in a reactive unit. According to this embodiment, a nucleic acid-template is associated with a reactive unit that contains a protected functional group. A transfer unit, comprising an oligonucleotide complimentary to the template codon region and a reagent capable of removing the protecting group, is annealed to the template, and the reagent reacts with the protecting group, removing it from the reactive unit. To further functionalize the reactive unit, the exposed functional group then is subjected to a reagent not linked to a nucleic acid. In some embodiments, the reactive unit contains two or more protected functional groups. In still other embodiments, the protecting groups are orthogonal protecting groups that are sequentially removed by iterated annealing with reagents linked to transfer units.

Another embodiment of the invention involves interconversions of functional groups present on a reactive unit. According to this embodiment, a transfer unit associated with a reagent that can catalyze a reaction is annealed to a template bearing the reactive unit. A reagent not linked to a nucleic acid is added to the reaction, and the transfer unit reagent catalyzes the reaction between the unlinked reagent and the reactive unit, yielding a newly functionalized reactive unit. In some embodiments, the reactive unit contains two or more functional groups which are sequentially interconverted by iterative exposure to different transfer unit-bound reagents.

(iv) Reaction Conditions

Nucleic acid-templated reactions can occur in aqueous or non-aqueous (i.e., organic) solutions, or a mixture of one or more aqueous and non-aqueous solutions. In aqueous solutions, reactions can be performed at pH ranges from about 2 to about 12, or preferably from about 2 to about 10, or more preferably from about 4 to about 10. The reactions used in DNA-templated chemistry preferably should not require very basic conditions (e.g., pH>12, pH>10) or very acidic conditions (e.g., pH<1, pH<2, pH<4), because extreme conditions may lead to degradation or modification of the nucleic acid template and/or molecule (for example, the polymer, or small molecule) being synthesized. The aqueous solution can contain one or more inorganic salts, including, but not limited to, NaCl, $Na_2SO_4$, KCl, $Mg^{+2}$, $Mn^{+2}$, etc., at various concentrations.

Organic solvents suitable for nucleic acid-templated reactions include, but are not limited to, methylene chloride, chloroform, dimethylformamide, and organic alcohols, including methanol and ethanol. To permit quantitative dissolution of reaction components in organic solvents, quaternized ammonium salts, such as, for example, long chain tetraalkylammonium salts, can be added (Jost et al. (1989) NUCLEIC ACIDS RES. 17: 2143; Mel'nikov et al. (1999) LANGMUIR 15: 1923-1928).

Nucleic acid-templated reactions may require a catalyst, such as, for example, homogeneous, heterogeneous, phase transfer, and asymmetric catalysis. In other embodiments, a catalyst is not required. The presence of additional, accessory reagents not linked to a nucleic acid are preferred in some embodiments. Useful accessory reagents can include, for example, oxidizing agents (e.g., $NaIO_4$); reducing agents (e.g., $NaCNBH_3$); activating reagents (e.g., EDC, NHS, and sulfo-NHS); transition metals such as nickel (e.g., $Ni(NO_3)_2$), rhodium (e.g. $RhCl_3$), ruthenium (e.g. $RuCl_3$), copper (e.g. $Cu(NO_3)_2$), cobalt (e.g. $CoCl_2$), iron (e.g. $Fe(NO_3)_3$), osmium (e.g. $OsO_4$), titanium (e.g. $TiCl_4$ or titanium tetraisopropoxide), palladium (e.g. $NaPdCl_4$), or Ln; transition metal ligands (e.g., phosphines, amines, and halides); Lewis acids; and Lewis bases.

Reaction conditions preferably are optimized to suit the nature of the reactive units and oligonucleotides used.

(v) Classes of Chemical Reactions

Known chemical reactions for synthesizing polymers, small molecules, or other chemical compounds can be used in nucleic acid-templated reactions. Thus, reactions such as those listed in *March's Advanced Organic Chemistry, Organic Reactions, Organic Syntheses*, organic text books, journals such as *Journal of the American Chemical Society Journal of Organic Chemistry, Tetrahedra*, etc., and Carruther's *Some Modern Methods of Organic Chemistry* can be used. The chosen reactions preferably are compatible with nucleic acids such as DNA or RNA or are compatible with the modified nucleic acids used as the template.

Reactions useful in nucleic-acid templated chemistry include, for example, substitution reactions, carbon-carbon bond forming reactions, elimination reactions, acylation reactions, and addition reactions. An illustrative but not exhaustive list of aliphatic nucleophilic substitution reactions useful in the present invention includes, for example, $S_N2$ reactions, $S_N1$ reactions, $S_Ni$ reactions, allylic rearrangements, nucleophilic substitution at an aliphatic trigonal carbon, and nucleophilic substation at a vinylic carbon.

Specific aliphatic nucleophilic substitution reactions with oxygen nucleophiles include, for example, hydrolysis of alkyl halides, hydrolysis of gen-dihalides, hydrolysis of 1,1,1-trihalides, hydrolysis of alkyl esters or inorganic acids, hydrolysis of diazo ketones, hydrolysis of acetal and enol ethers, hydrolysis of epoxides, hydrolysis of acyl halides, hydrolysis of anhydrides, hydrolysis of carboxylic esters, hydrolysis of amides, alkylation with alkyl halides (Williamson Reaction), epoxide formation, alkylation with inorganic esters, alkylation with diazo compounds, dehydration of alcohols, transetherification, alcoholysis of epoxides, alkylation with onium salts, hydroxylation of silanes, alcoholysis of acyl halides, alcoholysis of anhydrides, esterfication of carboxylic acids, alcoholysis of carboxylic esters (transesterfication), alcoholysis of amides, alkylation of carboxylic acid salts, cleavage of ether with acetic anhydride, alkylation of carboxylic acids with diazo compounds, acylation of caroxylic acids with acyl halides, acylation of carboxylic acids with carboxylic acids, formation of oxonium salts, preparation of peroxides and hydroperoxides, preparation of inorganic esters (e.g., nitrites, nitrates, sulfonates), preparation of alcohols from amines, and preparation of mixed organic-inorganic anhydrides.

Specific aliphatic nucleophilic substitution reactions with sulfur nucleophiles, which tend to be better nucleophiles than their oxygen analogs, include, for example, attack by SH at an alkyl carbon to form thiols, attack by S at an alkyl carbon to form thioethers, attack by SH or SR at an acyl carbon, formation of disulfides, formation of Bunte salts, alkylation of sulfonic acid salts, and formation of alkyl thiocyanates.

Aliphatic nucleophilic substitution reactions with nitrogen nucleophiles include, for example, alkylation of amines, N-arylation of amines, replacement of a hydroxy by an amino group, transamination, transamidation, alkylation of amines with diazo compounds, amination of epoxides, amination of oxetanes, amination of aziridines, amination of alkanes, formation of isocyanides, acylation of amines by acyl halides, acylation of amines by anhydrides, acylation of amines by carboxylic acids, acylation of amines by carboxylic esters, acylation of amines by amides, acylation of amines by other acid derivatives, N-alkylation or N-arylation of amides and imides, N-acylation of amides and imides, formation of aziridines from epoxides, formation of nitro compounds, formation of azides, formation of isocyanates and isothiocyanates, and formation of azoxy compounds.

Aliphatic nucleophilic substitution reactions with halogen nucleophiles include, for example, attack at an alkyl carbon, halide exchange, formation of alkyl halides from esters of sulfuric and sulfonic acids, formation of alkyl halides from alcohols, formation of alkyl halides from ethers, formation of halohydrins from epoxides, cleavage of carboxylic esters with lithium iodide, conversion of diazo ketones to α-halo ketones, conversion of amines to halides, conversion of tertiary amines to cyanamides (the von Braun reaction), formation of acyl halides from carboxylic acids, and formation of acyl halides from acid derivatives.

Aliphatic nucleophilic substitution reactions using hydrogen as a nucleophile include, for example, reduction of alkyl halides, reduction of tosylates, other sulfonates, and similar compounds, hydrogenolysis of alcohols, hydrogenolysis of esters (Barton-McCombie reaction), hydrogenolysis of nitriles, replacement of alkoxyl by hydrogen, reduction of epoxides, reductive cleavage of carboxylic esters, reduction of a C—N bond, desulfurization, reduction of acyl halides, reduction of carboxylic acids, esters, and anhydrides to aldehydes, and reduction of amides to aldehydes.

Although certain carbon nucleophiles may be too nucleophilic and/or basic to be used in certain embodiments of the invention, aliphatic nucleophilic substitution reactions using carbon nucleophiles include, for example, coupling with silanes, coupling of alkyl halides (the Wurtz reaction), the reaction of alkyl halides and sulfonate esters with Group I (I A) and II (II A) organometallic reagents, reaction of alkyl halides and sulfonate esters with organocuprates, reaction of alkyl halides and sulfonate esters with other organometallic reagents, allylic and propargylic coupling with a halide substrate, coupling of organometallic reagents with esters of sulfuric and sulfonic acids, sulfoxides, and sulfones, coupling involving alcohols, coupling of organometallic reagents with carboxylic esters, coupling of organometallic reagents with compounds containing an esther linkage, reaction of organometallic reagents with epoxides, reaction of organometallics with aziridine, alkylation at a carbon bearing an active hydrogen, alkylation of ketones, nitriles, and carboxylic esters, alkylation of carboxylic acid salts, alkylation at a position α to a heteroatom (alkylation of 1,3-dithianes), alkylation of dihydro-1,3-oxazine (the Meyers synthesis of aldehydes, ketones, and carboxylic acids), alkylation with trialkylboranes, alkylation at an alkynyl carbon, preparation of nitriles, direct conversion of alkyl halides to aldehydes and ketones, conversion of alkyl halides, alcohols, or alkanes to carboxylic acids and their derivatives, the conversion of acyl halides to ketones with organometallic compounds, the conversion of anhydrides, carboxylic esters, or amides to ketones with organometallic compounds, the coupling of acyl halides, acylation at a carbon bearing an active hydrogen, acylation of carboxylic esters by carboxylic esters (the Claisen and Dieckmann condensation), acylation of ketones and nitriles with carboxylic esters, acylation of carboxylic acid salts, preparation of acyl cyanides, and preparation of diazo ketones, ketonic decarboxylation.

Reactions which involve nucleophilic attack at a sulfonyl sulfur atom may also be used in the present invention and include, for example, hydrolysis of sulfonic acid derivatives (attack by OH), formation of sulfonic esters (attack by OR), formation of sulfonamides (attack by nitrogen), formation of sulfonyl halides (attack by halides), reduction of sulfonyl chlorides (attack by hydrogen), and preparation of sulfones (attack by carbon).

Aromatic electrophilic substitution reactions may also be used in nucleotide-templated chemistry. Hydrogen exchange reactions are examples of aromatic electrophilic substitution reactions that use hydrogen as the electrophile. Aromatic electrophilic substitution reactions which use nitrogen electrophiles include, for example, nitration and nitro-de-hydrogenation, nitrosation of nitroso-de-hydrogenation, diazonium coupling, direct introduction of the diazonium group, and amination or amino-de-hydrogenation. Reactions of this type with sulfur electrophiles include, for example, sulfonation, sulfo-de-hydrogenation, halosulfonation, halosulfo-de-hydrogenation, sulfurization, and sulfonylation. Reactions using halogen electrophiles include, for example, halogenation, and halo-de-hydrogenation. Aromatic electrophilic substitution reactions with carbon electrophiles include, for example, Friedel-Crafts alkylation, alkylation, alkyl-de-hydrogenation, Friedel-Crafts arylation (the Scholl reaction), Friedel-Crafts acylation, formylation with disubstituted formamides, formylation with zinc cyanide and HCl (the Gatterman reaction), formylation with chloroform (the Reimer-Tiemann reaction), other formylations, formyl-de-hydrogenation, carboxylation with carbonyl halides, carboxylation with carbon dioxide (the Kolbe-Schmitt reaction), amidation with isocyanates, N-alkylcarbamoyl-de-hydrogenation, hydroxyalkylation, hydroxyalkyl-de-hydrogenation, cyclodehydration of aldehydes and ketones, haloalkylation, halo-de-hydrogenation, aminoalkylation, amidoalkylation, dialkylaminoalkylation, dialkylamino-de-hydrogenation, thioalkylation, acylation with nitriles (the Hoesch reaction), cyanation, and cyano-de-hydrogenation. Reactions using oxygen electrophiles include, for example, hydroxylation and hydroxy-de-hydrogenation.

Rearrangement reactions include, for example, the Fries rearrangement, migration of a nitro group, migration of a nitroso group (the Fischer-Hepp Rearrangement), migration of an arylazo group, migration of a halogen (the Orton rearrangement), migration of an alkyl group, etc. Other reaction on an aromatic ring include the reversal of a Friedel-Crafts alkylation, decarboxylation of aromatic aldehydes, decarboxylation of aromatic acids, the Jacobsen reaction, deoxygenation, desulfonation, hydro-de-sulfonation, dehalogenation, hydro-de-halogenation, and hydrolysis of organometallic compounds.

Aliphatic electrophilic substitution reactions are also useful. Reactions using the $S_E1$, $S_E2$ (front), $S_E2$ (back), $S_Ei$, addition-elimination, and cyclic mechanisms can be used in the present invention. Reactions of this type with hydrogen as the leaving group include, for example, hydrogen exchange (deuterio-de-hydrogenation, deuteriation), migration of a double bond, and keto-enol tautomerization. Reactions with halogen electrophiles include, for example, halogenation of aldehydes and ketones, halogenation of carboxylic acids and acyl halides, and halogenation of sulfoxides and sulfones. Reactions with nitrogen electrophiles include, for example, aliphatic diazonium coupling, nitrosation at a carbon bearing an active hydrogen, direct formation of diazo compounds, conversion of amides to α-azido amides, direct amination at an activated position, and insertion by nitrenes. Reactions with sulfur or selenium electrophiles include, for example, sulfenylation, sulfonation, and selenylation of ketones and carboxylic esters. Reactions with carbon electrophiles include, for example, acylation at an aliphatic carbon, conversion of aldehydes to β-keto esters or ketones, cyanation, cyano-de-hydrogenation, alkylation of alkanes, the Stork enamine reaction, and insertion by carbenes. Reactions with metal electrophiles include, for example, metalation with organometallic compounds, metalation with metals and strong bases, and conversion of enolates to silyl enol ethers. Aliphatic electrophilic substitution reactions with metals as leaving groups include, for example, replacement of metals by hydrogen, reactions between organometallic reagents and oxygen, reactions between organometallic reagents and peroxides, oxidation of trialkylboranes to borates, conversion of Grignard reagents to sulfur compounds, halo-de-metalation, the conversion of organometallic compounds to amines, the conversion of organometallic compounds to ketones, aldehydes, carboxylic esters and amides, cyano-de-metalation, transmetalation with a metal, transmetalation with a metal halide, transmetalation with an organometallic compound, reduction of alkyl halides, metallo-de-halogenation, replacement of a halogen by a metal from an organometallic compound, decarboxylation of aliphatic acids, cleavage of alkoxides, replacement of a carboxyl group by an acyl group, basic cleavage of β-keto esters and β-diketones, haloform reaction, cleavage of non-enolizable ketones, the Haller-Bauer reaction, cleavage of alkanes, decyanation, and hydro-de-cyanation. Electrophlic substitution reactions at nitrogen include, for example, diazotization, conversion of hydrazines to azides, N-nitrosation, N-nitroso-de-hydrogenation, conversion of amines to azo compounds, N-halogenation, N-halode-hydrogenation, reactions of amines with carbon monoxide, and reactions of amines with carbon dioxide.

Aromatic nucleophilic substitution reactions may also be used in the present invention. Reactions proceeding via the $S_NAr$ mechanism, the $S_N1$ mechanism, the benzyne mechanism, the $S_{RN}1$ mechanism, or other mechanism, for example, can be used. Aromatic nucleophilic substitution reactions with oxygen nucleophiles include, for example, hydroxy-dehalogenation, alkali fusion of sulfonate salts, and replacement of OR or OAr. Reactions with sulfur nucleophiles include, for example, replacement by SH or SR. Reactions using nitrogen nucleophiles include, for example, replacement by $NH_2$, NHR, or $NR_2$, and replacement of a hydroxy group by an amino group. Reactions with halogen nucleophiles include, for example, the introduction halogens. Aromatic nucleophilic substitution reactions with hydrogen as the nucleophile include, for example, reduction of phenols and phenolic esters and ethers, and reduction of halides and nitro compounds. Reactions with carbon nucleophiles include, for example, the Rosenmund-von Braun reaction, coupling of organometallic compounds with aryl halides, ethers, and carboxylic esters, arylation at a carbon containing an active hydrogen, conversions of aryl substrates to carboxylic acids, their derivatives, aldehydes, and ketones, and the Ullmann reaction. Reactions with hydrogen as the leaving group include, for example, alkylation, arylation, and amination of nitrogen heterocycles. Reactions with $N_2^+$ as the leaving group include, for example, hydroxy-de-diazoniation, replacement by sulfur-containing groups, iodo-de-diazoniation, and the Schiemann reaction. Rearrangement reactions include, for example, the von Richter rearrangement, the Sommelet-Hauser rearrangement, rearrangement of aryl hydroxylamines, and the Smiles rearrangement.

Reactions involving free radicals can also be used, although the free radical reactions used in nucleotide-templated chemistry should be carefully chosen to avoid modification or cleavage of the nucleotide template. With that limitation, free radical substitution reactions can be used in the present invention. Particular free radical substitution reactions include, for example, substitution by halogen, halogenation at an alkyl carbon, allylic halogenation, benzylic halogenation, halogenation of aldehydes, hydroxylation at an aliphatic carbon, hydroxylation at an aromatic carbon, oxidation of aldehydes to carboxylic acids, formation of cyclic ethers, formation of hydroperoxides, formation of peroxides, acyloxylation, acyloxy-de-hydrogenation, chlorosulfonation, nitration of alkanes, direct conversion of aldehydes to amides, amidation and amination at an alkyl carbon, simple coupling at a susceptible position, coupling of alkynes, arylation of aromatic compounds by diazonium salts, arylation of activated alkenes by diazonium salts (the Meerwein arylation), arylation and alkylation of alkenes by organopalladium compounds (the Heck reaction), arylation and alkylation of alkenes by vinyltin compounds (the Stille reaction), alkylation and arylation of aromatic compounds by peroxides, photochemical arylation of aromatic compounds, alkylation, acylation, and carbalkoxylation of nitrogen heterocycles Particular reactions in which $N_2^+$ is the leaving group include, for example, replacement of the diazonium group by hydrogen, replacement of the diazonium group by chlorine or bromine, nitro-de-diazoniation, replacement of the diazonium group by sulfur-containing groups, aryl dimerization with diazonium salts, methylation of diazonium salts, vinylation of diazonium salts, arylation of diazonium salts, and conversion of diazonium salts to aldehydes, ketones, or carboxylic acids. Free radical substitution reactions with metals as leaving groups include, for example, coupling of Grignard reagents, coupling of boranes, and coupling of other organometallic reagents. Reaction with halogen as the leaving group are included. Other free radical substitution reactions with various leaving groups include, for example, desulfurization with Raney Nickel, conversion of sulfides to organolithium compounds, decarboxylative dimerization (the Kolbe reaction), the Hunsdiecker reaction, decarboxylative allylation, and decarbonylation of aldehydes and acyl halides.

Reactions involving additions to carbon-carbon multiple bonds are also used in nucleotide-templated chemistry. Any mechanism may be used in the addition reaction including, for example, electrophilic addition, nucleophilic addition, free radical addition, and cyclic mechanisms. Reactions involving additions to conjugated systems can also be used. Addition to cyclopropane rings can also be utilized. Particular reactions include, for example, isomerization, addition of hydrogen halides, hydration of double bonds, hydration of triple bonds, addition of alcohols, addition of carboxylic acids, addition of $H_2S$ and thiols, addition of ammonia and amines, addition of amides, addition of hydrazoic acid, hydrogenation of double and triple bonds, other reduction of double and triple bonds, reduction of the double and triple bonds of conjugated systems, hydrogenation of aromatic rings, reductive cleavage of cyclopropanes, hydroboration, other hydrometalations, addition of alkanes, addition of alkenes and/or alkynes to alkenes and/or alkynes (e.g., pi-cation cyclization reactions, hydro-alkenyl-addition), ene reactions, the Michael reaction, addition of organometallics to double and triple bonds not conjugated to carbonyls, the addition of two alkyl groups to an alkyne, 1,4-addition of organometallic compounds to activated double bonds, addition of boranes to activated double bonds, addition of tin and mercury hydrides to activated double bonds, acylation of activated double bonds and of triple bonds, addition of alcohols, amines, carboxylic esters, aldehydes, etc., carbonylation of double and triple bonds, hydrocarboxylation, hydroformylation, addition of aldehydes, addition of HCN, addition of silanes, radical addition, radical cyclization, halogenation of double and triple bonds (addition of halogen, halogen), halolactonization, halolactamization, addition of hypohalous acids and hypohalites (addition of halogen, oxygen), addition of sulfur compounds (addition of halogen, sulfur), addition of halogen and an amino group (addition of halogen, nitrogen), addition of NOX and $NO_2X$ (addition of halogen, nitrogen), addition of $XN_3$ (addition of halogen, nitrogen), addition of alkyl halides (addition of halogen, carbon), addition of acyl halides (addition of halogen, carbon), hydroxylation (addition of oxygen, oxygen) (e.g., asymmetric dihydroxylation reaction with $OsO_4$), dihydroxylation of aromatic rings, epoxidation (addition of oxygen, oxygen) (e.g., Sharpless asymmetric epoxidation), photooxidation of dienes (addition of oxygen, oxygen), hydroxysulfenylation (addition of oxygen, sulfur), oxyamination (addition of oxygen, nitrogen), diamination (addition of nitrogen, nitrogen), formation of aziridines (addition of nitrogen), aminosulfenylation (addition of nitrogen, sulfur), acylacyloxylation and acylamidation (addition of oxygen, carbon or nitrogen, carbon), 1,3-dipolar addition (addition of oxygen, nitrogen, carbon), Diels-Alder reaction, heteroatom Diels-Alder reaction, all carbon 3+2 cycloadditions, dimerization of alkenes, the addition of carbenes and carbenoids to double and triple bonds, trimerization and tetramerization of alkynes, and other cycloaddition reactions.

In addition to reactions involving additions to carbon-carbon multiple bonds, addition reactions to carbon-hetero multiple bonds can be used in nucleotide-templated chemistry. Exemplary reactions include, for example, the addition of water to aldehydes and ketones (formation of hydrates), hydrolysis of carbon-nitrogen double bond, hydrolysis of aliphatic nitro compounds, hydrolysis of nitriles, addition of alcohols and thiols to aldehydes and ketones, reductive alkylation of alcohols, addition of alcohols to isocyanates, alcoholysis of nitriles, formation of xanthates, addition of $H_2S$ and thiols to carbonyl compounds, formation of bisulfite addition products, addition of amines to aldehydes and ketones, addition of amides to aldehydes, reductive alkylation of ammonia or amines, the Mannich reaction, the addition of amines to isocyanates, addition of ammonia or amines to nitriles, addition of amines to carbon disulfide and carbon dioxide, addition of hydrazine derivative to carbonyl compounds, formation of oximes, conversion of aldehydes to nitriles, formation of gem-dihalides from aldehydes and ketones, reduction of aldehydes and ketones to alcohols, reduction of the carbon-nitrogen double bond, reduction of nitriles to amines, reduction of nitriles to aldehydes, addition of Grignard reagents and organolithium reagents to aldehydes and ketones, addition of other organometallics to aldehydes and ketones, addition of trialkylallylsilanes to aldehydes and ketones, addition of conjugated alkenes to aldehydes (the Baylis-Hillman reaction), the Reformatsky reaction, the conversion of carboxylic acid salts to ketones with organometallic compounds, the addition of Grignard reagents to acid derivatives, the addition of organometallic compounds to $CO_2$ and $CS_2$, addition of organometallic compounds to C=N compounds, addition of carbenes and diazoalkanes to C=N compounds, addition of Grignard reagents to nitriles and isocyanates, the Aldol reaction, Mukaiyama Aldol and related reactions, Aldol-type reactions between carboxylic esters or amides and aldehydes or ketones, the Knoevenagel reaction (e.g., the Nef reaction, the Favorskii reaction), the Peterson alkenylation reaction, the addition of active hydrogen compounds to $CO_2$ and $CS_2$, the Perkin reaction, Darzens glycidic ester condensation, the Tollens' reaction, the Wittig reaction, the Tebbe alkenylation, the Petasis alkenylation, alternative alkenylations, the Thorpe reaction, the Thorpe-Ziegler reaction, addition of silanes, formation of cyanohydrins, addition of HCN to C=N and C=N bonds, the Prins reaction, the benzoin condensation, addition of radicals to C=O, C=S, C=N compounds, the Ritter reaction, acylation of aldehydes and ketones, addition of aldehydes to aldehydes, the addition of isocyanates to isocyanates (formation of carbodiimides), the conversion of carboxylic acid salts to nitriles, the formation of epoxides from aldehydes and ketones, the formation of episulfides and episulfones, the formation of β-lactones and oxetanes (e.g., the Paterno-Büchi reaction), the formation of β-lactams, etc. Reactions involving addition to isocyanides include the addition of water to isocyanides, the Passerini reaction, the Ug reaction, and the formation of metalated aldimines.

Elimination reactions, including α, β, and γ eliminations, as well as extrusion reactions, can be performed using nucleotide-templated chemistry, although the strength of the reagents and conditions employed should be considered. Preferred elimination reactions include reactions that go by E1, E2, E1cB, or E2C mechanisms. Exemplary reactions include, for example, reactions in which hydrogen is removed from one side (e.g., dehydration of alcohols, cleavage of ethers to alkenes, the Chugaev reaction, ester decomposition, cleavage of quarternary ammonium hydroxides, cleavage of quaternary ammonium salts with strong bases, cleavage of amine oxides, pyrolysis of keto-ylids, decomposition of toluene-p-solfonylhydrazones, cleavage of sulfoxides, cleavage of selenoxides, cleavage of sulfornes, dehydrogalogenation of alkyl halides, dehydrohalogenation of acyl halides, dehydrohalogenation of sulfonyl halides, elimination of boranes, conversion of alkenes to alkynes, decarbonylation of acyl halides), reactions in which neither leaving atom is hydrogen (e.g., deoxygenation of vicinal diols, cleavage of cyclic thionocarbonates, conversion of epoxides to episulfides and alkenes, the Ramberg-Bäcklund reaction, conversion of aziridines to alkenes, dehalogenation of vicinal dihalides, dehalogenation of $\alpha$-halo acyl halides, and elimination of a halogen and a hetero group), fragmentation reactions (i.e., reactions in which carbon is the positive leaving group or the electrofuge, such as, for example, fragmentation of $\gamma$-amino and $\gamma$-hydroxy halides, fragmentation of 1,3-diols, decarboxylation of $\beta$-hydroxy carboxylic acids, decarboxylation of $\beta$-lactones, fragmentation of $\alpha,\beta$-epoxy hydrazones, elimination of CO from bridged bicyclic compounds, and elimination of $CO_2$ from bridged bicyclic compounds), reactions in which C≡C or C≡N bonds are formed (e.g., dehydration of aldoximes or similar compounds, conversion of ketoximes to nitriles, dehydration of unsubstituted amides, and conversion of N-alkylformamides to isocyanides), reactions in which C=O bonds are formed (e.g., pyrolysis of $\beta$-hydroxy alkenes), and reactions in which N=N bonds are formed (e.g., eliminations to give diazoalkenes). Extrusion reactions include, for example, extrusion of $N_2$ from pyrazolines, extrusion of $N_2$ from pyrazoles, extrusion of $N_2$ from triazolines, extrusion of CO, extrusion of $CO_2$, extrusion of $SO_2$, the Story synthesis, and alkene synthesis by twofold extrusion.

Rearrangements, including, for example, nucleophilic rearrangements, electrophilic rearrangements, prototropic rearrangements, and free-radical rearrangements, can also be performed using nucleotide-templated chemistry. Both 1,2 rearrangements and non-1,2 rearrangements can be performed. Exemplary reactions include, for example, carbon-to-carbon migrations of R, H, and Ar (e.g., Wagner-Meerwein and related reactins, the Pinacol rearrangement, ring expansion reactions, ring contraction reactions, acid-catalyzed rearrangements of aldehydes and ketones, the dienone-phenol rearrangement, the Favorskii rearrangement, the Arndt-Eistert synthesis, homologation of aldehydes, and homologation of ketones), carbon-to-carbon migrations of other groups (e.g., migrations of halogen, hydroxyl, amino, etc.; migration of boron; and the Neber rearrangement), carbon-to-nitrogen migrations of R and Ar (e.g., the Hofmann rearrangement, the Curtius rearrangement, the Lossen rearrangement, the Schmidt reaction, the Beckman rearrangement, the Stieglits rearrangement, and related rearrangements), carbon-to-oxygen migrations of R and Ar (e.g., the Baeyer-Villiger rearrangement and rearrangement of hydroperoxides), nitrogen-to-carbon, oxygen-to-carbon, and sulfur-to-carbon migration (e.g., the Stevens rearrangement, and the Wittig rearrangement), boron-to-carbon migrations (e.g., conversion of boranes to alcohols (primary or otherwise), conversion of boranes to aldehydes, conversion of boranes to carboxylic acids, conversion of vinylic boranes to alkenes, formation of alkynes from boranes and acetylides, formation of alkenes from boranes and acetylides, and formation of ketones from boranes and acetylides), electrocyclic rearrangements (e.g., of cyclobutenes and 1,3-cyclohexadienes, or conversion of stilbenes to phenanthrenes), sigmatropic rearrangements (e.g., (1,j) sigmatropic migrations of hydrogen, (1,j) sigmatropic migrations of carbon, conversion of vinylcyclopropanes to cyclopentenes, the Cope rearrangement, the Claisen rearrangement, the Fischer indole synthesis, (2,3) sigmatropic rearrangements, and the benzidine rearrangement), other cyclic rearrangements (e.g., metathesis of alkenes, the di-$\pi$-methane and related rearrangements, and the Hofmann-Löffler and related reactions), and non-cyclic rearrangements (e.g., hydride shifts, the Chapman rearrangement, the Wallach rearrangement, and dyotropic rearrangements).

Oxidative and reductive reactions may also be performed using nucleotide-templated chemistry. Exemplary reactions may involve, for example, direct electron transfer, hydride transfer, hydrogen-atom transfer, formation of ester intermediates, displacement mechanisms, or addition-elimination mechanisms. Exemplary oxidations include, for example, eliminations of hydrogen (e.g., aromatization of six-membered rings, dehydrogenations yielding carbon-carbon double bonds, oxidation or dehydrogenation of alcohols to aldehydes and ketones, oxidation of phenols and aromatic amines to quinones, oxidative cleavage of ketones, oxidative cleavage of aldehydes, oxidative cleavage of alcohols, ozonolysis, oxidative cleavage of double bonds and aromatic rings, oxidation of aromatic side chains, oxidative decarboxylation, and bisdecarboxylation), reactions involving replacement of hydrogen by oxygen (e.g., oxidation of methylene to carbonyl, oxidation of methylene to OH, $CO_2R$, or OR, oxidation of arylmethanes, oxidation of ethers to carboxylic esters and related reactions, oxidation of aromatic hydrocarbons to quinones, oxidation of amines or nitro compounds to aldehydes, ketones, or dihalides, oxidation of primary alcohols to carboxylic acids or carboxylic esters, oxidation of alkenes to aldehydes or ketones, oxidation of amines to nitroso compounds and hydroxylamines, oxidation of primary amines, oximes, azides, isocyanates, or notroso compounds, to nitro compounds, oxidation of thiols and other sulfur compounds to sulfonic acids), reactions in which oxygen is added to the substrate (e.g., oxidation of alkynes to $\alpha$-diketones, oxidation of tertiary amines to amine oxides, oxidation of thioesters to sulfoxides and sulfones, and oxidation of carboxylic acids to peroxy acids), and oxidative coupling reactions (e.g., coupling involving carbanoins, dimerization of silyl enol ethers or of lithium enolates, and oxidation of thiols to disulfides).

Exemplary reductive reactions include, for example, reactions involving replacement of oxygen by hydrogen (e.g., reduction of carbonyl to methylene in aldehydes and ketones, reduction of carboxylic acids to alcohols, reduction of amides to amines, reduction of carboxylic esters to ethers, reduction of cyclic anhydrides to lactones and acid derivatives to alcohols, reduction of carboxylic esters to alcohols, reduction of carboxylic acids and esters to alkanes, complete reduction of epoxides, reduction of nitro compounds to amines, reduction of nitro compounds to hydroxylamines, reduction of nitroso compounds and hydroxylamines to amines, reduction of oximes to primary amines or aziridines, reduction of azides to primary amines, reduction of nitrogen compounds, and reduction of sulfonyl halides and sulfonic acids to thiols), removal of oxygen from the substrate (e.g., reduction of amine oxides and azoxy compounds, reduction of sulfoxides and sulfones, reduction of hydroperoxides and peroxides, and reduction of aliphatic nitro compounds to oximes or nitriles), reductions that include cleavage (e.g., de-alkylation of amines and amides, reduction of azo, azoxy, and hydrazo compounds to amines, and reduction of disulfides to thiols), reductive couplic reactions (e.g., bimolecular reduction of aldehydes and ketones to 1,2-diols, bimolecular reduction of aldehydes or ketones to alkenes, acyloin ester condensation, reduction of nitro to azoxy compounds, and reduction of nitro to azo compounds), and reductions in which an organic substrate is both oxidized and reduced (e.g., the Cannizzaro reaction, the Tishchenko reaction, the Pummerer rearrangement, and the Willgerodt reaction).

(vi) Stereoselectivity

The chiral nature of nucleic acids raises the possibility that nucleic acid-templated synthesis can proceed stereoselectively without the assistance of chiral groups beyond those present in the nucleic acid, thereby transferring not only sequence but also stereochemical information from the template to the product. Previous studies have demonstrated that the chirality of nucleic acid templates can induce a preference for the template-directed ligation of (D)-nucleotides over (L)-nucleotides (Kozlov et al. (2000) ANGEW. CHEM. INT. ED. 39: 4292-4295; Bolli et al. (1997) A. CHEM. BIOL. 4: 309-320).

During nucleic acid-templated synthesis it is possible to transfer the chirality of a nucleic acid template transfer unit, catalyst or a combination of the foregoing to reaction products that do not resemble the nucleic acid backbone. In some embodiments, the reactive unit with a chiral center is associated with the template and the reactive unit associated with the transfer unit is achiral, while in other embodiments, the transfer unit's reactive unit is chiral and the template's reactive unit is achiral. Alternatively, both reactive units can possess chiral centers. In each of these cases, the chirality of the template directs which of the chiral reactive unit's stereoisomers reacts preferentially (i.e., with a higher rate constant) with the other reactive unit.

Useful template architectures include the H type, E type, Ω type and T type architecture. One or more template or transfer unit nucleotides may be replaced with non-nucleotide linkers, however, replacement of the nucleotides nearest the reactive units may result in loss of stereoselectivity. Preferably, 5 or more consecutive aromatic nucleotides are adjacent to the reactive units, and more preferably 6 or more consecutive aromatic nucleotides are adjacent to the reactive units.

At high salt concentrations, double-stranded DNA sequences rich in (5-Me-C)G repeats can adopt a left-handed helix (Z-form) rather than the usual right-handed helix (B-form). During DNA-templated synthesis, template-transfer unit complexes in the Z-form cause preferential reaction with one stereoisomer of a reactive unit, while template-transfer unit complexes in the B-form cause preferential reaction with the other stereoisomer of a reactive unit. Therefore, in some embodiments, a high concentration (e.g., at least 2.5 M, or at least 5 M) of a salt, such as, for example, sodium chloride (NaCl) or sodium sulfate ($Na_2SO_4$) is used during DNA-templated synthesis. In other embodiments, the concentration of salt is low (e.g., not greater than 100 mM) or is not present at all. The principles of DNA-templated stereospecific reactions are discussed in more detail in Example 6.

(vii) Otherwise Incompatible Reactions

It has been discovered that during nucleic acid-templated synthesis, oligonucleotides can simultaneously direct several different types of synthetic reactions within the same solution, even though the reactants involved would be cross-reactive and therefore incompatible under traditional synthesis conditions (see, Example 7). As a result, nucleic acid-templated synthesis permits one-pot diversification of synthetic library precursors into products of multiple reaction types.

In one embodiment, one or more templates associated with a single reactive unit are exposed to two or more transfer units, each associated with a different reagent that is capable of reacting with the templates reactive unit. In other embodiments, one or more transfer units associated with a single reagent are exposed to two or more templates, each associated with a different reactive unit that is capable of reacting with the reagent. Under the conditions of nucleic acid-templated synthesis, it is possible to have in a single solution multiple reactive units (attached to the template and/or the transfer units) that in normal synthetic reactions would cross react with one another. The nucleic acid-templated chemistries described herein use very low concentrations of reactants that because of concentration effects do not react with one another. It is only when the reactants are brought together via annealing of the oligonucleotide in the transfer unit to the template that their local concentrations are increased to permit a reaction occur. In some embodiments, a single accessory reagent (i.e., a reagent not linked to a nucleic acid or nucleic acid analog), such as, for example, a reducing agent, an oxidizing agent, or an activating agent, is added to the reaction. In other embodiments, no accessory reagent is added. In all cases, only the reactive units and reagents that are associated with complimentary oligonucleotides (i.e., that contain complimentary codon/anti-codon sequences) react to form a reaction product, demonstrating the ability of nucleic acid-templated synthesis to direct the selective one-pot transformation of a single functional group into multiple distinct types of products.

In another embodiment, templates and transfer units are provided as described above, but the template reactive units and transfer unit reagents react with one another using multiple different reaction types. In some embodiments, multiple different accessory reagents are added to the reaction. Again, only reaction products resulting from complimentary template/transfer unit sequences are formed in appreciable amounts.

In certain embodiments, multiple transfer unit reagents are capable of reacting with each template reactive unit, and some of the transfer unit reagents can cross react with one another. Even in the presence of several different cross-reactive functional groups, only reaction products resulting from complimentary template/transfer unit sequences are formed in appreciable amounts. These findings indicate that reactions of significantly different rates requiring a variety of accessory reagents can be directed by nucleic acid-templated synthesis in the same solution, even when both templates and reagents contain several different cross-reactive functional groups. The ability of nucleic acid templates to direct multiple reactions at concentrations that exclude non-templated reactions from proceeding at appreciable rates mimics, in a single solution, a spatially separated set of reactions.

(viii) Identification of New Chemical Reactions

Figure 12:
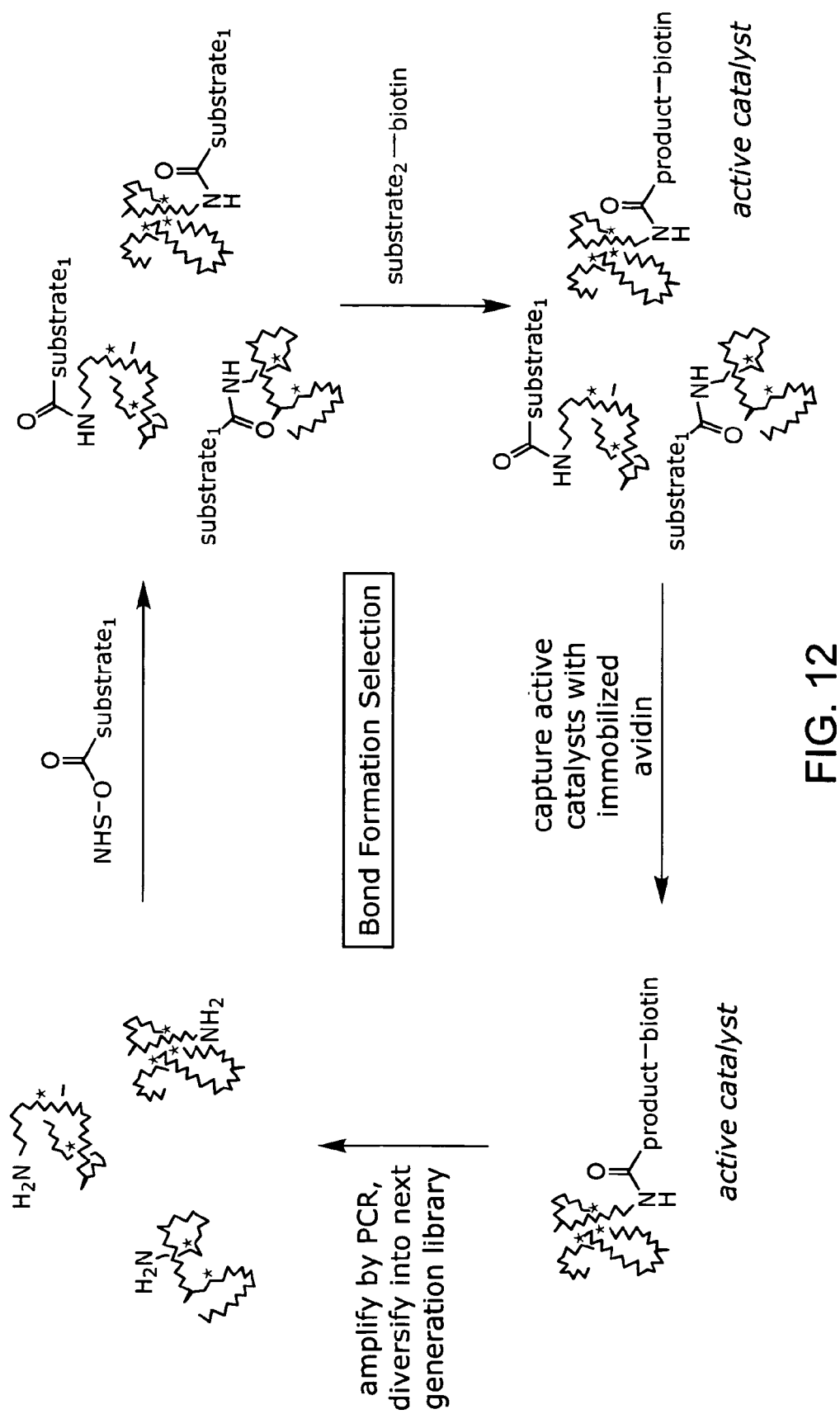
FIG. 12 is a schematic representation of an in vitro selection scheme for identifying non-natural polymer catalysts of bond-forming reactions.

In another aspect of the invention, as illustrated in FIG. 12, nucleic acid-templated synthesis can be used to discover previously unknown chemical reactions between two or more reactive units. To facilitate reaction discovery, multiple templates are synthesized, each comprising a different reactive unit coupled to a different oligonucleotide. Each template oligonucleotide contains a coding region, which identifies the reactive unit attached to the template, and an annealing region. In some embodiments, other sequences are included in the template oligonucleotide, including, for example, PCR primer sites. Multiple transfer units are also prepared, each comprising a different reagent coupled to a different oligonucleotide.

To test for new bond-forming reactions, one or more templates are combined with one or more transfer units under conditions that allow for hybridization of the transfer units to the templates. In some embodiments, non-DNA linked accessory molecules are added to the reaction, such as, for example, an activating agent or a catalyst. In other embodiments, reaction conditions, including, for example, reaction duration, temperature, solvent, and pH, are varied to select reactions that proceed at different rates and under different conditions.

The crude reaction mixture then is selected for particular reaction products. The reaction products preferably still are associated with their respective templates whose nucleotide sequence encodes the bond forming reactions that produced the reaction products. In some embodiments, the transfer unit is coupled to a capturable molecule, such as, for example, biotin. Following creation and selection of the reaction products the associated templates can be selected by capturing the biotin by streptavidin. In one embodiment, the streptavidin is immobilized to a solid support, for example, by linkage to a magnetic bead. The selected templates then are amplified by PCR and subjected to DNA sequencing to determine the identities of the reactive unit and the reagent. In another embodiment, the reactions revealed by the above approach are characterized in a non-DNA-templated format in both aqueous and organic solvents using traditional reaction analysis methods including, for example, thin-layer chromatography, NMR, HPLC, and mass spectroscopy.

It is theoretically possible that some of the reactions discovered will require some aspect of the DNA template to proceed efficiently. However, the vast majority, if not all, of the reactions discovered in this system will take place in the absence of DNA template when performed at typical non-DNA-templated synthesis concentrations (e.g., about 0.1 M). Reactions discovered in this manner also are naturally well-suited for DNA-templated small molecule library synthesis. An illustrative example of this embodiment appears in Example 12, describing the discovery of a new palladium-mediated coupling reaction between a terminal alkyne and a simple alkene.

(ix) Preparing Product Libraries

A major practical difference between traditional and nucleic acid-templated library synthesis is the scale of each manipulation. Due to the amounts of material needed for screening and compound identification, traditional combinatorial syntheses typically proceed on the nmol-μmol scale per library member. In contrast, nucleic acid-templated library synthesis can take place on the fmol-pmol scale because only minute quantities (e.g., about $10^{-20}$ mol) of each nucleic acid-linked synthetic molecule are needed for selection and PCR amplification. This vast difference in scale, combined with the single-solution format of the nucleic acid-templated libraries, simplifies significantly the preparation of materials required for nucleic acid-templated library syntheses.

Libraries can be produced via the template mediated syntheses described herein. For example, the template may comprise one or more reactive units (for example, scaffold molecules). However, in each case the template contains a coding sequence that identifies the particular reactive unit associated with the oligonucleotide. A library of templates is initially subjected to one or more nucleic acid-templated bond formation reactions using reagents attached to decoding oligonucleotides through a linker as described above. Depending upon the circumstances, the template library can be subjected to multiple iterations of bond formation reactions, wherein each intermediate product is purified before the subsequent round of reactions. In other circumstances, the intermediate products are not purified between reaction iterations. Preferably less than 20 bond forming reactions are required to create a library. In other embodiments, less than 10 bond forming reaction steps are needed, and more preferably, between 3 and 7 steps are needed to create a full library.

After the final round of nucleic acid-templated bond formation reactions has been performed accessory reagents can be added to protect exposed reactive functional groups on the reaction product, if necessary. In some embodiments, accessory reagents are added to initiate a subsequent reaction with the reaction product, such as, for example, a cyclization reaction. The resulting library of reaction products attached to template oligonucleotides then are purified and/or selected as discussed herein. As would be appreciated by one skilled in this art, libraries of small molecules or polymers can be synthesized using the principles discussed herein.

Using similar approaches, it is possible to create a library of non-natural polymers from a library of template oligonucleotides that are not initially associated with a reactive unit. In this case, the template encodes two or more codons which when annealed to corresponding anti-codons attached to monomer units bring together the monomer units in a sequence specific manner. The transfer units then are allowed to contact the template under conditions that permit hybridization of the anti-codons on each transfer unit to the complementary codon on the template. Polymerization of the monomer units along the template then produces the polymer. The polymerization may be step-by step or may be essentially simultaneous with the chain being formed in one large reaction with one reaction between adjacent monomers leading to the attachment of the next monomer. In some embodiments, the functional group or groups of each monomer are protected, and must be deprotected prior to polymerization. The newly synthesized polymer can then be cleaved from the anti-codons and the template, and selected for a desired activity or characteristic, as described herein. DNA-templated polymer synthesis reactions are described in more detail in Example 9A and 9C.

IV. Selection and Screening

Selection and/or screening for reaction products with desired activities (such as catalytic activity, binding affinity, or a particular effect in an activity assay) may be performed according to any standard protocol. For example, affinity selections may be performed according to the principles used in library-based selection methods such as phage display, polysome display, and mRNA-fusion protein displayed peptides. Selection for catalytic activity may be performed by affinity selections on transition-state analog affinity columns (Baca et al. (1997) PROC. NATL. ACAD. SCI. USA 94(19): 10063-8) or by function-based selection schemes (Pedersen et al. (1998) PROC. NATL. ACAD. SCI. USA 95(18): 10523-8). Since minute quantities of DNA (~$10^{-20}$ mol) can be amplified by PCR (Kramer et al. (1999) CURRENT PROTOCOLS IN MOLECULAR BIOLOGY (ed. Ausubel, F. M.) 15.1-15.3, Wiley), these selections can be conducted on a scale ten or more orders of magnitude less than that required for reaction analysis by current methods, making a truly broad search both economical and efficient.

(i) Selection for Binding to Target Molecule

The templates and reaction products can be selected (or screened) for binding to a target molecule. In this context, selection or partitioning means any process whereby a library member bound to a target molecule is separated from library members not bound to target molecules. Selection can be accomplished by various methods known in the art.

The templates of the present invention contain a built-in function for direct selection and amplification. In most applications, binding to a target molecule preferably is selective, such that the template and the resulting reaction product bind preferentially with a specific target molecule, perhaps preventing or inducing a specific biological effect. Ultimately, a binding molecule identified using the present invention may be useful as a therapeutic and/or diagnostic agent. Once the selection is complete, the selected templates optionally can be amplified and sequenced. The selected reaction products, if present in sufficient quantity, can be separated from the templates, purified (e.g., by HPLC, column chromatography, or other chromatographic method), and further characterized.

(it) Target Molecules

Binding assays provide a rapid means for isolating and identifying reaction products that bind to, for example, a surface (such as metal, plastic, composite, glass, ceramics, rubber, skin, or tissue); a polymer; a catalyst; or a target biomolecule such as a nucleic acid, a protein (including enzymes, receptors, antibodies, and glycoproteins), a signal molecule (such as cAMP, inositol triphosphate, peptides, or prostaglandins), a carbohydrate, or a lipid. Binding assays can be advantageously combined with activity assays for the effect of a reaction product on a function of a target molecule.

The selection strategy can be carried out to allow selection against almost any target. Importantly, the selection strategy does not require any detailed structural information about the target molecule or about the molecules in the libraries. The entire process is driven by the binding affinity involved in the specific recognition and binding of the molecules in the library to a given target. Examples of various selection procedures are described below.

The libraries of the present invention can contain molecules that could potentially bind to any known or unknown target. The binding region of a target molecule could include a catalytic site of an enzyme, a binding pocket on a receptor (for example, a G-protein coupled receptor), a protein surface area involved in a protein-protein or protein-nucleic acid interaction (preferably a hot-spot region), or a specific site on DNA (such as the major groove). The natural function of the target could be stimulated (agonized), reduced (antagonized), unaffected, or completely changed by the binding of the reaction product. This will depend on the precise binding mode and the particular binding site the reaction product occupies on the target.

Functional sites (such as protein-protein interaction or catalytic sites) on proteins often are more prone to bind molecules than are other more neutral surface areas on a protein. In addition, these functional sites normally contain a smaller region that seems to be primarily responsible for the binding energy: the so-called "hot-spot regions" (Wells, et al., (1993) RECENT PROG. HORMONE RES. 48: 253-262). This phenomenon facilitates selection for molecules affecting the biological function of a certain target.

The linkage between the template molecule and reaction product allows rapid identification of binding molecules using various selection strategies. This invention broadly permits identifying binding molecules for any known target molecule. In addition, novel unknown targets can be discovered by isolating binding molecules against unknown antigens (epitopes) and using these binding molecules for identification and validation. In another preferred embodiment, the target molecule is designed to mimic a transition state of a chemical reaction; one or more reaction products resulting from the selection may stabilize the transition state and catalyze the chemical reaction.

(iii) Binding Assays

The template-directed synthesis of the invention permits selection procedures analogous to other display methods such as phage display (Smith (1985) SCIENCE 228: 1315-1317). Phage display selection has been used successfully on peptides (Wells et al. (1992) CURR. OP. STRUCT. BIOL. 2: 597-604), proteins (Marks et al. (1992) J. BIOL. CHEM. 267: 16007-16010) and antibodies (Winter et al. (1994) ANNU. REV. IMMUNOL. 12: 433-455). Similar selection procedures also are exploited for other types of display systems such as ribosome display Mattheakis et al. (1994) PROC. NATL. ACAD. SCI. 91: 9022-9026) and mRNA display (Roberts, et al. (1997) PROC. NATL. ACAD. SCI. 94:12297-302). The libraries of the present invention, however, allow direct selection of target-specific molecules without requiring traditional ribosome-mediated translation. The present invention also allows the display of small molecules which have not previously been synthesized directly from a nucleic acid template.

Selection of binding molecules from a library can be performed in any format to identify optimal binding molecules. Binding selections typically involve immobilizing the desired target molecule, adding a library of potential binders, and removing non-binders by washing. When the molecules showing low affinity for an immobilized target are washed away, the molecules with a stronger affinity generally remain attached to the target. The enriched population remaining bound to the target after stringent washing is preferably eluted with, for example, acid, chaotropic salts, heat, competitive elution with a known ligand or by proteolytic release of the target and/or of template molecules. The eluted templates are suitable for PCR, leading to many orders of amplification, whereby essentially each selected template becomes available at a greatly increased copy number for cloning, sequencing, and/or further enrichment or diversification.

Figure 10:
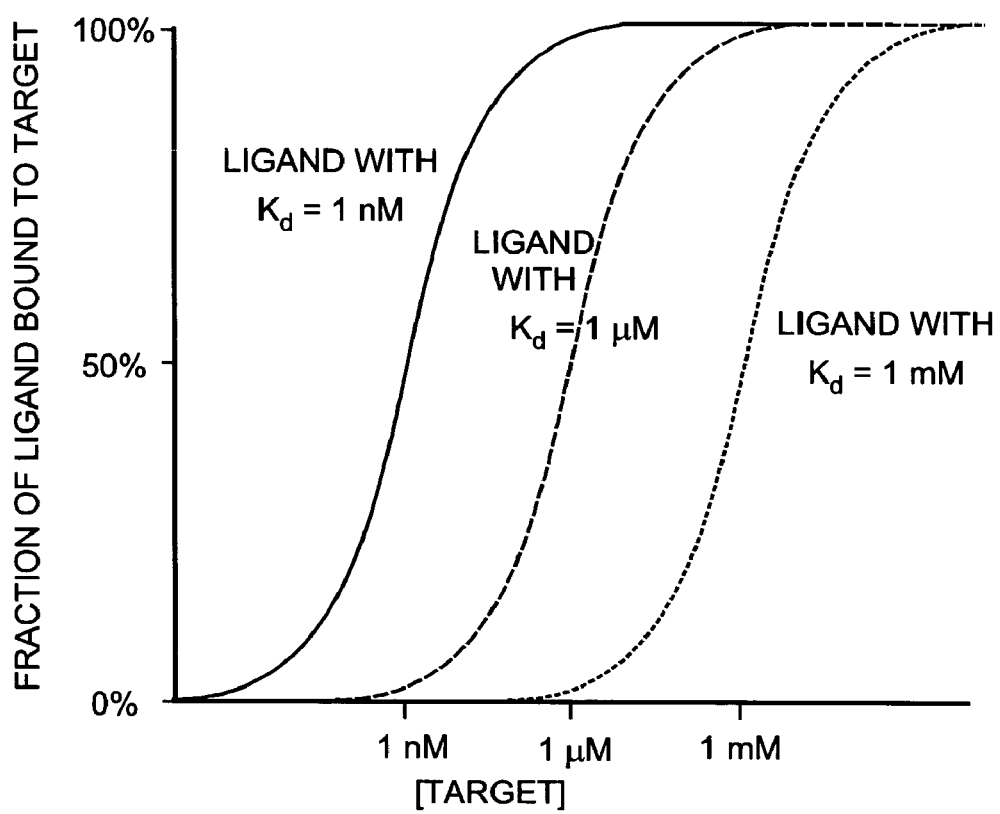
FIG. 10 is a graph showing the relationship between the effective concentration of target protein and the fraction of ligand that binds the target.

In a binding assay, when the concentration of ligand is much less than that of the target (as it would be during the selection of a DNA-templated library), the fraction of ligand bound to target is determined by the effective concentration of the target protein (see, FIG. 10). The fraction of ligand bound to target is a sigmoidal function of the concentration of target, with the midpoint (50% bound) at [target]=$K_d$ of the ligand-target complex. This relationship indicates that the stringency of a specific selection—the minimum ligand affinity required to remain bound to the target during the selection—is determined by the target concentration. Therefore, selection stringency is controllable by varying the effective concentration of target.

The target molecule (peptide, protein, DNA or other antigen) can be immobilized on a solid support, for example, a container wall, a wall of a microtiter plate well. The library preferably is dissolved in aqueous binding buffer in one pot and equilibrated in the presence of immobilized target molecule. Non-binders are washed away with buffer. Those molecules that may be binding to the target molecule through their attached DNA templates rather than through their synthetic moieties can be eliminated by washing the bound library with unfunctionalized templates lacking PCR primer binding sites. Remaining bound library members then can be eluted, for example, by denaturation.

Alternatively, the target molecule can be immobilized on beads, particularly if there is doubt that the target molecule will adsorb sufficiently to a container wall, as may be the case for an unfolded target eluted from an SDS-PAGE gel. The derivatized beads can then be used to separate high-affinity library members from nonbinders by simply sedimenting the beads in a benchtop centrifuge. Alternatively, the beads can be used to make an affinity column. In such cases, the library is passed through the column one or more times to permit binding. The column then is washed to remove nonbinding library members. Magnetic beads are essentially a variant on the above; the target is attached to magnetic beads which are then used in the selection.

There are many reactive matrices available for immobilizing the target molecule, including matrices bearing —NH$_2$ groups or —SH groups. The target molecule can be immobilized by conjugation with NHS ester or maleimide groups covalently linked to Sepharose beads and the integrity of known properties of the target molecule can be verified. Activated beads are available with attachment sites for —NH$_2$ or —COOH groups (which can be used for coupling). Alternatively, the target molecule is blotted onto nitrocellulose or PVDF. When using a blotting strategy, the blot should be blocked (e.g., with BSA or similar protein) after immobilization of the target to prevent nonspecific binding of library members to the blot.

Library members that bind a target molecule can be released by denaturation, acid, or chaotropic salts. Alternatively, elution conditions can be more specific to reduce background or to select for a desired specificity. Elution can be accomplished using proteolysis to cleave a linker between the target molecule and the immobilizing surface or between the reaction product and the template. Also, elution can be accomplished by competition with a known competitive ligand for the target molecule. Alternatively, a PCR reaction can be performed directly in the presence of the washed target molecules at the end of the selection procedure. Thus, the binding molecules need not be elutable from the target to be selectable since only the template is needed for further amplification or cloning, not the reaction product itself. Indeed, some target molecules bind the most avid ligands so tightly that elution would be difficult.

To select for a molecule that binds a protein expressible on a cell surface, such as an ion channel or a transmembrane receptor, the cells themselves can be used as the selection agent. The library preferably is first exposed to cells not expressing the target molecule on their surfaces to remove library members that bind specifically or non specifically to other cell surface epitopes. Alternatively, cells lacking the target molecule are present in large excess in the selection process and separable (by fluorescence-activated cell sorting (FACS), for example) from cells bearing the target molecule. In either method, cells bearing the target molecule then are used to isolate library members bearing the target molecule (e.g., by sedimenting the cells or by FACS sorting). For example, a recombinant DNA encoding the target molecule can be introduced into a cell line; library members that bind the transformed cells but not the untransformed cells are enriched for target molecule binders. This approach is also called subtraction selection and has successfully been used for phage display on antibody libraries (Hoogenboom et al. (1998) IMMUNOTECH 4: 1-20).

A selection procedure can also involve selection for binding to cell surface receptors that are internalized so that the receptor together with the selected binding molecule passes into the cytoplasm, nucleus, or other cellular compartment, such as the Golgi or lysosomes. Depending on the dissociation rate constant for specific selected binding molecules, these molecules may localize primarily within the intracellular compartments. Internalized library members can be distinguished from molecules attached to the cell surface by washing the cells, preferably with a denaturant. More preferably, standard subcellular fractionation techniques are used to isolate the selected library members in a desired subcellular compartment.

An alternative selection protocol also includes a known, weak ligand affixed to each member of the library. The known ligand guides the selection by interacting with a defined part of the target molecule and focuses the selection on molecules that bind to the same region, providing a cooperative effect. This can be particularly useful for increasing the affinity of a ligand with a desired biological function but with too low a potency.

Other methods for selection or partitioning are also available for use with the present invention. These include, for example: immunoprecipitation (direct or indirect) where the target molecule is captured together with library members; mobility shift assays in agarose or polyacrylamide gels, where the selected library members migrate with the target molecule in a gel; cesium chloride gradient centrifugation to isolate the target molecule with library members; mass spectroscopy to identify target molecules labeled with library members. In general, any method where the library member/target molecule complex can be separated from library members not bound to the target is useful.

The selection process is well suited for optimizations, where the selection steps are made in series, starting with the selection of binding molecules and ending with an optimized binding molecule. The procedures in each step can be automated using various robotic systems. Thus, the invention permits supplying a suitable library and target molecule to a fully automatic system which finally generates an optimized binding molecule. Under ideal conditions, this process should run without any requirement for external work outside the robotic system during the entire procedure.

The selection methods of the present invention can be combined with secondary selection or screening to identify reaction products capable of modifying target molecule function upon binding. Thus, the methods described herein can be employed to isolate or produce binding molecules that bind to and modify the function of any protein or nucleic acid. For example, nucleic acid-templated chemistry can be used to identify, isolate, or produce binding molecules (1) affecting catalytic activity of target enzymes by inhibiting catalysis or modifying substrate binding; (2) affecting the functionality of protein receptors, by inhibiting binding to receptors or by modifying the specificity of binding to receptors; (3) affecting the formation of protein multimers by disrupting the quaternary structure of protein subunits; or (4) modifying transport properties of a protein by disrupting transport of small molecules or ions.

Functional assays can be included in the selection process. For example, after selecting for binding activity, selected library members can be directly tested for a desired functional effect, such as an effect on cell signaling. This can, for example, be performed via FACS methodologies.

The binding molecules of the invention can be selected for other properties in addition to binding. For example, to select for stability of binding interactions in a desired working environment. If stability in the presence of a certain protease is desired, that protease can be part of the buffer medium used during selection. Similarly, the selection can be performed in serum or cell extracts or in any type of medium, aqueous or organic. Conditions that disrupt or degrade the template should however be avoided to allow subsequent amplification.

(iv) Other Selections

Selections for other desired properties, such as catalytic or other functional activities, can also be performed. Generally, the selection should be designed such that library members with the desired activity are isolatable on that basis from other library members. For example, library members can be screened for the ability to fold or otherwise significantly change conformation in the presence of a target molecule, such as a metal ion, or under particular pH or salinity conditions. The folded library members can be isolated by performing non-denaturing gel electrophoresis under the conditions of interest. The folded library members migrate to a different position in the gel and can subsequently be extracted from the gel and isolated.

Similarly, reaction products that fluoresce in the presence of specific ligands may be selected by FACS based sorting of translated polymers linked through their DNA templates to beads. Those beads that fluoresce in the presence, but not in the absence, of the target ligand are isolated and characterized. Useful beads with a homogenous population of nucleic acid-templates on any bead can be prepared using the split-pool synthesis technique on the bead, such that each bead is exposed to only a single nucleotide sequence. Alternatively, a different anti-template (each complementary to only a single, different template) can by synthesized on beads using a split-pool technique, and then can anneal to capture a solution-phase library.

Figure 11A:
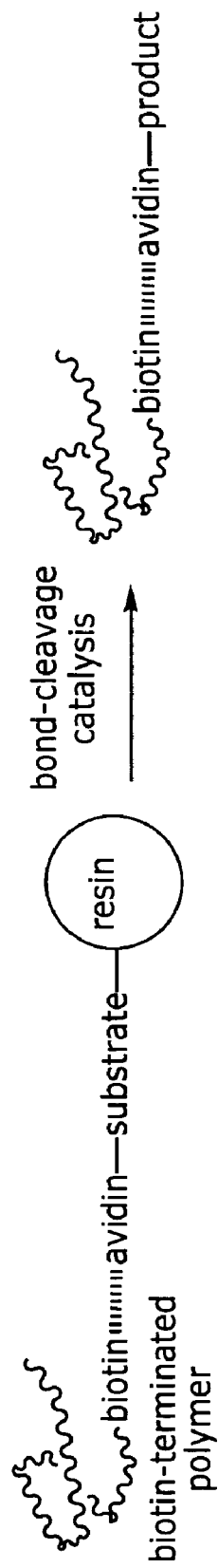
FIGS. 11A-B are schematic representations of methods for screening a library for bond-cleavage (FIG. 11A) and bond-formation (FIG. 11B) catalysts.
Figure 11B:
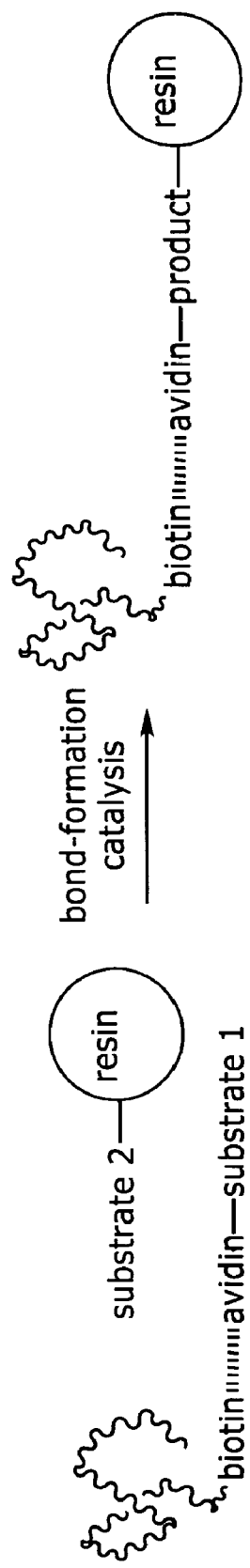

Biotin-terminated biopolymers can be selected for the actual catalysis of bond-breaking reactions by passing these biopolymers over a resin linked through a substrate to avidin (FIG. 11A). Those biopolymers that catalyze substrate cleavage self-elute from a column charged with this resin. Similarly, biotin-terminated biopolymers can be selected for the catalysis of bond-forming reactions (see, FIG. 11B). One substrate is linked to resin and the second substrate is linked to avidin. Biopolymers that catalyze bond formation between the substrates are selected by their ability to react the substrates together, resulting in attachment of the biopolymer to the resin.

Library members can also be selected for their catalytic effects on synthesis of a polymer to which the template is or becomes attached. For example, the library member may influence the selection of monomer units to be polymerized as well as how the polymerization reaction takes place (e.g., stereochemistry, tacticity, activity). The synthesized polymers can be selected for specific properties, such as, molecular weight, density, hydrophobicity, tacticity, stereoselectivity, using standard techniques, such as, electrophoresis, gel filtration, centrifugal sedimentation, or partitioning into solvents of different hydrophobicities. The attached template that directed the synthesis of the polymer can then be identified.

Figure 13:
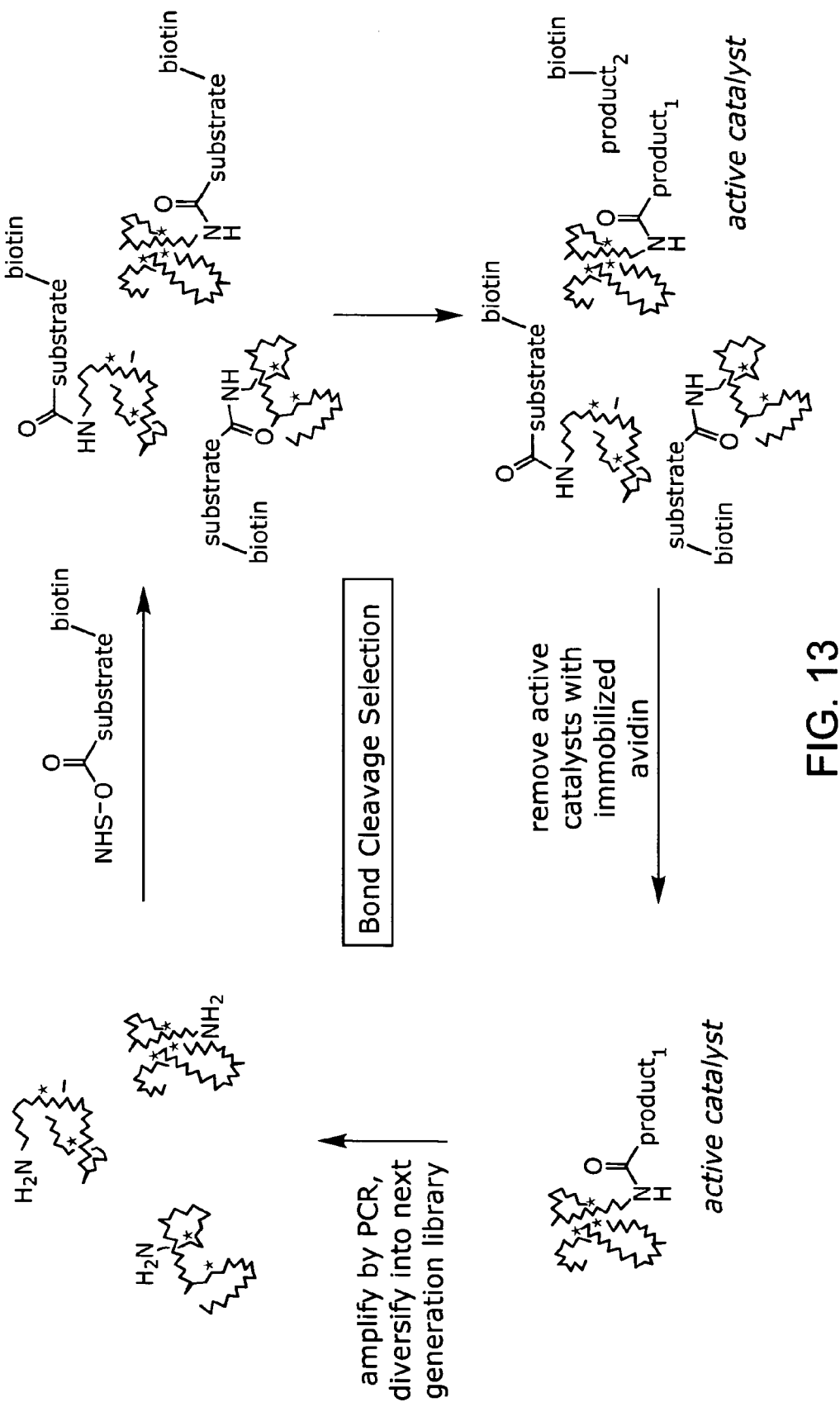
FIG. 13 is a schematic representation of an in vitro selection scheme for identifying non-natural polymer catalysts of bond-cleaving reactions.

Library members that catalyze virtually any reaction causing bond formation between two substrate molecules or resulting in bond breakage into two product molecules can be selected using the schemes proposed in FIGS. 12 and 13. To select for bond forming catalysts (for example, hetero Diels-Alder, Heck coupling, aldol reaction, or olefin metathesis catalysts), library members are covalently linked to one substrate through their 5' amino or thiol termini. The other substrate of the reaction is synthesized as a derivative linked to biotin. When dilute solutions of library-substrate conjugate are combined with the substrate-biotin conjugate, those library members that catalyze bond formation cause the biotin group to become covalently attached to themselves. Active bond forming catalysts can then be separated from inactive library members by capturing the former with immobilized streptavidin and washing away inactive library members (FIG. 12).

In an analogous manner, library members that catalyze bond cleavage reactions such as retro-aldol reactions, amide hydrolysis, elimination reactions, or olefin dihydroxylation followed by periodate cleavage can be selected. In this case, library members are covalently linked to biotinylated substrates such that the bond breakage reaction causes the disconnection of the biotin moiety from the library members (FIG. 13). Upon incubation under reaction conditions, active catalysts, but not inactive library members, induce the loss of their biotin groups. Streptavidin-linked beads can then be used to capture inactive polymers, while active catalysts are able to be eluted from the beads. Related bond formation and bond cleavage selections have been used successfully in catalytic RNA and DNA evolution (Jäschke et al. (2000) CURR. OPIN. CHEM. BIOL. 4: 257-62) Although these selections do not explicitly select for multiple turnover catalysis, RNAs and DNAs selected in this manner have in general proven to be multiple turnover catalysts when separated from their substrate moieties (Jäschke et al. (2000) CURR. OPIN. CHEM. BIOL. 4: 257-62; Jaeger et al. (1999) PROC. NATL. ACAD. SCI. USA 96: 14712-7; Bartel et al., (1993) SCIENCE 261: 1411-8; Sen et al., (1998) CURR. OPIN. CHEM. BIOL. 2: 680-7).

In addition to simply evolving active catalysts, the in vitro selections described above are used to evolve non-natural polymer libraries in powerful directions difficult to achieve using other catalyst discovery approaches. Substrate specificity among catalysts can be selected by selecting for active catalysts in the presence of the desired substrate and then selecting for inactive catalysts in the presence of one or more undesired substrates. If the desired and undesired substrates differ by their configuration at one or more stereocenters, enantioselective or diastereoselective catalysts can emerge from rounds of selection. Similarly, metal selectivity can be evolved by selecting for active catalysts in the presence of desired metals and selecting for inactive catalysts in the presence of undesired metals. Conversely, catalysts with broad substrate tolerance can be evolved by varying substrate structures between successive rounds of selection.

(v) Iterative Selection

Iterating a selection by loading eluant from a first selection into a second selection multiplies the net enrichment. No intervening amplification of template is required. For example, a selection for binding to carbonic anhydrase beads permitted a 330-fold enrichment of a ligand. Application of the eluant directly to fresh carbonic anhydrase beads (see, Example 11) enriched the template encoding the carbonic anhydrase ligand $\geq$10,000-fold. Where the selection was repeated a third time, a 5,000,000-fold net enrichment of the ligand was observed. This result indicates that iterating library selections can lead to very large enrichments of desired molecules. In certain embodiments, a first round of selection provides at least a 50-fold increase in the number of binding ligands. Preferably, the increase in enrichments is over 100-fold, more preferably over 1,000 fold, and even more preferably over 100,000-fold. Subsequent rounds of selection may further increase the enrichment 100-fold over the original library, preferably 1,000-fold, more preferably over 100,000-fold, and most preferably over 1,000,000-fold.

Alternatively, following PCR amplification of DNA templates encoding selected synthetic molecules, additional rounds of translation, selection, and amplification can be conducted to enrich the library for high affinity binders. The stringency of the selection is gradually increased by increasing the salt concentration of the binding and washing buffers, decreasing the duration of binding, elevating the binding and washing temperatures, and increasing the concentration of washing additives such as template DNA or unrelated proteins.

Importantly, in vitro selections can also select for specificity in addition to binding affinity. Library screening methods for binding specificity typically require duplicating the entire screen for each target or non-target of interest. In contrast, selections for specificity can be performed in a single experiment by selecting for target binding as well as for the inability to bind one or more non-targets. Thus, the library can be pre-depleted by removing library members that bind to a non-target. Alternatively, or in addition, selection for binding to the target molecule can be performed in the presence of an excess of one or more non-targets, as described in Example 11. To maximize specificity, the non-target can be a homologous molecule. If the target molecule is a protein, appropriate non-target proteins include, for example, a generally promiscuous protein such as an albumin. If the binding assay is designed to target only a specific portion of a target molecule, the non-target can be a variation on the molecule in which that portion has been changed or removed.

(vi) Amplification and Sequencing

Once all rounds of selection are complete, the templates which are, or formerly were, associated with the selected reaction product preferably are amplified using any suitable technique to facilitate sequencing or other subsequent manipulation of the templates. Natural oligonucleotides can be amplified by any state of the art method. These methods include, for example, polymerase chain reaction (PCR); nucleic acid sequence-based amplification (see, for example, Compton (1991) NATURE 350: 91-92), amplified anti-sense RNA (see, for example, van Gelder et al. (1988) PROC. NATL. ACAD. SCI. USA 5: 77652-77656); self-sustained sequence replication systems (Gnatelli et al. (1990) PROC. NATL. ACAD. SCI. USA 87: 1874-1878); polymerase-independent amplification (see, for example, Schmidt et al. (1997) NUCLEIC ACIDS RES. 25: 4797-4802, and in vivo amplification of plasmids carrying cloned DNA fragments. Descriptions of PCR methods are found, for example, in Saiki et al. (1985) SCIENCE 230: 1350-1354; Scharf et al. (1986) SCIENCE 233: 1076-1078; and in U.S. Pat. No. 4,683,202. Ligase-mediated amplification methods such as Ligase Chain Reaction (LCR) may also be used. In general, any means allowing faithful, efficient amplification of selected nucleic acid sequences can be employed in the method of the present invention. It is preferable, although not necessary, that the proportionate representations of the sequences after amplification reflect the relative proportions of sequences in the mixture before amplification.

For non-natural nucleotides the choices of efficient amplification procedures are fewer. As non-natural nucleotides can be incorporated by certain enzymes including polymerases it will be possible to perform manual polymerase chain reaction by adding the polymerase during each extension cycle.

For oligonucleotides containing nucleotide analogs, fewer methods for amplification exist. One may use non-enzyme mediated amplification schemes (Schmidt et al. (1997) NUCLEIC ACIDS RES. 25: 4797-4802). For backbone-modified oligonucleotides such as PNA and LNA, this amplification method may be used. Alternatively, standard PCR can be used to amplify a DNA from a PNA or LNA oligonucleotide template. Before or during amplification the templates or complementing templates may be mutagenized or recombined in order to create an evolved library for the next round of selection or screening.

(vii) Sequence Determination

Sequencing can be done by a standard dideoxy chain termination method, or by chemical sequencing, for example, using the Maxam-Gilbert sequencing procedure. Alternatively, the sequence of the template (or, if a long template is used, the variable portion(s) thereof) can be determined by hybridization to a chip (see, Example 12). For example, a single-stranded template molecule associated with a detectable moiety such as a fluorescent moiety is exposed to a chip bearing a large number of clonal populations of single-stranded nucleic acids or nucleic acid analogs of known sequence, each clonal population being present at a particular addressable location on the chip. The template sequences are permitted to anneal to the chip sequences. The position of the detectable moieties on the chip then is determined. Based upon the location of the detectable moiety and the immobilized sequence at that location, the sequence of the template can be determined. It is contemplated that large numbers of such oligonucleotides can be immobilized in an array on a chip or other solid support.

(viii) Diversification

Inventive libraries can be evolved by introducing mutations at the DNA level, for example, using error-prone PCR (Cadwell et al. (1992) PCR METHODS APPL. 2: 28) or by subjecting the DNA to in vitro homologous recombination (Stemmer (1994) PROC. NATL. ACAD. SCI. USA 91: 10747; Stemmer (1994) NATURE 370: 389).

Small molecule evolution using mutation and recombination offers two potential advantages over simple enrichment. If the total diversity of the library is much less than the number of molecules made (typically $10^{12}$ to $10^{15}$), every possible library member is present at the start of the selection. In this case, diversification is still useful because selection conditions can change as rounds of evolution progress. For example, later rounds of selection can be conducted under higher stringencies and can involve counterselections against binding to non-target molecules. Diversification gives library members that have been discarded during earlier rounds of selection the chance to reappear in later rounds under altered selection conditions in which their fitness relative to other members may be greater. In addition, it is quite possible to generate a synthetic library that has a theoretical diversity greater than $10^{15}$ molecules. In this case, diversification allows molecules that never existed in the original library to emerge in later rounds of selections on the basis of their similarity to selected molecules, similar to the way in which protein evolution searches the vastness of protein sequence space one small subset at a time.

(viii)(a) Error-Prone PCR

Random point mutagenesis is performed by conducting the PCR amplification step under error-prone PCR (Cadwell et al. (1992) PCR METHODS APPLIC. 2: 28-33) conditions. Because the genetic code of these molecules are written to assign related codons to related chemical groups, similar to the way that the natural protein genetic code is constructed, random point mutations in the templates encoding selected molecules will diversify progeny towards chemically related analogs. Because error-prone PCR is inherently less efficient than normal PCR, error-prone PCR diversification is preferably conducted with only natural dATP, dTTP, dCTP, and dGTP and using primers that lack chemical handles or biotin groups.

(viii)(b) Recombination

Figure 14:
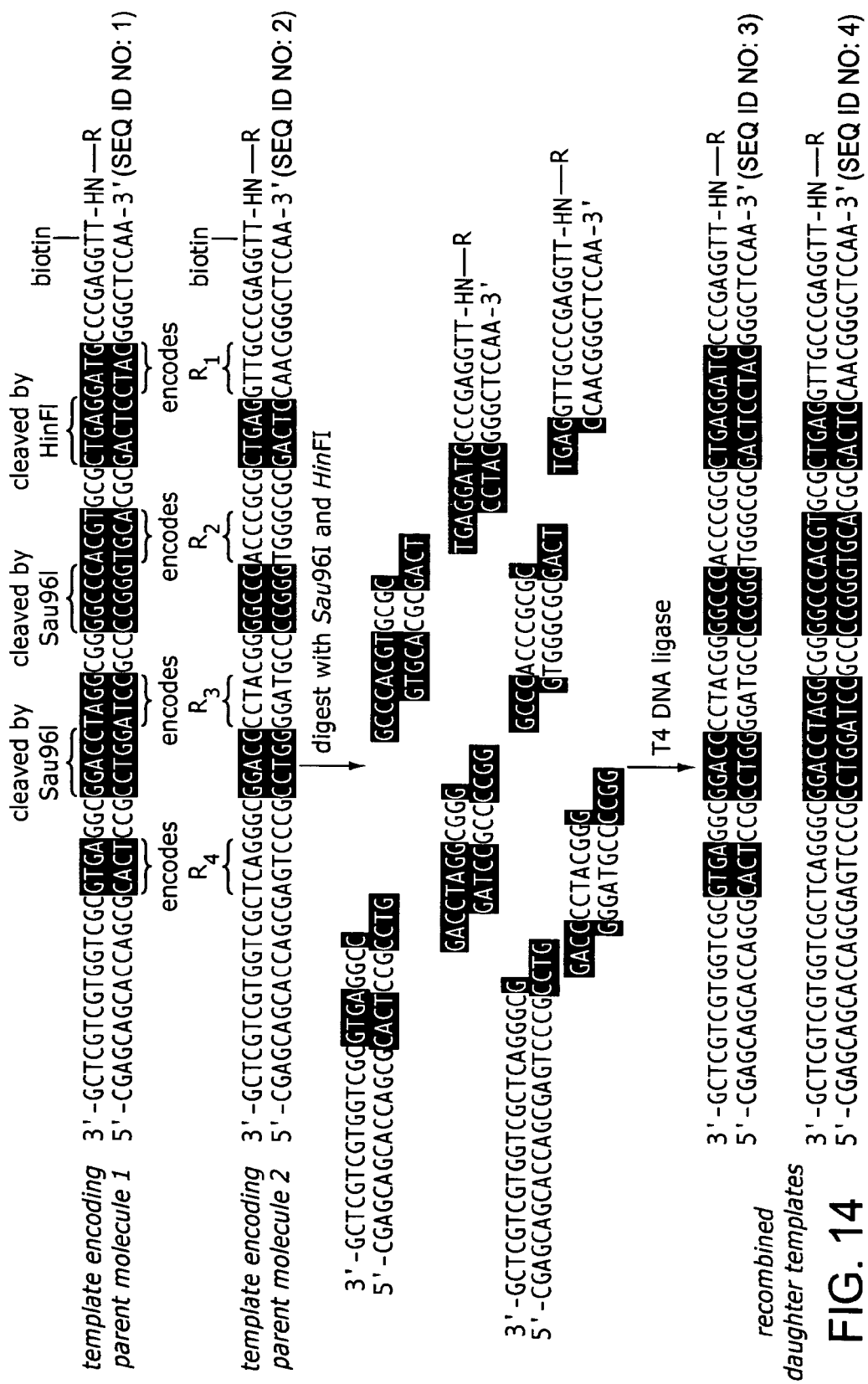
FIG. 14 is a schematic representation of exemplary reagents and their use in a recombination method for diversifying a template library.

Libraries may be diversified using recombination. For example, templates to be recombined may have the structure shown in FIG. 14, in which codons are separated by five-base non-palindromic restriction endonuclease cleavage sites such as those cleaved by AvaII (G/GWCC, W=A or T), Sau96I (G/GNCC, N=A, G, T, or C), DdeI (C/TNAG), or HinFI (G/ANTC). Following selections, templates encoding desired molecules are enzymatically digested with these commercially available restriction enzymes. The digested fragments then are recombined into intact templates with T4 DNA ligase. Because the restriction sites separating codons are nonpalindromic, template fragments can only reassemble to form intact recombined templates (FIG. 14). DNA-templated translation of recombined templates provides recombined small molecules. In this way, functional groups between synthetic small molecules with desired activities are recombined in a manner analogous to the recombination of amino acid residues between proteins in Nature. It is well appreciated that recombination explores the sequence space of a molecule much more efficiently than point mutagenesis alone (Minshull et al. (1999) CURR. OPIN. CHEM. BIOL. 3: 284-90; Bogarad et al., (1999) PROC. NATL. ACAD. SCI. USA 96: 2591-5; Stemmer NATURE 370: 389-391).

A preferred method of diversifying library members is through nonhomologous random recombination, as described, for example, in WO 02/074978; US Patent Application Publication No. 2003-0027180-A1; and Bittker et al. (2002) NATURE BIOTECH. 20(10): 1024-9.

(iiiv)(c) Random Cassette Mutagenesis

Random cassette mutagenesis is useful to create a diversified library from a fixed starting sequence. Thus, such a method can be used, for example, after a library has been subjected to selection and one or more library members have been isolated and sequenced. Generally, a library of oligonucleotides with variations on the starting sequence is generated by traditional chemical synthesis, error-prone PCR, or other methods. For example, a library of oligonucleotides can be generated in which, for each nucleotide position in a codon, the nucleotide has a 90% probability of being identical to the starting sequence at that position, and a 10% probability of being different. The oligonucleotides can be complete templates when synthesized, or can be fragments that are subsequently ligated with other oligonucleotides to form a diverse library of templates.

V. Uses

The methods and compositions of the present invention represent new ways to generate molecules with desired properties. This approach marries extremely powerful genetic methods, which molecular biologists have taken advantage of for decades, with the flexibility and power of organic chemistry. The ability to prepare, amplify, and evolve unnatural polymers by genetic selection may lead to new classes of catalysts that possess activity, bioavailability, stability, fluorescence, photolability, or other properties that are difficult or impossible to achieve using the limited set of building blocks found in proteins and nucleic acids. Similarly, developing new systems for preparing, amplifying, and evolving small molecules by iterated cycles of mutation and selection may lead to the isolation of novel ligands or drugs with properties superior to those isolated by slower traditional drug discovery methods.

For example, unnatural biopolymers useful as artificial receptors to selectively bind molecules or as catalysts for chemical reactions can be isolated. Characterization of these molecules would provide important insight into the ability of polycarbamates, polyureas, polyesters, polycarbonates, polypeptides with unnatural side chain and stereochemistries, or other unnatural polymers to form secondary or tertiary structures with binding or catalytic properties.

The present invention further allows the discovery of new chemical reactions. The field of chemistry is continually being transformed by the discovery of new chemical reactions providing access to previously inaccessible molecules, allowing for expedited syntheses, and revealing new chemical principles. Guided by predictions of reactivity based on literature precedent, chemists typically search for a new reaction to overcome a particular shortcoming in current synthetic methodology. Until now, it has not been feasible to conduct a broad, non-biased search for chemical reactivity in which a large number of diverse reactants are simultaneously evaluated for their ability to react with one another under many different conditions. Both the amount of material required for executing thousands of diverse reactions and the difficulty of analyzing the outcome of such an experiment makes this goal intractable using current reaction discovery approaches. A broad, non-biased search for chemical reactivity is appealing because it is not limited by conventional wisdom or by our ability to predict functional group reactivity.

The inventive method of discovering new chemical reactions and chemical reactivity has several advantages over existing methods. For example, several groups have developed high-throughput screens to test the efficiency of a particular reaction under a variety of conditions (Kuntz et al. (1999) CURR. OPIN. CHEM. BIOL. 3: 313-319; Francis et al. (1998) CURR. OPIN. CHEM. BIOL. 2: 422-428; Pawlas et al. (2002) J. AM. CHEM. SOC. 124: 3669-3679; Lober et al. (2001) J. AM. CHEM. SOC. 123: 4366-4367; Evans et al. (2002) CURR. OPIN. CHEM. BIOL. 6: 333-338; Taylor et al. (1998) SCIENCE 280: 267-270; and Stambuli et al. (2001) J. AM. CHEM. SOC. 123: 2677-2678); however, the screens are limited to a small set of reaction types. Reactions have been analyzed in a high-throughput manner using fluorescence spectroscopy, colorimetric assay, thermographic analysis, and traditional chromatography (Dahmen et al. (2001) SYNTHESIS-STUTTGART 1431-1449 and Wennemers (2001) COMBINATORIAL CHEMISTRY & HIGH THROUGHPUT SCREENING 4: 273-285). Most high-throughput screens for chemical reactivity are useful for only a small set of reaction types because the screen depends on a particular property of the reaction such as the disappearance of an amine or the production of protons. As a result, high throughput screening methods can be useful for discovering catalysts for a known or anticipated reason, but are poorly suited to discover novel reactivity different from a reaction of interest. A non-biased search for chemical reactions would examine a broad range of both reaction conditions and reactants in a highly efficient manner that is practical on the scale of thousands of different reactions. The inventive method of discovering chemical reactions offers a much greater chance of discovering unexpected and unprecedented reactivity that may lead to new insights into reactivity and to useful new reactions for chemical synthesis.

Discovering new reactions from very large and diverse collections of reactants and conditions entails (1) a general assay for reactivity that does not depend on a particular substrate or product, and (2) increasing the overall efficiency of assaying reactions such that both reaction condition space and reactant space can be searched extensively. For example, researchers evolving catalytic nucleic acids routinely select for bond formation catalysts by attaching one reactant to the pool of evolving nucleic acids and linking another reactant to a handle that can be easily immobilized such as biotin (Wilson et al. (1999) ANNU. REV. BIOCHEM. 68: 611-647; Jaschke (2001) CURR. OPIN. STRUCT. BIOL. 11: 321-326; Jaschke et al. (2000) CURR. OPIN. CHEM. BIOL. 4: 257-262; Jaschke (2001) BIOL. CHEM. 382: 1321-1325). Active nucleic acids become linked to the handle and are separated from the inactive sequences. Because this type of selection does not depend on the consumption or generation of a specific substrate or product, the scope of reactants that can be tested in this type of selection is much larger than the scope of reactants that can be evaluated in current reactivity screens.

Nucleic acid-templated synthesis provides a way to use bond formation selections to discover new chemical reactivity independent of nucleic acid catalysis (Gartner et al. (2002) ANGEW. CHEM. INT. ED. 41: 1796-1800; Gartner et al. (2001) supra). Nucleic acid templates can direct a wide variety of chemical reactions in a highly sequence-specific manner without any obvious requirements for reaction geometry. By attaching reactants to appropriately designed nucleic acid sequences, it becomes possible to test thousands of unprecedented reactions in a single pot with individual sequences encoding each reaction. Pools of nucleic acid-linked reactants would be truly selected (not simply screened) for covalent bond formation with members of a second nucleic acid-linked reactant pool. PCR amplification and DNA sequencing would reveal which combinations of reactants successfully undergo bond formation.

In certain embodiments, the searchable reactions are those transformations that can occur in aqueous or substantially aqueous medium. In other embodiments, the searchable reactions are limited to those that do not degrade nucleic acids rapidly. The known chemical robustness of DNA suggests that a wide range of reaction conditions spanning different temperatures, pH ranges, and additives such as transition metals are compatible with the proposed approach. A DNA-templated Heck reaction demonstrates that transition metal catalyzed reactions are viable in a DNA-templated format, consistent with extensive evidence (Patolsky et al. (2002) J. AM. CHEM. SOC. 124: 770-772; Weizman et al. (2002) J. AM. CHEM. SOC. 124: 1568-1569; Gartner et al. (2002) ANGEW. CHEM. INT. ED. 41: 1796-1800; Czlapinski et al. (2001) J. AM. CHEM. SOC. 123: 8618-8619; Holmlin et al. (1998) J. AM. CHEM. SOC. 120: 9724-9725; Bashkin et al. (1994) J. AM. CHEM. SOC. 116: 5981-5982; Magda et al. (1994) J. AM. CHEM. SOC. 116: 7439-7440; and Dandliker et al. (1997) SCIENCE 275: 1465-1468) that DNA is compatible with many transition metal complexes, including those containing Pd, Ni, Mn, Pt, Ru, Os, Cu, Eu, and Rh. Further, the rapid increase in the number of known water-compatible organic reactions (Li et al. *Organic reaction in aqueous media* (Wiley and Sons, New York, 1997) and the inherent benefits of working in aqueous solvents suggests that water is a rich medium for discovering new reactions. Reactions discovered in this effort may be of general utility when performed in a standard non-nucleic acid-templated mode, and are also natural candidates for use in generating nucleic acid-templated synthetic libraries.

Nucleic acid-templated chemistry is combined with in vitro selection and PCR amplification in certain embodiments to efficiently search for novel bond-forming reactions independent of reactant structures. The ability to select directly for covalent bond formation, the minute scale required for analysis, and compatibility of nucleic acids with a wide variety of reaction conditions may permit the first search for unprecedented reactivity that can examine thousands of combinations of reactants and reaction conditions in one or several experiments.

Figure 9:
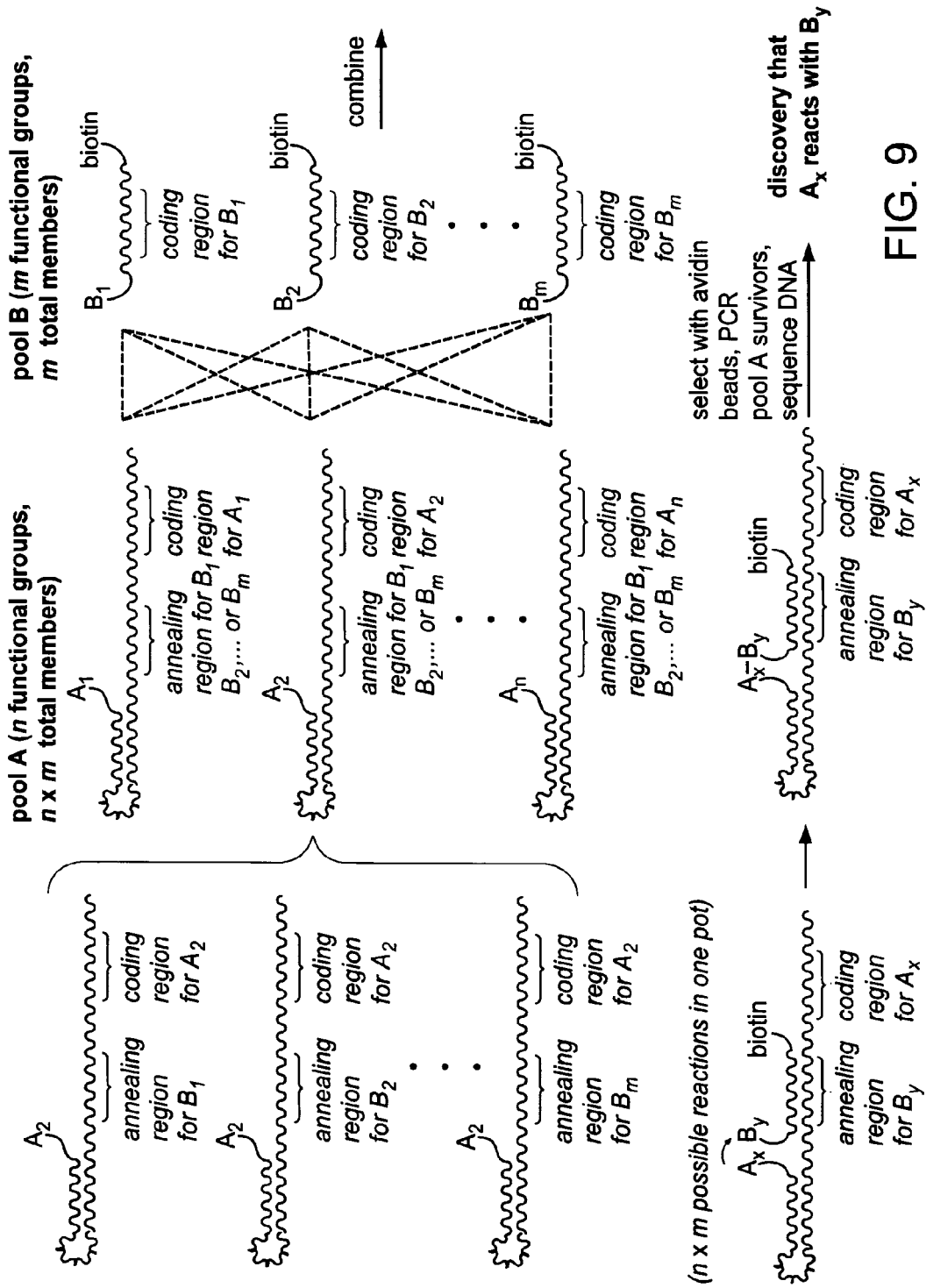
FIG. 9 is a schematic representation of a general method for making a library of reaction products.

The reaction generality and distance independence of DNA-templated synthesis allows for a system for discovering new chemical reactions by selection. DNA-linked reactants (i.e., templates and/or transfer units) suitable for in vitro selection for bond formation exist in one or two forms designated pool A and pool B in FIG. 9. Each reactant in pool B contains a functional group being tested linked to a short segment of biotinylated DNA (a coding region) encoding that functional group. Each reactant in pool A contains a functional group being tested, a corresponding coding region, and an "annealing region" or anti-codon that complements one of the pool B coding regions. Each functional group in pool A is linked to one of every possible annealing region. This arrangement allows any functional group in pool A to join any functional group in pool B on the same DNA duplex, providing the opportunity for DNA-templated bond formation if the reactants are mutually reactive. Generating these two pools of DNA-linked reactants in a format suitable for in vitro selection for bond formation requires the development of methods to efficiently assemble a small molecule reactant, a coding region, and in the case of pool A, a library of annealing regions.

The inventive system is particularly useful for the identification of small-molecule/target binding pairs. For instance, inventive DNA-templated small molecule libraries may be contacted with other solution or solid-phase libraries of potential target compounds such that small molecules within the inventive library that bind or interact with one or more compounds in the target libraries are identified. Preferably, bound pairs may be identified by selection (e.g., by tagging one of the components, combined with PCR to identify the other). In certain particularly preferred embodiments of this aspect of the invention, the target library or libraries comprise polypeptides and/or proteins.

As described herein, the present invention also provides new modes of nucleic acid-templated synthesis, including simultaneous incompatible reactions and one pot multi-step ordered synthesis (e.g., incubating three DNA-linked amino acids and one template so that only a single tripeptide, of specified sequence, is produced). The invention also provides nucleic acid-templated synthesis in organic solvents (e.g., methylene chloride, dimethylformamide).

Yet another application of the inventive system is to identify and/or evolve new templates for nucleic acid-templated synthesis. For instance, the present invention allows identification of nucleic acid templates that, when contacted with reagents that are sufficient to participate in a reaction to generate a selectable product, most efficiently lead to production of that product.

The invention also provides information useful to inform the development of chemical reaction pathways. For instance, according to the present invention, a researcher can select from within a library of nucleic acid-templated substrates those that permit a complex chemical reaction to take place (e.g., macrocyclization, which can be selected for by, for example, loss of a biotin leaving group). When successful reaction conditions have been identified, the inventive system allows ready identification of participating components. Thus, new chemistries can be developed without prior knowledge of the reagents and/or pathways likely to be useful in the reaction.

VI. Kits

The present invention also provides kits and compositions for use in the inventive methods. The kits may contain any item or composition useful in practicing the present invention. The kits may include, but are not limited to, templates, (e.g., end-of-helix, hairpin, omega, and T architectures), anti-codons, transfer units, monomer units, building blocks, reactants, small molecule scaffolds, buffers, solvents, enzymes (e.g., heat stable polymerase, reverse transcriptase, ligase, restriction endonuclease, exonuclease, Klenow fragment, polymerase, alkaline phosphatase, polynucleotide kinase), linkers, protecting groups, polynucleotides, nucleosides, nucleotides, salts, acids, bases, solid supports, or any combinations thereof.

A kit for preparing unnatural polymers should contain items needed to prepare unnatural polymers using the methods described herein. Such a kit may include templates, anti-codons, transfer units, monomers units, or combinations thereof. A kit for synthesizing small molecules may include templates, anti-codons, transfer units, building blocks, small molecule scaffolds, or combinations thereof.

The inventive kit can also be equipped with items needed to amplify and/or evolve a polynucleotide template such as a heat stable polymerase for PCR, nucleotides, buffer, and primers. In certain other embodiments, the inventive kit includes items commonly used in performing DNA shuffling such as polynucleotides, ligase, and nucleotides.

In addition to the templates and transfer units described herein, the present invention also includes compositions comprising complex small molecules, scaffolds, or unnatural polymer prepared by any one or more of the methods of the invention as described herein.

A kit for identifying new chemical reactions or functionality may include template associated with reactive units (reactants), transfer units associated with reactive units (reactants), reagents, acids, bases, catalysts, solvents, biotin, avidin, avidin beads, etc. The kit can also include reagents for generating the template associated with a reactive group (e.g., biotin, polynucleotides, reactive units, Klenow fragment of DNA pol I, nucleotides, avidin beads, etc.). The kit can also include reagents for PCR (e.g., buffers, heat stable polymerase, nucleotides, primers, etc.).

The following examples contain important additional information, exemplification and guidance that can be adapted to the practice of this invention in its various embodiments and equivalents thereof.

EXAMPLES

Examples 1 and 2 describe the preparation of materials for use in nucleic acid-templated synthesis and describe specific synthetic reactions. Example 3 discusses multi-step synthesis. Example 4 describes the compatibility of nucleic acid-templated synthesis with organic solvents. Example 5 describes specific template architectures useful in the practice of certain DNA-templated syntheses. Example 6 describes stereoselectivity in nucleic acid-templated synthesis. Example 7 describes the use of DNA-templated synthesis to direct otherwise incompatible reactions in a single solution. Example 8 describes functional group transformation reactions that can be carried out by nucleic acid-templated synthesis. Example 9 describes the synthesis of exemplary compounds and libraries. Example 10 describes the use of polymerases to translate DNA into nonnatural polymers. Example 11 describes in vitro selection protocols. Example 12 describes the application of DNA-templated synthesis toward the discovery of new chemical reactions.

Example 1

The Generality of DNA-Templated Synthesis

Nucleic acid-templated synthesis is extremely versatile and permits the synthesis of a variety of chemical compounds. This Example demonstrates that it is possible to perform DNA-templated synthesis using two different DNA template architectures.

Figure 15:
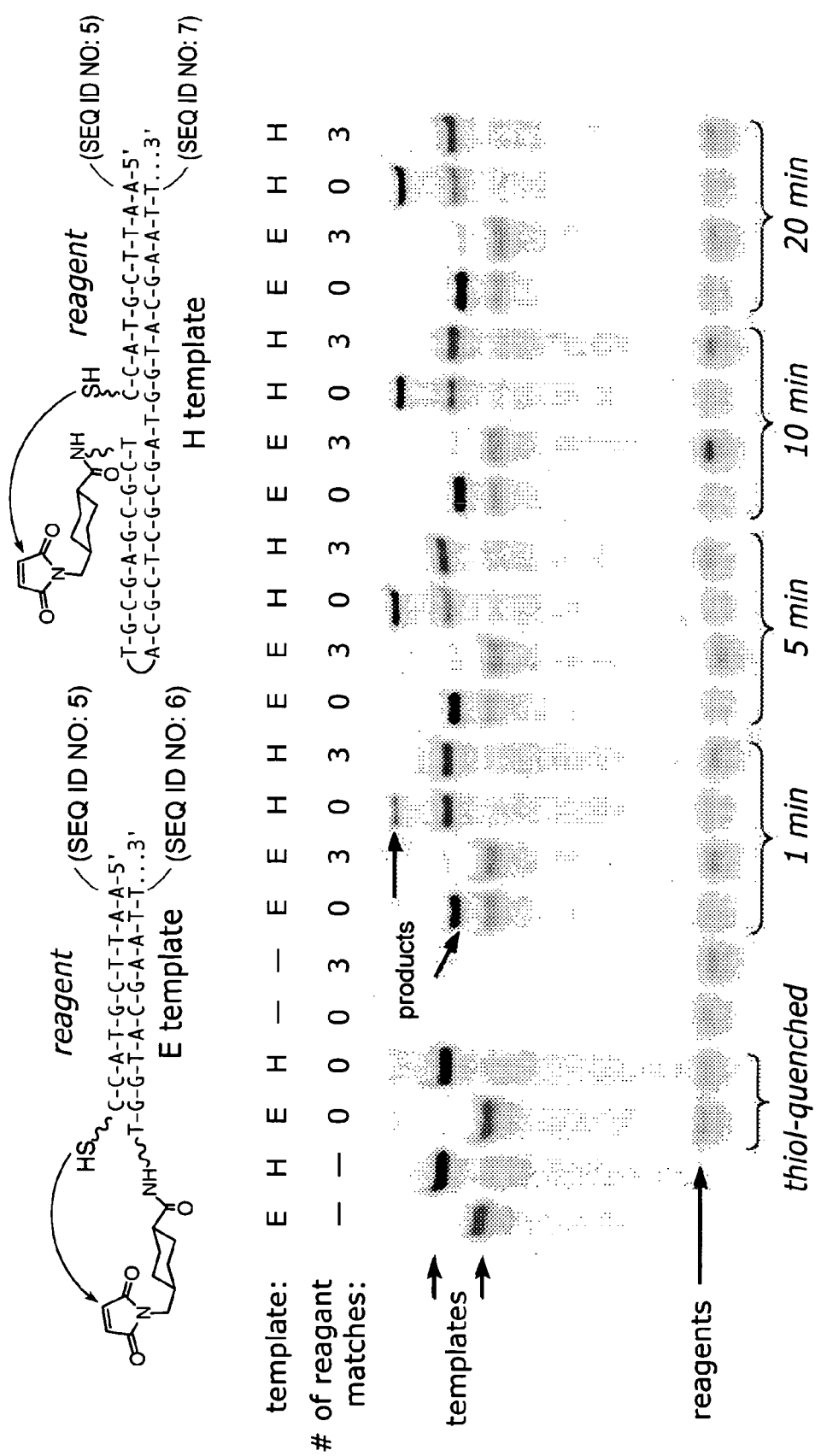
FIG. 15 depicts synthetic reactions directed by hairpin (H) and end-of-helix (E) DNA templates. Reactions were analyzed by denaturing polyacrylamide gel electrophoresis (PAGE) after the indicated reaction times. Lanes 3 and 4 contained templates quenched with excess β-mercaptoethanol prior to reaction.

As shown in FIG. 15, templates with a hairpin (H) or end-of-helix (E) architecture bearing electrophilic maleimide groups were prepared to test their reactivity with a transfer unit comprising, a complementary DNA oligonucleotide associated with a thiol reagent. Both the H and E templates reacted efficiently with one equivalent of the DNA-linked thiol reagent to yield the thioether product in minutes at 25° C. DNA-templated reaction rates ($k_{app}$~$10^5$ M$^{-1}$s$^{-1}$) were similar for H and E architectures despite significant differences in the relative orientation of their reactive groups. In contrast, no product was observed when using reagents containing sequence mismatches, or when using templates prequenched with excess β-mercaptoethanol (see FIG. 15). Thus, both DNA templates support a sequence-specific DNA-templated reaction even though the structures of the resulting products differ markedly from the structure of the natural DNA backbone. Little or no non-templated intermolecular reaction products were observed under the reaction conditions (pH 7.5, 25° C., 250 mM NaCl, 60 nM template transfer unit), demonstrating the specificity of the DNA-templated reaction.

Figure 16:
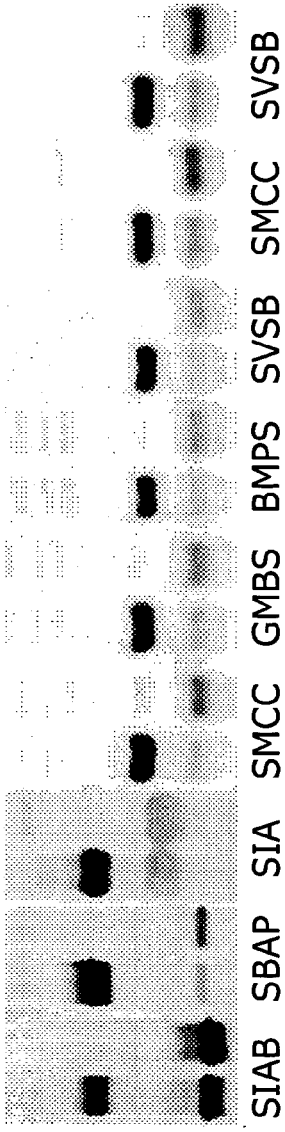
FIG. 16 depicts the results of reactions between matched (M) or mismatched (X) reagents linked to thiols (S) or primary amines (N) and templates functionalized with the variety of electrophiles.
Figure 16:
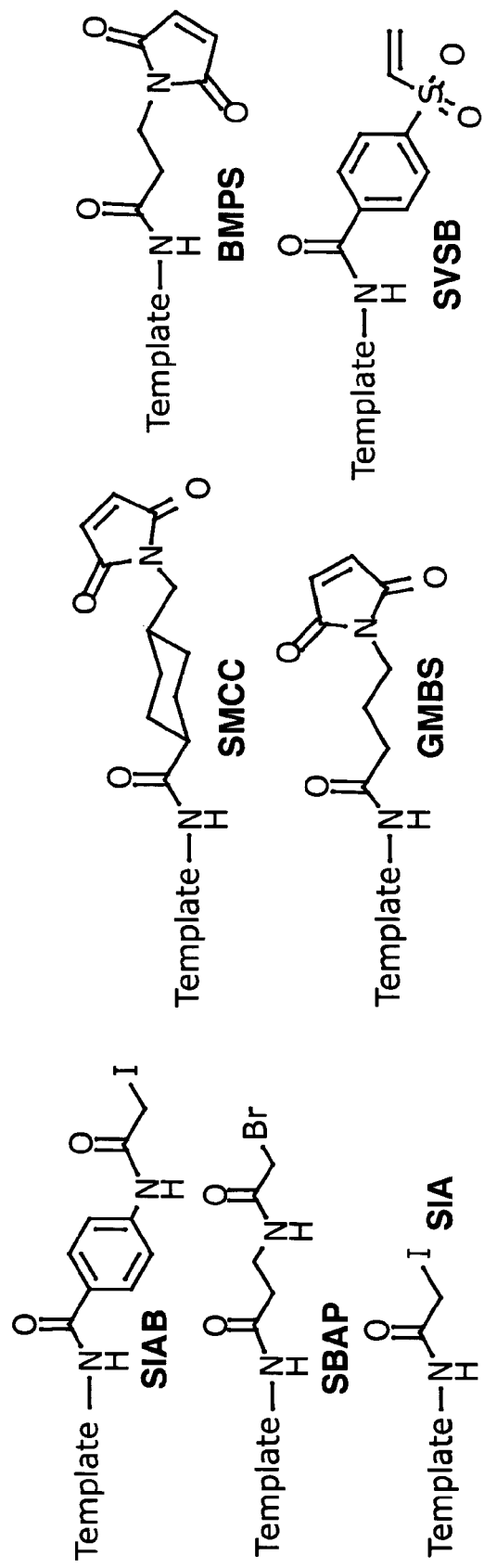

Indeed, sequence-specific DNA-templated reactions spanning a variety of reaction types ($S_N2$ substitutions, additions to α,β-unsaturated carbonyl systems, and additions to vinyl sulfones), nucleophiles (thiols and amines), and reactant structures all proceeded with good yields and excellent sequence selectivity (see, FIG. 16). Matched (M) or mismatched (X) reagents linked to thiols (S) or primary amines (N) were mixed with 1 equivalent of template functionalized with the variety of electrophiles shown in FIG. 16. Reactions with thiol reagents were conducted at pH 7.5 under the following conditions: SIAB and SBAP: 37° C., 16 hours; SIA: 25° C., 16 hours, SMCC, GMBS, BMPS, SVSB: 25° C., 10 minutes. Reactions with amine reagents were conducted at 25° C., pH 8.5 for 75 minutes. Expected product masses were verified by mass spectrometry. In each case, matched but not mismatched reagents afforded product efficiently despite considerable variations in their transition state geometry, steric hindrance, and conformational flexibility. Collectively these findings indicate that nucleic acid-templated synthesis is a general phenomenon capable of supporting a range of reaction types, and is not limited to the creation of structures resembling nucleic acid backbones.

Sequence discrimination is important for the faithful translation of a nucleic acid into a synthetic reaction product. To test the sequence discrimination of DNA-templated synthesis, hairpin templates linked to an iodoacetamide group were reacted to thiol-bearing transfer units containing 0, 1, or 3 mismatches. At 25° C., the initial rate of reaction of the thiol-bearing transfer unit with no mismatches was 200-fold faster than that of transfer units bearing a single mismatch ($k_{app}$=2.4×10$^4$ M$^{-1}$s$^{-1}$ vs. 1.1×10$^2$ M$^{-1}$s$^{-1}$; FIG. 17A).

In addition, small amounts of products arising from the annealing of mismatched reagents could be eliminated by elevating the reaction temperature beyond the melting temperature $T_m$ of the mismatched reagents (FIG. 17B). In FIG. 17B, the reactions in FIG. 17B were repeated at the indicated temperatures for 16 hours. The calculated reagent Tm values were found to be 38° C. (matched) and 28° C. (single mismatch). The inverse relationship between product formation and temperature indicates that product formation proceeds by a DNA-templated mechanism rather than by a simple intermolecular mechanism.

Figure 18:
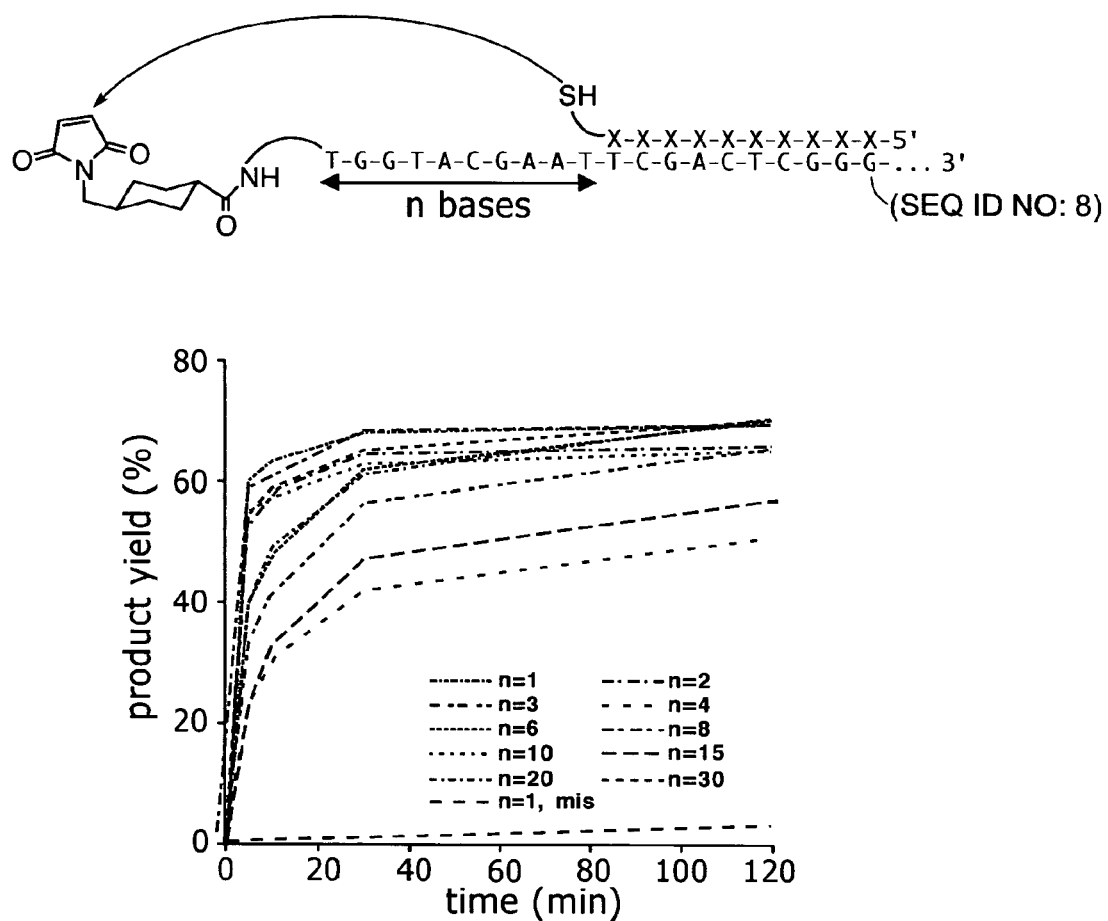
FIG. 18 depicts a reaction performed using a 41-base E template and a 10-base reagent designed to anneal 1-30 bases from the 5' end of the template.

In addition to reaction generality and sequence specificity, DNA-templated synthesis, under certain circumstances, also demonstrates remarkable distance independence. Both H and E templates linked to maleimide or α-iodoacetamide groups promoted sequence-specific reaction with matched, but not mismatched, thiol reagents annealed anywhere on the templates examined thus far (up to 30 bases away from the reactive group on the template). Reactants annealed one base away reacted with similar rates as those annealed 2, 3, 4, 6, 8, 10, 15, 20, or 30 bases away (FIG. 18). The reaction illustrated in FIG. 18 used a 41-base E template and a 10-base reagent designed to anneal 1-30 bases from the 5' end of the template. The kinetic profiles of FIG. 18 show the average of two trials (deviations <10%). The "n=1 mis" reagent contained three mismatches. In all cases, templated reaction rates were several hundred-fold higher than the rate of untemplated (mismatched) reaction ($k_{app}$=10$^4$-10$^5$ M$^{-1}$s$^{-1}$ vs. 5×10$^1$ M$^{-1}$s$^{-1}$). At intervening distances of 30 bases, products were efficiently formed presumably through transition states resembling 200-membered rings.

In order to further characterize the basis of the distance independence of DNA-templated synthesis, a series of modified E templates were first synthesized in which the intervening bases were replaced by a series of DNA analogs designed to evaluate the possible contribution of (i) interbase interactions, (ii) conformational preferences of the DNA backbone, (iii) the charged phosphate backbone, and (iv) backbone hydrophilicity. Templates in which the intervening bases were replaced with any of the analogs in FIG. 19 showed little effect on the rates of product formation.

Figure 19:
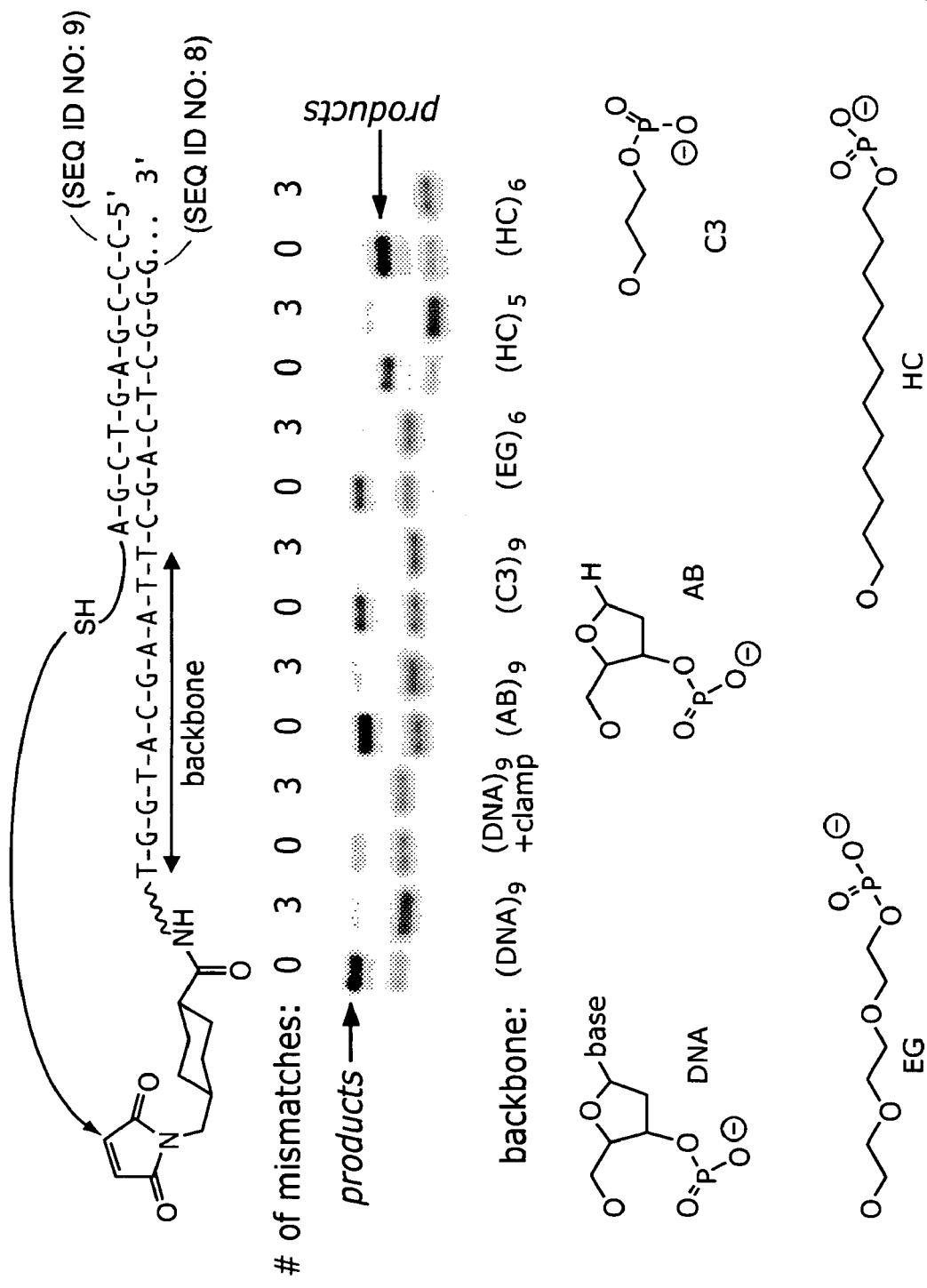
FIG. 19 depicts a repeat of the n=10 reaction in FIG. 18 in which the nine bases following the 5'-NH2-dT were replaced with various backbone analogues.

In the experiment shown in FIG. 19, the n=10 reaction in FIG. 18 was repeated using templates in which the nine bases following the 5'-NH$_2$-dT were replaced with the backbone analogues shown. Five equivalents of a DNA oligonucleotide complementary to the intervening bases were added to the "DNA+clamp" reaction. Reagents were either completely matched (0) or contained three mismatches (3). The gel shows reactions after 25 minutes at 25° C. FIG. 19 shows that the backbone structural elements specific to DNA are not responsible for the observed distance independence of DNA-templated synthesis. However, the addition of a 10-base DNA oligonucleotide "clamp" complementary to the single-stranded intervening region significantly reduced product formation (FIG. 19), suggesting that the flexibility of this region is critical to efficient DNA-templated synthesis.

Figure 20:
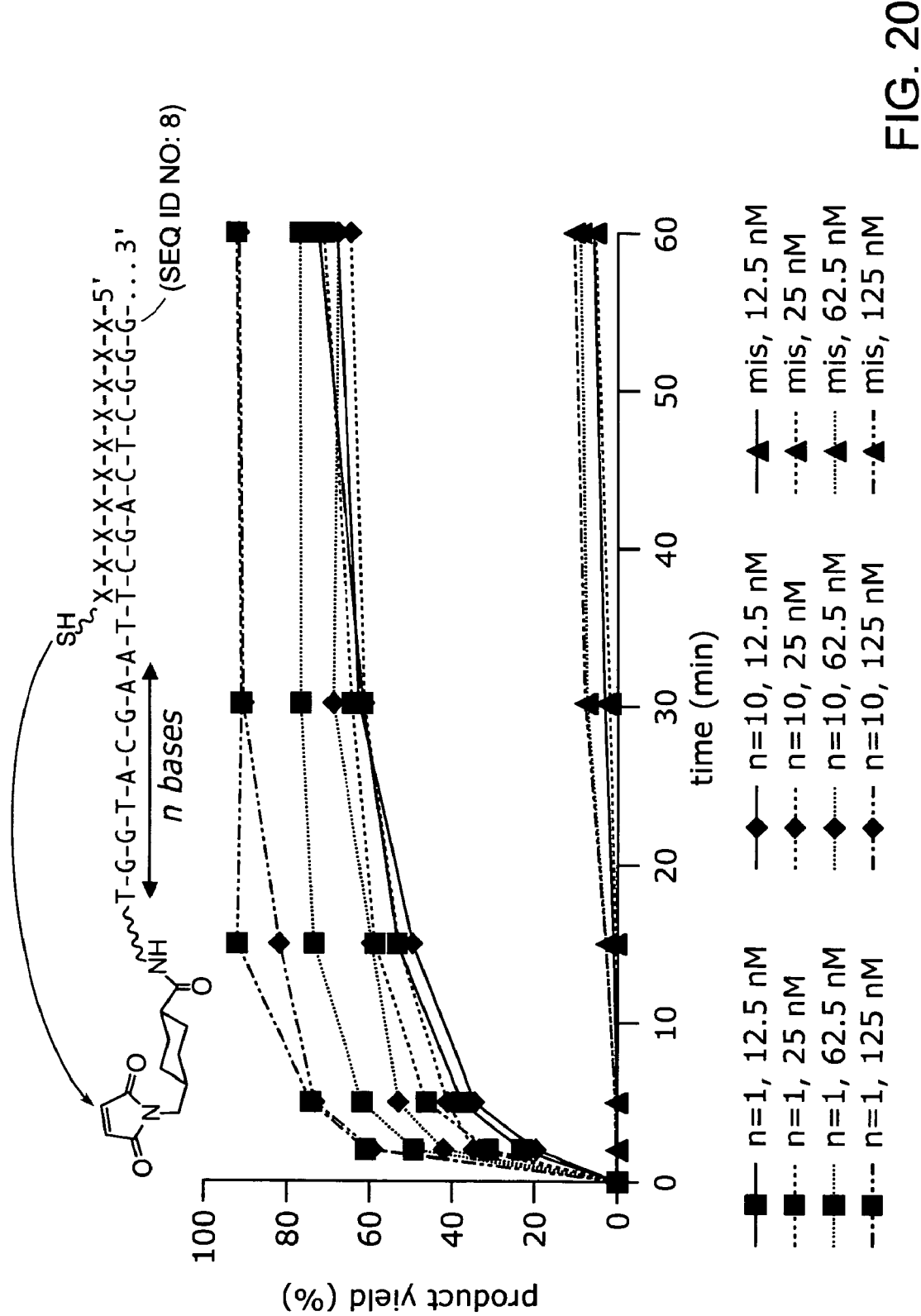
FIG. 20 depicts the n=1, n=10, and n=1 mismatched (mis) reactions described in FIG. 18 which were repeated with template and reagent concentrations of 12.5, 25, 62.5 or 125 nM.

The distance independent reaction rates may be explained if the bond-forming events in a DNA-templated format are sufficiently accelerated relative to their nontemplated counterparts such that DNA annealing, rather than bond formation, is rate-determining. If DNA annealing is at least partially rate limiting, then the rate of product formation should decrease as the concentration of reagents is lowered because annealing, unlike templated bond formation, is a bimolecular process. FIG. 20 shows the results of experiments in which the n=1, n=10, and n=1 mismatched (mis) reactions described in FIG. 18 were repeated with template and reagent concentrations of 12.5, 25, 62.5 or 125 nM. FIG. 20 shows that decreasing the concentration of reactants in the case of the E template with one or ten intervening bases between reactive groups resulted in a marked decrease in the observed reaction rate. This observation suggests that proximity effects in DNA-templated synthesis can enhance bond formation rates to the point that DNA annealing becomes rate-determining.

These findings raise the possibility of using DNA templated synthesis to translate in one pot libraries of DNA into solution-phase libraries of synthetic molecules suitable for PCR amplification and selection. The sequence specificity described above suggests that mixtures of reagents may be able to react predictably with complementary mixtures of templates. Finally, the observed distance independence suggests that different template codons can be used to encode different reactions without impairing reactions rates.

Figure 21A:
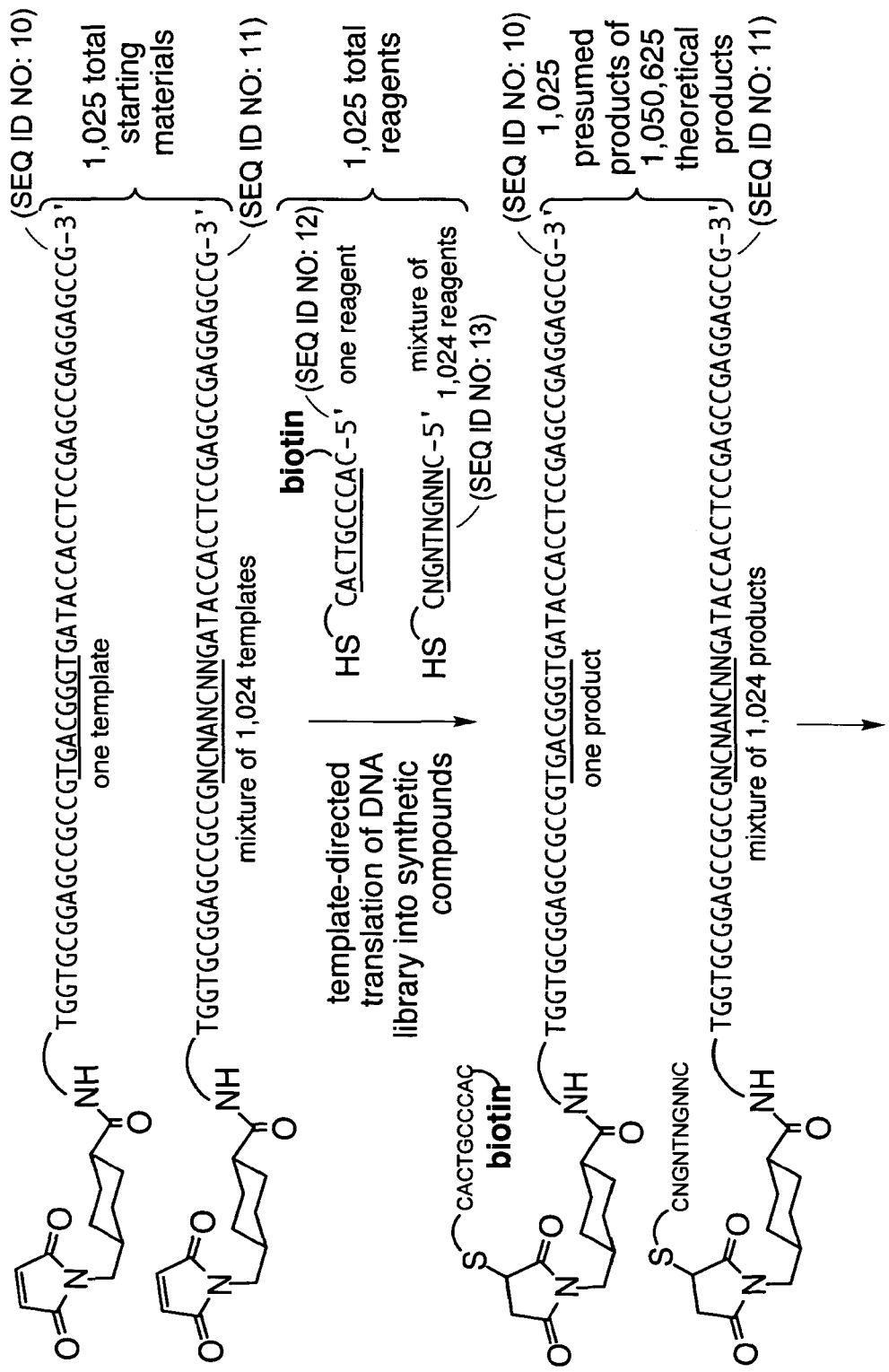
FIGS. 21A-21B are a schematic representation of a method for translating, selecting, and amplifying a synthetic molecule that binds streptavidin from a DNA-encoded library.
Figure 21B:
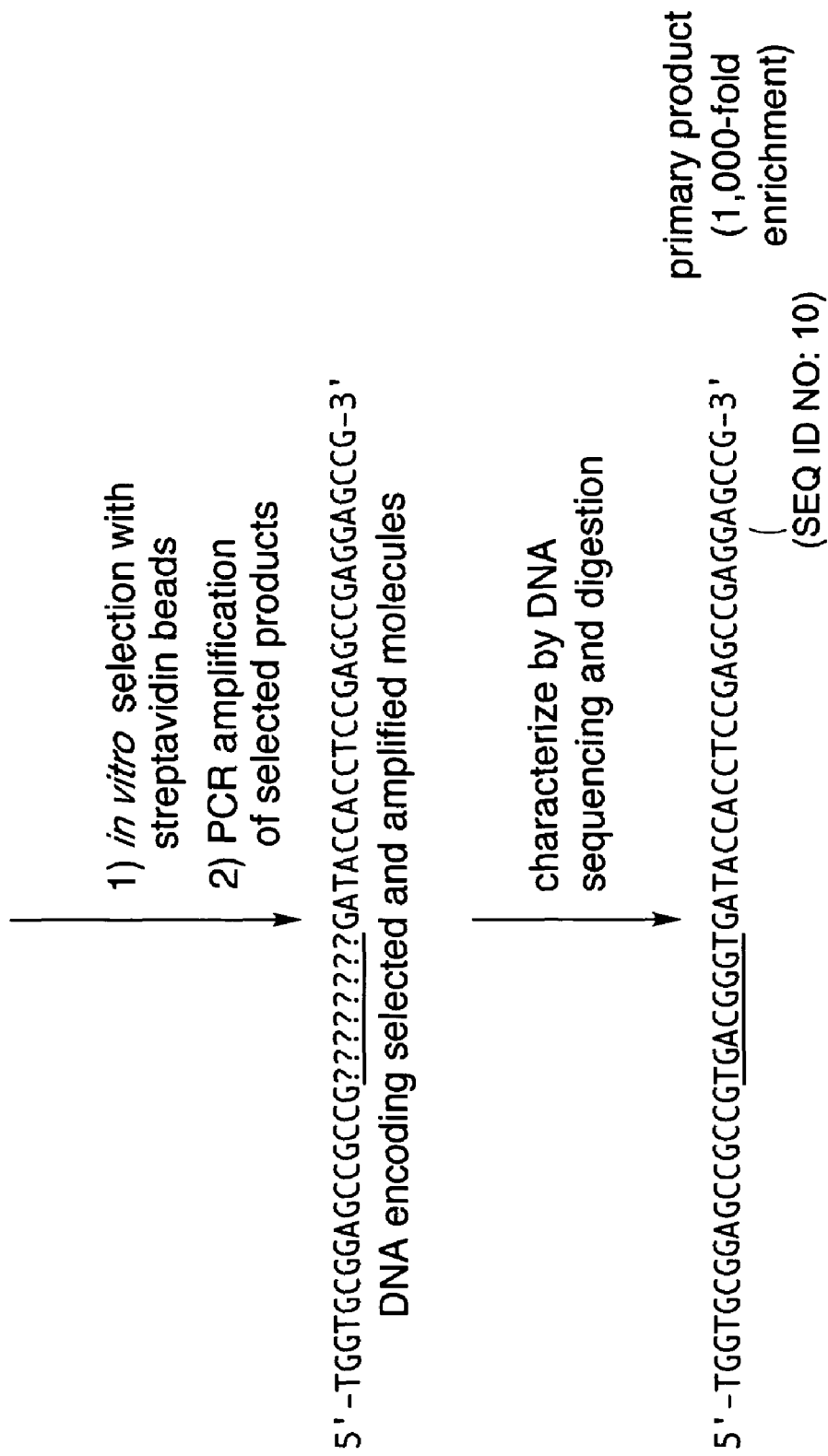

As a demonstration of this approach, a library of 1,025 maleimide-linked templates was synthesized, each with a different DNA sequence in an eight-base encoding region (FIGS. 21A-21B). One of these sequences, 5'-TGACGGGT-3', was arbitrarily chosen to code for the attachment of a biotin group to the template. A library of thiol reagents linked to 1,025 different oligonucleotides was also generated. The reagent linked to 3'-ACTGCCCA-5' contained a biotin group, while the other 1,024 reagents (transfer units) contained no biotin. Equimolar ratios of all 1,025 templates and 1,025 reagents were mixed in one pot for 10 minutes at 25° C. and the resulting products were selected in vitro for binding to streptavidin. Molecules surviving the selection were amplified by PCR and analyzed by restriction digestion and DNA sequencing.

Figure 22A:
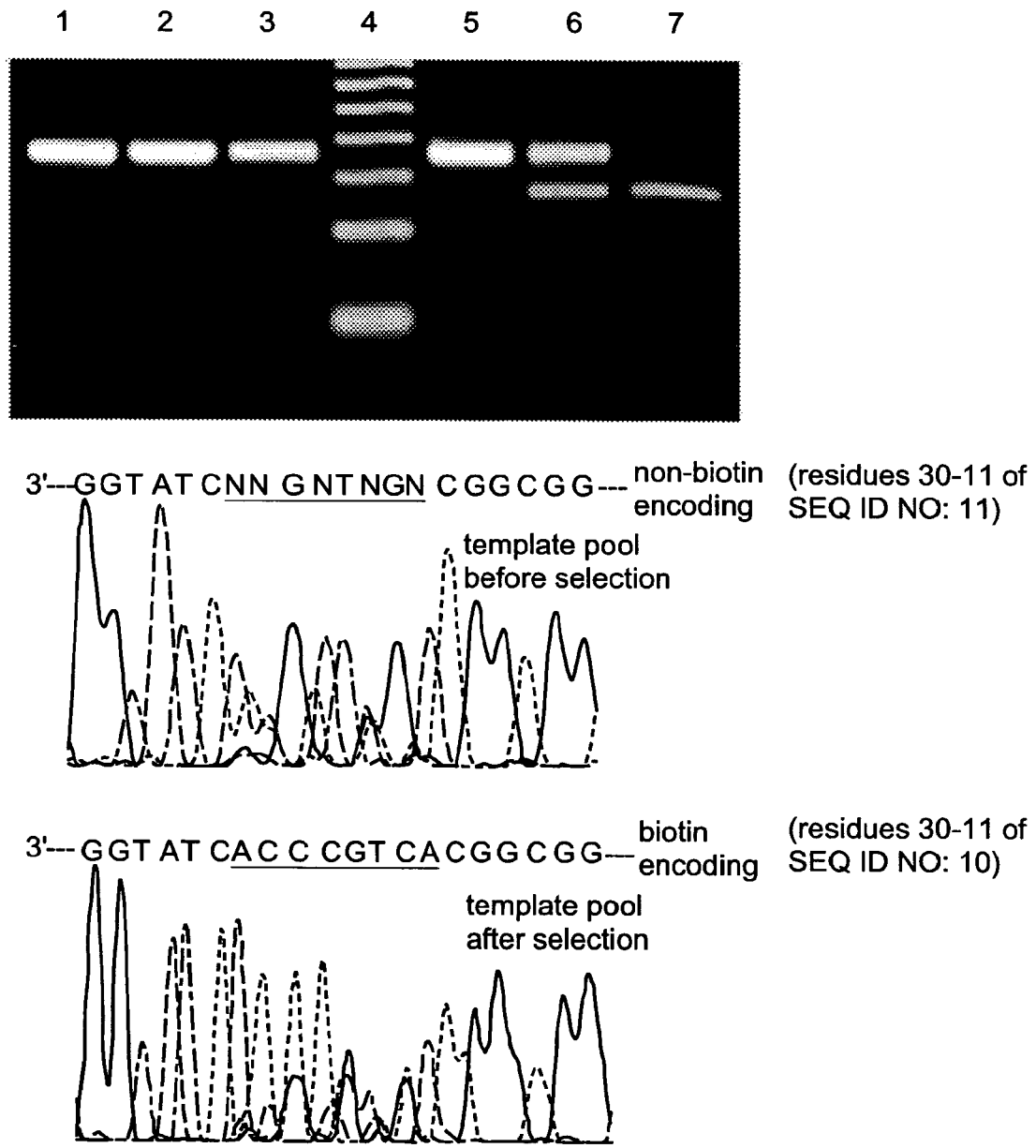
FIG. 22A depicts DNA sequencing results of a PCR amplified pool of nucleic acid templates of FIGS. 21A-21B before and after selection.

Digestion with the restriction endonuclease Tsp45I, which cleaves GTGAC and therefore cuts the biotin encoding template but none of the other templates, revealed a 1:1 ratio of biotin encoding to non-biotin encoding templates following selection. In the experiments shown in FIG. 22A, lanes 1 and 5 represent the PCR-amplified library before streptavidin binding selection; lanes 2 and 6 represent the PCR-amplified library after selection; lanes 3 and 7 represent the PCR amplified authentic biotin-encoding template; and lane 4 represents a 20 bp ladder. Lanes 5-7 were digested with Tsp45I. DNA sequencing traces of the amplified templates before and after selection are also shown, together with the sequences of the non-biotin-encoding and biotin-encoding templates. The results summarized in FIG. 22A represent a 1,000-fold enrichment compared with the unselected library. DNA sequencing of the PCR amplified pool before and after selection suggested a similar degree of enrichment and indicated that the biotin-encoding template is the major product after selection and amplification (FIG. 22A). The ability of DNA-templated synthesis to support the simultaneous sequence-specific reaction of 1,025 reagents, each of which faces a 1,024:1 ratio of non-partner to partner templates, demonstrates its potential as a method to create synthetic libraries in one pot.

Figure 22B:
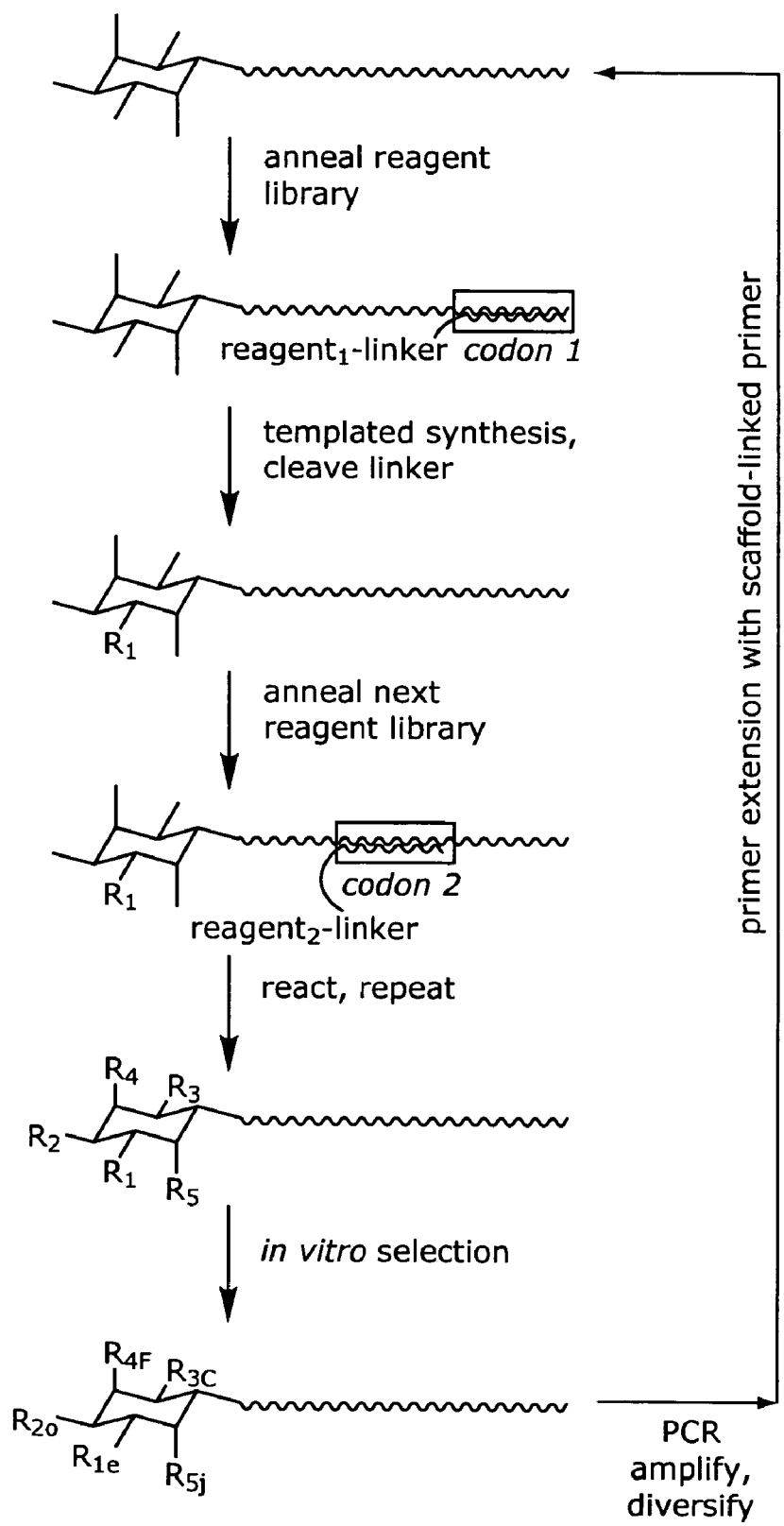
FIG. 22B is a schematic representation of a method for creating and evolving libraries of non-natural molecules using nucleic acid-templated synthesis, where —$R_1$ represents the library of product functionality transferred from reagent library 1 and —$R_{1B}$ represents a selected product.

Taken together, these results show that it is possible to translate, select, and amplify a synthetic library member having a specific property (for example, bind avidin) as shown in FIG. 22B. Furthermore, these results indicate that nucleic acid-templated synthesis is a surprisingly general phenomenon capable of directing, rather than simply encoding, a range of chemical reactions to form products unrelated in structure to nucleic acid backbones. For several reactions examined, the DNA-templated format accelerates the rate of bond formation beyond the rate of a 10-base DNA oligonucleotide annealing to its complement, resulting in surprising distance independence. The facile nature of long-distance DNA-templated reactions may also arise in part from the tendency of water to contract the volume of nonpolar reactants (see, C.-J. Li et al. Organic Reactions in Aqueous Media, Wiley and Sons: New York, 1997) and from possible compactness of the intervening single-stranded DNA between reactive groups.

Materials and Methods

DNA Synthesis. DNA oligonucleotides were synthesized on a PerSeptive Biosystems Expedite 8909 DNA synthesizer using standard protocols and purified by reverse phase HPLC. Oligonucleotides were quantitated spectrophotometrically and by denaturing polyacrylamide gel electrophoresis (PAGE) followed by staining with ethidium bromide or SYBR Green (Molecular Probes) and quantitation using a Stratagene Eagle Eye II densitometer. Phosphoramidites enabling the synthesis of 5'-NH$_2$-dT, 5' tetrachlorofluorescein, a basic backbone spacer, C3 backbone spacer, 9-bond polyethylene glycol spacer, 12-bond saturated hydrocarbon spacer, and 5' biotin groups were purchased from Glen Research, Sterling, Va., USA. Thiol-linked oligonucleotide reagents were synthesized on C3 disulfide controlled pore glass from Glen Research, Sterling, Va., USA.

Template Functionalization. Templates bearing 5'-NH$_2$-dT groups were transformed into a variety of electrophilic functional groups by reaction with the appropriate electrophile-N-hydroxysuccinimide (NHS) ester (Pierce, Rockford, Ill., USA). Reactions were performed in 200 mM sodium phosphate pH 7.2 with 2 mg/mL electrophile-NHS ester, 10% dimethylsulfoxide (DMSO), and up to 100 µg of 5'-amino template at 25° C. for 1 hours. Desired products were purified by reverse-phase HPLC and characterized by gel electrophoresis and MALDI mass spectrometry.

DNA-templated synthesis reactions. Reactions were initiated by mixing equimolar quantities of reagent (transfer unit) and template in buffer containing 50 mM N-[3-morpholinopropane]sulfonic acid (MOPS) pH 7.5 and 250 mM NaCl at the desired temperature (25° C. unless stated otherwise). Concentrations of reagents and templates were 60 nM unless otherwise indicated. At various time points, aliquots were removed, quenched with excess β-mercaptoethanol, and analyzed by denaturing PAGE. Reaction products were quantitated by densitometry using their intrinsic fluorescence or by staining followed by densitometry. Representative products were also verified by MALDI mass spectrometry.

In Vitro Selection for Avidin Binding. Products of the library translation reaction (FIG. 21A-21B) were isolated by ethanol precipitation and dissolved in binding buffer (10 mM Tris pH 8, 1 M NaCl, 10 mM ethylenediaminetetraacetic acid (EDTA)). Products were incubated with 30 µg of streptavidin-linked magnetic beads (Roche Biosciences) for 10 minute at room temperature in 100 µL total volume. The beads were washed 16 times with binding buffer and eluted by treatment with 1 µmol free biotin in 100 uL binding buffer at 70° C. for 10 minutes. The eluted molecules were isolated by ethanol precipitation and amplified by standard PCR protocols (2 mM $MgCl_2$, 55° C. annealing, 20 cycles) using the primers 5'-TG-GTGCGGAGCCGCCG [SEQ ID NO: 35] and 5'-CCACT-GTCCGTGGCGCGACCCCGGCTCCTCGGCTCGG [SEQ ID NO: 36]. Automated DNA sequencing used the primer 5'-CCACTGTCCGTGGCGCGACCC [SEQ ID NO: 37].

DNA Sequences. Sequences not provided in the Figures are as follows: matched reagent in FIG. 16 SIAB and SBAP reactions: 5'-CCCGAGTCGAAGTCGTACC-SH [SEQ ID NO: 38]; mismatched reagent in FIG. 16 SIAB and SBAP reactions: 5'-GGGCTCAGCTTCCCCATAA-SH [SEQ ID NO: 39]; mismatched reagents for other reactions in FIGS. 16, and 17A-17B; 5'-FAAATCTTCCC-SH tetrachlorofluorescein) [SEQ ID NO: 40]; reagents in FIG. 16 containing one mismatch: 5'-FAATTCTTACC-SH [SEQ ID NO: 41]; E templates in FIGS. 15 and 16 SMCC, GMBS, BMPS, and SVSB reactions, and FIGS. 17A-17B: 5'-($NH_2$dT)-CGCGAGCG-TACGCTCGCGATGGTACGAATTCGACTCGGGAATAC CACCTTCGACTCGAGG [SEQ ID NO: 42]; H template in FIG. 16 SIAB, SBAP, and SIA reactions: 5'-($NH_2$dT)-CGC-GAGCGTACGCTCGCGATGGTACGAATTC [SEQ ID NO: 43]; clamp oligonucleotide in FIG. 19: 5'-ATTCG-TACCA [SEQ ID NO: 44].

Example 2

Exemplary Reactions for Use in DNA-Templated Synthesis

This Example demonstrates that DNA-templated synthesis can direct a modest collection of chemical reactions without requiring the precise alignment of reactive groups into DNA-like conformations. Furthermore, this Example also demonstrates that it is possible to simultaneously translate in one-pot a library of more than 1,000 templates into the corresponding thioether products, one of which could be enriched by in vitro selection for binding to streptavidin and amplification by PCR.

As described in detail herein, a variety of chemical reactions for example. DNA-templated organometallic couplings and carbon-carbon bond forming reactions other than pyrimidine photodimerization can be utilized to construct small molecules. These reactions represent an important step towards the in vitro evolution of non-natural synthetic molecules by permitting the DNA-templated construction of a diverse set of structures.

The ability of DNA-templated synthesis to direct reactions that require a non-DNA-linked activator, catalyst or other reagent in addition to the principal reactants has also been demonstrated herein. To test the ability of DNA-templated synthesis to mediate such reactions without requiring structural mimicry of the DNA-templated backbone, DNA-templated reductive aminations between an amine-linked template (1) and benzaldehyde- or glyoxal-linked reagents (3) with millimolar concentrations of sodium cyanoborohydride ($NaBH_3CN$) at room temperature in aqueous solutions can be performed (see, FIG. 23A). Significantly, products formed efficiently when the template and reagent sequences were complementary, while control reactions in which the sequence of the reagent did not complement that of the template, or in which $NaBH_3CN$ was omitted, yielded no significant product (see FIGS. 23A-23D and 24). Although DNA-templated reductive aminations to generate products closely mimicking the structure of double-stranded DNA have been previously reported (see, for example, Li et al. (2002) J. AM. CHEM. SOC. 124: 746 and Gat et al. (1998) BIOPOLYMERS 48: 19), these results demonstrate that reductive amination to generate structures unrelated to the phosphoribose backbone can take place efficiently and sequence-specifically.

Figure 24:
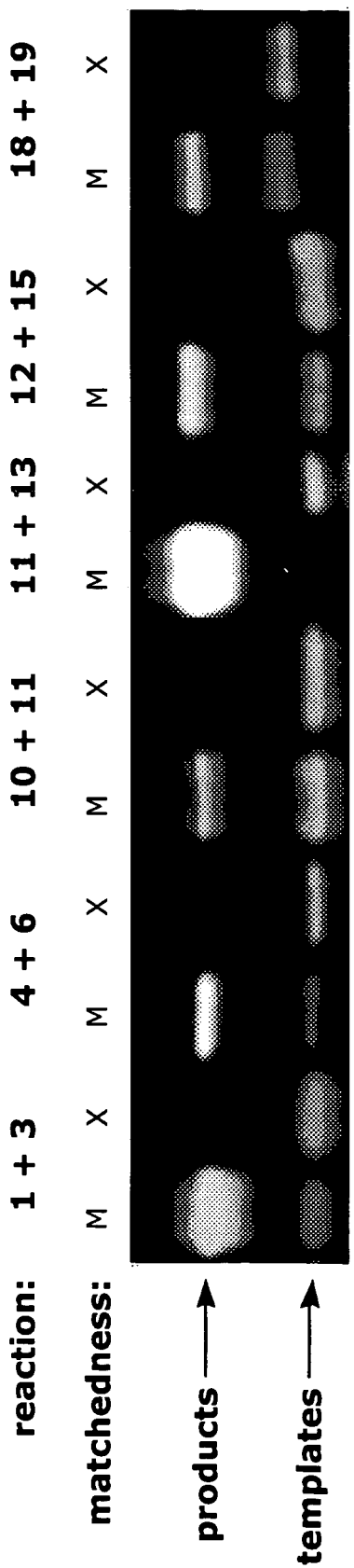
FIG. 24 depicts analysis by denaturing PAGE of representative DNA-templated reactions listed in FIGS. 23 and 25.
Figure 25A:
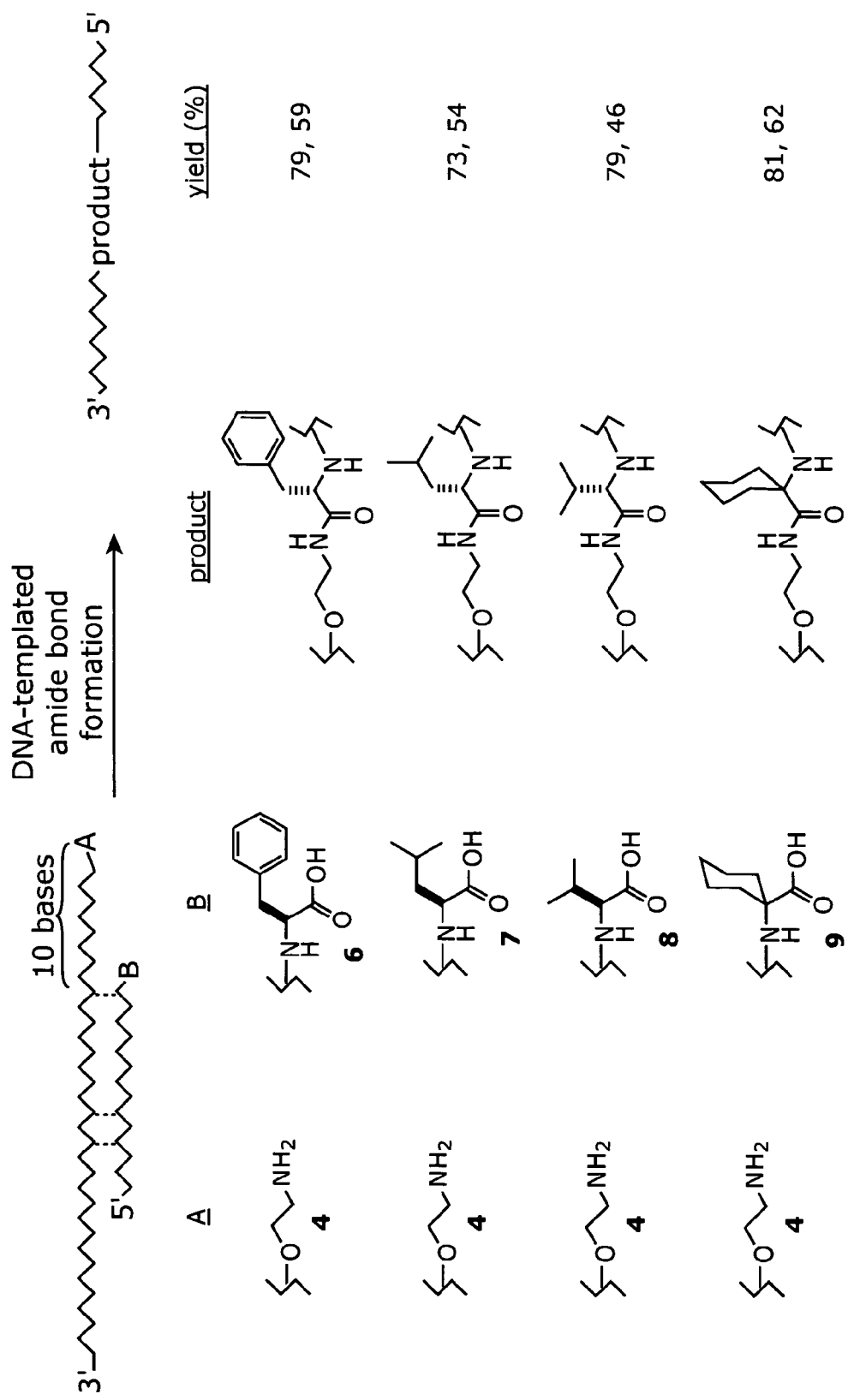
FIGS. 25A-25B are schematic representations of DNA-templated amide bond formation reactions mediated by EDC and sulfo-NHS or by DMT-MM for a variety of substituted carboxylic acids and amines.
Figure 25B:
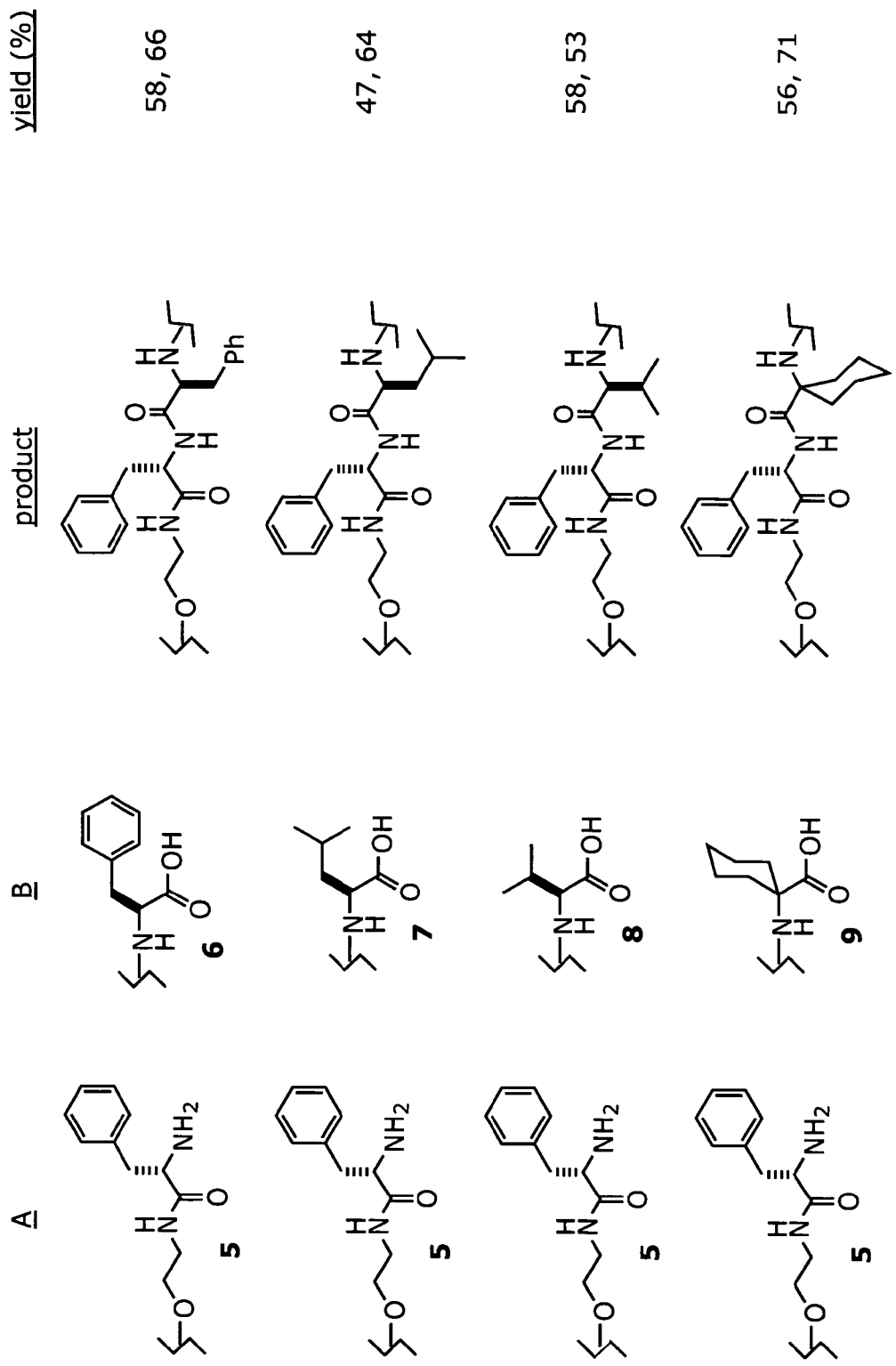

Referring to FIGS. 25A-25B, DNA-templated amide bond formations between amine-linked templates 4 and 5 and carboxylate-linked reagents 6-9 mediated by 1-(3-dimethylaminopropyl)-3-ethylcarbodiimide (EDC) and N-hydroxylsulfo-succinimide (sulfo-NHS) generated amide products in good yields at pH 6.0, 25° C. Product formation was (i) sequence-specific, (ii) dependent on the presence of EDC, and (iii) insensitive to the steric encumbrance of the amine or carboxy-late. Efficient DNA-templated amide formation was also mediated by the water-stable activator 4-(4,6-dimethoxy-1,3, 5-trizin-2-yl)-4-methylmorpholinium chloride (DMT-MM) instead of EDC and sulfo-NHS (FIGS. 24 and 25A-25B). The efficiency and generality of DNA-templated amide bond formation under these conditions, together with the large number of commercially available chiral amines and carboxylic acids, make this reaction an attractive candidate in future DNA-templated syntheses of structurally diverse small molecule libraries.

Figure 23A:
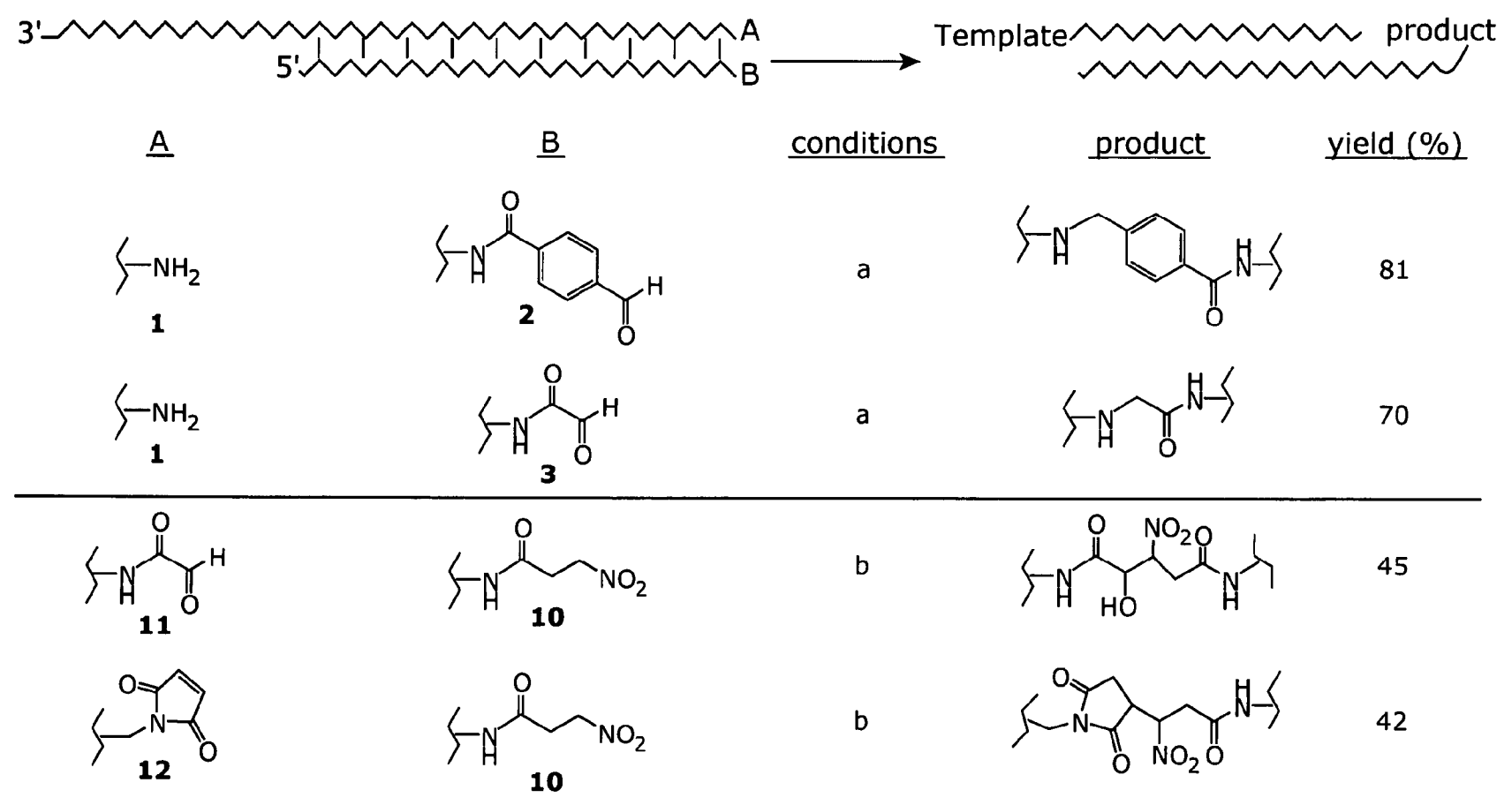
Figure 23B:
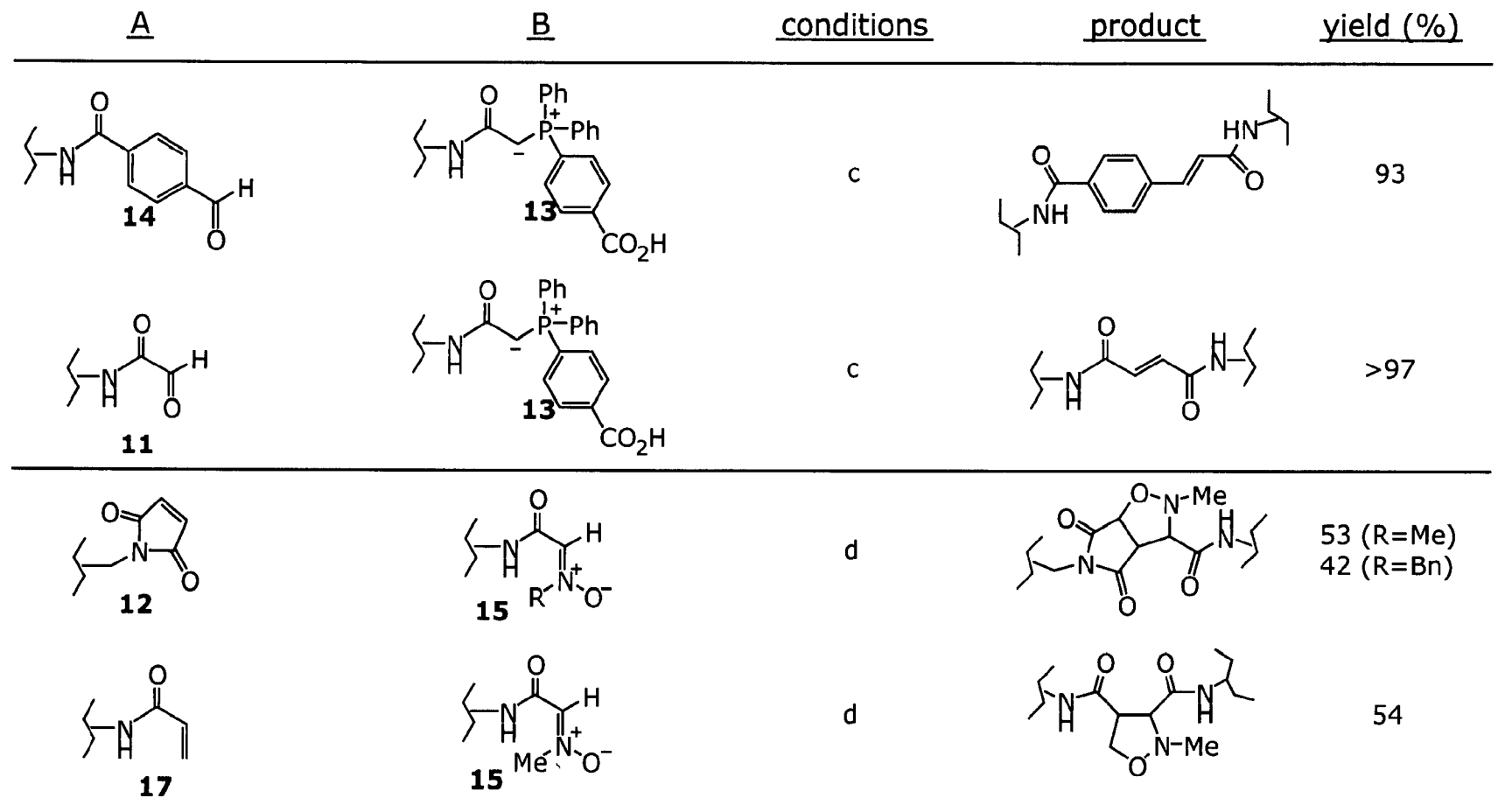
Figure 23C:
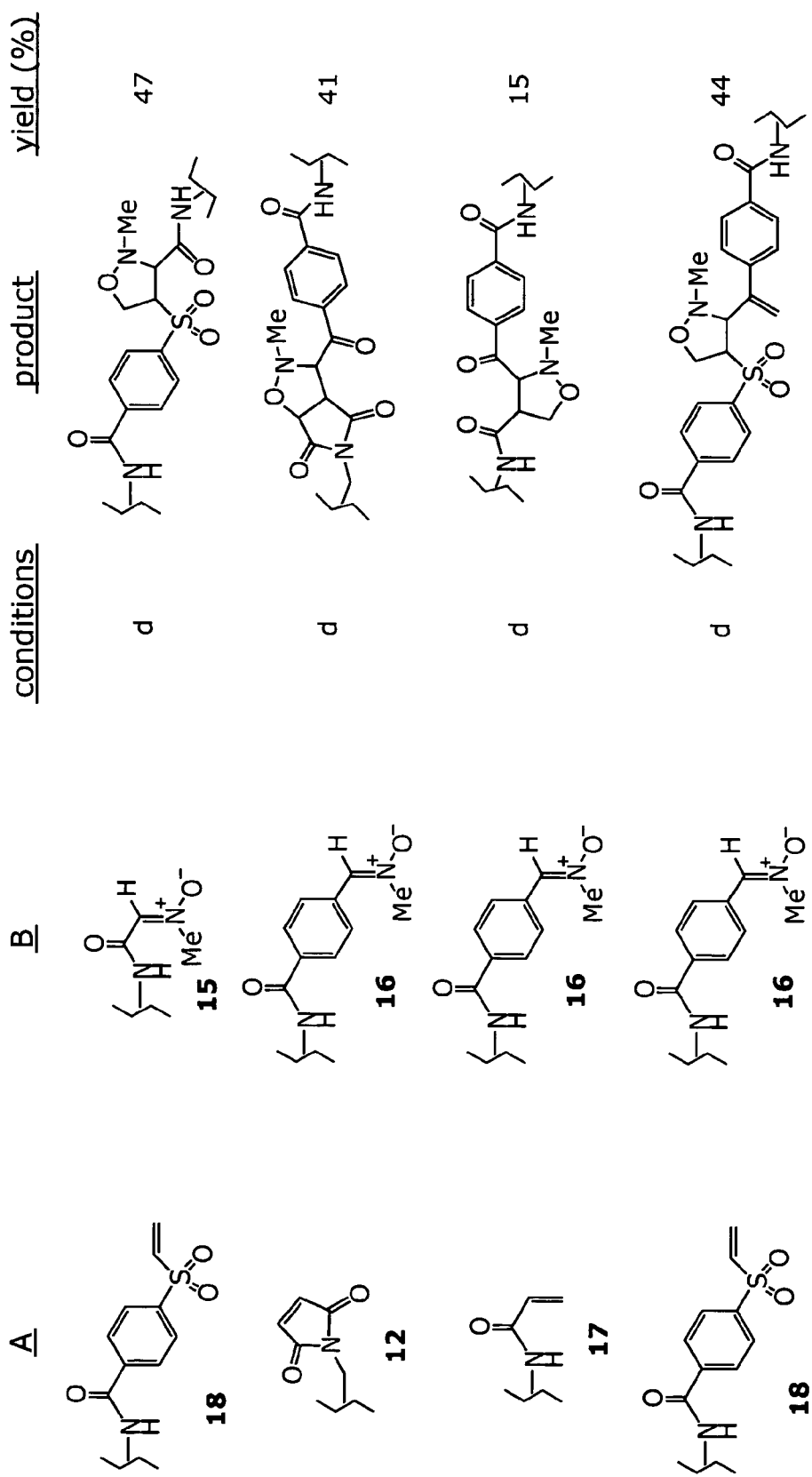

Carbon-carbon bond forming reactions are also important in both chemical and biological syntheses and thus several such reactions can be utilized in a nucleic acid-templated format. Both the reaction of nitroalkane-linked reagent (10) with aldehyde-linked template (11) (nitro-aldol or Henry reaction) and the conjugate addition of 10 to maleimide-linked template (12) (nitro-Michael addition) proceeded efficiently and with high sequence specificity at pH 7.5-8.5, 25° C. (FIGS. 23A and 24). In addition, the sequence-specific DNA-templated Wittig reaction between stabilized phosphorus ylide reagent 13 and aldehyde-linked templates 14 or 11 provided the corresponding olefin products in excellent yields at pH 6.0-8.0, 25° C. (FIGS. 23B and 24). Similarly, the DNA templated 1,3-dipolar cycloaddition between nitrone-linked reagents 15 and 16 and olefin-linked templates 12, 17 or 18 also afforded products sequence specifically at pH 7.5, 25° C. (FIGS. 23B, 23C and 24).

Figure 23D:
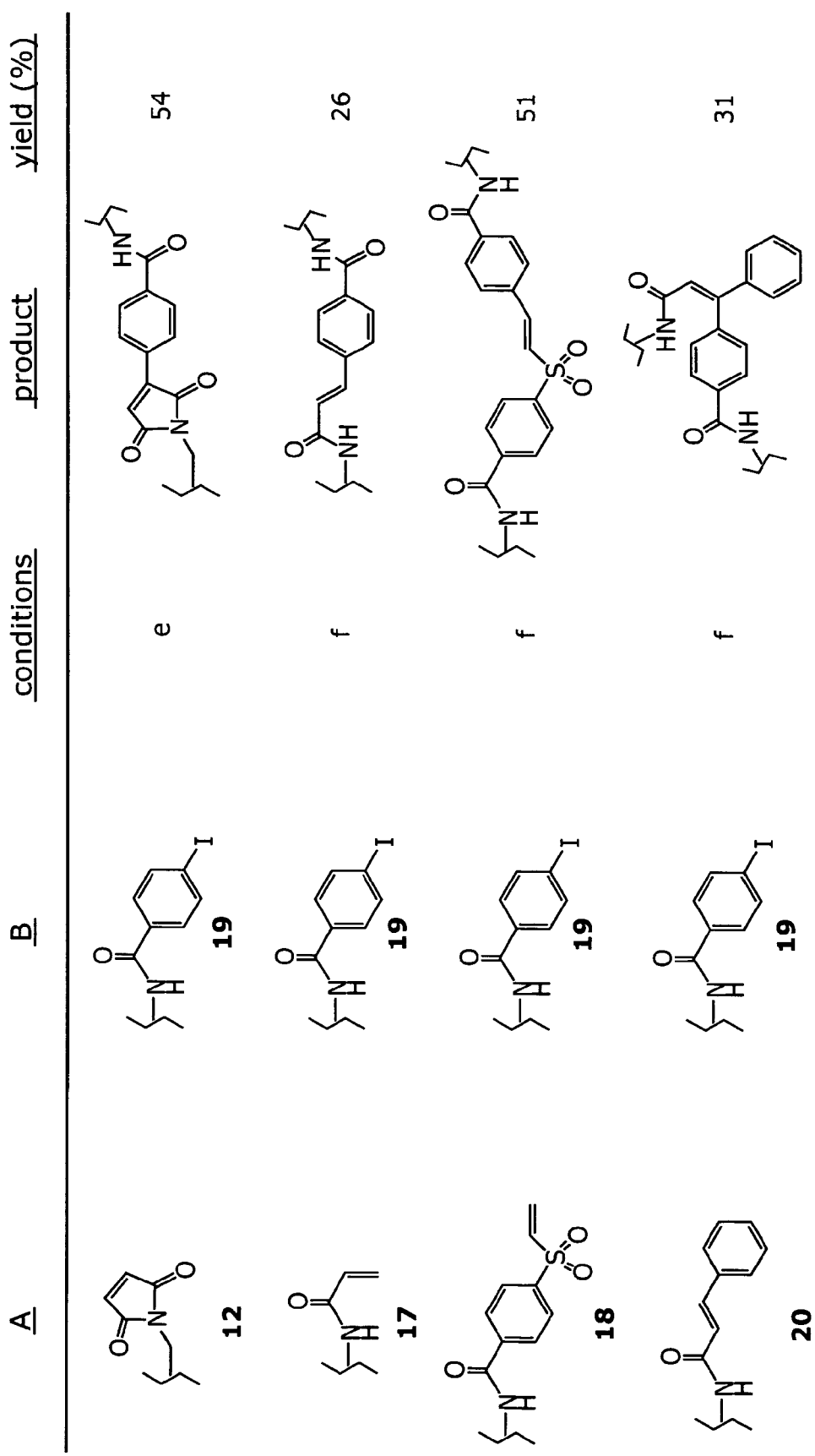

In addition to the reactions described above, organometallic coupling reactions can also be utilized in the present invention. For example, DNA-templated Heck reactions were performed in the presence of water-soluble Pd precatalysts. In the presence of 170 mM $Na_2PdCl_4$, aryl iodide-linked reagent 19 and a variety of olefin-linked templates including maleimide 12, acrylamide 17, vinyl sulfone 18 or cinnamamide 20 yielded Heck coupling products in modest yields at pH 5.0, 25° C. (FIGS. 23D and 24). For couplings with olefins 17, 18 and 20, adding two equivalents of P(p-SO$_3$C$_6$H$_4$)$_3$ per equivalent of Pd prior to template and reagent addition typically increased overall yields by 2-fold. Control reactions containing sequence mismatches or lacking Pd precatalyst yielded no product.

Figure 26A:
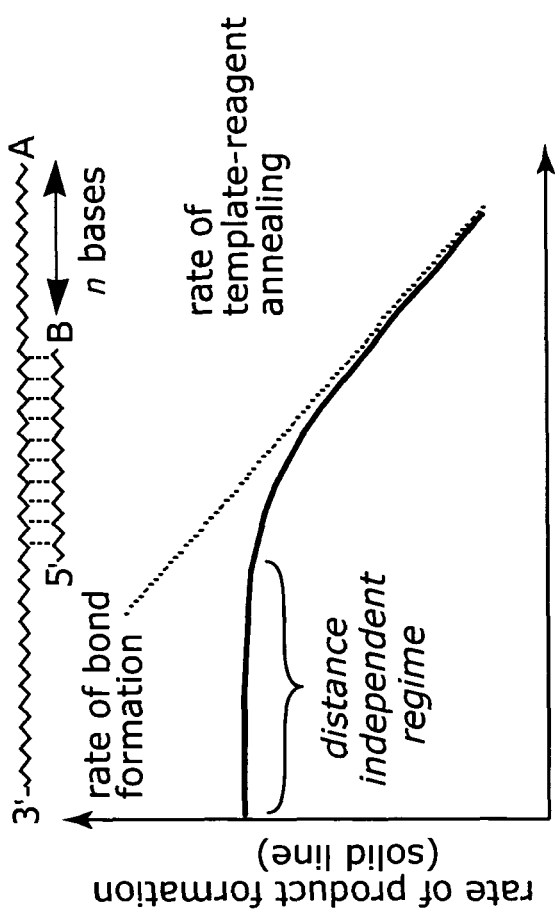
FIGS. 26A-26B depict an analysis of the distance independent nature of certain nucleic acid-templated reactions.
Figure 26B:
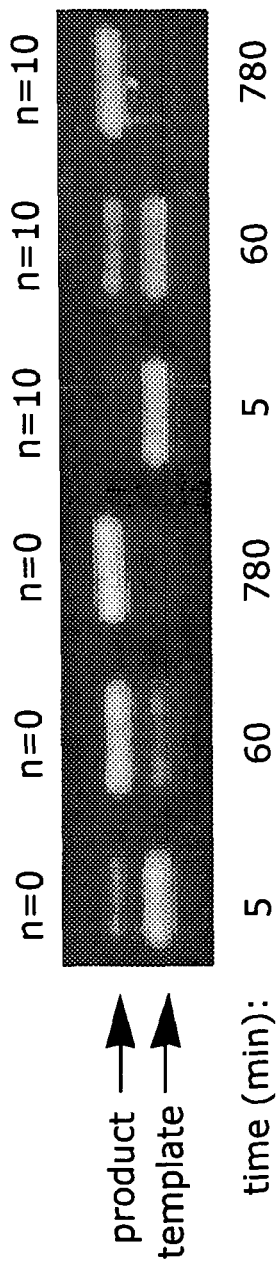

Example 1 above shows that certain DNA-templated reactions demonstrate distance independence. Distance independence may arise when the rate of bond formation in the DNA-templated reaction is greater than the rate of template-reagent annealing. Although only a subset of chemistries fall into this category, any DNA-templated reaction that affords comparable product yields when the reagent is annealed at various distances from the reactive end of the template is of special interest because it can be encoded at a variety of template positions. In order to evaluate the ability of the DNA-templated reactions developed in this Example to take place efficiently when reactants are separated by distances relevant to library encoding, the yields of reductive amination, amide formation, nitro-aldol addition, nitro-Michael addition, Wittig olefination, dipolar cycloaddition, and Heck coupling reactions were compared when either zero (n=0) or ten (n=10) bases separated the annealed reactive groups (FIG. 26A). Among the reactions described here or in Example 1, amide bond formation, nitro-aldol addition, Wittig olefination, Heck coupling, conjugate addition of thiols to maleimides and S$_N$2 reaction between thiols and α-iodo amides demonstrate comparable product formation when reactive groups are separated by zero or ten bases (FIG. 26B). FIG. 26B shows the results of denaturing polyacrylamide gel electrophoresis of a DNA-templated Wittig olefination between complementary 11 and 13 with either zero bases (lanes 1-3) or ten bases (lanes 4-6) separating the annealed reactants. Although the apparent second order rate constants for the n=0 and n=10 reactions differ by three-fold (kapp (n=0)=9.9×10$^3$ M$^{-1}$s$^{-1}$ while kapp (n=10)=3.5×10$^3$ M$^{-1}$s$^{-1}$), product yields after 13 hours at both distances were nearly quantitative. Control reactions containing sequence mismatches yielded no detectable product. These findings indicate that these reactions can be encoded during synthesis by nucleotides that are distal from the reactive end of the template without significantly impairing product formation.

Figure 27:
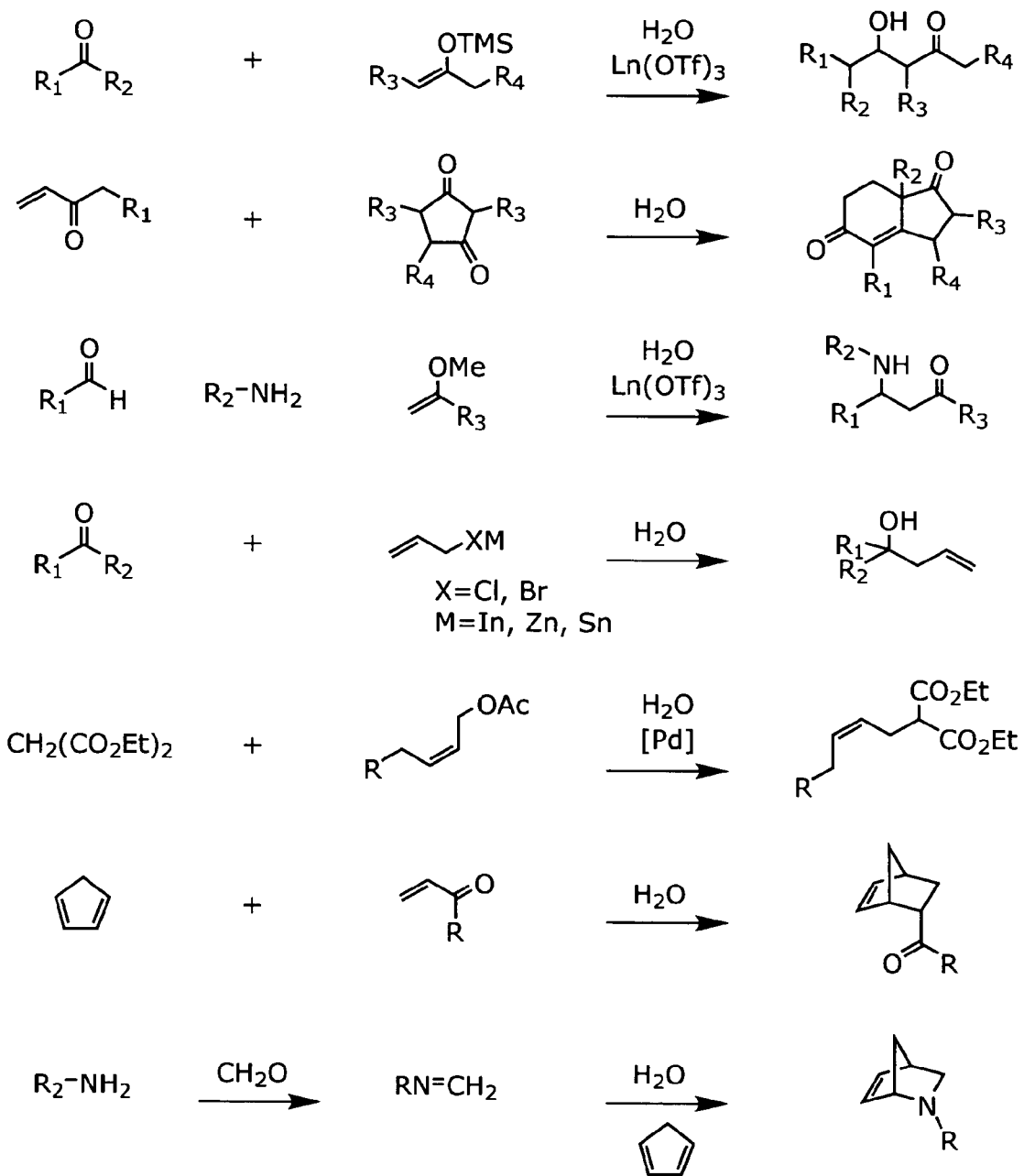
FIG. 27 is a schematic representation of exemplary nucleic acid-templated complexity building reactions.

In addition to the DNA-templated S$_N$2 reaction, conjugate addition, vinyl sulfone addition, amide bond formation, reductive amination, nitro-aldol (Henry reaction), nitro Michael, Wittig olefination, 1,3-dipolar cycloaddition and Heck coupling reactions described directly above, a variety of additional reagents can also be utilized in the method of the present invention. For example, as depicted in FIG. 27, powerful aqueous DNA-templated synthetic reactions including, but not limited to, the Lewis acid-catalyzed aldol addition, Mannich reaction, Robinson annulation reactions, additions of allyl indium, zinc and tin to ketones and aldehydes, Pd-assisted allylic substitution, Diels-Alder cycloadditions, and hetero-Diels-Alder reactions can be utilized efficiently in aqueous solvent and are important complexity-building reactions.

Taken together, these results expand considerably the reaction scope of DNA-templated synthesis. A wide variety of reactions can proceed efficiently and selectively when the corresponding reactants are programmed with complementary sequences. By augmenting the repertoire of known DNA-templated reactions to include carbon-carbon bond forming and organometallic reactions (nitro-aldol additions, nitro-Michael additions, Wittig olefinations, dipolar cycloadditions, and Heck couplings) in addition to previously reported amide bond formation (see, Schmidt et al. (1997) NUCLEIC ACIDS RES. 25: 4792; Bruick et al. (1996) CHEM. BIOL. 3: 49), imine formation (Czlapinski et al. (2001) J. AM. CHEM. SOC. 123: 8618), reductive amination (Li et al. (2002) J. AM. CHEM. SOC. 124: 746; Gat et al. (1998) BIOPOLYMERS 48: 19), S$_N$2 reactions (Gartner et al. (2001) J. AM. CHEM. SOC. 123: 6961; Xu et al. (2001) NAT. BIOTECHNOL. 19: 148; Herrlein et al. (1995) J. AM. CHEM. SOC. 117: 10151) conjugate addition of thiols (Gartner et al. (2001) J. AM. CHEM. SOC. 123: 6961), and phosphoester or phosphonamide formation (Orgel et al. (1995) ACC. CHEM. RES. 28: 109; Luther et al. (1998) NATURE 396: 245), these results may permit the sequence-specific translation of libraries of DNA into libraries of structurally and functionally diverse synthetic products.

Because minute quantities of templates encoding desired molecules can be amplified by PCR, the yields of DNA-templated reactions arguably are less critical than the yields of traditional synthetic transformations. Nevertheless, many of the reactions discussed in this Example proceed efficiently.

Materials and Methods

Functionalized templates and reagents were typically prepared by reacting 5'-NH$_2$ terminated oligonucleotides (for template 1), 5'-NH$_2$—(CH$_2$O)$_2$ terminated oligonucleotides (for all other templates) or 3'-OPO$_3$—CH$_2$CH(CH$_2$OH)(CH$_2$)$_4$NH$_2$ terminated nucleotides (for all reagents) with the appropriate NHS esters (0.1 volumes of a 20 mg/mL solution in DMF) in 0.2 M sodium phosphate buffer, pH 7.2, 25° C., for 1 hour to provide the template and reagent structures shown in FIGS. 23A-23D and 25A-25B. For amino acid linked reagents 6-9, 3% OPO$_3$CH$_2$CH(CH$_2$OH)(CH$_2$)$_4$NH$_2$ terminated oligonucleotides in 0.2 M sodium phosphate buffer, pH 7.2 were reacted with 0.1 volumes of a 100 mM bis[2-(succinimidyloxycarbonyloxy)ethyl]sulfone (BSO-COES, Pierce, Rockford, Ill., USA) solution in DMF for 10 minutes at 25° C., followed by 0.3 volumes of a 300 mM amino acid in 300 mM sodium hydroxide (NaOH) for 30 minutes at 25° C.

Functionalized templates and reagents were purified by gel filtration using Sephadex G-25 followed by reverse-phase HPLC (0.1 triethylammonium acetate-acetonitrile gradient) and characterized by MALDI mass spectrometry.

For the DNA templated reactions described in FIGS. 23A-23D, reactions were conducted at 25° C. with one equivalent each of template and reagent at 60 nM final concentration unless otherwise specified. Conditions: (a) 3 mM NaBH$_3$CN, 0.1 M N-[2-morpholinoethane]sulfonic acid (MES) buffer pH 6.0, 0.5 M NaCl, 1.5 hours; b) 0.1 M N-tris[hydroxymethyl]methyl-3-aminopropanesulfonic acid (TAPS) buffer pH 8.5, 300 mM NaCl, 12 hours; c) 0.1 M pH 8.0 TAPS buffer, 1 M NaCl, 5° C., 1.5 hours; d) 50 mM MOPS buffer pH 7.5, 2.8 M NaCl, 22 hours; e) 120 nM 19, 1.4 mM Na$_2$PdCL$_4$, 0.5 M NaOAc buffer pH 5.0, 18 hours; (f) Premix Na$_2$PdCl$_4$ with two equivalents of P(p-SO$_3$C$_6$H$_4$)$_3$ in water for 15 minutes, then add to reactants in 0.5 M NaOAc buffer pH 5.0, 75 mM NaCl. 2 hours (final [Pd]=0.3 mM, [19]=120 nM). The olefin geometry of products from 13 and the regiochemistries of cycloaddition products from 14 and 16 are presumed but not verified (FIGS. 23A-23D). Products were characterized by denaturing polyacrylamide gel electrophoresis and MALDI mass spectrometry. For all reactions under the specified conditions, product yields of reactions with matched template and reagent sequences were greater than 20-fold higher than that of control reactions with scrambled reagent sequences.

The conditions for the reactions described in FIGS. 25A-25B were: 60 nM template, 120 nM reagent, 50 mM DMT-MM in 0.1 M MOPS buffer pH 7.0, 1 M NaCl, for 16 hours at, 25° C.; or 60 nM template, 120 nM reagent, 20 mM EDC, 15 mM sulfo-NHS, 0.1 M MES buffer pH 6.0, 1 M NaCl, for 16 hours at 25° C. In each row of the table in FIGS. 25A-25B, yields of DMT-MM-mediated reactions between reagents and templates complementary in sequence were followed by yields of EDC and sulfo-NHS mediated reactions. In all cases, control reactions with mismatched reagent sequences yielded little or no detectable product and products were characterized by denaturing polyacrylamide gel electrophoresis and MALDI mass spectrometry.

FIG. 24 depicts the analysis by denaturing polyacrylamide gel electrophoresis of representative DNA-templated reactions listed in FIGS. 23A-23D and 25A-25B. The structures of reagents and templates correspond to the numbering in FIGS. 23A-23D and 25A-25B. Lanes 1, 3, 5, 7, 9, 11: reaction of matched (complementary or "M") reagents and templates under conditions listed in FIGS. 23A-23D and 25A-25B (the reaction between 4 and 6 was mediated by DMT-MM). Lanes 2, 4, 6, 8, 10, 12: reaction of mismatched (non-complementary or "X") reagents and templates under conditions identical to those in lanes 1, 3, 5, 7, 9 and 11, respectively.

The sequences of oligonucleotide templates and reagents are as follows (5' to 3' direction, n refers to the number of bases between reactive groups when template and reagent are annealed as shown in FIG. 26A). 1: TGGTACGAATTC-GACTCGGG [SEQ ID NO: 45]; 2 and 3 matched: GAGTC-GAATTCGTACC [SEQ ID NO: 46]; 2 and 3 mismatched: GGGCTCAGCTTCCCCA [SEQ ID NO: 47]; 4 and 5: GGTACGAATTCGACTCGGGAATACCACCTT [SEQ ID NO: 48]; 6-9 matched (n=10): TCCCGAGTCG [SEQ ID NO: 49]; 6 matched (n=0): AATTCGTACC [SEQ ID NO: 50]; 6-9 mismatched: TCACCTAGCA [SEQ ID NO: 51]; 11, 12, 14, 17, 18, 20: GGTACGAATTCGACTCGGGA [SEQ ID NO: 52]; 10, 13, 16, 19 matched: TCCCGAGTCGAATTCG-TACC [SEQ ID NO: 53]; 10, 13, 16, 19 mismatched: GGGCTCAGCTTCCCCATAAT [SEQ ID NO: 54]; 15 matched: AATTCGTACC [SEQ ID NO: 55]; 15 mismatched: TCGTATTCCA [SEQ ID NO: 56]; template for n=10 vs. n=0 comparison: TAGCGATTACGGTACGAATTC-GACTCGGGA [SEQ ID NO: 57].

Reaction yields were quantitated by denaturing PAGE followed by ethidium bromide staining, UV visualization, and charge-coupled device (CCD)-based densitometry of product and template starting material bands. Yield calculations assumed that templates and products stained with equal intensity per base; for those cases in which products were partially double-stranded during quantitation, changes in staining intensity may have resulted in higher apparent yields.

Example 3

Multi-Step Small Molecule Synthesis Programmed by DNA Templates

This Example demonstrates that it is possible to perform multi-step small molecule synthesis via DNA-templated chemistries.

DNA-templated synthesis can direct a wide variety of powerful chemical reactions with high sequence-specificity and without requiring structural mimicry of the DNA backbone. The application of this approach to synthetic molecules of useful complexity, however, requires the development of general methods to permit the product of a DNA-templated reaction to undergo subsequent DNA-templated transformations.

Multi-step DNA-templated small molecule synthesis faces two major challenges beyond those associated with DNA-templated synthesis in general. First, the DNA used to direct reagents to appropriate templates must be removed from the product of a DNA-templated reaction prior to subsequent DNA-templated synthetic steps in order to prevent undesired hybridization to the template. Second, multi-step synthesis often requires the purification and isolation of intermediate products. To address these challenges, three distinct strategies have been developed (i) to link chemical reagents (reactive units) with their decoding DNA oligonucleotides and (ii) to purify product after any DNA-templated synthetic step.

When possible, an ideal reagent-oligonucleotide linker for DNA-templated synthesis positions the oligonucleotide as a leaving group of the reagent. Under this "autocleaving" linker strategy, the oligonucleotide-reagent bond is cleaved as a natural chemical consequence of the reaction (see, FIG. 28A).

Figures 28A, 28B, 28C:
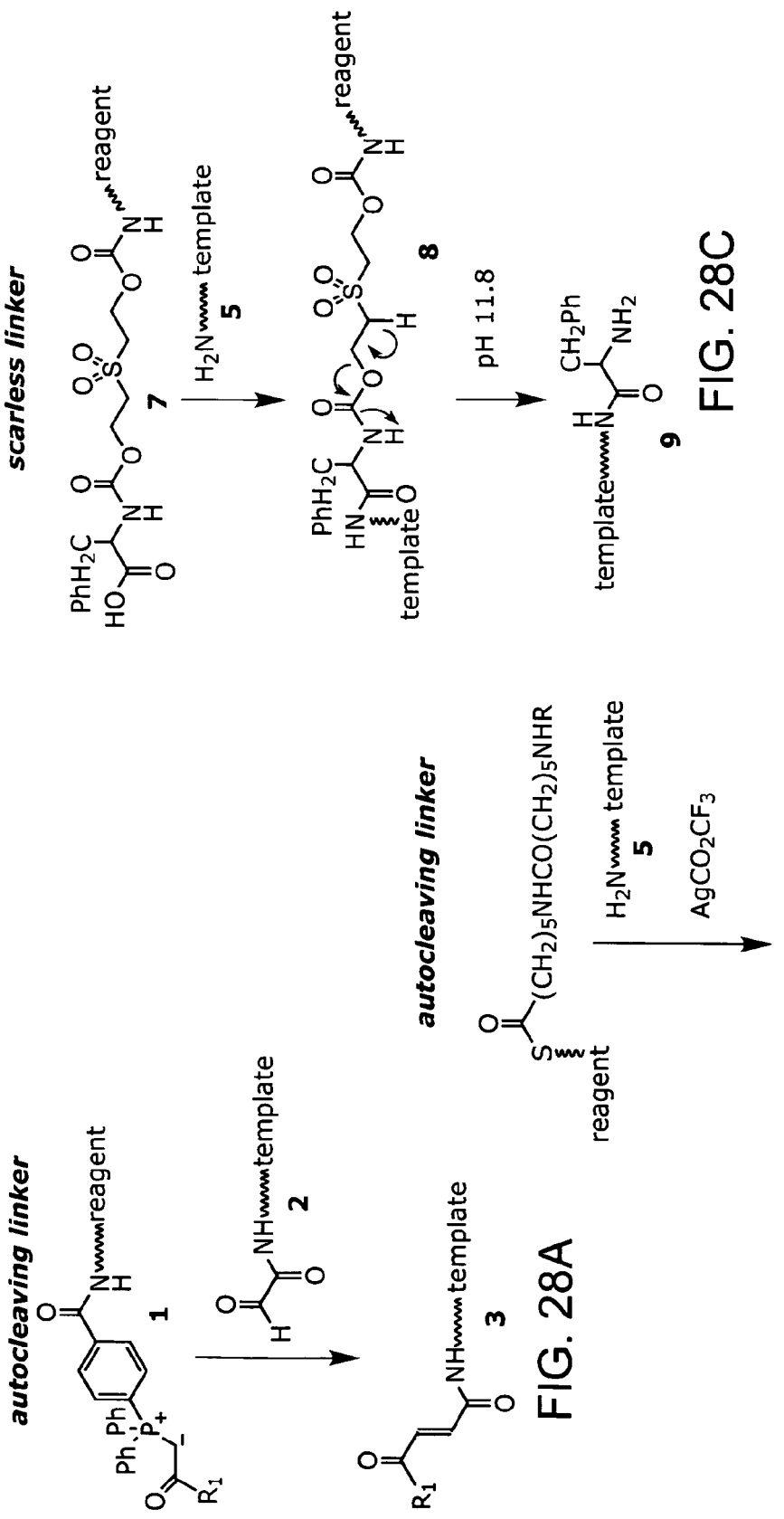
FIGS. 28A-28B depict strategies for DNA-templated synthesis using autocleaving linkers (FIGS. 28A and 28B), scarless linkers (FIG. 28C), and useful scar linkers (FIG. 28D).

As the first example of this approach applied to DNA-templated chemistry, a dansylated Wittig phosphorane reagent (1) was synthesized in which the decoding DNA oligonucleotide was attached to one of the aryl phosphine groups (Hughes (1996) TETRAHEDRON LETT. 37: 7595). DNA-templated Wittig olefination with aldehyde-linked template 2 resulted in the efficient transfer of the fluorescent dansyl group from the reagent to the template to provide olefin 3 (FIG. 28A). As a second example of an autocleaving linker, DNA-linked thioester 4, when activated with Ag(I) at pH 7.0 (Zhang et al. (1999) J. AM. CHEM. SOC. 121: 3311) acylated amino-terminated template 5 to afford amide product 6 (FIG. 28B).

Figure 30A:
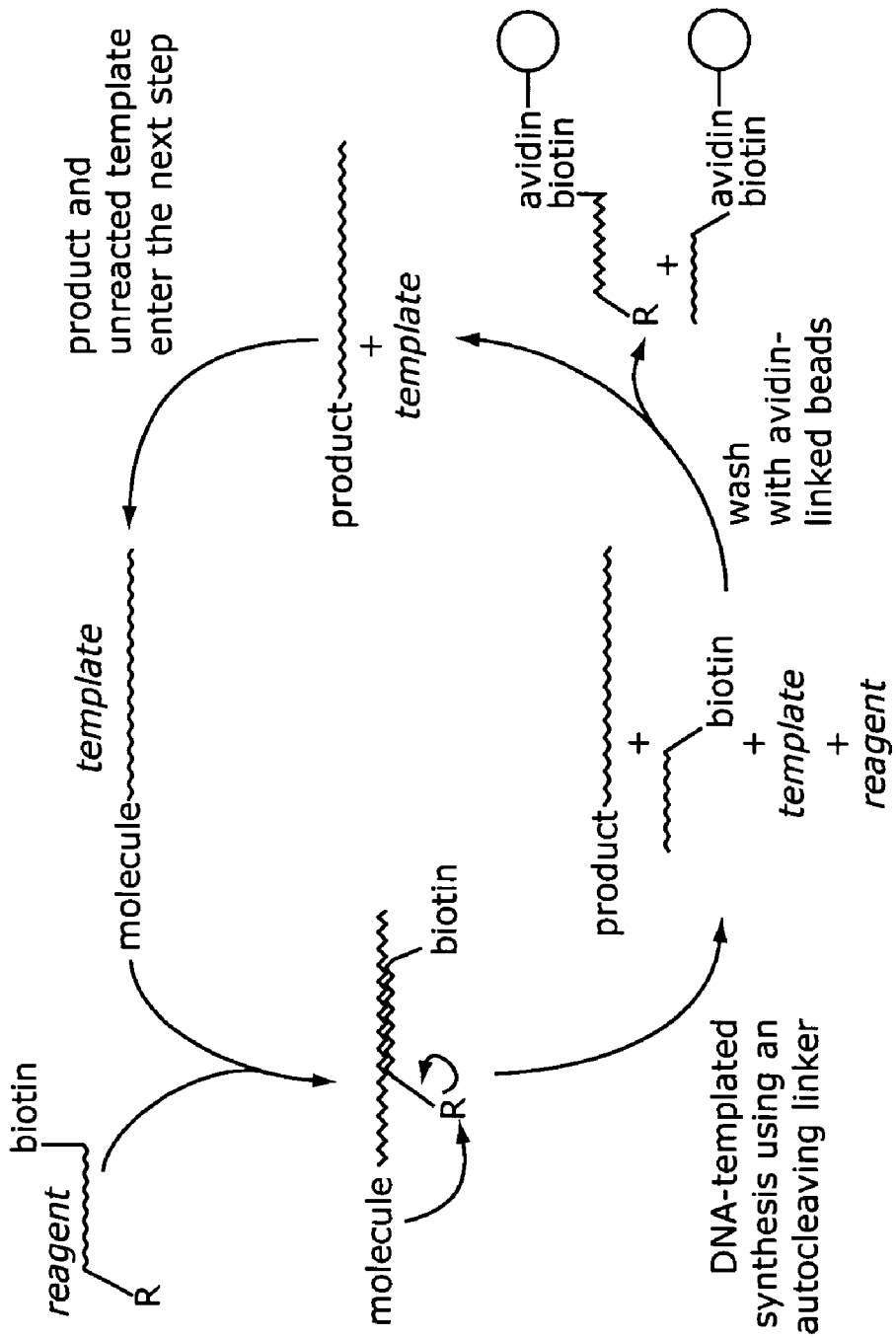
FIGS. 30A-30B are schematic representations depicting strategies for purifying products of DNA-templated synthesis using an autocleaving reagent linker (FIG. 30A) or scar and non scar linkers (FIG. 30B).

Ribosomal protein biosynthesis uses aminoacylated tRNAs in a similar autocleaving linker format to mediate RNA-templated peptide bond formation. To purify desired products away from unreacted reagents and from cleaved oligonucleotides following DNA-templated reactions using autocleaving linkers, biotinylated reagent oligonucleotides and washing crude reactions with streptavidin-linked magnetic beads (see, FIG. 30A) were utilized. Although this approach does not separate reacted templates from unreacted templates, unreacted templates can be removed in subsequent DNA-templated reaction and purification steps.

Reagents bearing more than one functional group can be linked to their decoding DNA oligonucleotides through second and third linker strategies. In the "scarless linker" approach (FIG. 28C), one functional group of the reagent is reserved for DNA-templated bond formation, while the second functional group is used to attach a linker that can be cleaved without introducing additional unwanted chemical functionality. The DNA-templated reaction then is followed by cleavage of the linker attached through the second functional group to afford desired products (FIG. 28C). For example, a series of aminoacylation reagents such as (D)-Phe derivative 7 were synthesized in which the α-amine is connected through a carbamoylethylsulfone linker (Zarling et al. (1980) J. IMMUNOLOGY 124: 913) to its decoding DNA oligonucleotide. The product (8) of DNA-templated amide bond formation using this reagent and an amine-terminated template (5) was treated with aqueous base to effect the quantitative elimination and spontaneous decarboxylation of the linker, affording product 9 containing the cleanly transferred amino acid group (FIG. 28C). This sulfone linker is stable in pH 7.5 or lower buffer at 25° C. for more than 24 hours yet undergoes quantitative cleavage when exposed to pH 11.8 buffer for 2 hours at 37 C.

In some cases it may be advantageous to introduce one or more atoms new chemical groups as a consequence of linker cleavage. Under a third linker strategy, linker cleavage generates a "useful scar" that can be functionalized in subsequent steps (FIG. 28C). As an example of this class of linker, amino acid reagents such as the (L)-Phe derivative 10 were generated linked through 1,2-diols (Fruchart et al. (1999) TETRAHEDRON LETT. 40: 6225) to their decoding DNA oligonucleotides. Following DNA-templated amide bond formation with amine terminated template (5), this linker was quantitatively cleaved by oxidation with 50 mM aqueous sodium periodate ($NaIO_4$) at pH 5.0 to afford product 12 containing an aldehyde group appropriate for subsequent functionalization (for example, in a DNA-templated Wittig olefination, reductive amination, or nitrolaldol addition).

Figure 29:
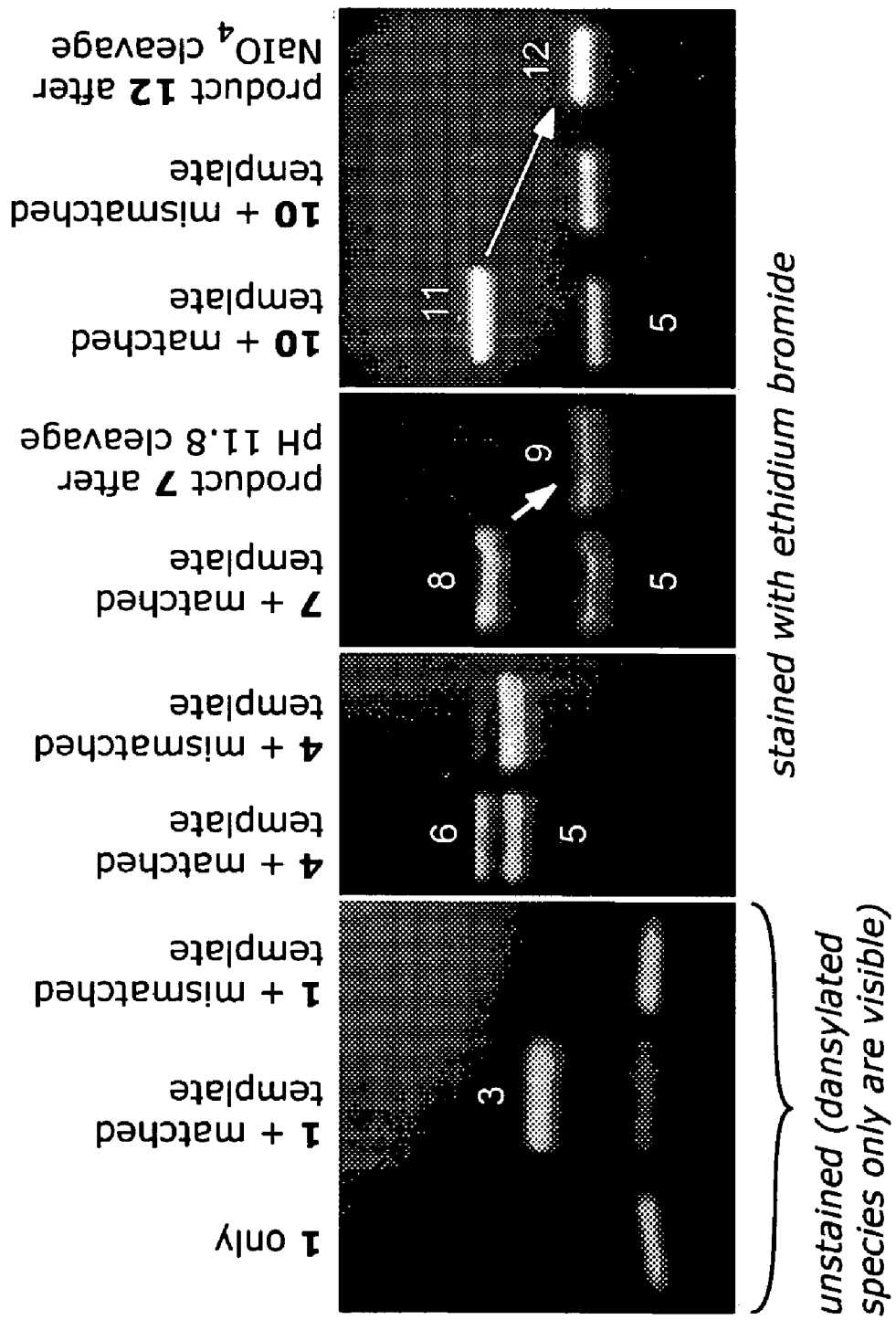
FIG. 29 depicts results from nucleic acid-templated reactions with various linkers.

FIG. 29 shows the results of exemplary DNA-templated synthesis experiments using autocleaving linkers, scarless linkers, and useful scar linkers. The depicted reactions were analyzed by denaturing PAGE. Lanes 1-3 were visualized using UV light without DNA staining; lanes 4-10 were visualized by staining, with ethidium bromide following by UV transillumination. Conditions for 1 to 3 were: one equivalent each of reagent and template, 0.1 M TAPS buffer pH 8.5, 1 M NaCl, at 25° C. for 1.5 hours. Conditions for 5 to 6 were: three equivalents of 4, 0.1 M MES buffer pH 7.0, 1 M sodium nitrite ($NaNO_2$) 10 mM silver nitrate ($AgNO_3$), at 37° C. for 8 hours. Conditions for 8 to 9 were 0.1 M 3-(cyclohexylamino)-1-propanesulfonic acid (CAPS) buffer pH 11.8, 60 mM β-mercaptoethanol (BME), at 37° C. for 2 hours. Finally, conditions for 11 to 12 were: 50 mM aqueous $NaIO_4$, at 25° C. for 2 hours. $R_1$=$NH(CH_2)_2NH$-dansyl; $R_2$=biotin.

Figure 30B:
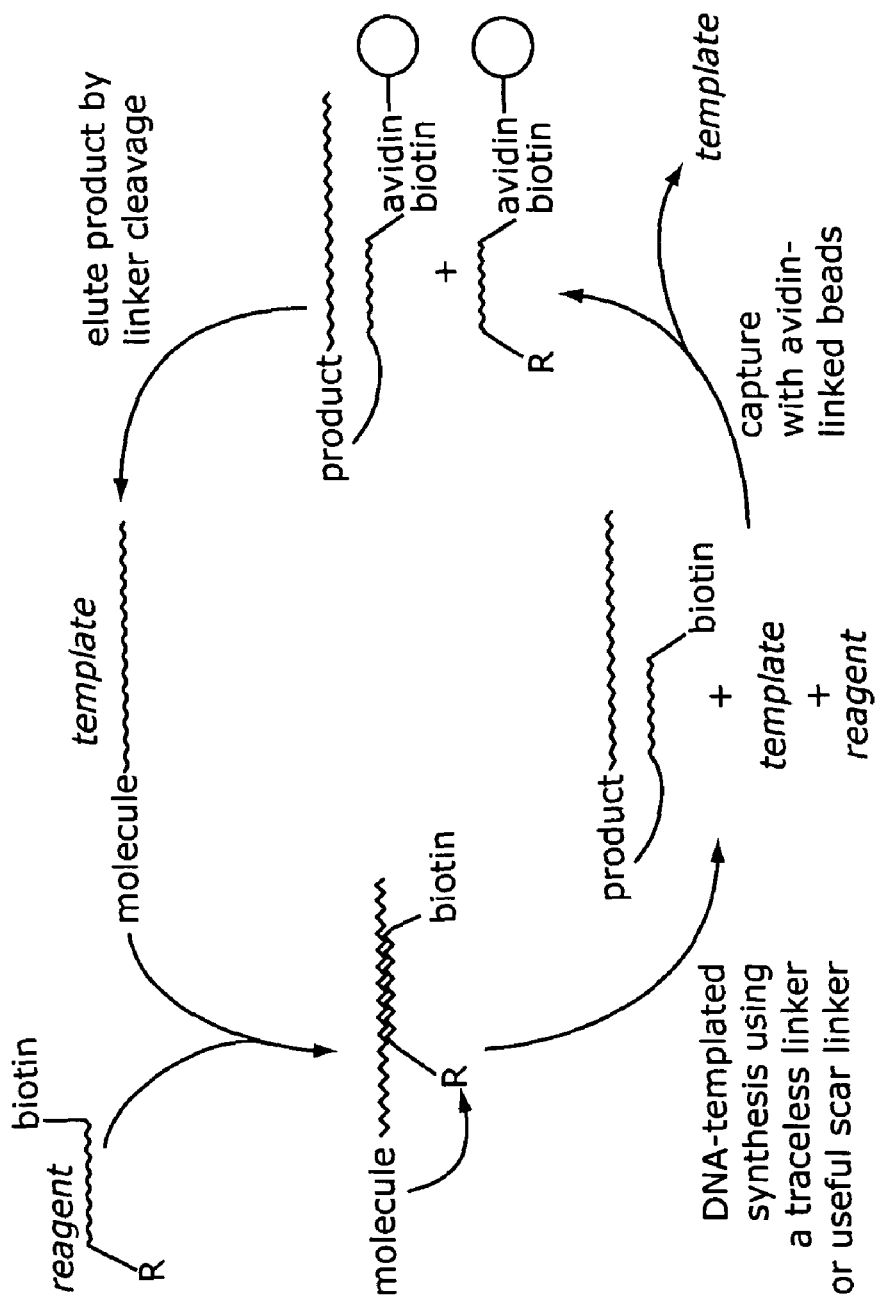

Desired products generated from DNA-templated reactions using the scarless or useful scar linkers can be readily purified using biotinylated reagent oligonucleotides (FIG. 30B). Reagent oligonucleotides together with desired products are first captured on streptavidin-linked magnetic beads. Any unreacted template bound to reagent by base pairing is removed by washing the beads with buffer containing 5 M guanidinium chloride. Biotinylated molecules remain bound to the streptavidin beads under these conditions. Desired product then is isolated in pure form by eluting the beads with linker cleavage buffer (in the examples above, either pH 11 or sodium periodate ($NaIO_4$)-containing buffer), while reacted and unreacted reagents remain bound to the beads.

Figure 31A:
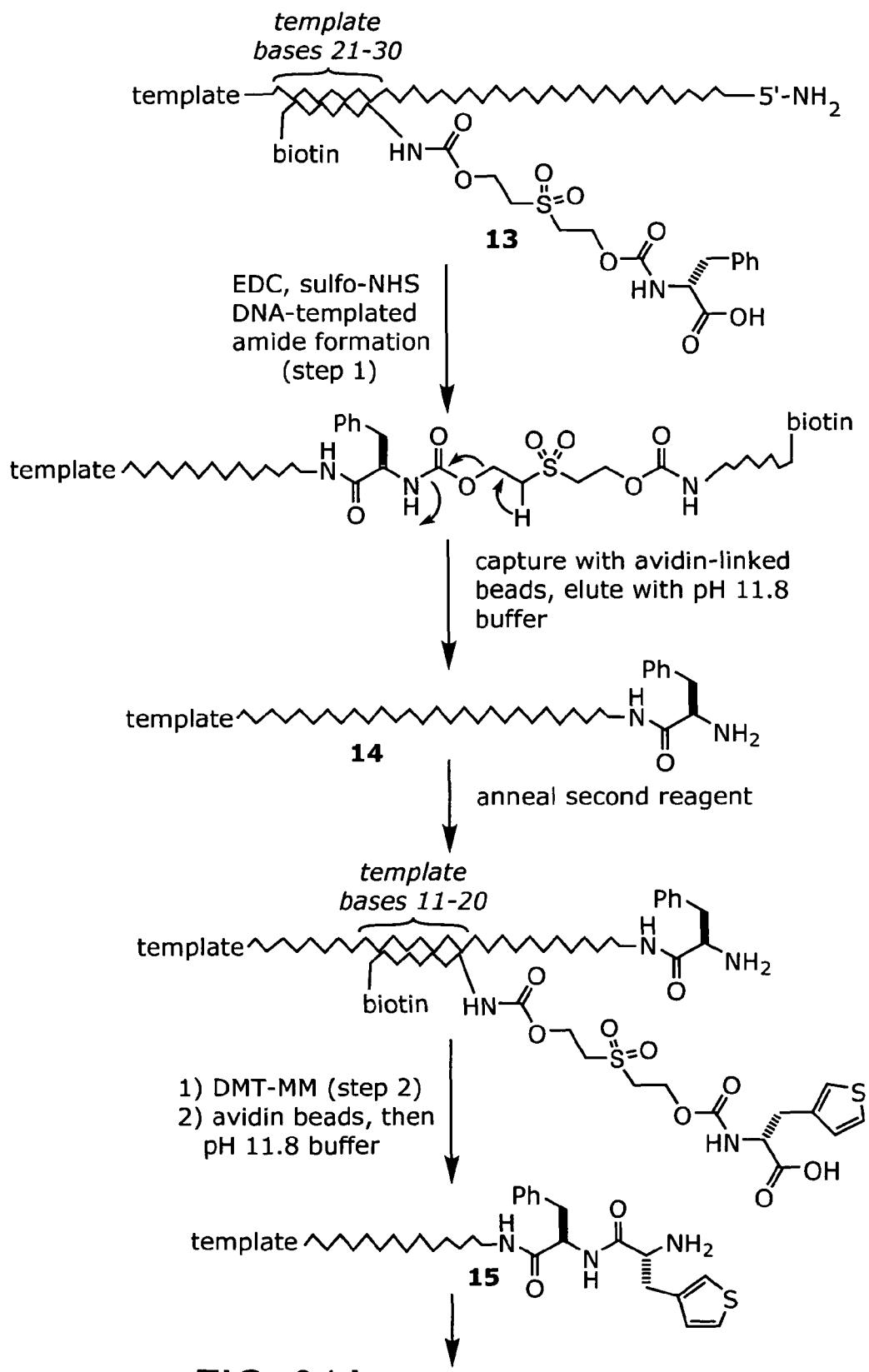
FIGS. 31A-B depict an exemplary DNA-templated multi-step tripeptide synthesis.
Figure 31B:
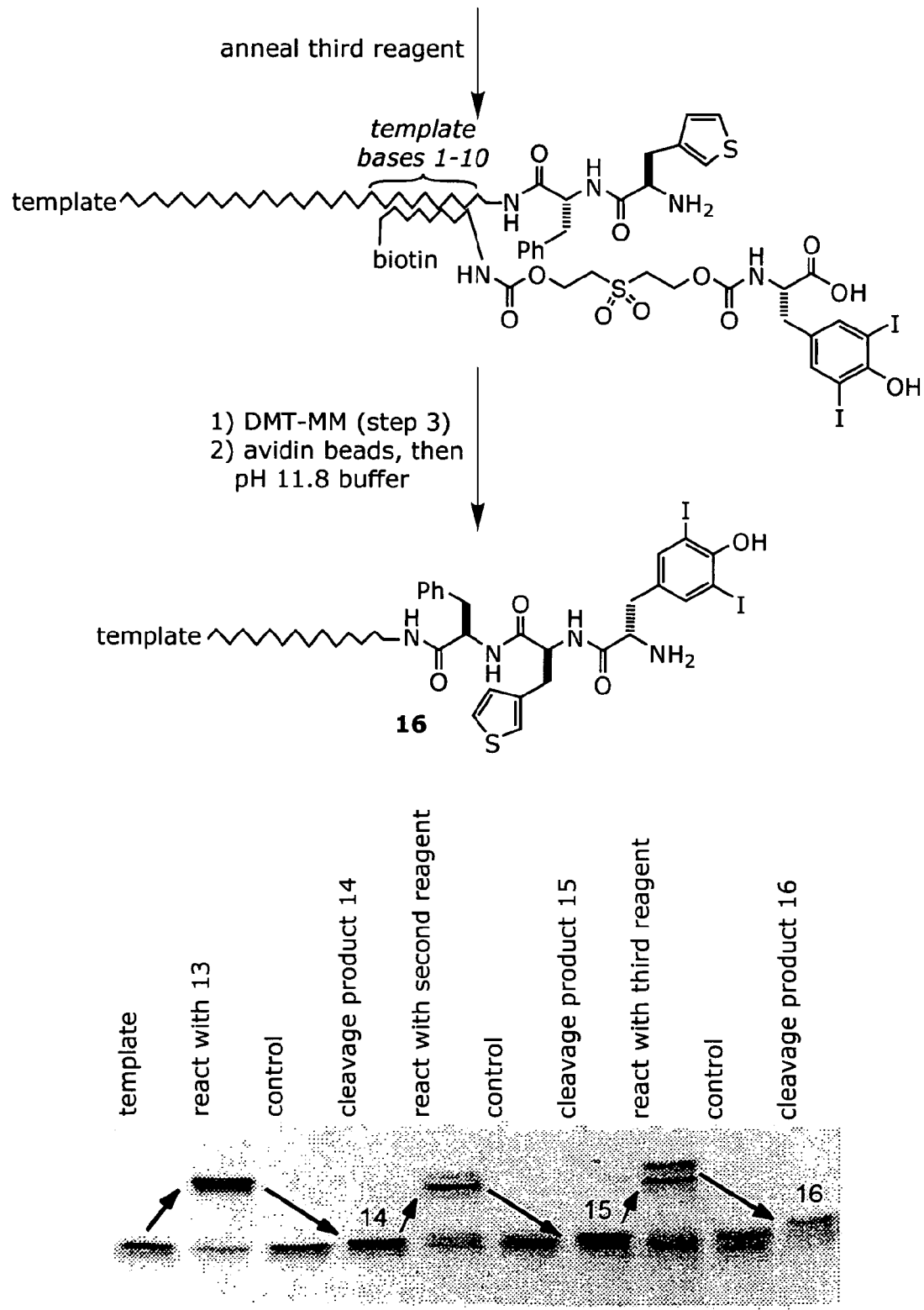

As one example of a specific library generated as described above, three iterated cycles of DNA-templated amide formation, traceless linker cleavage, and purification with streptavidin-linked beads were used to generate a non-natural tripeptide (FIGS. 31A-B). Each amino acid reagent was linked to a unique biotinylated 10-base DNA oligonucleotide through the sulfone linker described above. The 30-base amine-terminated template programmed to direct the tripeptide synthesis contained three consecutive 10-base regions that were complementary to the three reagents, mimicking the strategy that would be used in a multi-step DNA-templated small molecule library synthesis.

In the first step, two equivalents of 13 were activated by treatment with 20 mM EDC, 15 mM sulfo-NHS, 0.1 M MES buffer pH 5.5, and 1 M NaCl, for 10 minutes at 25° C. The template then was added in 0.1 M MOPS pH 7.5, and 1M NaCl, at 25° C. and was allowed to react for 1 hour. The free amine group in 14 then was elaborated in a second and third round of DNA-templated amide formation and linker cleavage to afford dipeptide 15 and tripeptide 16 using the following conditions: two equivalents of reagent, 50 mM DMT-MM, 0.1 M MOPS buffer pH 7.0, 1 M NaCl, at 25° C. for 6 hours. Desired product after each step was purified by capture on avidin-linked beads and elution with 0.1 M CAPS buffer pH 11.8, 60 mM BME, at 37° C. for 2 hours. The progress of each reaction and purification was followed by denaturing polyacrylamide gel electrophoresis (FIG. 31B, bottom). Lanes 3, 6, and 9 represent control reactions using reagents containing scrambled oligonucleotide sequences.

The progress of each reaction, purification, and sulfone linker cleavage step was followed by denaturing polyacrylamide gel electrophoresis. The final tripeptide linked to template 16 was digested with the restriction endonuclease EcoRI and the digestion fragment containing the tripeptide was characterized by MALDI mass spectrometry. Beginning with 2 nmol (~20 μg) of starting material, sufficient tripeptide product was generated to serve as the template for more than $10^6$ in vitro selections and PCR reactions (Kramer et al. (1999) CURRENT PROTOCOLS IN MOL. BIOL. 3: 15.1) (assuming 1/10,000 molecules survive selection). No significant product was generated when the starting material template was capped with acetic anhydride, or when control reagents containing sequence mismatches were used instead of the complementary reagents (FIG. 31B).

Figure 32A:
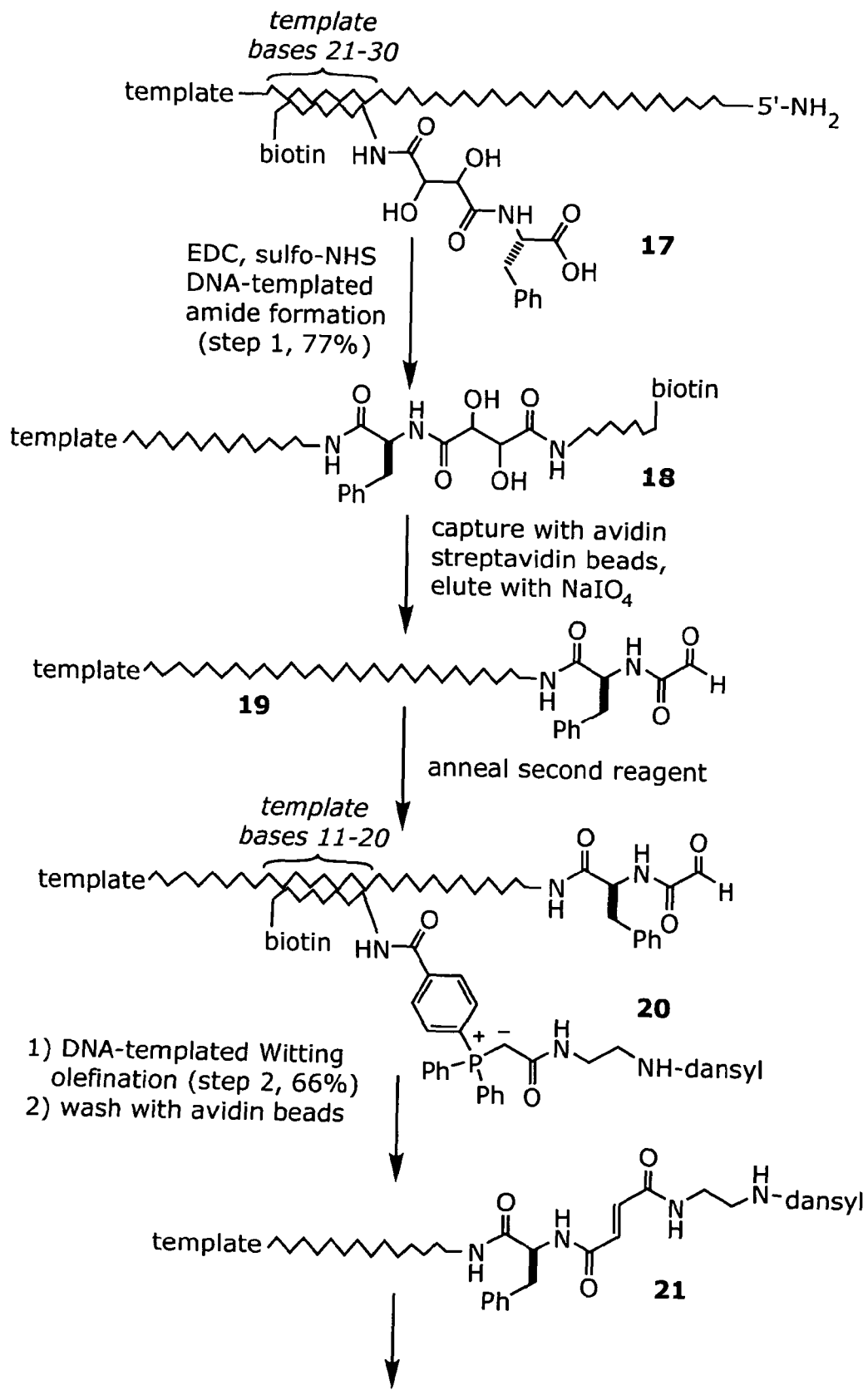
FIGS. 32A-B depict an exemplary DNA-templated multi-step synthesis.
Figure 32B:
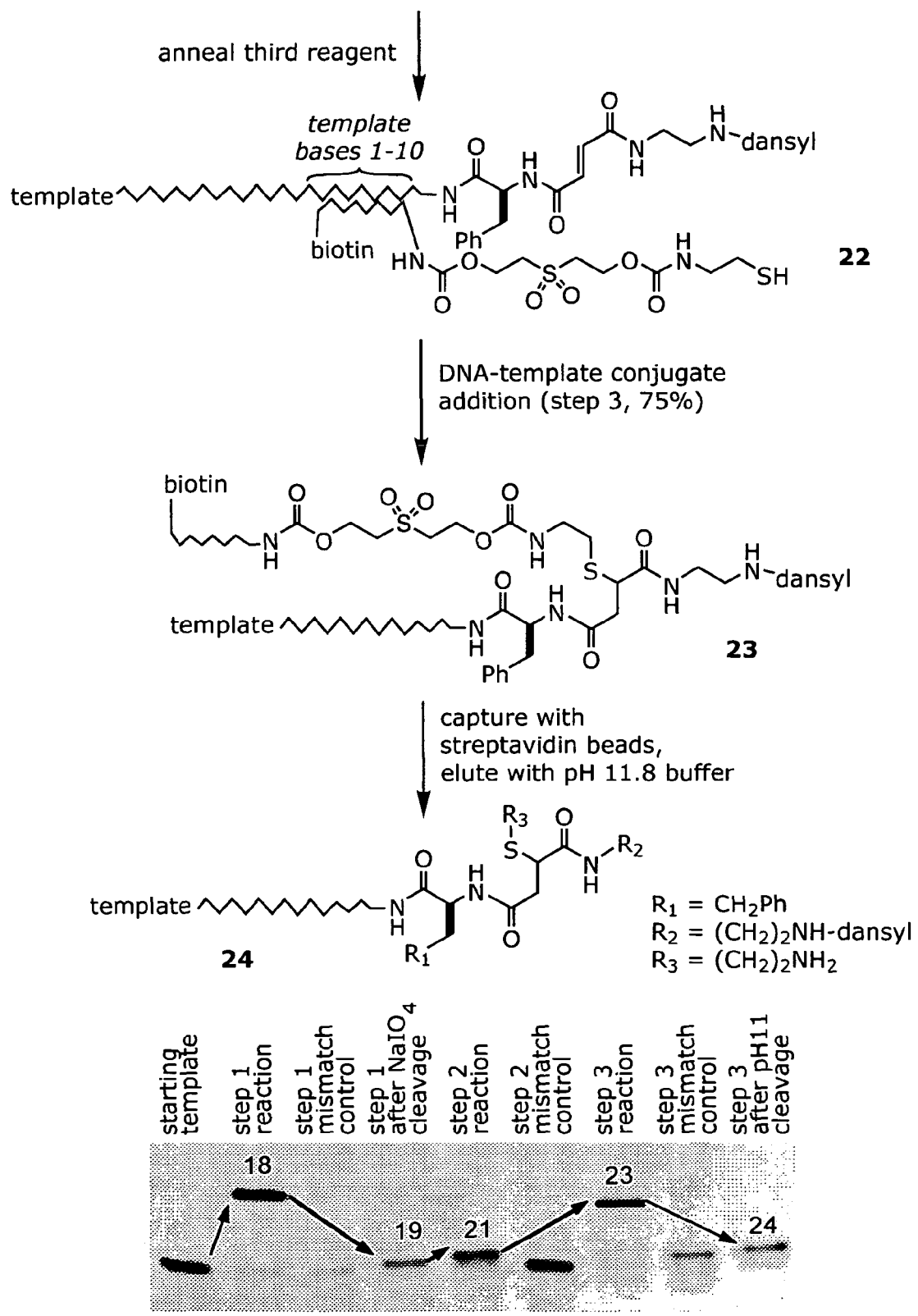

A non-peptidic multi-step DNA-templated small molecule synthesis that uses all three linker strategies developed above was also performed (FIG. 32A-32B). An amine-terminated 30-base template was subjected to DNA-templated amide bond formation using an aminoacyl donor reagent (17) containing the diol linker and a biotinylated 10-base oligonucleotide to afford amide 18 (two equivalents 17 in 20 mM EDC, 15 mM sulfo-NHS, 0.1 M MES buffer pH 5.5, 1 M NaCl, 10 minutes, 25° C., then add to template in 0.1 M MOPS pH 7.5, 1M NaCl at 16° C. for 8 hours). The desired product then was isolated by capturing the crude reaction on streptavidin beads followed by cleaving the linker with $NaIO_4$ to generate aldehyde 19. The DNA-templated Wittig reaction of 19 with the biotinylated autocleaving phosphorane reagent 20 afforded fumaramide 21 (three equivalents 20, 0.1 M TAPS pH 9.0, 3 M NaCl at 25° C. for 48 hours). The products from the second DNA-templated reaction were partially purified by washing with streptavidin beads to remove reacted and unreacted reagent. In the third DNA-templated step, fumaramide 21 was subjected to a DNA-templated conjugate addition (Gartner et al. (2001) J. AM. CHEM. SOC. 123: 6961) using thiol reagent 22 linked through the sulfone linker to a biotinylated oligonucleotide (three equivalents 22, 0.1 M TAPS pH 8.5, 1 M NaCl at 25° C. for 21 hours). The desired conjugate addition product (23) was purified by immobilization with streptavidin beads. Linker cleavage with pH 11 buffer afforded final product 24 in 5-10% overall isolated yield for the three bond forming reactions, two linker cleavage steps, and three purifications (FIGS. 32A-32B).

The final product was digested with EcoRI and the mass of the small molecule-linked template fragment was confirmed by MALDI mass spectrometry (exact mass: 2568, observed mass: 2566±5). As in the tripeptide example, each of the three reagents used during this multi-step synthesis annealed at a unique location on the DNA template, and control reactions with sequence mismatches yielded no product (FIG. 32B, bottom). In FIG. 32B, bottom lanes 3, 6, and 9 represent control reactions. As expected, control reactions in which the Wittig reagent was omitted (step 2) also did not generate product following the third step.

Taken together, the DNA-templated syntheses of compounds 16 and 24 demonstrate the ability of DNA to direct the sequence-programmed multi-step synthesis of both oligomeric and non-oligomeric small molecules unrelated in structure to nucleic acids.

Example 4

Exemplary Reactions in Organic Solvents

As demonstrated herein, a variety of DNA-templated reactions can occur in aqueous media. It has also been discovered that DNA-templated reactions can occur in organic solvents, thus greatly expanding the scope of DNA-templated synthesis. Specifically, DNA templates and reagents have been complexed with long chain tetraalkylammonium cations (see, Jost et al. (1989) NUCLEIC ACIDS RES. 17: 2143; Mel'nikov et al. (1999) LANGMUIR 15: 1923-1928) to permit quantitative dissolution of reaction components in anhydrous organic solvents including $CH_2Cl_2$, $CHCl_3$, DMF and methanol. Surprisingly, it was found that DNA-templated synthesis can indeed occur in anhydrous organic solvents with high sequence selectivity.

Figure 33:
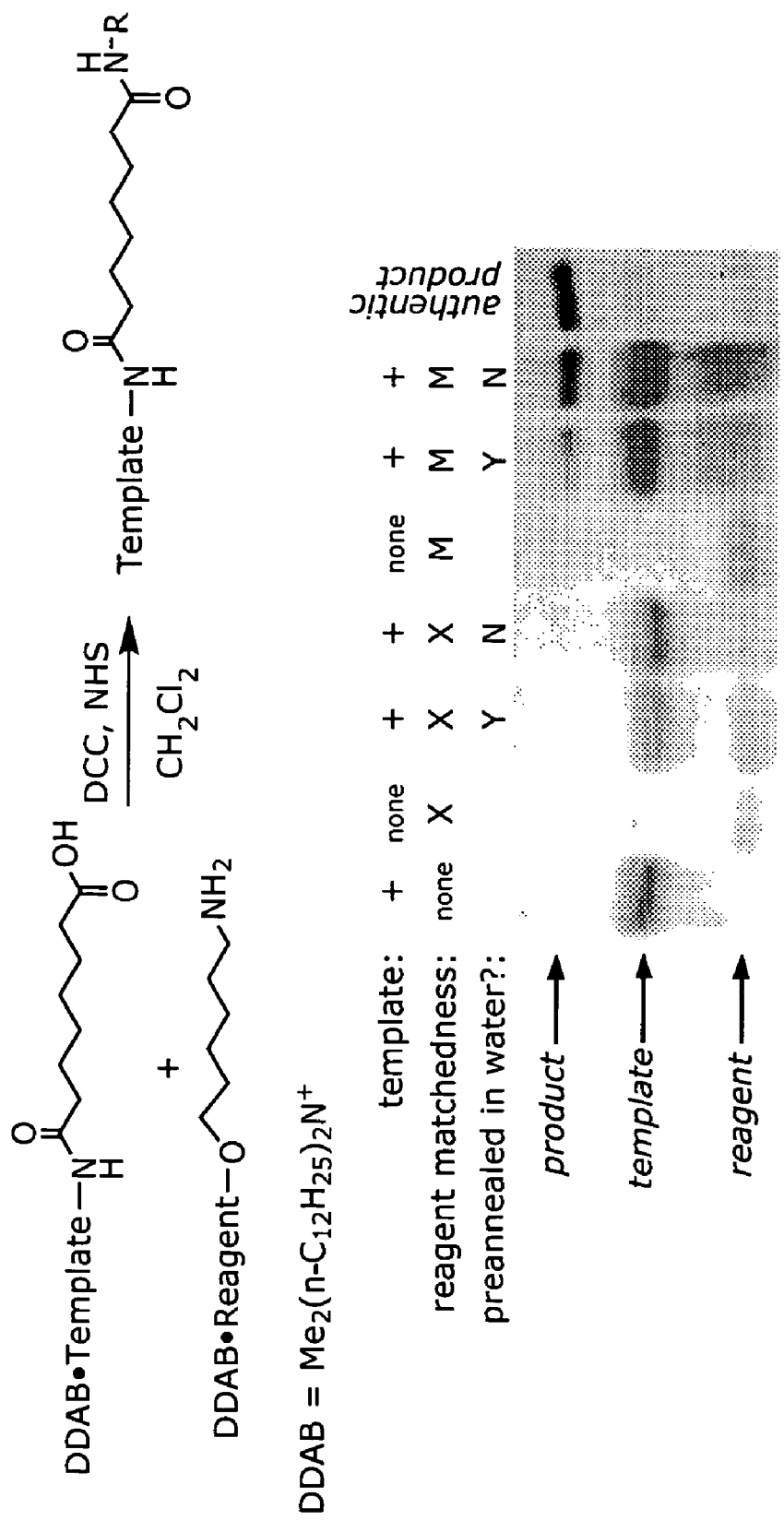
FIG. 33 depicts DNA-templated amide bond formation reactions in which reagents and templates are complexed with dimethyldidodecylammonium cations.

FIG. 33 shows DNA-templated amide bond formation reactions where the reagents and templates are complexed with dimethyldidodecylammonium cations either in separate vessels or after preannealing in water, lyophilized to dryness, dissolved in $CH_2Cl_2$, and mixed together. Matched, but not mismatched, reactions provided products both when reactants were preannealed in aqueous solution and when they were mixed for the first time in $CH_2Cl_2$ (FIG. 33). DNA-templated amide formation and Pd-mediated Heck coupling in anhydrous DMF also proceeded sequence-specifically.

These observations of sequence-specific DNA-templated synthesis in organic solvents imply the presence of at least some secondary structure within tetraalkylammonium-complexed DNA in organic media, and should permit DNA receptors and catalysts to be evolved towards stereoselective binding or catalytic properties in organic solvents. Specifically, DNA-templated reactions that are known to occur in aqueous media, including conjugate additions, cycloadditions, displacement reactions, and Pd-mediated couplings can also be performed in organic solvents.

It is contemplated that reactions in organic solvents may be utilized that are inefficient or impossible to perform in water. For example, while Ru-catalyzed olefin metathesis in water has been reported (Lynn et al., (1998) J. AM. CHEM. SOC. 120: 1627-1628; Lynn et al. (2000) J. AM. CHEM. SOC. 122: 6601-6609; Mohr et al. (1996) ORGANOMETALLICS 15: 4317-4325), the aqueous metathesis system is extremely sensitive to the identities of the functional groups. The functional group tolerance of Ru-catalyzed olefin metathesis in organic solvents, however, is significantly more robust. Some exemplary reactions to utilize in organic solvents include, but are not limited to 1,3-dipolar cycloaddition between nitrones and olefins which can proceed through transition states that are less polar than ground state starting materials.

Example 5

New Architectures for Nucleic Acid-Templated Synthesis

This Example discloses two different template architectures that further expand the scope of nucleic acid-templated synthesis.

During a nucleic acid-templated chemical reaction a portion of a template anneals to a complementary sequence of an oligonucleotide-linked reagent, holding functional groups on the template and transfer unit in reactive proximity. Template architecture can have a profound effect on the nature of the resulting reaction, raising the possibility of manipulating reaction conditions by rationally designing template-reagent complexes with different secondary structures.

During the course of DNA templated synthesis using the end-of-helix ("E") and hairpin ("H") templates (see, Example 1), two challenges emerged. First, some DNA-templated reactions do not proceed efficiently when the annealed reactive groups on the template and transfer unit (reagent) are separated by even small numbers of bases. Using the E or H architectures, "distance-dependent" reactions can only be encoded by template bases at the reactive end of the template. Second, the presence of double-stranded DNA between annealed reactive groups can greatly reduce the efficiency of templated reactions because, under certain circumstances a single-stranded template may need to be flexible. This may preclude the possibility of performing two or more reactions in a single DNA-templated step using the E or H architectures even though the template oligonucleotide may contain enough bases to encode multiple reactions. This Example discuses two new template architectures, which overcome each of these challenges.

It was hypothesized that the distance dependence of certain DNA-templated reactions such as 1,3-dipolar cycloadditions and reductive amination could be overcome by designing a new architecture that permits a reagent to anneal to two distinct and spatially separated regions of the template. In the "omega" or "Ω" architecture (see, FIG. 7), the template oligonucleotide contains a small number of constant bases at, for example, the reactive 5' end of the template in addition to distal coding regions. The oligonucleotide of the transfer unit for the Ω architecture contains at its reactive 3' end the bases that complement the constant region of the template followed by bases that complement a coding region anywhere on the template. The constant regions were designed to be of insufficient length to anneal in the absence of a complementary coding region. When the coding region of the template and transfer unit are complementary and anneal, the elevated effective molarity of the constant regions induces their annealing. Constant region annealing forms a bulge (resembling an Ω) in the otherwise double-stranded template-reagent complex and places groups at the ends of the template and reagent in reactive proximity. This design permits distance-dependent DNA-templated reactions to be encoded by bases distal from the reactive end of the template.

The efficiency of DNA-templated synthesis using the Ω architecture was compared with that of the standard E and H architectures. The Ω architectures studied comprise (i) three to five constant bases at the 5' end of the template followed by (ii) a five- to 17-base loop and (iii) a ten-base coding region. As a basis for comparison, four different classes of DNA-templated reactions were performed that collectively span the range of distance dependence observed to date.

Figure 34:
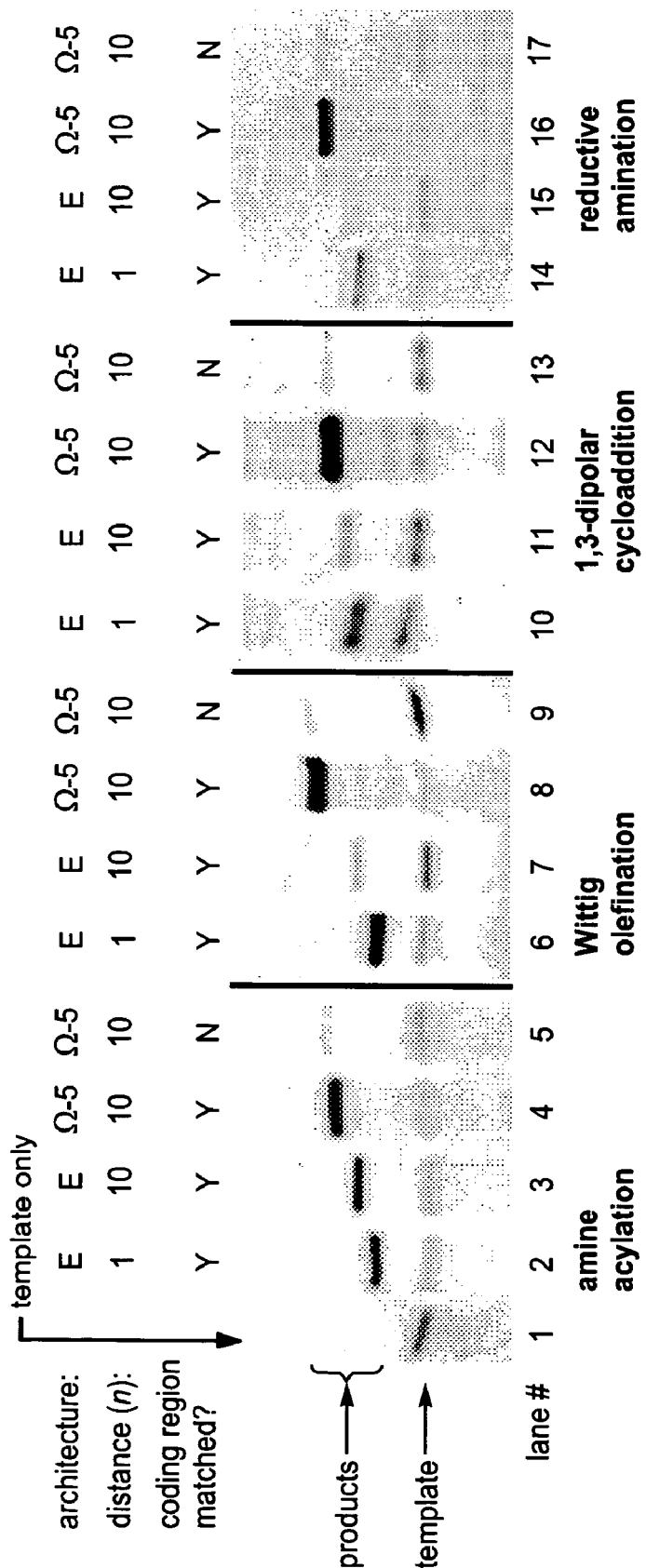
FIG. 34 shows denaturing PAGE gels with representative DNA-templated amine acylation, Wittig olefination, 1,3-dipolar cycloaddition, and reductive amination reactions using the end-of-helix (E) and omega (Ω) architectures.
Figure 35A:
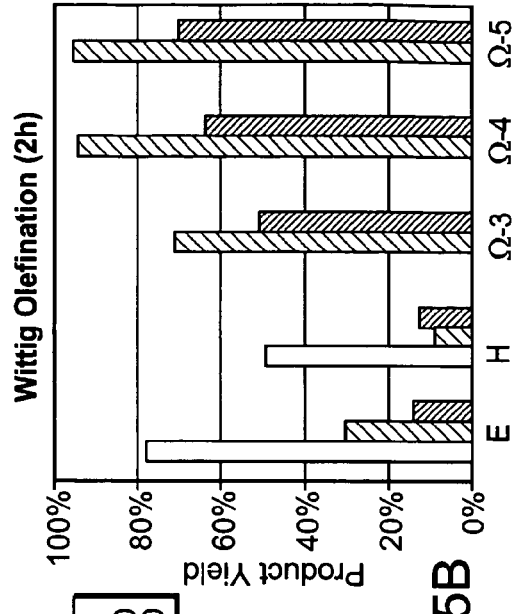
FIGS. 35A-35D are bar charts showing a comparison of end-of-helix (E), hairpin (H), and omega (Ω) architectures for mediating DNA-templated amine acylation (FIG. 35A), Wittig olefination (FIG. 35B), 1,3-dipolar cycloaddition (FIG. 35C), or reductive amination reactions (FIG. 35D).

Amine acylation reactions are representative of distance independent reactions that proceed efficiently even when considerable distances (e.g., 30 bases) separate the amine and carboxylate groups. As expected, amine acylation (20 mM DMT-MM, pH 7.0, at 30° C. for 12 hours) proceeded efficiently (46-96% yield) in all architectures with both small and large distances between reactive groups on the reagent and template (FIG. 34, lanes 1-5; and FIG. 35A). The Ω architecture mediated efficient amine acylation with three, four, or five constant bases at the reactive ends of the template and reagent and 10 or 20 bases between annealed reactants (n=10 or 20). Importantly, control reactions in which the distal coding region contained three sequence mismatches failed to generate significant product despite the presence of the complementary three- to five-base constant regions at the ends of the template and reagent (see, FIG. 34, lane 5 for a representative example). The Ω architecture, therefore, did not impede the efficiency or sequence-specificity of the distance-independent amine acylation reaction.

Figure 35B:
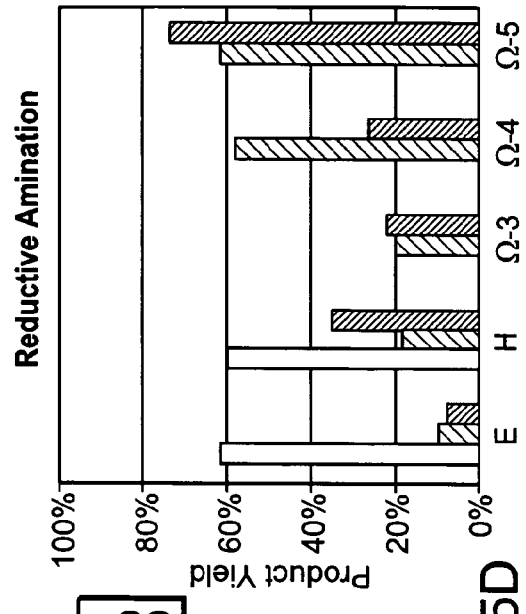

DNA-templated Wittig olefination reactions proceed at a significantly lower rate when the aldehyde and phosphorane are separated by larger numbers of template bases, even though product yields typically are excellent after 12 hours or more of reaction regardless of intervening distance. After only 2 hours of reaction (pH 7.5, 30° C.) in the E or H architectures, however, yields of olefin products were three- to six-fold lower when reactants were separated by ten or more bases (n=10 or 20) than when reactants are separated by only one base (n=1) (FIG. 34, lanes 6-7, and FIG. 35B). In contrast, the Ω architecture with four or five constant bases at the reactive end resulted in efficient and sequence-specific Wittig product formation after 2 hours of reaction even when 10 or 20 bases separated the coding region and reactive end of the template (FIG. 34, lanes 8-9, and FIG. 35B). These results suggest that the constant regions at the reactive ends of the template and transfer unit in the Ω architecture permit the aldehyde and phosphorane moieties to react at an effective concentration comparable to that achieved with the E-architecture when n=1 (FIG. 34).

Figure 35C:
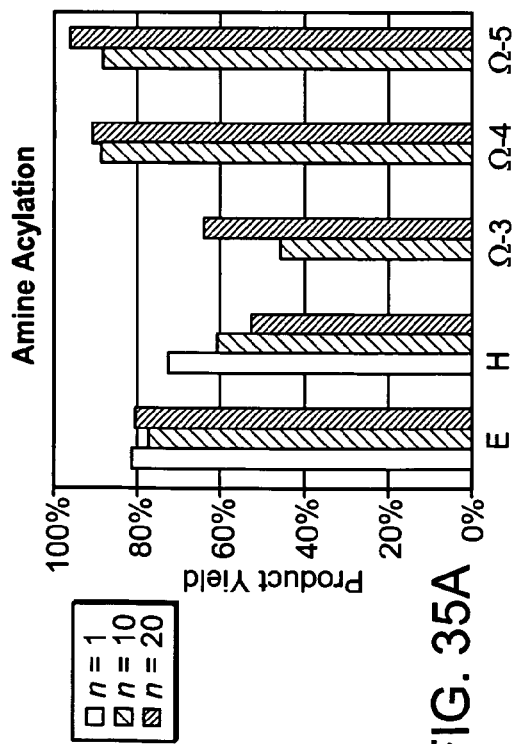
Figure 35D:
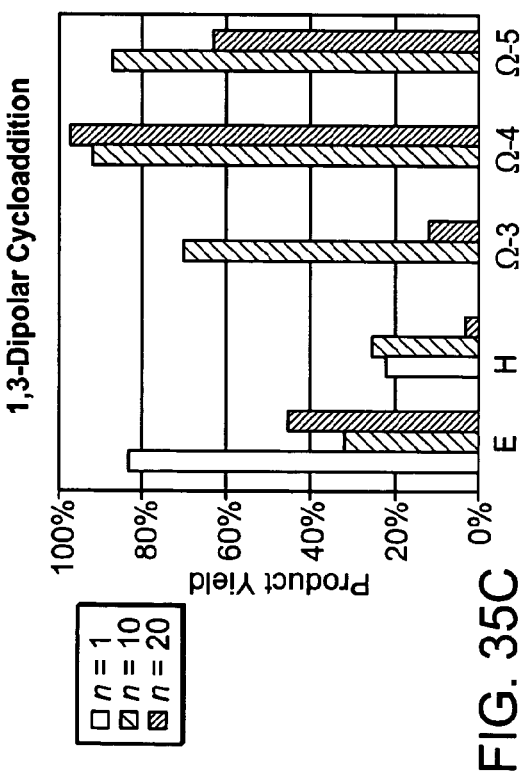

Among the many DNA-templated reactions studied to date, the 1,3-dipolar cycloaddition and reductive amination reactions demonstrate the most pronounced distance dependence. Both reactions proceed in low to modest efficiency (7%-44% yield) under standard reaction conditions using the E or H architectures when 10 or 20 bases separate the annealed reactive groups (FIG. 34, lanes 10-11 and 14-15, and FIGS. 35C-35D). This distance dependence limits the positions on a DNA template that can encode these or other similarly distant dependent reactions. In contrast, both 1,3-dipolar cycloaddition and reductive amination proceed efficiently (up to 97% yield) and sequence-specifically when encoded by template bases 15-25 bases away from the functionalized end of the template using the Ω architecture with four or five constant bases (FIG. 34, lanes 12-13 and 16-17, and FIGS. 35C-35D). These results demonstrate that the templates Ω architecture permits distance-dependent reactions to be efficiently directed by DNA bases far from the reactive end of the template. By overcoming the distance dependence of these reactions while preserving the efficiency of distant independent reactions, the Ω architecture may permit virtually any contiguous subset of bases in a single-stranded 30-base template to encode any viable DNA-templated reaction. Interestingly, the Ω templates with only three constant bases at their reactive ends do not consistently improve the efficiency of these reactions compared with the E-architecture (FIGS. 35C-35D), suggesting that four or five constant bases may be required in the Ω architecture to fully realize favorable proximity effects.

In order to probe the structural features underlying the observed properties of the Ω architecture, the thermal denaturation of the Ω-5 and E architectures using n=10 and n=20 reagents were characterized. For all template-reagent combinations, only a single cooperative melting transition was observed. Compared to the E architecture reagent lacking the five-base constant region, the Ω-5 reagent increased the hypochromicity upon annealing by ~50% but did not significantly affect melting temperature in either phosphate-buffered saline (PBS) or in 50 mM sodium phosphate pH 7.2 with 1 M NaCl (FIG. 36). These results are consistent with a model in which template-reagent annealing in the Ω architecture is dominated by coding region interactions even though the constant region forms secondary structure once the coding region is annealed. The entropic cost of partially ordering the loop between the coding and constant regions may, therefore, be offset by the favorable interactions that arise upon annealing of the constant region.

DNA templates of arbitrary length are easy to synthesize and undesired cross reactivity between reactants in the same solution can be avoided using concentrations that are too low to allow non-complementary reactants to react intermolecularly. These features of DNA-templated synthesis permit more than one DNA-templated reaction to take place on a single template in one solution, saving the effort associated with additional DNA-templated steps and product purifications.

Multiple DNA-templated reactions per step can be difficult using the E, H, or Ω architectures, because the reagent oligonucleotide that remains annealed to the template following the first reaction forms a relatively rigid double helix that can prevent a second reagent annealed further away along the template from encountering the reactive end of the template. To overcome this, the reactive group on the template was moved from the end of the oligonucleotide to the middle, attaching the reactive group to the non-Watson-Crick face of a base. This "T" architecture (see, FIG. 7G) was designed to permit two DNA-templated reactions, one with a reagent coupled to the 5' end of the oligonucleotide of a first transfer unit and one with a reagent coupled to the 3' end of the oligonucleotide of a second transfer unit, to take place sequence-specifically in the same solution on a single template.

Figure 37:
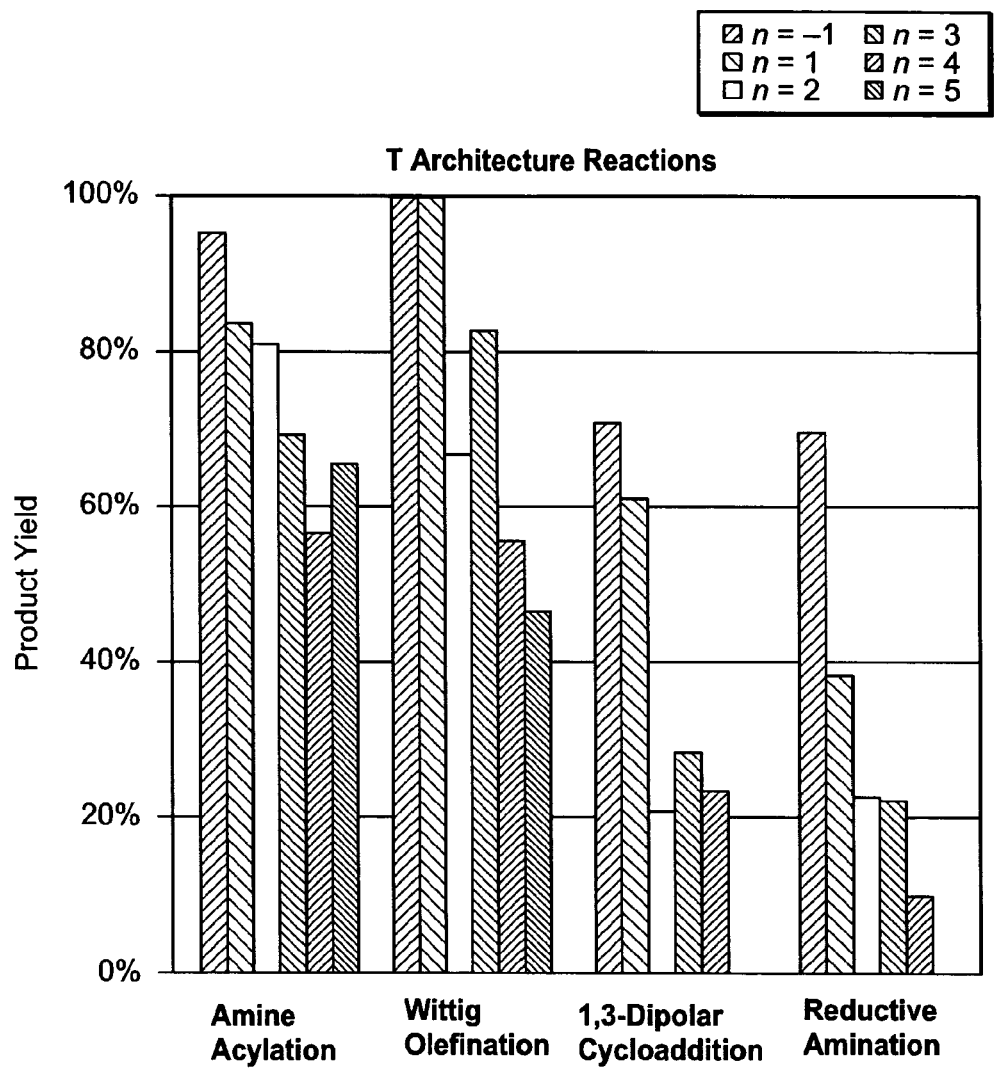
FIG. 37 is a bar chart showing the efficiencies of DNA-templated reactions mediated by a template having the T architecture.

To test the viability of the T architecture in DNA-templated reactions, the efficiency of the amine acylation, Wittig olefination, 1,3-dipolar cycloaddition, and reductive amination reactions using the T architecture was studied. The T architecture sequence-specifically directed these four reactions with efficiencies comparable to or greater than those of the E or H architectures (FIG. 37, 69-100% yield when n=1). The observed degree of distance dependence using the T architecture for each of the four reactions was consistent with the above findings (compare FIG. 37 and FIG. 35). Together these results demonstrate that the T architecture can mediate sequence-specific and efficient DNA-templated synthesis.

Figure 38A:
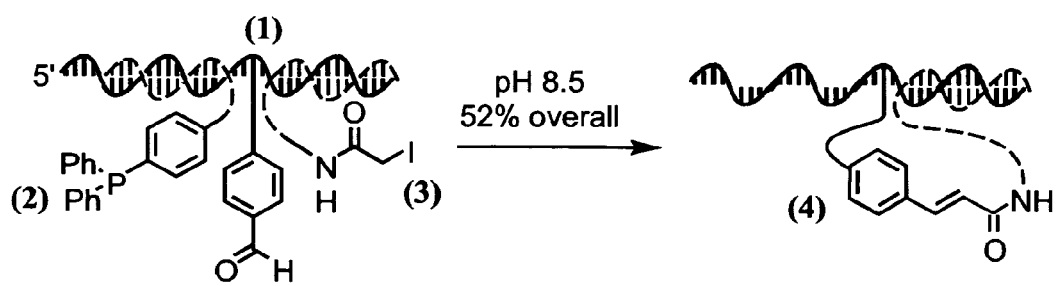

Once the ability of the T architecture to support efficient DNA-templated synthesis was established, the ability of the T architecture to direct two DNA-templated reactions on one template in one solution was studied. Two different two-reaction schemes using the T architecture were performed. In the first scheme, depicted in FIG. 38A, a benzaldehyde-linked T template (1) was combined with a phosphine-linked reagent (2) and an α-iodoamide-linked reagent (3) in a single solution (pH 8.5, 1 M NaCl, at 25° C. for 1 hour). The phosphine-linked oligonucleotide complemented ten bases of the template 5' of the aldehyde (n=−4), while the iodide-linked oligonucleotide complemented ten bases 3' of the aldehyde (n=0). DNA-templated $S_N2$ reaction between the phosphine and α-iodoamide generated the corresponding phosphorane, which then participated in a DNA-templated Wittig reaction to generate cinnanamide 4 in 52% overall yield after 1 hour (FIG. 38B, lanes 9-10). Control reactions containing sequence mismatches in either reagent generated no detectable product. The additional control reaction lacking the aldehyde group on the template generated only the $S_N2$ reaction product (FIG. 38B, lanes 3-4) while control reactions lacking either the phosphine group or the α-iodoamide group did not generate any detectable products (FIG. 38B, lanes 5-8).

In a second two-reaction scheme mediated by the T architecture, depicted in FIG. 38C, an amine-linked T template (5) was combined with a propargylglycine-linked 5' reagent (6) at n=−1 and a phenyl azide-linked 3' reagent (7) at n=1. The addition of 20 mM DMT-MM at pH 7.0 to induce amide formation followed by the addition of 500 μM copper(II) sulfate and sodium ascorbate to induce the recently reported Sharpless-modified Huisgen 1,3-dipolar cycloaddition provided 1,4-disubstituted triazoyl alanine adduct 8 in 32% overall yield.

Taken together, these observations show that the T architecture permits two sequence-specific DNA-templated reactions to take place on one template in one solution. Importantly, the T architecture templates described above were accepted as efficient templates for both a single cycle of primer extension as well as standard PCR amplification using Taq DNA polymerase, consistent with the known tolerance of several DNA polymerases for modifications to the non-Watson-Crick face of DNA templates. In addition to reducing the number of separate DNA-templated steps needed to synthesize a target structure, this architecture may also permit three-component reactions commonly used to build structural complexity in synthetic libraries to be performed in a DNA-templated format.

In summary, the Ω and T architectures significantly expand the scope of DNA-templated synthesis. By enabling distance-dependent DNA-templated reactions to be encoded by bases far away from the reactive end of the template, the omega architecture expands the types of reactions that can be encoded anywhere on a DNA template. The T architecture permits two DNA-templated reactions to take place on a single template in one step.

Materials and Methods

Oligonucleotide synthesis. Unless otherwise specified, DNA oligonucleotides were synthesized and functionalized as previously described using 2-[2-(4-monomethoxytrityl)aminoethoxy]ethyl-(2-cyanoethyl)-N,N-diisopropyl-phosphoramidite (Glen Research, Sterling, Va., USA) for 5'-functionalized oligonucleotides, and using (2-dimethoxytrityloxymethyl-6-fluorenylmethoxycarbonylamino-hexane-1-succinoyl)-long chain alkylamino-CPG (Glen Research, Sterling, Va., USA) for 3'-functionalized oligonucleotides (Calderone et al. (2002) ANGEW. CHEM. INT. ED. ENGL. 41: 4104; (2002) ANGEW. CHEM. 114: 4278). In the case of templates for the T architecture, amine groups were added using 5'-dimethoxytrityl-5-[N-(trifluoroacetylaminohexyl)-3-acrylimido]-2'-deoxyuridine-3'-[(2-cyanoethyl)-(N,N-diisopropyl)]-phosphoramidite (Glen Research, Sterling, Va., USA) and then acylated as reported previously (Calderone et al. (2002) supra).

Amine Acylation. Amine-labeled and carboxylic acid-labeled DNA were combined in aqueous 100 mM MOPS buffer, 1 M NaCl, pH 7.0 (60 nM in template DNA, 120 nM in reagent DNA) in the presence of 20 mM DMT-MM. Reactions proceeded for 12 hours at 25° C.

Wittig Olefination. Aldehyde-labeled and phosphorane-labeled DNA were combined in aqueous 100 mM MOPS, 1 M NaCl, pH 7.5 (60 nM in template DNA, 120 nM in reagent DNA). Reactions proceeded for 2 hours at 30° C.

1,3-Dipolar Cycloaddition. Dialdehyde-labeled DNA was incubated in 260 mM N-methylhydroxylamine hydrochloride for 1 hour at room temperature (Gartner et al. (2002) J. AM. CHEM. SOC. 124: 10304). It was subsequently combined with succinimide-labeled DNA in aqueous 50 mM MOPS, 2.8 M NaCl, pH 7.5 (final concentrations of N-methylhydroxylamine hydrochloride 0.75 mM, 60 nM in template DNA and 90 nM in reagent DNA). Reactions proceeded for 12 hours at 37° C.

Reductive Amination. Amine-labeled and aldehyde-labeled DNA were combined in aqueous 100 mM MES buffer, 1 M NaCl, pH 6.0 (60 nM in template DNA, 120 nM in reagent DNA). Sodium cyanoborohydride was added as a 5 M stock in 1 M NaOH to a final concentration of 38 mM, and reactions proceeded for 2 hours at 25° C. Reactions were quenched by ethanol precipitation in the presence of 15 mM methylamine.

T Architecture-mediated Conversion of Compound 1 to 4. The 5'-phosphine-linked oligonucleotide (2) was generated by coupling N-succinimidyliodoacetate (SIA) to the amine derived from 12-(4-monomethoxytritylamino)dodecyl-(2-cyanoethyl)-(N,N-diisopropyl)-phosphoramidite (Glen Research, Sterling, Va., USA) using the T (n=−4) oligonucleotide listed below, followed by treatment with 4-diphenylphosphinobenzoic acid as described previously (Gartner et al. (2002) supra). The 3'-Ω-iodoamide-linked reagent (3) was prepared by reacting the T (n=1) oligonucleotide (see below) with SIA as described previously (Gartner et al. (2001) supra). Aldehyde-labeled template (1) was prepared by reacting the "T template" oligonucleotide (see below) with para-formyl benzoic acid N-hydroxysuccinimidyl ester as described previously (Gartner et al. (2002) ANGEW. CHEM. INT. ED. 41: 1796; (2002) ANGEW. CHEM. 114: 1874). Template 1 was combined with reagents 2 and 3 in aqueous 200 mM N-(2-hydroxyethyl)piperazine-N'-(2-ethanesulfonic acid) (HEPES) buffer at pH 8.5 with 1 M NaCl, (63 nM template and 125 nM of each reagent). Reactions proceeded for up to 1 hour at 25° C.

The results of denaturing polyacrylamide gel electrophoresis analysis of these reactions is shown in FIG. 38B. The 30-base T architecture template (1) containing an aldehyde group was present in lanes 1-2 and lanes 5-10. A template lacking the aldehyde group but otherwise identical to (1) was present in lanes 3 and 4. DNA-linked phosphine reagent (2) was present in lanes 3-6 and lanes 9-10. DNA-linked α-iodoamide reagent (3) was present in lanes 3-4 and lanes 7-10. Lanes 1, 3, 5, 7, and 9 show reactions after 30 minutes. Lanes 2, 4, 6, 8, and 10 show reactions after 1 hour.

T Architecture-mediated Conversion of Compound 5 to 8. The 5'-propargylglycine linked oligonucleotide (6) was generated by combining the corresponding T (n=−1) 5'-amine-linked reagent oligonucleotide (see below) with 2 mg/mL bis(sulfosuccinimidyl)suberate in 9:1 200 mM sodium phosphate pH 7.2:DMF for 10 minutes at 25° C., followed by treatment with 0.3 vol of 300 mM racemic propargylglycine in 300 mM NaOH for 2 hours at 25° C. The 3'-azido linked oligonucleotide (7) was generated by combining the T (n=1) amine-linked reagent oligonucleotide (see below) with 2 mg/mL (N-hydroxysuccinimidyl)-4-azidobenzoate in 9:1 200 mM sodium phosphate pH 7.2:DMF for 2 hours at 25° C. Reagents 6 and 7 were purified by gel filtration and reverse-phase HPLC. Template 5 and reagents 6 and 7 were combined in aqueous 100 mM MOPS pH 7.0 in the presence of 1 M NaCl and 20 mM DMT-MM for 12 hours (60 nM template, 120 nM reagents) at 25° C. Copper (II) sulfate pentahydrate and sodium ascorbate were then added to 500 µM each. After 1 hour at 25° C., reactions were quenched by ethanol precipitation.

DNA Oligonucleotide Sequences Used. E or Ω template: 5'-H$_2$N-GGT ACG AAT TCG ACT CGG GAA TAC CAC CTT [SEQ ID NO: 58]. H template: 5'-H$_2$N-CGC GAG CGT ACG CTC GCG GGT ACG AAT TCG ACT CGG GAA TAC CAC CTT [SEQ ID NO: 59]. T template: 5'-GGT ACG AAT TCG AC(dT-NH$_2$) CGG GAA TAC CAC CTT [SEQ ID NO: 60]. E or H reagent (n=1): 5'-AAT TCG TAC C-NH$_2$ [SEQ ID NO: 61]. E or H reagent (n=10): 5'-TCC CGA GTC G-NH$_2$ [SEQ ID NO: 62]. E or H reagent (n=20): 5'-AAG GTG GTA T-NH$_2$ [SEQ ID NO: 63]. Mismatched E or H reagent: 5'-TCC CTG ATC G-NH$_2$ [SEQ ID NO: 64]. Ω-3 reagent (n=10): 5'-TCC CGA GTC GAC C-NH$_2$ [SEQ ID NO: 65]. Ω-4 reagent (n=10): 5'-TCC CGA GTC GTA CC-NH$_2$ [SEQ ID NO: 66]. Ω-5 reagent (n=10): 5'-TCC CGA GTC GGT ACC-NH$_2$-[SEQ ID NO: 67]. Ω-3 reagent (n=20): 5'-AAG GTG GTA TAC C-NH$_2$ [SEQ ID NO: 68]. Ω-4 reagent (n=20): 5'-AAG GTG GTA TTA CC-NH₂ [SEQ ID NO: 69]. Ω-5 reagent (n=20): 5'-AAG GTG GTA TGT ACC-NH₂ [SEQ ID NO: 70]. Mismatched Ω-3 reagent: 5'-TCC CTG ATC GAC C-NH₂ [SEQ ID NO: 71]. Mismatched Ω-4 reagent: 5'-TCC CTG ATC GTA CC-NH₂ [SEQ ID NO: 72]. Mismatched Ω-5 reagent: 5'-TCC CTG ATC GGT ACC-NH₂ [SEQ ID NO: 73]. T reagent (n=1): 5'-GGT ATT CCC G-NH₂ [SEQ ID NO: 74]. T reagent (n=2): 5'-TGG TAT TCC C-NH₂ [SEQ ID NO: 75]. T reagent (n=3): 5'-GTG GTA TTC C-NH₂ [SEQ ID NO: 76]. T reagent (n=4): 5'-GGT GGT ATT C-NH₂ [SEQ ID NO: 77]. T reagent (n=5): 5'-AGG TGG TAT T-NH₂ [SEQ ID NO: 78]. T reagent (n=−1): 5'-NH₂-GTC GAA TTC G [SEQ ID NO: 79]. T reagent (n=−4) for 2: 5'-[C₁₂-amine linker]-AAT TCG TAC C [SEQ ID NO: 80].

Reaction yields were quantitated by denaturing polyacrylamide gel electrophoresis followed by ethidium bromide staining, UV visualization, and CCD-based densitometry of product and template starting material bands. Yield calculations assumed that templates and products were denatured and, therefore, stained with comparable intensity per base; for those cases in which products are partially double-stranded during quantitation, changes in staining intensity may result in higher apparent yields. Representative reaction products were characterized by MALDI mass spectrometry in addition to denaturing polyacrylamide gel electrophoresis.

Melting curves were obtained on a Hewlett-Packard 8453 UV-visible spectrophotometer using a Hewlett-Packard 89090A Peltier thermocontroller. Absorbances of template-reagent pairs (1.5 µM each) at 260 nm were measured every 1° C. from 20° C. to 80° C. holding for 1 minute at each temperature in either phosphate-buffered saline ("PBS," 137 mM NaCl, 2.7 mM potassium chloride, 1.4 mM potassium phosphate, 10 mM sodium phosphate, pH 7.4) or in high salt phosphate buffer ("HSB," 50 mM sodium phosphate pH 7.2, 1 M NaCl).

Example 6

Stereoselectivity in Nucleic Acid-Templated Synthesis

This Example demonstrates that it is possible to perform stereoselective nucleic acid-templated syntheses. The chiral nature of DNA raises the possibility that DNA-templated synthesis can proceed stereoselectively without the assistance of chiral groups beyond those present in DNA, thereby transferring not only sequence but also stereochemical information from the template to the product.

Stereoselectivity was examined in the context of DNA-templated nucleophilic substitution reactions. Hairpin architecture templates conjugated at their 5' amino termini directly to (S)- or (R)-2-bromopropionamide were combined with 3' thiol-linked reagent oligonucleotides at 25° C. (FIG. 39A) (Gartner et al. (2001) supra; Gartner et al. (2003) ANGEW. CHEM. INT. ED. 42: 1370). The exact structure of the hairpin template and its complimentary reagent (FIG. 39A) were as follows:

```
Template:  5'-BrCH(CH₃)CONH-TCG CGA GCG TAC GCT CGC
           GAG GTA CGA ATT C-3'
           [SEQ ID NO: 81]

Reagent:   5'-GAA TTC GTA CC-(CH₂)₃SH-3'
           [SEQ ID NO: 82]
```

The stability of the bromides under the reaction conditions was confirmed by several independent methods. Initial rates of thioether product formation were determined by denaturing gel electrophoresis and the products were additionally characterized by MALDI-TOF mass spectrometry. Apparent rates of product formation were 4.0±0.2-fold higher for (S)-bromide-linked templates than for (R)-bromide-linked templates. Because template-reagent annealing could be partially rate-determining, this value is a lower limit of the actual ratio of $k_S/k_R$, assuming annealing rates are unaffected by bromide stereochemistry.

Surprisingly, similar preferences favoring the (5)-bromide were also observed using end-of-helix template architectures (FIG. 39B), even when 12 nucleotides separated the thiol and bromide in the template-reagent complexes. The exact structure of the end-of-helix template and its complimentary reagent (FIG. 39B) were as follows:

```
Template:  5'-BrCH(CH₃)CONH-TAC GCT CGC GAT GGT
           ACG AAT TC-3'
           [SEQ ID NO: 83]

Reagent:   5'-GAA TTC GTA CC-(CH₂)₃SH-3'
```

Figures 39A, 39B, 39C:
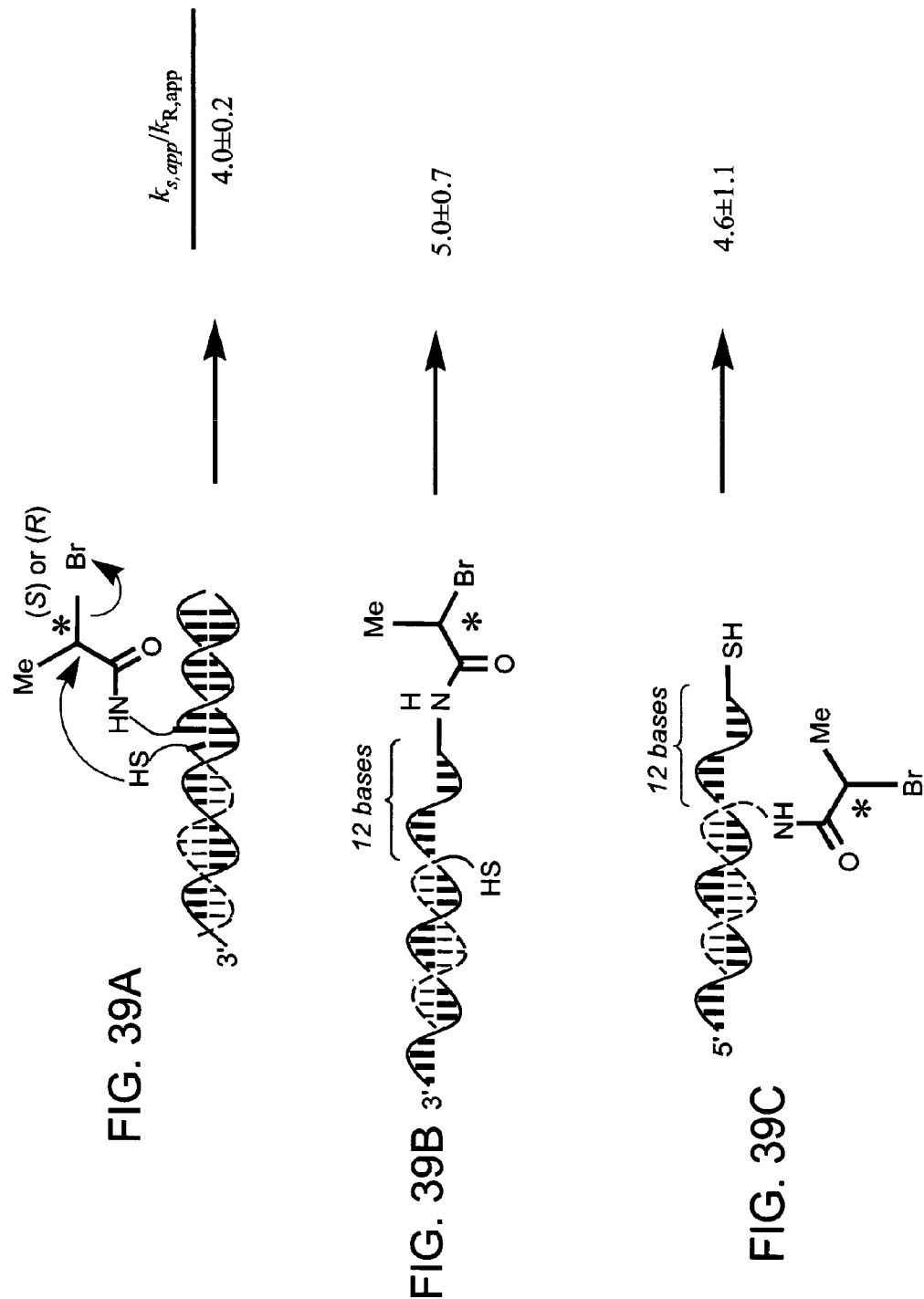
FIGS. 39A-39C are schematic illustrations showing the relative rates of product formation from (S)- and (R)-bromides in H template (FIG. 39A) or E template (FIGS. 39B and 39C) mediated stereoselective DNA-templated substitution reactions.

Stereoselectivity appeared to be independent of whether the bromide or the thiol was conjugated to the template (FIGS. 39B and 39C). The exact structure of the end-of-helix template conjugated to the thiol and its complimentary reagent (FIG. 39C) were as follows:

```
Template:  5'-GAA TTC GTA CAT AGC GCT CGC
           AT-(CH₂)₃SH-3'
           [SEQ ID NO: 84]

Reagent:   5'-BrCH(CH₃)CONH-TGT ACG AAT TC-3'
           [SEQ ID NO: 85]
```

Similar selectivities emerged from pseudo-kinetic resolutions containing both bromide stereoisomers in which thioether products arising from (S)- and (R)-bromides were distinguished using templates of two distinct lengths ($k_S/k_R$=4.2±0.4 to 4.9±0.3). Taken together, these findings indicate that the chirality of a DNA template can be transferred to products of DNA-templated synthesis that do not resemble the DNA backbone.

In order to probe the origins of the observed stereo selectivity, a series of template and reagent analogs were synthesized in which nucleotides near the thiol or bromide were replaced with flexible achiral linkers. Replacing the 12 template nucleotides separating the bromide and thiol in either of the end-of-helix reactions with an achiral polyethylene glycol linker of similar length (72 bonds) resulted in the loss of stereoselectivity. Stereoselectivity was also abolished when flexible achiral linkers consisting of three or five consecutive methylene or ether oxygens were inserted between the 5' end of the template oligonucleotide and the thiol or bromide groups, or between the 3' end of the reagent oligonucleotide and the thiol or bromide. Chiral linkers between reactants, therefore, are required for stereoselectivity in this DNA-templated reaction. These results also suggest that both the thiol and the bromide participate in the rate-determining step of the reaction, consistent with an $S_N2$ mechanism.

Figure 40A:
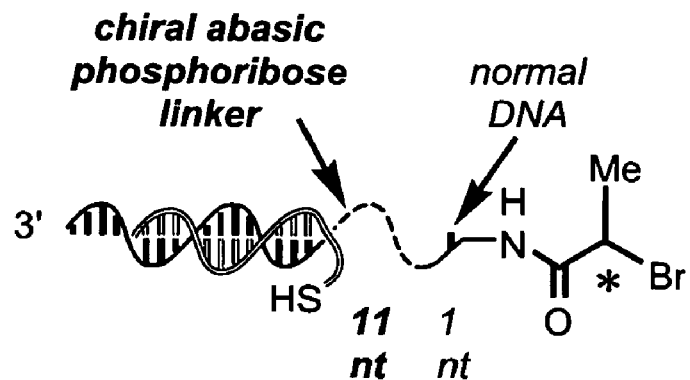
FIGS. 40A-40D depict results on reaction stereoselectivity when aromatic bases between the reactive groups are deleted and restored. The Figures show changes in stereoselectivity as a result of restoring aromatic DNA bases from the 5' end (FIGS. 40A-40C) or from the 3' end (FIG. 40D) of the 12-base intervening region.

The known sensitivity of single- and double-stranded DNA conformations on distal base stacking or base pairing interactions suggests that groups distal from the bromide or thiol could play important roles in inducing stereoselectivity. To test these possibilities, 11 of the 12 template nucleotides closest to the 5' bromide were replaced in the end-of-helix reaction with chiral abasic phosphoribose linkers in which the aromatic base was replaced with a proton (FIG. 40A). The exact structure of the end-of-helix template was the same as in FIG. 39, except that bases 2-12 were replaced with abasic phosphoribose units (prepared from the corresponding phosphoramidite from Glen Research, Sterling, Va., USA). Even though the 5' thymidine nucleotide closest to the bromide was unchanged, the resulting reactions were not stereoselective, indicating that the nucleotide closest to the bromide was not sufficient to induce the observed stereoselectivity.

Figure 40B:
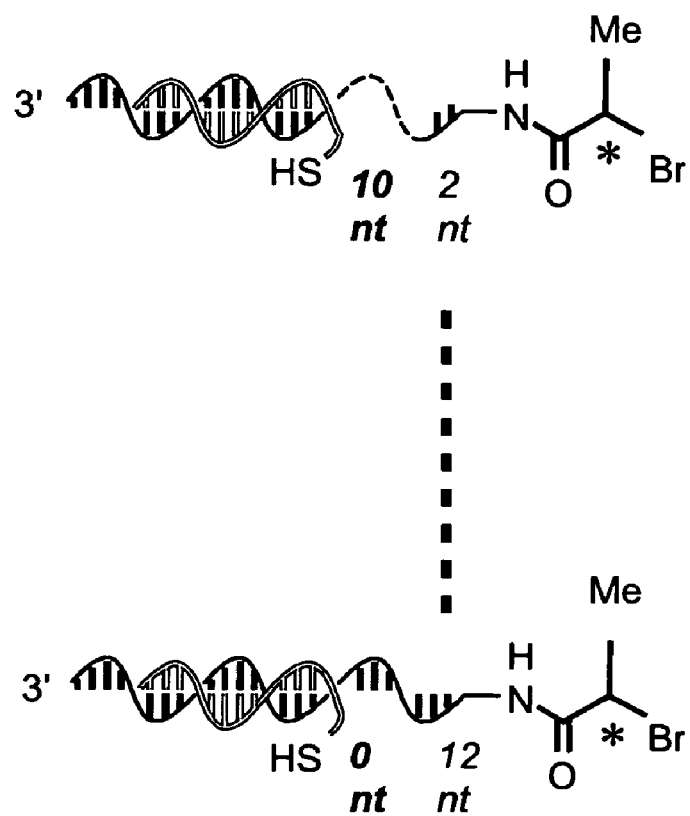
Figure 40C:
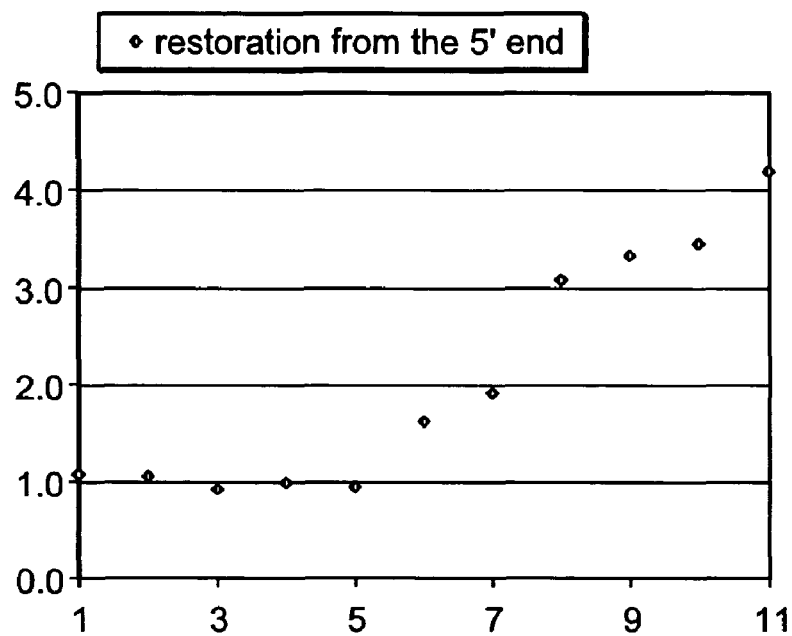
Figure 40D:
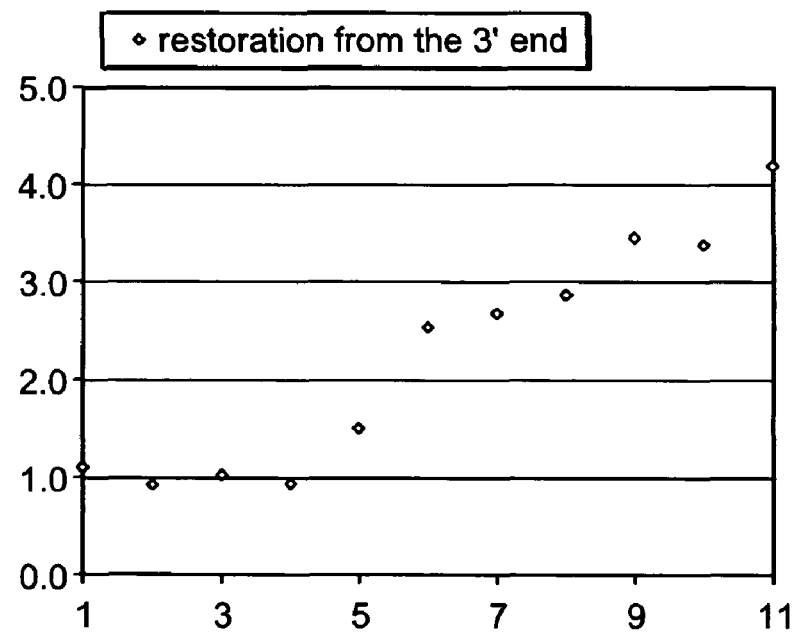

Each of the 11 missing aromatic bases from the 5' end were then restored (FIG. 40B) and measured rates of (S)-bromide and (R)-bromide reaction for each resulting template. Surprisingly, no stereoselectivity was observed when up to five bases were restored. Stereoselectivity increased steadily up to $k_S/k_R$=4.3 when 6 through 11 bases were restored (FIG. 40C). Restoration of the missing aromatic bases from the 3' end of the abasic region instead of from the 5' end also induced stereoselectivity only after several bases were restored (five to 11 bases in this case) (FIG. 40D). Collectively, these findings suggest that stereoselectivity arises from the conformation of nucleotides adjacent to either reactant, and that the conformation(s) leading to stereoselectivity require at least 5-6 consecutive aromatic bases.

This model of stereoselectivity predicts that global conformational changes in the template-reagent complex may alter stereoselectivity even if the covalent structure and absolute stereochemistry of all reactants were preserved. Double-stranded DNA sequences rich in (5-Me-C)G repeats can adopt a left-handed helix (Z-form) rather than the usual right-handed helix (B-form) at high salt concentrations (Rich et al. (1984) J. ANNO. REV. BIOCHEM. 53: 791-846; Behe et al. (1981) PROC. NATL. ACAD. SCI. USA 78: 1619-1623; Mao et al. (1999) NATURE 397: 144-146). Bromide-linked (5-Me-C)G-rich hairpin templates and complementary thiol-linked reagents protected as unreactive disulfides were prepared. When combined in equimolar ratios, the circular dichroism (CD) spectra of the resulting template-reagent complexes in low salt (100 mM NaCl) were characteristic of B-form DNA (see, for example, FIG. 42D). In the presence of high salt concentrations (5 M NaCl or 2.5 M $Na_2SO_4$), the same template-reagent complexes exhibited CD spectra representative of Z-form DNA. In contrast, the CD spectra of template-reagent complexes of normal sequence were representative of B-form DNA under both low salt and high salt conditions (see, for example, FIG. 42C).

Figure 41A:
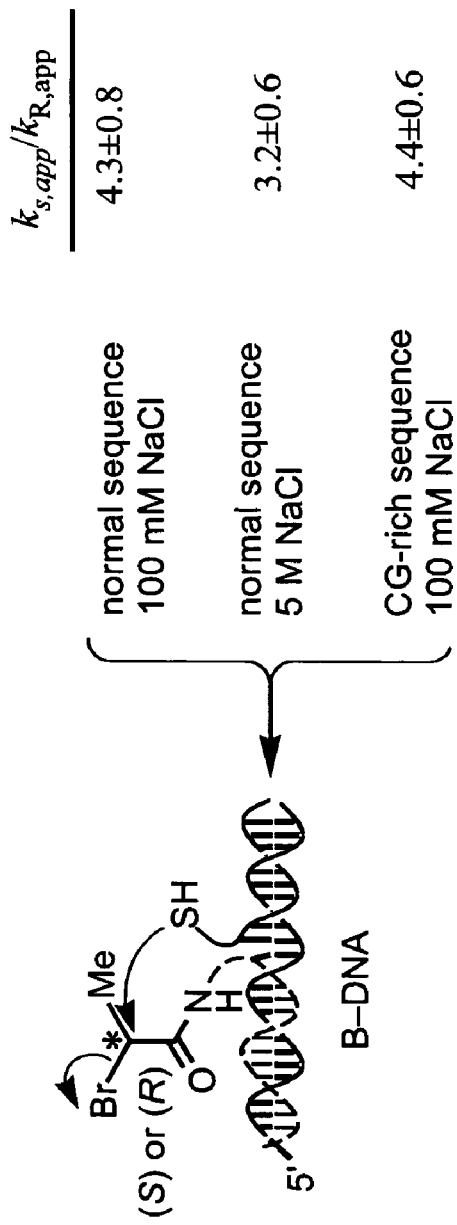
FIGS. 41A-41B show the stereoselectivities of DNA-templated reactions mediated by right-handed helix (B-form) (FIG. 41A) or left-handed helix (Z-form) (FIGS. 41A and 41B) hairpin architectures.
Figure 41B:
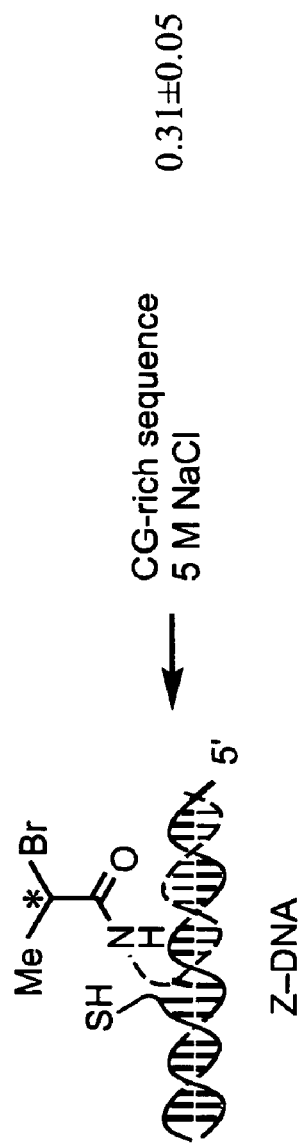

The stereoselectivity of DNA-templated reactions between bromide-linked templates and thiol-linked reagents using either the mixed or (5-Me-C)G-rich sequences was examined in the presence of low or high salt concentrations. The mixed sequence templates and reagents (B-form DNA) in the presence of low or high salt concentrations favored the (S)-bromide by 4.3- or 3.2-fold, respectively (FIG. 41A). The (5-Me-C)G-rich template and reagent in low salt concentrations (B-form DNA) exhibited a 4.4-fold preference for reaction of the (S)-bromide (FIG. 41A). Remarkably, repeating this reaction in the presence of high salt concentrations that induce Z-form DNA resulted in a 14-fold change in stereoselectivity now favoring the (R)-bromide by 3.2-fold ($k_S/k_R$=0.31) (FIG. 41B). This inversion of stereoselectivity as a result of changing the handedness of the DNA double helix is consistent with the theory implicating the conformation of the template and reagent in determining the stereoselectivity of this DNA-templated reaction.

These experiments demonstrate that stereoselectivity can be imparted during nucleic acid-templated organic synthesis. Conformations of DNA dependent on base stacking together with a partially constrained presentation of reactants appear to be responsible for the observed stereoselectivity. These experiments further demonstrate that a single structure with one absolute stereochemistry can induce opposite stereoselectivities when its macromolecular conformation is altered.

Oligonucleotides

The exact structures of the templates containing mixed and (5-Me-C)G-rich sequence, and their corresponding reagents used, are as follows:

```
Mixed sequence:
Template:   5'-GAA TTC TGG ACA CTT AGC TAT TCA TCG
            AGC GTA CGC TCG ATG AAT AGC-(CH2)3SH-3'
            [SEQ ID NO: 86]

Reagent:    5'-BrCH(CH3)CONH-TAA GTG TCC AGA ATT
            C-3'
            [SEQ ID NO: 87]

(5-Me-C)G-rich sequence:
Template:   5'-GAA TTC C*GC* GC*G C*GC* AC*G C*GC*
            GC*G C*GG AGC GTA CGC TCC* GC*G C*GC*
            GC*G-(CH2)3SH-3'
            [SEQ ID NO: 88]

Reagent:    5'-BrCH(CH3)CONH-TGC* GC*G C*GC* GGA
            ATT-3'
            [SEQ ID NO: 89]

C* = 5-methyl cytosine. The thiols in both the
mixed and (5-Me-C)G-rich sequences were protected
as disulfides (-(CH2)3S-S(CH2)3OH) for circular
dichroism measurements.
```

DNA Synthesis and Analysis

DNA oligonucleotides were synthesized on a PerSeptive Biosystems Expedite 8090 DNA synthesizer using standard phosphoramidite protocols and were purified by reverse phase HPLC with a triethylammonium acetate (TEAA)/$CH_3CN$ gradient. Oligonucleotides were quantitated by UV and by denaturing PAGE after staining with ethidium bromide. Quantitation of DNA by denaturing PAGE was performed with a Stratagene Eagle Eye II densitometer. Synthetically modified oligonucleotide analogs were incorporated using the corresponding phosphoramidites or controlled pore glass (CPG) beads purchased from Glen Research, Sterling, Va. USA.

DNA Functionalization 2-bromopropionamide-NHS esters. 200 mg N-hydroxysuccinimide (Pierce, Rockford, Ill., USA) was dissolved in anhydrous $CH_2Cl_2$ together with 1.1 equivalents of a 2-bromopropionic acid (either racemic, (R)-, or (S)-) and 2 equivalents of 1-(3-dimethylaminopropyl)-3-ethylcarbodiimide (EDC) (Aldrich). The 2-bromopropionic acid enantiomers were >95% enantiopure as judged by chiral HPLC (5% isopropanol in hexanes, (R,R) WHELK 01 chiral phase, detection at 220 nm). The reaction was maintained at room temperature and complete after 1.5 hours as judged by TLC (EtOAc). The crude reaction mixture was extracted with 2.5% sodium hydrogen sulfate ($NaHSO_4$) to remove the excess EDC. The organic phase was washed with brine, dried over magnesium sulfate ($MgSO_4$), and concentrated in vacuo. The residue was dried and used directly for DNA functionalization.

5'-functionalization of oligonucleotides. An NHS ester prepared as described above was dissolved in DMSO. Up to 150 µg of a 5'-amino DNA oligonucleotide was combined with 3 mg/mL NHS ester (final reaction=10% DMSO) in 200 mM sodium phosphate (pH=7.2) at room temperature for 2 hours. The functionalized oligonucleotides were purified by gel filtration and reverse-phase HPLC, and were characterized by denaturing PAGE and MALDI-TOF mass spectrometry.

3'-thiol modified oligonucleotides. The 3' thiol group was incorporated by standard automated DNA synthesis using 3'-disulfide-linked CPG (Glen Research, Sterling, Va., USA). Following oligonucleotide synthesis, the disulfide was cleaved with 50 mM DTT, 1M TAPS (pH=8.0) at room temperature for 1 hour and purified by gel filtration before being used in DNA-templated reactions.

DNA-Templated Reactions

Reactions were performed with 60 nM template and 60 nM reagent in 50 mM MOPS (pH=7.5) and 250 mM NaCl at 25° C. unless otherwise specified. Reaction aliquots were removed at time points from 2 minutes to 120 minutes and quenched with excess β-mercaptoethanol. Starting materials and products were ethanol-precipitated from the quenched reaction mixtures, analyzed by denaturing PAGE, quantified as described above. Relative initial rates of product formation were determined from the fitting the raw yield vs. time data and were used to calculate $k_S/k_R$. Representative data are shown in FIG. 42.

Figure 42A:
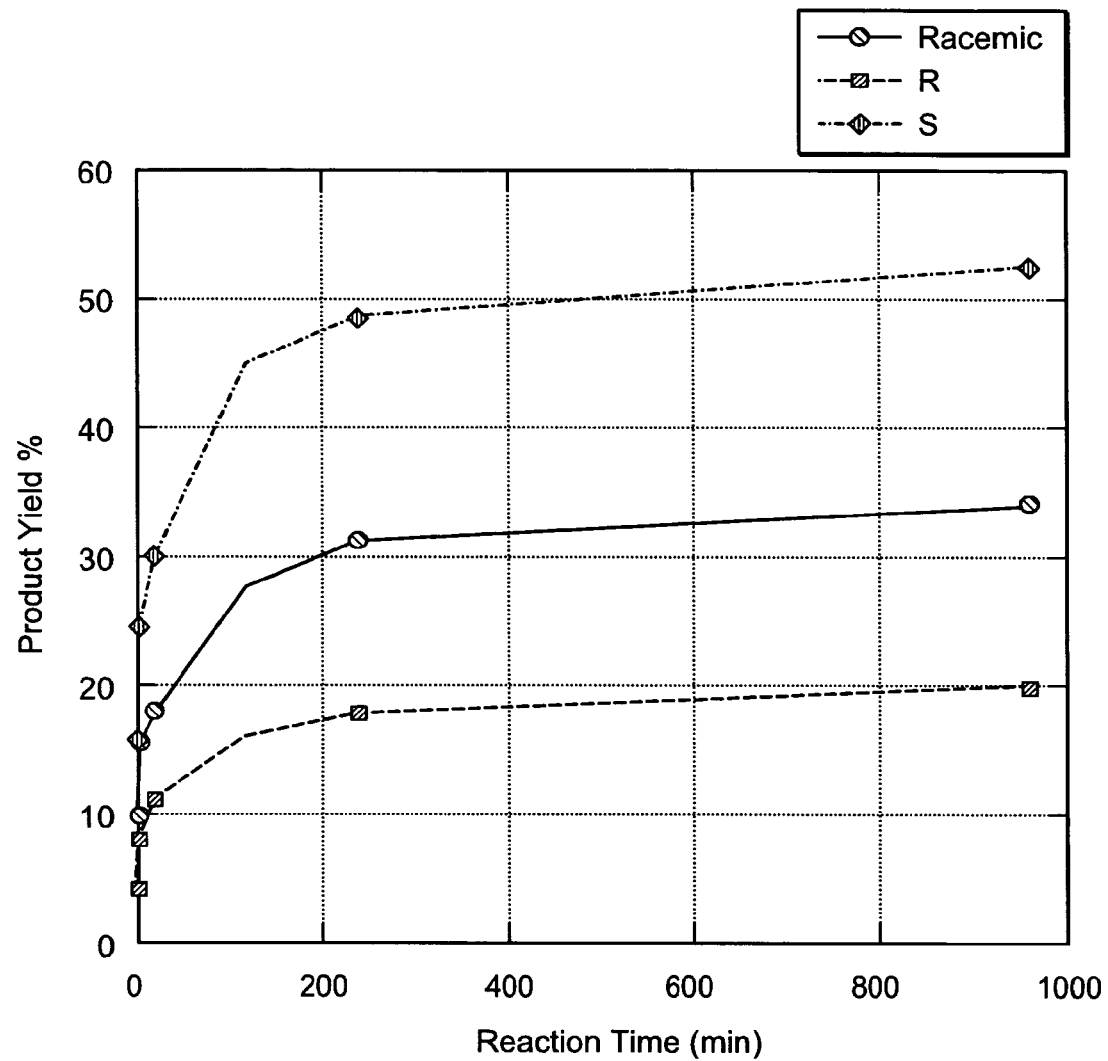
FIGS. 42A-42D shows graphical representations of product yield versus time for exemplary stereoselective DNA-templated reactions used to calculate $k_S/k_R$.

For the representative data sets shown in FIG. 42, the apparent second order rate constants derived from the initial rates are as follows:

FIGS. 39A and 42A:

$$k_{R,app}=1.94\times10^3\,M^{-1}s^{-1}; k_{S,app}=7.07\times10^3\,M^{-1}s^{-1}; k_{rac,app}=4.58\times10^3\,M^{-1}s^{-1}$$

Figure 42B:
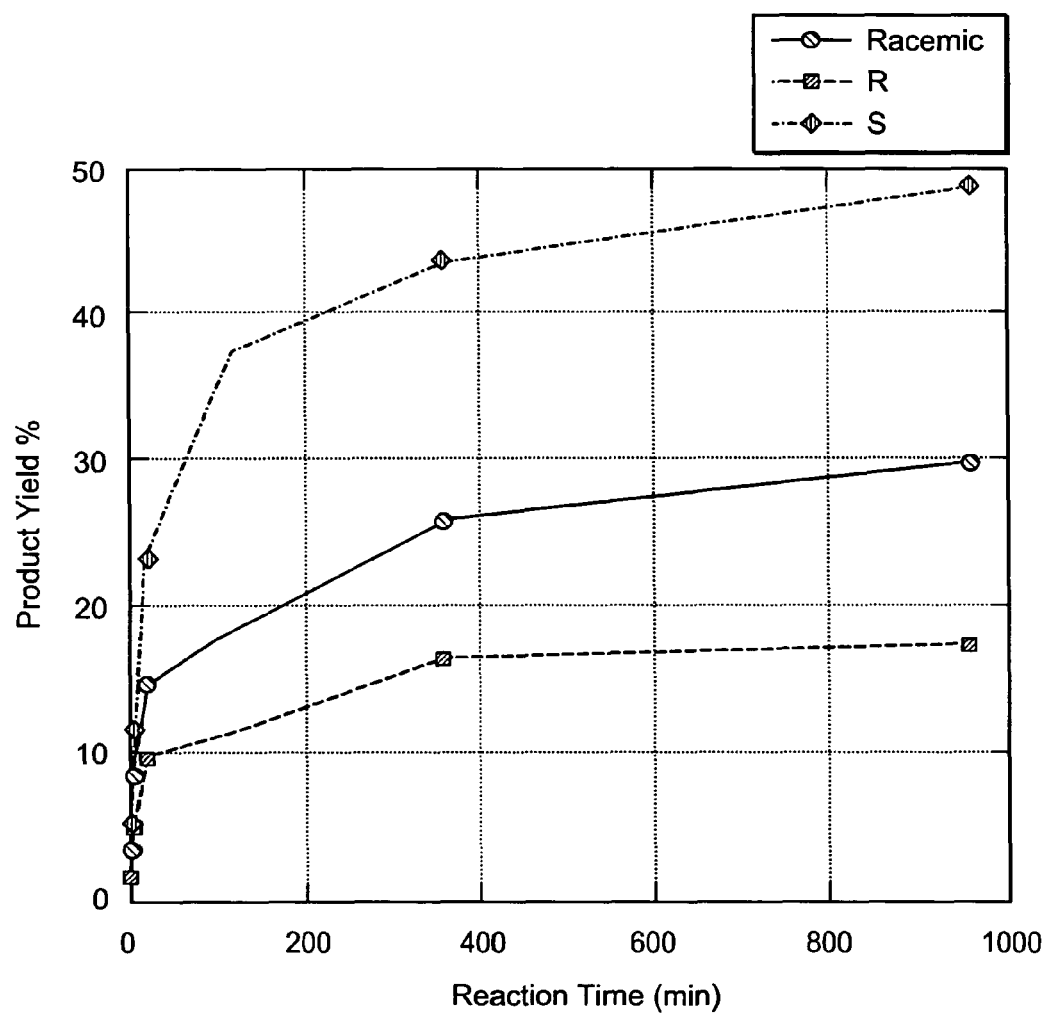

FIGS. 39B and 42B:

$$k_{R,app}=5.83\times10^3\,M^{-1}s^{-1}; k_{S,app}=21.9\times10^3\,M^{-1}s^{-1}; k_{rac,app}=13.6\times10^3\,M^{-1}s^{-1}$$

Figure 42C:
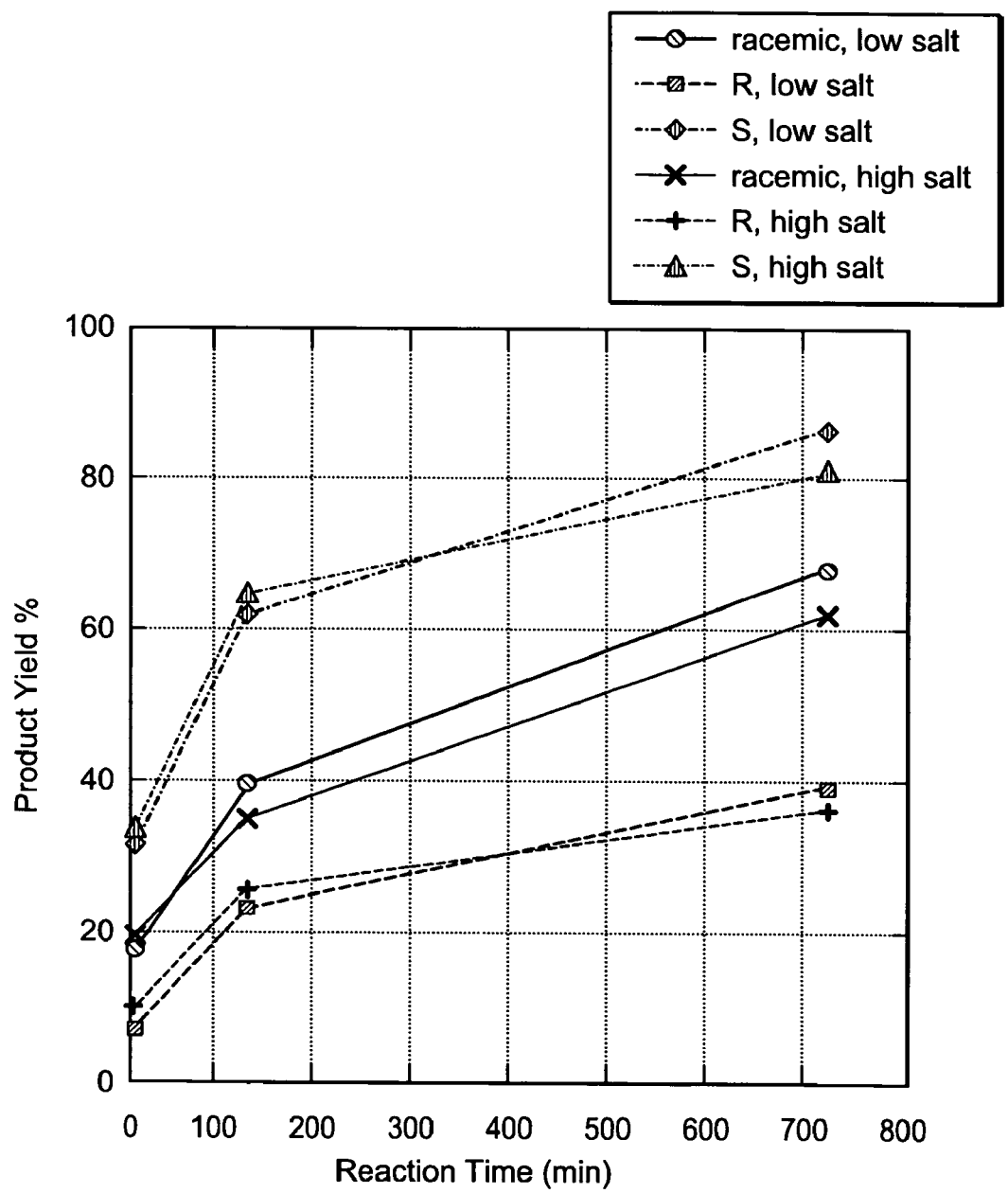
Figure 44A:
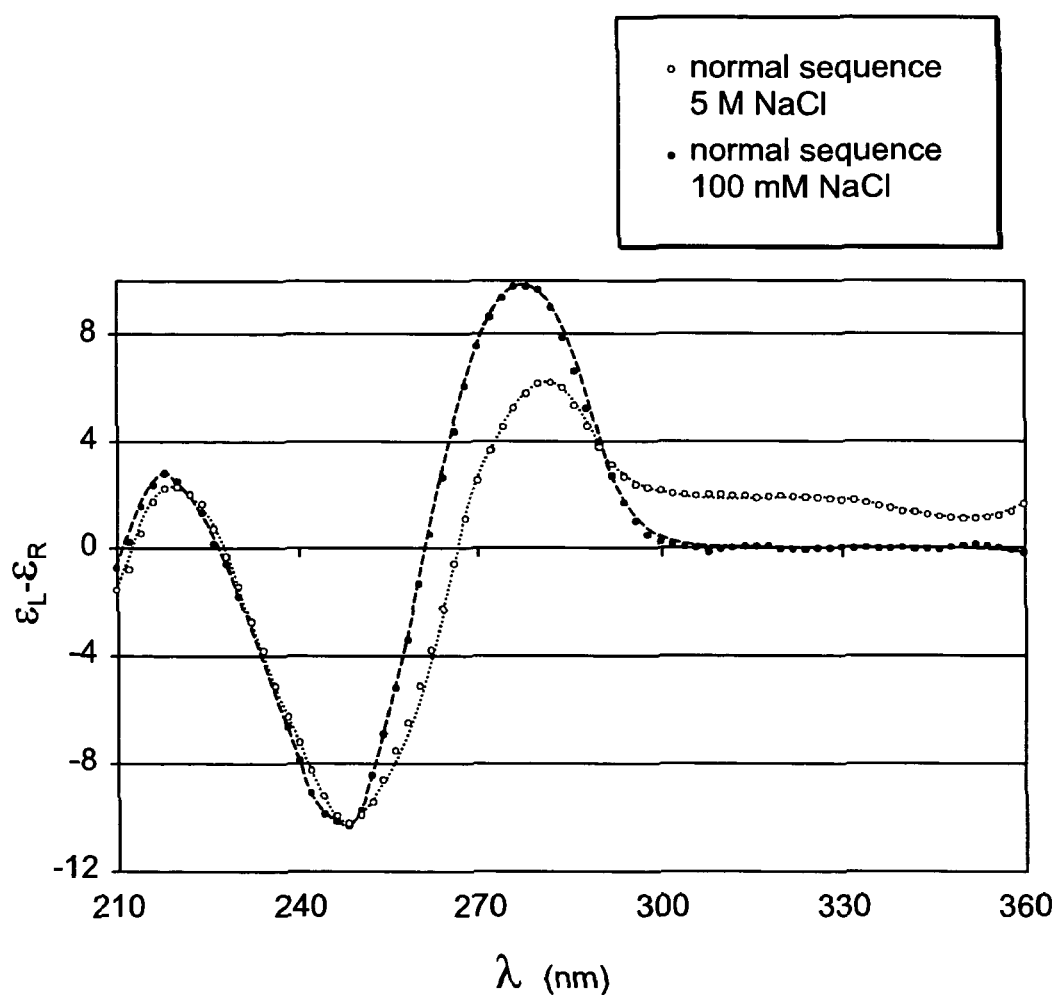
FIG. 44A-44B are graphical representations of circular dichroism spectra obtained for B-form (FIG. 44A) and Z-form (FIG. 44B) template-reagent complexes.

FIGS. 42C and 44A, low salt:

$$k_{R,app}=4.00\times10^3\,M^{-1}s^{-1}; k_{S,app}=17.6\times10^3\,M^{-1}s^{-1}; k_{rac,app}=9.88\times10^3\,M^{-1}s^{-1}$$

FIGS. 42C and 44A, high salt:

$$k_{R,app}=5.95\times10^3\,M^{-1}s^{-1}; k_{S,app}=18.8\times10^3\,M^{-1}s^{-1}; k_{rac,app}=10.8\times10^3\,M^{-1}s^{-1}$$

Figure 42D:
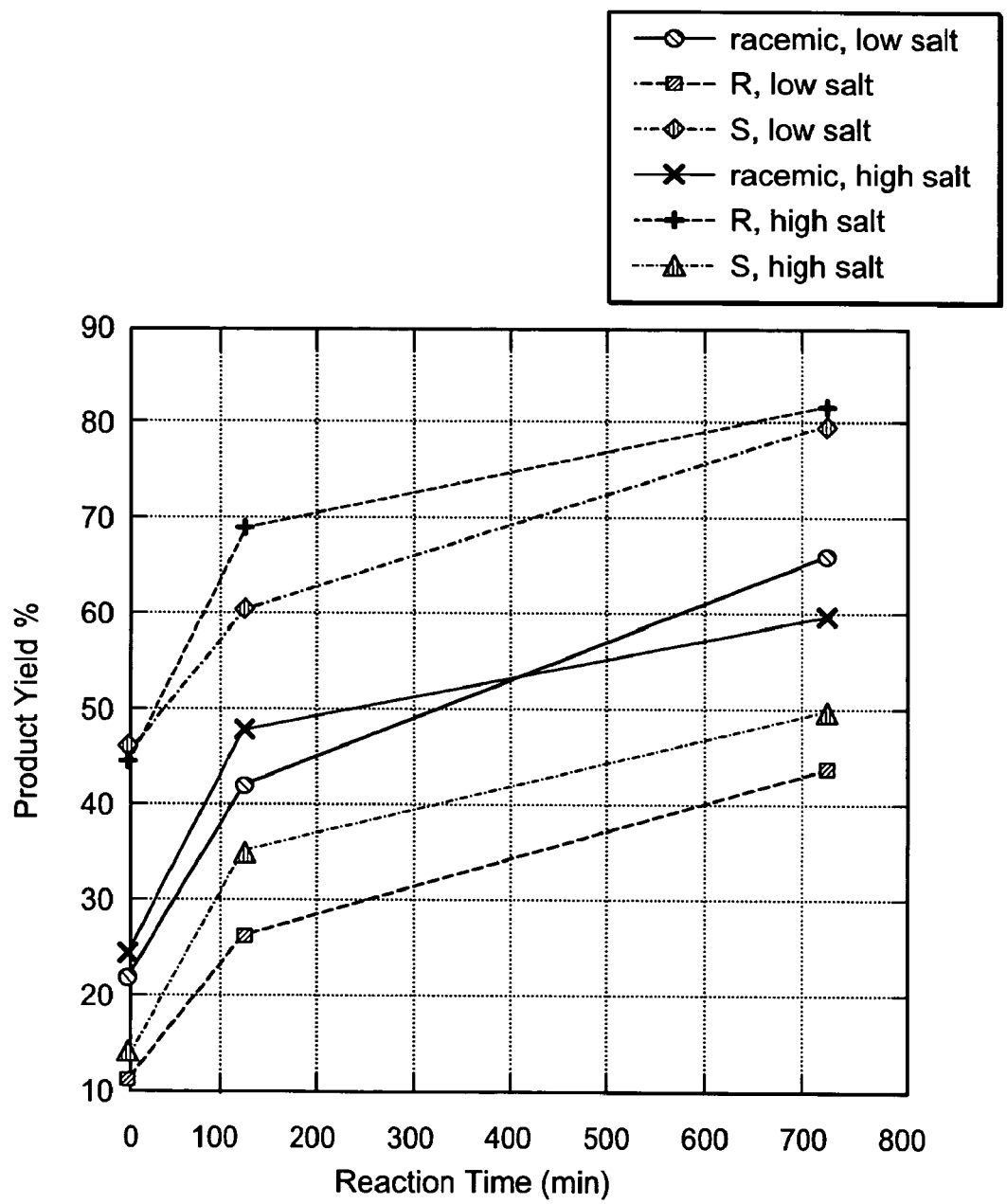
Figure 44B:
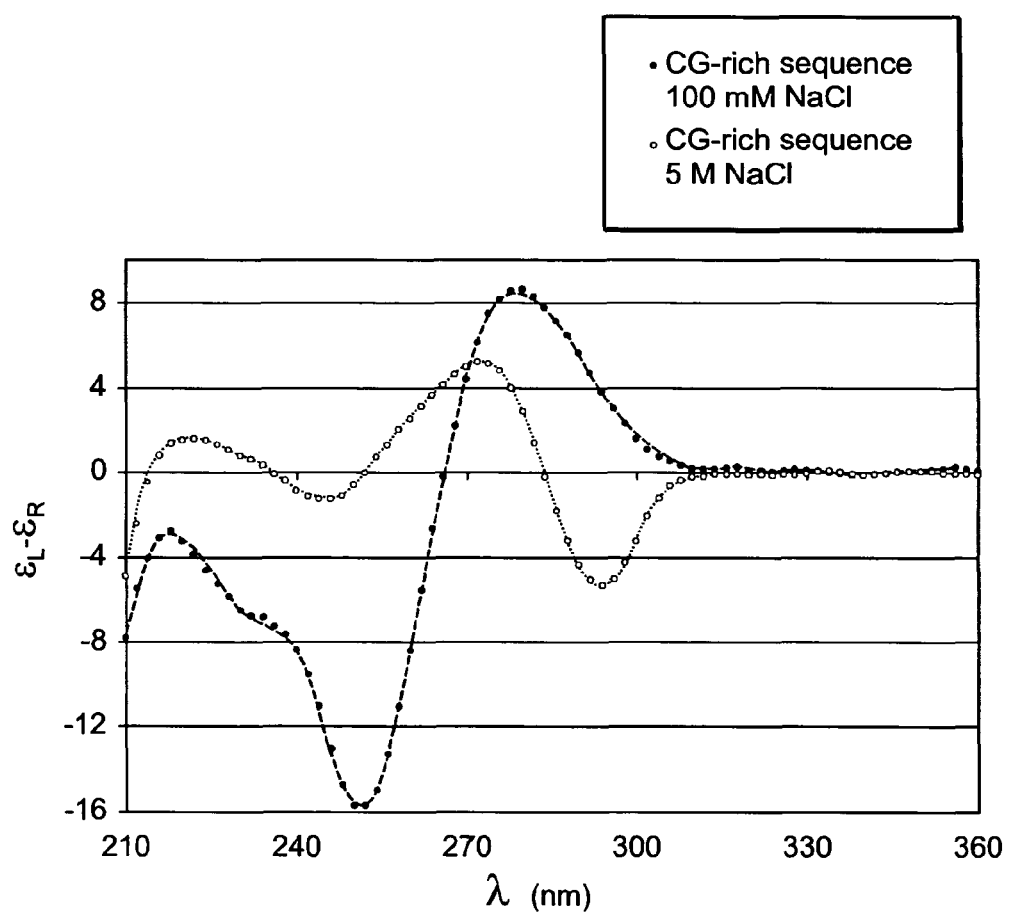

FIGS. 42D and 44B, low salt:

$$k_{R,app}=6.11\times10^3\,M^{-1}s^{-1}; k_{S,app}=25.4\times10^3\,M^{-1}s^{-1}; k_{rac,app}=12.1\times10^3\,M^{-1}s^{-1}$$

FIGS. 42D and 44B, high salt:

$$k_{R,app}=24.6\times10^3\,M^{-1}s^{-1}; k_{S,app}=7.66\times10^3\,M^{-1}s^{-1}; k_{rac,app}=13.6\times10^3\,M^{-1}s^{-1}$$

Evaluating Bromide Stability

The structural and configurational stability of the bromides under the reaction conditions was confirmed by several independent methods. Each bromide-linked template or reagent oligonucleotide was pre-incubated for up to 72 hours at 25° C., and up to 48 hours at 37° C. under the reaction conditions in the absence of thiol. Following the pre-incubation, stereoselectivity was measured as described above and always found to be unchanged as a result of the pre-incubation. In addition, large-scale (250 pmol) quantities of bromide-linked templates ((R), (S), and pseudo-racemic) were each incubated under the reaction conditions for 16 hours and analyzed by MALDI-TOF mass spectrometry. No evidence of bromide displacement (by water or by chloride) was observed as shown in Tables 11 and 12.

TABLE 11

| End-of-helix template (expected mass = 7202.1) | |
| --- | --- |
| Isomer | Observed Mass |
| (R) bromide: | before incubation = 7203.3 ± 7 |
| | after incubation = 7206.4 ± 7 |

TABLE 11-continued

| End-of-helix template (expected mass = 7202.1) | |
| --- | --- |
| Isomer | Observed Mass |
| (S) bromide: | before incubation = 7206.0 ± 7 |
| | after incubation = 7201.9 ± 7 |
| (±) bromide: | mass before incubation = 7201.7 ± 7 |
| | mass after incubation = 7204.7 ± 7 |

TABLE 12

| Hairpin template (expected mass = 9682.4) | |
| --- | --- |
| Isomer | Observed Mass |
| (R) bromide: | mass before incubation = 9686.6 ± 10 |
| | mass after incubation = 9685.7 ± 10 |
| (S) bromide: | mass before incubation = 9683.8 ± 10 |
| | mass after incubation = 9680.6 ± 10 |
| (±) bromide: | mass before incubation = 9680.6 ± 10 |
| | mass after incubation = 9684.7 ± 10 |

Finally, small molecule analogs of the above bromide-linked DNAs (both enantiomers of N-methyl 2-bromopropionamide) were incubated for 16 hours under the reaction conditions and analyzed by chiral HPLC under conditions that resolve the (S)- and (R)-enantiomers. No change in retention time was observed.

Stereoselectivities Using Achiral Flexible Linkers

Figure 43F:
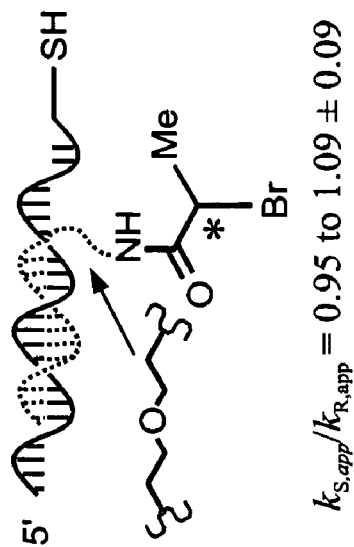
Figure 43E:
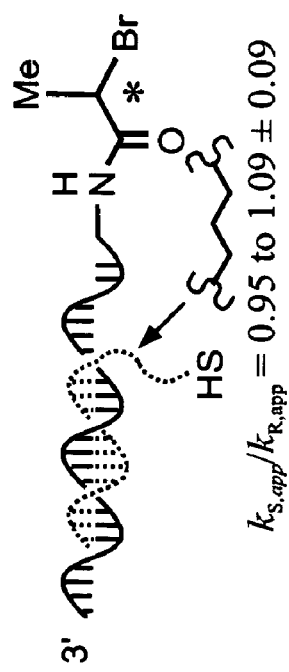

FIG. 43 shows modified template or reagent structures that result in loss of stereoselectivity during DNA-templated $S_N2$ reactions. In all cases, $k_{S,app}/k_{R,app}$ values fell within the range of 0.95 to 1.09 (±0.09), which reflects the mean and standard deviation of at least three independent experiments. The exact structures of the templates containing achiral linkers and their corresponding reagents were as follows:

FIG. 43A:

| Template | 5'-BrCH(CH$_3$)CONH-[(CH$_2$)$_2$O]$_2$OPO$_3^-$-{[(CH$_2$)$_2$O]$_6$OPO$_3^-$}$_3$-GGT ACG AAT TC-3' [SEQ ID NO: 90] |
| --- | --- |
| Reagent: | 5'-GAA TTC GTA CC-(CH$_2$)$_3$SH-3' [SEQ ID NO: 91] |

FIG. 43B:

| Template: | 5'-GAA TTC GTA CA-(CH$_2$)$_3$OPO$_3^-$-{[(CH$_2$)$_2$O]$_6$OPO$_3^-$}$_3$-(CH$_2$)$_3$SH-3' [SEQ ID NO: 92] |
| --- | --- |
| Reagent: | 5'-BrCH(CH$_3$)CONH-TGT ACG AAT TC-3' [SEQ ID NO: 93] |

FIG. 43C:

| Template: | 5'-BrCH(CH$_3$)CONH-[(CH$_2$)$_2$O]$_2$OPO$_3^-$-AC GCT CGC GAT GGT ACG AAT TC-3' [SEQ ID NO: 94] |
| --- | --- |
| Reagent: | 5'-GAA TTC GTA CC-(CH$_2$)$_3$SH-3' [SEQ ID NO: 95] |

FIG. 43D:

Template: 5'-GAA TTC GTA CAT AGC GCT CGC A-(CH₂)₃OPO⁻-(CH2)₃SH-3'
[SEQ ID NO: 96]

Reagent: 5'-BrCH(CH₃)CONH-TGT ACG AAT TC-3'
[SEQ ID NO: 97]

FIG. 43E:

Template: 5'-BrCH(CH₃)CONH-TAC GCT CGC GAT GGT ACG AAT TC-3'
[SEQ ID NO: 98]

Reagent: 5'-GAA TTC GTA CC-(CH₂)₃OPO₃⁻-(CH₂)₃SH-3'
[SEQ ID NO: 99]

FIG. 43F:

Template: 5'-GAA TTC GTA CAT AGC GCT CGC AT-(CH₂)₃SH-3'
[SEQ ID NO: 100]

Reagent: 5'-BrCH(CH₃)CONH-[(CH₂)₂O]OPO₃⁻-TGT ACG AAT TC-3'
[SEQ ID NO: 101]

Circular Dichroism (CD) of B-DNA and Z-DNA

The DNA templates and reagents were prepared as described above. Thiol-linked reagents were not deprotected and remained in their disulfide forms during CD analysis. CD samples contained 215 nM template and 215 nM protected reagent in 50 mM phosphate buffer (pH=7.5) with either 100 mM or 5 M NaCl. A background sample lacking DNA was also prepared for each sample. The CD measurements were performed in a 1 mm path cuvette at 25° C. scanning from 360 nm to 200 nm at 2 nm/sec on a JASCO polarized spectrometer with a 2.0 nm resolution. The resulting CD spectra of B-form and Z-form template-reagent complexes are shown in FIG. 44. FIG. 44A shows circular dichroism (CD) spectra of template-reagent complexes containing normal (mixed composition) sequences which are characteristic of B-DNA. FIG. 44B shows CD spectra of (5-Me-C)G-rich complexes having a B-DNA conformation at low salt concentrations, and having a Z-DNA conformation at high salt concentrations. The exact structures of the templates containing mixed and (5-Me-C) G-rich sequence, and their corresponding reagents used, are as follows:

Mixed sequence:
Template: 5'-GAA TTC TGG ACA CTT AGC TAT TCA TCG AGC GTA CGC TCG ATG AAT AGC-(CH₂)₃SH-3'
[SEQ ID NO: 102]
(The thiol was protected as a disulfide [(CH₂)₃S-S(CH₂)₃OH] for circular dichroism measurements).

Reagent: 5'-BrCH(CH₃)CONH-TAA GTG TCC AGA ATT C-3'
[SEQ ID NO: 103]

(5-Me-C)G-rich sequence:
Template: 5'-GAA TTC C*GC* GC*G C*GC* AC*G C*GC* GC*G C*GG AGC GTA CGC TCC* GC*G C*GC* GC*G-(CH₂)₃SH-3'
[SEQ ID NO: 104]
(The thiol was protected as a disulfide [(CH₂)₃S-S(CH₂)₃OH] for circular dichroism measurements)

Reagent: 5'-BrCH(CH₃)CONH-TGC* GC*G C*GC* GGA ATT-3'
[SEQ ID NO: 105]
C* = 5-methyl cytosine

Stereoselectivity Induced by B-Form and Z-Form DNA

Figure 45:
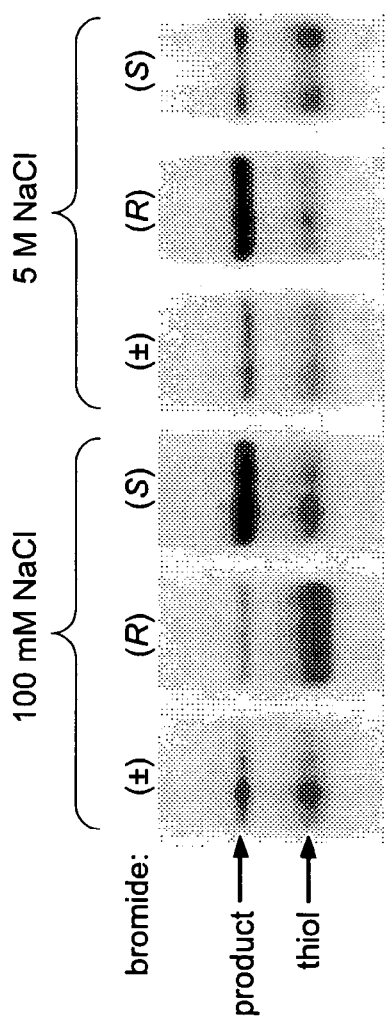
FIG. 45 shows a representative denaturing PAGE analysis of reactions using the CG-rich sequences at low and high salt concentrations.

FIG. 45 shows a representative denaturing gel electrophoresis analysis of reactions using the CG-rich sequences at 100 mM NaCl (lanes 1-3) or at 5 M NaCl (lanes 4-6) (6 hour time point). Lanes 1 and 4: racemic bromide; lanes 2 and 5: (R)-bromide; lanes 3 and 6: (S)-bromide. The bromide-linked reagent is not visible. Similar results were observed using Na₂SO₄ instead of NaCl.

DNA-Templated Reactions in the Presence of Na₂SO₄ Instead of NaCl

In order to ascertain that the observed stereoselectivities were not affected by the presence of chloride, the experiments shown in FIGS. 39 and 44 were repeated in the presence of Na₂SO₄ instead of NaCl (keeping the concentration of sodium constant). The results of three independent trials were very similar to those reported in the presence of NaCl, and are as follows:

FIG. 39A with Na₂SO₄ instead of NaCl: $k_S/k_R$=5.4±0.5
FIG. 39B with Na₂SO₄ instead of NaCl: $k_S/k_R$=3.9±0.3
FIG. 39C with Na₂SO₄ instead of NaCl: $k_S/k_R$=4.7±0.7
FIG. 44A, low salt with Na₂SO₄ instead of NaCl: $k_S/k_R$=3.7±0.7
FIG. 44A, high salt with Na₂SO₄ instead of NaCl: $k_S/k_R$=3.1±0.6
FIG. 44B, low salt with Na₂SO₄ instead of NaCl: $k_S/k_R$=3.6±0.5
FIG. 44B, high salt with Na₂SO₄ instead of NaCl: $k_S/k_R$=0.25±0.03

MALDI-TOF Mass Spectrometry of Representative Products

The products from the representative DNA-templated reactions (240 pmol scale) in FIG. 39 were purified by preparative denaturing polyacrylamide gel electrophoresis followed by extraction with 0.1 M triethylammonium acetate at 37° C. overnight. The lyophilized products were subjected to MALDI-TOF mass spectrometry, the results of which are summarized in Table 13. In all cases the observed mass is consistent with the expected mass.

TABLE 13

| FIG. | Expected Mass | Observed Mass |
|---|---|---|
| 39A | 13067.5 | 13015.6 ± 65 |
| 39B | 10562.0 | 10587.2 ± 53 |
| 39C | 10558.1 | 10600.1 ± 53 |

Example 7

Directing Otherwise Incompatible Reactions in a Single Solution

This Example demonstrates that oligonucleotides can simultaneously direct several different synthetic reaction types within the same solution, even though the reactants involved would be cross-reactive and, therefore, incompatible under traditional synthesis conditions. These findings also demonstrate that it is possible to perform a one-pot diversification of synthetic library precursors into products using multiple, simultaneous and not necessarily compatible reaction types.

Figure 46:
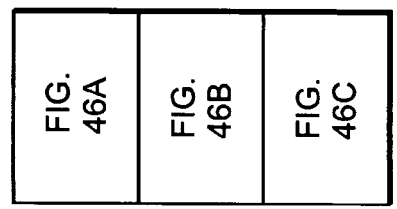
FIG. 46 is a schematic representation of a DNA-templated synthesis in which maleimides, aldehydes, or amines are subjected to multiple DNA-templated reaction types in a single solution.
Figure 46A:
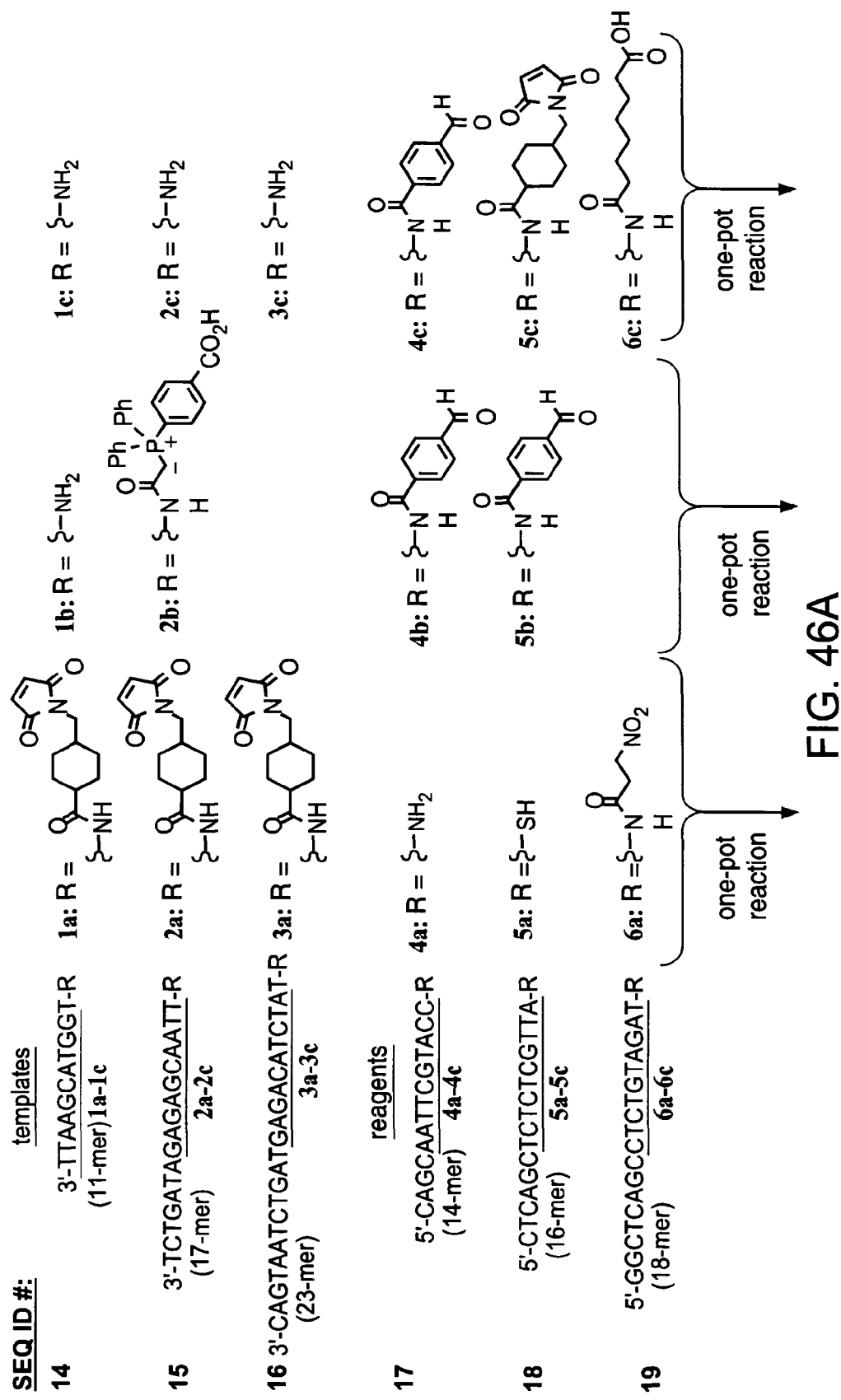
Figure 46B:
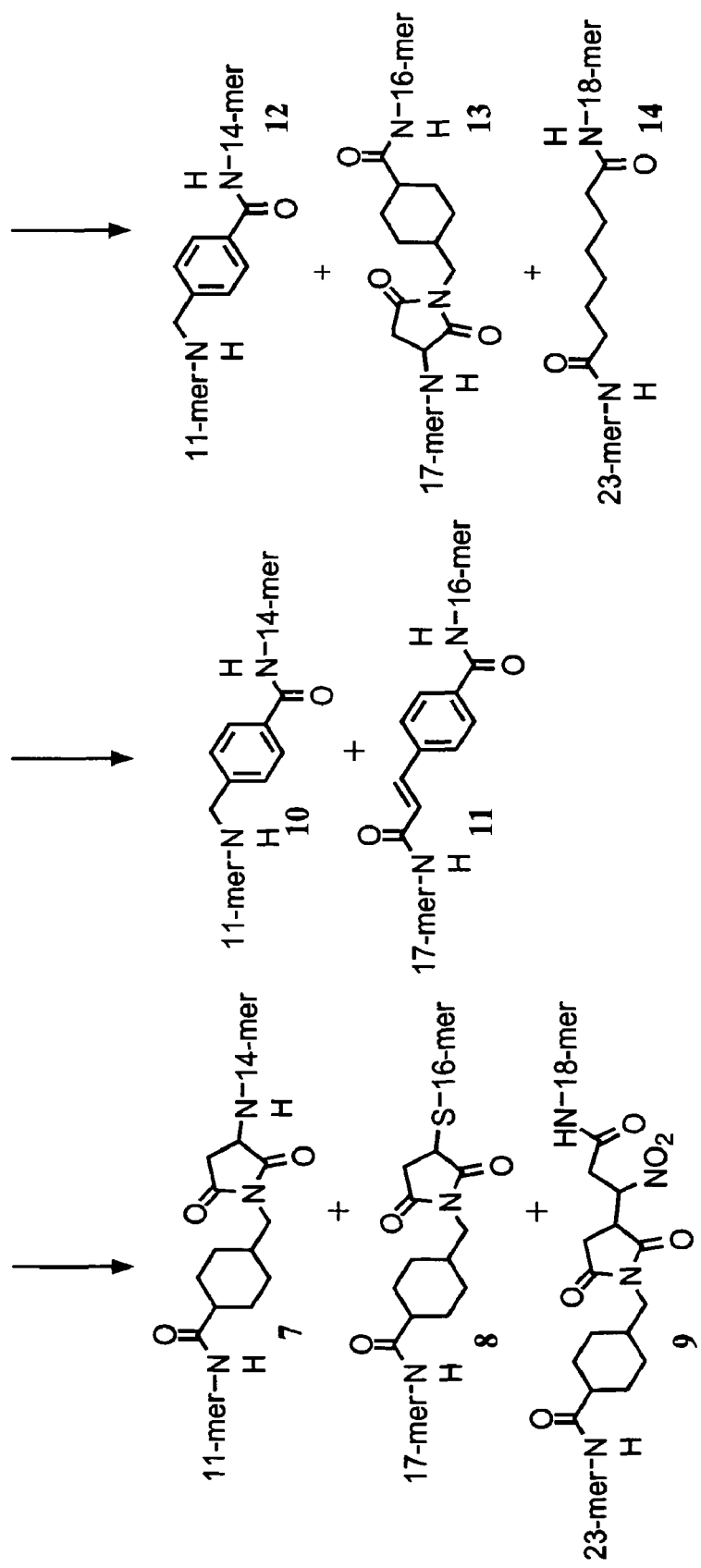
Figure 46C:
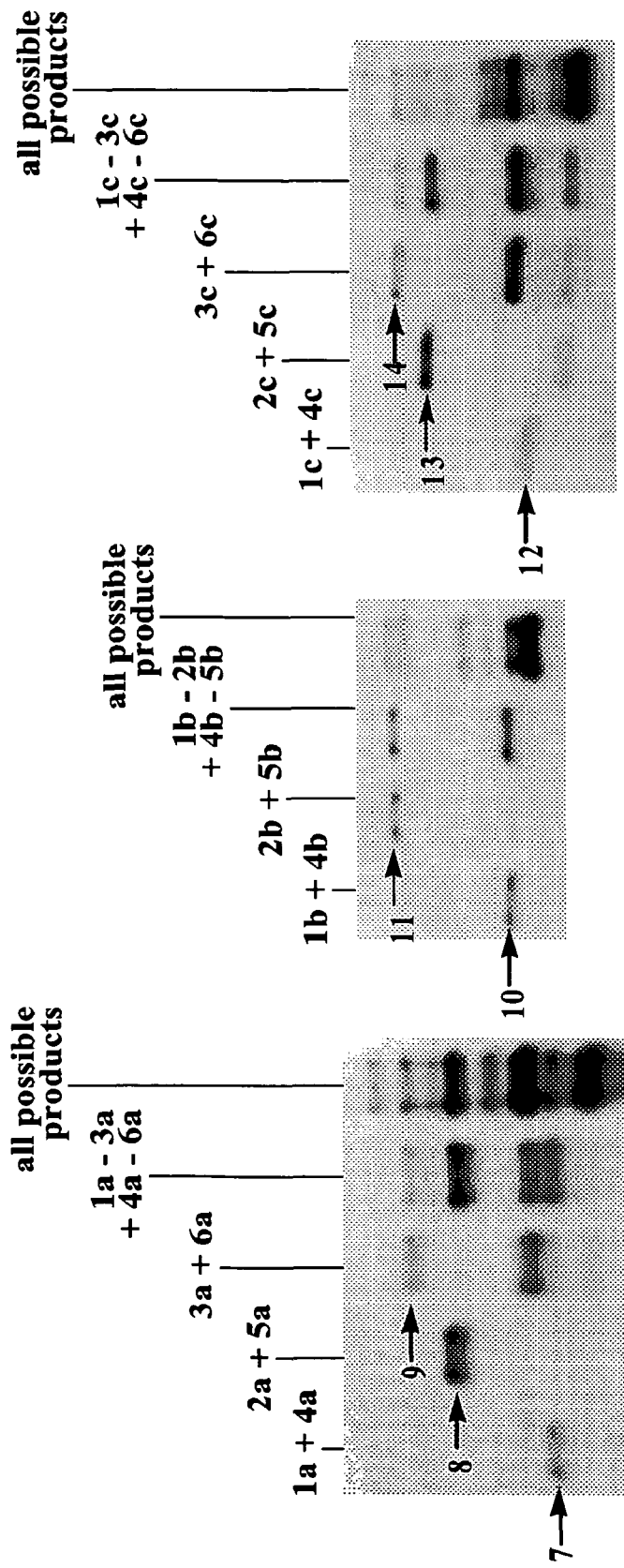

The ability of DNA templates to mediate diversification using different reaction types without spatial separation was initially tested by preparing three oligonucleotide templates of different DNA sequences (1a-3a) functionalized at their 5' ends with maleimide groups and three oligonucleotide reagents (4a-6a) functionalized at their 3' ends with an amine, thiol, or nitroalkane group, respectively (FIG. 46). The DNA sequences of the three reagents each contained a different 10-base annealing region that was complementary to ten bases near the 5' end of each of the templates. Combining 1a with 4a, 2a with 5a, or 3a with 6a in three separate vessels at pH 8.0 resulted in the expected DNA-templated amine conjugate addition, thiol conjugate addition, or nitro-Michael addition products 7-9 (FIG. 46, lanes 1-3).

To distinguish the nine possible reaction products that could be generated upon combining 1a-6a, the lengths of template oligonucleotides were varied to include 11, 17, or 23 bases and the lengths of reagent oligonucleotides were varied to include 14, 16, or 18 bases. Differences in oligonucleotide length were achieved using extensions distal from the reactive groups that did not significantly affect the efficiency of DNA-templated reactions. This design permitted all nine possible reaction products (linked to 25, 27, 29, 31, 33, 35, 37, 39, or 41 bases of DNA) to be distinguished by denaturing polyacrylamide gel electrophoresis.

A solution containing all three templates (1a-3a) was combined with a solution containing all three reagents (4a-6a) at pH 8.0. The resulting reaction exclusively generated the three desired products 7, 8, and 9 of lengths 25, 33, and 41 bases indicating that only the three reactions corresponding to the complementary template-reagent pairs took place (FIG. 46, lane 4). Formation of the other six possible reaction products was not detected by densitometry (<5% reaction). In contrast, individually reacting templates and reagents containing the same, rather than different, 10-base annealing regions permitted the formation of all possible products (FIG. 46, lane 5). This result demonstrates the ability of DNA-templated synthesis to direct the selective one-pot transformation of a single functional group into three distinct types of products (in this Example, maleimide into secondary amine, thioether, or α-branched nitroalkane).

To test the ability of this diversification mode to support one-pot reactions requiring non-DNA-linked accessory reagents, an analogous experiment was conducted with two aldehyde-linked reagents either 14 or 16 bases in length (4b or 5b, respectively) and a complementary 11-base amine-linked template (1b) or a 17-base phosphorane-linked template (2b). Combining 1b and 4b at pH 8.0 in the presence of 3 mM NaBH$_3$CN resulted in the DNA-templated reductive amination product 10, while 2b and 5b under the same conditions generated Wittig olefination product 11 (FIG. 46). Mixing all four reactants together in one pot resulted in an identical product distribution as the combined individual Wittig olefination or reductive amination reactions (FIG. 46). No reaction between amine 1b and aldehyde 5b or between phosphorane 2b and aldehyde 4b was detected (FIG. 46, lane 8 versus lane 9).

The generality of this approach was explored by including multiple reaction types that required different accessory reagents. Three amine-linked templates (1c-3c) of length 11, 17, or 23 bases were combined with an aldehyde-, carboxylic acid-, or maleimide-linked reagent (4c-6c) 14, 16, or 18 bases in length, respectively, at pH 8.0 in the presence of 3 mM NaBH$_3$CN, 10 mM 1-(3-dimethyl-aminopropyl)-3-ethylcarbodiimide (EDC), and 7.5 mM N-hydroxylsulfosuccinimide (sulfo-NHS). The reactions containing all six reactants afforded the same three reductive amination, amine acylation, or conjugate addition products (12-14) that were generated from the individual reactions containing one template and one reagent and did not produce detectable quantities of the six possible undesired products arising from non-DNA-templated reactions (FIG. 46, lanes 10-14). Collectively, these results indicate that DNA-templated synthesis can direct simultaneous reactions between several mutually cross-reactive groups in a single pot to yield only the sequence-programmed subset of many possible products.

Figure 47B:
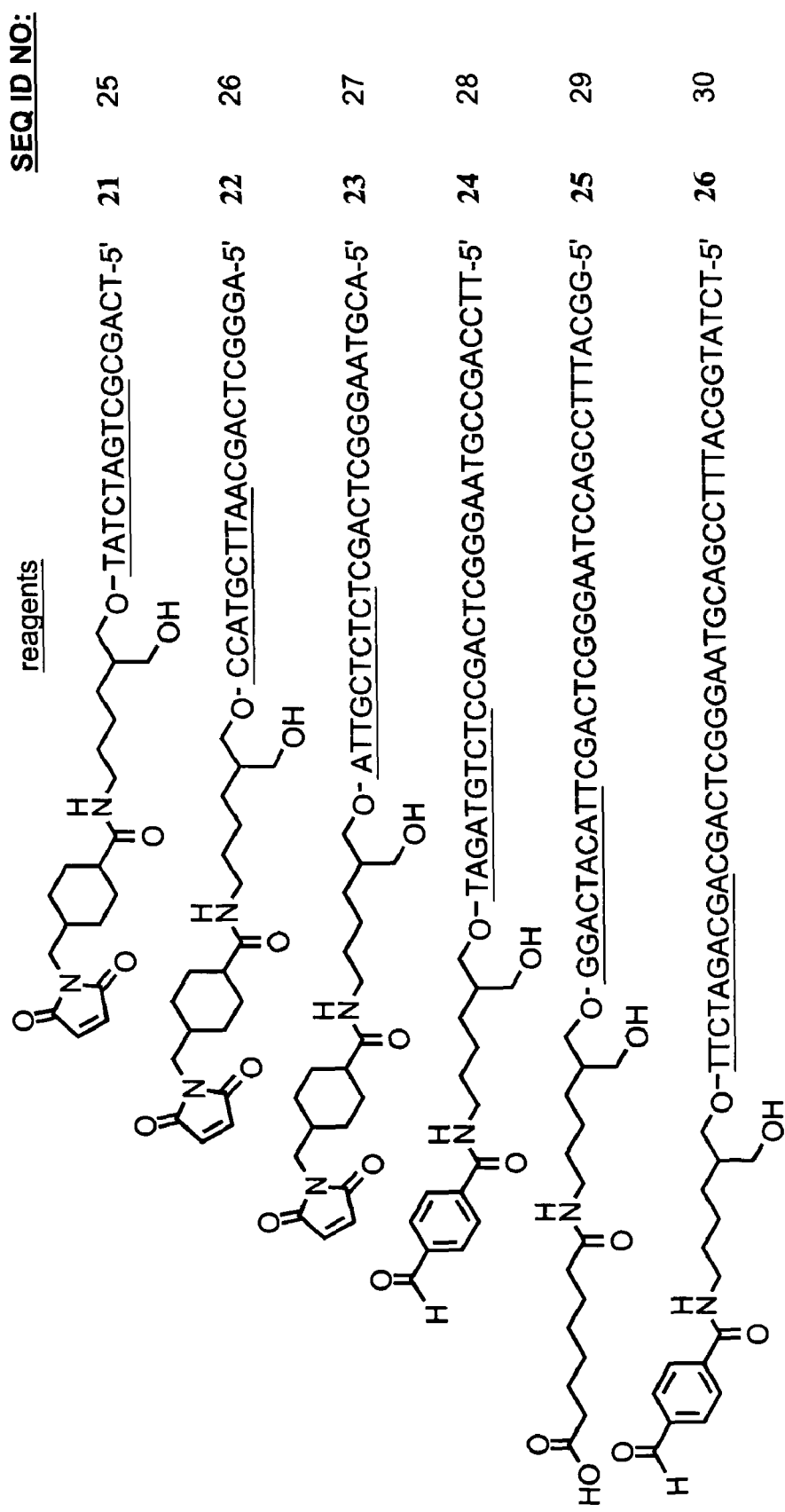
FIG. 47 depicts templates and reagents used pairwise in 12-reactant one-pot DNA-templated reactions.
Figure 47C:
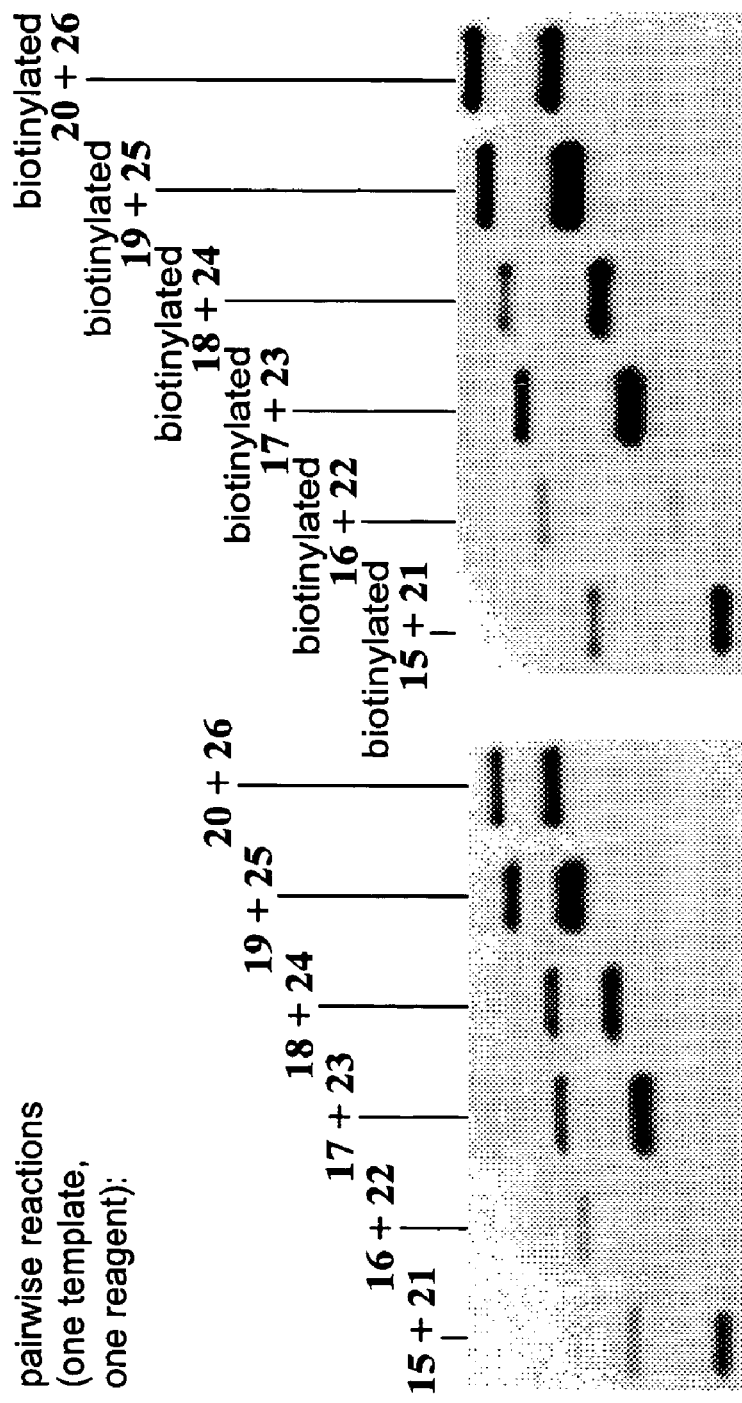

The above three examples each diversified a single functional group (maleimide, aldehyde, or amine) into products of different reaction types. A more general format for the one-pot diversification of a DNA-templated synthetic library into products of multiple reaction types would involve the simultaneous reaction of different functional groups linked to both reagents and templates. To examine this possibility, six DNA-linked nucleophile templates (15-20) and six DNA-linked electrophile reagents (21-25) collectively encompassing all of the functional groups used in the above three examples (amine, aldehyde, maleimide, carboxylic acid, nitroalkane, phosphorane, and thiol) were prepared (FIG. 47). These twelve DNA-linked reactants could, in theory, undergo simultaneous amine conjugate addition, thiol conjugate addition, nitro-Michael addition, reductive amination, amine acylation, and Wittig olefination in the same pot, although the apparent second order rate constants of these six reactions vary by more than 10-fold.

Determining the outcome of combining all twelve reagents and templates in a single pot by using oligonucleotides of varying lengths is difficult due the large number (at least 28) of possible products that could be generated. Accordingly, the length of the reagents as 15, 20, 25, 30, 35, or 40 bases were varied but the length of the templates was fixed at 11 bases (FIG. 47). Each of the six complementary template-reagent pairs when reacted separately at pH 8.0 in the presence of 3 mM NaBH$_3$CN, 10 mM EDC, and 7.5 mM sulfo-NHS generated the expected amine conjugate addition, thiol conjugate addition, nitro-Michael addition, reductive amination, amine acylation, or Wittig olefination products (FIG. 47). Reaction efficiencies were greater than 50% relative to the corresponding individual reactions despite having to compromise between differing optimal reaction conditions. Templates 15-20 were also prepared in a 3'-biotinylated form. The biotinylated templates demonstrated reactivities indistinguishable from those of their non-biotinylated counterparts (FIG. 47).

Figures 48, 48A:
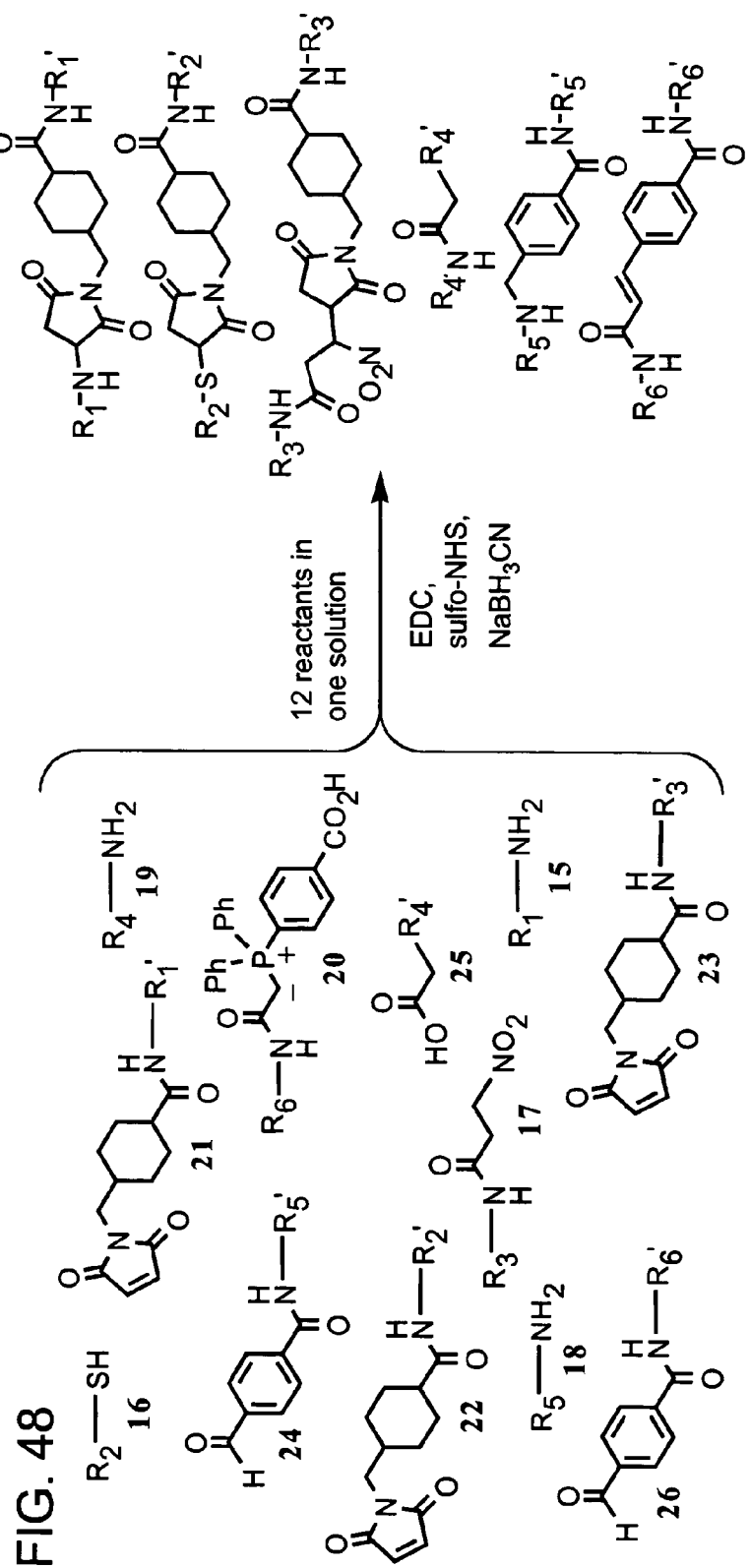
FIG. 48 depicts a "one-pot" DNA-templated reaction containing 12 reactants and at least seven possible reaction types which generates only 6 sequence-programmed products out of at least 28 possible products.
Figure 48B:
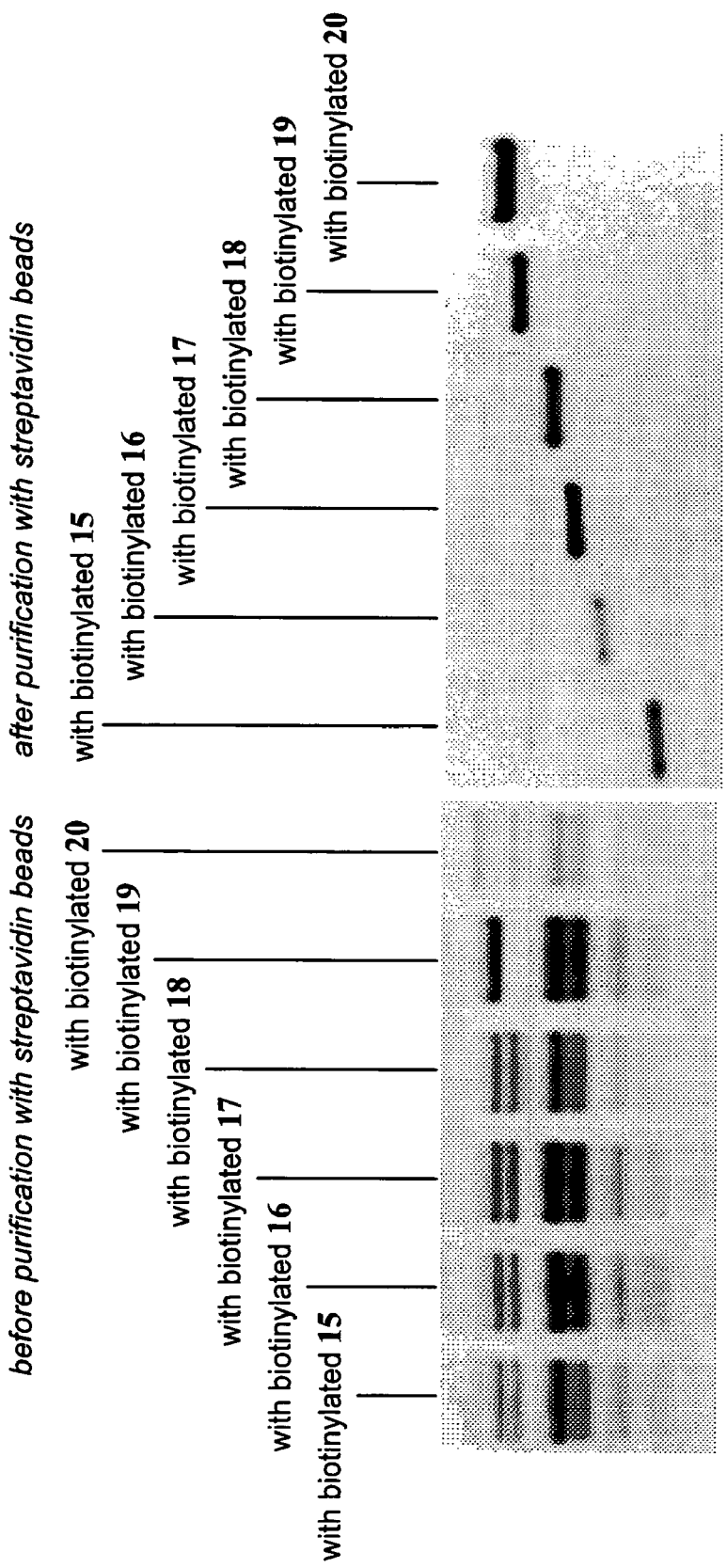

Six separate reactions each containing twelve reactants then were performed at pH 8.0 in the presence of 3 mM NaBH$_3$CN, 10 mM EDC, and 7.5 mM sulfo-NHS (FIG. 48). Each reaction contained a different biotinylated template (15, 16, 17, 18, 19, or 20) together with five non-biotinylated templates (from 15-20) and six reagents (21-25). These reactions were initiated by combining a solution containing 15-20 with a solution containing 21-25. The products that arose from each biotinylated template were captured with streptavidin-coated magnetic beads and identified by denaturing gel electrophoresis. Because the six reagents in each reaction contained oligonucleotides of unique lengths, the formation of any reaction products involving the biotinylated templates and any of the reagents could be detected. In all six cases, the biotinylated template formed only the single product programmed by its DNA sequence (FIG. 48) despite the possibility of forming up to five other products in each reaction. Taken together, these findings indicate that reactions of significantly different rates requiring a variety of non-DNA-linked accessory reagents can be directed by DNA-templated synthesis in the same solution, even when both templates and reagents contain several different cross-reactive functional groups. The ability of DNA templates to direct multiple reactions at concentrations that exclude non-templated reactions from proceeding at appreciable rates mimics, in a single solution, a spatially separated set of reactions.

Compared to the use of traditional synthetic methods, generating libraries of small molecules by DNA-templated synthesis is limited by several factors including the need to prepare DNA-linked reagents, the restriction of aqueous, DNA-compatible chemistries, and the reliance on characterization methods such as mass spectrometry and electrophoresis that are appropriate for molecular biology-scale (pg to µg) reactions. On the other hand, DNA-templated synthesis (i) allows the direct in vitro selection (as opposed to screening) and amplification of synthetic molecules with desired properties, (ii) permits the preparation of synthetic libraries of unprecedented diversity, and (iii) requires only minute quantities of material for selection and identification of active library members. In addition, this Example demonstrates that potentially useful modes of reactivity not possible using current synthetic methods can be achieved in a DNA-templated format. For example, six different types of reactions can be performed simultaneously in one solution, provided that required non-DNA-linked accessory reagents are compatible. This reaction mode permits the diversification of synthetic small molecule libraries using different reaction types in a single solution.

Materials and Methods

Synthesis of Templates and Reagents

Oligonucleotides were synthesized using standard automated solid-phase techniques. Modified phosphoramidites and controlled-pore glass supports were obtained from Glen Research, Sterling, Va., USA. Unless otherwise noted, functionalized templates and reagents were synthesized by reacting 5'-$H_2N(CH_2O)_2$ terminated oligonucleotides (for templates) or 3'-$OPO_3$—$CH_2CH(CH_2OH)(CH_2)_4NH_2$ terminated oligonucleotides (for reagents) in a 9:1 mixture of aqueous 200 mM pH 7.2 sodium phosphate buffer:DMF containing 2 mg/mL of the appropriate N-hydroxysuccinimide ester (Pierce, Rockford, Ill., USA) at 25° C.

For the aldehyde and nitroalkane-linked oligonucleotides (4b, 4c, 5b, 6a, 17, 24, and 26, FIGS. 46 and 47) the NHS esters were generated by combining the appropriate carboxylic acid (900 mM in DMF) with equal volumes of dicyclohexylcarbodiimide (900 mM in DMF) and NHS (900 mM in DMF) for 90 minutes. Phosphorane-linked oligonucleotides (2b and 20, FIGS. 46 and 47) were prepared by a 90 minute reaction of the appropriate amino-terminated oligonucleotide with 0.1 volumes of a 20 mg/mL DMF solution of the NHS ester of iodoacetic acid (SIA, Pierce, Rockford, Ill., USA) in pH 7.2 buffer as above, followed by addition of 0.1 volumes of a 20 mg/mL solution of 4-diphenylphosphinobenzoic acid in DMF. Thiol-linked template 16 was synthesized by reacting ethylene glycol bis(succinimidylsuccinate) (EGS, Pierce, Rockford, Ill., USA) with the appropriate oligonucleotide for 15 minutes, followed by addition of 0.1 volumes of 300 mM 2-aminoethanethiol. Reagent 5a was synthesized using 3'$OPO_3$—$(CH_2)_3SS(CH_2)_3ODMT$ functionalized controlled-pore glass (CPG) support and reduced prior to use according to the manufacturer's protocol.

The 3'-biotinylated oligonucleotides were prepared using biotin-TEG CPG (Glen Research, Sterling, Va., USA). Products arising from biotinylated templates were purified by mixing with 1.05 equivalents of streptavidin-linked magnetic beads (Roche), washing twice with 5 M guanidinium hydrochloride, and eluting with aqueous 10 mM Tris pH 7.6 with 1 mM biotin at 80° C.

Synthesis of Linkers

Linkers between DNA oligonucleotides and the functional groups in 1a-6c are as follows. 1b and 1c: DNA-5'-$NH_2$; 1a, 2a-2c, 3a, and 3c: DNA-5'-$O(CH_2)_2O(CH_2)_2$—NH—; 5a: DNA-3'-O—$(CH_2)_3SH$; 4a-4-c, 5b, 5c, 6a, and 6c: DNA-3'-O—$CH_2CH(CH_2OH)(CH_2)_4NH$—. Oligonucleotide sequences used to generate all possible products in FIG. 46 (lanes 5, 9, and 14), with annealing regions underlined: R-T ATCTACAGAG-3' [SEQ ID NO: 106] (1a-1c); R-T ATCTACAGAGTAGTCT-3' [SEQ ID NO: 107] (2a-2c); R-T ATCTACAGAGTAGTCTAATGAC-3' [SEQ ID NO: 108] (3a-3c); 5'-CAGCCTCTGTAGAT-R [SEQ ID NO: 109] (4a-4-c); 5'-CTCAGCCTCTGTAGAT-R [SEQ ID NO: 110] (5a-5c); 5'-GGCTCAGCCTCTGTAGAT-R [SEQ ID NO: 111] (6a-6c). Functionalized templates and reagents were purified by gel filtration (Sephadex G-25) followed by reverse-phase HPLC (0.1 M triethylammonium acetate/acetonitrile gradient). Representative functionalized templates and reagents were further characterized by MALDI mass spectrometry.

Reaction Conditions

All reactions were performed by dissolving reagents and templates in separate vessels in pure water before combining them into a solution of 50 mM aqueous TAPS buffer, pH 8.0, 250 mM NaCl at 25° C. for 16 hours with DNA-linked reactants at 60 nM (FIG. 47) or at 12.5 nM (FIGS. 47 and 48). $NaBH_3CN$, EDC, and sulfo-NHS were present when appropriate as described. Products were analyzed by denaturing polyacrylamide gel electrophoresis using ethidium bromide staining and UV transillumination. Differences in charge states, attached functional groups, and partial secondary structure resulted in modest variations in gel mobility for different functionalized oligonucleotides of the same length (FIGS. 46-48).

Example 8

DNA-Templated Functional Group Transformations

Figure 49:
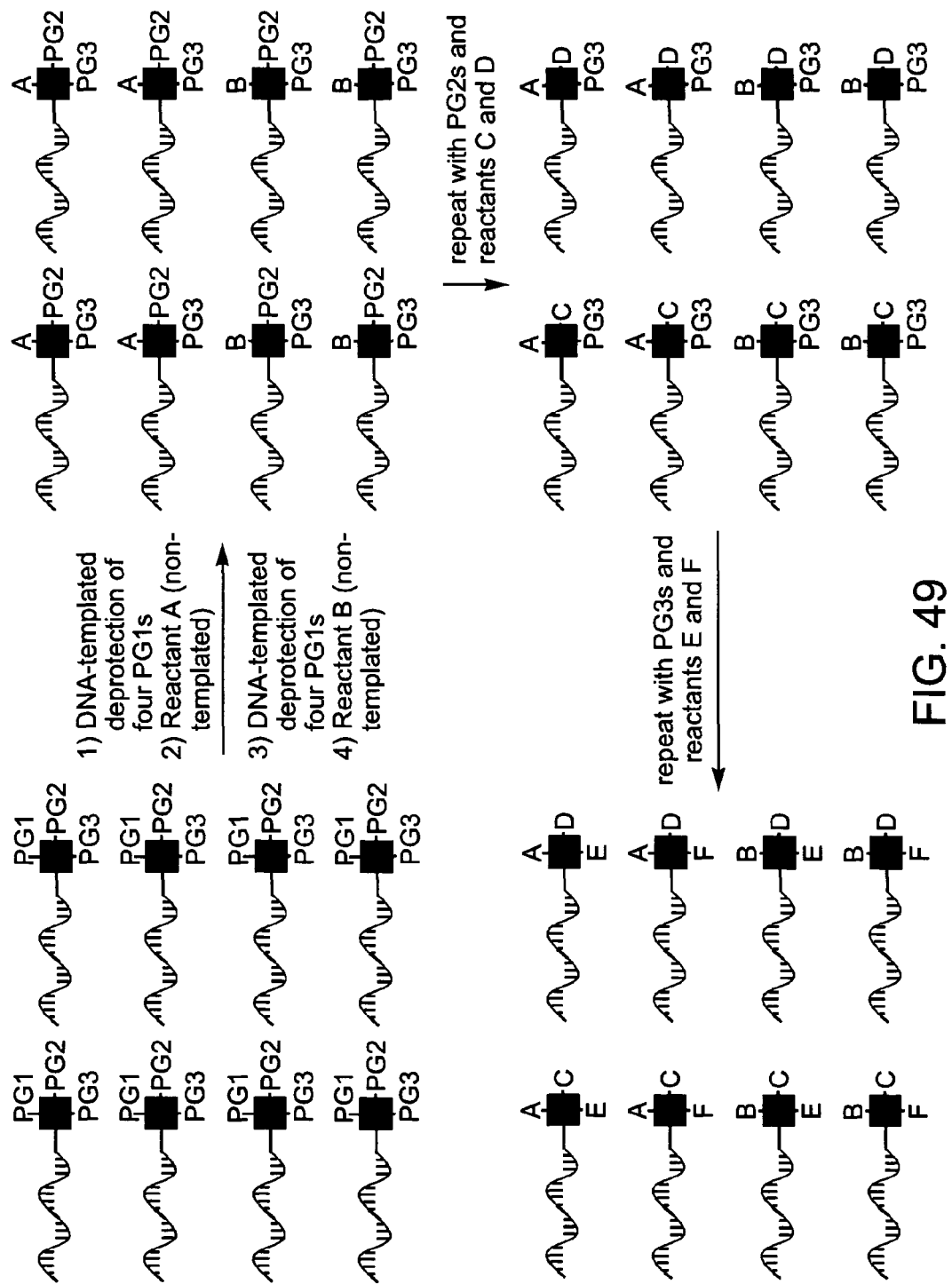
FIG. 49 is a schematic representation of a method for diversifying a DNA-templated library by sequentially exposing or creating reactive groups.

While coupling reactions are useful for building molecular diversity, the development of DNA-templated functional group transformations can significantly expand the types of structures that can be generated. DNA-templated synthesis can be used to transform functional groups by unmasking or interconverting functionalities used in coupling reactions. By exposing or creating a reactive group within a sequence-programmed subset of a library, DNA-templated functional group interconversions permit library diversity to be generated by sequential unmasking (FIG. 49). In FIG. 49, PG1-PG3 represent three different protecting groups, and A-F represent reactants capable of reacting with deprotected functionalities of a scaffold molecule. The sequential unmasking approach offers the major advantage of permitting reactants that would normally lack the ability to be linked to DNA (for example, simple alkyl halides) to contribute to library diversity by reacting with a sequence-specified subset of templates in an intermolecular, non-templated reaction mode. This advantage significantly increases the types of structures that can be generated. On the other hand, sequential unmasking has the drawback of requiring more manipulations per "step" because previously used small molecule reactants must be removed between DNA-templated functional group unmaskings. This removal can be rapidly performed on the entire library using a simple gel filtration cartridge.

DNA-Templated Deprotection

The first class of DNA-templated functional group transformations sequence-specifically unmask amine, thiol, alcohol, carboxylate, or aldehyde groups from protected forms. In the Staudinger reaction, azides react with phosphines to yield aza-ylides (Staudinger et al. (1919) HELV. CHIM. ACTA. 2: 635-646). When this reaction is performed in aqueous media, the aza-ylides undergo spontaneous hydrolysis to provide amines and phosphine oxides (Scriven et al. (1988) CHEM. REV. 88: 297-368). DNA-linked aryl and alkyl phosphine reagents, when combined with azide-linked DNA templates, permit sequence-specific amine deprotection (FIG. 50A). DNA-linked phosphines and DNA-linked azides have both been used successfully in previous DNA-templated reactions. As an alternative DNA-templated amine deprotection, the nucleophilic aromatic ipso-substitution of o-nitrobenzene-sulfonamides (prepared from amines and commercially available o-nitrobenzene sulfonylchloride) can yield free amines (FIG. 50B). This reaction is known to proceed efficiently in the presence of deprotonated thiophenols, so at pH>8 the DNA-templated attack of thiophenol-linked reagents on o-nitrobenzenesulfonamide-linked templates can permit sequence-specific amine deprotection (Fukuyama et al. (1999) SYNLETT 8: 1301-1303).

Once optimized, DNA-templated amine deprotection reactions can be extended to include deprotection reactions for alcohols and thiols. Kusumoto and co-workers have reported that 4-aminobutyryl esters undergo spontaneous intramolecular lactam formation to afford 2-pyrrolidinone and the liberated hydroxyl group in excellent yields (Kusumoto et al. (1986) BULL. CHEM. SOC. JPN. 59: 1296-1298). Kahne and co-workers have used this reaction effectively in aqueous media (Thomson et al. (1999) J. AM. CHEM. SOC. 121: 1237-1244). A DNA-templated hydroxyl group deprotection is shown in FIG. 50C. If lactam formation is slow, the reaction can be heated or Lewis acids can be added since sequence specificity is not required after amine deprotection. An analogous DNA-templated thiol deprotection that uses 4-azidobutyryl thioesters is shown in FIG. 50C. It is contemplated that these groups will be stable to hydrolysis under a wide range of conditions.

Palladium-mediated deallylation can also be used in DNA-templated carboxylate, amine, hydroxyl, or thiol deprotections. Allyloxycarbonyl (Alloc) esters, carbonates, thiocarbonates, and carbamates are treated with DNA-linked Pd ligands such as the 2,2'-bis(diphenylphosphino)-1,1'-binaphthyl (BINAP) reagent as shown in FIG. 50D (prepared from the known BINAP-6-butanoic acid) in the presence of pM to µM concentrations of water-soluble Pd sources such as $Na_2PdCl_4$ (Bayston et al. (1998) J. ORG. CHEM. 63: 3137-3140). The DNA-linked Pd ligands increase the effective molarity of Pd at complementary templates, but not at mismatched templates, to permit the sequence-specific deprotection of carboxylate, hydroxyl, thiol, and amine groups from the corresponding Alloc esters, carbonates, thiocarbonates, and carbamates, respectively (FIG. 50D) (Genêt et al. (1994) TETRAHEDRON 50: 497-503). It is particularly encouraging that the rates of BINAP ligand dissociation from Pd have been measured during Pd-mediated aryl aminations and found to be much slower than the rates of association and dissociation of substrate and products (Singh et al. (2002) J. AM. CHEM. SOC. 124: 14104-14114). The Pd source and the DNA-linked Pd ligands can be pre-incubated at high concentrations, and then the resulting complexes added either to complementary or mismatched templates at 60 nM concentrations. This procedure also results in sequence-specific Alloc deprotection if ligand-metal dissociation is slow relative to DNA annealing and Pd-catalyzed deallylation.

Finally, transition metal salts including $Sc^{3+}$ and $Yb^{3+}$ are known to catalyze acetal hydrolysis to yield aldehydes (Fukuzawa et al. (2001) CHEM. LETT. 5: 430-436). Conjugating the crown ether shown in FIG. 50E to oligonucleotides permits DNA-templated aldehyde deprotections in the presence of lanthanide triflates. These crown ether-$Ln^{3+}$ complexes have been previously reported to catalyze aqueous aldol reactions while completely sequestering one equivalent of $Ln^{3+}$ (Kobayashi et al. (2001) ORG. LETT. 3). Aldehyde deprotection is highly sequence-specific because the concentration of free $Ln^{3+}$ should be negligible.

DNA-Templated Functional Group Interconversions

The second class of DNA-templated functional group transformations interconverts groups generated from or used by DNA-templated reactions. Two functional group interconversions are shown in FIG. 51. Ruthenium(II) porphyrins in the presence of 2,6-disubstituted pyridine N-oxides catalyze the remarkably efficient epoxidation of a wide variety of simple and electron-deficient olefins (Higuchi et al. (1989) TETRAHEDRON LETT. 30: 6545-6548; Groves et al. (1985) J. AM. CHEM. SOC. 107: 5790-5792; Zhang et al. (2002) ORG. LETT. 4: 1911-1914; Yu et al. (2000) J. AM. CHEM. SOC. 122: 5337-5342). Single-stranded DNA is stable in the presence of aqueous tetrakis(4-carboxyphenyl) porphyrin complexed with Ru(II), and Ru(II)-DNA conjugates have been previously reported (Hartmann et al. (1997) J. BIOL. INORG. CHEM. 2: 427-432; Pascaly et al. (2002) J. AM. CHEM. SOC. 124: 9083-9092). DNA-templated olefin epoxidations using DNA-linked Ru(II) porphyrin catalysts are shown in FIG. 51A, which are prepared by coupling commercially available tetrakis(4-carboxyphenyl) porphyrin to amine-terminated oligonucleotides (Hoimlin et al. (1999) BIOCONJUG. CHEM. 10: 1122-1130). The resulting DNA-linked porphyrin is metalated with $Ru_3(CO)_{12}$ as described previously to afford the reagent shown in FIG. 51A. This functional group interconversion bridges several versatile reactions by permitting products of DNA-templated Wittig olefinations and Heck couplings to become substrates for epoxide addition reactions.

As a second functional group interconversion, lanthanide triflate-catalyzed aqueous Diels-Alder and hetero Diels-Alder cycloadditions proceed efficiently in water, and DNA-linked Lewis acid chelators such as binapthol, bis-trifylamides, or the crown ether shown in FIG. 50E permit the sequence-specific Diels-Alder reaction between a template-linked aldehyde and a free diene in solution (FIG. 51B). When Danishefsky's diene is used, this functional group transformation provides α,β unsaturated ketones that serve as substrates for subsequent DNA-templated conjugate addition reactions. Fully coordinated $Ln^{3+}$ complexes (such as those that arise from the crown ether) have been reported to be kinetically stable yet permit efficient catalysis through facile ligand exchange (Chappell et al. (1998) INORG. CHEM. 37: 3989-3998). Moreover, DNA-linked lanthanide complexes have been previously used as stable luminescent agents in aqueous solutions and, therefore, these complexes are compatible with the functionality present in DNA (Li et al. (1997) BIOCONJUG. CHEM. 8: 127-132).

Example 9

Synthesis of Exemplary Compounds and Libraries of Compounds

A) Synthesis of a Polycarbamate Library

This Example demonstrates a strategy for producing an amplifiable polycarbamate library.

Overview

Of the sixteen possible dinucleotide codons used to encode the library, one is assigned a start codon function, and one is assigned to serve as a stop codon. An artificial genetic code then is created assigning each of the up to 14 remaining dinucleotides to a different monomer. For geometric reasons one monomer actually contains a dicarbamate containing two side chains. Within each monomer, the dicarbamate is attached to the corresponding dinucleotide (analogous to a tRNA anticodon) through a silyl enol ether linker which liberates the native DNA and the free carbamate upon treatment with fluoride.

The dinucleotide moiety exists as the activated 5'-2-methylimidazole phosphate, that has been demonstrated to serve as an excellent leaving group for template-directed oligomerization of nucleotides yet is relatively stable under neutral or basic aqueous conditions (Inoue et al. (1982) J. MOL. BIOL. 162: 201; Rembold et al., (1994) J. MOL. EVOL. 38: 205; Chen et al. (1985) J. MOL. BIOL. 181: 271; Acevedo et al. (1987) J. MOL. BIOL. 197: 187; Inoue et al. (1981) J. AM. CHEM. SOC. 103: 7666; Schwartz et al. (1985) SCIENCE 228: 585). The dicarbamate moiety exists in a cyclic form linked through a vinyloxycarbonate linker. The vinylcarbonate group has been demonstrated to be stable in neutral or basic aqueous conditions and further has been shown to provide carbamates in very high yields upon the addition of amines Olofson et al. (1977) TETRAHEDRON LETT. 18: 1563; Olofson et al. (1977) TETRAHEDRON LETT. 18: 1567; Olofson et al. (1977) TETRAHEDRON LETT. 18: 1571).

When attacked by an amine from a nascent polycarbamate chain, the vinyl carbonate linker, driven by the aromatization of m-cresol, liberates a free amine. This free amine subsequently serves as the nucleophile to attack the next vinyloxycarbonate, propagating the polymerization of the growing carbamate chain. Such a strategy minimizes the potential for cross-reactivity and bi-directional polymerization by ensuring that only one nucleophile is present at any time during polymerization.

Figure 52:
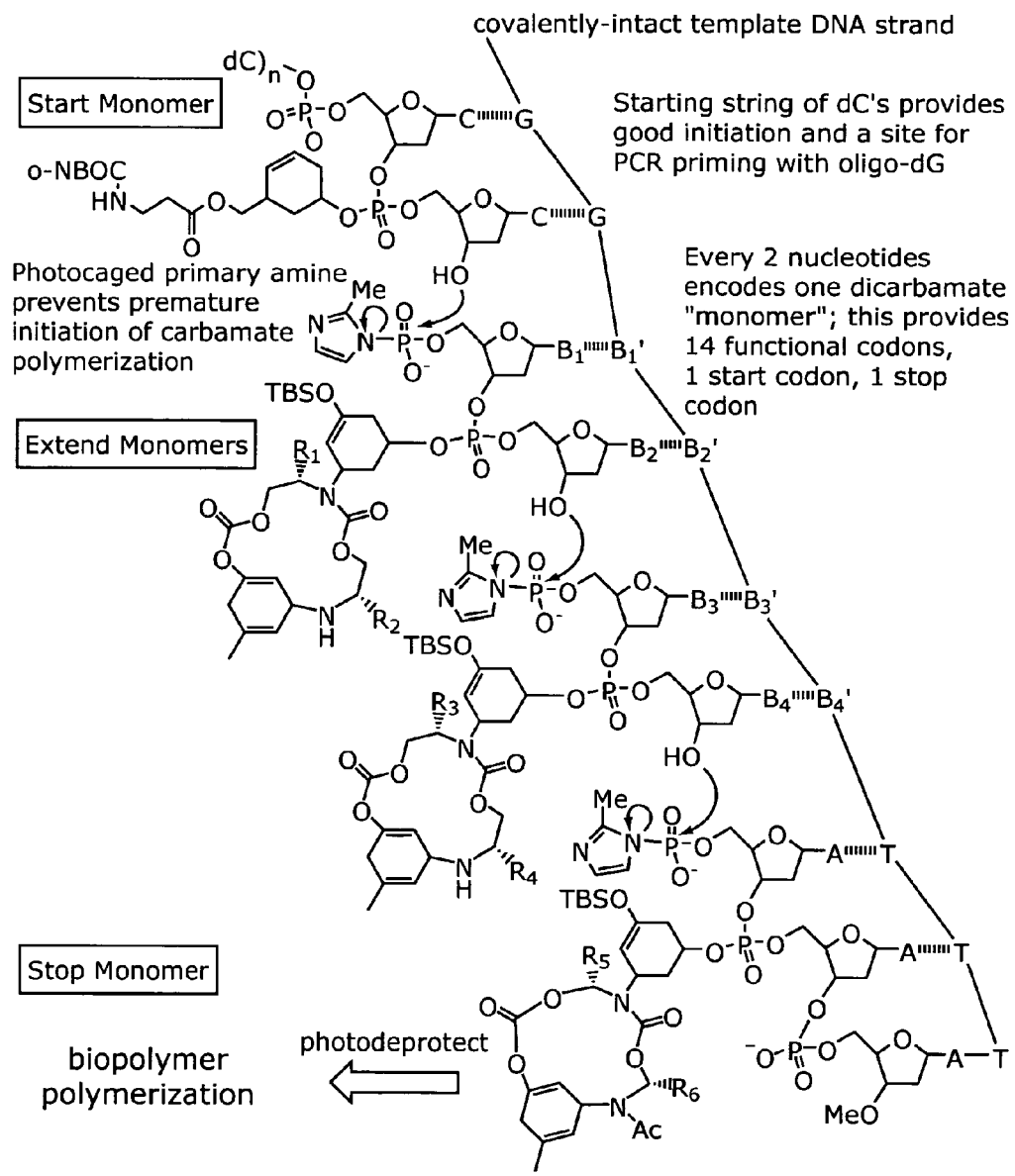
FIG. 52 is a schematic representation showing the assembly of transfer units along a nucleic acid template.

Using the monomer described above, artificial translation of DNA into a polycarbamate can be viewed as a three-stage process. In the first stage, single stranded DNA templates encoding the library are used to guide the assembly of the dinucleotide moieties of the monomers, terminating with the "stop" monomer which possesses a 3' methyl ether instead of a 3' hydroxyl group (FIG. 52).

Figure 53:
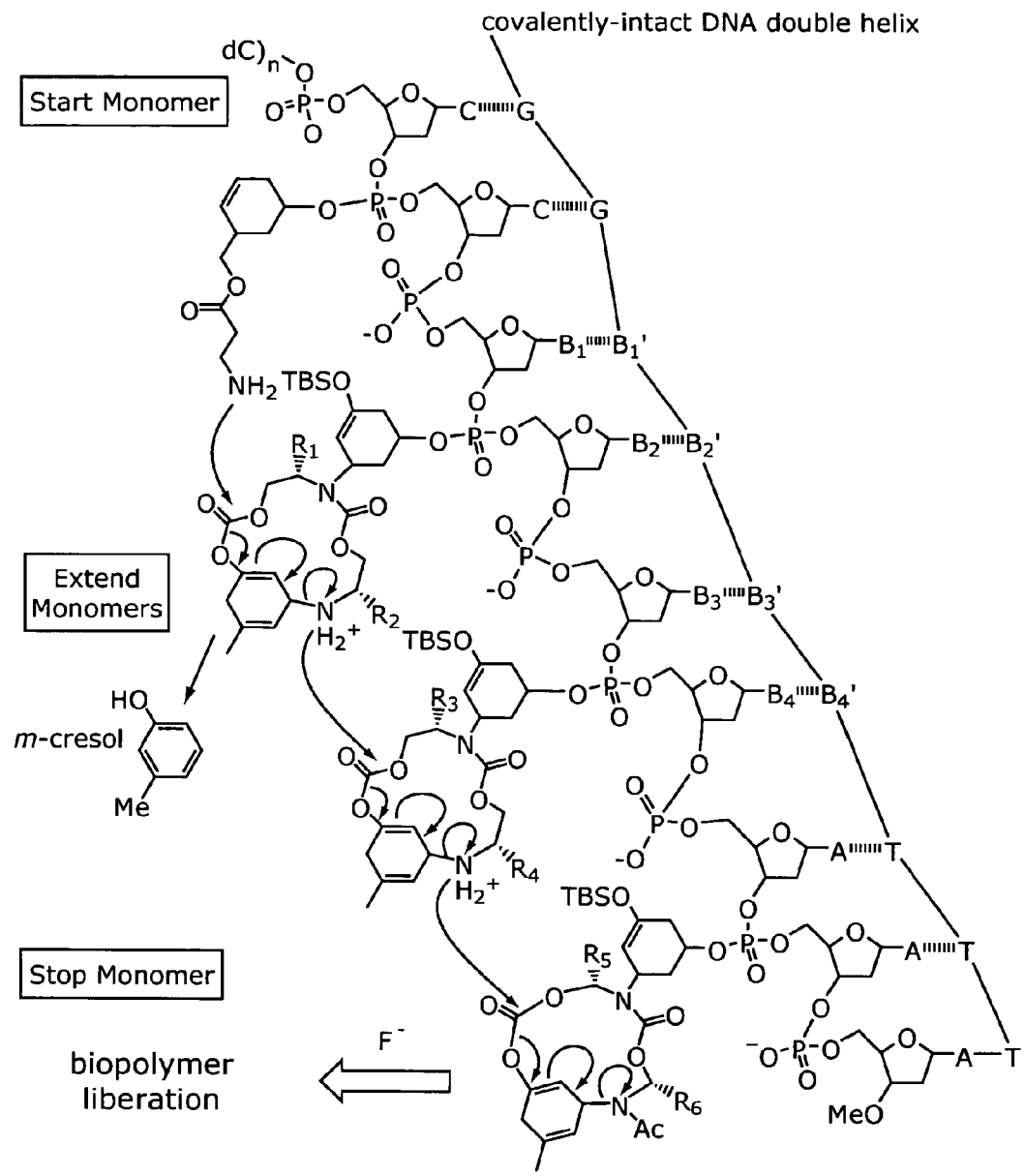
FIG. 53 is a schematic representation showing the polymerization of dicarbamate units along a nucleic acid template to form a polycarbamate.

Once the nucleotides have assembled, the "start" monomer ending in a o-nitrobenzylcarbamates is photodeprotected to reveal the primary amine that initiates carbamate polymerization. Polymerization proceeds in the 5' to 3' direction along the DNA backbone, with each nucleophilic attack resulting in the subsequent unmasking of a new amine nucleophile. Attack of the "stop" monomer liberates an acetamide rather than an amine, thereby terminating polymerization (FIG. 53). Because the DNA at this stage exists in a stable double-stranded form, variables such as temperature and pH may be explored to optimize polymerization efficiency.

Figure 54:
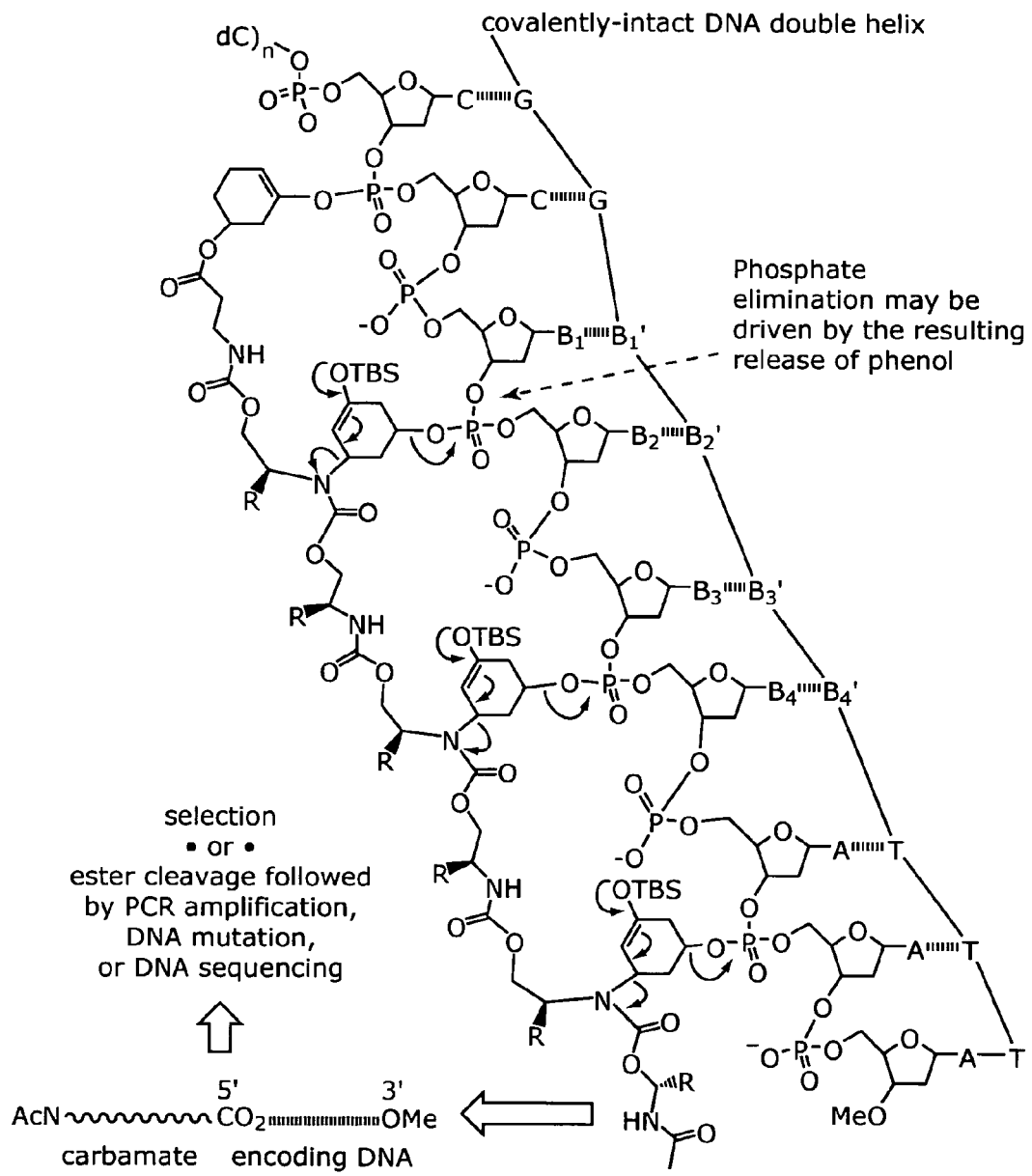
FIG. 54 is a schematic representation showing cleavage of a polycarbamate polymer from a nucleotide backbone.

Following polymerization, the polycarbamate can be cleaved from the phosphate backbone of the DNA upon treatment with fluoride. Desilylation of the enol ether linker and the elimination of the phosphate driven by the resulting release of phenol provides the polycarbamate covalently linked at its carboxy terminus to its encoding single-stranded DNA (FIG. 54).

At this stage, the polycarbamate may be completely liberated from the DNA by base hydrolysis of the ester linkage. The liberated polycarbamate can be purified by HPLC and retested to verify that its desired properties are intact. The free DNA can be amplified using PCR, mutated with error-prone PCR (Cadwell et al., (1992) PCR METHODS APPL. 2: 28) or DNA shuffling (Stemmer (1994) PROC. NATL. ACAD. SCI. USA 91: 10747; Stemmer (1994) NATURE 370: 389; U.S. Pat. No. 5,811,238), and/or sequenced to reveal the primary structure of the polycarbamate polymer.

Synthesis of Monomer Units

After the monomers are synthesized, the assembly and polymerization of the monomers on the DNA scaffold should occur spontaneously. Shikimic acid 1, available commercially, biosynthetically (Davis (1955) ADV. ENZYMOL. 16: 287), or by short syntheses from D-mannose (Fleet et al. (1984) J. CHEM. SOC. 905; Harvey et al. (1991) TETRAHEDRON LETT. 32: 4111), serves as a convenient starting point for the monomer synthesis. The syn hydroxyl groups are protected as the p-methoxybenzylidene, and remaining hydroxyl group as the tert-butyldimethylsilyl ether to afford 2. The carboxylate moiety of the protected shikimic acid then is completely reduced by lithium aluminum hydride (LAH) reduction, tosylation of the resulting alcohol, and further reduction with LAH to provide 3.

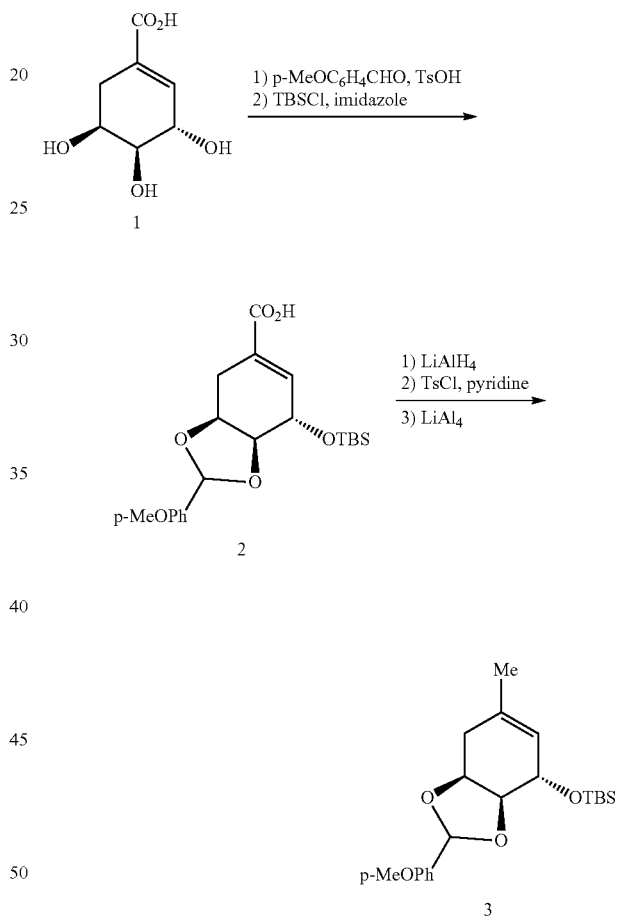

Commercially available and synthetically accessible N-protected amino acids can serve as the starting materials for the dicarbamate moiety of each monomer. Reactive side chains are protected as photolabile ethers, esters, acetals, carbamates, or thioethers. Using chemistry previously developed (Cho et al. (1993) SCIENCE 261: 1303), a desired amino acid 4 is converted to the corresponding amino alcohol 5 by mixed anhydride formation with isobutylchloroformate followed by reduction with sodium borohydride. The amino alcohol then is converted to the activated carbonate by treatment with p-nitrophenylchloroformate to afford 6, which then is coupled to a second amino alcohol 7 to provide, following hydroxyl group silylation and FMOC deprotection, carbamate 8.

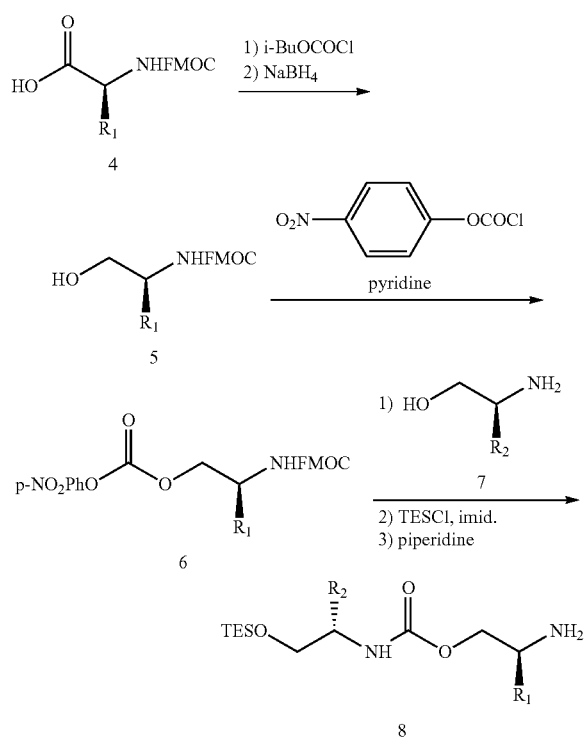

Coupling of carbamate 8 onto the shikimic acid-derived linker proceeds as follows. The allylic hydroxyl group of 3 is deprotected with tetra-butylammonium fluoride (TBAF), treated with triflic anhydride to form the secondary triflate, then displaced with aminocarbamate 8 to afford 9. Presence of the vinylic methyl group in 3 should assist in minimizing the amount of undesired product resulting from $S_N2'$ addition (Magid (1980) TETRAHEDRON 36: 1901). Michael additions of deprotonated carbamates to α,β-unsaturated esters have been well documented (Collado et al. (1994) TETRAHEDRON LETT. 35: 8037; Hirama et al. (1985) J. AM. CHEM. SOC. 107: 1797; Nagasaka et al. (1989) HETEROCYCLES 29: 155; Shishido et al. (1987) J. CHEM. SOC. 993; Hirama et al. (1989) HETEROCYCLES 28: 1229). By analogy, the secondary amine is protected as the o-nitrobenzyl carbamate (NBOC), and the resulting compound is deprotonated at the carbamate nitrogen. This deprotonation can typically be performed with either sodium hydride or potassium tert-butyloxide (Collado et al. (1994) supra; Hirama et al. (1985) supra; Nagasaka et al. (1989) supra; Shishido et al. (1987) supra; Hirama et al. (1989) supra), although other bases may be utilized to minimize deprotonation of the nitrobenzylic protons. Additions of the deprotonated carbamate to α,β-unsaturated ketone 10, followed by trapping of the resulting enolate with tert-butyldimethyl silyl chloride (TBSCl), should afford silyl enol ether 11. The previously found stereoselectivity of conjugate additions to 5-substituted enones such as 10 (House et al. (1968) J. ORG. CHEM. 33: 949; Still et al. (1981) TETRAHEDRON 37: 3981) suggests that 11 should be formed preferentially over its diastereomer. Ketone 10, the precursor to the fluoride-cleavable carbamate-phosphate linker, may be synthesized from 2 by one pot decarboxylation (Barton et al. (1985) TETRAHEDRON 41: 3901) followed by treatment with tetrabutylammonium fluoride (TBAF), Swern oxidation of the resulting alcohol to afford 12, deprotection with 2,3-dichloro-5,6-dicyano-1,4-benzoquinone (DDQ), selective nitrobenzyl ether formation of the less-hindered alcohol, and reduction of the α-hydroxyl group with samarium iodide (Molander (1994) ORGANIC REACTIONS 46: 211).

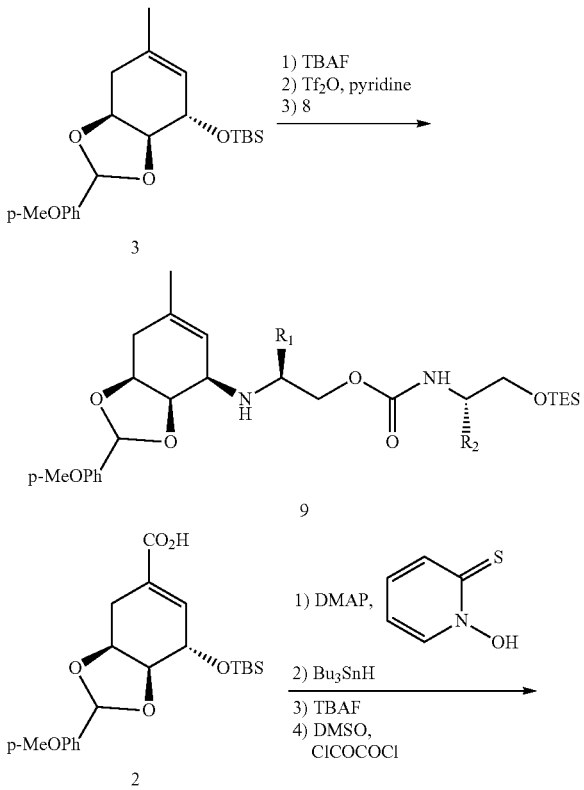

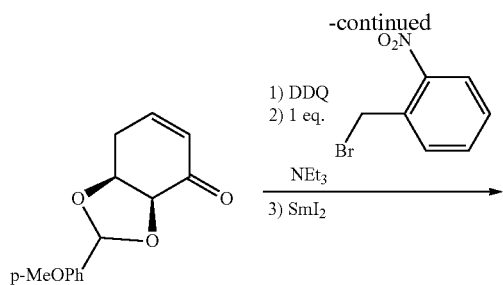
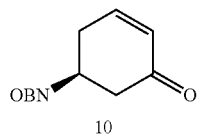
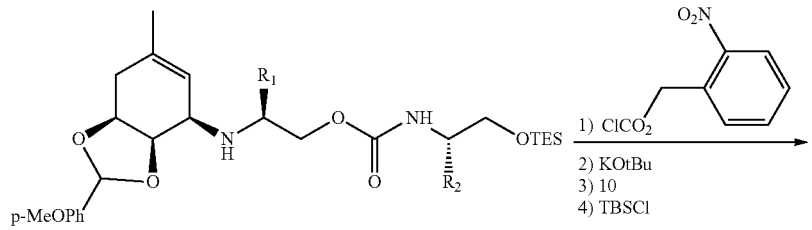
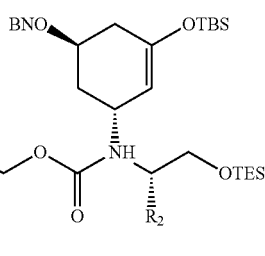

The p-methoxybenzylidiene group of 11 is transformed into the α-hydroxy p-methoxybenzyl (PMB) ether using sodium cyanoborohydride and trimethylsilyl chloride (TM-SCl) (Johansson et al. (1984) J. CHEM. SOC. 2371) and the TES group deprotected with 2% HF (conditions that should not affect the TBS ether (Boschelli et al. (1985) TETRAHEDRON LETT. 26: 5239)) to provide 13. The PMB group, following precedent (Johansson et al. (1984) J. CHEM. SOC. 2371; Sutherlin et al. (1993) TETRAHEDRON LETT. 34: 4897), should remain on the more hindered secondary alcohol. The two free hydroxyl groups may be macrocyclized by very slow addition of 13 to a solution of p-nitrophenyl chloroformate (or another phosgene analog), providing 14. The PMB ether is deprotected, and the resulting alcohol is converted into a triflate and eliminated under kinetic conditions with a sterically hindered base to afford vinyloxycarbonate 15. Photodeprotection of the nitrobenzyl either and nitrobenzyl carbamate yields alcohol 16.

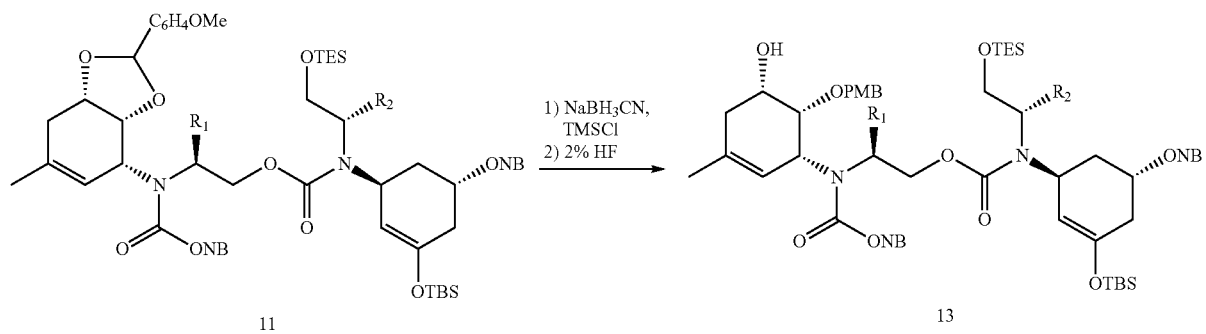
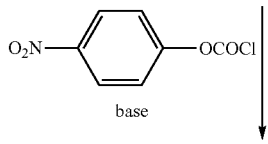

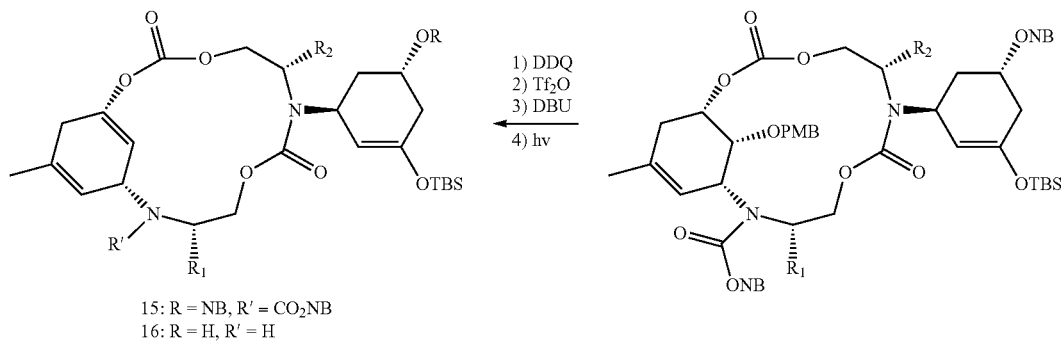

15: R = NB, R' = CO₂NB
16: R = H, R' = H

The monomer synthesis is completed by the sequential coupling of three components. Chlorodiisopropylaminophosphine 17 is synthesized by the reaction of PCl₃ with diisopropylamine (King et al., (1984) J. ORG. CHEM. 49: 1784). Resin-bound (or 3'-o-nitrobenzylether protected) nucleoside 18 is coupled to 17 to afford phosphoramidite 19. Subsequent coupling of 19 with the nucleoside 20 (Inoue et al. (1981) J. AM. CHEM. SOC. 103: 7666) provides 21. Alcohol 16 then is reacted with 21 to yield, after careful oxidation using m-chloroperbenzioc acid (MCPBA) or I₂ followed by cleavage from the resin (or photo-deprotection), the completed monomer 22. This strategy of sequential coupling of 17 with alcohols has been successfully used to generate phosphates bearing three different alkoxy substituents in excellent yields (Bannwarth et al. (1987) HELV. CHIM. ACTA 70: 175).

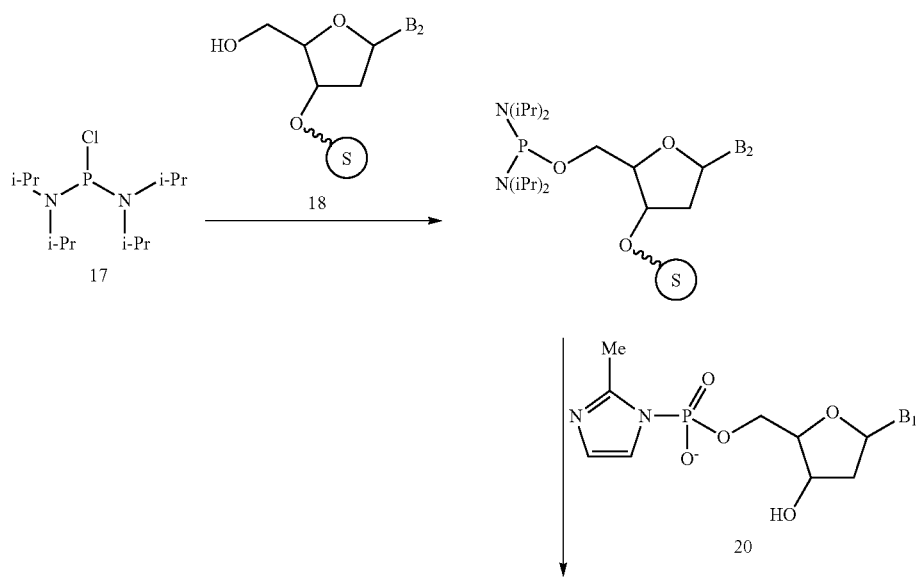

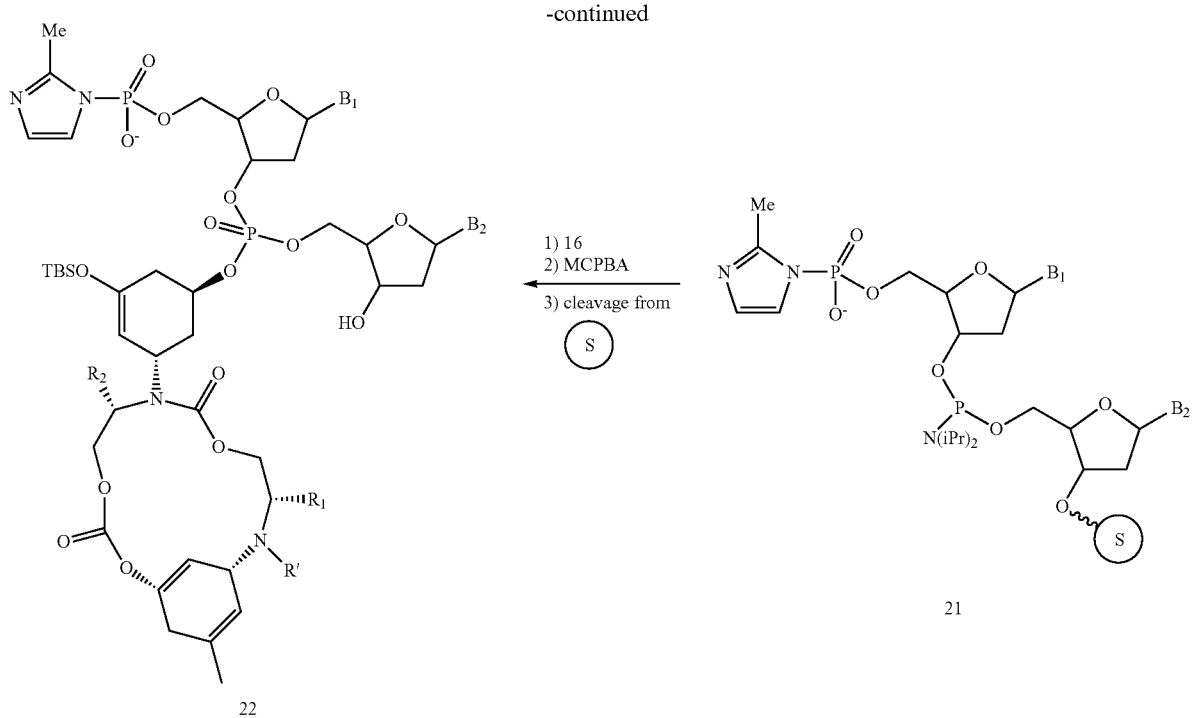

The unique start and stop monomers used to initiate and terminate carbamate polymerization may be synthesized by simple modification of the above scheme.

B) Macrocyclic Fumaramide Library

Figure 55:
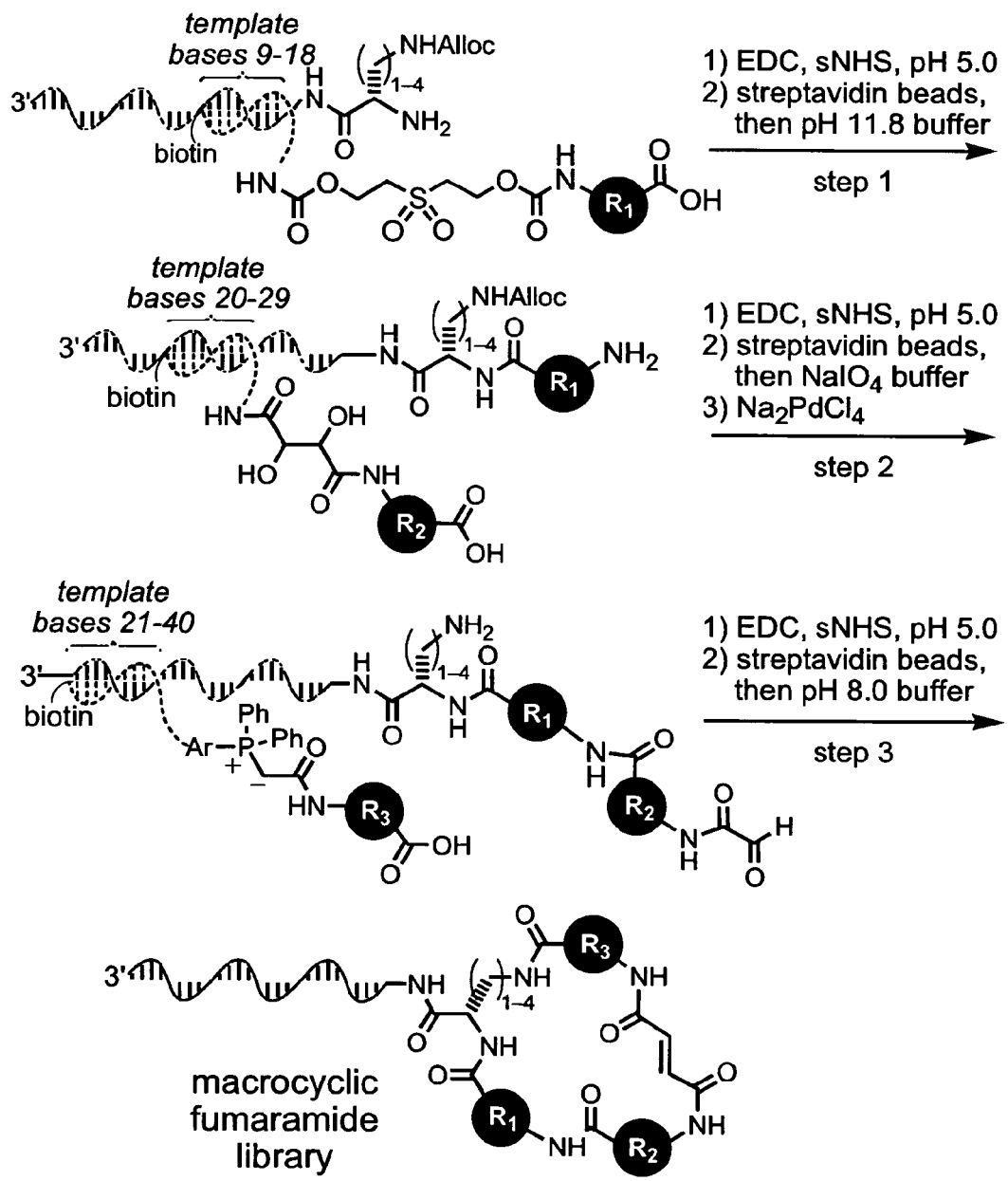
FIG. 55 is a schematic representation showing the synthesis of a DNA-templated macrocyclic fumaramide library.

This Example demonstrates that DNA templated-synthesis can be used to create a library of small molecules. In particular, it has been possible to create a DNA-templated macrocyclic fumaramide library as shown in FIG. 55.

Figure 56:
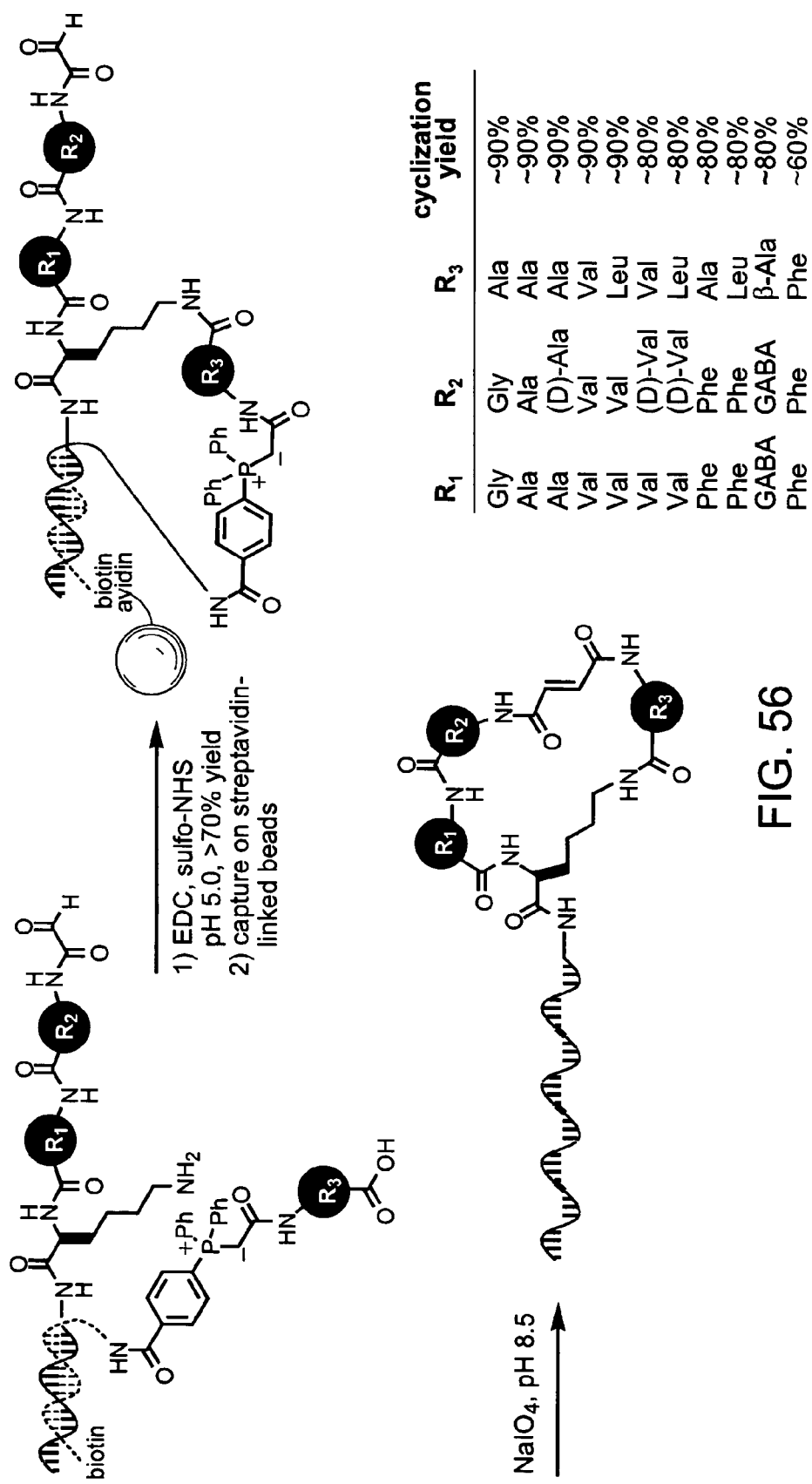
FIG. 56 is a schematic representation of the amine acylation and cyclization steps of various fumaramide library members of FIG. 55.

The library synthesis scheme employs robust DNA-templated amine acylation and intramolecular Wittig olefination reactions to generate diverse and partially rigid macrocyclic fumaramides. The fumaramide group is stable to neutral solutions but is sufficiently electrophilic to covalently capture nucleophiles when presented at elevated effective molarities. Nucleophilic side chains found in target protein active sites may, therefore, be covalently trapped by the fumaramide functionality. The key steps in the library synthesis are (i) DNA-templated amine acylation using the sulfone linker, (ii) DNA-templated amine acylation using the diol linker, (iii), DNA-templated amine acylation using a phosphorane linker, and (iv) intramolecular Wittig olefination to afford macrocyclic fumaramides linked to their corresponding DNA templates (FIG. 55).

macrocyclization is potentially the most challenging step of the library synthesis. To test this, seven model step 3 substrates were prepared to validate the third DNA-templated step and the subsequent macrocyclization (FIG. 56). Each substrate contained a variety of $R_1$ and $R_2$ groups of varying steric hindrances, stereochemistries, and backbone chain lengths. The model substrates were each mixed with one of four biotinylated DNA-linked reagents containing both a carboxylic acid and a phosphorane under DNA-templated amine acylation conditions. To evaluate both amide bond formation and Wittig macrocyclization, a two-stage purification strategy was implemented. The ten products of the DNA-templated amine acylation (FIG. 56 and step 3 in FIG. 55) were purified away from unreacted templates by capture with streptavidin-linked magnetic beads. The captured intermediates then were treated with pH 8.0 buffer to induce Wittig olefination-mediated macrocyclization. Macrocyclization created the fumaramide products (lacking the biotinylated reagent oligonucleotide) to self-elute from the magnetic beads. In every case, amine acylation and macrocyclization proceeded efficiently (FIG. 56) despite the wide range of steric, stereochemical, and backbone diversity in the intermediates. Control reactions at pH≦6 (too low to form the phosphorane), or at pH 8.0 but lacking the aldehyde group, failed to elute any product. In summary, the DNA-templated amine acylation-Wittig macrocyclization sequence is a highly efficient route to produce desired macrocyclic fumaramides.

Figure 57:
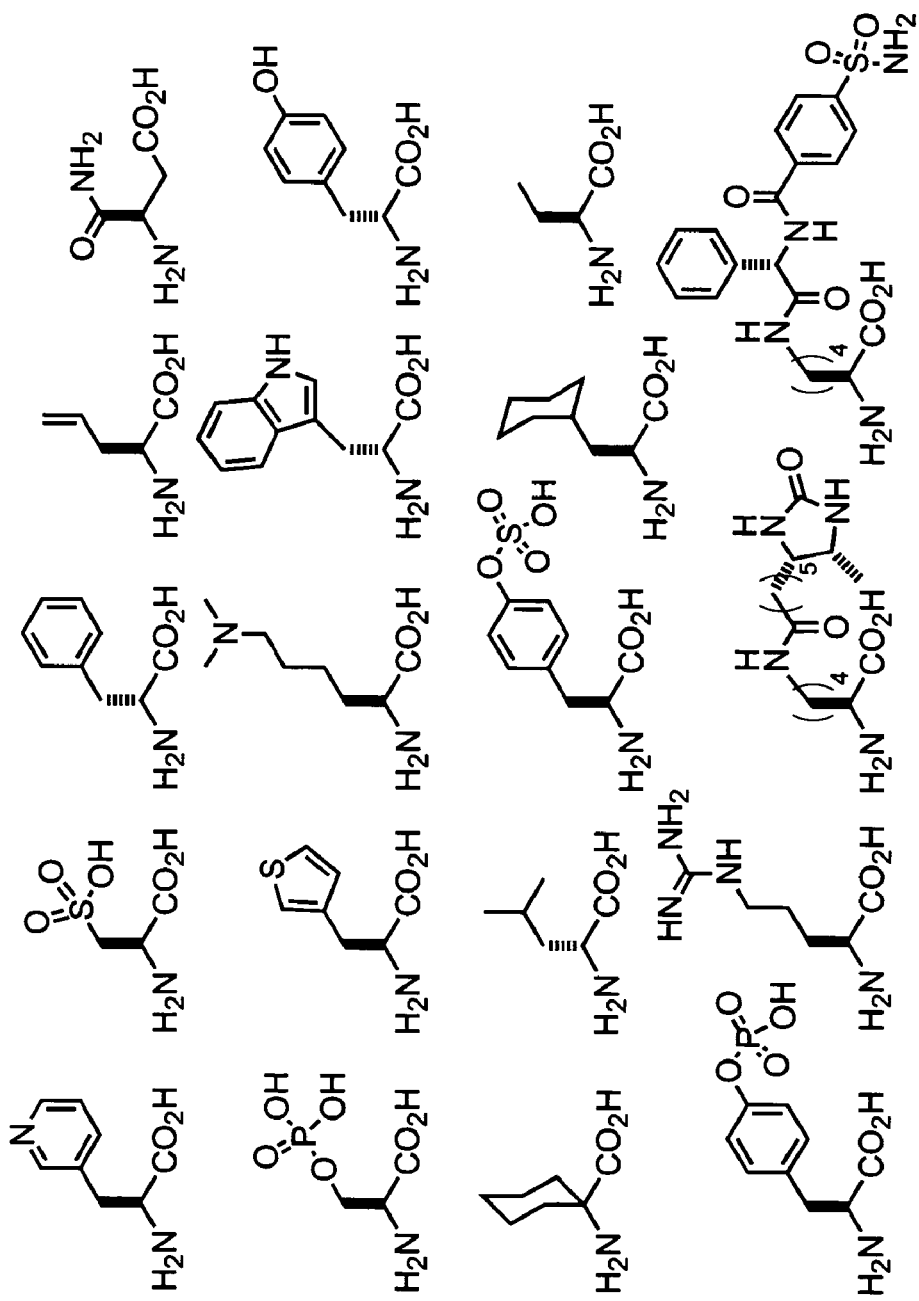
FIG. 57 shows exemplary amino acid building blocks for the synthesis of a DNA-templated macrocyclic fumaramide library.

After validating the macrocyclization step, a DNA-templated macrocyclic fumaramide library was synthesized. The pilot library was restricted to 83 macrocyclic fumaramides containing 4×4×5=80 macrocycles plus three macrocycles containing either an aryl sulfonamide, a desthiobiotin group, or both groups as positive controls for binding to carbonic anhydrase or avidin. Reagent oligonucleotides consisted of the six-base codons flanked by two constant bases on either side conjugated at their 3' ends to aminoacyl donors through the sulfone, diol, or phosphorane linker as previously reported. Multi-μg quantities of each of the 19 DNA-linked amine acylation reagents shown in FIG. 57 were created in a single day starting from commercially available free amino acids, linker precursors, and reagent oligonucleotides as described previously. The building blocks were chosen to sample structural and functional group diversity and include (L) and (D) α-amino acids, α,α'-disubstituted amino acids, and β-amino acids bearing alkyl, alkenyl, aryl, polar, heterocyclic, negatively charged, and positively charged side chains (FIG. 57). Each of the 19 reagents was successfully tested in single template reactions and generated product with <30% variance in efficiency. All 19 reagents reacted with high sequence-specificity, generating no significant product with mismatched templates even when five equivalents of reagent were used.

Figure 58:
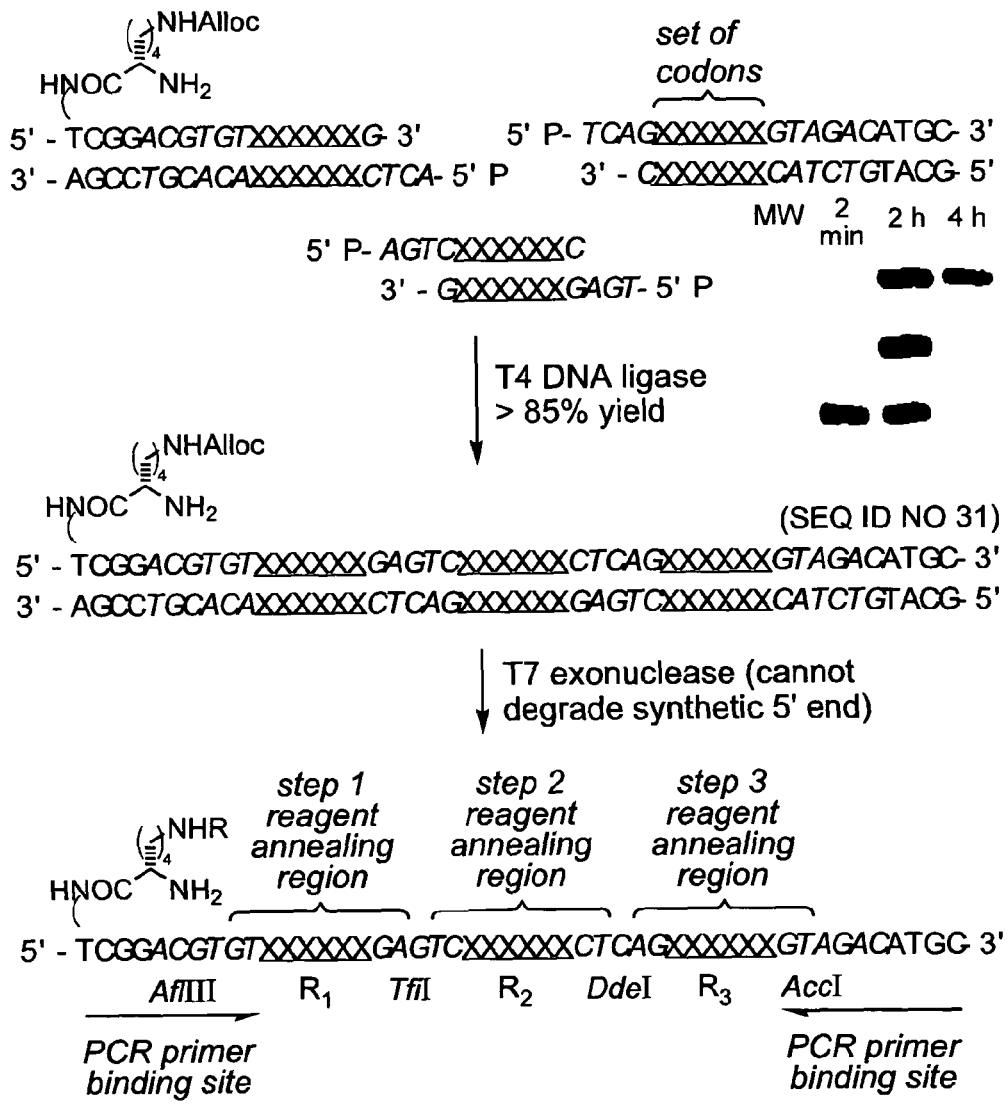
FIG. 58 is a schematic representation of a method of creating a template used in the synthesis of a DNA-templated macrocyclic fumaramide library.

The macrocyclic fumaramide-encoding template library was prepared from modular coding region cassettes in a single solution (FIG. 58). Oligonucleotides representing all reagent annealing regions were combined together with T4 DNA ligase in a single solution. Due to the sequence design of the oligonucleotide termini, the desired assembled template library is the only possible product when the ligation is complete. Excellent yields of the desired template library resulted from a 4 hour ligation reaction. Following ligation, T7 exonuclease was added to degrade the non-coding template strand (the desired coding strand is protected by its non-natural 5'-aminoethylene glycol linker). This procedure provided 20 nmol of the 5' functionalized single-stranded template library in 6 hours. The constant 10-base primer binding regions at the ends of each template were sufficient to permit PCR amplification of as few as 1,000 molecules ($10^{-21}$ mol) of template from this assembled material. Three positive control templates were added to produce a library containing 83 templates which were then combined with 3.0 equivalents of five step 1 reagents to produce the first library synthesis step. Products were purified as described above, then subjected to the second DNA-templated library synthesis step with five new reagents complementing the step 2 coding regions. The efficiency of both DNA-templated pilot library steps was judged to exceed 70% by denaturing gel electrophoresis and densitometry.

As a model for the deprotection prior to step 3, the Pd-mediated deprotection of DNA-linked Alloc carbamates was executed with excellent efficiency as judged by the liberation of ~1 equivalent of free amine groups. The products from each library synthesis step were analyzed by mass spectrometry. In the hope of eliminating the deprotection step, the necessity of protecting and deprotecting the side chain amine in the starting material was tested because the lower $pK_a$ of the α-amine may permit selective reaction of the α-amine at a pH that ensures protonation of the side chain amine. It was found that the α-amine group indeed could be selectively and efficiently acylated in a DNA-templated reaction in the presence of unprotected side-chain amine at pH 6.0. This may eliminate the need for a deprotection step following the second DNA-templated amide formation in step 2.

Figure 59:
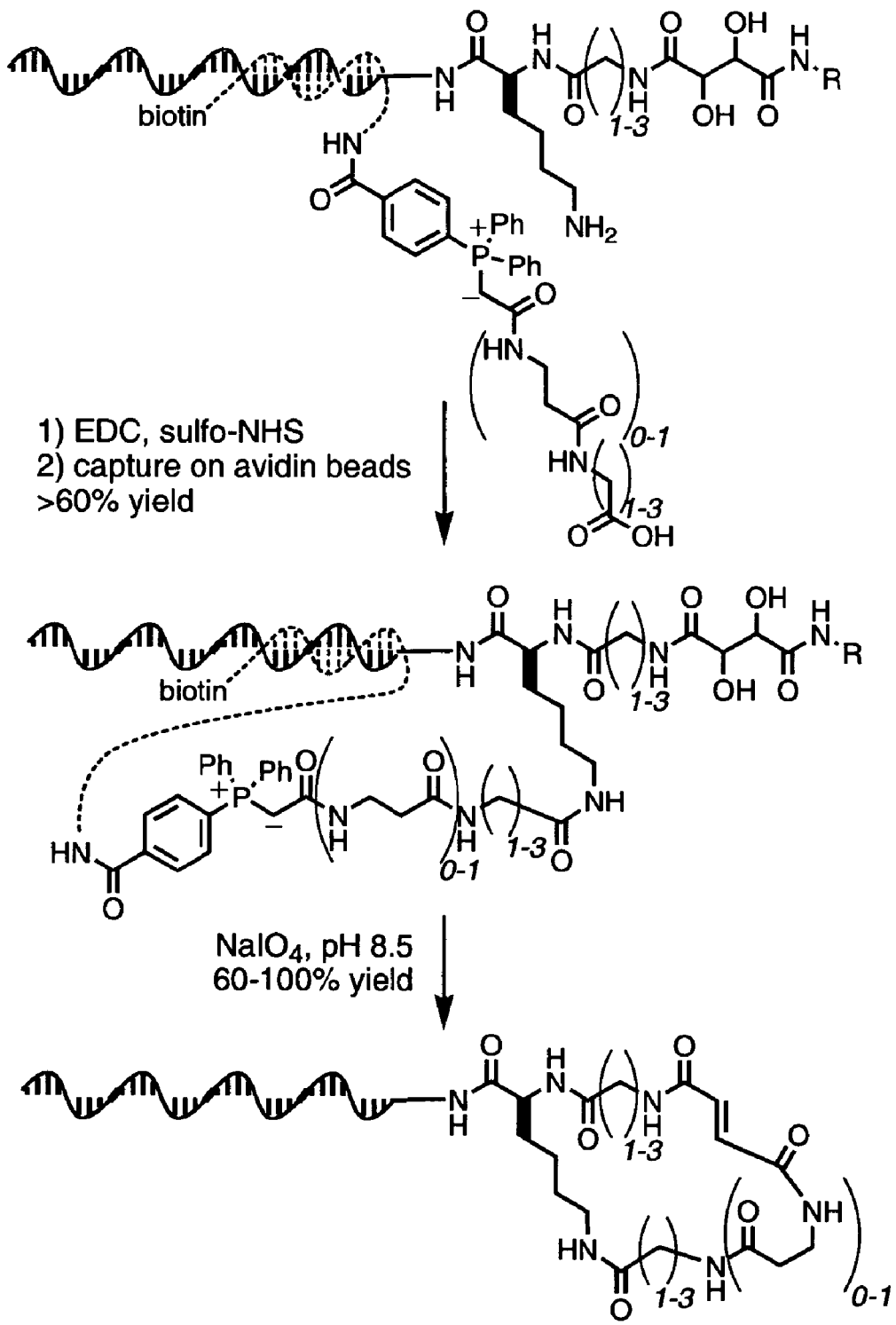
FIG. 59 is a schematic representation of an amine acylation and cyclization reaction useful in the synthesis of macrocyclic fumaramide library.

Several model substrates then were synthesized to validate the third DNA-templated step and the subsequent macrocyclization. Each model substrate consisted of a template-linked intermediate containing a free amine group and a diol linker separated by varying numbers of bonds to simulate groups of differing sizes during library synthesis. The model substrates were each mixed with one of several biotinylated DNA-linked reagents containing both a carboxylic acid and a phosphorane under DNA-templated amide formation conditions (pH 6.0, 20 mM EDC, 15 mM sulfo-NHS). DNA-templated amide formation proceeded in >60% yields and products were captured with avidin-linked magnetic beads. Bead-bound product was treated with 10 mM $NaIO_4$ at pH 8.5 to effect diol cleavage. The resulting aldehyde group reacted with the phosphorane in a spontaneous Wittig olefination reaction to furnish a cyclic fumaramide, free from the biotin group, that self-elutes from the avidin-linked beads (FIG. 59). Importantly, all of the model substrates under went macrocyclization in >60% yield, suggesting that this reaction is tolerant of a variety of substrate geometries. Control reactions confirmed that fumaramide formation was dependent on (i) periodate cleavage, (ii) the presence of the phosphorane group, and (iii) successful DNA-templated amide formation (required for capture onto avidin-linked beads).

C) PNA Polymer Library Formation

Despite significant successes, the generality and sequence-specificity of template-directed polymerization is still largely unexplored. For example, the efficient and sequence-specific templated polymerization of easily functionalized synthetic monomers lacking a ribose backbone has not been reported. Such a system would raise the possibility of evolving polymers comprised of these synthetic monomers through iterated cycles of translation (polymerization), selection, and amplification presently available only to DNA, RNA, and proteins.

The minimal requirements of a system for synthetic polymer evolution are: (i) distance-dependent nucleic acid-templated monomer coupling reactions to ensure that oligomerization proceeds exclusively between adjacently annealed monomers; (ii) efficient nucleic acid-templated oligomerization to provide sufficient yields of full-length products for in vitro selections; (iii) stable linkage of each synthetic polymer to its encoding template to ensure the survival of the appropriate template during polymer selection; and (iv) a readily functionalized synthetic monomer backbone to introduce tailor made functionality into the polymer.

In order to test the feasibility of producing polymers by DNA templated synthesis, DNA-templated amine acylation, Wittig olefination, reductive amination, and olefin metathesis reactions were tested for their ability to translate DNA sequences into functionalized peptide nucleic acid (PNA) polymers. The proposed PNA monomers are stable and can be easily synthesized from commercially available α-amino acids containing a wide variety of functional groups (Haaima et al. (1996) ANGEW. CHEM. INT. ED. ENGL. 35: 1939-1942; Puschl et al. (1998) TETRAHEDRON LETT. 39: 4707). PNAs containing functionalized side chains are known to retain their ability to hybridize to DNA sequence-specifically (Haaima et al. (1996) supra; Puschl et al. (1998) supra).

In the first strategy, PNA serves as the backbone of the functional polymer and displays the functional groups of each monomer. In another strategy, the DNA-templated PNA polymerizations organize reactive functional groups, enabling a second polymerization reaction between these functional groups (for example, an olefin metathesis or Wittig olefination reaction) to form the synthetic polymer backbone of interest.

Figure 60:
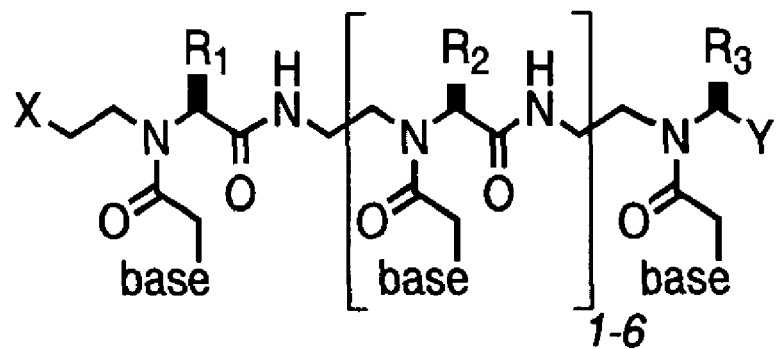
FIG. 60 depicts representative monomer structures that can be incorporated into a PNA polymer.
Figure 60:
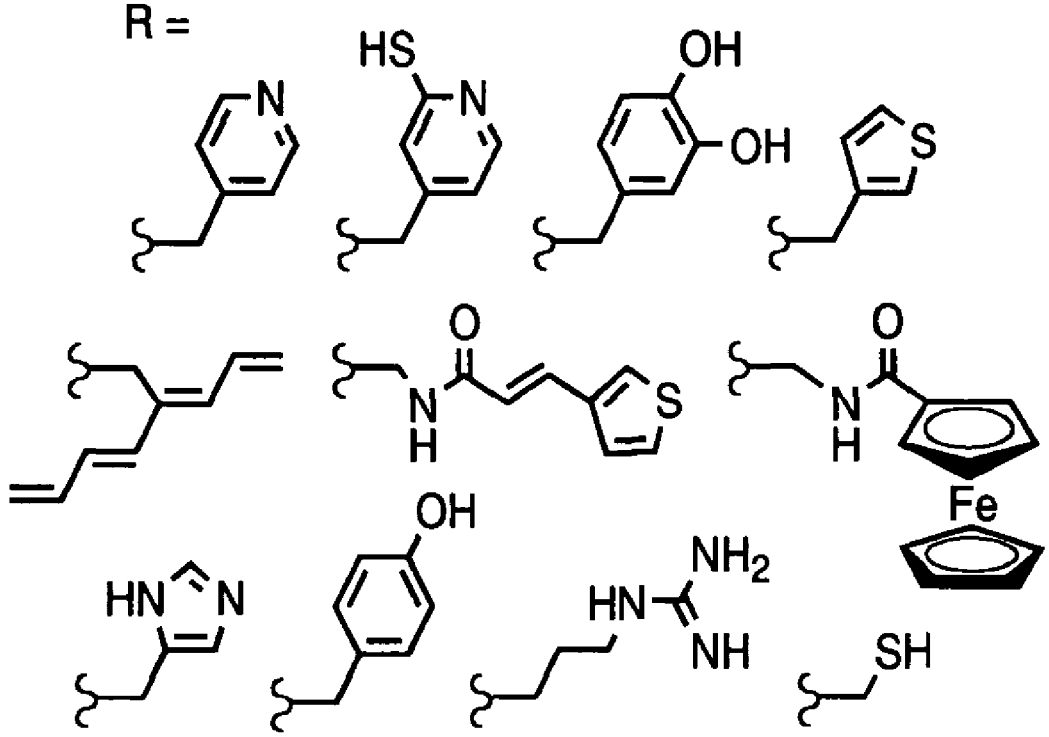

In both strategies templates consist of 5'-functionalized, single stranded DNA libraries 50-200 bases long that contain a central region of variable bases. These templates are made by standard solid-phase oligonucleotide synthesis combined with enzyme-catalyzed ligation for longer templates. Monomer structures are chosen to provide chemical functionalities including (i) Brønsted acidic and basic groups, (ii) nucleophilic and electrophilic groups, (iii) conjugated olefins suitable for post-PNA polymerization metathesis, and (iv) metal-binding groups capable of forming complexes with chemically potent transition metals. Representative monomer structures containing these functionalities are shown in FIG. 60. The DNA bases encoding each monomer (the "genetic code" of these polymers) are chosen from the examples shown in Table 10 to preclude the possibility of out-of-frame annealing. These genetic codes should prevent undesired frameshifted DNA-templated polymer translation.

Figure 61:
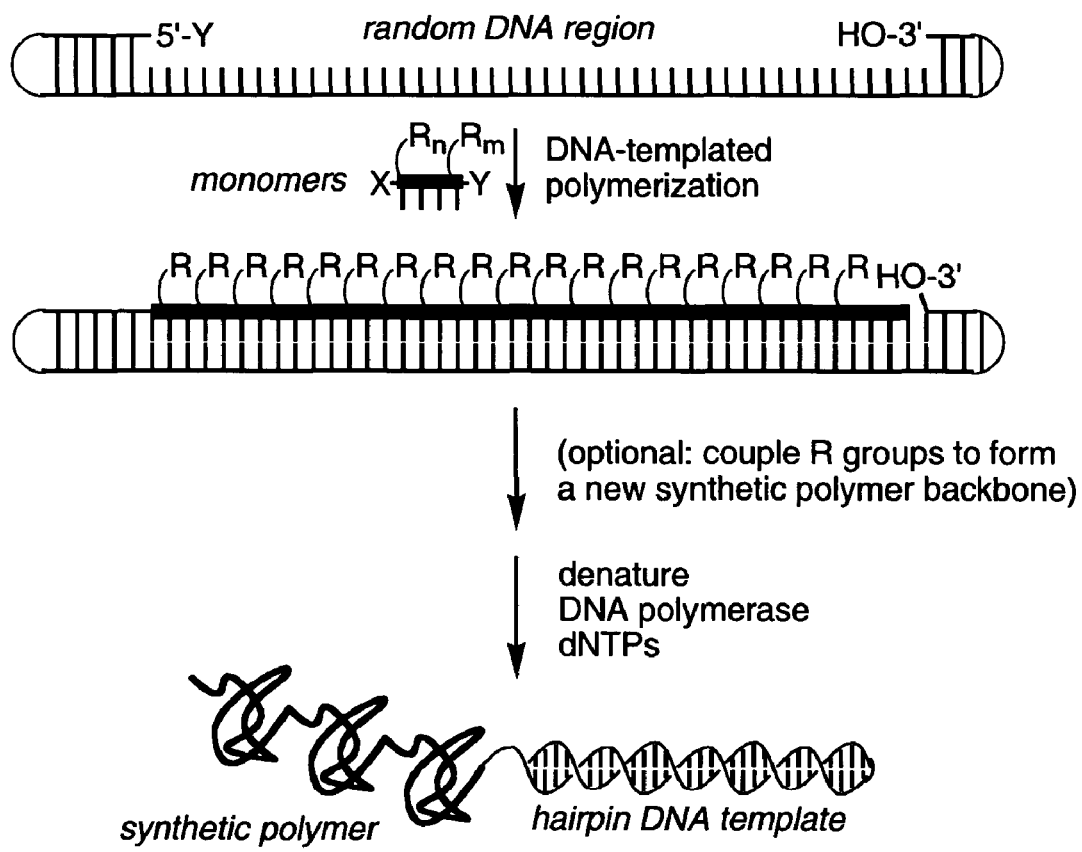
FIG. 61 is a schematic representation of a method for making functional polymers. As shown the polymer is still associated with the template.

Libraries of 5'-functionalized hairpin DNA templates containing up to $10^{15}$ different sequences are combined with sets of monomers under conditions that optimize the efficiency and sequence fidelity of each DNA-templated polymerization. Synthetic polymer strands then are de-annealed from their DNA templates by denaturation, and the 3' DNA hairpin primer extended using DNA polymerase to generate hairpin DNA templates linked to now liberated single-stranded synthetic polymers (FIG. 61). Libraries are characterized by gel electrophoresis and MALDI mass spectrometry, and individual representative library members are also characterized from single template reactions to confirm expected reaction efficiencies.

Once the libraries of DNA-linked PNAs are characterized, they can be subjected to three types of in vitro selections for: (i) folding, (ii) target binding, or (iii) catalysis. Prior to selection, polymers with anticipated metal binding ability are incubated with one or more water-compatible metal sources. Selections for folding are performed using the gel electrophoresis selection described in Example 10. Polymers capable of folding in the presence, but not in the absence, of metals serve as especially attractive starting points for the next two types of selections.

Selections for target binding can be conducted by incubating the solution-phase polymer library with either immobilized target or with biotinylated target followed by streptavidin-linked beads. Non-binders are removed by washing, and polymers with desired binding properties are eluted by chemical denaturation or by adding excess authentic free ligand. To complete one cycle of functionalized PNA evolution, the DNA templates corresponding to the desired PNA library members are amplified by PCR using one primer containing the 5'-functionalized hairpin primer and a biotinylated second primer, optionally diversified by error-prone PCR (Caldwell et al. (1992) PCR METHODS APPLIC. 2: 28-33), and then denatured into single stranded DNA and washed with streptavidin beads to remove the non-coding template strand. The resulting pool of selected single-stranded, 5'-functionalized DNA completes the evolution cycle and enters subsequent rounds of DNA-templated translation, selection, diversification, and amplification.

Selection for synthetic polymers that catalyze bond-forming or bond-cleaving reactions can also be performed. To select for bond-forming catalysts (for example, hetero Diels-Alder, Heck coupling, aldol reaction, or olefin metathesis catalysts), functionalized PNA library members are covalently linked to one substrate through their 5' hairpin termini. The other substrate of the reaction is synthesized as a derivative linked to biotin. When dilute solutions of library-substrate conjugate are reacted with the substrate-biotin conjugate, those library members that catalyze bond formation induce self-biotinylation. Active bond forming catalysts then are separated from inactive library members by capturing the former with immobilized streptavidin. In an analogous manner, functionalized PNAs that catalyze bond cleavage reactions such as retro-aldol reactions, amide hydrolysis, elimination reactions, or olefin dihydroxylation followed by sodium periodate cleavage can also be selected. In this case, library members are linked to biotinylated substrates such that the bond breakage reaction causes the disconnection of the biotin moiety from the library members. Active catalysts self-elute from streptavidin-linked beads while inactive catalysts remain bound.

Validation of PNA Polymer Library Formation

Peptide nucleic acids (PNAs) are attractive candidates for synthetic polymer evolution because of their known ability to bind DNA sequence-specifically, and their simple preparation from synthetically accessible amino acids. Previous efforts to oligomerize PNAs on DNA or RNA templates have used amine acylation as the coupling reaction and proceeded with modest efficiency and sequence specificity (Bohler et al. (1995) NATURE 376: 578-581; Schmidt et al. (1997) NUC. ACIDS RES. 25: 4792-4796).

When five PNA tetramers were combined using a variety of aqueous amine acylation conditions in the presence of DNA templates containing complementary 20-base annealing regions, only modest formation (<20% yield) of full-length PNAs, representing five successive coupling reactions, were observed. Even more problematic, however, was the formation of higher molecular weight products independent of the position of a mismatched 4-base annealing region in the template. These observations indicate that PNAs are able to couple using amine acylation chemistry even when not adjacently annealed, leading to an unpredictable mixture of products.

It was contemplated that the distance independence previously observed in DNA-templated amine acylation reactions was the origin of the poor regiospecificity of amine acylation-mediated PNA couplings. This Example shows that it is possible to overcome this problem by replacing the distance independent amine acylation reaction with a distance dependent DNA-templated reaction, such as a reductive amination reaction.

Figure 62:
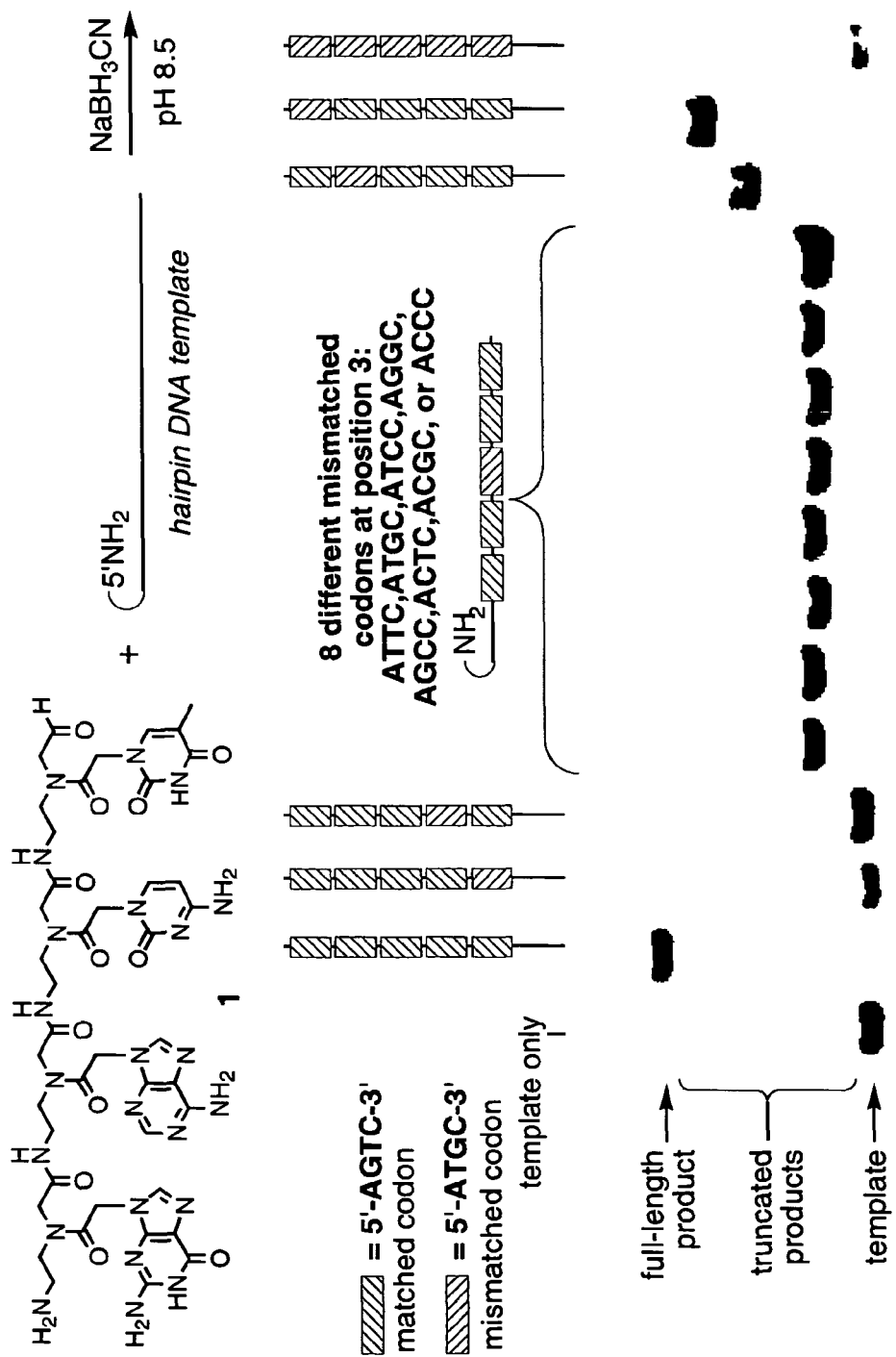
FIG. 62 depicts a DNA-templated aldehyde polymerization reaction.

In order to test this, a thymine-containing PNA monomer amino aldehyde was synthesized and coupled to threonine-linked resin following the method of Ede and Bray (Ede et al. (1997) TETRAHEDRON LETTERS 38, 7119-7122). Standard FMOC peptide synthesis was used to extend the peptide by three PNA monomers (final sequence: $NH_2$-gact-CHO), and aqueous acidic cleavage from the resin yielded the desired tetrameric peptide aldehyde 1 (FIG. 62).

A DNA template containing a 5'-amine-terminated hairpin and five successive repeats of the "codon" complementary to 1 (5'-AGTC-3') was combined with 8 µM 1 in aqueous pH 8.5 buffer. The reactants were annealed (95° C. to 25° C.) and $NaCNBH_3$ was added to 80 mM. The reactions were quenched by buffer exchange with a Sephadex column, and subjected to denaturation (95° C. for 10 minutes in 50% formamide) and 15% denaturing PAGE. In FIG. 62, lanes 1 and 2 show that the starting template was almost entirely consumed, and the higher molecular weight product was formed in >90% yield. Gel purification of the product following removal of the DNA template with DNase I and MALDI-TOF mass spectrometry confirmed full-length pentamer of the gact PNA aldehyde. This result indicates that DNA-templated reductive amination can mediate the highly efficient oligomerization of PNA aldehydes.

In order to examine the regio- and sequence-specificity of this reaction, the oligomerization reactions were repeated using a variety of template sequences. When a mismatched DNA template codon (5'-ATGC-3') was introduced at the second, third, fourth, or fifth 4-base coding region (i.e., the codon) of the template, highly efficient formation of products corresponding to the coupling of exactly one, two, three, or four copies of 1, respectively, was observed (see, FIG. 62, lanes 4-14). When the mismatched codon was placed at only the first coding position, or at all five coding positions, no product formation was observed (see, FIG. 62, lanes 3 and 15). The termination of oligomerization at the first mismatched codon in every case indicates that the DNA-templated PNA aldehyde coupling requires functional group adjacency (i.e., is highly distance dependent), and, therefore, is ideally suited for templated polymerization.

The sequence specificity of this system was probed by performing oligomerization experiments using DNA templates containing eight different mismatched codons (ATTC, ATGC, ATCC, AGGC, AGCC, ACTC, ACGC, or ACCC) in the third coding region. Even though four of these codons differ from the matched sequence (ATGC) in only one base, in each case only two copies of 1 were coupled to the template (see FIG. 62, lanes 5-12). This high degree of sequence specificity raises the possibility that libraries of different DNA sequences may be faithfully translated into libraries of corresponding polymers using this system, analogous to DNA-templated small molecule synthesis.

Figure 63:
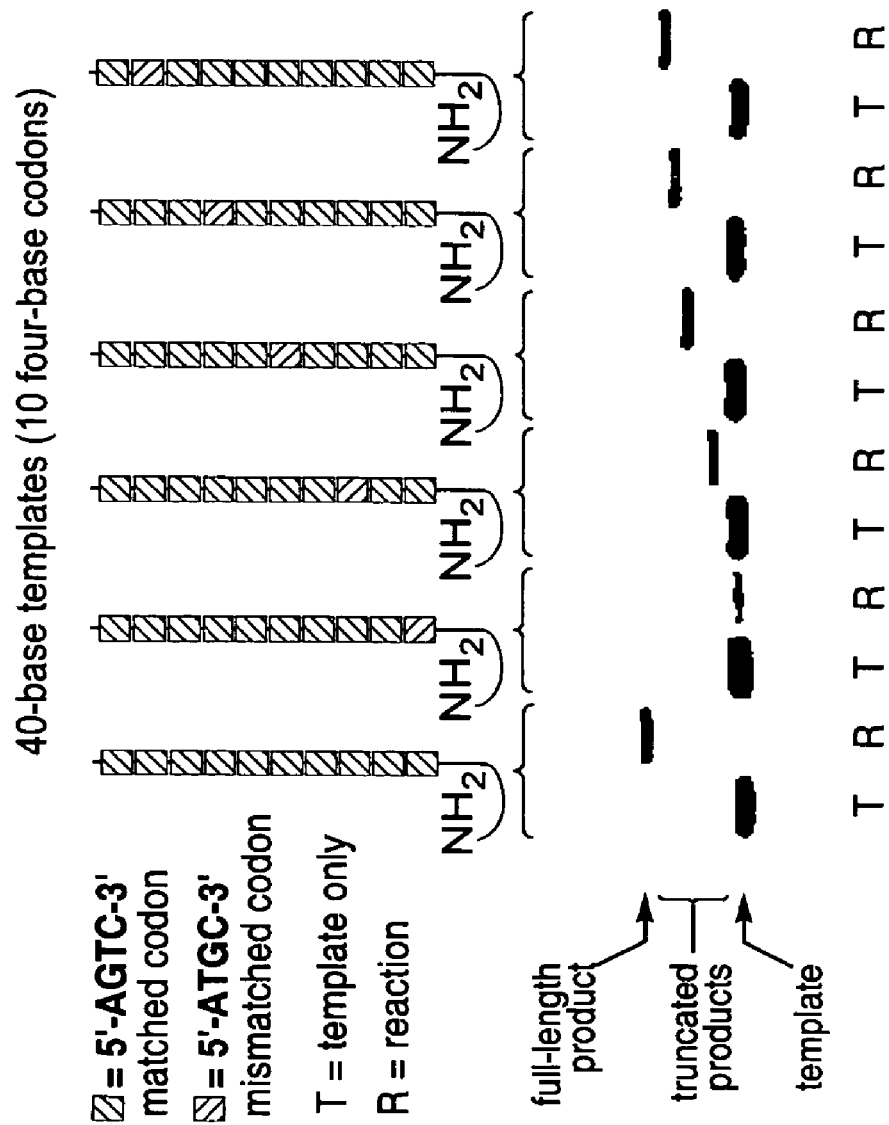
FIG. 63 depicts PNA polymerization reactions using a 40 base template with mismatched codons located at certain positions of the template.

It is contemplated that synthetic polymers with desired properties (e.g., binding or catalytic properties) may require lengths beyond those previously achieved efficiently using nucleic acid-templated synthesis. In order to test the ability of the above system to generate longer polymers in an efficient and sequence-specific manner, DNA templates were translated with 40-base coding regions encoding ten repeats of the above matched or mismatched codon into corresponding PNA aldehyde polymers. Polymerizations were carried out as in FIG. 62, except that the PNA peptide aldehyde concentration was 16 µM and the reaction time with NaCNBH$_3$ was 15 minutes. The results of these experiments are shown in FIG. 63, where the lanes alternate between template (with mismatch at indicated position) and reactions (template plus the gact monomer). As FIG. 63 illustrates, both denaturing PAGE and MALDI-TOF mass spectrometry revealed a single predominant product corresponding to the polymerization of a full length 40-mer PNA after 15 minutes. Introducing a mismatched codon in the first, third, fifth, seventh, or ninth coding positions on the template again resulted in truncation (FIG. 63, lanes 4, 6, 8, 10, and 12, respectively). This efficient translation of DNA sequences into 40 PNA bases (10 couplings) provides a polymer of length similar to DNA and RNA oligonucleotides with binding or catalytic properties, but made entirely of synthetic building blocks.

Figure 64:
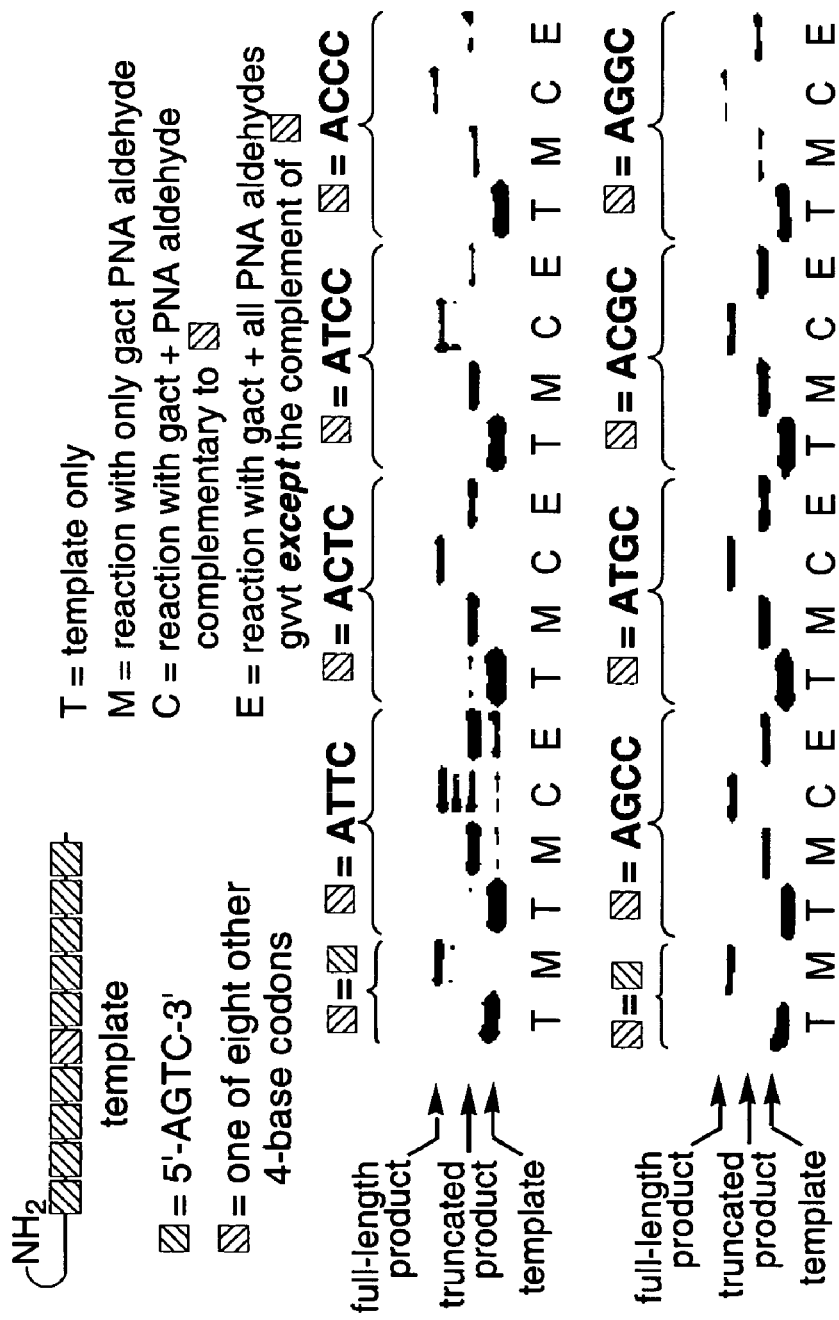
FIG. 64 shows the specificity of DNA-templated polymerization reactions.

A challenging requirement of creating libraries of sequence-defined synthetic polymers in this manner is maintaining sequence specificity in the presence of multiple monomers of closely related sequence. In order to study the specificity of DNA-templated polymerization using multiple PNA building blocks in a single solution, nine PNA aldehyde tetramers of the sequence NH$_2$-gvvt-CHO (v=g, a, or c) were synthesized. In addition, nine DNA templates containing one of nine codons complementary to gvvt at codon 5, and containing AGTC at the other nine positions were prepared. Reaction conditions were identical to those from FIG. 63, except that the reaction time with NaCNBH$_3$ was further shortened to 5 minutes and incubation was carried out at 37° C. The first two lanes of each panel in FIG. 64 show a positive control polymerization. Each additional set of four lanes corresponds to: (i) 20 pmol template, (ii) reaction with 14.4 µM gact, (iii) reaction with 14.4 µM gact plus 1.6 µM PNA aldehyde complementary to the highlighted codon, and (iv) reaction with 14.4 µM gact plus 0.2 µM of each PNA aldehyde of the sequence gvvt except the PNA complementary to the highlighted codon. As expected, each of the nine templates was translated into a single predominant truncated product corresponding to the incorporation of four copies of 1 when 1 was the only PNA building block included in the reaction (37° C., 5 min) (see, FIG. 64). Full-length product was efficiently generated for all nine templates, however, when the PNA aldehyde complementary to the fifth coding sequence was included in addition to 1. When all PNA aldehyde tetramers were included in the reaction except the PNA complementary to the fifth coding region, only the truncated product was efficiently generated (see, FIG. 64).

Taken together, these experiments reveal that DNA-templated PNA aldehyde polymerizations maintain sequence specificity even when a mixture of different PNA building blocks are present in a single solution.

D) Evolving Plastics

Figure 65A:
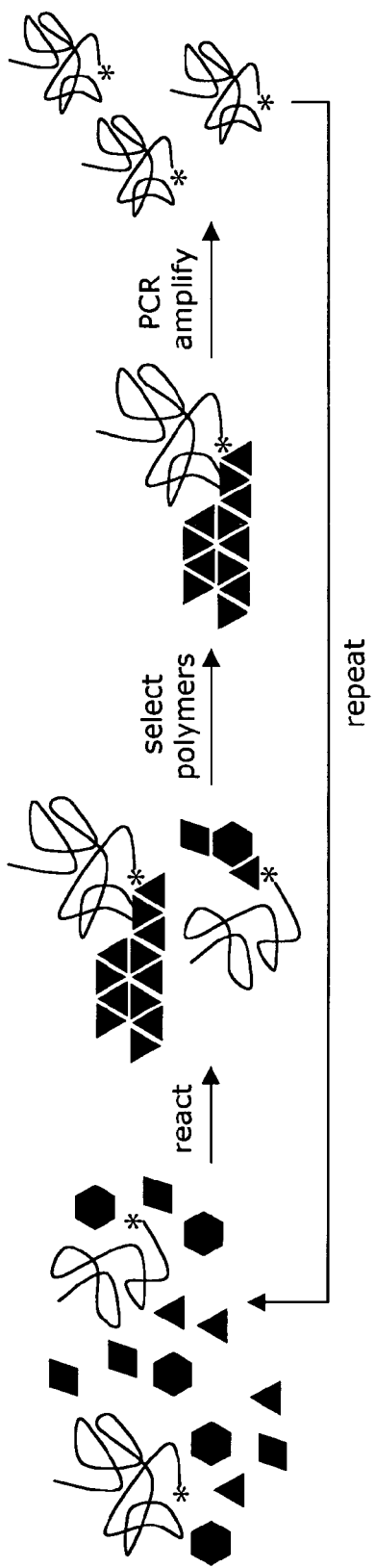
FIG. 65A is a schematic representation showing a method of using a nucleic acid to direct the synthesis of new polymers and plastics.

In yet another embodiment, a nucleic acid (e.g., DNA, RNA, derivative thereof) is attached to a polymerization catalyst. Since nucleic acids can fold into complex structures, the nucleic acid can be used to direct and/or affect the polymerization of a growing polymer chain. For example, the nucleic acid may influence the selection of monomer units to be polymerized as well as how the polymerization reaction takes place (e.g., stereochemistry, tacticity, activity). The synthesized polymers may be selected for specific properties such molecular, weight, density, hydrophobicity, tacticity, stereoselectivity, etc., and the nucleic acid which formed an integral part of the catalyst which directed its synthesis may be amplified and evolved (FIG. 65A). Iterated cycles of ligand diversification, selection, and amplification allow for the true evolution of catalysts and polymers towards desired properties.

Figure 65B:
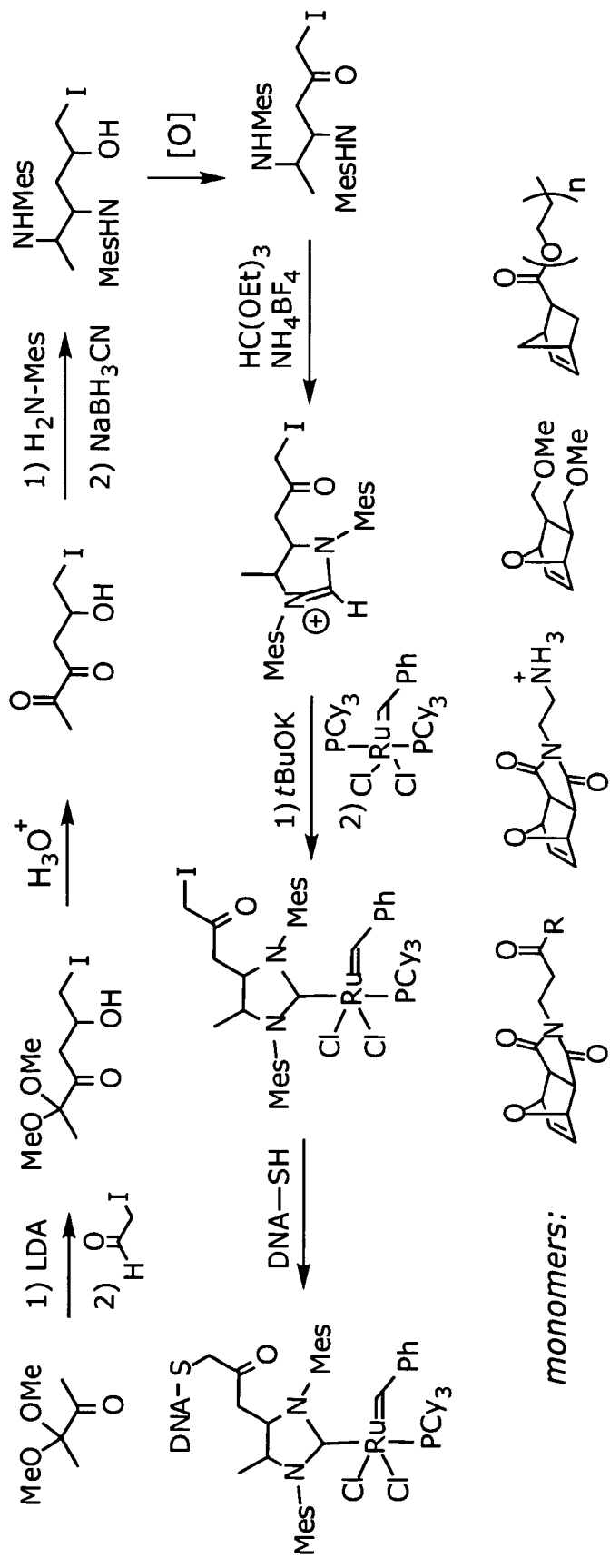
FIG. 65B is a schematic representation showing the use of Grubbs' ring-opening metathesis polymerization catalysis to evolve plastics.
Figure 66:
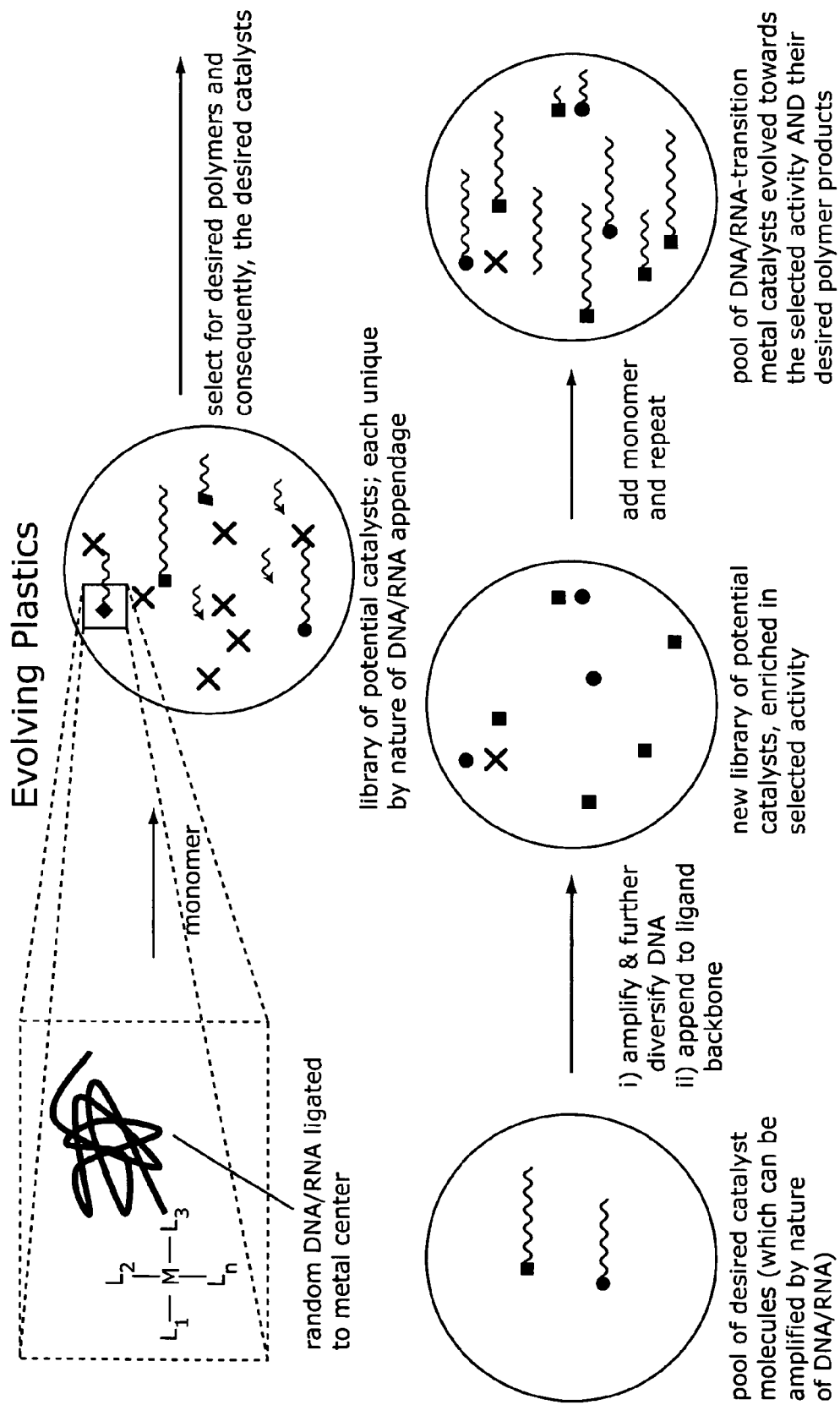
FIG. 66 is a schematic representation showing the evolution of plastics through iterative cycles of ligand diversification, selection, and amplification to create polymers with desired properties.

By way of example, a library of DNA molecules is attached to Grubbs' ruthenium-based ring opening metathesis polymerization (ROMP) catalyst through a dihydroimidazole ligand (Scholl et al. (1999) ORG. LETT. 1(6): 953) creating a large, diverse pool of potential catalytic molecules, each unique by nature of the functionalized ligand (see, FIG. 65B). Functionalizing the catalyst with a relatively large DNA-dehydroimidazole (DNA-DHI) ligand can alter the activity of the catalyst. Each DNA molecule has the potential to fold into a unique stereoelectronic shape which potentially has different selectivities and/or activities in the polymerization reaction (FIG. 66). Therefore, the library of DNA ligands can be "translated" into a library of plastics upon the addition of various monomers. In certain embodiments, DNA-DHI ligands capable of covalently inserting themselves into the growing polymer, thus creating a polymer tagged with the DNA that encoded its creation, are used. Using the synthetic scheme shown in FIG. 65A, dehydroimidazole (DHI) ligands are produced containing two chemical handles, one used to attach the DNA to the ligand, the other used to attach a pedant olefin to the DHI backbone. Rates of metathesis are known to vary widely based upon olefin substitution as well as the identity of the catalyst. Through alteration of these variable, the rate of pendant olefin incorporation can be modulated such that $k_{pendant\ olefin\ metathesis} \ll k_{ROMP}$, thereby, allowing polymers of moderate to high molecular weights to be formed before insertion of the DNA tag and corresponding polymer termination. Vinylic ethers are commonly used in ROMP to functionalize the polymer termini (Gordon et al., (2000) CHEM. BIOL. 7: 9-16), as well as produce polymers of decreased molecular weight.

A polymer from the library is subsequently selected based on a desired property by electrophoresis, gel filtration, centrifugal sedimentation, partitioning into solvents of different hydrophobicities, etc. Amplification and diversification of the coding nucleic acid via techniques such as error-prone PCR or DNA shuffling followed by attachment to a DHI backbone will allow for production of another pool of potential ROMP catalysts enriched in the selected activity (FIG. 66). This method provides a new approach to generating polymeric materials and the catalysts that create them.

Example 10

Development of Catalysts by Templated Synthesis

An alternative approach to translating DNA into non-natural, evolvable polymers takes advantage of the ability of some DNA polymerases to accept certain modified nucleotide triphosphate substrates (Perrin et al. (2001) J. AM. CHEM. SOC. 123: 1556; Perrin et al. (1999) NUCLEOSIDES NUCLEOTIDES 18: 377-91; Gourlain et al. (2001) NUCLEIC ACIDS RES. 29: 1898-1905; Lee et al. (2001) NUCLEIC ACIDS RES. 29: 1565-73; Sakthievel et al. (1998) ANGEW. CHEM. INT. ED. 37: 2872-2875). Several deoxyribonucleotides and ribonucleotides bearing modifications to groups that do not participate in Watson-Crick hydrogen bonding are known to be inserted with high sequence fidelity opposite natural DNA templates. Importantly, single-stranded DNA containing modified nucleotides can serve as efficient templates for the DNA-polymerase-catalyzed incorporation of natural or modified mononucleotides.

Figure 67:
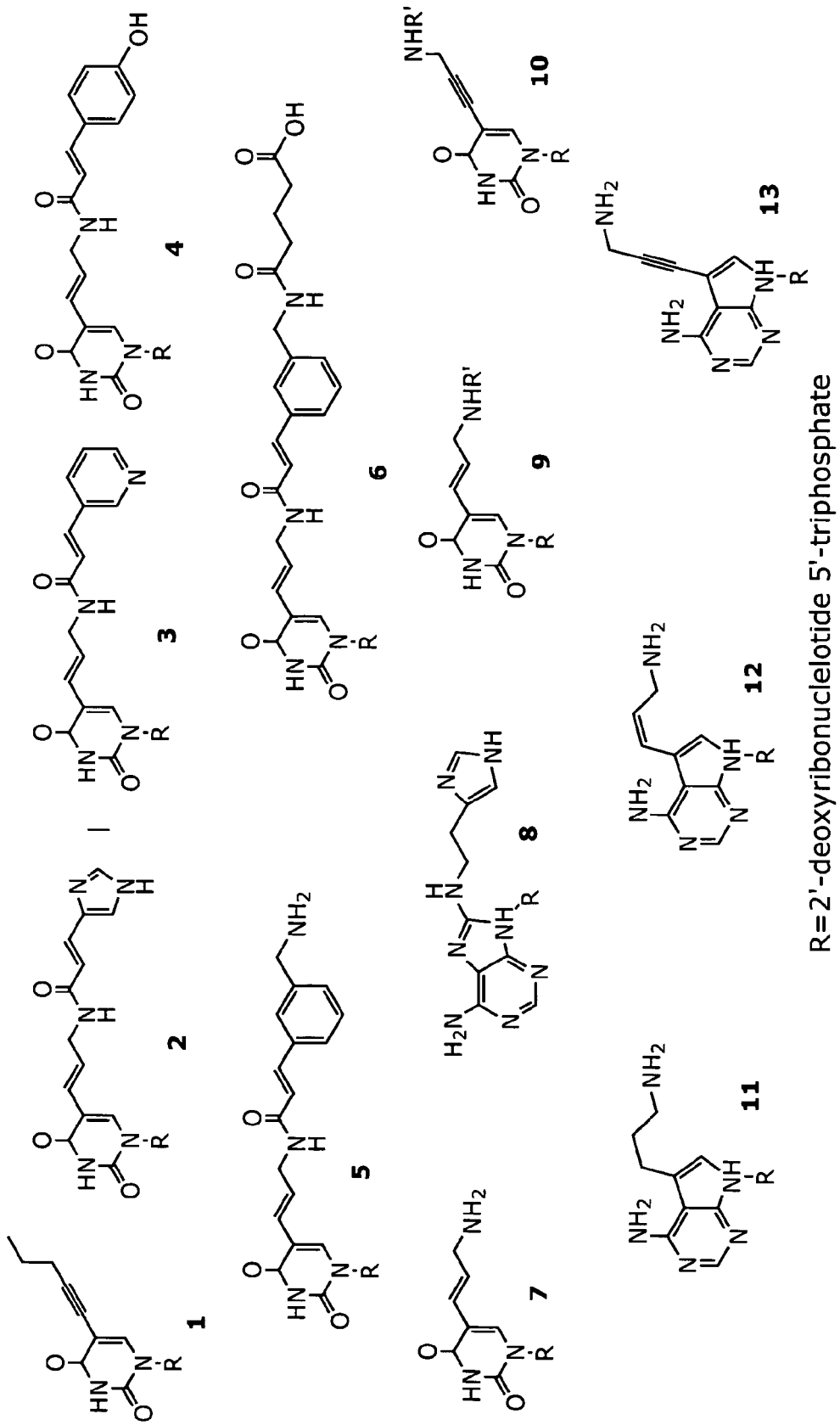
FIG. 67 depicts exemplary functionalized nucleotides that can be incorporated by DNA polymerase.

The functionalized nucleotides incorporated by DNA polymerases to date are shown in FIG. 67. In one of the earliest examples of modified nucleotide incorporation by DNA polymerase, Toole and co-workers reported the acceptance of 5-(1-pentynyl)-deoxyuridine 1 by Vent DNA polymerase under PCR conditions (Latham et al. (1994) NUCLEIC ACIDS RES. 22: 2817-22). Several additional 5-functionalized deoxyuridines (2-7) derivatives were subsequently found to be accepted by thermostable DNA polymerases suitable for PCR (Sakthievel et al. (1998) supra). The first functionalized purine accepted by DNA polymerase, deoxyadenosine analog 8, was incorporated into DNA by T7 DNA polymerase together with deoxyuridine analog 7 (Perrin et al. (1999) NUCLEOSIDES NUCLEOTIDES 18: 377-91). DNA libraries containing both 7 and 8 were successfully selected for metal-independent RNA cleaving activity (Perrin et al. (2001) J. Am. Chem. Soc. 123: 1556-63). Williams and co-workers recently tested several deoxyuridine derivatives for acceptance by Taq DNA polymerases and concluded that acceptance is greatest when using C5-modified uridines bearing rigid alkyne or trans-alkene groups such as 9 and 10 (Lee et al. (2001) NUCLEIC ACIDS RES. 29: 1565-73). A similar study (Gourlain et al. (2001) NUCLEIC ACIDS RES. 29: 1898-1905) on C7-functionalized 7-deaza-deoxyadenosines revealed acceptance by Taq DNA polymerase of 7-aminopropyl- (11), cis-7-aminopropenyl-(12), and 7-aminopropynyl-7-deazadeoxyadenosine (13).

With simple general acid and general base functionality, chiral metal centers would expand considerably the chemical scope of nucleic acids. Functionality aimed at binding chemically potent metal centers has yet to been incorporated into nucleic acid polymers. Natural DNA has demonstrated the ability to fold in complex three-dimensional structures capable of stereospecifically binding target molecules (Lin et al. (1997) CHEM. BIOL. 4: 817-32; Lin et al. (1998) CHEM. BIOL. 5: 555-72; Schultze et al. (1994) J. MOL. BIOL. 235: 1532-47) or catalyzing phosphodiester bond manipulation (Santoro et al. (1997) PROC. NATL. ACAD. SCI. USA 94: 4262-6; Breaker et al. (1995) CHEM. BIOL. 2: 655-60; Li et al. (2000) BIOCHEMISTRY 39: 3106-14; Li et al. (1999) PROC. NATL. ACAD. SCI. USA 96: 2746-51), DNA depurination (Sheppard et al. (2000) PROC. NATL. ACAD. SCI. USA 97: 7802-7807) and porphyrin metallation (Li et al. (1997) BIOCHEMISTRY 36: 5589-99; Li et al. (1996) NAT. STRUCT. BIOL. 3: 743-7). Non-natural nucleic acids augmented with the ability to bind chemically potent, water-compatible metals such Cu, La, Ni, Pd, Rh, Ru, or Sc may possess greatly expanded catalytic properties. For example, a Pd-binding oligonucleotide folded into a well-defined structure may possess the ability to catalyze Pd-mediated coupling reactions with a high degree of regiospecificity or stereospecificity. Similarly, non-natural nucleic acids that form chiral Sc binding sites may serve as enantioselective cycloaddition or aldol addition catalysts. The ability of DNA polymerases to translate DNA sequences into these non-natural polymers coupled with in vitro selections for catalytic activities would therefore permit the direct evolution of desired catalysts from random libraries.

Evolving catalysts in this approach addresses the difficulty of rationally designing catalytic active sites with specific chemical properties that has inspired recent combinatorial approaches (Kuntz et al. (1999) CURR. OPIN. CHEM. BIOL. 3: 313-319; Francis et al. (1998) CURR. OPIN. CHEM. BIOL. 2: 422-8) to organometallic catalyst discovery. For example, Hoveyda and co-workers identified Ti-based enantioselective epoxidation catalysts by serial screening of peptide ligands (Shimizu et al. (1997) ANGEW. CHEM. INT. ED. 36). Serial screening was also used by Jacobsen and co-workers to identify peptide ligands that form enantioselective epoxidation catalysts when complexed with metal cations (Francis et al. (1999) ANGEW. CHEM. INT. ED. ENGL. 38: 937-941). Recently, a peptide library containing phosphine side chains was screened for the ability to catalyze malonate ester addition to cyclopentenyl acetate in the presence of Pd (Gilbertson et al. (2000) J. AM. CHEM. SOC. 122: 6522-6523).

The current approach differs fundamentally from previous combinatorial catalyst discovery efforts in that it permits catalysts with desired properties to spontaneously emerge from one pot, solution-phase libraries after evolutionary cycles of diversification, amplification, translation, and selection. This strategy allows up to $10^{15}$ different catalysts to be generated and selected for desired properties in a single experiment. The compatibility of this approach with one-pot in vitro selections allows the direct selection for reaction catalysis rather than screening for a phenomenon associated with catalysis such as metal binding or heat generation. In addition, properties difficult to screen rapidly such as substrate stereospecificity or metal selectivity can be directly selected using approaches disclosed herein.

Key intermediates for a number of C5-functionalized uridine analogs and C7-functionalized 7-deazaadenosine analogs have been synthesized for incorporation into non-natural DNA polymers. In addition, the synthesis of six C8-functionalized adenosine analogs as deoxyribonucleotide triphosphates has been completed.

Synthesis of Metal-Binding Nucleotides

Figure 68:
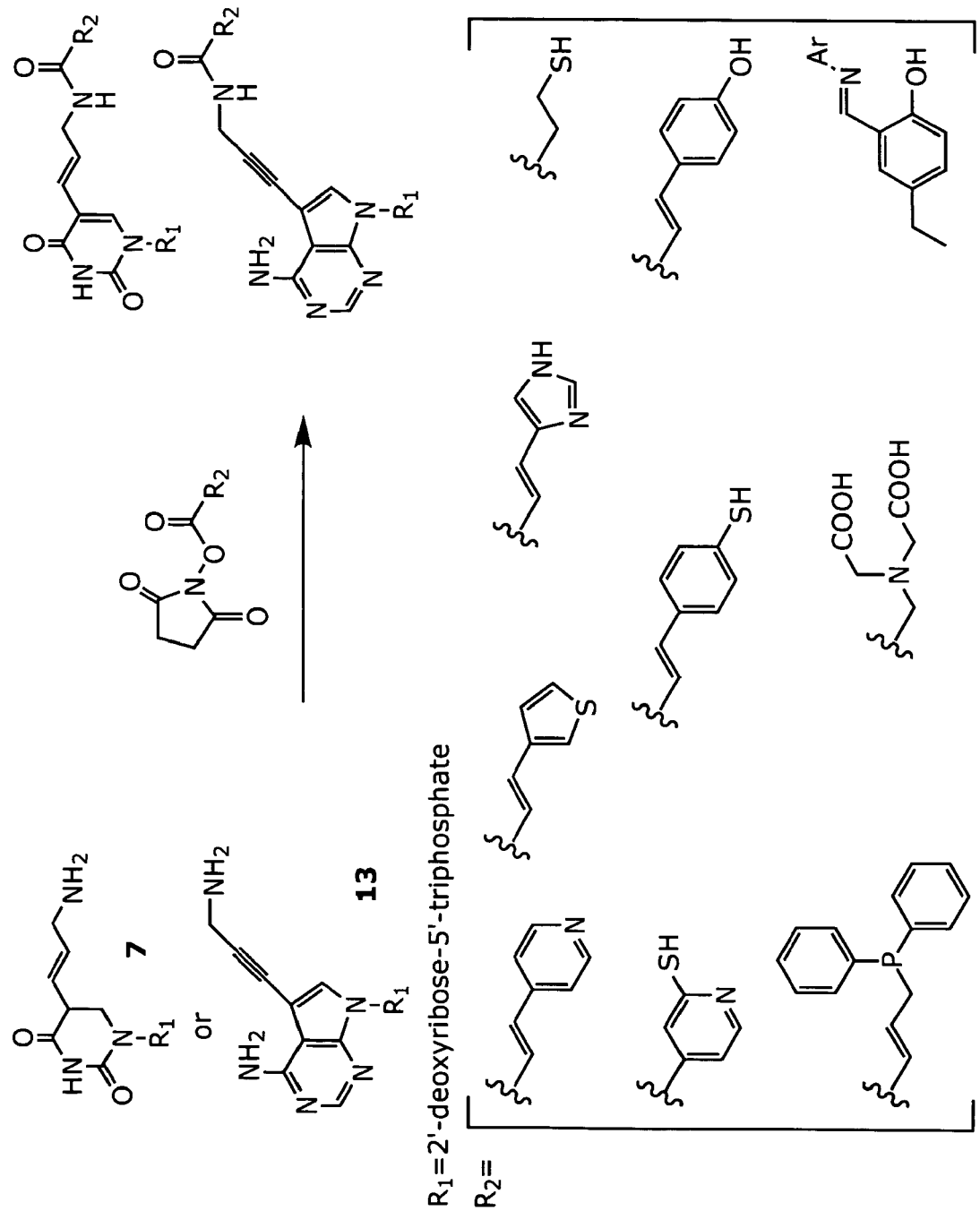
FIG. 68 depicts exemplary metal binding uridine and 7-deazaadenosine analogs.
Figure 69:
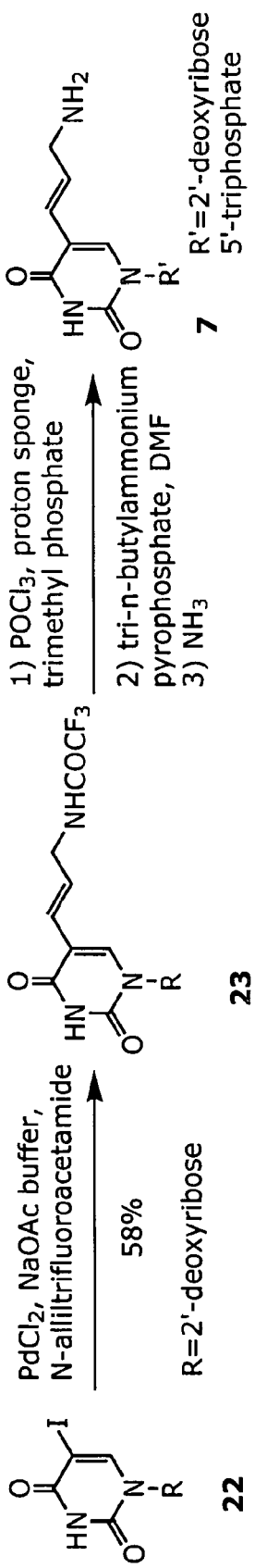
FIG. 69 depicts an exemplary synthesis of analog 7 from FIG. 67.

A strategy for synthesizing metal-binding uridine and 7-deazaadenosine analogs is shown in FIG. 68. Both routes end with amide bond formation between NHS esters of metal-binding functional groups and amino modified deoxyribonucleotide triphosphates (7 and 13). Analogs 7 and 13 as well as acetylated derivatives of 7 have been previously shown to be tolerated by DNA polymerases, including thermostable DNA polymerases suitable for PCR (Perrin et al. (2001) supra; Perrin et al. (1999) supra; Latham et al. (1994) NUCLEIC ACIDS RES. 22: 2817-22; Gourlain et al. (2001) Nucleic Acids Res. 29: 1898-1905; Lee et al. (2001) NUCLEIC ACIDS RES. 29: 1565-73; Sakthivel et al. (1998) ANGEW. CHEM. INT. ED. ENGL. 37: 2872-2875). This approach allows a wide variety of metal-binding ligands to be rapidly incorporated into either nucleotide analog. Amino modified deoxy-ribonucleotide triphosphate 7 has been synthesized using a previously reported route (Sakthivel et al. (1998) supra). As illustrated in FIG. 69, Heck coupling of commercially available 5-iodo-2'-deoxyuridine (22) with N-allyltrifluoroacetamide provided compound 23. The 5'-triphosphate group was incorporated by treatment of compound 23 with trimethylphosphate, phosphorous oxychloride ($POCl_3$), and proton sponge (1,8-bis (dimethylamino)-naphthalene) followed by tri-n-butylammonium pyrophosphate, and the trifluoroacetamide group then removed with aqueous ammonia to afford C5-modified uridine intermediate 7.

Figure 70:
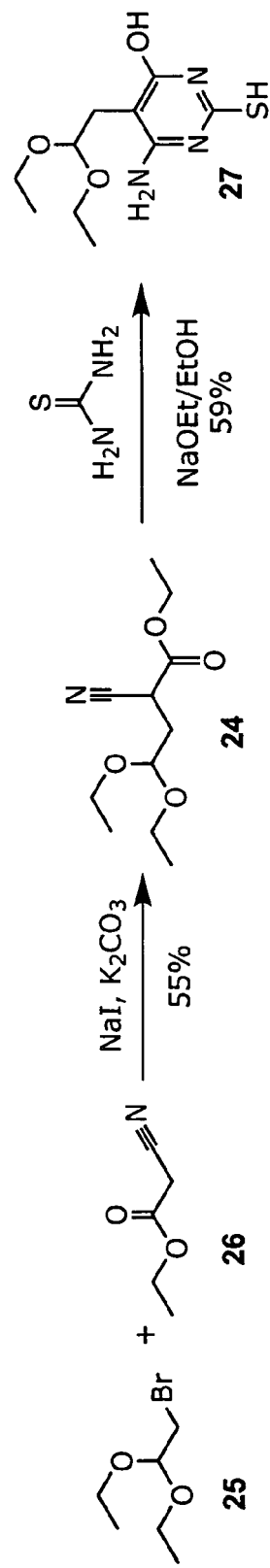
FIG. 70 depicts an exemplary synthesis of compound 30, a precursor to compound 13 from FIG. 67.
Figure 71:
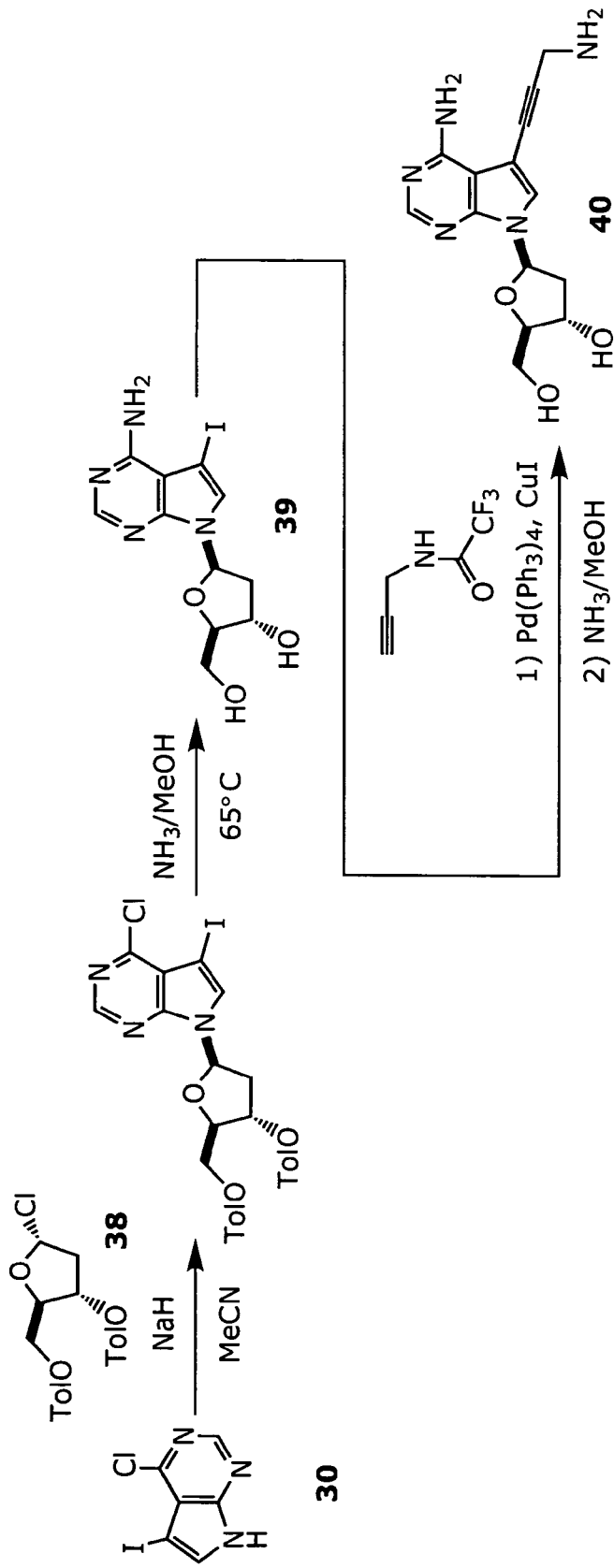
FIG. 71 depicts an exemplary synthesis of compound 40, a precursor to compound 13 from FIG. 67.
Figure 72:
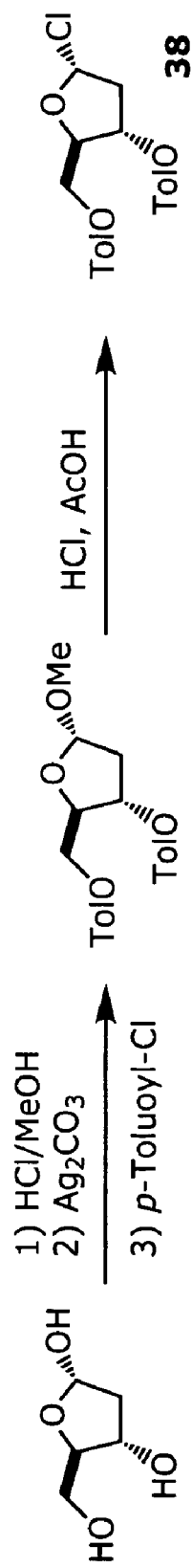
FIG. 72 depicts an exemplary synthesis of compound 38, a precursor to compound 40 from FIG. 71.
Figure 73:
FIG. 73 depicts exemplary deoxyadenosine derivatives.
Figure 74:
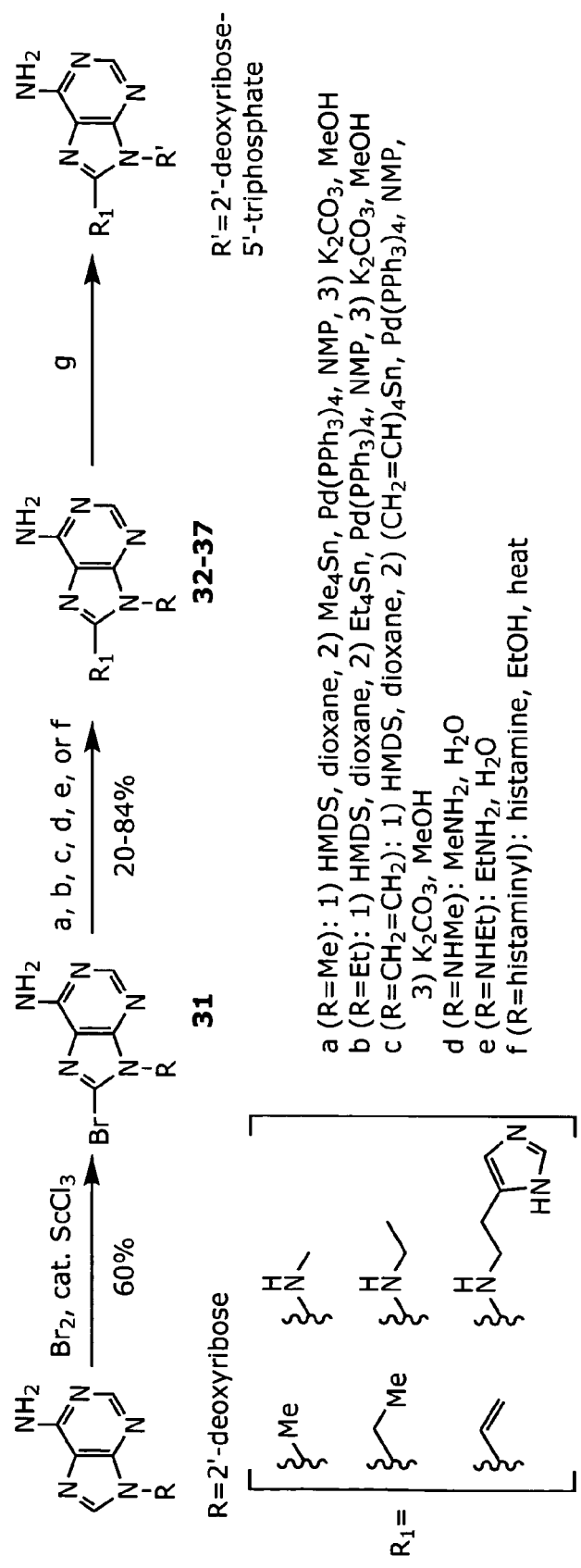
FIG. 74 depicts an exemplary synthesis of modified deoxyadenosine triphosphates.

C7-modified 7-deazaadenosine intermediate 13, the key intermediate for 7-deazaadenosine analogs, has been synthesized. As shown in FIG. 70, diethoxyethylcyanoacetate 24 was synthesized from bromoacetal 25 and ethyl cyanoacetate 26 following a known protocol (Davoll (1960) J. AM. CHEM. SOC. 82: 131-138). Condensation of 24 with thiourea provided pyrimidine 27, which was desulfurized with Raney nickel and then cyclized to pyrrolopyrimidine 28 with dilute aqueous HCl. Treatment of 28 with $POCl_3$ afforded 4-chloro-7-deazaadenine 29. The aryl iodide group which can serve as a Sonogashira coupling partner for installation of the propargylic amine in 13 was incorporated by reacting 29 with N-iodosuccinimide to generate 4-chloro-7-iodo-7-deazaadenine 30 in 13% overall yield from bromoacetal 25. FIG. 71 shows glycosylation of compound 30 with protected deoxyribosyl chloride 38 (generated from deoxyribose as shown in FIG. 72), followed by ammonolysis afforded 7-iodo-adenosine 39 (Gourlain et al. (2001) NUCLEIC ACIDS RES. 29: 1898-1905). Pd-mediated Sonogashira coupling (Seela et al. (1999) HELV. CHEM. ACTA 82: 1878-1898) of 39 with N-propynyltrifluoroacetamide provides 40, which is then converted to the 5' nucleotide triphosphate and deprotected with ammonia to yield C7-modified 7-deazaadenosine intermediate 13.

In order to create a library of metal-binding uridine and adenosine analogs, a variety of metal-binding groups as NHS esters can be coupled to C5-modified uridine intermediate 7 and C7-modified 7-deazaadenosine intermediate 13. Exemplary metal binding groups are shown in FIG. 68 and include phosphines, thiopyridyl groups, and hemi-salen moieties. Additional deoxyadenosine derivatives, such as, for example, compounds 41 and 42 shown in FIG. 73, can be prepared by coupling alkyl- and vinyl trifluoroacetamides to 8-bromodeoxyadenosine (31). These intermediates then are coupled with the NHS esters shown in FIG. 68 to generate a variety of metal-binding 8-functionalized deoxyadenosine triphosphates.

As alternative functionalized adenine analogs that will both probe the structural requirements of DNA polymerase acceptance and provide potential metal-binding functionality, six 8-modified deoxyadenosine triphosphates (FIG. 74) have been synthesized. All functional groups were installed by addition to 8-bromo-deoxyadenosine (31), which was prepared by bromination of deoxyadenosine in the presence of scandium chloride ($ScCl_3$), which we found to greatly increase product yield. Methyl- (32), ethyl- (33), and vinyladenosine (34) were synthesized by Pd-mediated Stifle coupling of the corresponding alkyl tin reagent and 31 (Mamos et al. (1992) TETRAHEDRON LETT. 33: 2413-2416). Methylamino- (35) (Nandanan et al. (1999) J. MED. CHEM. 42: 1625-1638), ethylamino- (36), and histaminoadenosine (37) were prepared by treatment of 23 with the corresponding amine in water or ethanol. The 5'-nucleotide triphosphates of 32-37 were synthesized as described above.

Acceptance of Nucleotides by Polymerase

Figure 75:
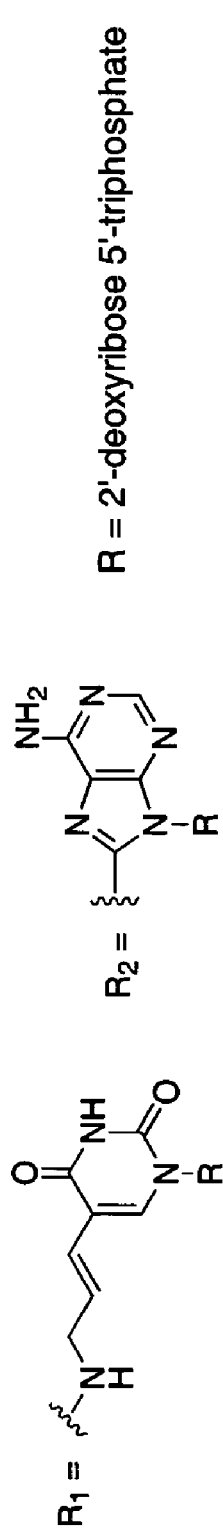
FIG. 75 depicts a summary of modified nucleotide triphosphates containing metal-binding functionalities which are or are not incorporated by DNA-polymerase.
Figure 75:
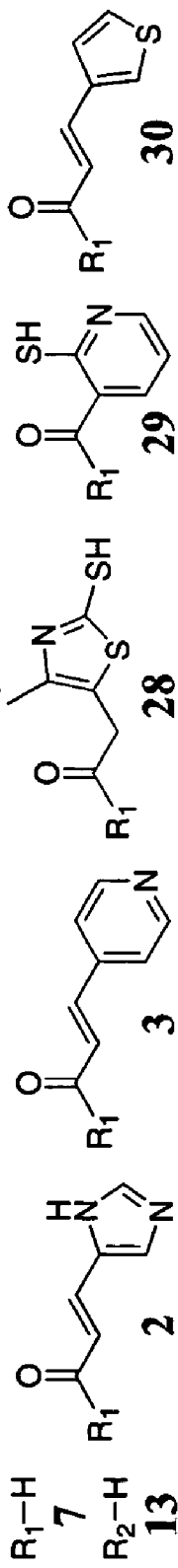
Figure 75:
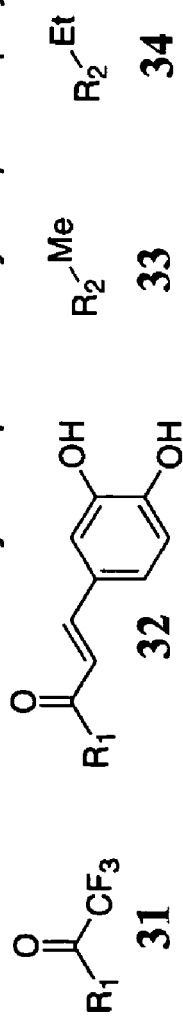
Figure 76:
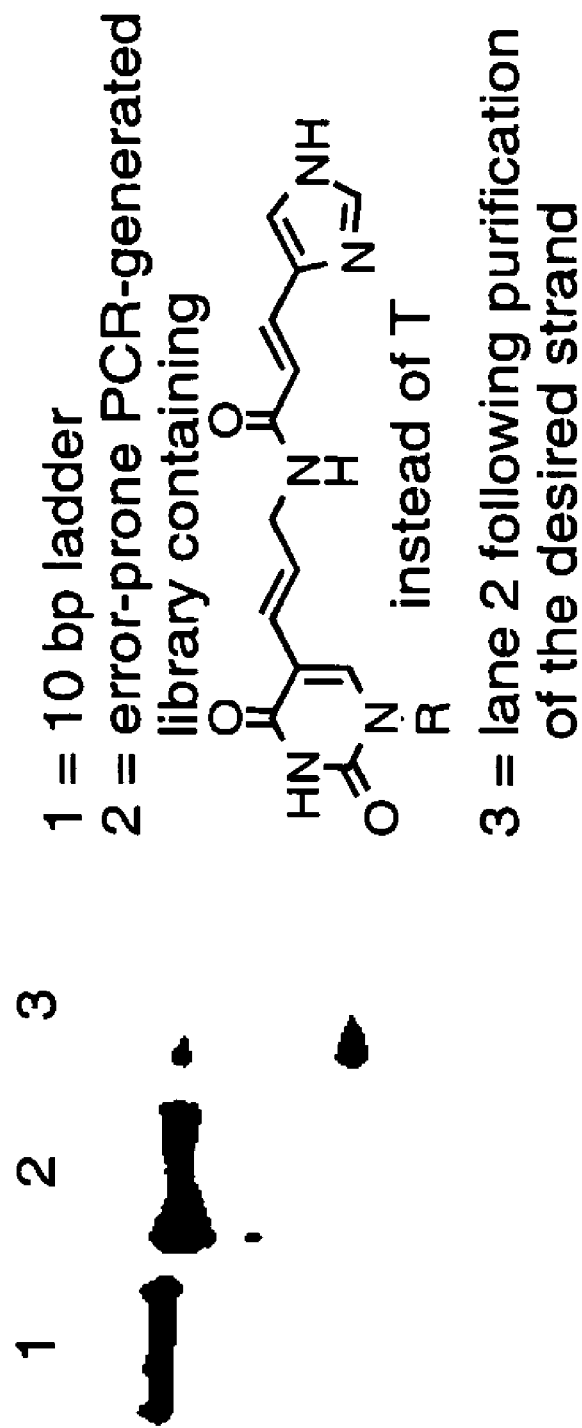
FIG. 76 depicts a non-natural polymer library containing a synthetic metal-binding nucleotide that is compatible with DNA polymerases.

The ability of the modified nucleotide triphosphates containing metal-binding functionality shown in FIG. 75 to be accepted by DNA polymerase enzymes was studied. Synthetic nucleotide triphosphates were purified by ion exchange and reverse-phase HPLC and were added to PCR reactions containing Taq DNA polymerase, three natural deoxynucleotide triphosphates, pUC19 template DNA, and two DNA primers. The primers were chosen to generate PCR products ranging from 50 to 200 base pairs in length. Control PCR reactions contained the four natural deoxynucleotide triphosphates and no non-natural nucleotides. PCR reactions were analyzed by gel electrophoresis and the results indicate that functionalized uridine analogs 2, 3, 7, 13, 28, 29, and 30 were efficiently incorporated by Taq DNA polymerase over 30 PCR cycles, while uridine analogs 31 and 32 were not efficiently incorporated (see, FIG. 75). These results demonstrate that synthetic nucleotides containing metal binding functionality can both be read as templates and incorporated as building blocks into non-natural nucleic acids using DNA polymerases. The 8-modified adenosine triphosphates 32 and 33 were not accepted by Taq DNA polymerase, suggesting possible rejection of modifications at C8 (see, FIG. 75).

Functionalized nucleotides that are especially interesting yet are not compatible with Taq, Pfu, or Vent thermostable DNA polymerases can be tested for their ability to participate in primer extension using other commercially available DNA polymerases including the Klenow fragment of *E. coli* DNA polymerase I, T7 or T4 DNA polymerase, or M-MuLV reverse transcriptase.

Generation of Polymer Libraries

Non-natural polymer libraries containing synthetic metal-binding nucleotides that are compatible with DNA polymerases have been created. Libraries of $10^{15}$ different modified nucleic acids consisting of 40 random bases flanked by two primer binding regions and containing the imidazole-linked thymine base shown in FIG. 76 have been created. These libraries were efficiently generated by three methods: standard PCR, error-prone PCR, and primer extension using large quantities of template and stoichiometric quantities of only one primer. The resulting double-stranded libraries were denatured and the desired strand isolated using the avidin-based purification system described hereinabove. Two rounds of in vitro selection on this library for polymers that fold only in the presence of $Cu^{2+}$ have been performed using the gel electrophoresis selection for folded nucleic acids as described herein.

Figure 77:
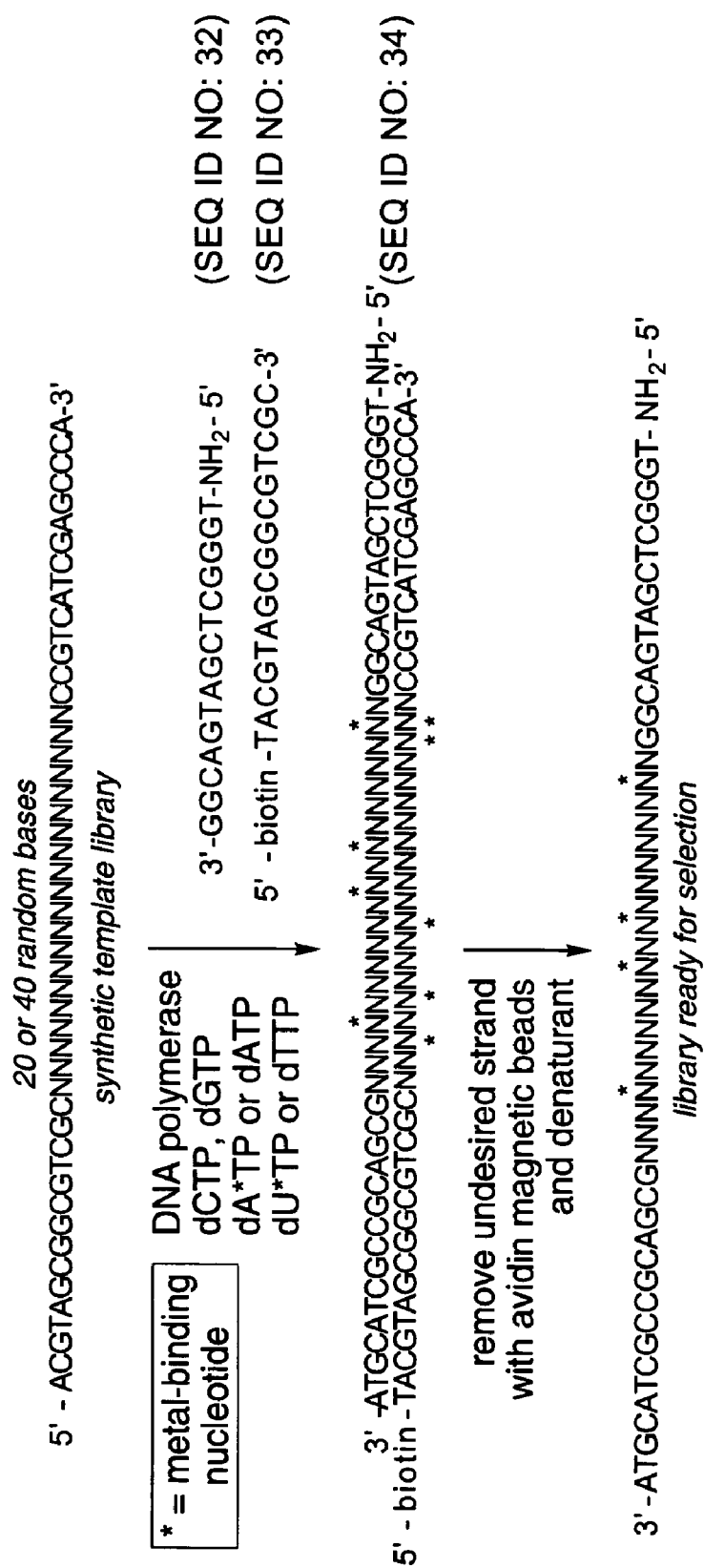
FIG. 77 is a schematic representation showing the generation of libraries of nucleic acids containing polymerase-accepted metal binding nucleotides.

Libraries of nucleic acids containing the most promising polymerase-accepted metal-binding nucleotides, including 28-30 (FIG. 75), can also be generated. Libraries can be generated by PCR amplification or by primer extension of a synthetic DNA template library consisting of a random region of 20 or 40 nucleotides flanked by two 15-base constant priming regions (FIG. 77). The priming regions contain restriction endonuclease cleavage sites to allow DNA sequencing of pools or individual library members. One primer contains a primary amine group at its 5' terminus and will become the coding strand of the library. The other primer contains a biotinylated 5' terminus and will become the non-coding strand. The PCR reaction includes one or two non-natural metal-binding deoxyribonucleotide triphosphates, three or two natural deoxyribonucleotide triphosphates, and a DNA polymerase compatible with non-natural nucleotides. Following PCR to generate the double-stranded form of the library, library members then are denatured and the non-coding strands removed by washing with streptavidin-linked magnetic beads to ensure that no biotinylated strands remain in the library. Libraries of up to $10^{15}$ different members can be generated by this method, far exceeding the combined diversity of previously reported combinatorial metal-binding catalyst discovery efforts.

Each library then is incubated in aqueous solution with a metal of interest from the following non-limiting list of water compatible metal salts: $ScCl_3$, $CrCl_3$, $MnCl_2$, $FeCl_2$, $FeCl_3$, $CoCl_2$, $NiCl_2$, $CuCl_2$, $ZnCl_2$, $GaCl_3$, $YCl_3$, $RuCl_3$, $RhCl_3$, $Na_2PdCl_4$, $AgCl$, $CdCl_2$, $InCl_3$, $SnCl_2$, $La(OTf)_3$, $Ce(OTf)_3$, $Pr(OTf)_3$, $Nd(OTf)_3$, $Sm(OTf)_3$, $Eu(OTf)_3$, $Gd(OTf)_3$, $Tb(OTf)_3$, $Dy(OTf)_3$, $Ho(OTf)_3$, $Er(OTf)_3$, $Tm(OTf)_3$, $Yb(OTf)_3$, $Lu(OTf)_3$, $IrCl_3$, $PtCl_2$, $AuCl$, $HgCl_2$, $HgCl$, $PbCl_2$, and $BiCl_3$ (Kobayashi et al. (1998) J. AM. CHEM. SOC. 120: 8287-8288; Fringuelli et al. (2001) EUR. J. ORG. CHEM. 2001: 439-455). The metals are chosen in part based on the specific chemical reactions to be catalyzed. For example, libraries aimed at reactions such as aldol condensations or hetero Diels-Alder reactions that are known to be catalyzed by Lewis acids are incubated with $ScCl_3$ or with one of the lanthanide triflates (Fringuelli et al. (2001) supra). In other cases, metals not previously known to catalyze the transformations of interest are also used to evolve polymers with unprecedented activity. The metal-incubated library is purified away from unbound metal salts using gel filtration cartridges (available from, for example, Princeton Separations) that separate DNA oligonucleotides 25 bases or longer from unbound smaller reaction components.

The ability of the polymer library (or of individual library members) to bind metals of interest is verified by treating the metalated library free of unbound metals with metal staining reagents, such as dithiooxamide, dimethylglyoxime, or potassium isothiocyanate (KSCN) (Francis et al. (1998) CURR. OPIN. CHEM. BIOL. 2: 422-8) or EDTA (Zaitoun et al. (1997) J. PHYS. CHEM. B 101: 1857-1860), that become distinctly colored in the presence of different metals. The approximate level of metal binding is measured by spectrophotometric comparison with solutions of free metals of known concentration and with solutions of positive control oligonucleotides containing an EDTA group (which can be introduced using a commercially available phosphoramidite from Glen Research, Sterling, Va., USA).

Selecting Nucleic Acid Polymers

Once the libraries of functionalized DNAs are synthesized and characterized, they are subjected to three types of in vitro selections for: (i) folding, (ii) target binding, or (iii) catalysis.

(i) Folding. Non-denaturing gel electrophoresis can be used as a simple selection, to be applied to inventive libraries of modified nucleic acids, to select for nucleic acid folding in the presence of specific metals of interest. In order to test this selection approach on molecules similar to future library members, three 60-base DNA oligonucleotides known (Schultze et al. (1994) J. MOL. BIOL. 235: 1532-1547) or predicted (SantaLucia (1998) PROC. NATL. ACAD. SCI. USA 95: 1460-1465) to have very different folded states were synthesized. Each oligonucleotide contained a core 30-base sequence flanked by two 15-base primer binding sequences. The unstructured control oligonucleotide contained a poly T core and an EcoR I restriction site. The second core sequence contained a perfect inverted repeat predicted to form a highly stable hairpin, while the third core sequence contained a poly G core known to fold in solution into an intramolecular G-quartet (Cheng et al. (1997) GENE 197: 253-260). The three DNA sequences were combined in equimolar ratios and the mixture subjected to preparative non-denaturing gel electrophoresis. The high mobility portion of the DNA was captured and compared by analytic electrophoresis to authentic poly T, hairpin, and poly G oligonucleotides. The results indicate that folded DNA sequences can be readily separated from a mixture of folded and unfolded DNA molecules by non-denaturing gel electrophoresis. This selection approach can be applied to the metal-binding polymer libraries, wherein polymers with anticipated metal binding ability will be incubated with one or more water-compatible metal sources prior to selection. Polymers capable of folding in the presence, but not in the absence, of metals will serve as especially attractive starting points for the next two types of selections.

(ii) Target Binding. Selections for target binding can be performed by incubating the solution-phase polymer library with either immobilized target or with biotinylated target followed by streptavidin-linked beads. Non-binders are removed by washing, and polymers with desired binding properties are eluted by chemical denaturation or by adding excess authentic free ligand. In order to complete one cycle of functionalized DNA evolution, the DNA templates are amplified by PCR using one primer containing the 5'-functionalized hairpin primer and a biotinylated second primer, optionally diversified by error-prone PCR (Caldwell (1992) PCR METHODS APPLIC. 2: 28-33) or by nonhomologous random recombination method, and then denatured into single stranded DNA and washed with streptavidin beads to remove the non-coding template strand. The resulting pool of selected single-stranded, 5'-functionalized DNA completes the evolution cycle and enters subsequent rounds of DNA-templated translation, selection, diversification, and amplification.

Figure 78A:
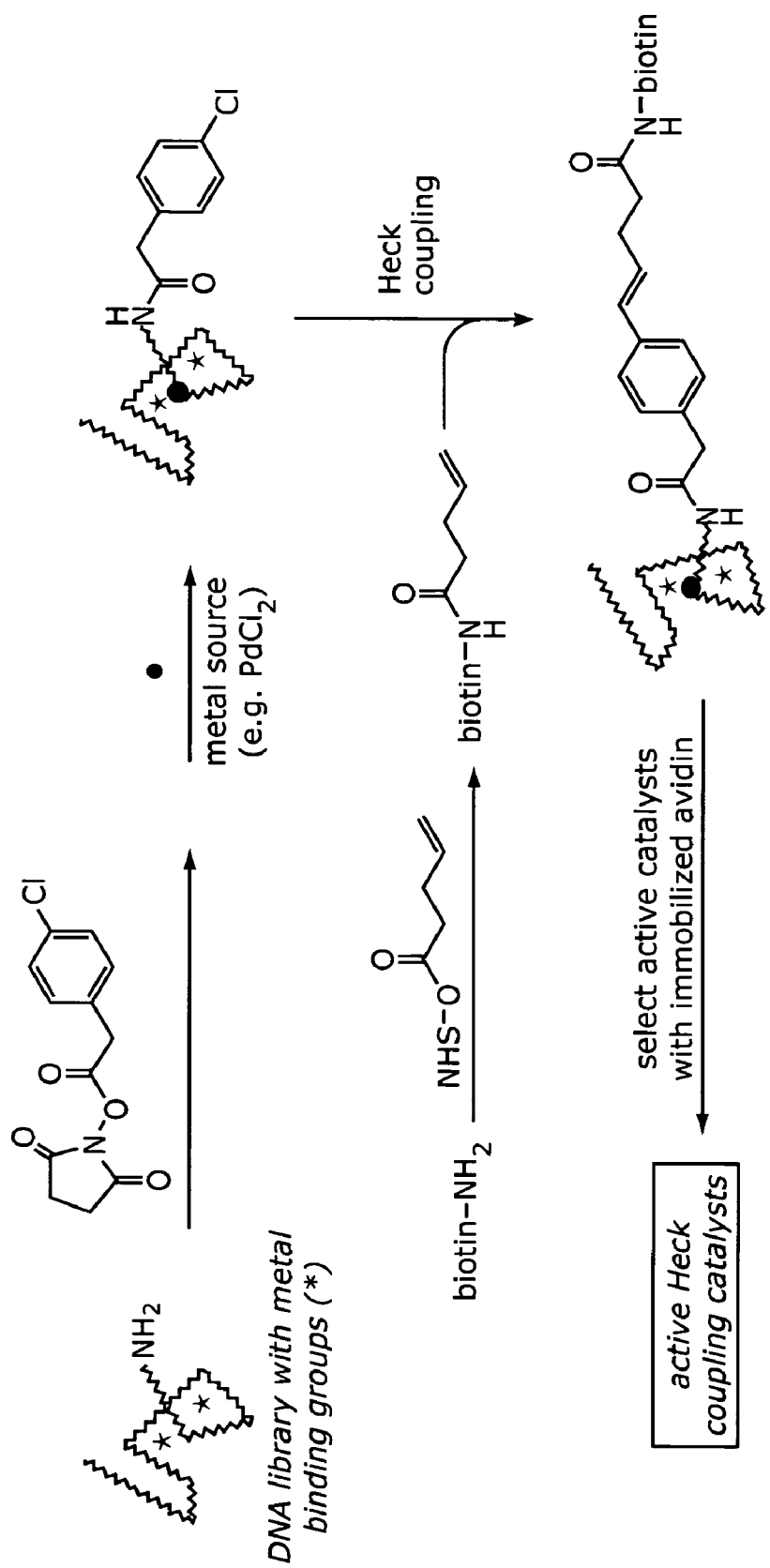
FIGS. 78A-78C show reaction schemes for identifying certain reaction catalysts.
Figure 78B:
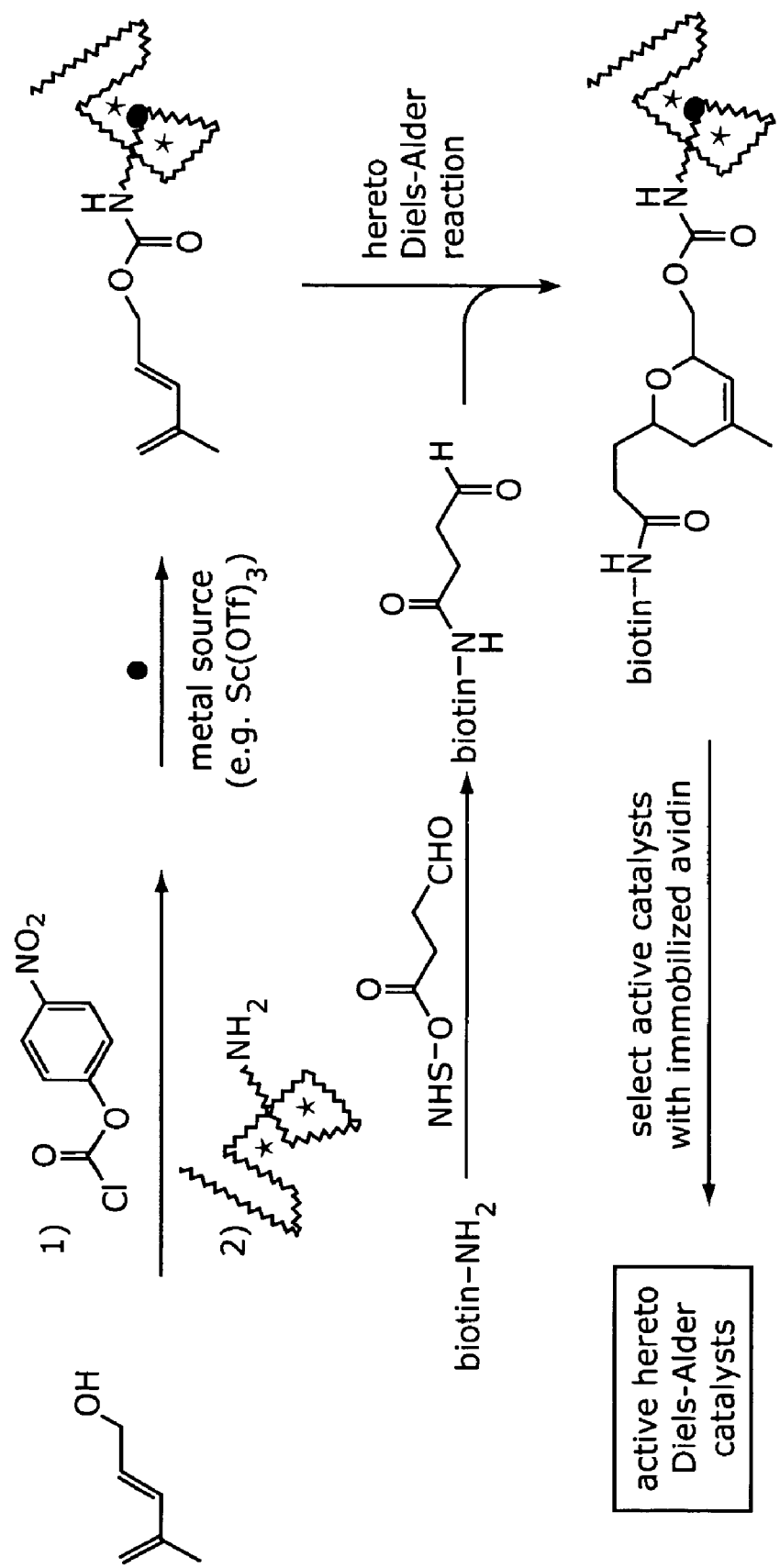
Figure 78C:
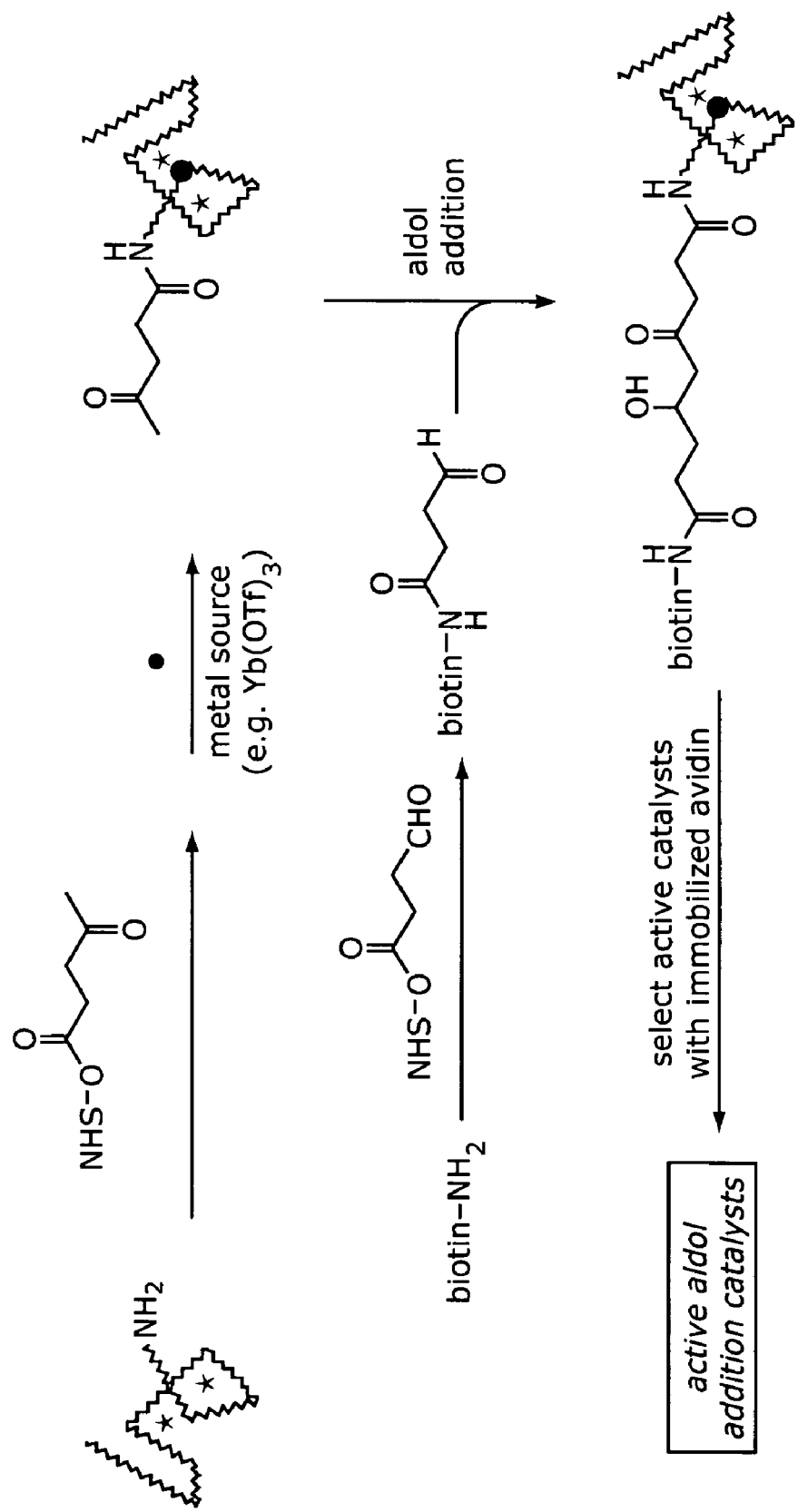

(iii) Catalysis. Selection for synthetic polymers that catalyze bond-forming or bond-cleaving reactions can also be performed. Library members that catalyze virtually any reaction that causes bond formation between two substrate molecules or that results in bond breakage into two product molecules can be selected using the schemes proposed in FIGS. 12 and 13. As illustrated in FIG. 12, in order to select for bond forming catalysts (for example, hetero Diels-Alder, Heck coupling, aldol reaction, or olefin metathesis catalysts), library members are covalently linked to one substrate through their 5' amino or thiol termini. The other substrate of the reaction is synthesized as a derivative linked to biotin. When dilute solutions of library-substrate conjugate are reacted with the substrate-biotin conjugate, those library members that catalyze bond formation cause the biotin group to become covalently attached to themselves. Active bond forming catalysts can then be separated from inactive library members by capturing the former with immobilized streptavidin and washing away inactive polymers. By way of example, the synthesis and selection of active Heck coupling catalysts, active hetero diels-alder catalysts and active aldol addition catalysts may be performed as shown in FIGS. 78A, 78B, and 78C, respectively.

In an analogous manner, library members that catalyze bond cleavage reactions such as retro-aldol reactions, amide hydrolysis, elimination reactions, or olefin dihydroxylation followed by periodate cleavage can also be selected, as illustrated in FIG. 13. In this case, metalated library members are covalently linked to biotinylated substrates such that the bond breakage reaction causes the disconnection of the biotin moiety from the library members. Upon incubation under reaction conditions, active catalysts, but not inactive library members, induce the loss of their biotin groups. Streptavidin-linked beads can then be used to capture inactive polymers, while active catalysts are able to elute from the beads. Related bond formation and bond cleavage selections have been used successfully in catalytic RNA and DNA evolution (Jäschke et al. (2000) CURR. OPIN. CHEM. BIOL. 4: 257-62). Although these selections do not explicitly select for multiple turnover catalysis, RNAs and DNAs selected in this manner have in general proven to be multiple turnover catalysts when separated from their substrate moieties (Jäschke et al. (2000) CURR. OPIN. CHEM. BIOL. 4: 257-62; Jaeger et al. (1999) PROC. NATL. ACAD. SCI. USA 96: 14712-7; Bartel et al. (1993) SCIENCE 261: 1411-8; Sen et al. (1998) CURR. OPIN. CHEM. BIOL. 2: 680-7).

It is contemplated that catalysts of three important and diverse bond-forming reactions (Heck coupling, hetero Diels-Alder cycloaddition, and aldol addition) can be created using the technologies described herein. All three reactions are water compatible (Kobayashi et al. (1998) J. AM. CHEM. SOC. 120: 8287-8288; Fringuelli et al. (2001) EUR. J. ORG. CHEM. 2001: 439-455; Li et al. (1997) ORGANIC REACTIONS IN AQUEOUS MEDIA) and are known to be catalyzed by metals.

Evolving Functionalized DNA Polymers

Following each round of selection, active library members can be amplified directly by PCR with the non-natural nucleotides and subjected to additional rounds of selection to enrich the library for desired catalysts. Libraries may be diversified by random mutagenesis using error-prone PCR or by nonhomologous recombination and characterized by DNA sequencing before and after selection. Because error-prone PCR is inherently less efficient than normal PCR, error-prone PCR diversification is conducted with only natural nucleotides. The mutagenized DNA templates then are translated into non-natural nucleic acid polymers as described above.

In addition to simply evolving active catalysts, the in vitro selections described herein may be used to evolve catalysts with properties difficult to achieve using current catalyst discovery approaches. For example, substrate specificity among catalysts can be evolved by selecting for active catalysts in the presence of the desired substrate and then selecting for inactive catalysts in the presence of one or more undesired substrates. Using this strategy, it is contemplated that it will be possible to evolve libraries of catalysts with unprecedented regio- and stereoselectivity. By way of example, four types of substrate specificity currently unachievable by known catalysts nor likely to be solvable by current catalyst discovery methods include: (i) Heck catalysts that operate on para- but not meta-aryl chlorides, (ii) aldol catalysts that accept ketones but not aldehydes as enolate acceptors, (iii) hetero Diels-Alder catalysts that reject olefin dienophiles, and (iv) hetero Diels-Alder catalysts that accept trans-trans but reject cis-trans or terminal dienes. Metal-binding polymers containing well-ordered, three-dimensional dispositions of key steric and electronic groups may be ideally suited to solving these problems. Similarly, metal selectivity can be evolved by selecting for active catalysts in the presence of desired metals and selecting against activity in the presence of undesired metals. Catalysts with broad substrate tolerance may be evolved by varying substrate structures between successive rounds of selection. Characterizing catalysts evolved by the above methods may provide new insights into developing analogous small molecule catalysts with powerful and unprecedented selectivities.

In addition, the observations of sequence-specific DNA-templated synthesis in DMF and $CH_2Cl_2$ suggested that DNA-tetralkylammonium cation complexes may form base-paired structures in organic solvents. These findings raise the possibility of evolving non-natural nucleic acid catalysts in organic solvents using slightly modified versions of the selections described above. The actual bond forming and bond cleavage selection reactions may be conducted in organic solvents, the crude reactions then will be ethanol precipitated to remove the tetraalkylammonium cations, and the immobilized avidin separation of biotinylated and non-biotinylated library members in aqueous solution will be performed. PCR amplification of selected members will then take place as described hereinabove. Successful evolution of reaction catalysts that function in organic solvents would expand considerably both the scope of reactions that can be catalyzed and the utility of the resulting evolved non-natural polymer catalysts.

Example 11

In Vitro Selection for Protein Binding and Affinity

This Example demonstrates that it is possible to perform in vitro selections for nucleic acid-linked synthetic small molecules with protein binding affinity. These selections (i) offer much greater sensitivities ($10^{-20}$ mol) than previously reported synthetic molecule screens for protein binding, (ii) can be rapidly iterated to achieve >$10^6$-fold net enrichments of active molecules, and (iii) can be adapted to select for binding specificity.

Because all molecules in a selection are processed simultaneously, selections offer much higher potential throughput than screens. Selections typically do not require sophisticated equipment and can be iterated to multiply the net enrichment of desired molecules. Certain properties such as binding specificity, although difficult to screen, can be readily selected. Finally, the outcomes of laboratory and natural selections usually are linked to amplifiable nucleic acids, permitting the selections to offer far greater sensitivities than screens. The covalent linkage of oligonucleotides to corresponding synthetic molecules, either as a consequence of nucleic acid-templated organic synthesis or as a result of conjugating a nucleic acid to synthetic molecules, allows synthetic molecules to be selected and then identified. Despite these attractions, selections for synthetic molecules have been largely unexplored.

At the outset, a variety of synthetic small molecules conjugated to 36- to 42-base DNA oligonucleotides (see, FIG. 79) were synthesized such that each small molecule was linked to a unique DNA sequence. The small molecules were chosen either for their known binding affinities to six proteins (see, FIG. 79), or as nonbinding negative controls. Solutions containing mixtures of DNA-linked protein ligands and DNA-linked negative controls were used to simulate DNA-templated synthetic small molecule libraries containing small fractions of library members with protein binding activities.

Selections for protein affinity were performed by incubating mixtures of DNA-linked synthetic small molecules for 1-2 hours with target proteins covalently conjugated to beads. The non-binders were removed by washing the beads with high salt buffer. The bound molecules were then PCR amplified to amplify the DNA oligonucleotides surviving selection. Sequences encoding known protein binding ligands were distinguished from DNA encoding non-binders by digestion with sequence-specific restriction endonucleases, permitting their relative ratio to be quantitated by gel electrophoresis and densitometry. The efficiency of each selection was assessed by the degree to which DNA-linked protein ligands were enriched relative to DNA-linked non-binders (the "enrichment factor").

Figure 80:
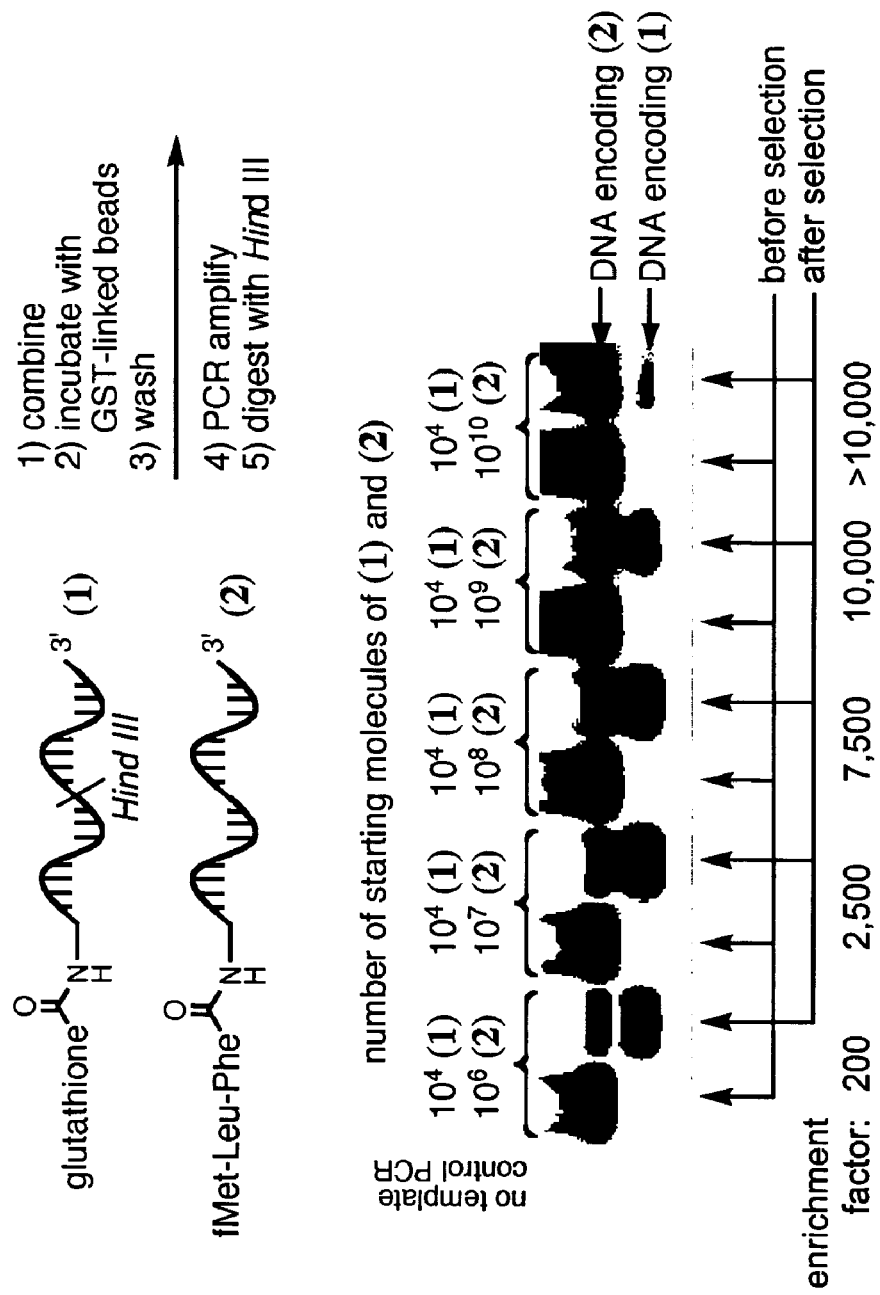
FIG. 80 depicts the results of an exemplary selection scheme.
Figure 81:
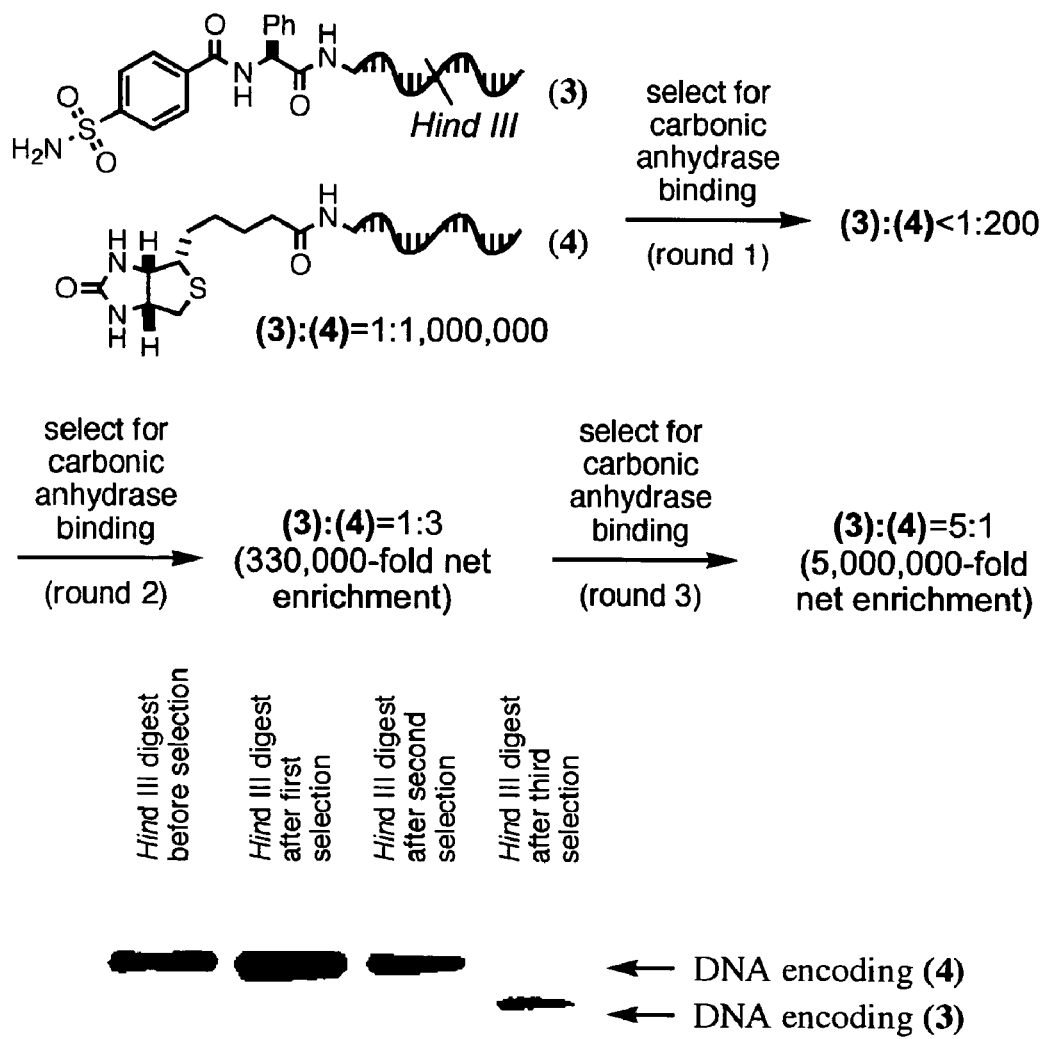
FIG. 81 depicts the net enrichment realized by three rounds of enrichment.

Among the protein-small molecule interactions considered, the binding of glutathione amide to glutathione S-transferase (GST) is among the lowest affinity ($K_d$=~10 µM) and, therefore, represents a stringent test of protein binding selections for DNA-linked synthetic small molecules. To measure the sensitivity and efficiency of these selections (see, FIG. 80), the number of DNA-linked glutathione molecules (1) were varied from $10^3$ to $10^7$ molecules. A 100- to $10^6$-fold molar excess of the negative control N-formyl-Met-Leu-Phe linked DNA (2) was combined with (1) and the resulting mixture was selected for binding to GST-linked agarose beads. The selection strongly enriched as few as 10,000 copies of the DNA-linked glutathione by 100- to >$10^4$-fold relative to the negative control (FIG. 80). Although the concentrations of DNA-linked molecules during selections were much lower than µM, the selections were successful because GST was immobilized at an effective concentration exceeding ~10 µM and, therefore, permitted a significant fraction of (1) to remain bound to GST. These results demonstrate that selections for modest protein affinities (for example, $K_d$=10 µM) are possible in this format.

Figure 79:
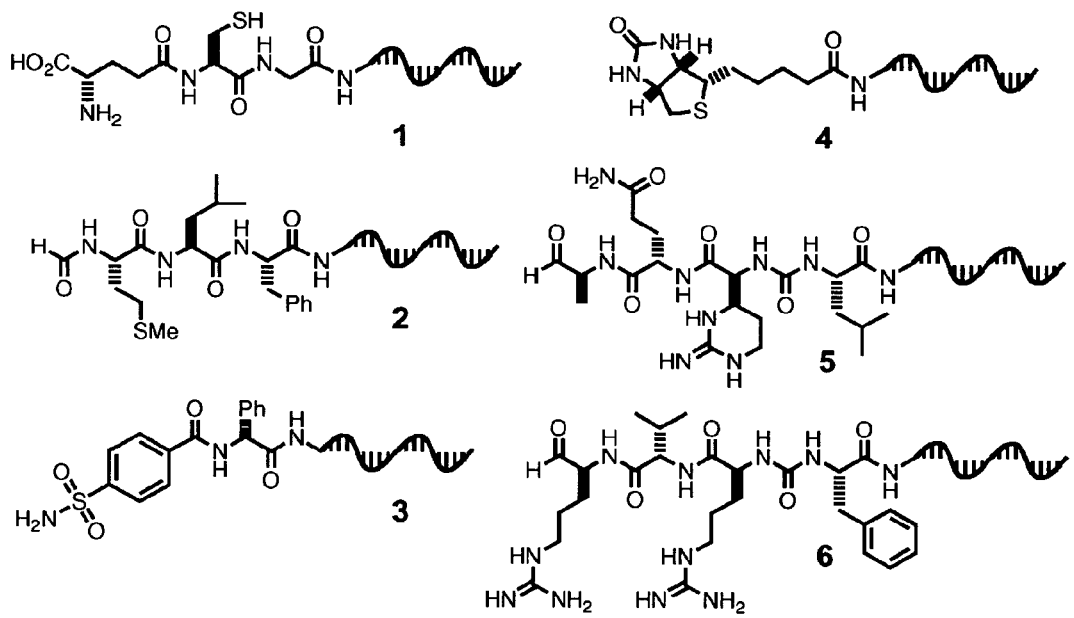
FIG. 79 depicts exemplary DNA-linked synthetic molecules subjected to protein binding selections, and enrichment factors for a single round of selection.

In order to evaluate the generality of this approach, analogous selections were performed for binding to streptavidin, carbonic anhydrase, papain, trypsin, and chymotrypsin in addition to GST (FIG. 79). Collectively these six functionally diverse proteins bind the ligands shown in FIG. 79 with predicted affinities that span more than eight orders of magnitude ($K_d$=~14 μM to ~40 fM) (D'Silva (1990) BIOCHEM. J. 271: 161-165) (Jain et al. (1994) J. MED. CHEM. 37: 2100-2105; Green (1990) METHODS ENZ. 184: 51-67; Otto et al. (1997) CHEM. REV. 97: 133-172). In each of these cases, selection enriched ≤$10^{-16}$ mol of a known small molecule ligand conjugated to DNA by at least 50-fold over a non-binding negative control (FIG. 79), indicating that DNA conjugation does not impair the ability of the ligands in FIG. 79 to bind their cognate protein targets and suggesting that these selections may be applicable to a wide variety of unrelated proteins.

Furthermore, selections can be iterated to multiply the net enrichment of desired molecules. To test this possibility with DNA-linked synthetic molecules, a 1:1,000 mixture of DNA-linked phenyl sulfonamide (3):DNA-linked N-formyl-Met-Leu-Phe (2) was subjected to a selection for binding carbonic anhydrase. The molecules surviving the first selection were eluted and directly subjected to a second selection using fresh immobilized carbonic anhydrase. PCR amplification and restriction digestion revealed that the first round of selection yielded a 1:3 ratio of (3):(2), representing a 330-fold enrichment for the DNA-linked phenyl sulfonamide. The second round of selection further enriched 3 by more than 30-fold, such that the ratio of (3):(2) following two rounds of selection exceeded 10:1 (>$10^4$-fold net enrichment). Similarly, three rounds of iterated selection were used to enrich a 1:$10^6$ starting ratio of (3):DNA-linked biotin (4) by a factor of 5×$10^6$ into a solution containing predominantly DNA-linked phenyl sulfonamide (3) (see, FIG. 81). These findings demonstate that enormous net enrichments for DNA-linked synthetic molecules can be achieved through iterated selection, and suggest that desired molecules represented as rarely as 1 part in $10^6$ (approximately the largest number of different small molecules generated in a single library to date) within DNA-templated synthetic libraries may be efficiently isolated in this manner.

In addition to binding affinity, binding specificity is a broadly important property of synthetic molecules. Library screening methods for binding specificity typically require duplicating the entire screen for each target or non-target of interest. In contrast, selections for specificity in principle can be performed in a single experiment by selecting for target binding as well as for the inability to bind one or more non-targets. In order to validate selections for specificity among DNA-linked synthetic small molecules, DNA-linked biotin (4), DNA-linked chymostatin (5), and DNA-linked antipain (6) were combined into a single solution in a 24:4:1 ratio, respectively. Because biotin has no significant affinity for chymotrypsin or papain, chymostatin binds to both proteases, and antipain binds only to papain, (see, FIG. 82) this mixture simulates a library containing predominantly nonbinding molecules with a minor fraction of nonspecific binders and an even smaller fraction of a target-specific binder.

Figure 82:
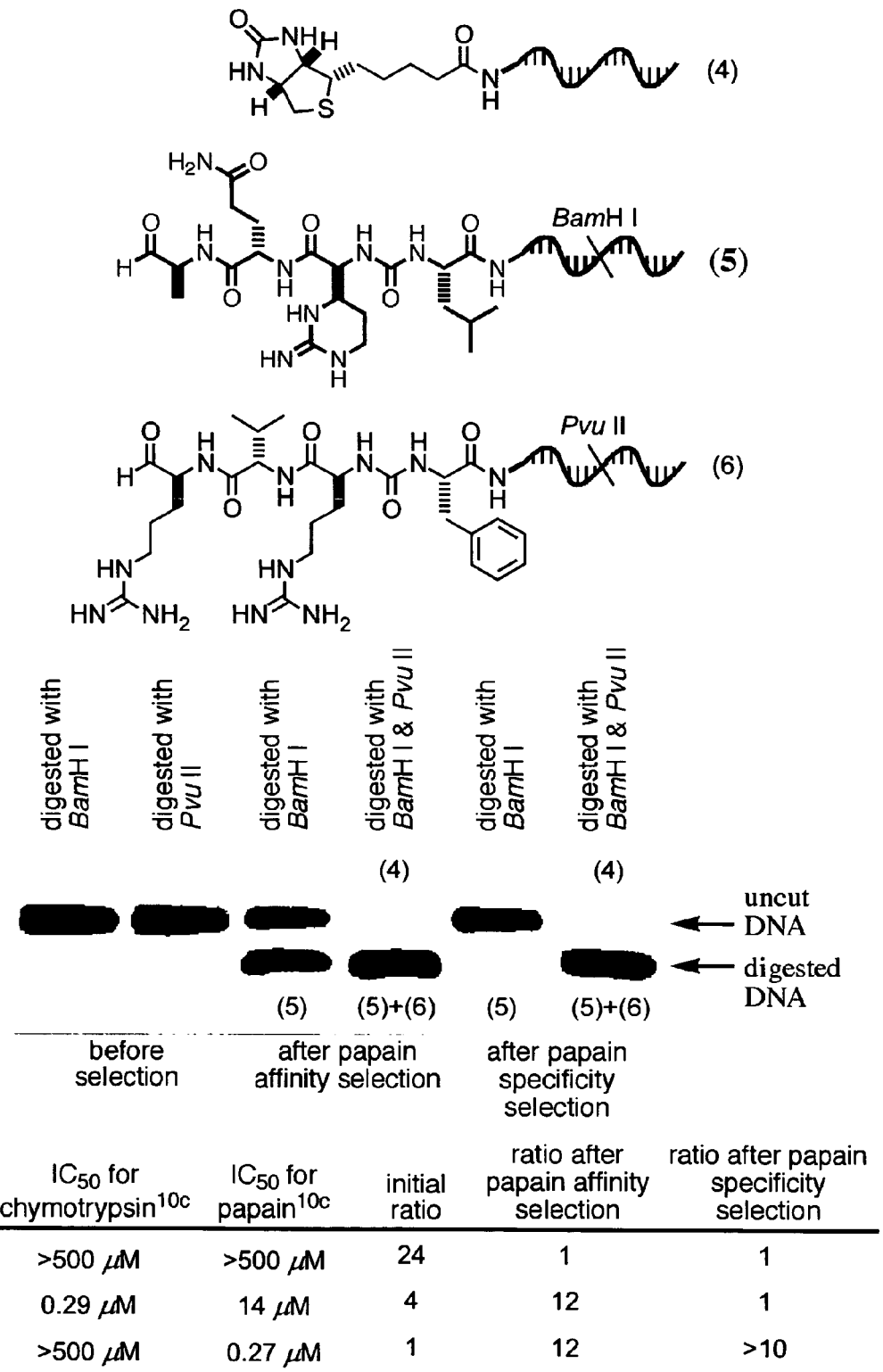
FIG. 82 depicts the separation of target-specific and non-specific DNA-linked synthetic molecules from a single solution.

When this mixture was subjected to two rounds of selection for binding to papain, both 5 and 6 were enriched at the expense of 4, as expected (FIG. 82). However, when the above mixture was washed with chymotrypsin-linked beads and selected for binding to papain in the presence of excess free chymotrypsin, only the papain-specific ligand (6) was enriched (FIG. 82). The ability of the selections described above to separate target-specific and non-specific DNA-linked synthetic molecules from a single solution suggests their use to discover synthetic molecules that exclusively bind a single member of a large family of related proteins (e.g., kinases, proteases, or glycotransferases), and that do not bind proteins that commonly reduce the biological efficacy of small molecules (e.g. by sequestering, exporting, or metabolizing them).

In summary, this Example demonstrates the feasibility of performing in vitro selections for DNA-linked synthetic small molecules with protein binding activities. The application of methods developed here to nucleic acid-templated (or nucleic acid-conjugated) libraries may play an important role in the discovery of synthetic molecules with desired properties using powerful selection and amplification strategies previously available only to biological molecules.

Materials and Methods

DNA Synthesis

DNA oligonucleotides were synthesized on a PerSeptive Biosystems Expedite 8090 DNA synthesizer using standard phosphoramidite protocols. All reagents were purchased from Glen Research, Sterling, Va., USA. The templates for the glutathione S-transferase (GST) selection were synthesized using a 5'-amino-modifier C12 and all other templates were synthesized using 5'-amino-modifier C5.

Preparation of Compound (1)

Glutathione was synthesized on the solid phase using standard Boc chemistry at room temperature. 200 mg PAM Resin (Advanced ChemTech) was swelled in 2 mL DMF for 20 minutes. N-Boc-glycine (Sigma, 640 μmol, 112 mg), diisopropylcarbodiimide (570 μmol, 89 μL), and 4-dimethylaminopyridine (DMAP, 57 μmol, 7 mg) were added to the resin and stirred for 4 hours. The resin was washed with DMF and then with DMF/$CH_2Cl_2$ (1:1). The N-Boc protecting group was removed using two 3 minute washes of trifluoroacetic acid (TFA):m-cresol (95:5). The resin then was washed with DMF:$CH_2Cl_2$ (1:1) and DMF:pyridine (1:1). A solution of N-Boc-Cys(Fm)-OH (ChemImpex, 800 μmol, 320 mg), O-(7-Azabenzotriazol-1-yl)-N,N,N',N'-tetramethyluronium hexafluorophosphate (Aldrich, 720 μmol, 274 mg), 2,6-lutidine (1.2 mmol, 131 μl) and N,N-diisopropylethylamine (DIPEA, 750 μmol, 131 μl) in 800 μL of 1-methyl-2pyrrolidinone was stirred for 15 minutes and then added to the resin, stirring for 30 minutes. The resin then was washed with DMF/$CH_2Cl_2$ (1:1). To remove the N-Boc protecting group on cysteine, a solution of trimethylsilyl triflate (TMS-Otf) (2.8 mmol, 0.5 mL) and 2,6-lutidine (4.58 mmol, 0.5 mL) in 1.75 mL $CH_2Cl_2$ was added to the resin and stirred for 1 hour. The resin then was washed with methanol and then with DMF:$CH_2Cl_2$ (1:1). Fmoc-Glu-OFm (ChemImpex, 800 μmol, 438 mg) was coupled as described above. The fully protected glutathione was cleaved from the resin with a solution of trifluoromethanesulfonic acid:m-cresol:thioanisole:TFA (2:1:1:8), stirring for 1 hours. The mixture was filtered and the filtrate was extracted into hexane. The crude extract was purified using preparative thin layer chromatography in hexane. The silica containing the crude product ($R_f$=0.35) was washed extensively with hexane:ethyl acetate (4:1). The filtrate was isolated under vacuum to afford a yellowish solid. Yields for this synthesis were not optimized.

A solution of protected glutathione (1.1 μmol, 1.3 mg) in 90 μl DMF with N-hydroxysuccinimide (NHS, 11 μmol, 1.3 mg), dicyclohexylcarbodiimide (DCC, 11 μmol, 2.3 mg), and DMAP (5.7 μmol, 0.7 mg) was agitated for 1 hour. The mixture was spun down and the supernatant was added to 5'-amino-terminated protected DNA on CPG beads. This mixture was agitated for 2 hours and then the beads were washed with DMF, with $CH_3CN$, and dried with nitrogen.

Preparation of Compound (2a)

N-formyl-Met-Leu-Phe (MLF) was purchased from Sigma and coupled to 5'-amino-terminated protected DNA on CPG beads using the conditions described for compound (1).

Preparation of Compound (2b)

MLF (10-100 µmol, 0.17 M) was dissolved in dry DMF with 1 equiv. 1-hydroxybenzotriazole (Novabiochem), 0.9 equiv. O-Benzotriazol-1-yl-N,N,N',N'-tetramethyluronium hexafluorophosphate (Aldrich), and 2.3 equivalents of DIPEA. The solution was agitated at room temperature for 1 hour and then added to a unique sequence of 5'-amino-terminated protected DNA on CPG beads. The mixture was agitated for 1 hour at room temperature. The beads then were washed with DMF, then with $CH_3CN$, and dried under nitrogen.

Preparation of Compound (3)

Fmoc-Lys(Mmt)-OH (Novabiochem) was attached to amino-terminated protected DNA on CPG beads using the method described for compound (2b). The Fmoc group was removed with three 2 minute washes with 20% piperidine in DMF. The mixture then was washed with DMF and then with $CH_3CN$. The α-amine then was capped with a solution of 5% 1-methylimidazole in acetic anhydride/pyridine/tetrahydrofuran (1:1.1:18) for 10 minutes at room temperature. The beads then were washed with DMF and $CH_3CN$, and then treated with 3% trichloroacetic acid, 1% thioanisole in $CH_2Cl_2$ for 5 minutes at room temperature to remove the Mmt protecting group. The mixture was washed with $CH_3CN$ and dried with nitrogen. Fmoc-Phg-OH (Novabiochem) was attached to the ε-amine of the Lys-linked DNA using the method described for compound (2b). After removal of the Fmoc protecting group, 4-carboxybenzenesulfonamide (Aldrich) was attached to the beads using the method described for compound (2b). The beads were washed with DMF, then with $CH_3CN$, and dried with nitrogen.

Figure 83:
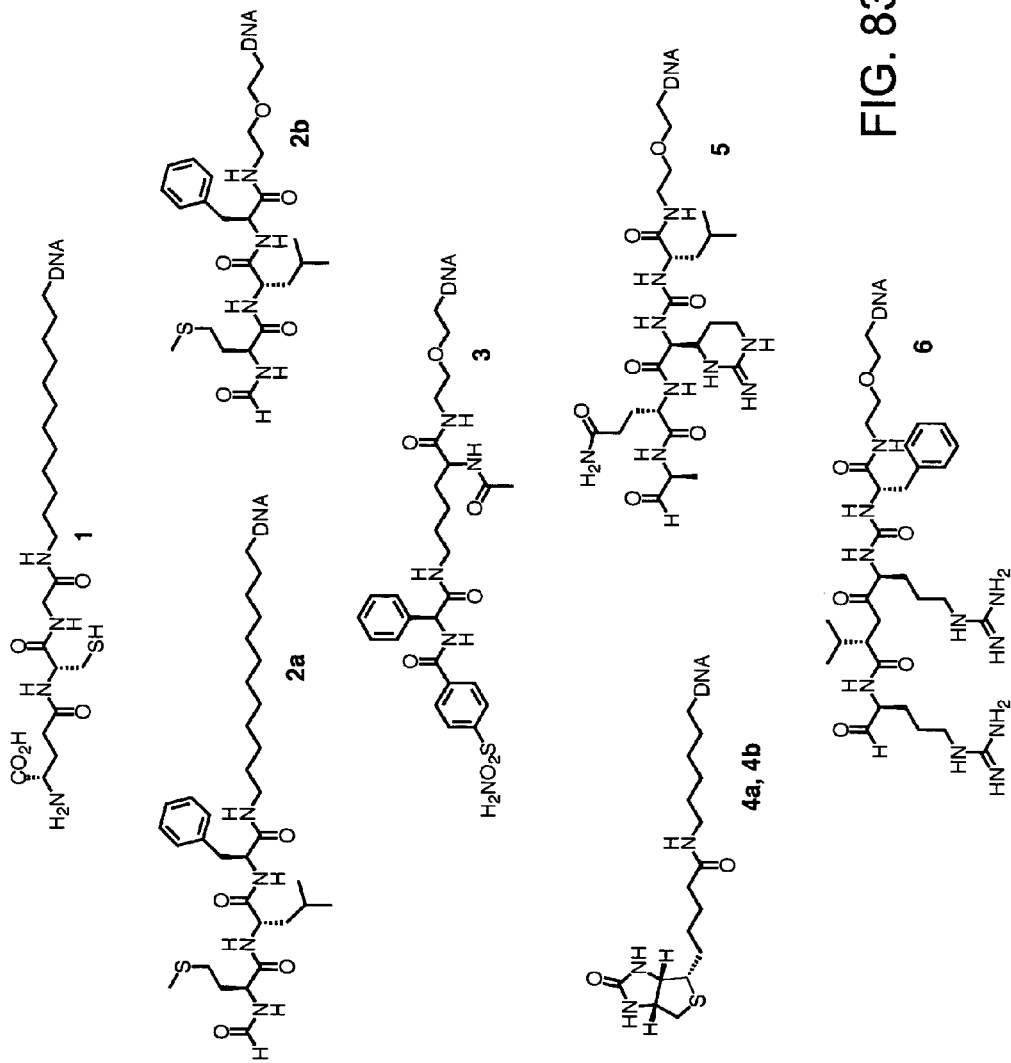
FIG. 83 depicts exemplary specific DNA-linked synthetic molecules selected in FIG. 79.
Figure 84:
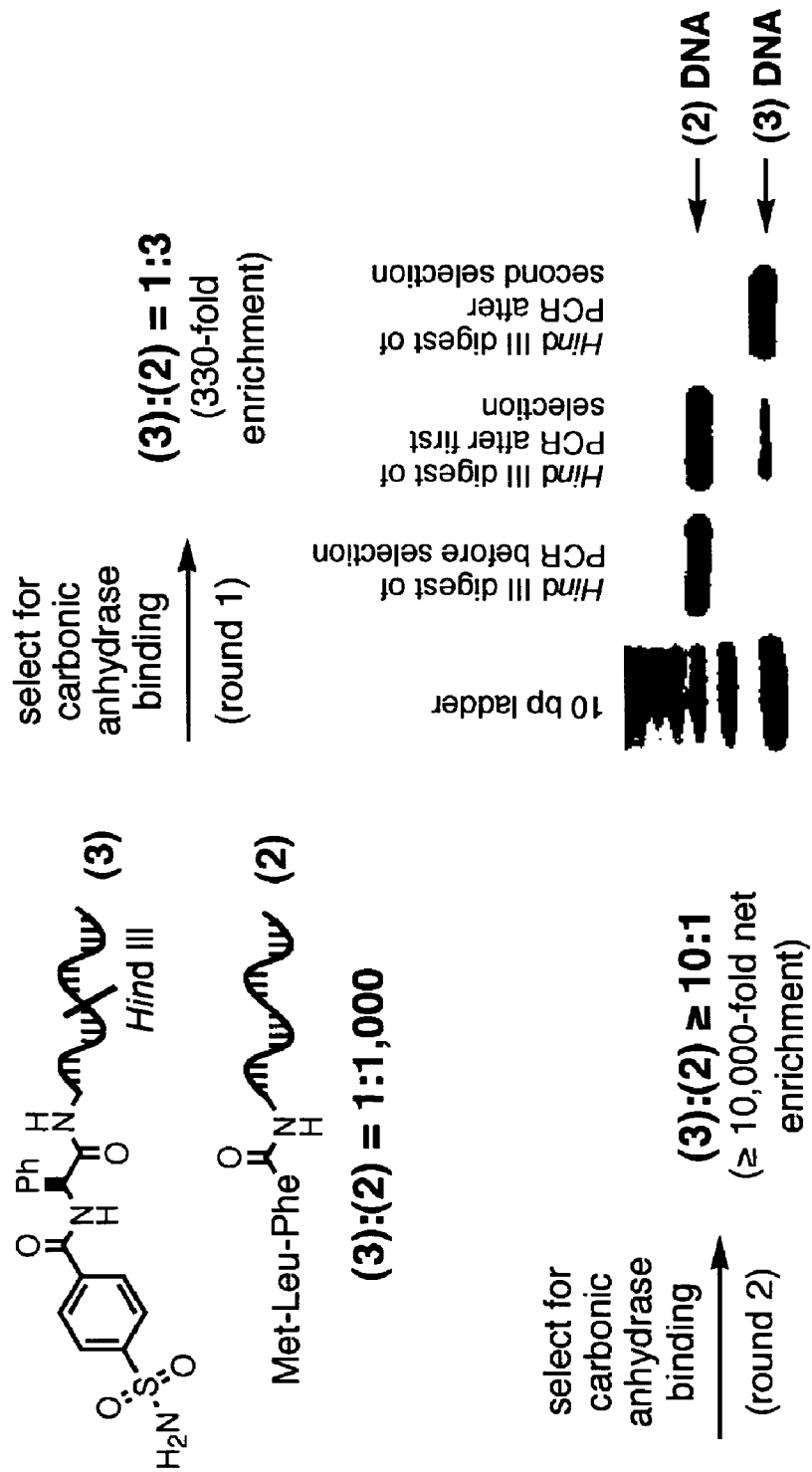
FIG. 84 depicts an exemplary iterated carbonic anhydrase selection scheme.

The complete structures of synthetic groups 1-6 linked to DNA are shown in FIG. 83.

Characterization of DNA-Linked Synthetic Molecules

Small molecule DNA conjugates were cleaved from the CPG beads with a solution of methylamine:ammonium hydroxide (1:1) at 55° C. for 1 hour. The solution was dried under vacuum and then purified by reverse phase HPLC using $TEAA/CH_3CN$ gradient and analyzed by MALDI-TOF mass spectrometry. Stock solution concentrations were determined using UV-Vis spectroscopy and serial dilutions were prepared for the selection experiments. Samples were stored in water at −20° C.

Preparation of Immobilized Target Proteins

NHS activated Sepharose 4 Fast Flow (Amersham Pharmacia) was prepared in accordance with the manufacturer's instructions. Equine GST, bovine carbonic anhydrase (CA), papain, Nα-p-tosyl-L-lysine chloromethyl ketone (TLCK)-treated bovine chymotrypsin, and N-p-tosyl-L-phenylalanine chloromethyl ketone (TPCK)-treated bovine trypsin were purchased from Sigma. Typically, proteins were dissolved in phosphate buffered saline (PBS) buffer pH 7.4-7.6 at concentrations of 20-100 µM. Protein concentrations were determined using UV-Vis spectrometry. Proteins were incubated with beads for 16 hours at 4° C. The beads were capped for two hours with Tris buffer, then washed extensively with the appropriate selection buffer containing 1 M NaCl and then exchanged into the appropriate selection buffer (see, Table 14). Beads were stored for up to 1 month at 4° C. in a volume of selection buffer equal to the initial volume of beads used. Before use, papain beads were activated using a solution of 5.5 mM cysteine HCl, 1.1 mM EDTA, and 0.067 mM β-mercaptoethanol for 30 minutes at 4° C. Streptavidin magnetic particles (Roche) were washed 3× with selection buffer before use.

TABLE 14

Selection and Wash Buffers

| Protein | Composition of Selection Buffer | Composition of Wash Buffers |
|---|---|---|
| GST | PBS pH 7.4 | |
| Carbonic Anhydrase | 10 mM Tris pH 7.4, 0.1M NaCl | 10 mM Tris pH 7.4, 0.25-0.5M NaCl |
| Papain | 50 mM Tris pH 7.4, 0.1M NaCl, 1 mM EDTA | 50 mM Tris pH 7.4, 0.5M NaCl, 1 mM EDTA |
| Trypsin | 50 mM Tris pH 8.0, 0.1M NaCl, 10 mM $CaCl_2$ | 50 mM Tris pH 8.0, 0.5M NaCl, 10 mM $CaCl_2$ |
| Chymotrypsin | 50 MM Tris pH 8.0, 0.1M NaCl, 10 mM $CaCl_2$ | 50 mM Tris pH 8.0, 0.5M NaCl, 10 mM $CaCl_2$ |
| Streptavidin | 10 mM Tris pH 7.4, 0.1M NaCl, 1 mM EDTA | 10 mM Tris pH 7.4, 1.0M NaCl, 1 mM EDTA |

Preparation of Compounds (4a, 4b)

A 5'-biotin modified phosphoramidite (Glen Research, Sterling, Va., USA) was used as the final monomer in the DNA synthesis.

Preparation of Compound (5)

Chymostatin (Sigma) was attached to amino-terminated protected DNA on CPG beads using the conditions described for compound (2b).

Preparation of Compound (6)

Antipain (Sigma, 1.5 µmol, 0.9 mg) was added to a 30 µL solution of 300 mM DCC and 300 mM NHS in DMF. After agitating for 1 hour at room temperature, this solution was added to 45 µL of 5'-amino terminated DNA (~200-300 µM) in 0.1 M MES buffer pH 6.0. This DNA had previously been cleaved from the CPG beads and purified by HPLC as described in the next section. After 2 hours, this solution was purified by gel filtration using Sephadex G-25 followed by reverse-phase HPLC.

GST Selection

The amount of compound (1), the binding ligand, was varied between $10^3$ and $10^7$ molecules and compound (2a), the non-binding ligand, was used in $10^2$-$10^6$ molar excess. (1) and (2a) were added to 40 µl, of GST beads and agitated at 4° C. for 1 hour. The mixture was transferred to a 5.0 µm low-binding Durapore membrane spin filter (Millipore), washed with 2×150 µL PBS pH 7.4, 1×100 µL 0.1 M Tris pH 8.0, 0.5 M NaCl, and 1×150 µL PBS. The bound ligands were eluted by agitating the beads with 100 µL 0.1 M glutathione (Sigma) at room temperature. The eluant was ethanol precipitated with 3 M sodium acetate and 1 µl, glycogen. The precipitate was used directly for PCR.

Carbonic Anhydrase Selection

Compound (2b), the non-binding ligand, and compound (3), the binding ligand, were added to 40 µL of resuspended beads and were diluted to 400 µL with selection buffer. Ratios were similar to those for the GST selection. The mixture was agitated at 4° C. for 1-2 hours. Selections then were carried out at room temperature. Each mixture was transferred to a spin filter and washed 3× with 400 µL of wash buffer and 1×400 µL with selection buffer. The resin was removed from the spin filter with 60 µL of selection buffer and the resulting beads were subjected to PCR.

Papain Selection

Compound (4a), the non-binding ligand, and compounds (5) or (6), the binding ligands, were incubated with papain beads and selected as described for the carbonic anhydrase selection.

Chymotrypsin Selection

Compound (4a), the non-binding ligand, and compound (5), the binding ligand, were incubated with chymotrypsin beads and selected as described for the carbonic anhydrase selection.

Trypsin Selection

Compound (4a), the non-binding ligand, and compound (6), the binding ligand, were incubated with trypsin beads and selected as described for carbonic anhydrase.

Streptavidin Selection

Compound (3), the non-binding ligand, and compound (4b), the binding ligand, were incubated with 15 µL streptavidin magnetic particles and agitated at room temperature for 20 minutes. Using a MPC-S magnet (Dynal), the beads were washed 2× with 0.1 M NaOH, 1 mM EDTA (100-200 pt), 4× with wash buffer (100-200 µL), and 1× with selection buffer. The beads then were resuspended in 15 µL double distilled $H_2O$.

Iterated Carbonic Anhydrase Selection $10^8$ molecules of compound (3) and $10^{11}$ molecules of compound (2b) were incubated with 40 µL carbonic anhydrase beads for 1 hours and then selected as described. After the first round of selection, 5 µL of resuspended agarose beads were removed for PCR. 6 M guanidinium HCl, 10 mM EDTA (40 µL) was added to the beads and the mixture was heated to 90° C. for 15 minutes. The beads were filtered away using a Wizard Minicolumn (Promega). The filtrate was buffer exchanged into selection buffer using a Centrisep Spin Column (Princeton Separations). A new aliquot of carbonic anhydrase beads was added to the eluted templates. After a second round of selection, the agarose beads were suspended in 30 µL of $H_2O$ and 15 µL were used for PCR. The PCR products were digested with Hind III, generating the results in FIG. 84.

The triple iteration selection was carried out essentially as described above with a few minor changes. The prepared carbonic anhydrase beads were incubated with $ZnSO_4$ (1 mM) for 1 hour and then washed extensively with selection buffer containing 2 M NaCl. The beads were exchanged back into selection buffer and used directly for the iterated selection. $10^9$ molecules of compound (3) and $10^{15}$ molecules of compound (4b) were added to the beads and selected as described above. After the first round of selection, 3 µL aliquot was removed for PCR. A second round of selection was carried out as described above and 8 µL aliquot of beads was removed for PCR. After a third round of selection, the resulting beads were removed from the spin filter using 30 µL of double distilled $H_2O$ and 15 µL of resuspended beads were used for PCR.

Papain Affinity and Papain Specificity Selections

Affinity selection: $6×10^9$ molecules of compound (6), $2.3×10^{10}$ molecules compound (5), and $1.4×10^{11}$ molecules of compound (4a) were added to 40 µA papain beads for 1 hour. The beads were washed with papain wash buffer (3×100 µL) and once with 100 µL papain selection buffer. The beads were removed from the spin filter with 30 µL of double distilled $H_2O$. A 3 µL aliquot of resuspended beads were removed for PCR. The DNA conjugates were eluted from the beads by adding 70 µL 6 M guanidinium HCl and heating the mixture to 90° C. for 15 minutes. The eluted material was buffer exchanged as described in the iterated carbonic anhydrase selection. After a second round of selection, the agarose beads were removed from the spin filter using 30 µL $H_2O$ and 15 µL of resuspended beads were used for PCR.

Specificity selection: The same amounts of antipain, chymostatin, and biotin were added to 40 µL chymotrypsin agarose beads in chymotrypsin selection buffer and incubated for 1 hour. The beads were spun down and the flow through was added to 40 µL fresh chymotrypsin beads and incubated for 1 hour. The beads were spun down and 15 µL of 100 µM chymotrypsin in papain selection buffer was added to the flow through and then incubated for 1 hour. This solution was added to 40 µL of papain beads and selected as described above. The small molecule-DNA conjugates were eluted and buffer exchanged as described, incubated with 15 µL 100 µM chymotrypsin for 1 hour and then subjected to a second round of selection. The beads were removed from the spin filter with 30 µL of $H_2O$ and 15 µL were used for PCR.

Contamination Controls

Due to the high sensitivity of these experiments, two important contamination controls were used throughout these studies. First, each selection was carried out as described above except no ligand-DNA conjugates were added to the protein-linked beads, which permitting testing for buffer contamination and any cross-contamination among samples. Secondly, a PCR reaction in which no material from the selection was added was used to test for contamination in primers, dNTPs, and PCR buffers.

PCR Conditions and Gel Electrophoresis Analysis

Templates surviving the selection were amplified using PCR. All reactions contained 1 µM of each primer and 250 µM of each dNTP (Promega). For the GST selection, the precipitated DNA was used in the PCR reaction and amplified with Platinum Taq (Invitrogen). PCR conditions were step 1: 94° C. 2'; step 2: 94° C., 30 s; step 3: 55° C. 1'; step 4:72° C., 30 s; step 5: go to step 2, ×29; step 6: 72° C., 5'; step 7: hold at 4° C. For all other selections, the agarose beads (3-15 µL) were used directly in the PCR reaction with Taq polymerase (Promega). PCR conditions were step 1: 94° C., 2' step 2: 94° C., 30 s; step 3: 55° C., 1'; step 4: 72° C., 30 s; step 5: go to step 2, ×24; step 6: 4° C.

The PCR products then were digested for 1-2 hours with the restriction enzymes (New England Biolabs, 5-10 units) that digest the ligand-encoding DNA. Digestion products were analyzed by electrophoresis on 3% agarose gels and quantitated by ethidium bromide staining and densitometry on a Strategene Eagle Eye II system.

Enrichment Calculations

Enrichment ratios are calculated as the ratio of the fraction of binding ligand surviving the selection as determined by restriction digestion to the fraction of binding ligand entering the selection as determined by the known concentrations of the stock solutions.

DNA Sequences of Templates and Primers

Restriction endonuclease cleavage sites are underlined.

DNA Sequences for Glutathione S Transferase Selections:

```
GSH template (1):   5'-GCC TCT GCG ACC GTT CGG AAG
                       CTT CGC GAG TTG CCC AGC GCG
                       (Hind III)
```

```
MLF-template (2a):      5'-GCC TCT GCG ACC GTT CGG GAA
                        TTC CGC GAG TTG CCC AGC GCG
                        (Eco RI)
                        [SEQ ID NO: 113]

Primer 1:               5'-GCC TCT GCG ACC GTT CGG
                        [SEQ ID NO: 114]

Primer 2:               5'-CGC GCT GGG CAA CTC GCG
                        [SEQ ID NO: 115]
```

DNA Sequences for Carbonic Anhydrase Selections:

```
Phenyl sulfonamide-     5'-CGA TGC TAG CGA AGG AAG
template (3):           CTT CCA CTG CAC GTC TGC
                        (Hind III)
                        [SEQ ID NO: 116]

MLF-template (2b):      5'-CGA TGC TAG CGA AGG GAA
                        TTC CCA CTG CAC GTC TGC
                        (Eco RI)
                        [SEQ ID NO: 117]

Biotin-template (4b):   5'-CGA TGC TAG CGA AGG GAA
                        TTC CCA CTG CAC GTC TGC
                        (Eco RI)
                        [SEQ ID NO: 118]

Primer 1:               5'CGA TGC TAG CGA AGG
                        [SEQ ID NO: 119]

Primer 2:               5'-GCA GAC GTG CAG TGG
                        [SEQ ID NO: 120]
```

DNA Sequences for Protease Selections:

```
Chymostatin-template (5):  5'-GCA GTC GAC TCG ACC
                           GGA TCC GGC TAC GAC GTG
                           CAC (BaM HI)
                           [SEQ ID NO: 121]

Antipain template (6):     5'-GCA GTC GAC TCG ACC
                           CAG CTG GGC TAC GAC GTG
                           CAC (Pvu II)
                           [SEQ ID NO: 122]

Biotin-template (4a):      5'-GCA GTC GAC TCG ACC
                           AAG CTT GGC TAC GAC GTG
                           CAC (Hind III)
                           [SEQ ID NO: 123]

Primer 1:                  5'-GCA GTC GAC TCG ACC
                           [SEQ ID NO: 124]

Primer 2:                  5'-GTG CAC GTC GTA GCC.
                           [SEQ ID NO: 125]
```

Example 12

Identification of New Chemical Reactions

This Example demonstrates that it is possible to identify the existence of new chemical reactions via nucleic acid-templated synthesis. New chemical reactions have been identified as a result of experiments to select for, and characterize, bond forming reactions.

Figure 85:
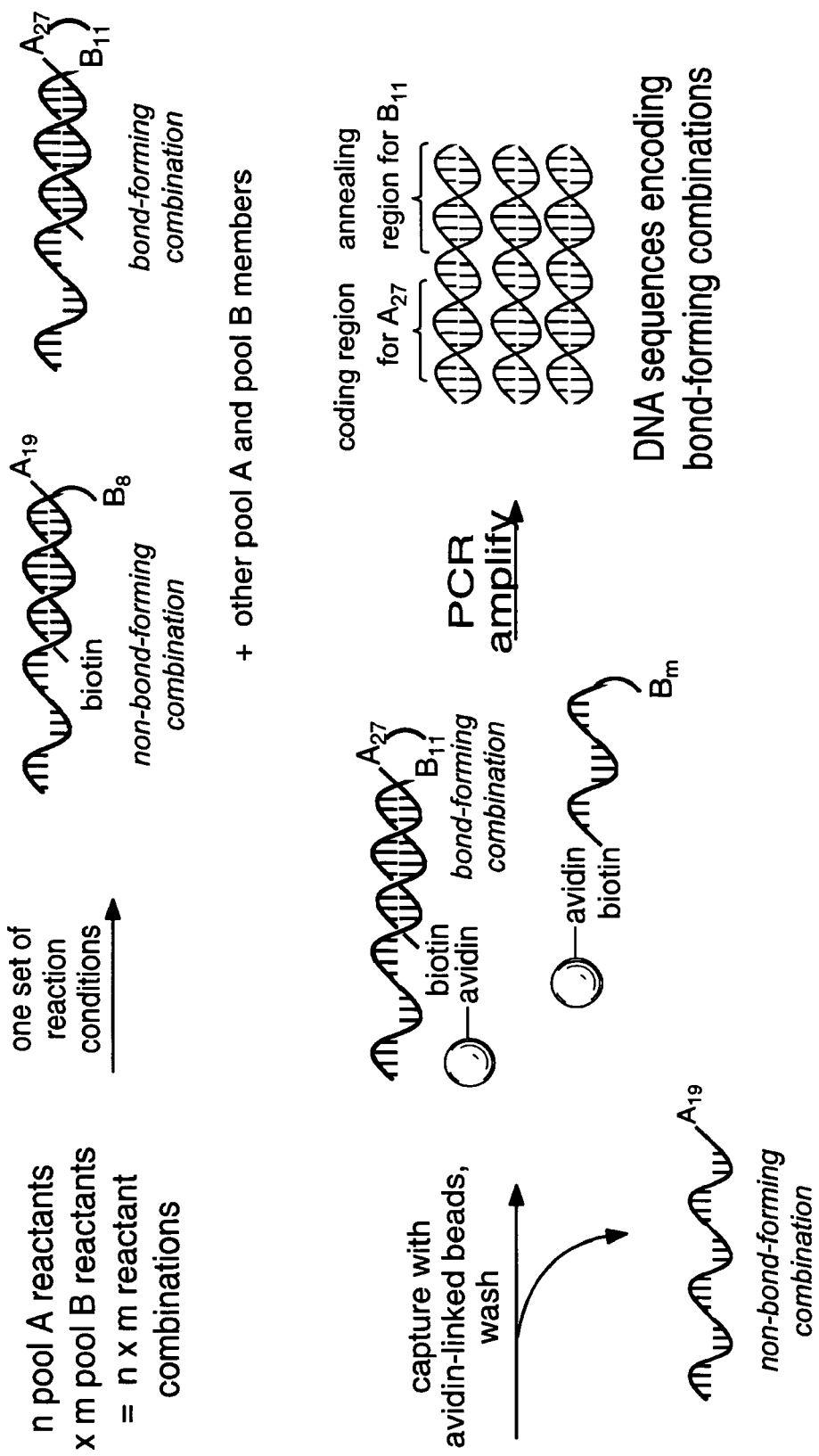
FIG. 85 is a schematic representation of a method for performing one-pot selections for bond-forming reactions.

A one-pot selection scheme to identify new bond forming reactions is summarized in FIG. 85. Briefly, when n pool A reactants are combined with m pool B biotinylated reactants, n×m possible reaction combinations are available. When the templated reaction is performed under a particular set of reaction conditions certain combinations of the template (e.g., reactant A27) reacts with certain combinations of the transfer unit (e.g., the reactant biotinylated B11). The reaction products are captured by avidin linked beads. Unreacted templates are not captured by the avidin and can be removed by washing. The avidin captured reaction product can then be amplified, for example, by PCR, and the template sequenced to determine its codon sequence. As shown, the amplified template included a sequence tag (coding region) for reactant A27 and a codon sequence (annealing region) for reactant B11.

Figure 86:
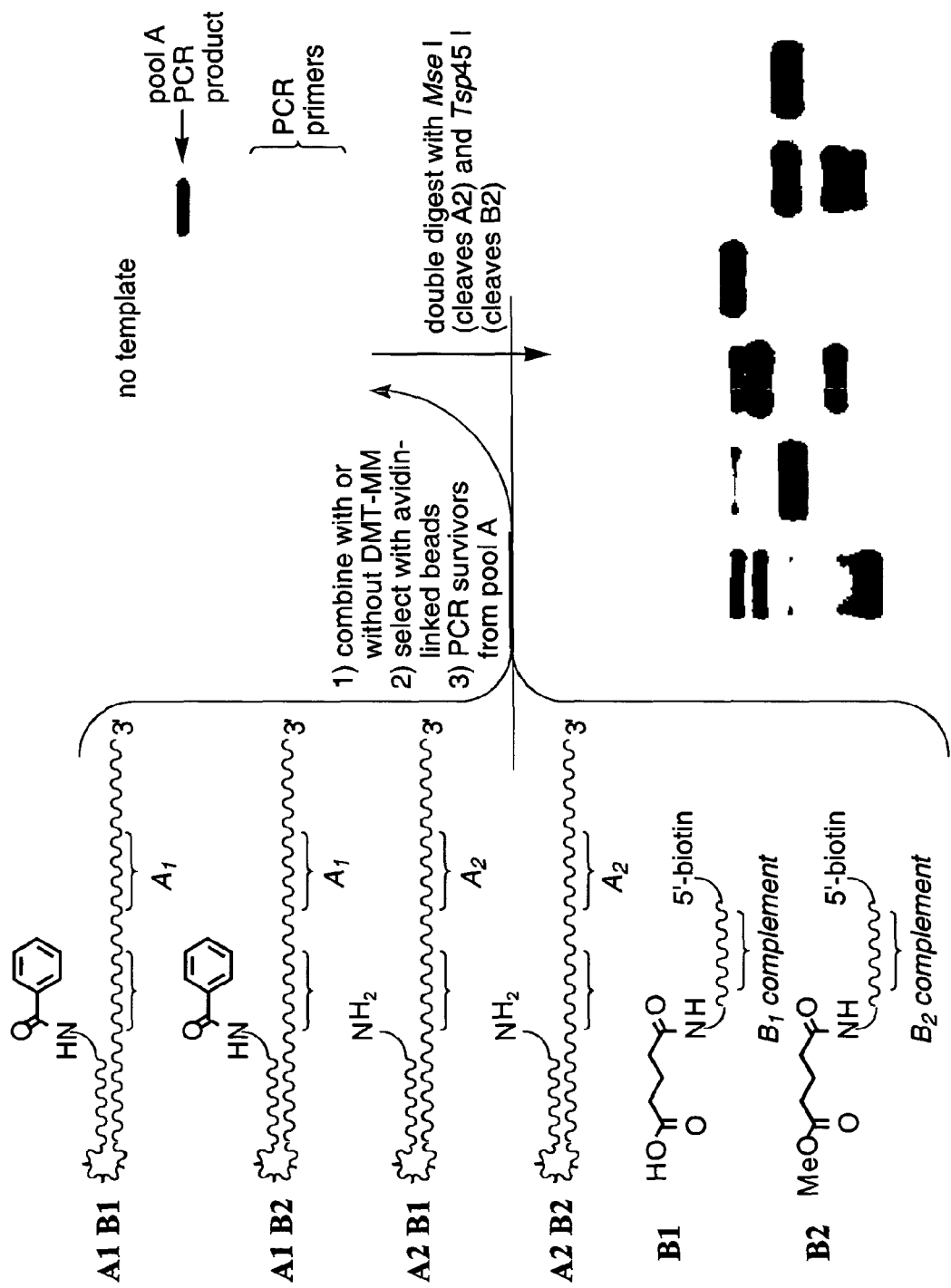
FIG. 86 is a schematic representation of a method for validating the discovery of new bond-forming reactions using DNA-templated synthesis.
Figure 87:
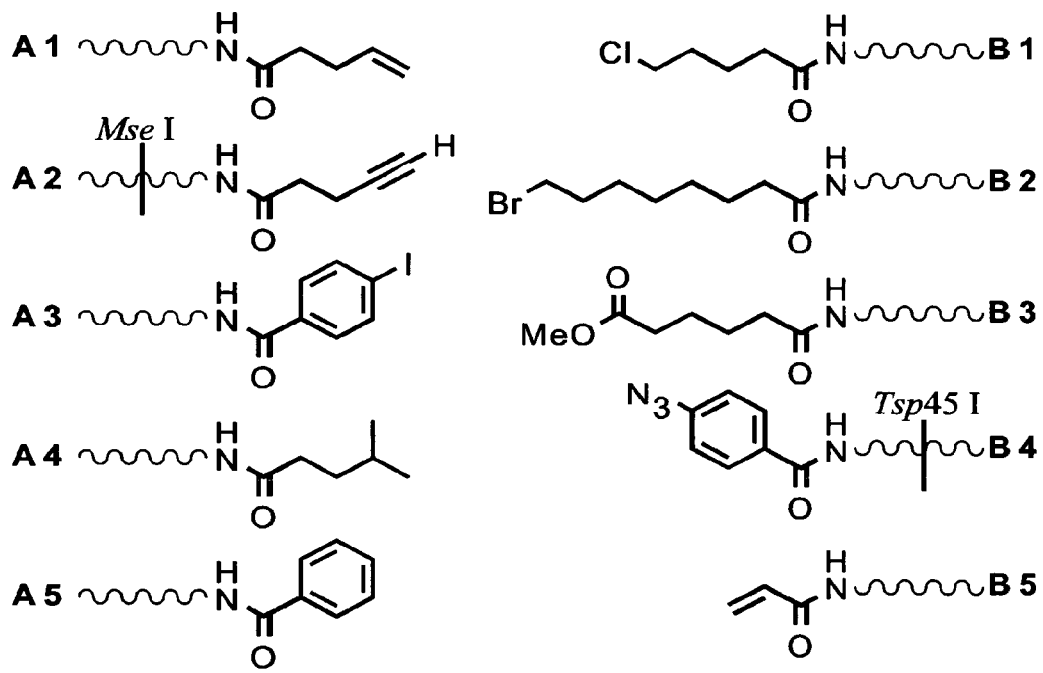
FIG. 87 depicts an example of reaction discovery using nucleic acid-templated synthesis.
Figure 87:
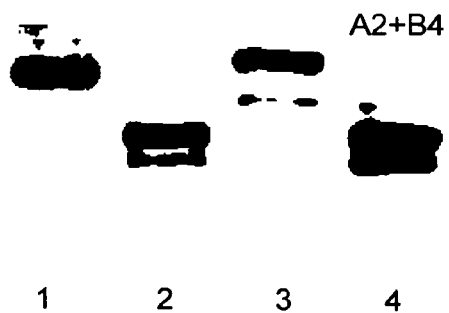
Figure 88:
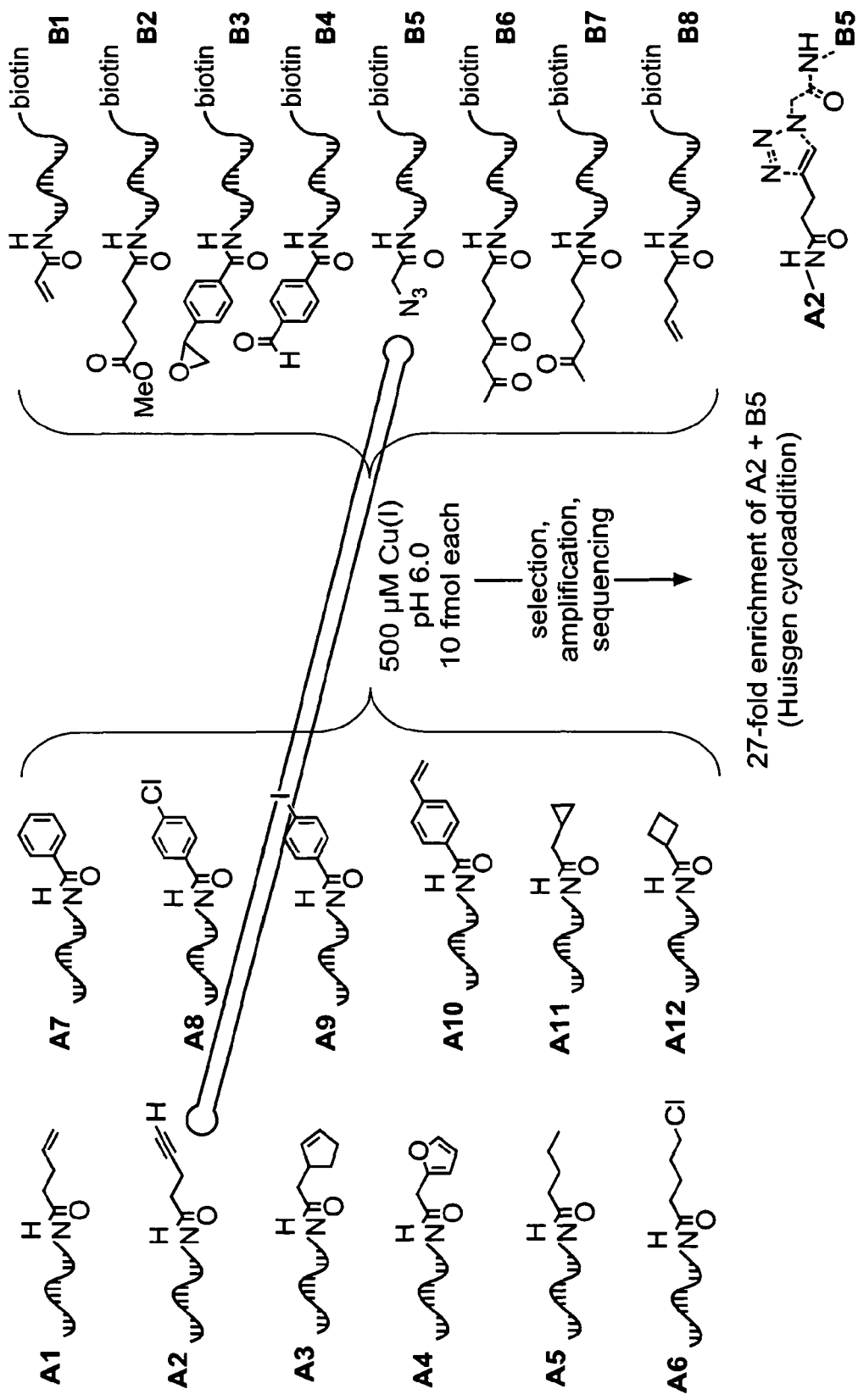
FIG. 88 depicts the discovery of Cu-mediated coupling reactions identified using nucleic acid-templated synthesis.

FIG. 86 provides a schematic overview of a scheme for producing a library of compounds, members of which were created by new identified chemical reactions. In order to select for bond-forming reactions, four pool A reactants presenting either a phenyl group (A1B1 and A1B2) or a primary amine (A2B1 and A2B2) and two biotinylated pool B reactants presenting either a carboxylic acid (B1) or a methyl ester (B2) were prepared. The two coding and two annealing regions contained different restriction digestion sites to permit the relative quantitation of each of the four pool A members from within a mixture. All six reactants (250 mol of each pool A reactant and 500 fmol of each of B1 and B2) were combined in a single pot either in the presence or absence of DMT-MM, which is known to mediate amide formation between amines and carboxylic acids (Gartner et al. (2002) AGNEW. CHEM. INT. ED. 41: 1796-1800; Kunishima et al. (2002) TETRAHEDRON 57: 1551-1558). The crude reactions were passed over streptavidin-linked magnetic beads to select for templates encoding bond-forming reactions and washed with denaturant to remove pool A members that did not undergo bond formation with a pool B member. The selected molecules were eluted with free biotin and formamide. A fraction of the eluant corresponding to 5 Fmol of initial total reactants was amplified by PCR and subjected to DNA sequencing and restriction digestion to determine the ratio of the four possible reaction-encoding sequences (i.e., reaction of the phenyl group with the carboxylic acid, reaction of the phenyl group with the ester, reaction of the amine group with the carboxylic acid, and reaction of the amine group with the ester) (FIG. 86).

Combining the reactants in the absence of DMT-MM resulted in very little PCR product formation following selection. In contrast, strong PCR product was observed when the reactants were combined in the presence of DMT-MM (FIG. 86), consistent with the effectiveness of capturing reacted pool A members and the thoroughness of the washing steps. This result suggests that the yield of PCR product following selection for bond-forming reactions can serve as a simple screen for the presence of bond formation within a pool of reactants. To determine the identity of the bond-forming reactants, the PCR products were digested with Mse I, which cleaves the coding region for A2 but not A1, and Tsp45 I, which cleaves the annealing region for B2 but not B1. An analysis of the digestion fragments revealed that reaction in the absence of DMT-MM followed by selection resulted in a mixture of all four possible reaction-encoding pool A members (FIG. 86). In contrast, reaction in the presence of DMT-MM followed by selection generated the A2B1 sequence and no significant amount of the other three sequences (FIG. 86), indicating strong enrichment for the DNA encoding bond formation between the amine and the carboxylic acid. DNA sequencing of the selected PCR products was consistent with the restriction digestion analysis. These results validate the basic principle of the proposed method and system for discovering new reactions.

In order to test the ability of the proposed reaction discovery system to select a single reactive combination out of an even larger excess of unreactive combinations, the system was programmed with three reaction possibilities (amine+ carboxylic acid, amide+ester, and amine+ester) and combined the corresponding DNA-linked reactants in proportions that favor the unreactive combinations (amide+ester and amine+ester) by 100-fold. In the presence of amide coupling reagent DMT-MM, in vitro selection of the resulting mixture for bond-forming reactions resulted in a >1.000-fold enrichment of the template encoding bond formation between the amine and carboxylic acid. No enrichment was observed when DMT-MM was omitted. This result further supports the possibility of selecting and decoding a single reactive bond-forming combination from the planned 30 by 30 matrix of 900 reaction possibilities.

Validation of New Reaction Discovery

Example A

This Example shows that it is indeed possible to discover new chemical reactions using DNA-templated synthesis. A 25-reaction matrix containing the DNA-linked functional groups shown in FIG. 87 was generated essentially as described in FIG. 9 using the omega architecture, the one-pot assembly method for pool A reactants, and an optimized codon set. Among the 25 possible reactions in this set is the Huisgen 1,3-dipolar cycloaddition (Huisgen et al. (1989) PURE APPL. CHEM. 61: 613) between an azide and an alkyne. Sharpless and co-workers recently reported (Rostoutseu et al., (2002) ANGEW CHEM. INT. ED. ENGL. 41: 2596) that catalytic $CuSO_4$ and sodium ascorbate dramatically improve the regioselectivity and efficiency of this process, permitting a robust reaction at room temperature. A reaction discovery selection was performed on a 1 pmol scale using this 25-reaction matrix either in the presence or the absence of $CuSO_4$ and sodium ascorbate.

In the presence of copper and ascorbate, selection for bond-forming reactions followed by PCR amplification and sequence analysis by restriction digestion highly enriched the pool A template encoding the alkyne- and azide-encoding reactants (see, Lane 2 in FIG. 87B). In contrast, omitting copper and ascorbate resulted in no enrichment for the alkyne- and azide-encoding template (see, Lane 3 in FIG. 87B. The reaction discovery selection system therefore successfully "rediscovered" the Cu(I)-mediated coupling of an alkyne and azide.

Validation of New Reaction Discovery

Example B

This Example shows that the reaction identified in Example A can also be identified in a 96-reaction matrix. Briefly, a 96-reaction matrix containing the DNA-linked functional groups shown in FIG. 88 was generated. Pool A contained 12 reactants (A1-A12) and pool B contained 8 biotinylated reactants (B1-B8). When combined, 96 different reactions were possible.

The reactants (10 fmol each) were combined in the presence of 500 µM Cu (I) at pH 6.0. Following reaction selection and amplification, one oligonucleotide sequence was enriched. In particular, there was a 27-fold enrichment for the template encoding the reaction between reactant A2 and reactant B5. The reaction product, like Example A appears to have resulted from a Huisgen cycloaddition reaction. In contrast, when no Cu (I) was present, there was very little PCR product with no enrichment for any combination of the reactants.

Validation of New Reaction Discovery

Example C

This Example shows another example that it is possible to discover new chemical reactions using nucleic acid-templated synthesis. In particular, this Example demonstrates the discovery of a novel Pd-mediated coupling reaction.

A library of reactants were created and combined to test for the ability of nucleic acid-templated Pd-mediated coupling reactions. Two pools of reactants (see, FIG. 89) were synthesized to give 12 pool A reactants (A1-A12) and 8 biotinylated pool B reactants (B1-B8). When combined, 96 different reactions were possible. The reactants (10 fmol each) were combined in the presence of 1 mM Pd(II) at pH 7.0. Following reaction selection and amplification, five oligonucleotide sequences were enriched between 10-fold and 22-fold. Analysis of the five oligonucleotide sequences revealed that reactions occurred between (i) reactant A2 and reactant B1 (ii) reactant A2 and reactant B4, (iii) reactant A2 and reactant B8 (iv) reactant A9 and reactant B1, and (v) reactant A 10 and reactant B4.

Figure 90:
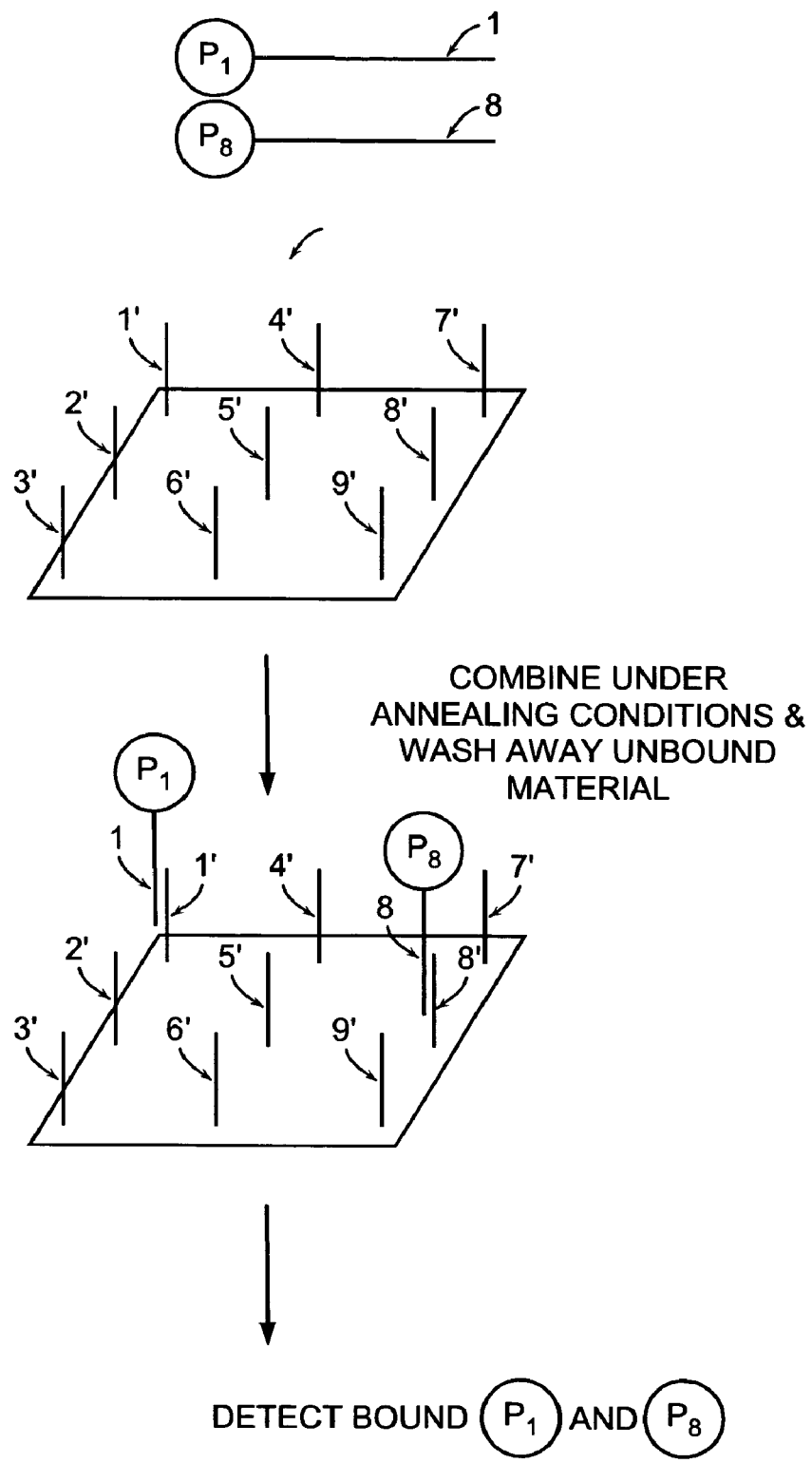
FIG. 90 is a schematic representation of a microarray based sequence analysis protocol.

As an alternative to sequencing the enriched oligonucleotides, the identity of the oligonucleotide sequences attached to the reaction products were determined by microarray analysis (see, FIG. 90). A library of anti-sense oligonucleotides complementary to each of the templates to be included in the reaction matrix are synthesized. Then, individual anti-sense oligonucleotides (1'-9' in FIG. 90) complementary to each template are immobilized at separate addressable locations of a microarray. The sequence of each anti-sense oligonucleotide immobilized in the microarray is known. After nucleic acid-templated synthesis, the oligonucleotides attached to the resulting reaction products (for example, P1 attached to template 1 and product P8 attached to template 8 in FIG. 90) are amplified under conditions to permit incorporation of a detectable moiety, for example, a fluorophore, into the amplified template. The amplified oligonucleotides then are denatured and combined with the microarray under conditions to permit the template oligonucleotide (for example, oligonucleotide 1 and oligonucleotide 8 in FIG. 90) to hybridize to its immobilized, complementary oligonucleotide. After washing to remove unbound material, the microarray may then be scanned to detect a specific binding event via detection of the detectable moiety at a particular location. Based on the location of the detectable moiety and the known sequence of the complementary oligonucleotide immobilized at that location, it is possible to determine the sequence of the bound template and thus the reactants that produced the reaction product.

This type of microarray analysis approach was used following reactions similar to those described in Example B (96-reaction matrix with Cu (I)) and in Example C hereinabove (96-reaction matrix with Pd (II)). The microarray analysis was found to agree with the DNA sequencing results. Furthermore, the microarray analysis was found to be more direct, more sensitive, and significantly faster (at least 5-fold faster) than standard sequencing methodologies.

Figure 89:
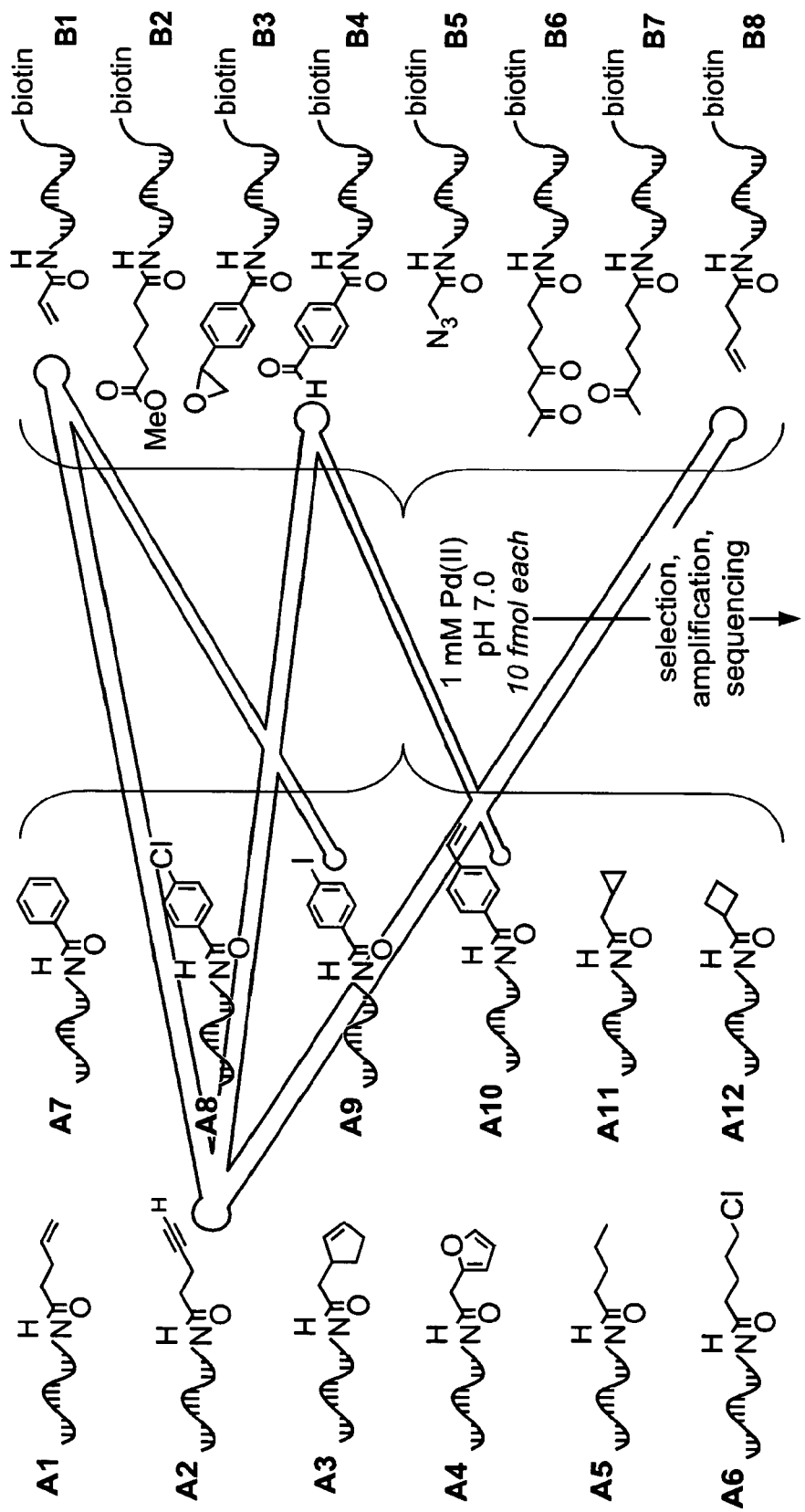
FIG. 89 depicts the discovery of Pd-mediated coupling reactions identified using nucleic acid-templated synthesis.
Figure 91:
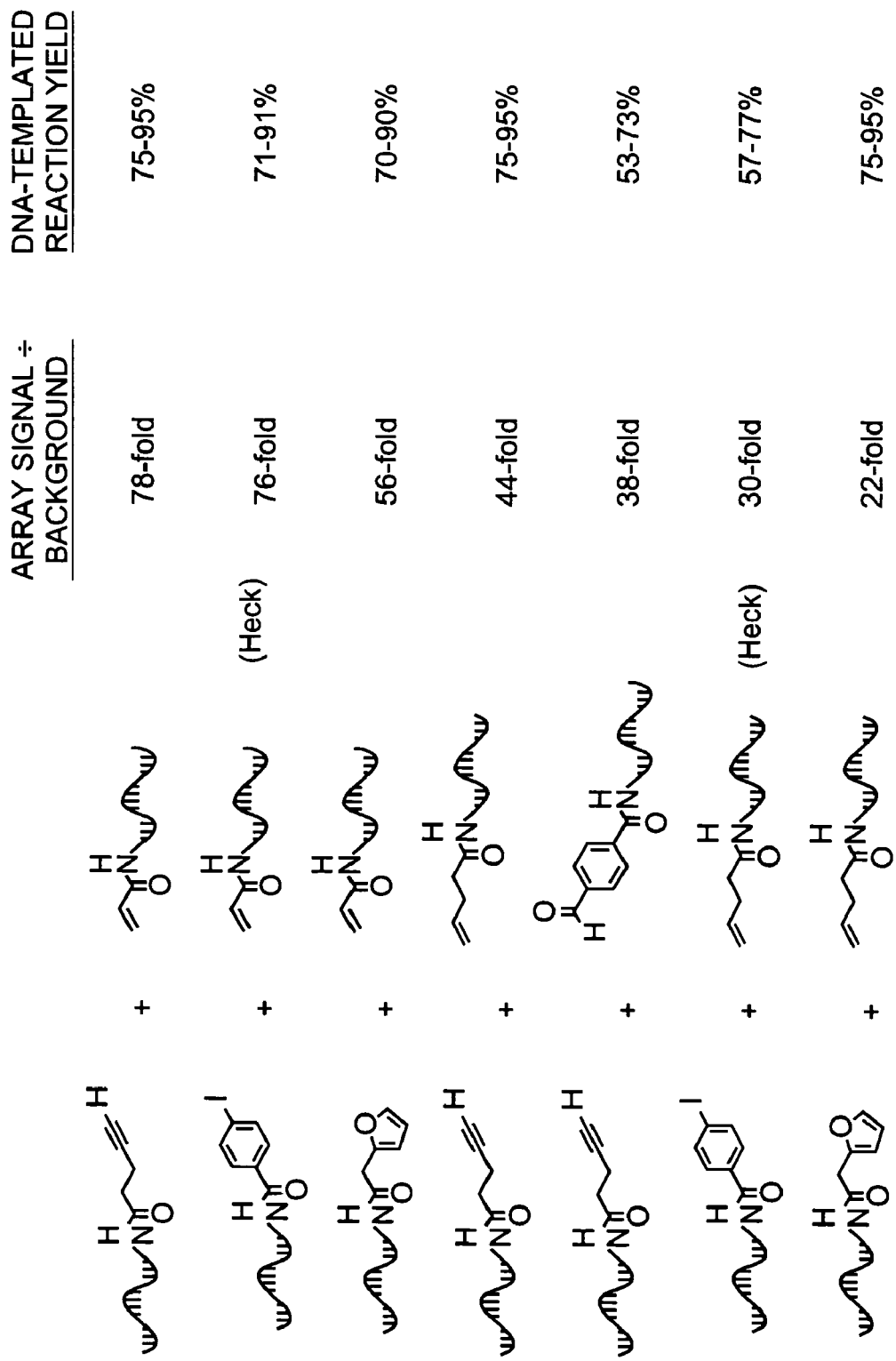
FIG. 91 depicts the analysis of the Pd-mediated reactions identified via microarray based sequence analysis.

By way of example, various products of the Pd (II) mediated reactions were detected via the microarray system, the results of which are summarized in FIG. 91. FIG. 91 summarizes which reactants in pool A reacted with which biotinylated reactants in pool B to create a product. FIG. 91 also summarizes the level of signal over background and DNA-templated reaction yield for each product. Of particular interest is the discovery using both sequence analysis approaches of a bond-forming reaction between DNA-linked terminal alkyne A2 and DNA-linked acrylamide B8 in the presence of 1 mM Pd(II) at pH 7 (see. FIGS. 89 and 91). This reaction is comparable in efficiency a DNA-templated Heck coupling reactions of aryl iodides and olefins and does not proceed in the absence of a Pd source. Although Pd-mediated couplings between terminal alkynes and aryl iodides are known (Amatore et al., (1995) J. ORG. CHEM. 60: 6829), the Pd-mediated coupling of terminal alkynes with simple or electron deficient olefins appears to be a new type of reaction scheme. This newly discovered reaction scheme may now be characterized in greater detail using more conventional larger scale reactions.

INCORPORATION BY REFERENCE

The entire contents of each of the publications, patents and patent applications cited herein are incorporated by reference into this application for all purposes.

EQUIVALENTS

The invention may be embodied in other specific forms without departing form the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. An in vitro method of enriching a product of a nucleic acid-templated synthesis, the method comprising the steps of:
(a) providing a first library of molecules comprising a plurality of reaction products of a nucleic acid templated synthesis, which are not nucleic acids, wherein each reaction product is covalently attached to a corresponding oligonucleotide that templated the synthesis of the reaction product, and wherein each oligonucleotide comprises a nucleotide sequence indicative of the reaction product associated therewith, and wherein a portion of said reaction products are capable of binding to a preselected binding moiety;
(b) exposing said first library of molecules to said binding moiety under conditions to permit reaction product capable of binding said binding moiety to bind thereto, wherein the reaction product has a $K_d$ for the binding moiety of no less than 0.9 nM;
(c) removing unbound reaction products; and
(d) eluting bound reaction product from said binding moiety to produce a second library of molecules enriched at least 50-fold for reaction product that binds said binding moiety relative to said first library.

2. The method of claim 1, wherein in step (b), said binding moiety is immobilized on a solid support.

3. The method of claim 1, wherein said binding moiety is a target biomolecule.

4. The method of claim 3, wherein said target biomolecule is a protein.

5. The method of claim 1, wherein in step (d), said second library is enriched at least 100-fold for reaction product that binds said binding moiety.

6. The method of claim 5, wherein in step (d), said second library is enriched at least 1,000-fold for reaction product that binds said binding moiety.

7. The method of claim 1, further comprising repeating steps (b), (c), and (d).

8. The method of claim 7, wherein repeating steps (b), (c), and (d) produces a third library enriched by at least 10,000-fold for reaction product that binds said binding moiety.

9. The method of claim 8, wherein said library is enriched by at least 100,000-fold for reaction product that binds said binding moiety.

10. The method of claim 1, wherein said oligonucleotide comprises a first sequence that identifies a first reactive unit that produced said reaction product capable of binding said preselected binding moiety.

11. The method of claim 10, wherein said oligonucleotide comprises a second sequence that identifies a second reactive unit that produced said reaction product capable of binding said preselected binding moiety.

12. The method of claim 1, comprising the additional step of amplifying oligonucleotide associated with the enriched reaction product.

13. The method of claim 1, comprising the additional step of determining the sequence of the oligonucleotide associated with the enriched reaction product.

14. The method of claim 12, comprising the additional step of determining the sequence of the amplified oligonucleotide.

15. The method of claim 13, further comprising the step of characterizing said reaction product from information in said sequence of said oligonucleotide.

16. The method of claim 15, further comprising the step of identifying a new chemical reaction that produced said reaction product.

17. The method of claim 14, further comprising the step of characterizing the reaction product from information in said sequence of said oligonucleotide.

18. The method of claim 17, further comprising the step of identifying a new chemical reaction that produced said reaction product.

19. An in vitro method of enriching a product of a nucleic acid-templated synthesis, the method comprising the steps of:
(a) providing a first library of molecules comprising a plurality of reaction products of a nucleic acid templated synthesis, which are not nucleic acids, wherein each reaction product is covalently attached to a corresponding oligonucleotide that templated the synthesis of the reaction product, wherein each oligonucleotide comprises a nucleotide sequence indicative of the reaction product associated therewith, wherein no oligonucleotide is linked by a direct or indirect covalent or non-covalent interaction to a capturable moiety selected from the group consisting of biotin, avidin and streptavidin; and wherein a portion of said reaction products are capable of binding to a preselected binding moiety;
(b) exposing said first library of molecules to said binding moiety under conditions to permit reaction product capable of binding said binding moiety to bind thereto;
(c) removing unbound reaction products; and
(d) eluting bound reaction product from said binding moiety to produce a second library of molecules enriched at least 50-fold for reaction product that binds said binding moiety relative to said first library.

* * * * *